(12) United States Patent
Niessen et al.

(10) Patent No.: US 12,371,499 B2
(45) Date of Patent: Jul. 29, 2025

(54) METHOD OF TREATING CANCER USING ANTI-AV8 ANTIBODIES

(71) Applicants: PFIZER INC., New York, NY (US); THE REGENTS OF THE UNIVERSITY OF CALIFORNIA, Oakland, CA (US)

(72) Inventors: Kyle Steven Niessen, Edina, MN (US); Dharmaraj Samuel, Dublin, CA (US); Charles Ray Holst, San Jose, CA (US); Matthew Ross Drever, Concord, CA (US); Dean Sheppard, Oakland, CA (US); Rosemary J. Akurst, Tiburon, CA (US); Amha Atakilit, Oakland, CA (US); Dominique Meyer, El Cerrito, CA (US); Isaac J. Rondon, San Francisco, CA (US); Joseph Dal Porto, Los Gatos, CA (US)

(73) Assignees: The Regents of the University of California, Oakland, CA (US); Pfizer, Inc., New York, NY (US)

( * ) Notice: Subject to any disclaimer, the term of this patent is extended or adjusted under 35 U.S.C. 154(b) by 119 days.

(21) Appl. No.: 17/743,578

(22) Filed: May 13, 2022

(65) Prior Publication Data
US 2022/0289850 A1 Sep. 15, 2022

Related U.S. Application Data

(62) Division of application No. 16/561,530, filed on Sep. 5, 2019, now Pat. No. 11,359,024.
(Continued)

(51) Int. Cl.
| A61K 39/395 | (2006.01) |
| C07K 16/28 | (2006.01) |
| A61K 39/00 | (2006.01) |

(52) U.S. Cl.
CPC ...... *C07K 16/2839* (2013.01); *C07K 16/2818* (2013.01); *C07K 16/2878* (2013.01);
(Continued)

(58) Field of Classification Search
None
See application file for complete search history.

(56) References Cited

U.S. PATENT DOCUMENTS

| 5,624,821 A | 4/1997 | Winter et al. |
| 7,501,121 B2 | 3/2009 | Tchistiakova et al. |

(Continued)

FOREIGN PATENT DOCUMENTS

| CN | 103857696 A | 6/2014 |
| CO | 2022011661 A2 | 8/2022 |

(Continued)

OTHER PUBLICATIONS

Ganesh et al., TGF-b Inhibition and Immunotherapy: Checkmate, Immunity, 48:626-628, Apr. 17, 2018.*
(Continued)

*Primary Examiner* — Claire Kaufman
(74) *Attorney, Agent, or Firm* — Kilpatrick Townsend & Stockton LLP

(57) ABSTRACT

The invention provides antibodies, and antigen-binding fragments thereof, that specifically bind to αvβ8 integrin. The invention includes uses, and associated methods of using the antibodies.

20 Claims, 51 Drawing Sheets

Specification includes a Sequence Listing.

Related U.S. Application Data

(60) Provisional application No. 62/890,945, filed on Aug. 23, 2019, provisional application No. 62/728,688, filed on Sep. 7, 2018.

(52) U.S. Cl.
CPC .... *A61K 39/3955* (2013.01); *A61K 2039/505* (2013.01); *A61K 2039/507* (2013.01); *C07K 2317/24* (2013.01); *C07K 2317/33* (2013.01); *C07K 2317/55* (2013.01); *C07K 2317/565* (2013.01); *C07K 2317/71* (2013.01)

(56) References Cited

U.S. PATENT DOCUMENTS

| | | | |
|---|---|---|---|
| 9,217,039 | B2 | 12/2015 | Pedersen et al. |
| 9,290,572 | B2 | 3/2016 | Nishimura et al. |
| 9,969,804 | B2 | 5/2018 | Sheppard et al. |
| 10,167,334 | B2 | 1/2019 | Mirza et al. |
| 10,597,455 | B2 | 3/2020 | Sheppard et al. |
| 11,359,024 | B2 | 6/2022 | Niessen et al. |
| 2009/0155256 | A1 | 6/2009 | Black et al. |
| 2016/0046717 | A1 | 2/2016 | Sheppard et al. |
| 2019/0144547 | A1 | 5/2019 | Celik et al. |
| 2020/0079855 | A1 | 3/2020 | Niessen et al. |
| 2020/0247891 | A1 | 8/2020 | Sheppard et al. |

FOREIGN PATENT DOCUMENTS

| | | | |
|---|---|---|---|
| EP | 2744823 | A2 | 6/2014 |
| JP | 2015-501285 | A | 1/2015 |
| RU | 2565539 | C2 | 10/2015 |
| RU | 2614252 | C2 | 3/2017 |
| WO | WO 2008/141276 | A1 | 11/2008 |
| WO | WO 2011/020529 | A2 | 2/2011 |
| WO | WO 2011/103490 | A2 | 8/2011 |
| WO | WO 2013/026004 | A2 | 2/2013 |
| WO | 2014/165524 | A2 | 10/2014 |
| WO | WO 2015/195835 | A2 | 12/2015 |
| WO | 2016/092419 | A1 | 6/2016 |
| WO | WO 2018/064478 | A1 | 4/2018 |

OTHER PUBLICATIONS

Tsuji et al., Somatic Hypermutation and Framework Mutations of Variable Region Contribute to Anti-Zika Virus-Specific Monoclonal Antibody Binding and Function, J. Virol. 96(11), doi.org/10.1128/jvi.00071-22, 18 page, Jun. 2022.*

Lan et al., Enhanced preclinical antitumor activity of M7824, a bifunctional fusion protein simultaneously targeting PD-L1 and TGF-β, Sci. Transl. Med. 10, eaan5488, 15 pages, Jan. 17, 2018.*

Duan et al., Impact of PD-L1, transforming growth factor-B expression and tumor-infiltrating CD8+ T cells on clinical outcome of patients with advanced thymic epithelial tumors, Thoracic Cancer 9 (2018) 1341-1353.*

Ravi et al., Bifunctional immune checkpoint-targeted antibody-ligand traps that simultaneously disable TGFβ enhance the efficacy of cancer immunotherapy, Nat. Commun. 9:417, Feb. 21, 2018.*

Herold et al., Determinants of the assembly and function of antibody variable domains, Scientific Reports, 7:12276, DOI:10.1038/s41598-017-12519-9, Sep. 2017.*

Kranz et al., Restricted reassociation of heavy and light chains from hapten-specific monoclonal antibodies, Proc. Natl. Acad. Sci., USA, 78(9):5807-5811, 1981.*

Sela-Culang et al., The structural basis of antibody-antigen recognition, Front. Immunol. 4:302, 13 pages, Oct. 2013.*

Wu et al., Integrins as receptor targets for neurological disorders, Pharmacol. Therap. 134:68-81, 2012.*

RS Nezlin, Biochemistry of Antibodies, (Plenum Press: New York) Translated by MC Vale, Ed. F. Karush, p. 160, 1970.*

JP2021-512751, "Office Action", Nov. 28, 2023, 8 pages.

Abe M. et al., "An Assay for Transforming Growth Factor-B Using Cells Transfected With a Plasminogen Activator Inhibitor-1 Promoter-Luciferase Construct", Analytical Biochemistry 216:276-284 (1994).

Akhurst R.J. et al., "Targeting TGF-B Signaling for Therapeutic Gain", Cold Spring Harb Perspect Biol 9:a022301 (2017).

Akhurst R.J. et al., "Targeting the TGFB Signalling Pathway in Disease", Nature Reviews Drug Discovery 11:790-811 (Oct. 2012).

Alegre M-L et al., "Effect of a Single Amino Acid Mutation on the Activating and Immunosuppressive Properties of a "Humanzed" OKT3 Monoclonal Antibody", The Journal of Immunology 148(11):3461-3468 (Jun. 1, 1992).

Annes J.P. et al., "Making Sense of Latent TGFB Activation", Journal of Cell Science 116(2):217-224 (2003).

Arnold T.D. et al., "Defective Retinal Vascular Endothelial Cell Development as a Consequence of Impaired Integrin aVB8-Mediated Activation of Transforming Growth Factor-B", The Journal of Neuroscience 32(4):1197-1206 (Jan. 25, 2012).

Ascierto P.A. et al., "Perspectives in Immunotherapy: Meeting Report from the "Immunotherapy Bridge", Napoli, Nov. 30, 2016", Journal of Translational Medicine 15:205, 21 pages, (2017).

Betts A. et al., "Linear Pharmacokinetic Parameters for Monoclonal Antibodies are Similar Within a Species and Across Different Pharmacological Targets: A Comparison Between Human, Cynomolgus Monkey and hFcRn Tg32 Transgenic Mouse Using a Population-Modeling Approach", MABS 10(5):751-764 (2018).

Chen C. et al., "Enhancement and Destruction of Antibody Function by Somatic Mutation: Unequal Occurrence is Controlled by V Gene Combinatorial Associations", EMBO J. 14(12):2784-2794 (1995).

Dodagatta-Marri et al., "a-PD-1 Therapy Elevates Treg/Th Balance and Increases Tumor Cell pSmad3 that are Both Targeted by a-TGFB Antibody to Promote Durable Rejection and Immunity in Squamous Cell Carcinomas", Journal of Immuno Therapy of Cancer 7:62, 15 pages, (2019).

Edwards J.P. et al., "Release of Active TGF-B1 from the Latent TGF-B1/GARP Complex on T Regulatory Cells is Mediated by Integrin B8", The Journal of Immunology 193:2843-2849 (2014).

Fenton TM et al., "Inflammatory Cues Enhance TGFB Activation by Distinct Subsets of Human Intestinal Dendritic Cells via Integrin avB8", Nature 10(3):624-634 (May 2017).

Flavell R.A. et al., "The Polarization of Immune Cells in the Tumour Environment by TGFB", Nature Reviews—Immunology 10:554-567 (Aug. 2010).

Franklin R.A. et al., "The Cellular and Molecular Origin of Tumor-Associated Macrophages", Science 344 (6186):921-925 (May 23, 2014).

Gorelik L. et al., "Immune-Mediated Eradication of Tumors Through the Blockade of Transforming Growth Factor-B Signaling in T Cells", Nature Medicine 7(10):1118-1122 (Oct. 2001).

Henderson N C et al., "Targeting of aV Integrin Identifies a Core Molecular Pathway that Regulates Fibrosis in Several Organs", Nature Medicine 19(12):1617-1624 (Dec. 2013).

Herold K.C. et al., "Anti-CD3 Monoclonal Antibody in New-Onset Type 1 Diabetes Mellitus", The New England Journal of Medicine 346(22):1692-1698 (May 30, 2002).

Hezareh M. et al., "Effector Function Activities of a Panel of Mutants of a Broadly Neutralizing Antibody Against Human Immunodeficiency Virus Type 1", Journal of Virology 75(24):12161-12168 (Dec. 2001).

Huang X. et al., "The Integrin avB6 is Critical for Keratinocyte Migration on Both its Known Ligand, Fibronectin, and on Vitronectin", Journal of Cell Science 111:2189-2195 (1998).

Kang S.W. et al., "Anti-CD137 Suppresses Tumor Growth by Blocking Reverse Signaling by CD137 Ligand", Cancer Research 77(21):5989-6000 (Sep. 2017).

Kueng W. et al., "Quantification of Cells Cultured on 96-Well Plates", Analytical Biochemistry 182:16-19 (1989).

Ladner R C, "Mapping the Epitopes of Antibodies", Biotechnol Genet Eng Rev 24:1-30 (2007).

Amminmaki U. et al., "Crystal Structure of a Recombinant Anti-Estradiol Fab Fragment in Complex With 17Beta-Estradiol", J Biol Chem 276:36687-36694 (2001).

(56) References Cited

OTHER PUBLICATIONS

Liu C. et al., "Randomised, Double Blind, Placebo Controlled Study of Interferon B-1a in Relapsing-Remitting Multiple Sclerosis Analysed by Area Under Disability/Time Curves", J Neurol Neurosurg Psychiatry 67:451-456 (1999).
MacCallum R M et al., "Antibody-Antigen Interactions: Contact Analysis and Binding Site Topography", J Mol Biol. 262(5):732-745 (Oct. 1996).
Mariathasan S. et al., "TGFB Attenuates Tumour Response to PD-L1 Blockade by Contributing to Exclusion of T Cells", Nature 554:544-548 and extended data (Feb. 22, 2018).
Melton A.C. et al., "Expression of avB8 Integrin on Dendritic Cells Regulates Th17 Cell Development and Experimental Autoimmune Encephalomyelitis in Mice", The Journal of Clinical Investigation 120(12):4436-4444 (Dec. 2010).
Movahedi K. et al., "Different Tumor Microenvironments Contain Functionally Distinct Subsets of Macrophages Derived from Ly6C(high) Monocytes", Cancer Research 70(14):5728-5739 (2010).
Mu D. et al., "The Integrin avB8 Mediates Epithelial Homeostasis Through MT1-MMP-Dependent Activation of TGF-B1", The Journal of Cell Biology 157(3):493-507 (Apr. 29, 2002).
Munger J.S. et al., "The Integrin avB6 Binds and Activates Latent TGFB1: A Mechanism for Regulating Pulmonary Inflammation and Fibrosis", Cell 96:319-328 (Feb. 5, 1999).
Muyldermans S., "Nanobodies: Natural Single-Domain Antibodies", Annu Rev Biochem. 82:775-797 (2013).
Nishimura H. et al., "Immunological Studies on PD-1-Deficient Mice: Implication of PD-1 as a Negative Regular for B Cell Responses", International Immunology 10(10):1563-1572 (1998).
Noy R. et al., "Tumor-Associated Macrophages: From Mechanisms to Therapy", Immunity 41:49-61 (Jul. 17, 2014).
Ostuni R. et al., "Macrophages and Cancer: From Mechanisms to Therapeutic Implications", Trends in Immunology 36(4):229-239 (Apr. 2015).
Portielje J.E.A. et al., "IL-12: A Promising Adjuvant for Cancer Vaccination", Cancer Immunol Immunother 52:133-144 (2003).
Proctor J.M. et al., "Vascular Development of the Brain Requires B8 Integrin Expression in the Neuroepithelium", The Journal of Neuroscience 25(43):9940-9948 (Oct. 26, 2005).
Rock J.R. et al., "Multiple Stromal Populations Contribute to Pulmonary Fibrosis Without Evidence for Epithelial to Mesenchymal Transition", PNAS 108(52):E1475-E1483 (Dec. 27, 2011).
Su G. et al., "Absence of Integrin avB3 Enhances Vascular Leak in Mice by Inhibiting Endothelial Cortical Actin Formation", Am J Respir Crit Care Med 185(1):58-66 (Jan. 1, 2012).
Su G. et al., "Integrin avB5 Regulates Lung Vascular Permeability and Pulmonary Endothelial Barrier Function", American Journal of Respiratory Cell and Molecular Biology 36:377-386 (2007).
Tauriello D.V.F. et al., "TGFB Drives Immune Evasion in Genetically Reconstituted Colon Cancer Metastasis", Nature 554:538-543 (Feb. 22, 2018).
Terabe M. et al., "Blockade of Only TGF-B 1 and 2 is Sufficient to Enhance the Efficacy of Vaccine and PD-1 Checkpoint Blockade Immunotherapy", Oncoimmunology 6(5):e1308616 (2017).
Thomas D.A. et al., "TGF-B Directly Targets Cytotoxic T Cell Functions During Tumor Evasion of Immune Surveillance", Cancer Cell 8:369-380 (Nov. 2005).
Travis M.A et al., "Loss of Integrin avB8 Dendritic Cells Causes Autoimmunity and Colitis in Mice", Nature 149:361-365 (Sep. 20, 2007).

Vanpouille-Box C. et al., "TGFB is a Master Regulator of Radiation Therapy-Induced Antitumor Immunity", Cancer Research 75(11):2232-2242 (Jun. 1, 2015).
Wei S.C. et al., "Distinct Cellular Mechanisms Underlie Anti-CTLA-4 and Anti-PD-1 Checkpoint Blockade", Cell 170:1120-1133 (Sep. 7, 2017).
Wu T-C et al., "Reprogramming Tumor-Infiltrating Dendritic Cells for CD103+CD8+ Mucosal T-Cell Differentiation and Breast Cancer Rejection", Cancer Immunology Research 2(5):487-500 (2014).
Yang J.C. et al., "A Randomized Trial of Bevacizumab, and Anti-Vascular Endothelial Growth Factor Antibody, for Metastatic Renal Cancer", The New England Journal of Medicine 349(5):427-434 (Jul. 31, 2003).
Young K.H. et al., "Optimizing Timing of Immunotherapy Improves Control of Tumors by Hypofractionated Radiation Therapy", PLoS One 11(6):e0157164 (2016).
Dahmani et al., TGF-$\beta$ in T Cell Biology: Implications for Cancer Immunotherapy. Cancers (Basel). Jun. 11, 2018;10(6):194. doi: 10.3390/cancers10060194, (21 pages).
Fenton et al., Inflammatory cues enhance TGF$\beta$ activation by distinct subsets of human intestinal dendritic cells via integrin $\alpha v \beta 8$. Mucosal Immunol. May 2017;10(3):624-634. doi: 10.1038/mi.2016.94. Epub Oct. 26, 2016.
International Search Report and Written Opinion for Application No. PCT/US2019/049748, mailed Dec. 16, 2019.
International Preliminary Report on Patentability for Application No. PCT/US2019/049748, mailed Mar. 18, 2021.
Hargadon et al., Immune checkpoint blockade therapy for cancer: An overview of FDA-approved immune checkpoint inhibitors. Int Immunopharmacol. Sep. 2018;62:29-39. doi: 10.1016/j.intimp.2018.06.001. Epub Jul. 2, 2018.
Leger et al., Humanization of Antibodies. Chapter 1 in: Antibody Drug Discovery. Imperial College Press, Eds. 2012; 4: 1-23. https://doi.org/10.1142/9781848166295_0001.
Mariuzza et al., The Structural Basis of Antigen-Antibody Recognition. Annu Rev Biophys Biophys Chem. 1987;16:139-59. doi: 10.1146/annurev.bb.16.060187.001035.
Rudikoff et al., Single amino acid substitution altering antigen-binding specificity. Proc Natl Acad Sci U S A. Mar. 1982;79(6):1979-83. doi: 10.1073/pnas.79.6.1979.
Safdari et al., Antibody humanization methods—a review and update. Biotechnol Genet Eng Rev. 2013;29:175-86. doi: 10.1080/02648725.2013.801235. Epub Aug. 2, 2013.
Stockis et al., Blocking immunosuppression by human Tregs in vivo with antibodies targeting integrin $\alpha V \beta 8$. Proc Natl Acad Sci U S A. Nov. 21, 2017;114(47):E10161-E10168. doi: 10.1073/pnas.1710680114. Epub Nov. 6, 2017.
Wang et al., IgG Fc engineering to modulate antibody effector functions. Protein Cell. Jan. 2018;9(1):63-73. doi: 10.1007/s13238-017-0473-8. Epub Oct. 6, 2017.
Dirks, Brain Tumor Stem Cells: Bringing Order to the Chaos of Brain Cancer. J Clin Oncol. Jun. 10, 2008;26(17):2916-24. doi: 10.1200/JCO.2008.17.6792.
LÓPEZ-LÁZARO, The migration ability of stem cells can explain the existence of cancer of unknown primary site. Rethinking metastasis. Oncoscience. May 1, 2015;2(5):467-75. doi: 10.18632/oncoscience.159. eCollection 2015.
Tran et al., Survival comparison between glioblastoma multiforme and other incurable cancers. J Clin Neurosci. Apr. 2010;17(4):417-21. doi: 10.1016/j.jocn.2009.09.004. Epub Feb. 18, 2010.
Singer, et al., Genes and Genomes—A changing perspective. University Science Books, Eds. 1991, p. 63.
CN2019980057769.8, "Office Action", Feb. 23, 2024, 6 pages.

* cited by examiner

FIG. 1A
HEAVY CHAIN

```
              1           11          21          31          41          51
IMGT:         EVQLVESGGG  LVQPGGSLRL  SCAASGFTFS  SYWMSWVRQA  PGKGLEWVAN  IKQDGSEKYY
mADWA11:      EVQLQQSGAE  LVRPGAFVKL  SCKASGFNIK  DYYMNWVLQR  PEQGLEWIGW  IDPDNGNTIY
huADWA11-2.4: EVQLVESGGG  LVQPGGSLRL  SCAASGFNIK  DYYMNWVRQA  PGKGLEWVGW  IDPDQGNTIY 61          71          81          91          101         111
IMGT:         VDSVKGRFTI  SRDNAKNSLY  LQMNSLRAED  TAVYYCAR                LMDYWGQGTS VTVSS
mADWA11:      DPKFQGKASI  TADTSSNTAY  LQLSSLTSED  TAVYYCARRL  LMDYWGQGTL  VTVSS
huADWA11-2.4: EPKFQGRFTI  SADTSKNSAY  LQMNSLRAED  TAVYYCARRL  LMDYWGQGTL  VTVSS
```

FIG. 1B
LIGHT CHAIN

```
              1           11          21          31          41          51
IMGT:         DIQMTQSPSS  LSASVGDRVT  ITCRASQSIS  ------S-YLNW YQQKPGKAPK  LLIYAASSLQ
mADWA11:      DIVMTQAAPS  VPVTPGESVS  ISCRSTKSLL  HFNGNTYLFW  FLQRPGQSPQ  RLIYYMSNLA
huADWA11-2.4: DIQMTQSPSS  LSASVGDRVT  ITCRSTKSLS  HFNGNTYLFW  YQQKPGKAPK  RLIYYMSSLA 61          71          81          91          101         111
IMGT:         SGVPSRFSGS  GSGTDFTLTI  SSLQPEDFAT  YYCQQSYSTP              FTFGTGTKLE IK
mADWA11:      SGVPDRFSGR  GSGTDFTLRI  SRVEAEDVGV  YYCMQSLEYP  FTFGGGTKVE  IK
huADWA11-2.4: SGVPSRFSGS  GSGTDFTLTI  SSLQPEDFAT  YYCQQSLEYP  FTFGGGTKVE  IK
```

IMGT:           IMGT sequences
                IGHV3-07 for Heavy Chain and
                IGKV1-39 for Light Chain mADWA11:        HYBRIDOMA MOUSE ADWA11 huADWA11-2.4:   HUMANIZED ADWA11 2.4

FIG. 6C

| Fab | species | ka (M⁻¹s⁻¹) | kd (s⁻¹) | KD (M) |
|---|---|---|---|---|
| Ms ADWA11 | human | 9.22E+04 | 4.86E-5 | 5.36E-10 |
| | cyno | 9.81E+04 | 4.97E-5 | 5.07E-10 |
| | mouse | 1.03E+05 | 5.03E-5 | 4.89E-10 |
| ADWA11 5-2 2.4 | human | 1.61E+05 | ≤3E-5 | ≤2E-10 |
| | cyno | 1.72E+05 | ≤2E-5 | ≤2E-10 |
| | mouse | 2.57E+05 | 1.82E-05 | ≤2E-10 |
| | rat | 3.41E+05 | ≤2E-5 | ≤2E-10 |

*Biacore binding data, n ≥ 3*

FIG. 12B
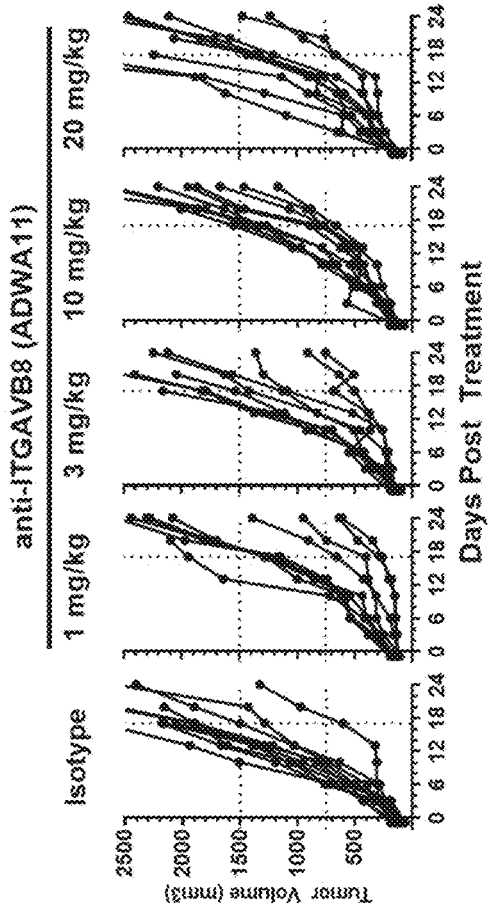
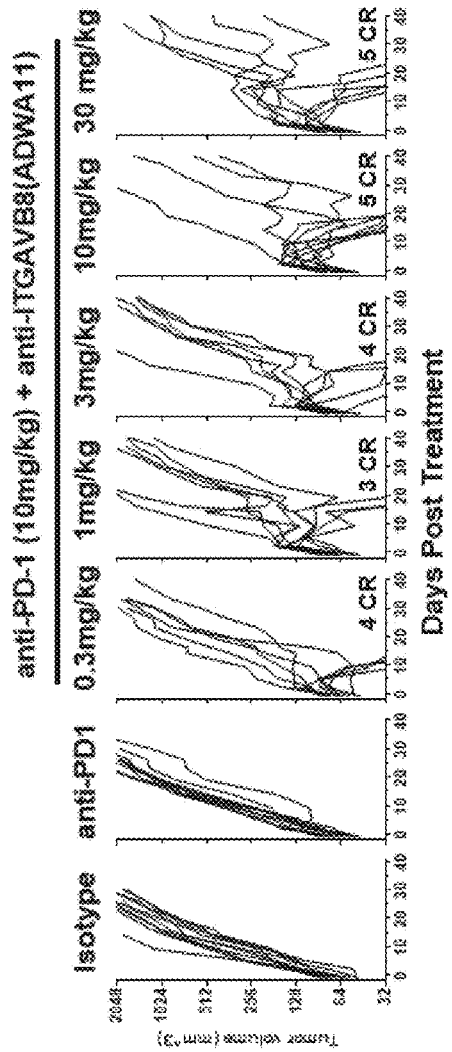

FIG. 14B
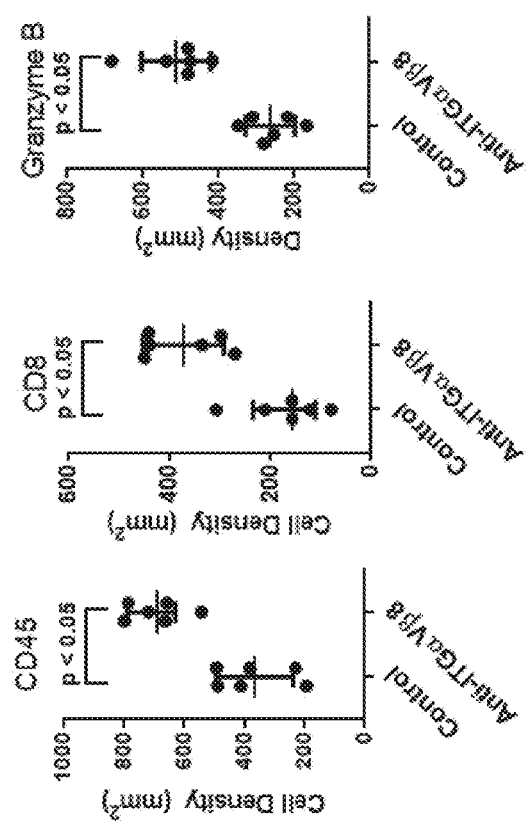
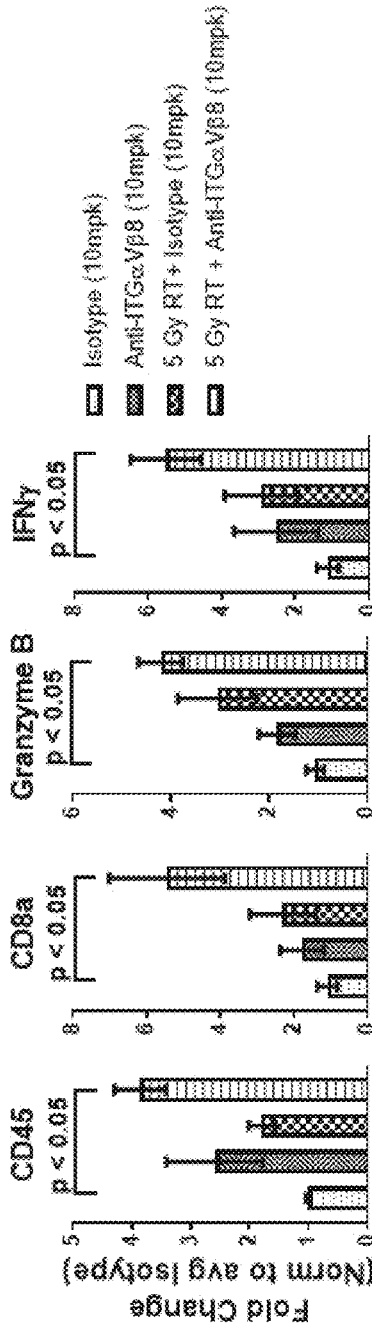

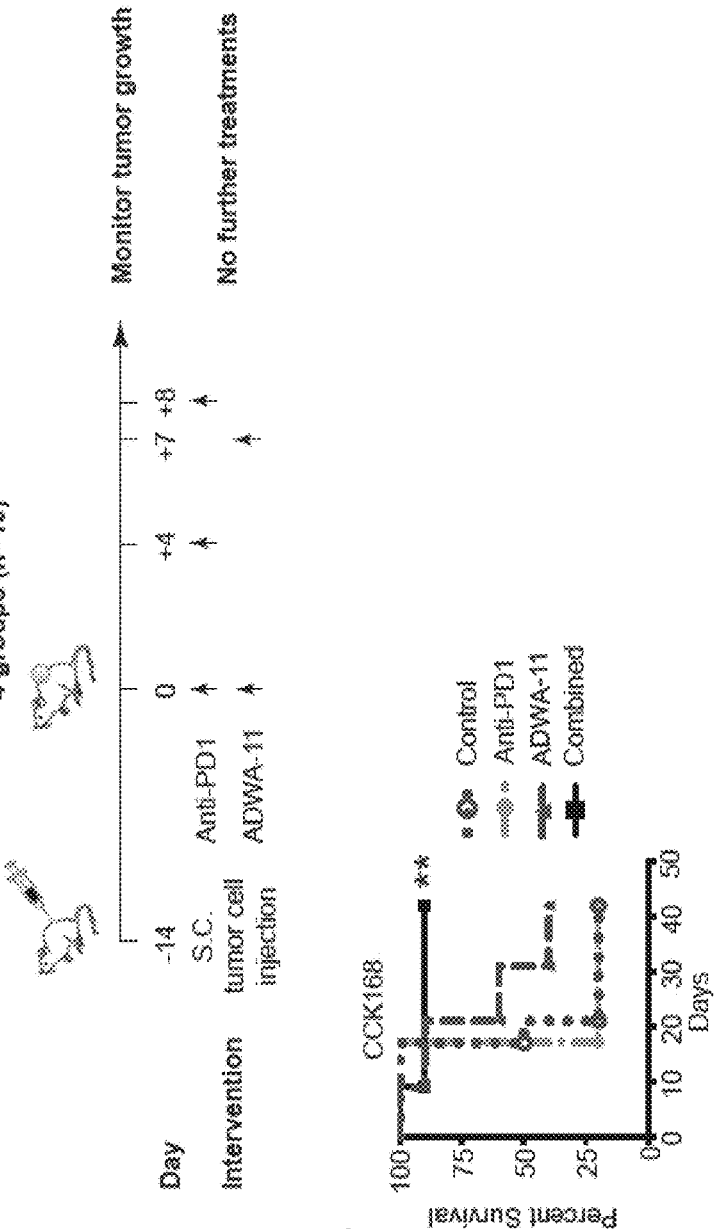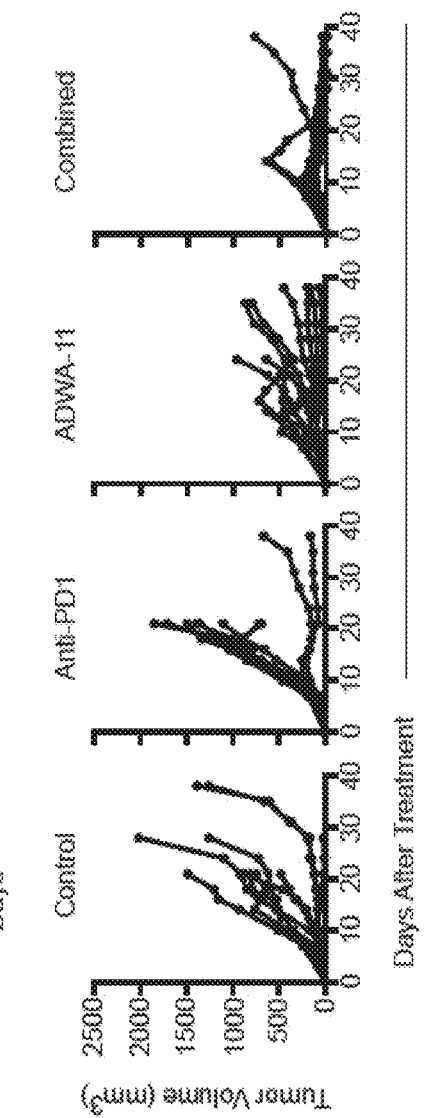
FIG. 16A
FIG. 16B
FIG. 16C

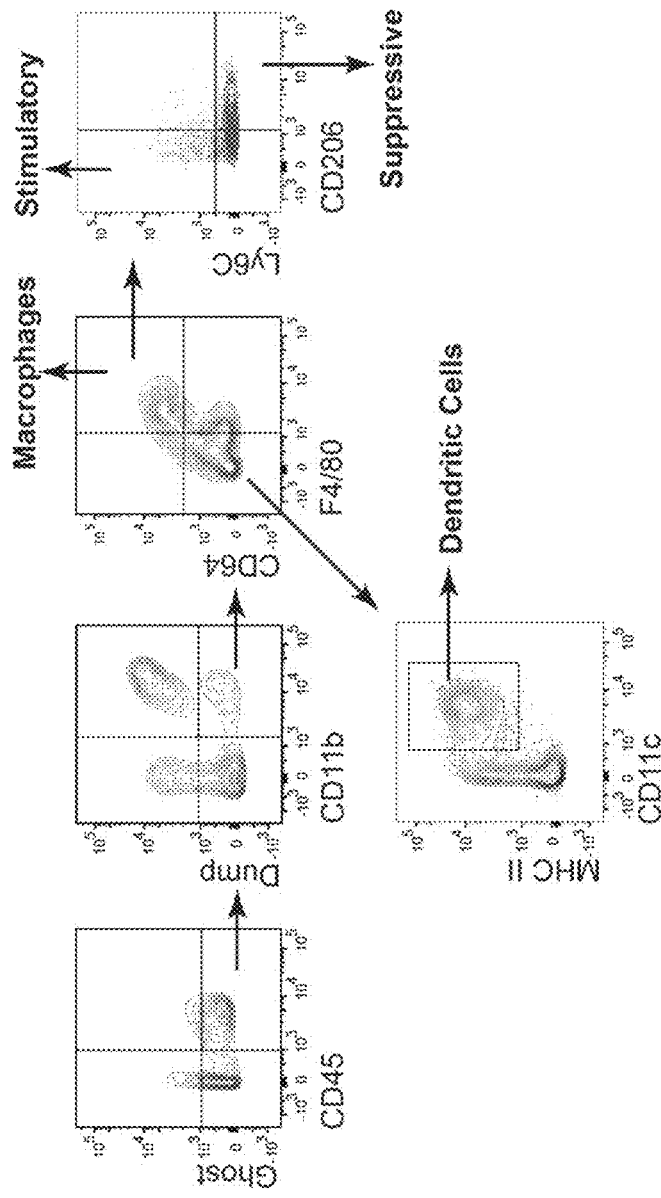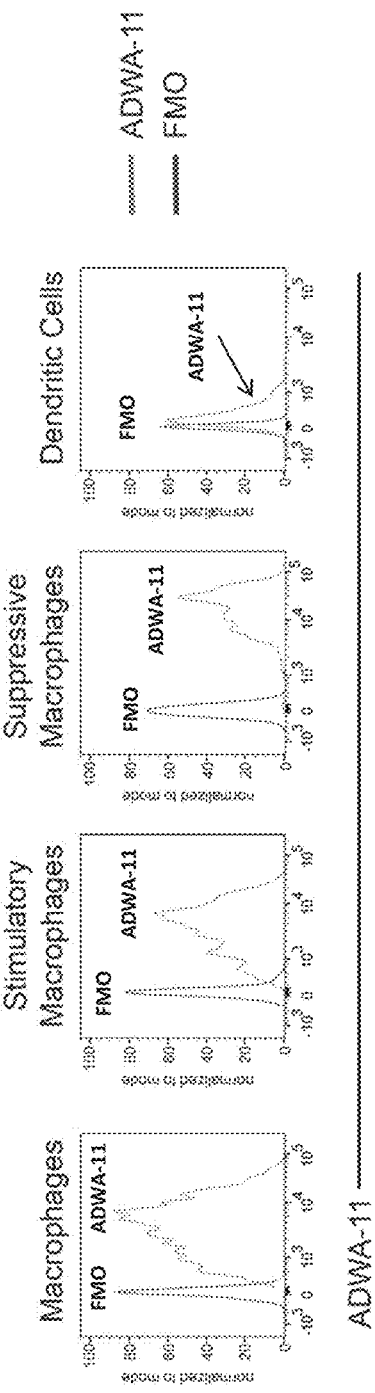
FIG. 17A
FIG. 17B

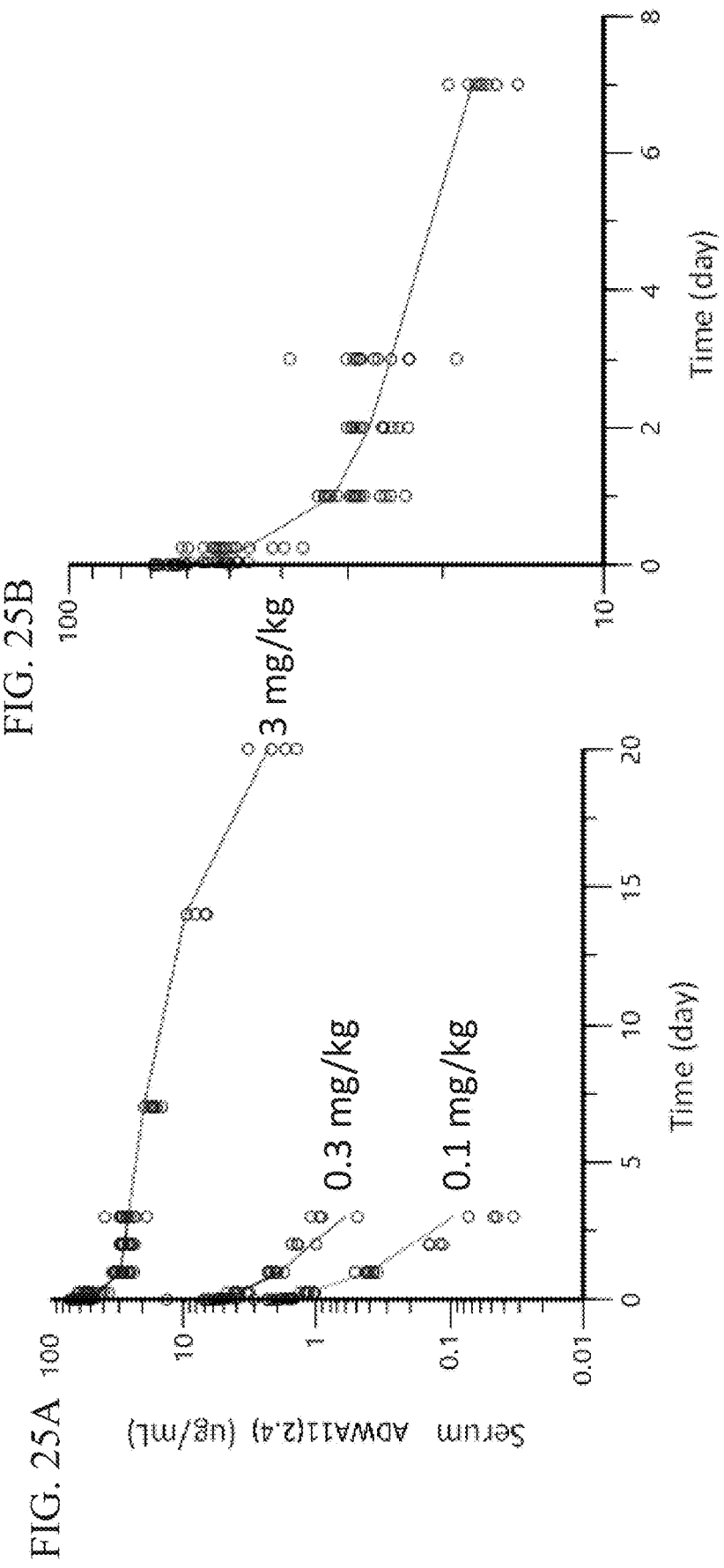

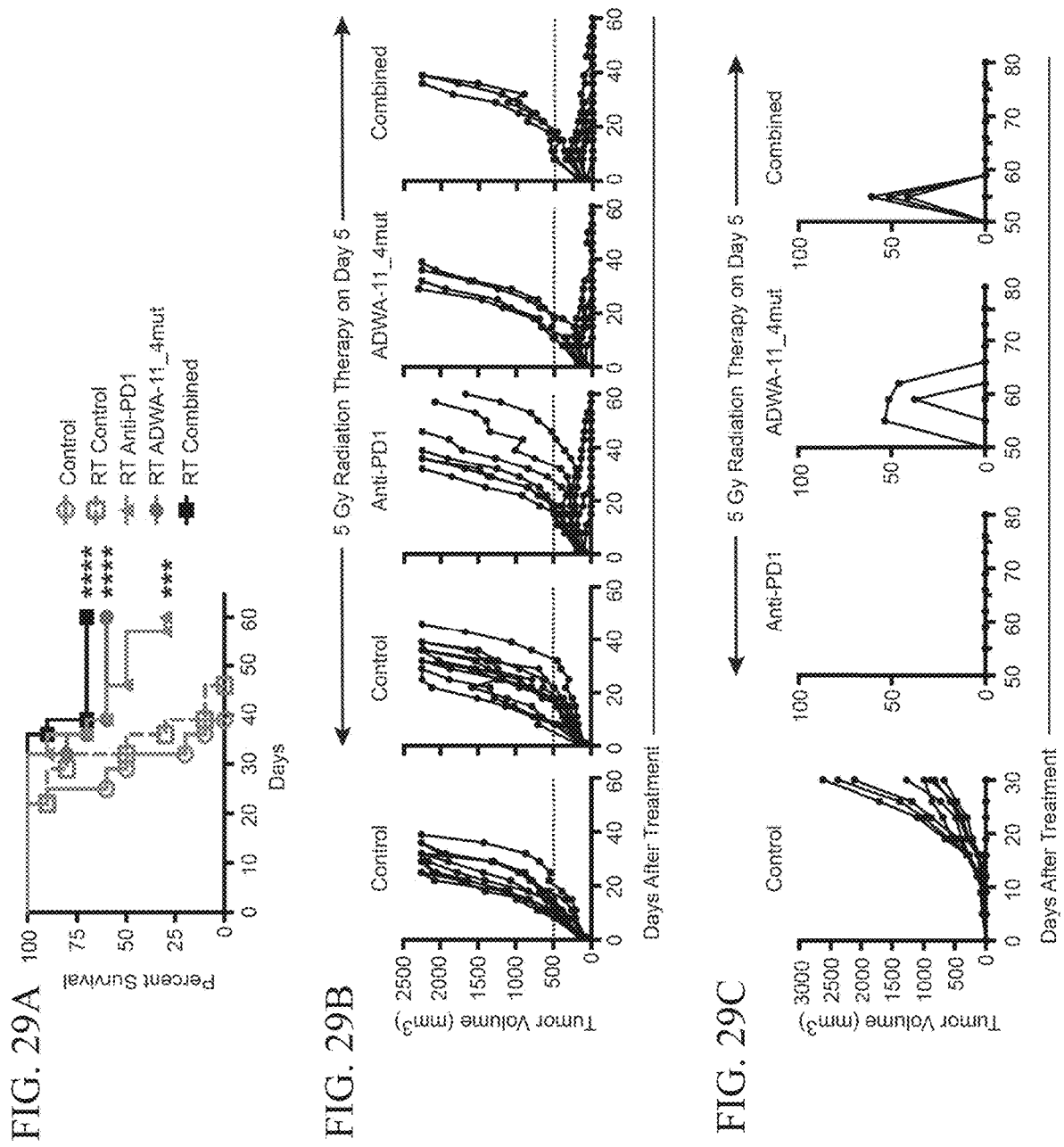

MC38 Tumor Growth Curves for Isotype Control, ADWA11, ADWA11 2.4, Anti-PD-1 (clone RMP1-14), and Combination Treated Mice

METHOD OF TREATING CANCER USING ANTI-AV8 ANTIBODIES

CROSS REFERENCE TO RELATED APPLICATIONS

This application is a divisional of U.S. patent application Ser. No. 16/561,530, filed Sep. 5, 2019, which claims priority to U.S. Ser. No. 62/890,945 filed Aug. 23, 2019, and U.S. Ser. No. 62/728,688 filed Sep. 7, 2018, the contents of each of which are incorporated herein by reference in their entirety.

INCORPORATION BY REFERENCE OF SEQUENCE LISTING

The Sequence Listing in the ASCII text file, named as 38972A_SequenceListing.txt of 184,222 bytes, created on May 5, 2022 and submitted in the United States Patent and Trademark Office via EFS-Web, is incorporated herein by reference.

PARTIES TO A JOINT RESEARCH STATEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are THE REGENTS OF THE UNIVERSITY OF CALIFORNIA on behalf of its SAN FRANCISCO CAMPUS and PFIZER INC.

FIELD

The present invention relates to antibodies, and antigen-binding fragments thereof, that specifically bind $\alpha v \beta 8$ integrin, and compositions, methods and uses thereof.

BACKGROUND

Transforming growth factor $\beta$ (TGF$\beta$) is a potent suppressor of adaptive and innate immunity and an important mediator of immune suppression by a subset of regulatory T cells. TGF$\beta$ is required for the induction of Th17 cells, which can promote tumor progression through induction of granulocytic inflammation and promotes epithelial to mesenchymal transformation of tumor cells and secretion and accumulation of a fibrotic tumor stroma that may contribute to exclusion of immune cells from some solid tumors. For all of these reasons, inhibition of TGF$\beta$ has been explored as an adjunctive immunotherapy, especially in so-called "immune-excluded" tumors (Gorelik et al. *Nat. Med.* 7:1118-1122, 2001; Tauriello et al. *Nature* 554:538-543, 2018; Mariathasan et al. *Nature* 554:544-548, 2018, Dodagatta et al. *J Immunother Cancer.* 7: 62. 2019; U.S. Pat. No. 10,167,334). However, since TGF$\beta$ plays important homeostatic roles in many biological systems, systemic targeting of TGF$\beta$ signaling presents numerous challenges due to unwanted side effects (Hata and Akhurst *Nat. Rev. Drug Dev.* 11, 791-811, 2012; Akhurst et al. *Cold Spring Harbor Perspectives.* 10, 2017; Flavell et al. *Nat. Rev. Immunol.* 10:554-567, 2010).

Previous studies have shown that inhibition of TGF$\beta$ signaling can enhance responses to radiation or vaccine therapies in combination with checkpoint inhibition (Vanpouille-Box et al. *Cancer Res.* 75:2232-2242, 2015; Terabe et al. *OncoImmunology* 6(5): e1308616, 2017). In vivo activity of TGF$\beta$ is regulated via several mechanisms. For example, TGF$\beta$ is secreted as an inactive or latent complex, where the cleaved latency associated peptide (LAP) domain encases the active TGF$\beta$ mature peptide. Latent-TGF$\beta$ can be covalently linked to the extracellular matrix through latent TGF$\beta$ binding protein (LTBP) or displayed on the cell surface by Glycoprotein-A Repetitions Predominant protein (GARP). Early in vitro data showed that the latent complex of TGF$\beta$ can be activated by high temperature, acidic pH, and various proteases (Annes et al. *J Cell Sci.* 116:217-24, 2003), however the importance of these mechanisms in vivo remains to be determined.

A role for members of the $\alpha v$ Integrin family, specifically $\alpha v \beta 1$, $\alpha v \beta 6$, and $\alpha v \beta 8$, has been demonstrated for latent-TGF$\beta$ activation. Integrin $\alpha v \beta 8$ is a transmembrane noncovalent heterodimer consisting of ITG$\alpha$V and ITG$\beta$8 subunits. $\alpha v \beta 8$ expression is unique among $\alpha v$ integrins, where its expression by immune cells such as dendritic cells, T regulatory cells, and tumor associated macrophages has emerged as a contextual activator of TGF$\beta$ for regulation of active immune responses. $\alpha v \beta 8$ expression by dendritic cells (DCs) acts as a mediator of TGF$\beta$ production during T-cell stimulation and strongly influences the differentiation and development of Tregs and Th17 cells at the expense of Th1 differentiation during immune responses. Mice with conditional deletion of Itgb8 in DCs or all leukocytes demonstrate a dramatic inhibition of TGF$\beta$-dependent induction of antigen-specific Th17 cells and are subsequently protected from organ dysfunction in certain preclinical models of autoimmunity, such as multiple sclerosis (experimental auto-immune encephalomyelitis) and allergic asthma (Travis et al. *Nature.* 449(7160):361-5, 2007; Melton et al. *J Clin. Invest.* 120(12):4436-44, 2010).

TGF$\beta$ plays a role in both the differentiation and recruitment of immune suppressor cells to the tumor, and as a tumor intrinsic factor that contributes to an immune suppressive tumor microenvironment. In some cancers, TGF$\beta$ can be tumor-promoting by influencing numerous aspects of the tumor microenvironment including angiogenesis, metastasis, epithelial-mesenchymal transition, and perhaps most importantly, suppression of infiltrating immune cells.

Accordingly, in view of the prominent role of TGF$\beta$ in the tumor microenvironment and the numerous challenges associated with the systemic targeting of TGF$\beta$ signaling (Hata and Akhurst *Nat. Rev. Drug Dev.* 11, 791-811, 2012; Akhurst et al. *Cold Spring Harbor Perspectives* 10, 2017; Flavell et al. *Nat. Rev. Immunol.* 10:554-567, 2010), the need exists for developing strategies for the selective inhibition of $\alpha v \beta 8$-dependent latent-TGF$\beta$ activation.

SUMMARY OF THE INVENTION

Disclosed herein are antibodies (e.g., humanized and chimeric antibodies), and antigen-binding fragments thereof, that specifically bind to $\alpha v \beta 8$ integrin (also interchangeably referred to herein as "AVB8", "$\alpha v \beta 8$" or "avb8") (e.g., $\alpha v \beta 8$ integrin from human, mouse, cynomolgus monkey, and/or rat). In certain aspects, antibodies and antigen-binding fragments thereof bind to $\alpha v \beta 8$ integrin, and ultimately reduce TGF$\beta$ (e.g., TGF$\beta 1$ and TGF$\beta 3$) signaling, e.g., in the tumor or tumor microenvironment.

Mature TGF$\beta$ is present in inactive or latent form in a complex with the latency associated peptide (LAP) domain. Binding of $\alpha v \beta 8$ integrin to LAP results in release of active TGF$\beta$ (e.g., TGF$\beta 1$ and TGF$\beta 3$). Reducing binding of $\alpha v \beta 8$ integrin to LAP can prevent the release of active TGFβ, thereby reducing TGFβ signaling. TGFβ is known to have immune suppressive effects, e.g., in the tumor microenvironment, thus reduction of TGFβ activity and/or signaling using the antibodies described herein can result in activation of an immune response, e.g., an anti-tumor response in vivo.

Because of the restricted expression of αvβ8 integrin on immune cells (e.g., dendritic cells, T regulatory cells, tumor-associated macrophages) and tumor cells, antibodies disclosed herein can result in a more targeted, non-systemic reduction of TGFβ signaling. Thus, antibodies, and antigen binding fragments thereof, of the disclosure enable a more selective antagonism of TGFβ activity in the immune system and/or the tumor microenvironment, thereby enhancing an anti-tumor immune response in a subject. In some embodiments disclosed herein, antibodies against αvβ8 integrin have been shown to cause growth suppression and/or complete tumor regression in animal models for several cancers, including, for example, squamous cell carcinoma, breast cancer, and/or colon cancer, alone or in combination with other immunomodulators, such as modulators of checkpoint inhibitors, (e.g., inhibitors of PD-1, PD-L1, CTLA-4 or agonists of 4-1BB), or anti-cancer therapies, e.g., radiotherapy.

Accordingly, in certain aspects, the disclosure provides antibodies, and antigen-binding fragments thereof, that bind to αvβ8 integrin with high affinity and specificity, nucleic acid molecules encoding antibodies and antigen-binding fragments thereof, expression vectors, host cells and methods for making the same. In certain aspects, antibodies, and antigen-binding fragments thereof, exhibit altered effector functions (e.g., have reduced antibody-dependent cell-mediated cytotoxicity (ADCC) activity and/or reduced complement dependent cytotoxicity (CDC) activity). In certain aspects, anti-αvβ8 integrin antibodies and antigen-binding fragments thereof exhibit enhanced binding affinity for αvβ8 integrin as compared to murine hybridoma antibodies, and antigen-binding fragments thereof, from which they are derived. Humanized anti-αvβ8 integrin antibodies and antigen-binding fragments thereof disclosed herein can be used alone, or in combination with other agents or therapeutic modalities, (e.g., immunomodulators or anti-cancer therapies) to treat, prevent and/or diagnose disorders, such as cancerous disorders (e.g., solid and soft-tissue tumors). Thus, compositions and methods for detecting αvβ8 integrin, as well as methods for treating various disorders, including cancer, using anti-αvβ8 integrin antibodies and antigen-binding fragments thereof are disclosed.

Those skilled in the art will recognize, or be able to ascertain using no more than routine experimentation, many equivalents to the specific embodiments of the invention described herein. Such equivalents are intended to be encompassed by the following embodiments (E).

E1. An isolated antibody, or antigen-binding fragment thereof, that specifically binds to αvβ8 integrin, wherein said antibody, or antigen-binding fragment thereof, has at least one of the following properties:
  i. a binding affinity, expressed as KD, for human αvβ8 integrin that is less than the KD for the murine antibody ADWA11 as disclosed in U.S. Pat. No. 9,969,804, which is herein incorporated by reference in its entirety, confirming the amino acid sequences and as set forth in, e.g., SEQ ID NO: 20-33 and 71-76 of the present description, e.g., the ADWA11 antibodies of the invention have a KD less than 536 pM (e.g., 1, 5, 10, 20, 30, 40, 50, 60, 70, 80, 90, 100, 150, 200, 250, 300, 350, 370, 400, 450, 500, 510, 520, 530, 531, 532, 533, 534, or 535 pM);
  ii. a KD for human αvβ8 integrin that is less than or equal to 200 pM (e.g., 1, 2, 3, 4, 5, 6, 7, 8, 9, 10, 15, 20, 30, 40, 50, 60, 70, 80, 90, 100, 150, 180, 190 or 200 pM), e.g., for purified human αvβ8 integrin;
  iii. a KD for human αvβ8 integrin that is less than or equal to 100 pM for purified human αvβ8 integrin;
  iv. a KD for mouse αvβ8 integrin that is less than the KD for the murine antibody ADWA11, e.g., less than 489 pM (e.g., 1, 5, 10, 20, 30, 40, 50, 60, 70, 80, 90, 100, 150, 200, 250, 300, 350, 370, 400, 450, 460, 470, 480, 485, 486, 487, or 488 pM);
  v. a $K_D$ for mouse αvβ8 integrin that is 70.8+/−19.9 pM for purified mouse αvβ8 integrin;
  vi. a KD for cynomolgus monkey αvβ8 integrin that is less than the KD for the murine antibody ADWA11, e.g., less than 507 pM (e.g., 1, 5, 10, 20, 30, 40, 50, 60, 70, 80, 90, 100, 150, 200, 250, 300, 350, 370, 400, 450, 500, 501, 502, 503, 504, 505, or 506 pM);
  vii. a KD for cynomolgus αvβ8 integrin that is less than or equal to 100 pM for purified cynomolgus αvβ8 integrin;
  viii. a KD for rat αvβ8 integrin that is about 160 pM;
  ix. approximately equivalent affinity for at least two, three, or all of human, cynomolgus, mouse, and rat αvβ8 integrin, e.g., with a KD that is less than 100 pM (e.g., 1, 2, 3, 4, 5, 6, 7, 8, 9, 10, 15, 20, 30, 40, 50, 60, 70, 80, 90, 95 or 98 pM), e.g., as determined using a Biacore affinity assay;
  x. an IC50 for inhibiting TGFβ transactivation that is less than that of the murine antibody ADWA11, e.g., less than 183 pM (e.g., 1, 2, 3, 4, 5, 6, 7, 8, 9, 10, 15, 20, 30, 40, 50, 60, 70, 80, 90, 100, 110, 120, 130, 140, 150, 160, 170, 175, 180, 181, or 182 pM);
  xi. an IC50 for inhibiting TGFβ transactivation in U251 cells of about 199+/−93.6 pM;
  xii. an IC50 for inhibiting TGFβ transactivation that is about 100 pM to about 300 pM;
  xiii. an EC50 for U251 cells of about 126+/−34 pM (e.g., about 50, 60, 70 80, 90, 100, 110, 115, 120, 121, 122, 123, 124, 125, 126, 127, 128, 129, 130, 140, 150, 160, 170, 180, or 190 pM);
  xiv. an EC50 for U251 cells of about 256+/−115 pM (e.g., about 120, 140, 160, 180, 200, 220, 240, 260, 280, 290, 300, 320, 340, 360, 380, 400 pM);
  xv. an EC50 for U251 cells of about 80 pM to about 400 pM;
  xvi. an EC50 for C8-S cells of about 115 pM;
  xvii. an EC50 for C8-S cells of about 145+/−23.7 pM;
  xviii. an EC50 for C8-S cells of about 110 pM to about 180 pM;
  xix. at least one predicted human pharmacokinetic (PK) parameter chosen from:
    a. a clearance from central compartment (CL) of about 0.12-0.15 mL/h/kg;
    b. an inter-compartmental distribution clearance (CLF) of about 0.15-0.51 mL/h/kg;
    c. a volume of distribution for the central compartment (V1) of about 36-39 mL/kg;
    d. a volume of distribution for the peripheral compartment (V2) of about 21-33 mL/kg; and/or
    e. a terminal half-life ($t_{1/2}$) of about 12 days;
    f. a terminal half-life ($t_{1/2}$) of about 15-17 days; or
  xx. no detectable binding to human Fcγ receptors or C1q.

E2. The isolated antibody, or antigen-binding fragment thereof, of embodiment E1, wherein the KD for human αvβ8 integrin is less than the KD for the murine antibody ADWA11, e.g., less than 536 pM (e.g., 1, 5, 10, 20, 30, 40, 50, 60, 70, 80, 90, 100, 150, 200, 250, 300, 350, 370, 400, 450, 500, 510, 520, 530, 531, 532, 533, 534, or 535 pM).

E3. The isolated antibody, or antigen-binding fragment thereof, of embodiment E1 or E2, wherein the KD for human αvβ8 integrin is less than or equal to 100 pM (e.g., 1, 2, 3, 4, 5, 6, 7, 8, 9, 10, 15, 20, 30, 40, 50, 60, 70, 80, 90, or 100 pM), e.g., for purified human αvβ8 integrin.

E4. The isolated antibody, or antigen-binding fragment thereof, of any of the preceding embodiments, wherein the KD for mouse αvβ8 integrin is less than the KD for the murine antibody ADWA11, e.g., less than 489 pM (e.g., 1, 5, 10, 20, 30, 40, 50, 60, 70, 80, 90, 100, 150, 200, 250, 300, 350, 370, 400, 450, 460, 470, 480, 485, 486, 487, or 488 pM).

E5. The isolated antibody, or antigen-binding fragment thereof, of any of the preceding embodiments, wherein the KD for mouse αvβ8 integrin is about 70.8+/−19.9 pM.

E6. The isolated antibody, or antigen-binding fragment thereof, of any of the preceding embodiments, wherein the KD for cynomolgus monkey αvβ8 integrin is less than the KD for the murine antibody ADWA11, e.g., less than 507 pM (e.g., 1, 5, 10, 20, 30, 40, 50, 60, 70, 80, 90, 100, 150, 200, 250, 300, 350, 370, 400, 450, 500, 501, 502, 503, 504, 505, or 506 pM).

E7. The isolated antibody, or antigen-binding fragment thereof, of any of the preceding embodiments, wherein the KD for cynomolgus monkey αvβ8 integrin is less than 100 pM.

E8. The isolated antibody, or antigen-binding fragment thereof, of any of the preceding embodiments, wherein the KD for rat αvβ8 integrin is about 160 pM.

E9. The isolated antibody, or antigen-binding fragment thereof, of any of the preceding embodiments, wherein the isolated antibody, or antigen-binding fragment thereof, shows approximately equivalent affinity for at least two, three, or all of human, cynomolgus, mouse, and rat αvβ8 integrin, e.g., with a KD that is less than 100 pM (e.g., 1, 2, 3, 4, 5, 6, 7, 8, 9, 10, 15, 20, 30, 40, 50, 60, 70, 80, 90, 95 pM), e.g., as determined using a Biacore affinity assay.

E10. The isolated antibody, or antigen-binding fragment thereof, of any of the preceding embodiments, wherein the isolated antibody, or antigen-binding fragment thereof, shows approximately equivalent affinity for at least two, three, or all of human, cynomolgus, mouse, and rat αvβ8 integrin, e.g., with a KD that is less than 100 pM (e.g., 1, 2, 3, 4, 5, 6, 7, 8, 9, 10, 15, 20, 30, 40, 50, 60, 70, 80, 90, 95 or 98 pM), e.g., as determined using a Biacore affinity assay.

E11. The isolated antibody, or antigen-binding fragment thereof, of any of the preceding embodiments, wherein the IC50 for inhibiting TGFβ transactivation is less than the murine antibody ADWA11, e.g., less than 183 pM (e.g., 1, 2, 3, 4, 5, 6, 7, 8, 9, 10, 15, 20, 30, 40, 50, 60, 70, 80, 90, 100, 110, 120, 130, 140, 150, 160, 170, 175, 180, 181, or 182 pM).

E12. The isolated antibody, or antigen-binding fragment thereof, of any of the preceding embodiments, wherein the IC50 for inhibiting TGFβ transactivation in U251 cells is about 199+/−93.6 pM.

E13. The isolated antibody, or antigen-binding fragment thereof, of any of the preceding embodiments, wherein the IC50 for inhibiting TGFβ transactivation is about 100 pM to about 300 pM.

E14. The isolated antibody, or antigen-binding fragment thereof, of any of the preceding embodiments, wherein the EC50 for U251 cells is about 126 pM with a standard deviation of plus or minus 34 pM.

E15. The isolated antibody, or antigen-binding fragment thereof, of any of the preceding embodiments, wherein the EC50 for U251 cells is about 256 pM with a standard deviation of plus or minus 115 pM.

E16. The isolated antibody, or antigen-binding fragment thereof, of any of the preceding embodiments, wherein the EC50 for U251 cells is about 100 pM to about 400 pM.

E17. The isolated antibody, or antigen-binding fragment thereof, of any of the preceding embodiments, wherein the EC50 for C8-S cells is about 115 pM.

E18. The isolated antibody, or antigen-binding fragment thereof, of any of the preceding embodiments, wherein the EC50 for C8-S cells is about 145+/−23.7 pM.

E19. The isolated antibody, or antigen-binding fragment thereof, of any of the preceding embodiments, wherein the EC50 for C8-S cells is about 110 pM to about 180 pM.

E20. The isolated antibody, or antigen-binding fragment thereof, of any of the preceding embodiments, having at least one predicted human pharmacokinetic (PK) parameter chosen from the group consisting of:
  (i) a clearance from central compartment (CL) of about 0.12-0.15 mL/h/kg;
  (ii) an inter-compartmental distribution clearance (CLF) of about 0.15-0.51 mL/h/kg;
  (iii) a volume of distribution for the central compartment (V1) of about 36-39 mL/kg;
  (iv) a volume of distribution for the peripheral compartment (V2) of about 21-33 mL/kg; and/or
  (v) a terminal half-life ($t_{1/2}$) of about 12-17 days.

E21. The isolated antibody, or antigen-binding fragment thereof, of any of the preceding embodiments, wherein the isolated antibody, or antigen-binding fragment thereof, shows no detectable binding to a human Fcγ receptor or C1q.

E22. The isolated antibody, or antigen-binding fragment thereof, of any one of the preceding embodiments, wherein the antibody, or antigen-binding fragment thereof, further has at least one of the following properties:
  (i) binds specifically to αvβ8 integrin (e.g., αvβ8 integrin from human, mouse, cynomolgus monkey, and/or rat);
  (ii) reduce an interaction between αvβ8 integrin and Latency Associated Peptide (LAP);
  (iii) reduces TGF-β signaling;
  (iv) effectively blocks the αvβ8 integrin-mediated TGFβ activation with an IC50≤10 nM;
  (v) has a comparable Kd (within 5-fold) towards a non-human primate (NHP) orthologue;
  (vi) selectivity binds human αvβ8 and does not detectably bind a homologue of αvβ8 (e.g., αvβ1, αvβ3, αvβ5 and αvβ6);
  (vii) causes growth suppression and/or complete tumor regression in an animal model for a cancer, alone or in combination with an immunomodulatory agent, e.g., a modulators of checkpoint inhibitors, e.g., inhibitors of PD-1, PD-L1, CTLA-4, or an agonist of a stimulatory molecule, e.g., 4-1BB;
  (viii) causes growth suppression and/or complete tumor regression in an animal model for a cancer in combination with an anti-cancer therapy, e.g., radiotherapy;
  (ix) shows at least 60% reduction in tumor growth in a syngeneic tumor graft model, e.g., when administered at ≤10 mg/kg, alone or in combination with an immunomodulatory agent (e.g., an inhibitor of PD-1, PD-L1, or CTLA-4);

(x) increases an anti-tumor response in the presence of one or more immunomodulators, e.g., an antagonist of a checkpoint inhibitor, e.g., an antagonist of PD-1, PD-L1, or CTLA-4, or an activator of an immune response, e.g., 4-1BB agonist, when administered to a subject;

(xi) has an efficacy that is not dependent upon the expression of αvβ8 integrin in a tumor model;

(xii) increases the abundance of CD8+ GzmB+ T cells in the tumor microenvironment;

(xiii) shows a decrease, e.g., at least a >80% decrease, in tumor growth when used in combination with an antagonist of a checkpoint inhibitor (e.g., an anti-PD-1 or anti-PD-L1 antibody), e.g., in a syngeneic model of squamous cell carcinoma, breast cancer, and/or colon cancer;

(xiv) shows a statistically significant improvement in overall survival of a subject, as determined by a Kaplan-Meier analysis;

(xv) has a high degree of thermal stability;

(xvi) shows minimal aggregation at high concentration; and (xvii) may show reproducible expression and purity in large-scale manufacturing conditions.

E23. An isolated antibody, or antigen-binding fragment thereof, that specifically binds to human αvβ8 integrin, comprising:
  one, two or three CDRs from a heavy chain variable region (e.g., H1, H2 or H3), and/or one, two, or three CDRs from a light chain variable region (e.g., L1, L2 or L3) selected from:
  (i) a CDR-H1 comprising the amino acid sequence of SEQ ID NO: 8 or 14,
    a CDR-H2 comprising the amino acid sequence of SEQ ID NO: 9 or 15,
    a CDR-H3 comprising the amino acid sequence of SEQ ID NO: 10 or 16,
    a CDR-L1 comprising the amino acid sequence of SEQ ID NO: 11 or 17,
    a CDR-L2 comprising the amino acid sequence of SEQ ID NO: 12 or 18, and
    a CDR-L3 comprising the amino acid sequence of SEQ ID NO: 13 or 19, or
  (ii) a CDR-H1 comprising at least one amino acid alteration, but not more than two, three or four alterations (e.g., a substitution, deletion, or insertion, e.g., conservative substitution) relative to SEQ ID NO: 8 or 14,
    a CDR-H2 comprising at least one amino acid alteration, but not more than two, three or four alterations (e.g., a substitution, deletion, or insertion, e.g., conservative substitution) relative to SEQ ID NO: 9 or 15,
    a CDR-H3 comprising at least one amino acid alteration, but not more than two, three or four alterations (e.g., a substitution, deletion, or insertion, e.g., conservative substitution) relative to SEQ ID NO: 10 or 16,
    a CDR-L1 comprising at least one amino acid alteration, but not more than two, three or four alterations (e.g., a substitution, deletion, or insertion, e.g., conservative substitution) relative to SEQ ID NO: 11 or 17,
    a CDR-L2 comprising at least one amino acid alteration, but not more than two, three or four alterations (e.g., a substitution, deletion, or insertion, e.g., conservative substitution) relative to SEQ ID NO: 12 or 18, or
    a CDR-L3 comprising at least one amino acid alteration, but not more than two, three or four alterations (e.g., a substitution, deletion, or insertion, e.g., conservative substitution) relative to SEQ ID NO: 13 or 19, optionally wherein:
  any of CDR-H1, CDR-H2, CDR-H3, CDR-L1, CDR-L2, or CDR-L3 do not comprise the amino acid sequence of any of:
    (a) SEQ ID NOs: 22, 23, 24, 25, 26, and 27, respectively,
    (b) SEQ ID NOs: 28, 29, 30, 31, 32, and 33, respectively,
    (c) SEQ ID NOs: 22, 23, 24, 71, 72, and 73, respectively, or
    (d) SEQ ID NOs: 28, 29, 30, 74, 75, and 76, respectively.

Alternatively, or in combination with any of the embodiments provided herein (e.g., E1-E23), the antibody, or antigen-binding fragment thereof, has one or more of the following aspects, features, and embodiments.

E24. An isolated antibody, or antigen-binding fragment thereof, that specifically binds to human αvβ8 integrin, comprising:
  one, two or three CDRs from a heavy chain variable region (e.g., H1, H2 or H3), and/or one, two, or three CDRs from a light chain variable region (e.g., L1, L2 or L3) selected from:
  (i) a CDR-H1 comprising the amino acid sequence of SEQ ID NO: 8,
    a CDR-H2 comprising the amino acid sequence of SEQ ID NO: 9,
    a CDR-H3 comprising the amino acid sequence of SEQ ID NO: 10,
    a CDR-L1 comprising the amino acid sequence of SEQ ID NO: 11,
    a CDR-L2 comprising the amino acid sequence of SEQ ID NO: 12, and
    a CDR-L3 comprising the amino acid sequence of SEQ ID NO: 13, or
  (ii) a CDR-H1 comprising at least one amino acid alteration, but not more than two, three or four alterations (e.g., a substitution, deletion, or insertion, e.g., conservative substitution) relative to SEQ ID NO: 8,
    a CDR-H2 comprising at least one amino acid alteration, but not more than two, three or four alterations (e.g., a substitution, deletion, or insertion, e.g., conservative substitution) relative to SEQ ID NO: 9,
    a CDR-H3 comprising at least one amino acid alteration, but not more than two, three or four alterations (e.g., a substitution, deletion, or insertion, e.g., conservative substitution) relative to SEQ ID NO: 10,
    a CDR-L1 comprising at least one amino acid alteration, but not more than two, three or four alterations (e.g., a substitution, deletion, or insertion, e.g., conservative substitution) relative to SEQ ID NO: 11,
    a CDR-L2 comprising at least one amino acid alteration, but not more than two, three or four alterations (e.g., a substitution, deletion, or insertion, e.g., conservative substitution) relative to SEQ ID NO: 12, or
    a CDR-L3 comprising at least one amino acid alteration, but not more than two, three or four alterations (e.g., a substitution, deletion, or insertion, e.g., conservative substitution) relative to SEQ ID NO: 13, optionally wherein:
  any of CDR-H1, CDR-H2, CDR-H3, CDR-L1, CDR-L2, or CDR-L3 do not comprise the amino acid sequence of any of:

(a) SEQ ID NOs: 22, 23, 24, 25, 26, and 27, respectively, or
(b) SEQ ID NOs: 22, 23, 24, 71, 72, and 73, respectively.

E25. An isolated antibody, or antigen-binding fragment thereof, that specifically binds to human αvβ8 integrin, comprising:
one, two, or three complementarity determining regions (CDRs) from a heavy chain variable region (e.g., H1, H2 or H3), and/or one, two, or three CDRs from a light chain variable region (e.g., L1, L2 or L3) selected from:
a CDR-H2 comprising the amino acid sequence of SEQ ID NO: 9,
a CDR-L1 comprising the amino acid sequence of SEQ ID NO: 11,
a CDR-L2 comprising the amino acid sequence of SEQ ID NO: 12, and
a CDR-L3 comprising the amino acid sequence of SEQ ID NO: 13.

E26. The isolated antibody, or antigen-binding fragment thereof, of embodiment E24 or E25, comprising:
a CDR-H1 comprising the amino acid sequence of SEQ ID NO: 8,
a CDR-H2 comprising the amino acid sequence of SEQ ID NO: 9, and
a CDR-H3 comprising the amino acid sequence of SEQ ID NO: 10.

E27. The isolated antibody, or antigen-binding fragment thereof, of any of embodiments E24-E26, comprising:
a CDR-L1 comprising the amino acid sequence of SEQ ID NO: 11,
a CDR-L2 comprising the amino acid sequence of SEQ ID NO: 12, and
a CDR-L3 comprising the amino acid sequence of SEQ ID NO: 13.

E28. An isolated antibody, or antigen-binding fragment thereof, that specifically binds to human αvβ8 integrin, comprising:
a CDR-H1 comprising the amino acid sequence of SEQ ID NO: 8,
a CDR-H2 comprising the amino acid sequence of SEQ ID NO: 9,
a CDR-H3 comprising the amino acid sequence of SEQ ID NO: 10,
a CDR-L1 comprising the amino acid sequence of SEQ ID NO: 11,
a CDR-L2 comprising the amino acid sequence of SEQ ID NO: 12, and
a CDR-L3 comprising the amino acid sequence of SEQ ID NO: 13.

E29. An isolated antibody, or antigen-binding fragment thereof, that specifically binds to human αvβ8 integrin, comprising one, two, or three complementarity determining regions (CDRs) from a heavy chain variable region (e.g., H1, H2 or H3), and/or one, two, or three CDRs from a light chain variable region (e.g., L1, L2 or L3):
a CDR-H1 comprising the amino acid sequence of DYYMN (SEQ ID NO: 8);
a CDR-H2 comprising the amino acid sequence of WIDPDX$_1$GNTIYX$_2$PKFQG (SEQ ID NO: 131), wherein X$_1$ can be any one of: an amino acid, an amino acid other than N, a conservative substitution of N, N, or Q; and X$_2$ can be any one of: an amino acid, an amino acid other than D, a conservative substitution of D, D, or E;
a CDR-H3 comprising the amino acid sequence of RLL-MDY (SEQ ID NO: 10);
a CDR-L1 comprising the amino acid sequence of RSTKSLX$_3$HFNGNTYLF (SEQ ID NO: 132), wherein X$_3$ can be any one of: an amino acid, an amino acid other than L, a conservative substitution of L, L, or S;
a CDR-L2 comprising the amino acid sequence of YYMSX$_4$LAS (SEQ ID NO: 133), wherein X$_4$ can be any one of: an amino acid, an amino acid other than N, a conservative substitution of N, N, or S; and/or
a CDR-L3 comprising the amino acid sequence of X$_5$QSLEYPFT (SEQ ID NO: 134), wherein X$_5$ can be any one of: an amino acid, an amino acid other than M, a conservative substitution of M, M, or Q;
e.g., wherein the CDR-H1, CDR-H2, CDR-H3, CDR-L1, CDR-L2, and CDR-L3 do not comprise the amino acid sequences of SEQ ID NOs: 22, 23, 24, 25, 26, and 27, respectively, or SEQ ID NOs: 22, 23, 24, 71, 72, and 73, respectively.

E30. The isolated antibody, or antigen-binding fragment thereof, of embodiment E29, wherein X$_1$ is Q and X$_2$ is E.

E31. The isolated antibody, or antigen-binding fragment thereof, of embodiment E29 or E30, wherein X$_3$ is S.

E32. The isolated antibody, or antigen-binding fragment thereof, of any of embodiments E29-E31, wherein X$_4$ is S.

E33. The isolated antibody, or antigen-binding fragment thereof, of any of embodiments E29-E32, wherein X$_5$ is Q.

E34. The isolated antibody, or antigen-binding fragment thereof, of embodiment E29, wherein X$_1$ is Q, X$_2$ is E, X$_3$ is S, and X$_5$ is Q.

E35. The isolated antibody, or antigen-binding fragment thereof, of embodiment E29, wherein X$_1$ is Q, X$_2$ is E, and X$_3$ is S.

E36. The isolated antibody, or antigen-binding fragment thereof, of embodiment E29, wherein X$_1$ is Q, X$_2$ is E, X$_3$ is S, X$_4$ is S, and X$_5$ is Q.

E37. An isolated antibody, or antigen-binding fragment thereof, that specifically binds to human αvβ8 integrin, comprising one, two, or three complementarity determining regions (CDRs) from a heavy chain variable region (e.g., H1, H2 or H3), and/or one, two, or three CDRs from a light chain variable region (e.g., L1, L2 or L3):
a CDR-H1 comprising the amino acid sequence of DYYMN (SEQ ID NO: 8);
a CDR-H2 comprising the amino acid sequence of WIDPDX$_1$GX$_2$TIYX$_3$X$_4$X$_5$X$_6$X$_7$G (SEQ ID NO: 167), wherein X$_1$ can be any one of: an amino acid, an amino acid other than N, a conservative substitution of N, N, or Q; X$_2$ can be any one of: an amino acid, an amino acid other than N, a conservative substitution of N, N, or Q; X$_3$ can be any one of: an amino acid, an amino acid other than D, a conservative substitution of D, D, or E; X$_4$ can be any one of: an amino acid, an amino acid other than P, a conservative substitution of P, P, Q, D, or A; X$_5$ can be any one of: an amino acid, an amino acid other than K, a conservative substitution of K, K, S, or A; X$_6$ can be any one of: an amino acid, an amino acid other than F, a conservative substitution of F, F, or V; and X$_7$ can be any one of: an amino acid, an amino acid other than Q, a conservative substitution of Q, Q, or K;
a CDR-H3 comprising the amino acid sequence of RLL-MDY (SEQ ID NO: 10);
a CDR-L1 comprising the amino acid sequence of RSTKSX$_8$X$_9$HFNGNX$_{10}$YLF (SEQ ID NO: 168), wherein X$_8$ can be any one of: an amino acid, an amino acid other than L, a conservative substitution of L, L, or I; X$_9$ can be any one of: an amino acid, an amino acid other than L, a conservative substitution of L, L, or S; and $X_{10}$ can be any one of: an amino acid, an amino acid other than T, a conservative substitution of T, T, or S;

a CDR-L2 comprising the amino acid sequence of $YX_{11}X_{12}SX_{13}LX_{14}S$ (SEQ ID NO: 169), wherein $X_{11}$ can be any one of: an amino acid, an amino acid other than Y, a conservative substitution of Y, Y, or A; $X_{12}$ can be any one of: an amino acid, an amino acid other than M, a conservative substitution of M, M, or A; Xu can be any one of: an amino acid, an amino acid other than N, a conservative substitution of N, N, or S; and Xu can be any one of: an amino acid, an amino acid other than A, a conservative substitution of A, A, or Q; and/or a CDR-L3 comprising the amino acid sequence of $X_{15}QSX_{16}X_{17}X_{18}PX_{19}T$ (SEQ ID NO: 170), wherein $X_{15}$ can be any one of: an amino acid, an amino acid other than M, a conservative substitution of M, M, or Q; $X_{16}$ can be any one of: an amino acid, an amino acid other than L, a conservative substitution of L, L, or Y; $X_{17}$ can be any one of: an amino acid, an amino acid other than E, a conservative substitution of E, E, or S; $X_{18}$ can be any one of: an amino acid, an amino acid other than Y, a conservative substitution of Y, Y, or T; and $X_{19}$ can be any one of: an amino acid, an amino acid other than F, a conservative substitution of F, F, L, or W;

e.g., wherein the CDR-H1, CDR-H2, CDR-H3, CDR-L1, CDR-L2, and CDR-L3 do not comprise the amino acid sequences of SEQ ID NOs: 22, 23, 24, 25, 26, and 27, respectively, or SEQ ID NOs: 22, 23, 24, 71, 72, and 73, respectively, optionally wherein:

$X_1$ is Q, $X_2$ is N, $X_3$ is E, $X_4$ is P, $X_5$ is K, $X_6$ is F, and $X_7$ is Q,
$X_8$ is L, $X_9$ is S, and $X_{10}$ is T,
$X_{11}$ is Y, $X_{12}$ is M, $X_{13}$ is S, and $X_{14}$ is A, and/or
$X_{15}$ is Q, $X_{16}$ is L, $X_{17}$ is E, $X_{18}$ is Y, and $X_{19}$ is F.

E38. An isolated antibody, or antigen-binding fragment thereof, that specifically binds to human αvβ8 integrin, comprising one, two, or three complementarity determining regions (CDRs) from a heavy chain variable region (e.g., H1, H2 or H3), and/or one, two, or three CDRs from a light chain variable region (e.g., L1, L2 or L3):

a CDR-H1 comprising the amino acid sequence of DYYMN (SEQ ID NO: 8);

a CDR-H2 comprising the amino acid sequence of $WIDPDX_1GNTIYX_2PKX_3QG$ (SEQ ID NO: 171), wherein $X_1$ can be any one of: an amino acid, an amino acid other than N, a conservative substitution of N, N, or Q; $X_2$ can be any one of: an amino acid, an amino acid other than D, a conservative substitution of D, D, or E; and $X_3$ can be any one of: an amino acid, an amino acid other than F, a conservative substitution of F, F, or V;

a CDR-H3 comprising the amino acid sequence of RLL-MDY (SEQ ID NO: 10);

a CDR-L1 comprising the amino acid sequence of $RSTKSLX_4HFNGNTYLF$ (SEQ ID NO: 172), wherein $X_4$ can be any one of: an amino acid, an amino acid other than L, a conservative substitution of L, L, or S;

a CDR-L2 comprising the amino acid sequence of $YYX_5SX_6LAS$ (SEQ ID NO: 173), wherein $X_5$ can be any one of: an amino acid, an amino acid other than M, a conservative substitution of M, M, or A; and $X_6$ can be any one of: an amino acid, an amino acid other than N, a conservative substitution of N, N, or S; and/or a CDR-L3 comprising the amino acid sequence of $X_7QSX_8EYPFT$ (SEQ ID NO: 174), wherein $X_7$ can be any one of: an amino acid, an amino acid other than M, a conservative substitution of M, M, or Q; and $X_8$ can be any one of: an amino acid, an amino acid other than L, a conservative substitution of L, L, or Y;

e.g., wherein the CDR-H1, CDR-H2, CDR-H3, CDR-L1, CDR-L2, and CDR-L3 do not comprise the amino acid sequences of SEQ ID NOs: 22, 23, 24, 25, 26, and 27, respectively, or SEQ ID NOs: 22, 23, 24, 71, 72, and 73, respectively, optionally wherein:

$X_1$ is Q, $X_2$ is E, and $X_3$ is F,
$X_4$ is S,
$X_5$ is M and $X_6$ is S, and/or
$X_7$ is Q and $X_8$ is L.

E39. An isolated antibody, or antigen-binding fragment thereof, that specifically binds to human αvβ8 integrin, comprising one, two, or three of the CDR sequences from a VH region comprising the amino acid sequence of SEQ ID NO: 6, wherein the CDR sequences are as defined according to Kabat.

E40. An isolated antibody, or antigen-binding fragment thereof, that specifically binds to human αvβ8 integrin, comprising one, two, or three of the CDR sequences from a VL region comprising the amino acid sequence of SEQ ID NO: 7, wherein the CDR sequences are as defined according to Kabat.

E41. An isolated antibody, or antigen-binding fragment thereof, that specifically binds to human αvβ8 integrin, comprising one, two, or three of the CDR sequences from a VH region comprising the amino acid sequence of SEQ ID NO: 6 and one, two, or three of the CDR-L1 sequences from a VL region comprising the amino acid sequence of SEQ ID NO: 7, wherein the CDR sequences are as defined according to Kabat.

E42. An isolated antibody, or antigen-binding fragment thereof, that specifically binds to human αvβ8 integrin, comprising one, two, or three of the CDR sequences from a polypeptide encoded by the nucleic acid sequence of SEQ ID NO: 189, 190 or 191, wherein the CDR sequences are as defined according to Kabat.

E43. An isolated antibody, or antigen-binding fragment thereof, that specifically binds to human αvβ8 integrin, comprising one, two, or three of the CDR sequences from a polypeptide encoded by the nucleic acid sequence of SEQ ID NO: 185 or 186, wherein the CDR sequences are as defined according to Kabat.

E44. An isolated antibody, or antigen-binding fragment thereof, that specifically binds to human αvβ8 integrin, comprising one, two, or three of the CDR sequences from a polypeptide encoded by the nucleic acid sequence of SEQ ID NO: 189, 190 or 191 and one, two, or three of the CDR sequences from a polypeptide encoded by the nucleic acid sequence of SEQ ID NO: 185 or 186, wherein the CDR sequences are as defined according to Kabat.

E45. An isolated antibody, or antigen-binding fragment thereof, that specifically binds to human αvβ8 integrin, comprising one or more complementarity determining regions (CDRs) selected from:

(i) a CDR-H1 comprising the amino acid sequence of SEQ ID NO: 14,
a CDR-H2 comprising the amino acid sequence of SEQ ID NO: 15,
a CDR-H3 comprising the amino acid sequence of SEQ ID NO: 16,
a CDR-L1 comprising the amino acid sequence of SEQ ID NO: 17, a CDR-L2 comprising the amino acid sequence of SEQ ID NO: 18, and
a CDR-L3 comprising the amino acid sequence of SEQ ID NO: 19; or
(ii) a CDR-H1 comprising at least one amino acid alteration, but not more than two, three or four alterations (e.g., a substitution, deletion, or insertion, e.g., conservative substitution) relative to SEQ ID NO: 14,
a CDR-H2 comprising at least one amino acid alteration, but not more than two, three or four alterations (e.g., a substitution, deletion, or insertion, e.g., conservative substitution) relative to SEQ ID NO: 15,
a CDR-H3 comprising at least one amino acid alteration, but not more than two, three or four alterations (e.g., a substitution, deletion, or insertion, e.g., conservative substitution) relative to SEQ ID NO: 16,
a CDR-L1 comprising at least one amino acid alteration, but not more than two, three or four alterations (e.g., a substitution, deletion, or insertion, e.g., conservative substitution) relative to SEQ ID NO: 17,
a CDR-L2 comprising at least one amino acid alteration, but not more than two, three or four alterations (e.g., a substitution, deletion, or insertion, e.g., conservative substitution) relative to SEQ ID NO: 18, or
a CDR-L3 comprising at least one amino acid alteration, but not more than two, three or four alterations (e.g., a substitution, deletion, or insertion, e.g., conservative substitution) relative to SEQ ID NO: 19, optionally wherein:
any of CDR-H1, CDR-H2, CDR-H3, CDR-L1, CDR-L2, or CDR-L3 do not comprise the amino acid sequence of any of
(a) SEQ ID NOs: 28, 29, 30, 31, 32, and 33, respectively, or
(b) SEQ ID NOs: 28, 29, 30, 74, 75, and 76, respectively.

E46. An isolated antibody, or antigen-binding fragment thereof, that specifically binds to human αvβ8 integrin, comprising one or more complementarity determining regions (CDRs) selected from:
a CDR-H2 comprising the amino acid sequence of SEQ ID NO: 15,
a CDR-L1 comprising the amino acid sequence of SEQ ID NO: 17, and
a CDR-L2 comprising the amino acid sequence of SEQ ID NO: 18.

E47. The isolated antibody, or antigen-binding fragment thereof, of embodiment E45 or E46, comprising:
a CDR-H1 comprising the amino acid sequence of SEQ ID NO: 14,
a CDR-H2 comprising the amino acid sequence of SEQ ID NO: 15, and
a CDR-H3 comprising the amino acid sequence of SEQ ID NO: 16.

E48. The isolated antibody, or antigen-binding fragment thereof, of any of embodiments E45-E47, comprising:
a CDR-L1 comprising the amino acid sequence of SEQ ID NO: 17,
a CDR-L2 comprising the amino acid sequence of SEQ ID NO: 18, and
a CDR-L3 comprising the amino acid sequence of SEQ ID NO: 19.

E49. An isolated antibody, or antigen-binding fragment thereof, that specifically binds to human αvβ8 integrin, comprising:
a CDR-H1 comprising the amino acid sequence of SEQ ID NO: 14,
a CDR-H2 comprising the amino acid sequence of SEQ ID NO: 15,
a CDR-H3 comprising the amino acid sequence of SEQ ID NO: 16,
a CDR-L1 comprising the amino acid sequence of SEQ ID NO: 17,
a CDR-L2 comprising the amino acid sequence of SEQ ID NO: 18, and
a CDR-L3 comprising the amino acid sequence of SEQ ID NO: 19.

E50. An isolated antibody, or antigen-binding fragment thereof, that specifically binds to human αvβ8 integrin, comprising:
a CDR-H1 comprising the amino acid sequence of GFNIKDYYMN (SEQ ID NO: 14);
a CDR-H2 comprising the amino acid sequence of WIDPDX$_1$GN (SEQ ID NO: 135), wherein X$_1$ can be any one of: an amino acid, an amino acid other than N, a conservative substitution of N, N, or Q;
a CDR-H3 comprising the amino acid sequence of RLLMDY (SEQ ID NO: 16);
a CDR-L1 comprising the amino acid sequence of STKSLX$_2$HFNGNTYL (SEQ ID NO: 136), wherein X$_2$ can be any one of: an amino acid, an amino acid other than L, a conservative substitution of L, L, or S;
a CDR-L2 comprising the amino acid sequence of YYMSX$_3$ (SEQ ID NO: 137), wherein X$_3$ can be any one of: an amino acid, an amino acid other than N, a conservative substitution of N, N, or S; and
a CDR-L3 comprising the amino acid sequence of QSLEYPFT (SEQ ID NO: 19);
e.g., wherein the CDR-H1, CDR-H2, CDR-H3, CDR-L1, CDR-L2, and CDR-L3 do not comprise the amino acid sequences of SEQ ID NOs: 28, 29, 30, 31, 32, and 33, respectively, or SEQ ID NOs: 28, 29, 30, 74, 75, and 76, respectively.

E51. The isolated antibody, or antigen-binding fragment thereof, of embodiment E50, wherein X$_1$ is Q, X$_2$ is S, and X$_3$ is S.

E52. An isolated antibody, or antigen-binding fragment thereof, that specifically binds to human αvβ8 integrin, comprising:
a CDR-H1 comprising the amino acid sequence of GFNIX$_1$DYYMN (SEQ ID NO: 175), wherein X$_1$ can be any one of: an amino acid, an amino acid other than K, a conservative substitution of K, K, or A;
a CDR-H2 comprising the amino acid sequence of WIDPDX$_2$GX$_3$ (SEQ ID NO: 176), wherein X$_2$ can be any one of: an amino acid, an amino acid other than N, a conservative substitution of N, N, or Q; and X$_3$ can be any one of: an amino acid, an amino acid other than N, a conservative substitution of N, N, or Q;
a CDR-H3 comprising the amino acid sequence of RLLMDY (SEQ ID NO: 16);
a CDR-L1 comprising the amino acid sequence of STKSX$_4$X$_5$HFNGNX$_6$YL (SEQ ID NO: 177), wherein X$_4$ can be any one of: an amino acid, an amino acid other than L, a conservative substitution of L, L, or I; X$_5$ can be any one of: an amino acid, an amino acid other than L, a conservative substitution of L, L, or S; and X$_6$ can be any one of: an amino acid, an amino acid other than T, a conservative substitution of T, T, or S;
a CDR-L2 comprising the amino acid sequence of YX$_7$X$_8$SX$_9$ (SEQ ID NO: 178), wherein X$_7$ can be any one of: an amino acid, an amino acid other than Y, a conservative substitution of Y, Y, or A; X$_8$ can be any one of: an amino acid, an amino acid other than M, a conservative substitution of M, M, or A; and X₉ can be any one of: an amino acid, an amino acid other than N, a conservative substitution of N, N, or S; and a CDR-L3 comprising the amino acid sequence of QSX₁₀X₁₁X₁₂PX₁₃T (SEQ ID NO: 197), wherein X₁₀ can be any one of: an amino acid, an amino acid other than L, a conservative substitution of L, L, or Y; X₁₁ can be any one of: an amino acid, an amino acid other than E, a conservative substitution of E, E, or S; X₁₂ can be any one of: an amino acid, an amino acid other than Y, a conservative substitution of Y, Y, or T; and X₁₃ can be any one of: an amino acid, an amino acid other than F, a conservative substitution of F, F, L, or W;

e.g., wherein the CDR-H1, CDR-H2, CDR-H3, CDR-L1, CDR-L2, and CDR-L3 do not comprise the amino acid sequences of SEQ ID NOs: 28, 29, 30, 31, 32, and 33, respectively, or SEQ ID NOs: 28, 29, 30, 74, 75, and 76, respectively, optionally wherein:

X₁ is Q, X₂ is N, X₃ is E, X₄ is P, X₅ is K, X₆ is F, and X₇ is Q,

X₈ is L, X₉ is S, and X₁₀ is T,

X₁₁ is Y, X₁₂ is M, X₁₃ is S, and X₁₄ is A, and/or

X₁₅ is Q, X₁₆ is L, X₁₇ is E, X₁₈ is Y, and X₁₉ is F.

E53. An isolated antibody, or antigen-binding fragment thereof, that specifically binds to human αvβ8 integrin, comprising:

a CDR-H1 comprising the amino acid sequence of GFNIKDYYMN (SEQ ID NO: 14);

a CDR-H2 comprising the amino acid sequence of WIDPDX₁GN (SEQ ID NO: 135), wherein X₁ can be any one of: an amino acid, an amino acid other than N, a conservative substitution of N, N, or Q;

a CDR-H3 comprising the amino acid sequence of RLL-MDY (SEQ ID NO: 16);

a CDR-L1 comprising the amino acid sequence of STKSLX₂HFNGNTYL (SEQ ID NO: 136), wherein X₂ can be any one of: an amino acid, an amino acid other than L, a conservative substitution of L, L, or S;

a CDR-L2 comprising the amino acid sequence of YYX₃SX₄ (SEQ ID NO: 179), wherein X₃ can be any one of: an amino acid, an amino acid other than M, a conservative substitution of M, M, or A; and X₄ can be any one of: an amino acid, an amino acid other than N, a conservative substitution of N, N, or S; and a CDR-L3 comprising the amino acid sequence of QSX₅EYPFT (SEQ ID NO: 180), wherein X₅ can be any one of: an amino acid, an amino acid other than L, a conservative substitution of L, L, or Y;

e.g., wherein the CDR-H1, CDR-H2, CDR-H3, CDR-L1, CDR-L2, and CDR-L3 do not comprise the amino acid sequences of SEQ ID NOs: 28, 29, 30, 31, 32, and 33, respectively, or SEQ ID NOs: 28, 29, 30, 74, 75, and 76, respectively, optionally wherein:

X₁ is Q,

X₂ is S,

X₃ is M and X₄ is S, and/or

X₅ is L.

E54. An isolated antibody, or antigen-binding fragment thereof, that specifically binds to human αvβ8 integrin, comprising one, two, or three of the CDR sequences from a VH region comprising the amino acid sequence of SEQ ID NO: 6, wherein the CDR sequences are as defined according to Chothia.

E55. An isolated antibody, or antigen-binding fragment thereof, that specifically binds to human αvβ8 integrin, comprising one, two, or three of the CDR sequences from a VL region comprising the amino acid sequence of SEQ ID NO: 7, wherein the CDR sequences are as defined according to Chothia.

E56. An isolated antibody, or antigen-binding fragment thereof, that specifically binds to human αvβ8 integrin, comprising one, two, or three of the CDR sequences from a VH region comprising the amino acid sequence of SEQ ID NO: 6 and one, two, or three of the CDR-L1 sequences from a VL region comprising the amino acid sequence of SEQ ID NO: 7, wherein the CDR sequences are as defined according to Chothia.

E57. An isolated antibody, or antigen-binding fragment thereof, that specifically binds to human αvβ8 integrin, comprising one, two, or three of the CDR sequences from a polypeptide encoded by the nucleic acid sequence of SEQ ID NO: 189, 190 or 191, wherein the CDR sequences are as defined according to Chothia.

E58. An isolated antibody, or antigen-binding fragment thereof, that specifically binds to human αvβ8 integrin, comprising one, two, or three of the CDR sequences from a polypeptide encoded by the nucleic acid sequence of SEQ ID NO: 185 or 186, wherein the CDR sequences are as defined according to Chothia.

E59. An isolated antibody, or antigen-binding fragment thereof, that specifically binds to human αvβ8 integrin, comprising one, two, or three of the CDR sequences from a polypeptide encoded by the nucleic acid sequence of SEQ ID NO: 189, 190 or 191 and one, two, or three of the CDR sequences from a polypeptide encoded by the nucleic acid sequence of SEQ ID NO: 185, 186, wherein the CDR sequences are as defined according to Chothia.

E60. The isolated antibody, or antigen-binding fragment thereof, of any of the preceding embodiments, wherein the antibody comprises a VH framework region (e.g., one, two, three, or four of FR1, FR2, FR3, or FR4) comprising an amino acid sequence having at least 80%, 85%, 87% 90%, 92%, 93%, 95%, 97%, 98%, or preferably 100% sequence identity to a VH framework region of a VH region comprising the amino acid sequence of any one of SEQ ID NOs: 6, 34-46, 88-91, or 93.

E61. The isolated antibody, or antigen-binding fragment thereof, of any of the preceding embodiments, wherein the antibody comprises a VL framework region (e.g., one, two, three, or four of FR1, FR2, FR3, or FR4) comprising an amino acid sequence having at least 80%, 85%, 87% 90%, 92%, 93%, 95%, 97%, 98%, or preferably 100% sequence identity to a VL framework region of a VL region comprising the amino acid sequence of any one of SEQ ID NOs: 7, 47-69, or 92.

E62. The isolated antibody, or antigen-binding fragment thereof, of any of the preceding embodiments, wherein the antibody comprises a VH framework region (e.g., one, two, three, or four of FR1, FR2, FR3, or FR4) comprising an amino acid sequence having at least 80%, 85%, 87% 90%, 92%, 93%, 95%, 97%, 98%, or 100% sequence identity to the germline amino acid sequence of IGHV3-07, IGHV1-46, IGHV3-23, IGHV3-30, IGHV1-69, or IGHV3-48.

E63. The isolated antibody, or antigen-binding fragment thereof, of any of the preceding embodiments, wherein the antibody comprises a VL framework region (e.g., one, two, three, or four of FR1, FR2, FR3, or FR4) comprising an amino acid sequence having at least 80%, 85%, 87% 90%, 92%, 93%, 95%, 97%, 98%, or 100% sequence identity to the germline amino acid sequence of IGKV1-39, IGKV2-28, IGKV2-30, IGKV4-1, or IGKV3-11.

E64. The isolated antibody, or antigen-binding fragment thereof, of any of the preceding embodiments, wherein the antibody comprises a VH framework region (e.g., one, two, three, or four of FR1, FR2, FR3, or FR4) comprising an amino acid sequence comprising 1, 2, 3, 4, 5, 6, 7, 8, 9, 10, 11, 12, 13, 14, 15, 16, 17, 18, 19, 20, 21, 22, or 23 substitutions relative to a VH framework region of a VH region comprising the amino acid sequence of any one of SEQ ID NOs: 6, 34-46, 88-91, or 93.

E65. The isolated antibody, or antigen-binding fragment thereof, of any of the preceding embodiments, wherein the antibody comprises a VL framework region (e.g., one, two, three, or four of FR1, FR2, FR3, or FR4) comprising an amino acid sequence comprising 1, 2, 3, 4, 5, 6, 7, 8, 9, 10, 11, 12, 13, 14, 15, 16, 17, 18, 19, 20, 21, 22, or 23 substitutions relative to a VL framework region of a VL region comprising the amino acid sequence of any one of SEQ ID NOs: 7, 47-69, or 92.

E66. The isolated antibody, or antigen-binding fragment thereof, of any of the preceding embodiments, wherein the antibody comprises a VH framework region (e.g., one, two, three, or four of FR1, FR2, FR3, or FR4) comprising an amino acid sequence comprising 1, 2, 3, 4, 5, 6, 7, 8, 9, 10, 11, 12, 13, 14, 15, 16, 17, 18, 19, 20, 21, 22, or 23 substitutions relative to the germline amino acid sequence of IGHV3-07, IGHV1-46, IGHV3-23, IGHV3-30, IGHV1-69, or IGHV3-48.

E67. The isolated antibody, or antigen-binding fragment thereof, of any of the preceding embodiments, wherein the antibody comprises a VL framework region (e.g., one, two, three, or four of FR1, FR2, FR3, or FR4) comprising an amino acid sequence comprising 1, 2, 3, 4, 5, 6, 7, 8, 9, 10, 11, 12, 13, 14, 15, 16, 17, 18, 19, 20, 21, 22, or 23 substitutions relative to the germline amino acid sequence of IGKV1-39, IGKV2-28, IGKV2-30, IGKV4-1, or IGKV3-11.

E68. The isolated antibody, or antigen-binding fragment thereof, of any of the preceding embodiments, comprising a murine IgG1 Fc region comprising a substitution at one or more positions selected from E233, E318, K320, and R322 (e.g., E233P, E318A, K320A, and R322A), e.g., wherein the murine IgG1 Fc region comprises one or more of the E233P, E318A, K320A, and R322A substitutions, as numbered according to the Eu numbering scheme (see e.g., U.S. Pat. No. 5,624,821).

E69. The isolated antibody, or antigen-binding fragment thereof, of any of the preceding embodiments, comprising a human IgG1 Fc region comprising a substitution at one or more positions selected from L234, L235, and G237 (e.g., L234A, L235A, and G237A), e.g., wherein the human IgG1 Fc region comprises one or more of the L234A, L235A, and G237A substitutions, as numbered according to the Eu numbering scheme.

E70. The isolated antibody, or antigen-binding fragment thereof, of any of the preceding embodiments, wherein the antibody further comprises a VH region comprising a variant of the germline VH amino acid sequence of IGHV3-07, IGHV1-46, IGHV3-23, IGHV3-30, IGHV1-69, or IGHV3-48, wherein the VH region comprises one or more substitutions at positions T28, F29, A49, R72, N74, A75, and/or L79 (e.g., one or more substitutions selected from T28N, F29I, A49G, R72A, N74T, A75S and L79A), as numbered according to the amino acid sequence of SEQ ID NO: 127, optionally wherein the VH region comprises the substitutions:

(i) T28N and F29I;
(ii) T28N, F29I, and R72A;
(iii) T28N, F29I, R72A, A49G, and L79A;
(iv) T28N, F29I, R72A, N74T, and A75S; or
(v) T28N, F29I, R72A, A49G, L79A, N74T, and A75S, wherein (i)-(v) are as numbered according to the amino acid sequence of SEQ ID NO: 127, optionally wherein:
the VH region comprises the substitutions T28N, F29I, R72A, A49G, L79A, N74T, and A75S, numbered according to the amino acid sequence of SEQ ID NO: 127.

E71. The isolated antibody, or antigen-binding fragment thereof, of any of the preceding embodiments, wherein the antibody further comprises a VH region comprising one or more (e.g., 2, 3, 4, 5, 6, or all) of the following:
(a) an Asn at position 28,
(b) an Ile at position 29,
(c) a Gly at position 49,
(d) an Ala at position 72,
(e) a Thr at position 74,
(f) a Ser at position 75, and
(g) an Ala at position 79, numbered according to the amino acid sequence of SEQ ID NO: 127, optionally wherein the VH region comprises:
(i) an Asn at position 28 and an Ile at position 29;
(ii) an Asn at position 28, an Ile at position 29, and an Ala at position 72;
(iii) an Asn at position 28, an Ile at position 29, an Ala at position 72, a Gly at position 49, and an Ala at position 79;
(iv) an Asn at position 28, an Ile at position 29, an Ala at position 72, a Thr at position 74, and a Ser at position 75; or
(v) an Asn at position 28, an Ile at position 29, an Ala at position 721, a Gly at position 49, an Ala at position 79, a Thr at position 74, and a Ser at position 75, numbered according to the amino acid sequence of SEQ ID NO: 127, optionally wherein:
the VH region comprises an Asn at position 28, an Ile at position 29, an Ala at position 72, a Gly at position 49, an Ala at position 79, a Thr at position 743, and a Ser at position 75, numbered according to the amino acid sequence of SEQ ID NO: 127.

E72. The isolated antibody, or antigen-binding fragment thereof, of any of the preceding embodiments, wherein the antibody further comprises a VL region comprising a variant of the germline VL amino acid sequence of IGKV1-39, IGKV2-28, IGKV2-30, IGKV4-1, or IGKV3-11, wherein the VH region comprises one or more substitutions at positions Y36 and/or L46 (e.g., Y36F and/or L46R), as numbered according to the amino acid sequence of SEQ ID NO: 128, optionally wherein the VL region comprises the substitutions:
(i) L46R; or
(ii) L46R and Y36F,
wherein (i)-(v) are as numbered according to the amino acid sequence of SEQ ID NO: 128, optionally wherein the VL region comprises the substitution L46R, numbered according to the amino acid sequence of SEQ ID NO: 128.

E73. The isolated antibody, or antigen-binding fragment thereof, of any of the preceding embodiments, wherein the antibody further comprises a VL region comprising one or both of the following:
(a) a Tyr at position 36, and
(b) a Leu at position 46, numbered according to the amino acid sequence of SEQ ID NO:128, optionally wherein the VL region comprises:

(i) a Leu at position 46; or
(ii) a Leu at position 46 and a Tyr at position 36, numbered according to the amino acid sequence of SEQ ID NO:128, optionally wherein:
the VL region comprises a Leu at position 46, numbered according to the amino acid sequence of SEQ ID NO:128.

E74. An isolated antibody, or antigen-binding fragment thereof, that specifically binds to human αvβ8 integrin, comprising one or more CDRs of any of the preceding embodiments, wherein the one or more CDRs comprise at least one amino acid alteration, but not more than two, three or four alterations (e.g., a substitution, deletion, or insertion, e.g., conservative substitution); wherein the CDR-H1, CDR-H2, CDR-H3, CDR-L1, CDR-L2, and CDR-L3 do not comprise the amino acid sequences of SEQ ID NOs: 22, 23, 24, 25, 26, and 27, respectively, SEQ ID NOs: 22, 23, 24, 71, 72, and 73, respectively, SEQ ID NOs: 28, 29, 30, 31, 32, and 33, respectively, or SEQ ID NOs: 28, 29, 30, 74, 75, and 76, respectively.

E75. The isolated antibody, or antigen-binding fragment thereof, of any of the preceding embodiments, further comprising a VH region comprising an amino acid sequence set forth in Table 1.

E76. The isolated antibody, or antigen-binding fragment thereof, of any of the preceding embodiments, further comprising a VL region comprising an amino acid sequence set forth in Table 1.

E77. The isolated antibody, or antigen-binding fragment thereof, of any of the preceding embodiments, comprising a VH region comprising an amino acid sequence having at least 80%, 85%, 90%, 91%, 92%, 93%, 94%, 95%, 96%, 97%, 98%, 99%, or 100% sequence identity to any one of SEQ ID NOs: 6, 34-46, 88-91, or 93.

E78. The isolated antibody, or antigen-binding fragment thereof, of embodiment E77, comprising a VH region comprising the amino acid sequence of SEQ ID NO: 6.

E79. The isolated antibody, or antigen-binding fragment thereof, of any of the preceding embodiments, comprising a VL region comprising an amino acid sequence having at least 80%, 85%, 90%, 91%, 92%, 93%, 94%, 95%, 96%, 97%, 98%, 99%, or 100% sequence identity to any one of SEQ ID NOs: 7, 47-69, or 92.

E80. The isolated antibody, or antigen-binding fragment thereof, of embodiment E79, comprising a VL region having at least 80%, 85%, 90%, 91%, 92%, 93%, 94%, 95%, 96%, 97%, 98%, 99%, or 100% sequence identity (e.g., 100%) to the amino acid sequence of SEQ ID NO: 7.

E81. An isolated antibody, or antigen-binding fragment thereof, that specifically binds to human αvβ8 integrin, comprising a VH region comprising an amino acid sequence having at least 80%, 85%, 90%, 91%, 92%, 93%, 94%, 95%, 96%, 97%, 98%, 99%, or 100% sequence identity to any one of SEQ ID NOs: 6, 34-46, 88-91, or 93.

E82. The isolated antibody, or antigen-binding fragment thereof, of embodiment E81, comprising a VH region having at least 80%, 85%, 90%, 91%, 92%, 93%, 94%, 95%, 96%, 97%, 98%, 99%, or 100% sequence identity (e.g., 100%) to the amino acid sequence of SEQ ID NO: 6.

E83. The isolated antibody, or antigen-binding fragment thereof, of embodiment E81 or E82, further comprising a VL region having at least 80%, 85%, 90%, 91%, 92%, 93%, 94%, 95%, 96%, 97%, 98%, 99%, or 100% sequence identity (e.g., 100%) to the amino acid sequence of SEQ ID NO: 7.

E84. The isolated antibody, or antigen-binding fragment thereof, of embodiment E81, comprising a VH region comprising the amino acid sequence of SEQ ID NO: 6.

E85. The isolated antibody, or antigen-binding fragment thereof, of embodiment E84, comprising a VL region comprising the amino acid sequence of SEQ ID NO: 7.

E86. An isolated antibody, or antigen-binding fragment thereof, that specifically binds to human αvβ8 integrin, comprising a VL region comprising an amino acid sequence having at least 80%, 85%, 90%, 91%, 92%, 93%, 94%, 95%, 96%, 97%, 98%, 99%, or 100% sequence identity to any one of SEQ ID NOs: 7, 47-69, or 92.

E87. The isolated antibody, or antigen-binding fragment thereof, of embodiment E86, comprising a VL region having at least 80%, 85%, 90%, 91%, 92%, 93%, 94%, 95%, 96%, 97%, 98%, 99%, or 100% sequence identity (e.g., 100%) to the amino acid sequence of SEQ ID NO: 7.

E88. The isolated antibody, or antigen-binding fragment thereof, of embodiment E86 or E87, further comprising a VH region having at least 80%, 85%, 90%, 91%, 92%, 93%, 94%, 95%, 96%, 97%, 98%, 99%, or 100% sequence identity (e.g., 100%) to the amino acid sequence of SEQ ID NO: 6.

E89. The isolated antibody, or antigen-binding fragment thereof, of embodiment E86, comprising a VL region comprising an amino acid sequence selected from SEQ ID NOs: 7, 47-69, or 92.

E90. An isolated antibody, or antigen-binding fragment thereof, that specifically binds to human αvβ8 integrin, comprising a VH region comprising the amino acid sequence of SEQ ID NO: 39, wherein one or more amino acid residues of said SEQ ID NO: 39 comprise one or more amino acid substitutions selected from K30A, N55Q, N57Q, D61E, P62A, K63A, and F64V, numbered according to SEQ ID NO: 39.

E91. An isolated antibody, or antigen-binding fragment thereof, that specifically binds to human αvβ8 integrin, comprising a VH region comprising at least one of the following:
(a) an Ala at position 30
(b) a Gln at position 55,
(c) a Gln at position 57,
(d) a Glu at position 61,
(e) an Ala at position 62,
(f) an Ala at position 63, and
(g) a Val at position 64, numbered according to SEQ ID NO: 39.

E92. The isolated antibody, or antigen-binding fragment thereof, of embodiment E90, wherein said SEQ ID NO: 39 comprises:
(i) N55Q and D61E; or
(ii) N55Q, D61E, and F64V, numbered according to SEQ ID NO: 39, optionally wherein said SEQ ID NO: 39 comprises N55Q and D61E substitutions, numbered according to SEQ ID NO: 39.

E93. The isolated antibody, or antigen-binding fragment thereof, of embodiment E91, wherein the VH region comprises:
(i) a Gln at position 55 and a Glu at position 61; or
(ii) a Gln at position 55, a Glu at position 61, and a Val at position 64, numbered according to SEQ ID NO: 39, optionally wherein the VH region comprises a Gln at position 55 and a Glu at position 61, numbered according to SEQ ID NO: 39.

E94. The isolated antibody, or antigen-binding fragment thereof, of embodiment E90 or E92, further comprising a VL region comprising the amino acid sequence of SEQ ID NO:

47, wherein one or more amino acid residues of said SEQ ID NO: 47 comprise one or more amino acid substitutions selected from L30S, Y55A, M56A, N58S, A60Q, M94Q, L97Y, F101L, F101W, and Q105G, or any combination thereof, numbered according to SEQ ID NO: 47, optionally wherein one or more amino acid residues of said SEQ ID NO: 47 comprise one or more amino acid substitutions selected from L30S, M56A, N58S, M94Q, L97Y, and Q105G.

E95. The isolated antibody, or antigen-binding fragment thereof, of embodiment E91 or E93, further comprising a VL region comprising at least one of the following:
(a) a Ser at position 30,
(b) an Ala at position 55,
(c) an Ala at position 56,
(d) a Ser at position 58,
(e) a Gln at position 60,
(f) a Gln at position 94,
(g) a Tyr at position 97,
(h) a Leu at position 101,
(i) a Trp at position 101, and
(j) a Gly at position 105, numbered according to SEQ ID NO: 47, optionally wherein the VL region comprises at least one of the following:
(a) a Ser at position 30,
(b) an Ala at position 56,
(c) a Ser at position 58,
(d) a Gln at position 94,
(e) a Tyr at position 97, and
(f) a Gly at position 105.

E96. The isolated antibody, or antigen-binding fragment thereof, of embodiment E94, wherein said SEQ ID NO: 47 comprises a L30S, M56A, N58S, M94Q, L97Y, and/or Q105G substitution, numbered according to SEQ ID NO: 47.

E97. The isolated antibody, or antigen-binding fragment thereof, of embodiment E95, wherein the VL region comprises a Ser at position 30, an Ala at position 56, a Ser at position 58, a Gln at position 94, a Tyr at position 97, and/or a Gly at position 105, numbered according to SEQ ID NO: 47.

E98. The isolated antibody, or antigen-binding fragment thereof, of embodiment E94, wherein said SEQ ID NO: 47 comprises a L30S, N58S, M94Q, and/or Q105G substitution, numbered according to SEQ ID NO: 47, optionally wherein said SEQ ID NO: 47 comprises all of L30S, N58S, M94Q, and Q105G substitutions.

E99. The isolated antibody, or antigen-binding fragment thereof, of embodiment E95, wherein the VL region comprises a Ser at position 30, a Ser at position 58, a Gln at position 94, and/or a Gly at position 105, numbered according to SEQ ID NO: 47, optionally wherein the VL region comprises all of: a Ser at position 30, a Ser at position 58, a Gln at position 94, and a Gly at position 105.

E100. The isolated antibody, or antigen-binding fragment thereof, of embodiment E94, wherein said SEQ ID NO: 39 comprises N55Q and D61E substitutions, numbered according to SEQ ID NO: 39, and said SEQ ID NO: 47 comprises L30S, N58S, M94Q, and Q105G substitutions, numbered according to SEQ ID NO: 47.

E101. The isolated antibody, or antigen-binding fragment thereof, of embodiment E95, wherein the VH region comprises a Gln at position 55 and a Glu at position 61, numbered according to SEQ ID NO: 39, and the VL region comprises a Ser at position 30, a Ser at position 58, a Gln at position 94, and a Gly at position 105, numbered according to SEQ ID NO: 47.

E102. An isolated antibody, or antigen-binding fragment thereof, that specifically binds to human $\alpha v \beta 8$ integrin, comprising a VL region comprising the amino acid sequence of SEQ ID NO: 47, wherein one or more amino acid residues of said SEQ ID NO: 47 comprise one or more amino acid substitutions selected from L30S, Y55A, M56A, N58S, A60Q, M94Q, L97Y, F101L, F101W, and Q105G, or any combination thereof (e.g., all of L30S, M56A, N58S, M94Q, L97Y, and Q105G), numbered according to SEQ ID NO: 47, optionally wherein one or more amino acid residues of said SEQ ID NO: 47 comprise one or more amino acid substitutions selected from L30S, M56A, N58S, M94Q, L97Y, and Q105G.

103. The isolated antibody, or antigen-binding fragment thereof, of embodiment E102, wherein said SEQ ID NO: 47 comprises a L30S, N58S, M94Q, and/or Q105G substitution, numbered according to SEQ ID NO: 47.

E104. The isolated antibody, or antigen-binding fragment thereof, of embodiment E102, further comprising a VH region comprising the amino acid sequence of SEQ ID NO: 39, wherein the sequence of SEQ ID NO: 39 comprises one or more amino acid substitutions selected from K30A, N55Q, N57Q, D61E, P62A, K63A, and F64V, or any combination thereof, numbered according to SEQ ID NO: 39.

E105. The isolated antibody, or antigen-binding fragment thereof, of embodiment E104, wherein said SEQ ID NO: 39 comprises N55Q and D61E substitutions.

E106. The isolated antibody, or antigen-binding fragment thereof, of any of the preceding embodiments, comprising a heavy chain comprising an amino acid sequence having at least 80%, 85%, 90%, 91%, 92%, 93%, 94%, 95%, 96%, 97%, 98%, 99%, or 100% sequence identity to SEQ ID NO: 2 or 3.

E107. The isolated antibody, or antigen-binding fragment thereof, of any of the preceding embodiments, further comprising a light chain comprising an amino acid sequence having at least 80%, 85%, 90%, 91%, 92%, 93%, 94%, 95%, 96%, 97%, 98%, 99%, or 100% sequence identity to SEQ ID NO: 5.

E108. An isolated antibody, or antigen-binding fragment thereof, that specifically binds to human $\alpha v \beta 8$ integrin, comprising a heavy chain variable region comprising the amino acid sequence of SEQ ID NO: 6 and a light chain variable region comprising the amino acid sequence of SEQ ID NO: 7.

E109. An isolated antibody, or antigen-binding fragment thereof, that specifically binds to human $\alpha v \beta 8$ integrin, comprising a heavy chain comprising the amino acid sequence of SEQ ID NO: 2 or 3, and a light chain comprising the amino acid sequence of SEQ ID NO: 5.

E110. An isolated antibody, or antigen-binding fragment thereof, that specifically binds to human $\alpha v \beta 8$ integrin, comprising
(a) a light chain comprising the amino acid sequence of SEQ ID NO: 5 and
(b) a heavy chain comprising the amino acid sequence of SEQ ID NO: 3, with or without a C-terminal lysine residue.

E111. An isolated antibody, or antigen-binding fragment thereof, that specifically binds to human $\alpha v \beta 8$ integrin, comprising a heavy chain comprising an amino acid sequence encoded by the insert of the plasmid deposited with the ATCC and having the Accession Number PTA-124917, a light chain comprising an amino acid sequence encoded by the insert of the plasmid deposited with the ATCC and having the Accession Number PTA-124918, or both.

E112. An isolated antibody, or antigen-binding fragment thereof, that specifically binds to human αvβ8 integrin, comprising a heavy chain comprising an amino acid sequence having at least 80%, 85%, 90%, 91%, 92%, 93%, 94%, 95%, 96%, 97%, 98%, 99%, or 100% (e.g., 100%) sequence identity to SEQ ID NO: 2 or 3, optionally wherein the heavy chain comprises the amino acid sequence of SEQ ID NO: 2.

E113. An isolated antibody, or antigen-binding fragment thereof, that specifically binds to human αvβ8 integrin, comprising a light chain comprising an amino acid sequence having at least 80%, 85%, 90%, 91%, 92%, 93%, 94%, 95%, 96%, 97%, 98%, 99%, or 100% (e.g., 100%) sequence identity to SEQ ID NO: 5, optionally wherein the light chain comprises the amino acid sequence of SEQ ID NO: 5, optionally wherein the isolated antibody, or antigen-binding fragment thereof, further comprises a heavy chain comprising the amino acid sequence of SEQ ID NO: 2.

E114. An isolated antibody, or antigen-binding fragment thereof, that specifically binds to human αvβ8 integrin, comprising a heavy chain comprising an amino acid sequence comprising SEQ ID NO: 2, and a light chain comprising an amino acid sequence comprising SEQ ID NO: 5.

E115. An isolated antibody, or antigen-binding fragment thereof, that specifically binds to human αvβ8 integrin, comprising a heavy chain comprising an amino acid sequence comprising SEQ ID NO: 3, and a light chain comprising an amino acid sequence comprising SEQ ID NO: 5.

E116. An isolated antibody, or antigen-binding fragment thereof, that specifically binds to human αvβ8 integrin, comprising:
  a CDR-H1 comprising the amino acid sequence of SEQ ID NO: 22,
  a CDR-H2 comprising the amino acid sequence of SEQ ID NO: 23,
  a CDR-H3 comprising the amino acid sequence of SEQ ID NO: 24,
  a CDR-L1 comprising the amino acid sequence of SEQ ID NO: 25,
  a CDR-L2 comprising the amino acid sequence of SEQ ID NO: 26, and
  a CDR-L3 comprising the amino acid sequence of SEQ ID NO: 27; and
  wherein the antibody further comprises a VH framework region (e.g., one, two, three or all four of FR1, FR2, FR3, or FR4) comprising an amino acid sequence having at least 80%, 85%, 87% 90%, 92%, 93%, 95%, 97%, 98%, or preferably 100% sequence identity to a VH framework region of a VH region comprising the amino acid sequence of any one of SEQ ID NOs: 6, 34-46, 88-91, or 93, or an amino acid sequence having at least one, but less than twenty alterations, e.g., an amino acid substitution or deletion, of the amino acid sequence of the entire VH framework region (including FR1, FR2, FR3 and FR4).

E117. An isolated antibody, or antigen-binding fragment thereof, that specifically binds to human αvβ8 integrin, comprising:
  a CDR-H1 comprising the amino acid sequence of SEQ ID NO: 22,
  a CDR-H2 comprising the amino acid sequence of SEQ ID NO: 23,
  a CDR-H3 comprising the amino acid sequence of SEQ ID NO: 24,
  a CDR-L1 comprising the amino acid sequence of SEQ ID NO: 25,
  a CDR-L2 comprising the amino acid sequence of SEQ ID NO: 26, and
  a CDR-L3 comprising the amino acid sequence of SEQ ID NO: 27; and
  wherein the antibody further comprises a VL framework region (e.g., FR1, FR2, FR3, or FR4) comprising an amino acid sequence having at least 80%, 85%, 87% 90%, 92%, 93%, 95%, 97%, 98%, or preferably 100% sequence identity to a VL framework region of a VL region comprising the amino acid sequence of any one of SEQ ID NOs: 7, 47-69, or 92, or an amino acid sequence having at least one, two, three, four, five, six, seven, ten, fifteen, but less than twenty alterations, e.g., an amino acid substitution or deletion, of the amino acid sequence of the entire VL framework region (including FR1, FR2, FR3, and FR4).

E118. An isolated antibody, or antigen-binding fragment thereof, that specifically binds to human αvβ8 integrin, comprising:
  a CDR-H1 comprising the amino acid sequence of SEQ ID NO: 22,
  a CDR-H2 comprising the amino acid sequence of SEQ ID NO: 23,
  a CDR-H3 comprising the amino acid sequence of SEQ ID NO: 24,
  a CDR-L1 comprising the amino acid sequence of SEQ ID NO: 25,
  a CDR-L2 comprising the amino acid sequence of SEQ ID NO: 26, and
  a CDR-L3 comprising the amino acid sequence of SEQ ID NO: 27; and wherein the antibody comprises a VH framework region (e.g., FR1, FR2, FR3, or FR4) comprising an amino acid sequence having at least 80%, 85%, 87% 90%, 92%, 93%, 95%, 97%, 98%, or 100% sequence identity to a VH framework region within the germline amino acid sequence of IGHV3-07, IGHV1-46, IGHV3-23, IGHV3-30, IGHV1-69, or IGHV3-48, or an amino acid sequence having at least one, two, three, four, five, six, seven, ten, fifteen, but less than twenty alterations, e.g., an amino acid substitution or deletion, of the amino acid sequence of the entire VH framework region (including FR1, FR2, FR3, and FR4).

E119. An isolated antibody, or antigen-binding fragment thereof, that specifically binds to human αvβ8 integrin, comprising:
  a CDR-H1 comprising the amino acid sequence of SEQ ID NO: 22,
  a CDR-H2 comprising the amino acid sequence of SEQ ID NO: 23,
  a CDR-H3 comprising the amino acid sequence of SEQ ID NO: 24,
  a CDR-L1 comprising the amino acid sequence of SEQ ID NO: 25,
  a CDR-L2 comprising the amino acid sequence of SEQ ID NO: 26, and
  a CDR-L3 comprising the amino acid sequence of SEQ ID NO: 27; and wherein the antibody comprises a VH region comprising a variant of the germline VH amino acid sequence of IGHV3-07, IGHV1-46, IGHV3-23, IGHV3-30, IGHV1-69, or IGHV3-48, wherein the VH region comprises one or more substitutions at positions T28, F29, A49, R71, N73, A74, and/or L78 (e.g., one or more substitutions selected from T28N, F29I, A49G, R72A, N74T, A75S and L79A), as numbered according to the amino acid sequence of SEQ ID NO: 127, optionally wherein the VH region comprises the substitutions:
(i) T28N and F29I;
(ii) T28N, F29I, and R72A;
(iii) T28N, F29I, R72A, A49G, and L79A;
(iv) T28N, F29I, R72A, N74T, and A75S; or
(v) T28N, F29I, R72A, A49G, L79A, N74T, and A75S,
wherein (i)-(v) are as numbered according to the amino acid sequence of SEQ ID NO: 127, optionally wherein:
the VH region comprises the substitutions T28N, F29L, R72A, A49G, L79A, N74T, and A75S, numbered according to the amino acid sequence of SEQ ID NO: 127.

E120. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 25,
a CDR-L2 comprising the amino acid sequence of SEQ ID NO: 26, and
a CDR-L3 comprising the amino acid sequence of SEQ ID NO: 27; and wherein the antibody comprises a VH region comprising one or more (e.g., 2, 3, 4, 5, 6, or all) of the following:
(a) an Asn at position 28,
(b) an Ile at position 29,
(c) a Gly at position 49,
(d) an Ala at position 72,
(e) a Thr at position 74,
(f) a Ser at position 75, and
(g) an Ala at position 79, numbered according to the amino acid sequence of SEQ ID NO: 127, optionally wherein the VH region comprises:
(i) an Asn at position 28 and an Ile at position 29;
(ii) an Asn at position 28, an Ile at position 29, and an Ala at position 72;
(iii) an Asn at position 28, an Ile at position 29, an Ala at position 72, a Gly at position 49, and an Ala at position 79;
(iv) an Asn at position 28, an Ile at position 29, an Ala at position 72, a Thr at position 74, and a Ser at position 75; or
(v) an Asn at position 28, an Ile at position 29, an Ala at position 72, a Gly at position 49, an Ala at position 79, a Thr at position 74, and a Ser at position 75, numbered according to the amino acid sequence of SEQ ID NO: 127, optionally wherein:
the VH region comprises an Asn at position 28, an Ile at position 29, an Ala at position 72, a Gly at position 49, an Ala at position 79, a Thr at position 74, and a Ser at position 75, numbered according to amino acid sequence of SEQ ID NO: 127.

E121. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 25,
a CDR-L2 comprising the amino acid sequence of SEQ ID NO: 26, and
a CDR-L3 comprising the amino acid sequence of SEQ ID NO: 27; and wherein the antibody comprises a VL framework region (e.g., FR1, FR2, FR3, or FR4) comprising an amino acid sequence having at least 80%, 85%, 87% 90%, 92%, 93%, 95%, 97%, 98%, or 100% sequence identity to the germline amino acid sequence of IGKV1-39, IGKV2-28, IGKV2-30, IGKV4-1, or IGKV3-11, or an amino acid sequence having at least one, two, three, four, five, six, seven, ten, fifteen, but less than twenty alternations, e.g., an amino acid substitution or deletion, of the amino acid sequence of the entire VL framework region (including FR1, FR2, FR3, and FR4).

E122. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 25,
a CDR-L2 comprising the amino acid sequence of SEQ ID NO: 26, and
a CDR-L3 comprising the amino acid sequence of SEQ ID NO: 27; and wherein the antibody comprises a VL region comprising a variant of the germline VL amino acid sequence of IGKV1-39, IGKV2-28, IGKV2-30, IGKV4-1, or IGKV3-11, wherein the VL region comprises one or more substitutions at positions Y36 and/or L46 (e.g., Y36F and/or L46R), as numbered according to the amino acid sequence of SEQ ID NO: 128, optionally wherein the VL region comprises the substitutions:
(i) L46R; or
(ii) L46R and Y36F,
wherein (i) and (ii) are numbered according to the amino acid sequence of SEQ ID NO: 128, optionally wherein the VL region comprises the substitution L46R, numbered according to the amino acid sequence of SEQ ID NO: 128.

E123. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 25,
a CDR-L2 comprising the amino acid sequence of SEQ ID NO: 26, and
a CDR-L3 comprising the amino acid sequence of SEQ ID NO: 27; and wherein the antibody comprises a VL region comprising one or both of the following:

(a) a Tyr at position 36, and
(b) a Leu at position 46, numbered according to the amino acid sequence of SEQ ID NO: 128, optionally wherein the VL region comprises:
(i) a Leu at position 46; or
(ii) a Leu at position 46 and a Tyr at position 36, numbered according to the amino acid sequence of SEQ ID NO: 128, optionally wherein:
the VL region comprises a Leu at position 46, numbered according to the amino acid sequence of SEQ ID NO: 128.

E124. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 25,
a CDR-L2 comprising the amino acid sequence of SEQ ID NO: 26, and
a CDR-L3 comprising the amino acid sequence of SEQ ID NO: 27; and further comprising a murine IgG1 Fc region comprising one or more substitutions selected from positions E233, E318, K320, and R322 (e.g., E233P, E318A, K320A, and R322A) as numbered according to the Eu numbering scheme, e.g., relative to murine IgG1 Fc set forth in Table 1.

E125. The isolated antibody, or antigen-binding fragment thereof, of embodiment E124, wherein the murine IgG1 Fc region comprises the E233P, E318A, K320A, and R322A substitutions as numbered according to the Eu numbering scheme, e.g., relative to murine IgG1 Fc set forth in Table 1.

E126. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 25,
a CDR-L2 comprising the amino acid sequence of SEQ ID NO: 26, and
a CDR-L3 comprising the amino acid sequence of SEQ ID NO: 27; and further comprising a human IgG1 Fc region comprising one or more substitutions selected from positions L234, L235, and G237 (e.g., L234A, L235A, and G237A) as numbered according to the Eu numbering scheme, e.g., relative to human IgG1 Fc set forth in Table 1.

E127. The isolated antibody, or antigen-binding fragment thereof, of embodiment E126, wherein the human IgG1 Fc region comprises the L234A, L235A, and G237A substitutions, as numbered according to the Eu numbering scheme, e.g., relative to human IgG1 Fc set forth in Table 1.

E128. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 71,
a CDR-L2 comprising the amino acid sequence of SEQ ID NO: 72, and
a CDR-L3 comprising the amino acid sequence of SEQ ID NO: 73; and
wherein the antibody further comprises a VH framework region (e.g., one, two, three, or four or FR1, FR2, FR3, or FR4) comprising an amino acid sequence having at least 80%, 85%, 87% 90%, 92%, 93%, 95%, 97%, 98%, or preferably 100% sequence identity to a VH framework region of a VH region comprising the amino acid sequence of any one of SEQ ID NOs: 6, 34-46, 88-91, or 93.

E129. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 71,
a CDR-L2 comprising the amino acid sequence of SEQ ID NO: 72, and
a CDR-L3 comprising the amino acid sequence of SEQ ID NO: 73; and
wherein the antibody further comprises a VL framework region (e.g., one, two, three, or four or FR1, FR2, FR3, or FR4) comprising an amino acid sequence having at least 80%, 85%, 87% 90%, 92%, 93%, 95%, 97%, 98%, or preferably 100% sequence identity to a VL framework region of a VL region comprising the amino acid sequence of any one of SEQ ID NOs: 7, 47-69, or 92.

E130. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 71,
a CDR-L2 comprising the amino acid sequence of SEQ ID NO: 72, and
a CDR-L3 comprising the amino acid sequence of SEQ ID NO: 73; and wherein the antibody further comprises a VH framework region (e.g., one, two, three, or four or FR1, FR2, FR3, or FR4) comprising an amino acid sequence having at least 80%, 85%, 87% 90%, 92%, 93%, 95%, 97%, 98%, or 100% sequence identity to a VH framework region within the germline amino acid sequence of IGHV3-07, IGHV1-46, IGHV3-23, IGHV3-30, IGHV1-69, or IGHV3-48.

E131. An isolated antibody, or antigen-binding fragment thereof, that specifically binds to human αvβ8 integrin, comprising:

a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 71,
a CDR-L2 comprising the amino acid sequence of SEQ ID NO: 72, and
a CDR-L3 comprising the amino acid sequence of SEQ ID NO: 73; and wherein the antibody further comprises a VL framework region (e.g., one, two, three, or four or FR1, FR2, FR3, or FR4) comprising an amino acid sequence having at least 80%, 85%, 87% 90%, 92%, 93%, 95%, 97%, 98%, or 100% sequence identity to the germline amino acid sequence of IGKV1-39, IGKV2-28, IGKV2-30, IGKV4-1, or IGKV3-11.

E132. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 71,
a CDR-L2 comprising the amino acid sequence of SEQ ID NO: 72, and
a CDR-L3 comprising the amino acid sequence of SEQ ID NO: 73; and further comprising a murine IgG1 Fc region comprising one or more substitutions selected from positions E233, E318, K320, and R322 (e.g., E233P, E318A, K320A, and R322A) as numbered according to the Eu numbering scheme, e.g., relative to murine IgG1 Fc set forth in Table 1.

E133. The isolated antibody, or antigen-binding fragment thereof, of embodiment E132, wherein the murine IgG1 Fc region comprises E233P, E318A, K320A, and R322A substitutions as numbered according to the Eu numbering scheme, e.g., relative to murine IgG1 Fc set forth in Table 1.

E134. An isolated antibody, or antigen-binding fragment thereof, that specifically binds to human αvβ8 integrin, comprising:
a CDR-H1 comprising the amino acid sequence of SEQ ID NO: 22,
a CDR-H2 comprising the amino acid sequence of SEQ ID NO: 23,
a CDR-H3 comprising the amino acid sequence of SEQ ID NO: 24,
a CDR-L1 comprising the amino acid sequence of SEQ ID NO: 71,
a CDR-L2 comprising the amino acid sequence of SEQ ID NO: 72, and
a CDR-L3 comprising the amino acid sequence of SEQ ID NO: 73; and further comprising a human IgG1 Fc region comprising L234A, L235A, and G237A substitutions as numbered according to the Eu numbering scheme, e.g., relative to human IgG1 Fc set forth in Table 1.

E135. An isolated antibody, or antigen-binding fragment thereof, that specifically binds to human αvβ8 integrin, comprising:
a CDR-H1 comprising the amino acid sequence of SEQ ID NO: 28, a CDR-H2 comprising the amino acid sequence of SEQ ID NO: 29,
a CDR-H3 comprising the amino acid sequence of SEQ ID NO: 30,
a CDR-L1 comprising the amino acid sequence of SEQ ID NO: 31,
a CDR-L2 comprising the amino acid sequence of SEQ ID NO: 32, and
a CDR-L3 comprising the amino acid sequence of SEQ ID NO: 33; and
wherein the antibody further comprises a VH framework region (e.g., one, two, three, or four of FR1, FR2, FR3, or FR4) comprising an amino acid sequence having at least 80%, 85%, 87% 90%, 92%, 93%, 95%, 97%, 98%, or preferably 100% sequence identity to a VH framework region of a VH region comprising the amino acid sequence of any one of SEQ ID NOs: 6, 34-46, 88-91, or 93.

E136. An isolated antibody, or antigen-binding fragment thereof, that specifically binds to human αvβ8 integrin, comprising:
a CDR-H1 comprising the amino acid sequence of SEQ ID NO: 28,
a CDR-H2 comprising the amino acid sequence of SEQ ID NO: 29,
a CDR-H3 comprising the amino acid sequence of SEQ ID NO: 30,
a CDR-L1 comprising the amino acid sequence of SEQ ID NO: 74,
a CDR-L2 comprising the amino acid sequence of SEQ ID NO: 75, and
a CDR-L3 comprising the amino acid sequence of SEQ ID NO: 76; and
wherein the antibody further comprises a VH framework region (e.g., one, two, three, or four of FR1, FR2, FR3, or FR4) comprising an amino acid sequence having at least 80%, 85%, 87% 90%, 92%, 93%, 95%, 97%, 98%, or preferably 100% sequence identity to a VH framework region of a VH region comprising the amino acid sequence of any one of SEQ ID NOs: 6, 34-46, 88-91, or 93.

E137. An isolated antibody, or antigen-binding fragment thereof, that specifically binds to human αvβ8 integrin, comprising:
a CDR-H1 comprising the amino acid sequence of SEQ ID NO: 28,
a CDR-H2 comprising the amino acid sequence of SEQ ID NO: 29,
a CDR-H3 comprising the amino acid sequence of SEQ ID NO: 30,
a CDR-L1 comprising the amino acid sequence of SEQ ID NO: 31,
a CDR-L2 comprising the amino acid sequence of SEQ ID NO: 32, and
a CDR-L3 comprising the amino acid sequence of SEQ ID NO: 33; and
wherein the antibody further comprises a VL framework region (e.g., one, two, three, or four of FR1, FR2, FR3, or FR4) comprising an amino acid sequence having at least 80%, 85%, 87% 90%, 92%, 93%, 95%, 97%, 98%, or preferably 100% sequence identity to a VL framework region of a VL region comprising the amino acid sequence of any one of SEQ ID NOs: 7, 47-69, or 92.

E138. An isolated antibody, or antigen-binding fragment thereof, that specifically binds to human αvβ8 integrin, comprising:

a CDR-H1 comprising the amino acid sequence of SEQ ID NO: 28,
a CDR-H2 comprising the amino acid sequence of SEQ ID NO: 29,
a CDR-H3 comprising the amino acid sequence of SEQ ID NO: 30,
a CDR-L1 comprising the amino acid sequence of SEQ ID NO: 31,
a CDR-L2 comprising the amino acid sequence of SEQ ID NO: 32, and
a CDR-L3 comprising the amino acid sequence of SEQ ID NO: 33; and wherein the antibody further comprises a VH framework region (e.g., one, two, three, or four of FR1, FR2, FR3, or FR4) comprising an amino acid sequence having at least 80%, 85%, 87% 90%, 92%, 93%, 95%, 97%, 98%, or 100% sequence identity to the germline amino acid sequence of IGHV3-07, IGHV1-46, IGHV3-23, IGHV3-30, IGHV1-69, or IGHV3-48.

E139. An isolated antibody, or antigen-binding fragment thereof, that specifically binds to human αvβ8 integrin, comprising:
a CDR-H1 comprising the amino acid sequence of SEQ ID NO: 28,
a CDR-H2 comprising the amino acid sequence of SEQ ID NO: 29,
a CDR-H3 comprising the amino acid sequence of SEQ ID NO: 30,
a CDR-L1 comprising the amino acid sequence of SEQ ID NO: 31,
a CDR-L2 comprising the amino acid sequence of SEQ ID NO: 32, and
a CDR-L3 comprising the amino acid sequence of SEQ ID NO: 33; and wherein the antibody further comprises a VL framework region (e.g., one, two, three, or four of FR1, FR2, FR3, or FR4) comprising an amino acid sequence having at least 80%, 85%, 87% 90%, 92%, 93%, 95%, 97%, 98%, or 100% sequence identity to the germline amino acid sequence of IGKV1-39, IGKV2-28, IGKV2-30, IGKV4-1, or IGKV3-11.

E140. An isolated antibody, or antigen-binding fragment thereof, comprising: a CDR-H1 comprising the amino acid sequence of SEQ ID NO: 28,
a CDR-H2 comprising the amino acid sequence of SEQ ID NO: 29,
a CDR-H3 comprising the amino acid sequence of SEQ ID NO: 30,
a CDR-L1 comprising the amino acid sequence of SEQ ID NO: 31,
a CDR-L2 comprising the amino acid sequence of SEQ ID NO: 32, and
a CDR-L3 comprising the amino acid sequence of SEQ ID NO: 33; and further comprising a human IgG1 Fc region comprising one or more substitutions selected from positions L234, L235, and G237 (e.g., L234A, L235A, and G237A) as numbered according to the Eu numbering scheme, e.g., relative to human IgG1 Fc set forth in Table 1.

E141. The isolated antibody, or antigen-binding fragment thereof, of embodiment E140, wherein the human IgG1 Fc region comprises L234A, L235A, and G237A substitutions as numbered according to the Eu numbering scheme, e.g., relative to human IgG1 Fc set forth in Table 1.

E142. The isolated antibody, or antigen-binding fragment thereof, of any of the preceding embodiments, wherein the antibody is a multispecific antibody (e.g., a bispecific antibody).

E143. The isolated antibody, or antigen-binding fragment thereof, of any of the preceding embodiments, wherein the antibody is a multivalent antibody (e.g., a bivalent antibody).

E144. The isolated antibody, or antigen-binding fragment thereof, of any of the preceding embodiments, wherein the antibody is a humanized antibody, a human antibody, a murine antibody, chimeric antibody, or a camelid antibody.

E145. An isolated antibody, or antigen-binding fragment thereof, that specifically binds to αvβ8 integrin, comprising a VH region and a VL region, wherein the VH region and VL region comprise the amino acid sequences of:
(i) SEQ ID NOs: 6 and 7, respectively, or an amino acid sequence having at least 80%, 85%, 87% 90%, 92%, 93%, 95%, 97%, 98%, or preferably 100% sequence identity thereto;
(ii) SEQ ID NOs: 34 and 65, respectively, or an amino acid sequence having at least 80%, 85%, 87% 90%, 92%, 93%, 95%, 97%, 98%, or preferably 100% sequence identity thereto;
(iii) SEQ ID NOs: 34 and 62, respectively, or an amino acid sequence having at least 80%, 85%, 87% 90%, 92%, 93%, 95%, 97%, 98%, or preferably 100% sequence identity thereto;
(iv) SEQ ID NOs: 34 and 66, respectively, or an amino acid sequence having at least 80%, 85%, 87% 90%, 92%, 93%, 95%, 97%, 98%, or preferably 100% sequence identity thereto;
(v) SEQ ID NOs: 34 and 63, respectively, or an amino acid sequence having at least 80%, 85%, 87% 90%, 92%, 93%, 95%, 97%, 98%, or preferably 100% sequence identity thereto;
(vi) SEQ ID NOs: 34 and 64, respectively, or an amino acid sequence having at least 80%, 85%, 87% 90%, 92%, 93%, 95%, 97%, 98%, or preferably 100% sequence identity thereto;
(vii) SEQ ID NOs: 37 and 65, respectively, or an amino acid sequence having at least 80%, 85%, 87% 90%, 92%, 93%, 95%, 97%, 98%, or preferably 100% sequence identity thereto;
(viii) SEQ ID NOs: 37 and 62, respectively, or an amino acid sequence having at least 80%, 85%, 87% 90%, 92%, 93%, 95%, 97%, 98%, or preferably 100% sequence identity thereto;
(ix) SEQ ID NOs: 37 and 66, respectively, or an amino acid sequence having at least 80%, 85%, 87% 90%, 92%, 93%, 95%, 97%, 98%, or preferably 100% sequence identity thereto;
(x) SEQ ID NOs: 37 and 63, respectively, or an amino acid sequence having at least 80%, 85%, 87% 90%, 92%, 93%, 95%, 97%, 98%, or preferably 100% sequence identity thereto;
(xi) SEQ ID NOs: 37 and 64, respectively, or an amino acid sequence having at least 80%, 85%, 87% 90%, 92%, 93%, 95%, 97%, 98%, or preferably 100% sequence identity thereto;
(xii) SEQ ID NOs: 36 and 65, respectively, or an amino acid sequence having at least 80%, 85%, 87% 90%, 92%, 93%, 95%, 97%, 98%, or preferably 100% sequence identity thereto;
(xiii) SEQ ID NOs: 36 and 62, respectively, or an amino acid sequence having at least 80%, 85%, 87% 90%, 92%, 93%, 95%, 97%, 98%, or preferably 100% sequence identity thereto;

(xiv) SEQ ID NOs: 36 and 66, respectively, or an amino acid sequence having at least 80%, 85%, 87% 90%, 92%, 93%, 95%, 97%, 98%, or preferably 100% sequence identity thereto;
(xv) SEQ ID NOs: 36 and 63, respectively, or an amino acid sequence having at least 80%, 85%, 87% 90%, 92%, 93%, 95%, 97%, 98%, or preferably 100% sequence identity thereto;
(xvi) SEQ ID NOs: 36 and 64, respectively, or an amino acid sequence having at least 80%, 85%, 87% 90%, 92%, 93%, 95%, 97%, 98%, or preferably 100% sequence identity thereto;
(xvii) SEQ ID NOs: 35 and 65, respectively, or an amino acid sequence having at least 80%, 85%, 87% 90%, 92%, 93%, 95%, 97%, 98%, or preferably 100% sequence identity thereto;
(xviii) SEQ ID NOs: 35 and 62, respectively, or an amino acid sequence having at least 80%, 85%, 87% 90%, 92%, 93%, 95%, 97%, 98%, or preferably 100% sequence identity thereto;
(xix) SEQ ID NOs: 35 and 66, respectively, or an amino acid sequence having at least 80%, 85%, 87% 90%, 92%, 93%, 95%, 97%, 98%, or preferably 100% sequence identity thereto;
(xx) SEQ ID NOs: 35 and 63, respectively, or an amino acid sequence having at least 80%, 85%, 87% 90%, 92%, 93%, 95%, 97%, 98%, or preferably 100% sequence identity thereto;
(xxi) SEQ ID NOs: 35 and 64, respectively, or an amino acid sequence having at least 80%, 85%, 87% 90%, 92%, 93%, 95%, 97%, 98%, or preferably 100% sequence identity thereto;
(xxii) SEQ ID NOs: 38 and 65, respectively, or an amino acid sequence having at least 80%, 85%, 87% 90%, 92%, 93%, 95%, 97%, 98%, or preferably 100% sequence identity thereto;
(xxiii) SEQ ID NOs: 38 and 62, respectively, or an amino acid sequence having at least 80%, 85%, 87% 90%, 92%, 93%, 95%, 97%, 98%, or preferably 100% sequence identity thereto;
(xxiv) SEQ ID NOs: 38 and 66, respectively, or an amino acid sequence having at least 80%, 85%, 87% 90%, 92%, 93%, 95%, 97%, 98%, or preferably 100% sequence identity thereto;
(xxv) SEQ ID NOs: 38 and 63, respectively, or an amino acid sequence having at least 80%, 85%, 87% 90%, 92%, 93%, 95%, 97%, 98%, or preferably 100% sequence identity thereto;
(xxvi) SEQ ID NOs: 38 and 64, respectively, or an amino acid sequence having at least 80%, 85%, 87% 90%, 92%, 93%, 95%, 97%, 98%, or preferably 100% sequence identity thereto;
(xxvii) SEQ ID NOs: 20 and 21, respectively, or an amino acid sequence having at least 80%, 85%, 87% 90%, 92%, 93%, 95%, 97%, 98%, or preferably 100% sequence identity thereto;
(xxviii) SEQ ID NOs: 88 and 47, respectively, or an amino acid sequence having at least 80%, 85%, 87% 90%, 92%, 93%, 95%, 97%, 98%, or preferably 100% sequence identity thereto;
(xxix) SEQ ID NOs: 89 and 47, respectively, or an amino acid sequence having at least 80%, 85%, 87% 90%, 92%, 93%, 95%, 97%, 98%, or preferably 100% sequence identity thereto;
(xxx) SEQ ID NOs: 90 and 47, respectively, or an amino acid sequence having at least 80%, 85%, 87% 90%, 92%, 93%, 95%, 97%, 98%, or preferably 100% sequence identity thereto;
(xxxi) SEQ ID NOs: 90 and 92, respectively, or an amino acid sequence having at least 80%, 85%, 87% 90%, 92%, 93%, 95%, 97%, 98%, or preferably 100% sequence identity thereto;
(xxxii) SEQ ID NOs: 39 and 47, respectively, or an amino acid sequence having at least 80%, 85%, 87% 90%, 92%, 93%, 95%, 97%, 98%, or preferably 100% sequence identity thereto;
(xxxiii) SEQ ID NOs: 6 and 67, respectively, or an amino acid sequence having at least 80%, 85%, 87% 90%, 92%, 93%, 95%, 97%, 98%, or preferably 100% sequence identity thereto;
(xxxiv) SEQ ID NOs: 6 and 68, respectively, or an amino acid sequence having at least 80%, 85%, 87% 90%, 92%, 93%, 95%, 97%, 98%, or preferably 100% sequence identity thereto;
(xxxv) SEQ ID NOs: 6 and 69, respectively, or an amino acid sequence having at least 80%, 85%, 87% 90%, 92%, 93%, 95%, 97%, 98%, or preferably 100% sequence identity thereto;
(xxxvi) SEQ ID NOs: 93 and 67, respectively, or an amino acid sequence having at least 80%, 85%, 87% 90%, 92%, 93%, 95%, 97%, 98%, or preferably 100% sequence identity thereto;
(xxxvii) SEQ ID NOs: 93 and 68, respectively, or an amino acid sequence having at least 80%, 85%, 87% 90%, 92%, 93%, 95%, 97%, 98%, or preferably 100% sequence identity thereto;
(xxxviii) SEQ ID NOs: 93 and 69, respectively, or an amino acid sequence having at least 80%, 85%, 87% 90%, 92%, 93%, 95%, 97%, 98%, or preferably 100% sequence identity thereto; or
(xxxix) SEQ ID NOs: 93 and 7, respectively, or an amino acid sequence having at least 80%, 85%, 87% 90%, 92%, 93%, 95%, 97%, 98%, or preferably 100% sequence identity thereto, optimally wherein:
the VH region and VL region comprise the amino acid sequences of
(i) SEQ ID NOs: 6 and 7, respectively;
(ii) SEQ ID NOs: 34 and 65, respectively;
(iii) SEQ ID NOs: 34 and 62, respectively;
(iv) SEQ ID NOs: 34 and 66, respectively;
(v) SEQ ID NOs: 34 and 63, respectively;
(vi) SEQ ID NOs: 34 and 64, respectively;
(vii) SEQ ID NOs: 37 and 65, respectively;
(viii) SEQ ID NOs: 37 and 62, respectively;
(ix) SEQ ID NOs: 37 and 66, respectively;
(x) SEQ ID NOs: 37 and 63, respectively;
(xi) SEQ ID NOs: 37 and 64, respectively;
(xii) SEQ ID NOs: 36 and 65, respectively;
(xiii) SEQ ID NOs: 36 and 62, respectively;
(xiv) SEQ ID NOs: 36 and 66, respectively;
(xv) SEQ ID NOs: 36 and 63, respectively;
(xvi) SEQ ID NOs: 36 and 64, respectively;
(xvii) SEQ ID NOs: 35 and 65, respectively;
(xviii) SEQ ID NOs: 35 and 62, respectively;
(xix) SEQ ID NOs: 35 and 66, respectively;
(xx) SEQ ID NOs: 35 and 63, respectively;
(xxi) SEQ ID NOs: 35 and 64, respectively;
(xxii) SEQ ID NOs: 38 and 65, respectively;
(xxiii) SEQ ID NOs: 38 and 62, respectively;
(xxiv) SEQ ID NOs: 38 and 66, respectively;
(xxv) SEQ ID NOs: 38 and 63, respectively;

(xxvi) SEQ ID NOs: 38 and 64, respectively;
(xxvii) SEQ ID NOs: 20 and 21, respectively;
(xxviii) SEQ ID NOs: 88 and 47, respectively;
(xxix) SEQ ID NOs: 89 and 47, respectively;
(xxx) SEQ ID NOs: 90 and 47, respectively;
(xxxi) SEQ ID NOs: 90 and 92, respectively;
(xxxii) SEQ ID NOs: 39 and 47, respectively;
(xxxiii) SEQ ID NOs: 6 and 67, respectively;
(xxxiv) SEQ ID NOs: 6 and 68, respectively;
(xxxv) SEQ ID NOs: 6 and 69, respectively;
(xxxvi) SEQ ID NOs: 93 and 67, respectively;
(xxxvii) SEQ ID NOs: 93 and 68, respectively;
(xxxviii) SEQ ID NOs: 93 and 69, respectively; or
(xxxix) SEQ ID NOs: 93 and 7, respectively.

E146. The isolated antibody, or antigen-binding fragment thereof, of any of the preceding embodiments, which comprises or has a heavy chain constant region (Fc) chosen from, e.g., the heavy chain constant regions of IgG1, IgG2, IgG3, IgG4, IgM, IgA1, IgA2, IgD, and IgE.

E147. The isolated antibody, or antigen-binding fragment thereof, of any of the preceding embodiments, wherein the antibody belongs to an isotype chosen from IgG1, IgG2, IgG3, IgG4, or any variant thereof.

E148. The isolated antibody, or antigen-binding fragment thereof, of any of the preceding embodiments, wherein the antibody comprises a heavy chain constant region of IgG1 or IgG2 (e.g., human IgG1 or human IgG2).

E149. The isolated antibody, or antigen-binding fragment thereof, of any of the preceding embodiments, which comprises or has a heavy chain constant region is human IgG1.

E150. The isolated antibody, or antigen-binding fragment thereof, of any of the preceding embodiments, which comprises or has a light chain constant region chosen from, e.g., the light chain constant regions of kappa or lambda.

E151. The isolated antibody, or antigen-binding fragment thereof, of any of the preceding embodiments, which comprises or has a kappa (e.g., human kappa) light chain constant region.

E152. The isolated antibody, or antigen-binding fragment thereof, of any of the preceding embodiments, which comprises an Fc region of the heavy chain having an altered hinge region to reduce effector cell function.

E153. The isolated antibody, or antigen-binding fragment thereof, of any of the preceding embodiments, which has reduced antibody dependent cellular cytotoxicity (ADCC) and/or reduced complement dependent cytotoxicity (CDC).

E154. The isolated antibody, or antigen-binding fragment thereof, of any of the preceding embodiments, which comprises a hinge region having a substitution at at least one position of L234, L235 or G237, e.g., as compared to a human IgG1, numbered according to the Eu numbering scheme.

E155. The isolated antibody, or antigen-binding fragment thereof, of any of the preceding embodiments, comprising a human IgG1 Fc region comprising at least one substitution selected from L234A, L235A, and G237A, numbered according to the Eu numbering scheme.

E156. The isolated antibody, or antigen-binding fragment thereof, of any of the preceding embodiments, which has a hinge region comprising the amino acid sequence of EPKSCDKTHTCPPCPAPEAAGAP (SEQ ID NO: 126).

E157. The isolated antibody, or antigen-binding fragment thereof, of any of the preceding embodiments, which is altered to remove an immunogenic T-cell epitope.

E158. The isolated antibody, or antigen-binding fragment thereof, of embodiment E157, which comprises a VL comprising at least one substitution selected from the group consisting of L30S, N58S, M56A, M94Q, L97Y and Q105G, numbered according to SEQ ID NO: 47.

E159. The antibody, or antigen-binding fragment thereof, of any of the preceding embodiments, wherein said antibody, or antigen-binding fragment thereof, has at least one of the following properties:
(i) a binding affinity, expressed as KD, for human αvβ8 integrin that is less than the murine antibody ADWA11, e.g., less than 536 pM;
(ii) a KD for human αvβ8 integrin that is less than or equal to 100 pM for purified human αvβ8 integrin;
(iii) a KD for mouse αvβ8 integrin that is less than 100 pM;
(iv) a KD for cynomolgus monkey αvβ8 integrin that is less 100 pM;
(v) a KD for rat αvβ8 integrin that is about 160 pM;
(vi) approximately equivalent affinity for at least two, three, or all of human, cynomolgus, mouse, and rat αvβ8 integrin, e.g., with a KD that is less than 100 pM, e.g., as determined using a Biacore affinity assay;
(vii) an IC50 for inhibiting TGFβ transactivation that is less than 183 pM; (viii) an IC50 for inhibiting TGFβ transactivation in U251 cells that is about 100 pM to about 300 pM;
(ix) an EC50 for U251 cells of about 100 pM to about 400 pM pM;
(x) an EC50 for C8-S cells of about 110 pM to about 180 pM;
(xi) at least one predicted human pharmacokinetic (PK) parameter chosen from:
  a. a clearance from central compartment (CL) of about 0.12-0.15 mL/h/kg;
  b. an inter-compartmental distribution clearance (CLF) of about 0.15-0.51 mL/h/kg;
  c. a volume of distribution for the central compartment (V1) of about 36-39 mL/kg;
  d. a volume of distribution for the peripheral compartment (V2) of about 21-33 mL/kg; and/or
  e. a terminal half-life ($t_{1/2}$) of about 12-17 days; and
(xii) no detectable binding to human Fcγ receptors or C1q.

E160. The antibody, or antigen-binding fragment thereof, of any of the preceding embodiments, wherein said antibody, or antigen-binding fragment thereof, has at least one of the following properties:
(i) binds specifically to αvβ8 integrin but not to other integrins;
(ii) reduces an interaction between αvβ8 integrin and Latency Associated Peptide (LAP);
(iii) reduces TGF-β signaling;
(iv) effectively blocks the αvβ8 integrin-mediated TGFβ activation with an IC50 ≤10 nM;
(v) has a comparable Kd (within 5-fold) towards a non-human primate (NHP) orthologue;
(vi) selectivity binds human αvβ8 and does not detectably bind a homologue of αvβ8 (e.g., αvβ1, αvβ3, αvβ5 and αvβ6);
(vii) causes growth suppression and/or complete tumor regression in a human subject or an animal model of cancer, for example, squamous cell carcinoma, breast cancer, and/or colon cancer, alone or in combination with an immunomodulatory agent, e.g., a modulators of checkpoint inhibitors, e.g., inhibitors of PD-1, PD-L1, CTLA-4, or an agonist of a stimulatory molecule, e.g., 4-1BB;
(viii) causes growth suppression and/or complete tumor regression in an animal model for a cancer in combination with an anti-cancer therapy, e.g., radiotherapy;

(ix) shows at least 60% reduction in tumor growth in a syngeneic tumor graft model, e.g., when administered at ≤10 mg/kg alone or in combination with an immunomodulatory agent (e.g., an inhibitor of PD-1, PD-L1, CTLA-4);
(x) increases an anti-tumor response in the presence of one or more immunomodulators, e.g., an antagonist of a checkpoint inhibitor or an agonist of a checkpoint activator, e.g., an antagonist of PD-1, PD-L1, or CTLA-4, or an activator of an immune response, e.g., 4-4BB agonist, when administered to a subject, e.g., a mouse or human subject;
(xi) has an efficacy that is not dependent upon the expression of αvβ8 integrin in a tumor model;
(xii) can increase the abundance of CD8+ GzmB+ T cells in the tumor microenvironment, e.g., as a monotherapy;
(xiii) shows a decrease, e.g., at least a >80% decrease, in tumor growth when used in combination with an antagonist of a checkpoint inhibitor (e.g., an anti-PD-1 or anti-PD-L1 antibody), e.g., in a syngeneic model of squamous cell carcinoma, breast cancer, and/or colon cancer;
(xiv) shows a statistically significant improvement in overall survival of a subject, as determined by a Kaplan-Meier analysis;
(xv) shows a high degree of thermal stability;
(xvi) shows minimal aggregation at high concentration; and
(xvii) may show reproducible expression and purity in large-scale manufacturing conditions.

E161. The antibody, or antigen-binding fragment thereof, of any of the preceding embodiments, wherein said antibody, or antigen-binding fragment thereof, has at least one of the following properties:
(i) a binding affinity, expressed as KD, for human αvβ8 integrin that is less than the KD for the murine antibody ADWA11, e.g., less than 536 pM;
(ii) a KD for human αvβ8 integrin that is less than or equal to 100 pM for purified human αvβ8 integrin;
(iii) a KD for mouse αvβ8 integrin that is less than 100 pM;
(iv) a KD for cynomolgus monkey αvβ8 integrin that is less than 100 pM; (v) a KD for rat αvβ8 integrin that is about 160 pM;
(vi) approximately equivalent affinity for at least two, three, or all of human, cynomolgus, mouse, and rat αvβ8 integrin, e.g., with a KD that is less than 100 pM, as determined using a Biacore affinity assay;
(vii) an IC50 for inhibiting TGFβ transactivation that is less than 183 pM; (viii) an IC50 for inhibiting TGFβ transactivation in U251 cells of about 100 pM to about 300 pM;
(ix) an EC50 for U251 cells of about 126 pM with a standard deviation of plus or minus 34 pM;
(x) an EC50 for U251 cells of about 256 pM with a standard deviation of plus or minus 115 pM;
(xi) an EC50 for U251 cells of about 80 pM to about 400 pM;
(xii) an EC50 for C8-S cells of about 115 pM;
(xiii) an EC50 for C8-S cells of about 145 pM with a standard deviation of plus or minus 23.7 pM;
(xiv) an EC50 for C8-S cells of about 110 pM to about 180 pM;
(xv) at least one predicted human pharmacokinetic (PK) parameter chosen from:
a. a clearance from central compartment (CL) of about 0.12-0.15 mL/h/kg;
b. an inter-compartmental distribution clearance (CLF) of about 0.15-0.51 mL/h/kg;
c. a volume of distribution for the central compartment (V1) of about 36-39 mL/kg;
d. a volume of distribution for the peripheral compartment (V2) of about 21-33 1 mL/kg; and/or
e. a terminal half-life ($t_{1/2}$) of about 12-17 days; and
(xvi) no detectable binding to human Fcγ receptors or C1q.

E162. The isolated antibody, or antigen-binding fragment thereof, of any of the preceding embodiments, which binds human αvβ8 integrin with a $K_D$ less than or equal to 100 pM for purified human αvβ8 integrin.

E163. The isolated antibody, or antigen-binding fragment thereof, of any of the preceding embodiments, which binds human αvβ8 integrin with a $K_D$ less than 536 pM.

E164. The isolated antibody, or antigen-binding fragment thereof, of any of the preceding embodiments, which inhibits TGFβ activation with an IC50 less than 183 pM.

E165. The isolated antibody, or antigen-binding fragment thereof, of any of the preceding embodiments, which inhibits TGFβ activation with an IC50 of 100 pM to about 300 pM.

E166. The isolated antibody, or antigen-binding fragment thereof, of any of the preceding embodiments, which inhibits TGFβ activation in U251 cells with an IC50 of 199+/−93.6 pM.

E167. A pharmaceutical composition comprising the antibody, or antigen-binding fragment thereof, of any of the preceding embodiments, and a pharmaceutically acceptable carrier or excipient.

E168. A nucleic acid molecule that encodes the antibody, or antigen-binding fragment thereof, of any of embodiments E1-E166.

E169. A nucleic acid molecule comprising:
(i) a nucleotide sequence having at least 80%, 85%, 87% 90%, 92%, 93%, 95%, 97%, 98%, or 100% sequence identity to SEQ ID NO: 1, 183, 189 or 191 and encoding a heavy chain;
(ii) a nucleotide sequence having at least 80%, 85%, 87% 90%, 92%, 93%, 95%, 97%, 98%, or 100% sequence identity to SEQ ID NO: 190 and encoding a heavy chain variable region;
(iii) a nucleotide sequence having at least 80%, 85%, 87% 90%, 92%, 93%, 95%, 97%, 98%, or 100% sequence identity to SEQ ID NO: 192 or 193 and encoding a heavy chain constant region; or
(iv) a nucleotide sequence having at least 80%, 85%, 87% 90%, 92%, 93%, 95%, 97%, 98%, or 100% sequence identity to a nucleic acid sequence of the insert of the plasmid deposited with the ATCC and having Accession Number PTA-124917.

E170. A nucleic acid molecule comprising:
(i) a nucleotide sequence having at least 80%, 85%, 87% 90%, 92%, 93%, 95%, 97%, 98%, or 100% sequence identity to SEQ ID NO: 4 or 185 and encoding a light chain;
(ii) a nucleotide sequence having at least 80%, 85%, 87% 90%, 92%, 93%, 95%, 97%, 98%, or 100% sequence identity to SEQ ID NO:186 and encoding a light chain variable region;
(iii) a nucleotide sequence having at least 80%, 85%, 87% 90%, 92%, 93%, 95%, 97%, 98%, or 100% sequence identity to SEQ ID NO: 194 and encoding a light chain constant region; or
(iv) a nucleotide sequence having at least 80%, 85%, 87% 90%, 92%, 93%, 95%, 97%, 98%, or 100% sequence identity to a nucleic acid sequence of the insert of the plasmid deposited with the ATCC and having Accession Number PTA-124918.

E171. A nucleic acid molecule comprising a nucleotide sequence having at least 80%, 85%, 87% 90%, 92%, 93%, 95%, 97%, 98%, or 100% sequence identity to SEQ ID NO: 1 or 183 and a nucleotide sequence having at least 80%, 85%, 87% 90%, 92%, 93%, 95%, 97%, 98%, or 100% sequence identity to SEQ ID NO: 4.

E172. A nucleic acid molecule comprising a nucleotide sequence having at least 80%, 85%, 87% 90%, 92%, 93%, 95%, 97%, 98%, or 100% sequence identity to SEQ ID NO: 189 or 191 and a nucleotide sequence having at least 80%, 85%, 87% 90%, 92%, 93%, 95%, 97%, 98%, or 100% sequence identity to SEQ ID NO: 185.

E173. A vector comprising the nucleic acid molecule of any of embodiments E168-E172.

E174. A host cell comprising the nucleic acid molecule of any of embodiments E168-E172 or the vector of embodiment E173.

E175. The host cell of embodiment E174, wherein the host cell is a mammalian cell, e.g., a human cell.

E176. The host cell of embodiment E175, wherein the host cell is a CHO cell, a COS cell, a HEK-293 cell, an NS0 cell, a PER.C6® cell, or an Sp2.0 cell.

E177. A method of making an isolated antibody, or antigen-binding fragment thereof, that specifically binds to human αvβ8 integrin, comprising culturing the host cell of any one of embodiments E174-E176, under conditions wherein said antibody or antigen-binding fragment is expressed by said host cell.

E178. The method of embodiment E177, further comprising isolating the antibody or antigen-binding fragment thereof.

E179. A method of reducing TGFβ signaling in a subject in need thereof, the method comprising administering to a subject in need thereof a therapeutically effective amount of the antibody, or antigen-binding fragment thereof, of any of embodiments E1-E166, or the pharmaceutical composition of any one of embodiment E167.

E180. A method of reducing αvβ8 integrin activity in a subject in need thereof, the method comprising administering to a subject in need thereof a therapeutically effective amount of the antibody, or antigen-binding fragment thereof, of any of embodiments E1-E166, or the pharmaceutical composition of embodiment E167.

E181. A method of treating a disease, disorder, or condition associated with or mediated by aberrant (e.g., increased) TGFβ signaling, comprising administering to a subject in need thereof a therapeutically effective amount of the antibody, or antigen-binding fragment thereof, of any of embodiments E1-E166, or the pharmaceutical composition of embodiment E167.

E182. A method of inducing an anti-tumor response in a subject, comprising administering to a subject in need thereof a therapeutically effective amount of the antibody, or antigen-binding fragment thereof, of any of embodiments E1-E166, or the pharmaceutical composition of any one of embodiment E167, optionally, wherein the antibody, or antigen-binding fragment thereof, is administered in combination with a second therapy, optionally wherein the antibody, or antigen-binding fragment thereof, and the second therapy are administered simultaneously, sequentially, or separately, optionally wherein:
(i) the antibody, or antigen-binding fragment thereof, is administered prior to the administration of the second therapy, or
(ii) the antibody, or antigen-binding fragment thereof, is administered after the administration of the second therapy.

E183. The antibody, or antigen-binding fragment thereof, of any of embodiments E1-E166, or the pharmaceutical composition of embodiment E167, for use in reducing the activity of αvβ8 integrin in a subject.

E184. A method of treating a cancer, comprising administering to a subject in need thereof a therapeutically effective amount of the antibody, or antigen-binding fragment thereof, of any of embodiments E1-E166, or the pharmaceutical composition of embodiment E167.

E185. The method of embodiment E184, wherein said antibody, or antigen-binding fragment thereof, has at least one of the following properties:
(i) binds specifically to αvβ8 integrin (e.g., αvβ8 integrin from human, mouse, cynomolgus monkey, and/or rat);
(ii) reduce an interaction between αvβ8 integrin and Latency Associated Peptide (LAP);
(iii) reduces TGF-β signaling;
(iv) blocks the αvβ8 integrin-mediated TGFβ activation with an IC50≤10 nM;
(v) has a comparable Kd (within 5-fold) towards a non-human primate (NHP) orthologue;
(vi) selectivity binds human αvβ8 and does not detectably bind a homologue of αvβ8 (e.g., αvβ1, αvβ3, αvβ5 and αvβ6);
(vii) causes growth suppression and/or complete tumor regression in an animal model for a cancer chosen from, for example, squamous cell carcinoma, breast, and colon cancer, alone or in combination with an immunomodulatory agent, e.g., a modulators of checkpoint inhibitors, e.g., inhibitors of PD-1, CTLA-4, or an agonist of a stimulatory molecule, e.g., 4-1BB;
(viii) causes growth suppression and/or complete tumor regression in an animal model for a cancer in combination with an anti-cancer therapy, e.g., radiotherapy;
(ix) shows at least 60% reduction in tumor growth in a syngeneic tumor graft model, e.g., when administered at ≤10 mg/kg;
(x) increases an anti-tumor response in the presence of one or more immunomodulators, e.g., an antagonist of a checkpoint inhibitor, e.g., an antagonist of PD-1 or CTLA-4, or an activator of an immune response, e.g., 4-1BB agonist, when administered to a subject, e.g., a mouse or human subject;
(xi) has an efficacy that is not dependent upon the expression of αvβ8 integrin in a tumor model;
(xii) is sufficient to increase the abundance of CD8+ GzmB+ T cell in the tumor microenvironment, e.g., as a monotherapy;
(xiii) shows at least an 80% decrease, in tumor growth when used in combination with an antagonist of a checkpoint inhibitor (e.g., an anti-PD-1 or anti-PD-L1 antibody), e.g., in a syngeneic model of squamous cell carcinoma, breast cancer, and/or colon cancer;
(xiv) shows a statistically significant improvement in overall survival of a subject, e.g., a human or a mouse, as determined by a Kaplan-Meier analysis;
(xv) shows a high degree of thermal stability;
(xvi) shows minimal aggregation at high concentration; and
(xvii) may show reproducible expression and purity in large-scale manufacturing conditions.

E186. The method of embodiment E184 or E185, wherein said antibody, or antigen-binding fragment thereof, has at least one of the following properties:

(i) a binding affinity, expressed as KD, for human αvβ8 integrin that is less than the KD for the murine antibody ADWA11, e.g., less than 536 pM;
(ii) a KD for human αvβ8 integrin that is less than or equal to 100 pM for purified human αvβ8 integrin;
(iii) a KD for mouse αvβ8 integrin that is less than 100 pM;
(iv) a KD for cynomolgus monkey αvβ8 integrin that is less than 100 pM;
(v) a KD for rat αvβ8 integrin that is about 160 pM;
(vi) shows approximately equivalent affinity for at least two, three, or all of human, cynomolgus, mouse, and rat αvβ8 integrin, e.g., with a KD that is less than 100 pM, e.g., as determined using a Biacore affinity assay.
(vii) an IC50 for inhibiting TGFβ transactivation that is less than 183 pM;
(viii) an IC50 for inhibiting TGFβ transactivation in U251 cells of about 199+/−93.6 pM;
(ix) an IC50 for inhibiting TGFβ transactivation that is about 100 pM to about 300 pM.
(x) an EC50 for U251 cells of about 126 pM with a standard deviation of plus or minus 34 pM;
(xi) an EC50 for U251 cells of about 256 pM with a standard deviation of plus or minus 115 pM;
(xii) an EC50 for U251 cells of about 80 pM to about 400 pM;
(xiii) an EC50 for C8-S cells of about 115 pM;
(xiv) an EC50 for C8-S cells of about 145 pM with a standard deviation of plus or minus 23.7 pM;
(xv) an EC50 for C8-S cells of about 110 pM to about 180 pM;
(xvi) at least one predicted human pharmacokinetic (PK) parameter chosen from:
  a. a clearance from central compartment (CL) of about 0.12-0.15 mL/h/kg;
  b. an inter-compartmental distribution clearance (CLF) of about 0.15-0.51 mL/h/kg;
  c. a volume of distribution for the central compartment (V1) of about 36-39 mL/kg;
  d. a volume of distribution for the peripheral compartment (V2) of about 21-33 mL/kg; and/or
  e. a terminal half-life ($t_{1/2}$) of about 12-17 days; and
(xvii) shows no detectable binding to human Fcγ receptors or C1q.

E187. The method of any of embodiments E184-E186, wherein said antibody, or antigen-binding fragment thereof, is according to any of embodiments E1-E166, or the pharmaceutical composition of embodiment E167.

E188. The method of any of embodiments E184-E187, wherein the antibody, or antigen-binding fragment thereof, is administered in an amount sufficient to increases CD45+ cell, CD3+ T cell, CD4+ T cell, CD8+ T cells, and/or Granzyme B expressing cell infiltration.

E189. The method of any of embodiments E184-E188, wherein the antibody, or antigen-binding fragment thereof, is administered in an amount sufficient to increases CD8+ T cells infiltration.

E190. The method of any of embodiments E184-E189, wherein the antibody, or antigen-binding fragment thereof, is administered in an amount sufficient to increase the expression of Granzyme B on CD8+ T cells.

E191. The method of any of embodiments E184-E190, wherein the antibody, or antigen-binding fragment thereof, is administered in an amount sufficient to increase the accumulation of inflammatory macrophages having an elevated level of Ly6G expression.

E192. The method of any of embodiments E184-E191, wherein the antibody, or antigen-binding fragment thereof, is administered in an amount sufficient to increase the accumulation of CD45+CD11b+CD11c−Ly6G−Ly6C$^{high}$CD206$^{low}$ inflammatory macrophages.

E193. The method of any of embodiments E184-E192, wherein the antibody, or antigen-binding fragment thereof, is administered in an amount sufficient to increase the response a second therapy.

E194. The method of any of embodiments E184-E193, wherein the efficacy of the antibody, or antigen-binding fragment thereof, when administered to an animal tumor model is not dependent upon expression of αvβ8 integrin by the tumor model.

E195. The method of any of embodiments E184-E194, wherein the administration of said antibody, or antigen-binding fragment thereof, occurs in combination with a second therapy.

E196. The method of embodiment E195, wherein the second therapy comprises an anti-cancer therapy, a cytotoxic or cytostatic agent, e.g., a chemotherapeutic agent, a hormone treatment, a vaccine, and/or an immunotherapy.

E197. The method of embodiment E195 or E196, wherein the second therapy is or comprises surgery, radiation, cryo-surgery, and/or thermotherapy.

E198. The method of any of embodiments E195-E197, wherein the second therapy comprises a modulator, e.g., an inhibitor or an agonist, of an immune checkpoint molecule, optionally wherein the second therapy is or comprises a modulator of an immune checkpoint molecule selected from the group consisting of PD1, PD-L1, 4-1BB, OX40, CTLA-4, PD-L2, TIM-3, LAG-3, VISTA, CD160, BTLA, TIGIT, 2B4, TGFβ, LAIR1 and a combination thereof.

E199. The method of embodiment E198, wherein the inhibitor of an immune checkpoint molecule is an inhibitor of PD1, PD-L1, CTLA-4, PD-L2, TIM-3, LAG-3, VISTA, BTLA, TIGIT, 2B4, TGFβ, or LAIR1.

E200. The method of embodiment E199, wherein the inhibitor of an immune checkpoint molecule is an inhibitor of PD1, e.g., an antibody against PD1.

E201. The method of embodiment E199, wherein the inhibitor of an immune checkpoint molecule is an inhibitor CTLA-4, e.g., an antibody against CTLA-4 or a soluble CTLA-4 fusion.

E202. The method of embodiments E195-E201, wherein the second therapy comprises an agonist of a costimulatory molecule.

E203. The method of embodiment E202, wherein the agonist of a costimulatory molecule is selected from at least one of 4-1BB (CD137), OX40, CD2, CD27, CDS, ICAM-1, LFA-1 (CD11a/CD18), ICOS (CD278), GITR, CD30, CD40, BAFFR, HVEM, CD7, LIGHT, NKG2C, SLAMF7, NKp80, CD160, or B7-H3.

E204. The method of embodiment E202, wherein the agonist of a costimulatory molecule is a 41-BB agonist.

E205. The method of embodiment E195-E204, wherein the second therapy comprises an inhibitor of PARP1 (e.g., olaparib, rucaparib, niraparib, veliparib, iniparib, talazoparib, 3-aminobenzamide, CEP 9722, E7016, BSI-201, KU-0059436, AG014699, MK-4827, or BGB-290).

E206. The method of embodiment E184-E205, wherein the cancer is selected from the group consisting of a solid tumor, a hematological cancer (e.g., leukemia, lymphoma, myeloma, e.g., multiple myeloma), and a metastatic lesion.

E207. The method of embodiment E206, wherein the cancer is a solid tumor.

E208. The method of embodiment E206 or E207, wherein the cancer is a solid tumor and is chosen from a malignancy, e.g., sarcomas and carcinomas, e.g., adenocarcinomas of the various organ systems, such as those affecting the lung (e.g., a non-small cell lung cancer (NSCLC)), breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck (e.g., head and neck squamous cell carcinoma (HNSCC), skin (e.g., melanoma, e.g., an advanced melanoma), pancreas, colon, rectal, a renal (e.g., a renal cell carcinoma), liver, cancer of the small intestine and cancer of the esophagus, gastro-esophageal cancer, thyroid cancer, and cervical cancer.

E209. The method of any of embodiment E184-E208, wherein the cancer is a lymphoproliferative disease (e.g., a post-transplant lymphoproliferative disease) or a hematological cancer, T-cell lymphoma, B-cell lymphoma, a non-Hodgkin lymphoma, or a leukemia (e.g., a myeloid leukemia or a lymphoid leukemia).

E210. The method of any of embodiment E184-E209, wherein the cancer is an early, intermediate, late stage or metastatic cancer.

E211. The method of any of embodiment E184-E210, wherein the cancer is selected from the group consisting of a renal cell carcinoma, an ovarian cancer, and a head and neck squamous cell carcinoma.

E212. The method of embodiment E211, further comprising administering an inhibitor of a checkpoint inhibitor, e.g., an inhibitor of PD-1, PD-L1, or CTLA-4.

E213. The method of embodiment E212, wherein the inhibitor of PD-L1 in not avelumab.

E214. The method of embodiment E211 or E212, wherein the cancer is a renal cancer, e.g., a renal cell carcinoma (RCC).

E215. The method of embodiment E214, wherein the cancer is a renal cancer selected from the group consisting of a metastatic RCC, a clear cell renal cell carcinoma (ccRCC)), a non-clear-cell renal cell carcinoma (ncRCC), and high risk renal cell carcinoma.

E216. The method of embodiment E215, wherein the antibody, or antigen-binding fragment thereof is administered as a $1^{st}$ line or $2^{nd}$ line therapy.

E217. The method of any of embodiments E184-E216, wherein the antibody, or antigen-binding fragment thereof, is administered as a $1^{st}$ line therapy.

E218. The method of any of embodiments E184-E216, wherein the antibody, or antigen-binding fragment thereof, is administered as a 2nd line therapy.

E219. The method of any of embodiments E184-E212, wherein the cancer is an ovarian cancer.

E220. The method of embodiment E219, wherein the second therapy is an inhibitor of PARP1 (e.g., olaparib, rucaparib, niraparib, veliparib, iniparib, talazoparib, 3-aminobenzamide, CEP 9722, E7016, BSI-201, KU-0059436, AG014699, MK-4827, or BGB-290).

E221. The method of embodiment E219, wherein the antibody, or antigen-binding fragment thereof is administered as a $2^{nd}$ line therapy, optionally wherein the subject is platinum-resistant.

E222. The method of embodiment E219, wherein the antibody, or antigen-binding fragment thereof is administered as a $1^{st}$ line therapy.

E223. The method of any of embodiments E184-E222, wherein the cancer is a head and neck squamous cell carcinoma.

E224. The method of embodiment E223, wherein the method further comprises administration of radiation therapy.

E225. The method of embodiment E223 or E224, wherein the cancer is platinum-resistant and/or recurrent cancer.

E226. The method of any of embodiments E179-E225, wherein said subject is a human.

E227. The method of any of embodiments E179-E226, comprising administering said antibody or antigen-binding fragment thereof, or pharmaceutical composition, intravenously.

E228. The method of any of embodiments E179-E227, comprising administering said antibody or antigen-binding fragment thereof, or pharmaceutical composition, subcutaneously.

E229. The method of any of embodiments E179-E228, wherein said antibody or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months.

E230. The method of any of embodiments E179-E229, wherein the antibody, or the antigen-binding fragments thereof, is administered every two weeks, e.g., up to 12 times (e.g., up to 10, 8, 6, 5, 4, or 3 times).

E231. The method of embodiment E230, wherein each administration comprises 5-10 mg/kg (e.g., 5, 6, 7, 8, 9, or 10 mg/kg) of the antibody, or the antigen-binding fragments thereof.

E232. The method of embodiment E231, wherein each administration comprises about 7 mg/kg.

E233. The method of any of embodiments E179-E229, wherein the antibody, or the antigen-binding fragments thereof, is administered every four weeks, e.g., up to 6 times (e.g., up to 6, 5, 4, 3, 2, or 1 time).

E234. The method of embodiment E233, wherein each administration comprises 10-15 mg/kg (e.g., 10, 11, 12, 13, 14, or 15 mg/kg) of the antibody, or the antigen-binding fragments thereof.

E235. The method of embodiment E234, wherein each administration comprises about 12 mg/kg.

E236. A method of detecting αvβ8 integrin (e.g., human αvβ8 integrin) in a sample, tissue, or cell using the antibody, or antigen-binding fragment thereof, of any of embodiments E1-E166, or the pharmaceutical composition of embodiment E167, comprising contacting the sample, tissue or cell with the antibody and detecting the antibody.

E237. A kit comprising the antibody, or antigen-binding fragment thereof, of any of embodiments E1-E166, or the pharmaceutical composition of embodiment E167.

E238. The antibody, or antigen-binding fragment thereof, of any of embodiments E1-E166, or the pharmaceutical composition of embodiment E167, for use as a medicament, e.g., in any of the method embodiments described herein.

E239. An isolated antibody, or antigen-binding fragment thereof, that specifically binds αvβ8 integrin, wherein the antibody or fragment is at least one antibody or fragment selected from the group consisting of:

(a) an antibody or antigen-binding fragment thereof, comprising a light chain complementarity determining region 1 (CDR-L1) comprising the amino acid sequence of SEQ ID NO:11; a CDR-L2 comprising the amino acid sequence of SEQ ID NO:12; a CDR-L3 comprising the amino acid sequence of SEQ ID NO:13; a heavy chain CDR1 (CDR-H1) comprising the amino acid sequence of SEQ ID NO:8; a CDR-H2 comprising the amino acid sequence of SEQ ID NO:9; and a CDR-H3 comprising the amino acid sequence of SEQ ID NO:10;

(b) an antibody or antigen-binding fragment thereof, comprising a CDR-L1 comprising the amino acid sequence of SEQ ID NO:17; a CDR-L2 comprising the amino acid sequence of SEQ ID NO:18; a CDR-L3 comprising the amino acid sequence of SEQ ID NO:19; a CDR-H1 comprising the amino acid sequence of SEQ ID NO:14; a CDR-H2 comprising the amino acid sequence of SEQ ID NO:15; and a CDR-H3 comprising the amino acid sequence of SEQ ID NO:16;

(c) an antibody or antigen-binding fragment thereof, comprising a variable light (VL) region comprising an amino acid sequence encoded by the insert of the plasmid deposited with the ATCC and having Accession Number PTA-124918, and a variable heavy (VH) region comprising an amino acid sequence encoded by the insert of the plasmid deposited with the ATCC having Accession Number PTA-124917;

(d) an antibody or antigen-binding fragment thereof, comprising a VL region comprising the amino acid sequence of SEQ ID NO:7, and a VH region comprising the amino acid sequence of SEQ ID NO:6;

(e) an antibody or antigen-binding fragment thereof, comprising a VL region comprising the amino acid sequence selected from the group consisting of SEQ ID NO:62-66, and a VH region comprising the amino acid sequence selected from the group consisting of SEQ ID NO:34-38;

(f) an antibody or antigen-binding fragment thereof, comprising a VL region comprising the amino acid sequence selected from the group consisting of SEQ ID NO:47 and 92, and a VH region comprising the amino acid sequence selected from the group consisting of SEQ ID NO:39 and 88-91;

(g) an antibody or antigen-binding fragment thereof, comprising a VL region comprising the amino acid sequence selected from the group consisting of SEQ ID NO:7 and 67-69, and a VH region comprising the amino acid sequence selected from the group consisting of SEQ ID NO:6 and 93;

(h) an antibody or antigen-binding fragment thereof, comprising a VL region comprising the amino acid sequence selected from the group consisting of SEQ ID NO:7, 47-69 and 92, and a VH region comprising the amino acid sequence selected from the group consisting of SEQ ID NO:6, 34-46, 88-91 and 93;

(i) an antibody or antigen-binding fragment thereof, comprising a light chain (LC) region comprising the amino acid sequence of SEQ ID NO:5, and a heavy chain (HC) region comprising the amino acid sequence of SEQ ID NO:2;

(j) an antibody or antigen-binding fragment thereof, comprising a LC region comprising the amino acid sequence of SEQ ID NO:5, and a HC region comprising the amino acid sequence of SEQ ID NO:3;

(k) an antibody or antigen-binding fragment thereof, comprising a LC region comprising the amino acid sequence of SEQ ID NO:123, and a HC region comprising the amino acid sequence of SEQ ID NO:124 or 182;

(l) an antibody or antigen-binding fragment thereof, comprising a VL region encoded by the nucleic acid sequence of SEQ ID NO:186, and a VH region encoded by the nucleic acid sequence of SEQ ID NO:190; and (m) an antibody or antigen-binding fragment thereof, comprising a LC region encoded by the nucleic acid sequence of SEQ ID NO:185, and a HC region encoded by the nucleic acid sequence of SEQ ID NO:189 or 191.

E240. The isolated antibody or antigen-binding fragment thereof of embodiment E239, comprising a VL region comprising the amino acid sequence of SEQ ID NO:7, and a VH region comprising the amino acid sequence of SEQ ID NO:6.

E241. The isolated antibody or antigen-binding fragment thereof of embodiments E239 or E240, comprising a VL region comprising an amino acid sequence at least 95% identical to SEQ ID NO:7, and a VH region comprising an amino acid sequence at least 95% identical to SEQ ID NO:6.

E242. The isolated antibody or antigen-binding fragment thereof of embodiment E239, comprising a LC region comprising the amino acid sequence of SEQ ID NO:5, and a HC region comprising the amino acid sequence of SEQ ID NO:2 or 3.

E243. The isolated antibody or antigen-binding fragment thereof of embodiments E239 or E242, comprising a LC region comprising an amino acid sequence at least 95% identical to SEQ ID NO:5, and a HC region comprising an amino acid sequence at least 95% identical to SEQ ID NO:2 or 3.

E244. An isolated antibody, or antigen-binding fragment thereof, that specifically binds αvβ8 integrin, wherein the antibody or fragment comprises a VH region comprising an amino acid sequence having at least 90%, 91%, 92%, 93%, 94%, 95%, 96%, 97%, 98%, 99%, or 100% sequence identity to an amino acid sequence selected from the group consisting of SEQ ID NO:6, 34-46, 88-91, and 93, and/or a VL region comprising an amino acid sequence having at least 90%, 91%, 92%, 93%, 94%, 95%, 96%, 97%, 98%, 99%, or 100% sequence identity to an amino acid sequence selected from the group consisting of SEQ ID NOs: 7, 47-69, and 92.

E245. An isolated antibody, or antigen-binding fragment thereof, that specifically binds αvβ8 integrin, wherein the antibody or fragment comprises:
  (i) an antibody HC comprising an amino acid sequence having at least 90%, 91%, 92%, 93%, 94%, 95%, 96%, 97%, 98%, 99%, or 100% sequence identity to SEQ ID NO: 2 or 3; and/or
  (ii) an antibody LC comprising an amino acid sequence having at least 90%, 91%, 92%, 93%, 94%, 95%, 96%, 97%, 98%, 99%, or 100% sequence identity to SEQ ID NO: 5.

E246. An isolated antibody that specifically binds αvβ8 integrin, comprising a LC consisting of the amino acid sequence of SEQ ID NO:5, and HC consisting of the amino acid sequence of SEQ ID NO:2 or 3.

E247. An isolated antibody that specifically binds αvβ8 integrin, comprising: an antibody VL region comprising the CDR-L1, CDR-L2 and CDR-L3 from the VL region comprising the amino acid sequence of SEQ ID NO:7; and an antibody VH region comprising the CDR-H1, CDR-H2, and CDR-H3 from the VH region comprising the amino acid sequence of SED ID NO:6.

E248. The isolated antibody of embodiment E247, comprising an antibody heavy chain constant region comprising the amino acid sequence of SEQ ID NO: 181 or 184 and an antibody light chain constant region comprising the amino acid sequence of SEQ ID NO: 83.

E249. An isolated antibody that specifically binds αvβ8 integrin, comprising:
   a) an antibody VL region comprising the first, second and third CDRs from the VL region comprising the amino acid sequence of SEQ ID NO:7;
   an antibody VH region comprising the first, second and third CDRs from the VH region comprising the amino acid sequence of SEQ ID NO:6;
   an antibody light chain constant (CL) region comprising the amino acid sequence of SEQ ID NO:83; and
   an antibody heavy chain (CH) constant region comprising the amino acid sequence of SEQ ID NO:181 or 184;
   b) an antibody VL region comprising an amino acid sequence at least 95% identical to SEQ ID NO: 7; and an antibody VH region comprising an amino acid sequence at least 95% identical to SEQ ID NO:6; or
   c) an antibody LC region comprising an amino acid sequence at least 95% identical to SEQ ID NO: 5, and an antibody HC comprising an amino acid sequence at least 95% identical to SEQ ID NO: 2 or 3.

E250. An isolated antibody, or antigen-binding fragment thereof, that specifically binds αvβ8 integrin, comprising an antibody VH comprising an amino acid sequence encoded by the insert deposited with the ATCC and having the Accession Number PTA-124917, and an antibody VL comprising an amino acid sequence encoded by the insert deposited with the ATCC and having the Accession Number PTA-124918.

E251. An isolated antibody, or antigen-binding fragment thereof, that specifically binds αvβ8 integrin, wherein the antibody or fragment has at least one of the following properties:
   a. a binding affinity, expressed as KD, for human αvβ8 integrin that is less than the KD for the murine antibody ADWA11, e.g., less than about 536 pM;
   b. a KD for human αvβ8 integrin that is less than or equal to about 100 pM
   c. a KD for mouse αvβ8 integrin that is less than the KD for the murine antibody ADWA11, e.g., less than about 489 pM;
   d. a KD for mouse αvβ8 integrin that is less than about 100 pM;
   e. a KD for cynomolgus monkey αvβ8 integrin that is less than the KD for the murine antibody ADWA11, e.g., less than about 507 pM;
   f. a KD for cynomolgus monkey αvβ8 integrin that is less than or equal to about 100 pM;
   g. a KD for rat αvβ8 integrin that is about 160 pM;
   h. approximately equivalent affinity for at least two, three, or all of human, cynomolgus, mouse, and rat αvβ8 integrin, e.g., with a KD that is less than about 100 pM as determined using a Biacore affinity assay;
   i. an IC50 for inhibiting TGFβ transactivation that is about 100 pM to about 300 pM;
   j. an EC30 for U251 cells of about 100 pM to about 400 pM;
   k. an EC50 for C8-S cells of about 110 pM to about 180 pM; and
   l. at least one predicted human pharmacokinetic (PK) parameter selected from:
      i. a clearance from central compartment (CL) of about 0.12 mL/h/kg;
      ii. an inter-compartmental distribution clearance (CLF) of about 0.51 mL/h/kg;
      iii. a volume of distribution for the central compartment (V1) of about 36 mL/kg;
      iv. a volume of distribution for the peripheral compartment (V2) of about 33 mL/kg;
      v. a terminal half-life ($t_{1/2}$) of about 15 to 17 days; and
      vi. no detectable binding to human Fcγ receptors or C1q.

E252. The isolated antibody or antigen-binding fragment thereof, of any of the preceding embodiments, comprising a human IgG1 Fc region comprising one or more substitutions selected from positions L234, L235, and G237 (e.g., one or more of L234A, L235A, and G237A), as numbered according to the Eu numbering of Kabat.

E253. The isolated antibody or antigen-binding fragment thereof, of any of the preceding embodiments, wherein the antibody is a humanized antibody, a human antibody, a murine antibody, chimeric antibody, or a camelid antibody.

E254. The isolated antibody or antigen-binding fragment thereof, of any of the preceding embodiments, wherein the antibody heavy chain isotype is selected from IgG1, IgG2, IgG3, IgG4, or any variant thereof; and/or wherein the light chain constant region is chosen from kappa or lambda.

E255. The isolated antibody or antigen-binding fragment thereof, of any of the preceding embodiments, wherein the antibody heavy chain isotype is IgG1 and/or wherein the light chain constant region is a kappa light chain.

E256. An antibody, or antigen binding fragment thereof, that competes for binding to αvβ8 integrin with an antibody, or antigen-binding fragment thereof, of embodiment E242.

E257. A pharmaceutical composition comprising the antibody or antigen-binding fragment thereof, of any of the preceding embodiments, and a pharmaceutically acceptable carrier or excipient.

E258. The pharmaceutical composition of embodiment E257, comprising i) an antibody or antigen-binding fragment thereof comprising an antibody heavy chain encoded by the amino acid sequence of SEQ ID NO:2 and an antibody light chain encoded by the amino acid sequence of SEQ ID NO:5, ii) an antibody or antigen-binding fragment thereof comprising an antibody heavy chain encoded by the amino acid sequence of SEQ ID NO:3 and an antibody light chain encoded by the amino acid sequence of SEQ ID NO:5, or iii) both.

E259. An isolated nucleic acid molecule that encodes the antibody or antigen-binding fragment thereof of any of embodiments E239-E256.

E260. The isolated nucleic acid of embodiment E259, wherein the isolated nucleic acid encodes the VH region, VL region, or both, of the antibody, or antigen-binding fragment thereof, and wherein said nucleic acid comprises: the nucleic acid sequence of SEQ ID NO:190, the nucleic acid sequence of SEQ ID NO:186, or both.

E261. The isolated nucleic acid of embodiment E259, wherein the isolated nucleic acid encodes the heavy chain constant region, the light chain constant region, or both, of the antibody, or antigen-binding fragment thereof, and wherein the nucleic acid comprises the nucleic acid sequence of SEQ ID NO: 192 or 193; the nucleic acid sequence of SEQ ID NO: 194; or both.

E262. The isolated nucleic acid of embodiment E259, wherein the isolated nucleic acid encodes the HC, LC, or both, of the antibody or antigen-binding fragment thereof, and wherein said nucleic acid comprises: the nucleic acid sequence of SEQ ID NO:189 or 190; the nucleic acid sequence of SEQ ID NO 185; or both.

E263. The isolated nucleic acid of embodiment E259, wherein the isolated nucleic comprises the nucleic acid sequence of the insert of the plasmid deposited with the ATCC and having the Accession Number PTA-124917, the nucleic acid sequence of the insert of the plasmid deposited with the ATCC and having the Accession Number PTA-124918, or both.

E264. The isolated nucleic acid of embodiment E259, wherein the isolated nucleic acid comprises a nucleic acid sequence having at least 80%, 85%, 87% 90%, 92%, 93%, 95%, 97%, 98%, or 100% sequence identity to SEQ ID NO: 189 or SEQ ID NO: 191; a nucleic acid sequence having at least 80%, 85%, 87% 90%, 92%, 93%, 95%, 97%, 98%, or 100% sequence identity to SEQ ID NO: 185; or both.

E265. A vector comprising the nucleic acid of any of embodiments E259-E264.

E266. A host cell comprising the nucleic acid of any of embodiments E259-E264 or the vector of embodiment E265.

E267. The host cell of embodiment E265, wherein the host cell is a mammalian cell selected from the group consisting of a CHO cell, a COS cell, a HEK-293 cell, an NS0 cell, a PER.C6® cell, and an Sp2.0 cell.

E268. A method of making an isolated antibody, or antigen-binding fragment thereof, comprising culturing the host cell of embodiment 266, under conditions wherein the antibody or fragment is expressed by the host cell and isolating the antibody or fragment.

E269. A method of reducing αvβ8 integrin activity in a subject in need thereof, the method comprising administering to the subject a therapeutically effective amount of the antibody, or antigen-binding fragment thereof, of any of embodiments E239-E256, or the pharmaceutical composition of embodiments E257 or E258.

E270. A method of treating cancer, comprising administering to a subject in need thereof, a therapeutically effective amount of the antibody or antigen-binding fragment thereof of any of embodiments E239-E256, or the pharmaceutical composition of embodiments E257 or E258.

E271. The method of embodiment E270, further administration of a cytotoxic agent, a cytostatic agent, a chemotherapeutic agent, a hormone treatment, a vaccine, an immunotherapy, surgery, radiation, cryosurgery, thermotherapy, or a combination thereof.

E272. The method of embodiment E271, wherein the further administration is simultaneous, sequential or separate from the administration of the therapeutically effective amount of the antibody, or antigen-binding fragment thereof, or the pharmaceutical combination.

E273. The method of embodiment E271, wherein the immunotherapy comprises a modulator of an immune checkpoint molecule selected from the group consisting of an anti-PD1 antibody, an anti-PD-L1 antibody, an anti-PD-L2 antibody, an anti-CTLA-4 antibody, a soluble CTLA-4 fusion protein and a combination thereof, and wherein the anti-PD-L1 antibody is not avelumab.

E274. The method of any one of embodiments E270-E273, wherein the cancer is selected from the group consisting of squamous cell carcinoma of the head and neck, renal cell carcinoma with clear cell or papillary cell type, ovarian cancer, fallopian tube cancer, primary peritoneal cancer, gastric cancer, gastroesophageal junction cancer, esophageal cancer, lung squamous cell cancer, pancreatic ductal adenocarcinoma, cholangiocarcinoma, uterine cancer, melanoma, urothelial carcinoma and combinations thereof.

E275. A method of detecting αvβ8 integrin in a sample, tissue or cell using the antibody, or antigen-binding fragment thereof, of embodiments E239-E256, comprising contacting the sample, tissue or cell with the antibody, or antigen-binding fragment thereof, and detecting the antibody, or antigen-binding fragment thereof.

E276. A kit comprising the antibody or fragment of any of embodiments E239-E256, or the pharmaceutical composition of embodiments E257 or E258 and optionally comprising the modulator of embodiment E273.

E277. The antibody or antigen-binding fragment thereof according to any of embodiments E239-E256, or the pharmaceutical composition of embodiments E257 or E258 for use in reducing αvβ8 integrin activity in a subject in need thereof, for treatment of cancer.

E278. The antibody, or antigen-binding fragment thereof, of any of embodiments E239-E256, or the pharmaceutical composition of embodiments E257 or E258 for use in treating cancer, optionally wherein the antibody, or antigen-binding fragment thereof, or the pharmaceutical composition is for administration simultaneously, sequentially or separately in combination with immunotherapy wherein the combination optionally provides a synergistic therapeutic effect.

E279. The antibody or antigen-binding fragment thereof, or the pharmaceutical composition for use according to embodiment E278, wherein the cancer is selected from the group consisting of squamous cell carcinoma of the head and neck, renal cell carcinoma with clear cell or papillary cell type, ovarian cancer, fallopian tube cancer, primary peritoneal cancer, gastric cancer, gastroesophageal junction cancer, esophageal cancer, lung squamous cell cancer, pancreatic ductal adenocarcinoma, cholangiocarcinoma, uterine cancer, melanoma, urothelial carcinoma and combinations thereof, optionally wherein the antibody, or antigen-binding fragment thereof, or the pharmaceutical composition or combination are for use together with administration of immunotherapy or radiation therapy.

E280. Use of an antibody, or antigen-binding fragment thereof, of any one of embodiments E239-E256, or the pharmaceutical composition of embodiments E257 or E258 for treating cancer.

E281. Use of an antibody, or antigen-binding fragment thereof, of any one of embodiments E239-E256 in the manufacture of a medicament for treating cancer.

E282. A method of treating cancer, comprising administering to a subject in need thereof, a therapeutically effective amount of (i) an antibody or antigen-binding fragment thereof that specifically binds αvβ8 integrin and (ii) a modulator of an anti-PD1, anti-PD-L1 or anti-PD-L2 immune checkpoint molecule.

E283. The method of embodiment E282, wherein the cancer is a squamous cell carcinoma.

E284. The method of embodiment E282, wherein the cancer is breast or colon cancer.

E285. The method of any one of embodiments E282-E284, wherein the modulator is selected from the group consisting of an anti-PD1 antibody, an anti-PD-L1 antibody, and an anti-PD-L2 antibody.

BRIEF DESCRIPTION OF THE DRAWINGS

The foregoing summary, as well as the following detailed description of the invention, will be better understood when read in conjunction with the appended drawings. For the purpose of illustrating the invention the following drawings embodiment(s) are shown, however, it should be understood that the invention is not limited to the precise arrangements and instrumentalities shown.

FIG. 1A shows a sequence alignment comparing the heavy chain variable region amino acid sequences of the mouse hybridoma antibody ADWA11 (referred to as "mADWA11" "ADWA11" or "Hybridoma mouse ADWA11"; SEQ ID NO: 20), the humanized ADWA11 VH05-2/VK01(2.4) antibody ("huADWA11-2.4", "ADWA11 2.4" or "humanized ADWA11-2.4"; SEQ ID NO: 6), and the IGHV3-07 germline ("IMGT" or "DP-54"; SEQ ID NO: 195) sequences. The underlined amino acid residues are the CDR sequences according to Kabat.

FIG. 1B shows a sequence alignment comparing the light chain variable region amino acid sequences of the mouse hybridoma antibody ADWA11 (referred to as "mADWA11" "AWDA11" or "Hybridoma mouse ADWA11"; SEQ ID NO: 21), the humanized ADWA11 VH05-2/VK01(2.4) antibody ("huADWA11-2.4", "ADWA11 2.4" or "humanized ADWA11 2.4"; SEQ ID NO: 7), and the IGKV1-39 germline ("IMGT" or "DPK-9"; SEQ ID NO: 196) sequences. The underlined amino acid residues are the CDR sequences according to Kabat.

FIG. 6C shows a representative table showing that the humanized Fab ADWA11, referred to herein as ADWA11 5-2 2.4 (also known as ADWA11 2.4, and ADWA11 VH05-2/VK01(2.4)), retains affinity for human αvβ8 and cross species reactivity as assessed by Biacore, as compared to the parental mouse antibody Fab ("MsADWA11"). ADWA11 5-2 2.4 demonstrated an equivalent affinity for human, cynomolgus, mouse, and rat αvβ8 with a KD of <200 pM. The parental mouse antibody demonstrated an equivalent affinity for human, cynomolgus, and mouse αvβ8 with a KD of 489-536 pM.

FIG. 12B shows representative graphs showing the efficacy of an anti-αvβ8 antibody (ADWA11) at 1, 3, 10, and 20 mg/kg as monotherapy and an isotype control (mIgG1_4mut isotype (2B8)) in the EMT6 breast cancer model in the top panel. Also shown is the combination of anti-αvβ8 antibody ADWA11 at 1, 3, 10, and 20 mg/kg with anti-PD1 antibody (RMP1-14, 10 mg/kg) and a rat IgG2a isotype (2A3) in the EMT6 breast cancer tumor model. Mice were treated with antibodies on Day 0, 4, and 8 of the study and tumor growth was measured using digital calipers three times per week and reported as tumor volume (length×width×width×0.5).

FIG. 14B top graph depicts the density of CD45, CD8, and Granzyme B expressing cells in CT26 tumor tissue collected on Day 12 from mice treated on Day 0, Day 4, and Day 8 with 10 mg/kg of isotype control (Control), or ADWA11 antibody (Anti-ITGαVβ8), n=6; p=P-value. The bottom graph depicts gene expression of CD45, CD8, GranzymeB, and IFNγ in tumor tissue collected 12 days after the first 10 mg/kg dose of isotype control (Isotype), ADWA11 antibody (Anti-ITGαVβ8), Isotype in combination with 5 Gy of tumor targeted radiation, or ADWA11 antibody in combination with 5Gy of tumor targeted radiation. Antibody treatments were administered intravenously on Day 1, Day 4, and Day 8 of the study and radiation therapy was administered on Day 5 of the study. Five mice were included in each treatment group; mean and standard error of the mean are graphed.

FIG. 16A shows a diagram showing a treatment regimen for the CCK168 tumor model. The time line for implantation of tumor cells and intraperitoneal (i.p.) antibody injection for four treatment groups is provided.

FIG. 16B shows representative Kaplan-Meier survival curves using a tumor volume of 2000 mm$^3$ as a cutoff for survival in the CCK168 tumor model. n=10 in each group. **p<0.01 by log-rank Mantel-Cox test.

FIG. 16C depicts representative graphs showing individual growth curves of tumors shown in FIG. 16B. Mice were euthanized prior to the 45-day endpoint when tumors reached ≥2000 mm$^3$ or if extensive tumor ulceration was observed. The combination of an anti-PD1 antibody and ADWA11 treatment synergistically inhibited tumor growth and improved overall survival to a greater extent than an anti-PD1 antibody, ADWA11, or isotype control treatment alone or the individual effects merely added together. Data shown are representative of 3 independent biological replicates.

FIG. 17A depicts the gating strategy for identification of tumor infiltrating monocytes, macrophages, and dendritic cells. Live single cells were first gated with a dump gate including Ly6G, SiglecF, CD90 and B220 to eliminate neutrophils, eosinophils, lymphocytes and B cells. Negatively staining cells were then analyzed by flow cytometry and gated. Macrophages were identified as CD45+CD11b+CD64$^{high}$F4/80$^{high}$ and dendritic cells were identified as CD45+CD11b+F4/80-CD64-MHCII$^{high}$CD11c$^{high}$. Of the macrophage population, profiles consistent with immunostimulatory macrophages were identified as Ly6C$^{high}$CD206$^{low}$ and immunosuppressive macrophages were identified as Ly6C$^{low}$CD206$^{high}$. Dump channel Ly6G+SiglecF+CD90.2+B220+.

FIG. 17B shows a representative graph showing cell surface staining for integrin αvβ8 analyzed as part of a multicolor flow cytometry panel in disaggregated tumors described in FIG. 17A. Representative flow cytometry plots showing fluorescence minus one control staining (FMO) and ADWA11 antibody staining in CCK168 tumor model. N=4 tumors.

FIG. 25A shows a representative graph depicting two-compartment non-linear pharmacokinetic model fitted to 0.1, 0.3, and 3 mg/kg i.v. dosing of ADWA11(2.4) in TG32 mice Circles: observed data. Lines: model fit.

FIG. 25B shows a representative graph depicting two-compartment pharmacokinetic model fitted to 3 mg/kg i.v. dosing of ADWA11 2.4 in TG32 mice. Circles: observed data. Lines: model fit.

FIG. 29A shows graphs depicting representative survival curves and FIG. 29B shows graphs depicting representative individual tumor growth curves in mice implanted with subcutaneous CT26 cells and treated with isotype control antibodies, anti-PD1, ADWA11_4mut, or a combination of anti-PD1 and ADWA11_4mut, plus 5 Gy radiation dose on day 5. One group of mice treated with isotype control antibody did not receive radiation therapy. Data reported as percent survival, n=10 in each group. *p<0.001, **p<0.0001 by log-rank Mantel-Cox test.

FIG. 29C shows graphs depicting representative tumor re-challenge in CT26-cured mice that survived 50 days post-treatment initiation. Parental CT26 cells were implanted into the flank contralateral to that of the original tumor implantation site of CT-26-cured mice, 51 days after initiating immunotherapy in combination with radiation therapy. Control mice did not receive radiation and were not previously exposed to tumor cells. Re-challenged mice were followed for 30 days. Control, n=10; RT plus anti-PD1, n=3; RT plus ADWA11_mut, n=5; RT plus ADWA11_mut and anti-PD1, n=7.

DETAILED DESCRIPTION

Figure 2:
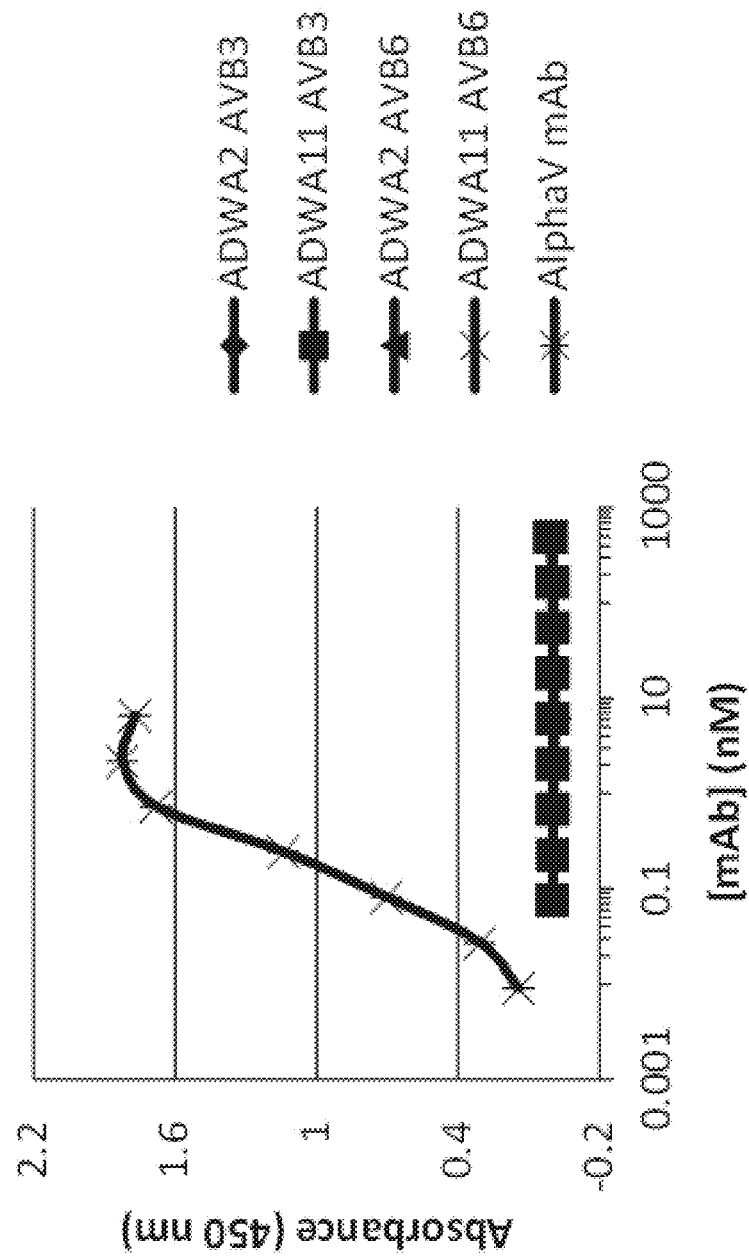
FIG. 2 shows a representative graph comparing the binding specificity of the mouse hybridoma antibodies ADWA2 and ADWA11 for human integrins αvβ3 ("AVB3") and αvβ6 ("AVB6"), as determined by ELISA. ADWA2 and ADWA11 did not bind integrins αvβ3 ("AVB3") and αvβ6 ("AVB6"), while the control αV binding antibody ("AlphaV mAb") bound both αvβ3 and αvβ6.

Disclosed herein are antibodies, and antigen-binding fragments thereof, that specifically bind to αvβ8 integrin (e.g., human αvβ8 integrin) and further, antibodies that antagonize αvβ8 integrin activity (e.g., antagonizes activation of TGFβ, antagonizes mediation of TGFβ production, antagonizes modulation of Tregs and Th17 cells) or its interaction with TGFβ 1 and TGFβ3, or the release of active TGFβ. Methods of making anti-αvβ8 integrin antibodies, compositions comprising anti-αvβ8 integrin antibodies, and methods of using anti-αvβ8 integrin antibodies are provided. In some embodiments, recombinant, e.g., humanized, antibodies that bind αvβ8 integrin (e.g., human αvβ8 integrin) are provided. In some embodiments, humanized antibody heavy chains and light chains that are capable of forming antibodies that bind αvβ8 integrin are also provided. In some embodiments, humanized antibodies, heavy chains, and light chains comprising one or more particular complementarity determining regions (CDRs) are provided. In some embodiments, humanized anti-αvβ8 integrin antibodies have altered effector functions. In some embodiments, the antibodies of the invention have reduced antibody-dependent cell-mediated cytotoxicity (ADCC) activity and/or complement dependent cytotoxicity (CDC) activity relative to otherwise identical anti-αvβ8 integrin antibodies of the invention.

Polynucleotides encoding antibodies that bind αvβ8 integrin (e.g., human αvβ8 integrin), or antigen-binding fragments thereof, are provided. Polynucleotides encoding antibody heavy chains or light chains are also provided. Host cells that express anti-αvβ8 integrin antibodies, including humanized antibodies, are provided. Methods of treatment using anti-αvβ8 integrin antibodies, including humanized antibodies, are provided.

Anti-αvβ8 integrin antibodies, and antigen-binding fragments thereof, including humanized antibodies, can be used in the prevention, treatment, and/or amelioration of diseases, disorders, or conditions caused by and/or associated with aberrant (e.g., increased) TGFβ signaling. Such diseases, disorders, or conditions include cancer (e.g., controlling the proliferation of cancer cells with aberrant (e.g., increased) TGFβ signaling).

Without wishing to be bound by any particular theory, mature TGFβ is present in inactive or latent form in a complex with the latency associated peptide (LAP) domain. Binding of αvβ8 integrin to LAP results in release of active TGFβ (e.g., TGFβ1 and TGFβ3). Reducing binding of αvβ8 integrin to LAP can prevent the release of active TGFβ, thereby reducing TGFβ signaling. TGFβ is known to have immune suppressive effects, e.g., in the tumor microenvironment, thus reduction of TGFβ activity and/or signaling using the antibodies described herein can result in activation of an immune response, e.g., an anti-tumor response in vivo. Thus, antibodies, and antigen-binding fragments thereof, of the disclosure enable selective antagonism of TGFβ activity in the immune system and/or the tumor microenvironment, thus enhancing an anti-tumor immune response in a subject. In some embodiments disclosed in the Examples herein, antibodies, and antigen-binding fragments thereof, against αvβ8 integrin have been shown to cause growth suppression and/or complete tumor regression in animal models for several cancers, including squamous cell carcinoma, breast, and colon cancer, alone or in combination with other immunomodulators, such as modulators of checkpoint inhibitors, (e.g., inhibitors of PD-1, PD-L1, CTLA-4 or agonists of 4-1BB), or anti-cancer therapies, e.g., radiotherapy. Thus, anti-αvβ8 integrin antibodies, and antigen-binding fragments thereof, including humanized antibodies, can be used, alone or in combination with a second therapy, in the prevention, treatment, and/or amelioration of a cancer, e.g., a solid tumor, e.g., a solid tumor chosen from: renal cell carcinoma (RCC), an ovarian cancer, or a head and neck squamous cell carcinoma (SCCHN).

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999)); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

I. Definitions

The present invention may be understood more readily by reference to the following detailed description of exemplary embodiments of the invention and the examples included therein.

Unless otherwise defined, all technical and scientific terms used herein have the same meaning as commonly understood by one of ordinary skill in the art to which this invention belongs. In case of conflict, the present specification, including definitions, will control.

Further, unless otherwise required by context or expressly indicated, singular terms shall include pluralities and plural terms shall include the singular.

It is understood that aspects and embodiments of the invention described herein include "consisting" and/or "consisting essentially of" aspects and embodiments. As used herein, the singular form "a", "an", and "the" includes plural references unless indicated otherwise.

In this application, the use of "or" means "and/or" unless expressly stated or understood by one skilled in the art. In the context of a multiple dependent claim, the use of "or" refers back to more than one preceding independent or dependent claim.

"About" or "approximately," when used in connection with a measurable numerical variable, refers to the indicated value of the variable and to all values of the variable that are within the experimental error of the indicated value (e.g. within the 95% confidence interval for the mean) or within 10 percent of the indicated value, whichever is greater. Numeric ranges are inclusive of the numbers defining the range.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

It is to be understood that the terminology used herein is for the purpose of describing particular embodiments only and is not intended to be limiting. In this specification and in the claims that follow, reference will be made to a number of terms that shall be defined to have the following meanings.

The term "isolated molecule" (where the molecule is, for example, a polypeptide, a polynucleotide, or an antibody or fragment thereof) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species. In certain embodiments a substantially pure material is at least 50% pure (i.e., free from contaminants), more preferably, at least 90% pure, more preferably, at least 95% pure, yet more preferably, at least 98% pure, and most preferably, at least 99% pure.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i.e. "algorithms").

The term "similarity" is a related concept, but in contrast to "identity," refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

Polypeptide or antibody "fragments" or "portions" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion"

variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown below under the heading of "conservative substitutions." If such substitutions result in a change in biological activity, then more substantial changes, denominated "exemplary substitutions" shown below, or as further described below in reference to amino acid classes, may be introduced and the products screened.

Amino Acids and Substitutions

| Original Residue | Conservative Substitutions | Exemplary Substitutions |
| --- | --- | --- |
| alanine Ala (A) | Val | Val; Leu; Ile |
| arginine Arg (R) | Lys | Lys; Gln; Asn |
| asparagine Asn (N) | Gln | Gln; His; Asp, Lys; Arg |
| aspartatic Asp (D) | Glu | Glu; Asn |
| cysteine Cys (C) | Ser | Ser; Ala |
| glutamine Gln (Q) | Asn | Asn; Glu |
| glutamic Glu (E) | Asp | Asp; Gln |
| glycine Gly (G) | Ala | Ala |
| histidine His (H) | Arg | Asn; Gln; Lys; Arg |
| isoleucine Ile (I) | Leu | Leu; Val; Met; Ala; Phe; Norleucine |
| leucine Leu (L) | Ile | Norleucine; Iie; Val; Met; Ala; Phe |
| lysine Lys (K) | Arg | Arg; Gln; Asn |
| methionine Met (M) | Leu | Leu; Phe; Ile |
| phenylalanine Phe (F) | Tyr | Leu; Val; Iie; Ala; Tyr |
| proline Pro (P) | Ala | Ala |
| serine Ser (S) | Thr | Thr |
| threonine Thr (T) | Ser | Ser |
| tryptophan Trp (W) | Tyr | Tyr; Phe |
| tyrosine Tyr (Y) | Phe | Trp; Phe; Thr; Ser |
| Original Residue | Conservative Substitutions | Exemplary Substitutions |
| valine Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a beta-sheet or helical conformation, (b) the charge or hydrophobicity of the molecule at the target site, or (c) the bulk of the side chain. Naturally occurring residues are divided into groups based on common side-chain properties:
 i. Non-polar: Norleucine, Met, Ala, Val, Leu, Ile;
 ii. Polar without charge: Cys, Ser, Thr, Asn, Gln;
 iii. Acidic (negatively charged): Asp, Glu;
 iv. Basic (positively charged): Lys, Arg;
 v. Residues that influence chain orientation: Gly, Pro; and
 vi. Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical (e.g., not preferred or common) cysteine. The substitution can be made in a CDR or framework region of a variable domain or in the constant region of an antibody. In some embodiments, the cysteine is canonical (e.g., preferred or most common). Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding fragment thereof that competes with the intact antibody for specific binding, fusion proteins comprising an antigen binding fragment, and any other modified configuration of the immunoglobulin molecule that comprises an antigen recognition site. Antigen binding fragments include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide.

An antibody includes an antibody of any class, such as IgG, IgA, or IgM (or sub-class thereof), and the antibody need not be of any particular class. Depending on the antibody amino acid sequence of the constant region of its heavy chains (HC), immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody (or simply "antibody portion"), as used interchangeably herein, refers to one or more fragments of an antibody that retain the ability to specifically bind to an antigen (e.g., αvβ8 integrin). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al., Science 242:423-426 (1988) and Huston et al., Proc. Natl. Acad. Sci. USA 85:5879-5883 (1988)). Such single chain antibodies are also intended to be encompassed within the term "antigen-binding fragment" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., Proc. Natl. Acad. Sci. USA 90:6444-6448 (1993); Poljak et al., 1994, Structure 2:1121-1123).

Antibodies may be derived from any mammal, including, but not limited to, humans, monkeys, pigs, horses, rabbits, dogs, cats, mice, etc., or other animals such as birds (e.g. chickens), fish (e.g., sharks) and camelids (e.g., llamas).

A "variable region" of an antibody refers to the variable region of the antibody light chain (VL) or the variable region of the antibody heavy chain (VH), either alone or in combination. As known in the art, the variable regions of the heavy and light chains each consist of four framework regions (FRs) connected by three "complementarity determining regions (CDRs)" also known as hypervariable regions (HVR) and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J. Mol. Biol. 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

There are several numbering methods in the art for numbering the amino acid residues that form the CDRs. The Kabat numbering method is a standard for numbering the residues in an antibody and is also typically used to identify CDRs. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198.

The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

"Contact residue" as used herein with respect to an antibody or the antigen specifically bound thereby, refers to an amino acid residue present on an antibody/antigen comprising at least one heavy atom (i.e., not hydrogen) that is within 4 Å or less of a heavy atom of an amino acid residue present on the cognate antibody/antigen.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4.

Residues in a variable domain are typically numbered according Kabat, which provides a numbering system used for heavy chain variable domains or light chain variable domains of the compilation of antibodies. See, Kabat et al., 1991, Sequences of Proteins of Immunological Interest, 5th Ed. Public Health Service, National Institutes of Health, Bethesda, MD. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the version 2.3.3 release of Abysis (www.abysis.org) can be used to assign Kabat numbering to variable regions CDR-L1, CDR-L2, CDR-L3, CDR-H2, and CDR-H3, and the AbM definition can then be used for CDR-H1.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

The antibody, or antigen-binding fragment thereof, of the invention may be affinity matured. For example, an affinity matured antibody can be produced by procedures known in the art (Marks et al., 1992, Bio/Technology, 10:'9-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and WO2004/058184).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody or vice versa. The term also encompasses an antibody comprising a V region from one individual from one species (e.g., a first mouse) and a constant region from another individual from the same species (e.g., a second mouse).

The term "antigen (Ag)" refers to the molecular entity used for immunization of an immunocompetent vertebrate to produce the antibody (Ab) that recognizes the Ag or to screen an expression library (e.g., phage, yeast or ribosome display library, among others). Herein, Ag is termed more broadly and is generally intended to include target molecules that are specifically recognized by the Ab, thus including fragments or mimics of the molecule used in an immunization process for raising the Ab or in library screening for selecting the Ab. Thus, for antibodies of the invention binding to αvβ8 integrin, full-length αvβ8 integrin from mammalian species (e.g., human, monkey, mouse, and rat αvβ8 integrin), including monomers and multimers, such as dimers, trimers, etc. thereof, as well as truncated and other variants of αvβ8 integrin, are referred to as an antigen.

Generally, the term "epitope" refers to the area or region of an antigen (e.g., a protein, nucleic acid, carbohydrate, or lipid, etc.) to which an antibody specifically binds, i.e., an area or region in physical contact with the antibody. Thus, the term "epitope" refers to that portion of a molecule capable of being recognized by and bound by an antibody at one or more of the antibody's antigen-binding regions. Typically, an epitope is defined in the context of a molecular interaction between an "antibody, or antigen-binding portion thereof" (Ab), and its corresponding antigen. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to αvβ8 integrin, e.g., the antibodies compete for binding to the antigen.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. For example, an antibody that specifically or preferentially binds to an αvβ8 integrin epitope is an antibody that binds this epitope with greater affinity, avidity, more readily, and/or with greater duration than it binds to other αvβ8 integrin epitopes or non-αvβ8 integrin epitopes. It is also understood by reading this definition, for example, that an antibody (or moiety or epitope) which specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody or a peptide receptor which recognizes and binds to a cognate ligand or binding partner (e.g., an anti-αvβ8 integrin antibody that binds αvβ8 integrin) in a sample, but does not substantially recognize or bind other molecules in the sample, specifically binds to that cognate ligand or binding partner. Thus, under designated assay conditions, the specified binding moiety (e.g., an antibody or antigen-binding fragment thereof or a receptor or a ligand binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, Biacore™ (GE Healthcare, Piscataway, NJ), KinExA, fluorescence-activated cell sorting (FACS), Octet™ (FortéBio, Inc., Menlo Park, CA) and Western blot analysis are among many assays that may be used to identify an antibody that specifically reacts with an antigen, or antigen-binding fragment thereof, or a receptor, or ligand binding portion thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background. Additionally, an antibody is said to "specifically bind" an antigen when the equilibrium dissociation constant ($K_D$) is ≤1 M, preferably ≤100 nM, more preferably ≤10 nM, even more preferably, ≤100 pM, yet more preferably, ≤10 pM, and even more preferably, ≤1 pM. In some embodiments, an antibody is said to "specifically bind" an antigen when the equilibrium dissociation constant ($K_D$) is ≤7 nM.

The term "binding affinity" is herein used as a measure of the strength of a noncovalent interaction between two molecules, e.g., and antibody, or fragment thereof, and an antigen. The term "binding affinity" is used to describe monovalent interactions (intrinsic activity).

Additionally, to determine the binding affinity of anti-αvβ8 integrin antibodies to αvβ8 integrin-expressing cells, cell binding experiments can be performed to determine the apparent affinity. The apparent affinity of antibody binding to cells expressing the target can be calculated as the $EC_{50}$ of equilibrium binding titration curves in which the geometric mean fluorescence intensity (gMFI) of the antigen binding population is quantified by flow cytometry.

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation using, e.g., the surface plasmon resonance (SPR) method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D = k_d/k_a$. The value of the dissociation constant can be determined directly by well-known methods and can be computed even for complex mixtures by methods such as those, for example, set forth in Caceci et al. (1984, Byte 9: 340-362). For example, the $K_D$ may be established using a double-filter nitrocellulose filter binding assay such as that disclosed by Wong & Lohman (1993, Proc. Natl. Acad. Sci. USA 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA.

A competitive binding assay can be conducted in which the binding of the antibody to the antigen is compared to the binding of the target by another ligand of that target, such as another antibody or a soluble receptor that otherwise binds the target. The concentration at which 50% inhibition occurs is known as the $K_i$. Under ideal conditions, the $K_i$ is equivalent to $K_D$. The $K_i$ value will never be less than the $K_D$, so measurement of $K_i$ can conveniently be substituted to provide an upper limit for $K_D$.

Following the above definition, binding affinities associated with different molecular interactions, e.g., comparison of the binding affinity of different antibodies for a given antigen, may be compared by comparison of the $K_D$ values for the individual antibody/antigen complexes. $K_D$ values for antibodies or other binding partners can be determined using methods well established in the art. One method for determining the $K_D$ is by using surface plasmon resonance, typically using a biosensor system such as a Biacore® system.

Similarly, the specificity of an interaction may be assessed by determination and comparison of the $K_D$ value for the interaction of interest, e.g., a specific interaction between an antibody and an antigen, with the $K_D$ value of an interaction not of interest, e.g., a control antibody known not to bind αvβ8 integrin.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold or greater than its affinity for binding to another non-αvβ8 integrin molecule.

The term "compete", as used herein with regard to an antibody, means that a first antibody, or antigen-binding fragment thereof, binds to an epitope in a manner sufficiently similar to the binding of a second antibody, or antigen-binding fragment thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE® system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to αvβ8 integrin. For example, a sequential binding competition assay may be used, with different antibodies being added sequentially. The first antibody may be added to reach binding that is close to saturation. Then, the second antibody is added. If the binding of second antibody to αvβ8 integrin is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other.

In addition, an exemplary antibody epitope binning assay using domain swapping between human and mouse αvβ8 integrin proteins to assess potential epitopes among several antibodies is provided in Example 9. The skilled artisan would appreciate, armed with the teachings provided herein, that there are a wide variety of assays known in the art that can be used to determine the binding to a target of at least two antibodies relative to each other, and such assays are included herein.

Anti-αvβ8 integrin antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999. In an additional example, epitope mapping can be used to determine the sequence to which an anti-αvβ8 integrin antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with anti-αvβ8 integrin antibody.

In addition, the epitope to which the anti-αvβ8 integrin antibody binds can be determined in a systematic screening by using overlapping peptides derived from the αvβ8 integrin sequence (e.g., a human αvβ8 integrin sequence) and determining binding by the antibody. According to the gene fragment expression assays, the open reading frame encoding αvβ8 integrin can be fragmented either randomly or by specific genetic constructions and the reactivity of the expressed fragments of αvβ8 integrin with the antibody to be tested is determined. The gene fragments may, for example, be produced by PCR and then transcribed and translated into protein in vitro, in the presence of radioactive amino acids. The binding of the antibody to the radioactively labeled αvβ8 integrin fragments is then determined by immunoprecipitation and gel electrophoresis.

Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant αvβ8 integrin in which various residues of the αvβ8 integrin polypeptide have been replaced with alanine. By assessing binding of the antibody to the mutant αvβ8 integrin, the importance of the particular αvβ8 integrin residues to antibody binding can be assessed.

Yet another method which can be used to characterize an anti-αvβ8 integrin antibody is to use competition assays with other antibodies known to bind to the same antigen, i.e., various fragments on αvβ8 integrin, to determine if an anti-αvβ8 integrin antibody binds to the same epitope as other antibodies. Competition assays are well known to those of skill in the art.

Furthermore, the epitope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, hydrogen/deuterium exchange Mass Spectrometry (H/D-MS) and various competition binding methods well-known in the art. As each method relies on a unique principle, the description of an epitope is intimately linked to the method by which it has been determined. Thus, the epitope for a given antibody/ antigen pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterion, e.g., by distance between atoms (e.g., heavy, i.e., non-hydrogen atoms) in the Ab and the Ag. At a further less detailed level the epitope can be characterized through function, e.g., by competition binding with other Abs. The epitope can also be defined more generically as comprising amino acid residues for which substitution by another amino acid will alter the characteristics of the interaction between the Ab and Ag (e.g., using alanine scanning).

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g., determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

The definition of the term "paratope" is derived from the above definition of "epitope" by reversing the perspective. Thus, the term "paratope" refers to the area or region on the antibody which specifically binds an antigen, i.e., the amino acid residues on the antibody which make contact with the antigen (αvβ8 integrin, or a portion thereof) as "contact" is defined elsewhere herein.

The epitope and paratope for a given antibody/antigen pair may be identified by routine methods. For example, the general location of an epitope may be determined by assessing the ability of an antibody to bind to different fragments or variant αvβ8 integrin polypeptides. The specific amino acids within αvβ8 integrin that make contact with an antibody (epitope) and the specific amino acids in an antibody that make contact with αvβ8 integrin (paratope) may also be determined using routine methods, such as those described in the examples. For example, the antibody and target molecule may be combined and the antibody/antigen complex may be crystallized. The crystal structure of the complex may be determined and used to identify specific sites of interaction between the antibody and its target.

An antibody according to the current invention may bind to the same epitope or domain of αvβ8 integrin (e.g., human αvβ8 integrin) as the antibodies of the invention that are specifically disclosed herein. Analyses and assays that may be used for the purpose of such identification include assays assessing the competition for binding of αvβ8 integrin between the antibody of interest and αvβ8 integrin receptor, in biological activity assays as described in Examples 1-26.

An antibody, or antigen-binding fragment thereof, may have the ability to compete or cross-compete with another antibody of the invention for binding to αvβ8 integrin (e.g., human αvβ8 integrin) as described herein. For example, an antibody of the invention may compete or cross-compete with antibodies described herein for binding to αvβ8 integrin, or to a suitable fragment or variant of αvβ8 integrin that is bound by the antibodies disclosed herein.

That is, if a first antibody competes with a second antibody for binding to αvβ8 integrin, but it does not compete where the second antibody is first bound to αvβ8 integrin, it is deemed to "compete" with the second antibody (also referred to as unidirectional competition). Where an antibody competes with another antibody regardless of which antibody is first bound to αvβ8 integrin, then the antibody "cross-competes" for binding to αvβ8 integrin with the other antibody. Such competing or cross-competing antibodies can be identified based on their ability to compete/cross-compete with a known antibody of the invention in standard binding assays. For example, SPR e.g. by using a Biacore™ system, ELISA assays or flow cytometry may be used to demonstrate competition/cross-competition. Such competition/cross-competition may suggest that the two antibodies bind to identical, overlapping or similar epitopes.

An antibody of the invention may therefore be identified by a method that comprises a binding assay which assesses whether or not a test antibody is able to compete/cross-compete with a reference antibody for a binding site on the target molecule. Methods for carrying out competitive binding assays are disclosed herein and/or are well known in the art. For example, they may involve binding a reference antibody of the invention to a target molecule using conditions under which the antibody can bind to the target molecule. The antibody/target complex may then be exposed to a test/second antibody and the extent to which the test antibody is able to displace the reference antibody of the invention from antibody/target complexes may be assessed. An alternative method may involve contacting a test antibody with a target molecule under conditions that allow for antibody binding, then adding a reference antibody of the invention that is capable of binding that target molecule and assessing the extent to which the reference antibody of the invention is able to displace the test antibody from antibody/target complexes or to simultaneously bind to the target (i.e., non-competing antibody).

The ability of a test antibody to inhibit the binding of a reference antibody of the invention to the target demonstrates that the test antibody can compete with a reference antibody of the invention for binding to the target and thus that the test antibody binds to the same, or substantially the same, epitope or region on the αvβ8 integrin protein as the reference antibody of the invention. A test antibody that is identified as competing with a reference antibody of the invention in such a method is also an antibody of the present invention. The fact that the test antibody can bind αvβ8 integrin in the same region as a reference antibody of the invention and can compete with the reference antibody of the invention suggests that the test antibody may act as a ligand at the same binding site as the antibody of the invention and that the test antibody may therefore mimic the action of the reference antibody and is, thus, an antibody of the invention. This can be confirmed by comparing the activity of αvβ8 integrin in the presence of the test antibody with the activity of αvβ8 integrin in the presence of the reference antibody under otherwise identical conditions, using an assay as more fully described elsewhere herein.

The reference antibody, or antigen-binding fragment thereof, of the invention may be an antibody as described herein, e.g., an antibody in Table 1, and any variant, or fragment thereof, as described herein that retains the ability to bind to αvβ8 integrin.

As stated previously elsewhere herein, specific binding may be assessed with reference to binding of the antibody to a molecule that is not the target. This comparison may be made by comparing the ability of an antibody to bind to the target and to another molecule. This comparison may be made as described above in an assessment of $K_D$ or $K_i$. The other molecule used in such a comparison may be any molecule that is not the target molecule. Preferably, the other molecule is not identical to the target molecule. Preferably the target molecule is not a fragment of the target molecule.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule, e.g., αvβ8 integrin (e.g., human αvβ8 integrin). By ensuring that the antibody of the invention has specificity for αvβ8 integrin over another such molecule, unwanted in vivo cross-reactivity may be avoided.

The antibody of the invention may retain the ability to bind to some molecules that are related to the target molecule.

Alternatively, the antibody of the invention may have specificity for a particular target molecule. For example, it may bind to one target molecule as described herein, but may not bind, or may bind with significantly reduced affinity to a different target molecule as described herein. For example, a full length mature human αvβ8 integrin may be used as the target, but the antibody that binds to that target may be unable to bind to or may bind with lesser affinity to, e.g. other αvβ8 integrin proteins from other species, such as other mammalian αvβ8 integrin. In some embodiments, the antibody binds to both human and mouse αvβ8 integrin.

An "Fc fusion" protein is a protein wherein one or more polypeptides are operably linked to an Fc polypeptide. An Fc fusion combines the Fc region of an immunoglobulin with a fusion partner.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As known in the art, a "constant region" of an antibody refers to the constant region of the antibody light chain or the constant region of the antibody heavy chain, either alone or in combination.

The terms "IgG Fc region", "Fc region", "Fc domain" and "Fc", as interchangeably used herein refer to the portion of an IgG molecule that correlates to a crystallizable fragment obtained by papain digestion of an IgG molecule. As used herein, the terms relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain. For IgG, Fc comprises immunoglobulin domains Cγ2 and Cγ3 (C gamma 2 and C gamma 3) and the hinge between Cγ1 (C gamma 1) and Cγ2 (C gamma 2). Although the boundaries of the Fc region may vary, the human IgG heavy chain Fc region is usually defined to comprise residues C226 or P230 to its carboxyl-terminus, wherein the numbering is according to the Eu index of Edelman et al., 1969, Proc. Natl. Acad. Sci. USA 63(1):78-85 as described in Kabat et al., 1991. Typically, the Fc domain comprises from about amino acid residue 236 to about 447 of the human IgG1 constant domain. An exemplary human wild type IgG1 Fc domain amino acid sequence is set forth in SEQ ID NO: 81 and SEQ ID NO: 82 (including an optional terminal lysine (K) residue). Fc polypeptide may refer to this region in isolation, or this region in the context of an antibody, or antigen-binding fragment thereof, or Fc fusion protein.

The heavy chain constant domain comprises the Fc region and further comprises the CH1 domain and hinge as well as the CH2 and CH3 (and, optionally, CH4 of IgA and IgE) domains of the IgG heavy chain.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain or antigen-binding fragment thereof) and can be assessed using various assays known in the art for evaluating such antibody effector functions.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (IT AM) in its cytoplasmic domain Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, macrophages, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al., Proc. Natl. Acad. Sci. (USA) 95:652-656 (1998). Additional antibodies with altered Fc region amino acid sequences and increased or decreased ADCC activity are described, e.g., in U.S. Pat. Nos. 7,923,538, and 7,994,290.

An antibody having an "enhanced ADCC activity" refers to an antibody that is more effective at mediating ADCC in vitro or in vivo compared to the parent antibody, wherein the antibody and the parent antibody differ in at least one structural aspect, and when the amounts of such antibody and parent antibody used in the assay are essentially the same. In some embodiments, the antibody and the parent antibody have the same amino acid sequence, but the antibody is afucosylated while the parent antibody is fucosylated. In some embodiments, ADCC activity will be determined using the in vitro ADCC assay as herein disclosed, but other assays or methods for determining ADCC activity, e.g. in an animal model etc., are contemplated. In some embodiments, an antibody with enhanced ADCC activity has enhanced affinity for Fc gamma RIIIA.

An antibody with "altered" FcR binding affinity or ADCC activity is one which has either enhanced or diminished FcR binding activity and/or ADCC activity compared to a parent antibody, wherein the antibody and the parent antibody differ in at least one structural aspect. An antibody that "displays increased binding" to an FcR binds at least one FcR with better affinity than the parent antibody. An antibody that "displays decreased binding" to an FcR, binds at least one FcR with lower affinity than a parent antibody. Such antibodies that display decreased binding to an FcR may possess little or no appreciable binding to an FcR, e.g., 0-20 percent binding to the FcR compared to a native sequence IgG Fc region.

"Enhanced affinity for Fc gamma RIIIA" refers to an antibody that has greater affinity for Fc gamma RIIIA (also referred to, in some instances, as CD 16a) than a parent antibody, wherein the antibody and the parent antibody differ in at least one structural aspect.

"Glycoform" refers to a complex oligosaccharide structure comprising linkages of various carbohydrate units. Such structures are described in, e.g., Essentials of Glycobiology Varki et al., eds., Cold Spring Harbor Laboratory Press, Cold Spring Harbor, NY (1999), which also provides a review of standard glycobiology nomenclature. Such glycoforms include, but are not limited to, G2, G1, G0, G-1, and G-2 (see, e.g., International Patent Publication No. WO 99/22764).

"Glycosylation pattern" is defined as the pattern of carbohydrate units that are covalently attached to a protein (e.g., the glycoform) as well as to the site(s) to which the glycoform(s) are covalently attached to the peptide backbone of a protein, more specifically to an immunoglobulin protein.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202: 163 (1996), may be performed. Antibodies with altered Fc region amino acid sequences and increased or decreased C1q binding capability are described, e.g., in U.S. Pat. No. 6,194,551 B 1, U.S. Pat. Nos. 7,923,538, 7,994,290 and WO 1999/51642. See also, e.g., Idusogie et al., J.

As used herein, the terms "wild-type amino acid," "wild-type IgG," "wild-type antibody," or "wild-type mAb," refer to a sequence of amino or nucleic acids that occurs naturally within a certain population (e.g., human, mouse, rats, cell, etc.).

The term "αvβ8 integrin," as used herein, generally refers to a protein complex comprising an alpha integrin subunit (e.g., an integrin alpha-V subunit, e.g., ITGAV, e.g., comprising the amino acid sequence of SEQ ID NO: 77) and a beta integrin subunit (e.g., an integrin subunit beta 8, e.g., ITGB8, e.g., comprising the amino acid sequence of SEQ ID NO: 78). A "human αvβ8 integrin," as used herein, generally refers to an αvβ8 integrin, e.g., comprising a human ITGAV alpha subunit, e.g., comprising the sequence of SEQ ID NO: 77, and a human ITGB8 beta subunit, e.g., comprising the sequence of SEQ ID NO: 78. A "murine αvβ8 integrin" or "mouse αvβ8 integrin," as used herein, generally refers to an αvβ8 integrin, e.g., comprising a murine ITGAV alpha subunit, e.g., comprising the sequence of SEQ ID NO: 79, and a murine ITGB8 beta subunit, e.g., comprising the sequence of SEQ ID NO: 80. The term αvβ8 integrin typically includes αvβ8 integrin homologs and orthologs, including, but not limited to, human, cynomolgus monkey, rat, rabbit, and mouse. As used herein, "αvβ8 integrin" typically refers to a mammalian αvβ8 integrin, e.g., human, rat, mouse, non-human primate, bovine, ovine, or porcine αvβ8 integrin (e.g., comprising an integrin alpha-V subunit and an integrin beta 8 subunit from human, rat, mouse, non-human primate, bovine, ovine, or porcine, respectively). Non-limiting exemplary examples of integrin alpha-V subunits include human (see, e.g., Genbank Accession Number P06756.2, SEQ ID NO: 77), cynomolgus monkey (see, e.g., SEQ ID NO:84), and mouse (see, e.g., SEQ ID NO: 79) αvβ8 integrin. Non-limiting exemplary examples of integrin beta 8 subunits include human (see, e.g., Genbank Accession Number P26012.1, SEQ ID NO: 78), cynomolgus monkey (see, e.g., SEQ ID NO: 85), and mouse (see, e.g., SEQ ID NO:80) αvβ8 integrin. The term "αvβ8 integrin" also encompasses fragments, variants, isoforms, and other homologs of such αvβ8 integrin subunit molecules. Variant αvβ8 integrin molecules will generally be characterized by having the same type of activity as naturally occurring αvβ8 integrin, such as the ability to bind an αvβ8 integrin ligand, e.g., as described herein, the ability to induce receptor-mediated activity, and the ability to bind, or not, the antibody, or antigen-fragment thereof, of the invention.

Exemplary amino acid and nucleotide sequences for TGFβ and LAP are known in the art. For example, a precursor polypeptide comprising TGFβ1 and LAP (e.g., human sequence UniProt Accession No. P01137) is post-translationally processed into about amino acids 30-278 of UniProt Accession No. P01137 corresponding to LAP and about amino acids 279-390 of UniProt Accession No. P01137 corresponding to human TGFβ1. Similarly, a precursor polypeptide comprising TGFβ3 and LAP (e.g., human sequence UniProt Accession No. P10600) is post-translationally processed into about amino acids 24-300 of UniProt Accession No. P10600 corresponding to LAP and about amino acids 301-412 of UniProt Accession No. 10600 corresponding to human TGFβ3.

The αvβ8 integrin may comprise one or more, two or more, three or more, four or more, five or more, six or more, seven or more, eight or more, nine or more, ten or more, twelve or more or fifteen or more surface accessible residues of αvβ8 integrin. The target molecule may comprise a known epitope from αvβ8 integrin.

As outlined elsewhere herein, certain positions of the antibody molecule can be altered. By "position" as used herein is meant a location in the sequence of a protein. Positions may be numbered sequentially, or according to an established format, for example the EU index and Kabat index can be used to number amino acid residues of an antibody. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR₂ ("amidate"), P(O)R, P(O)OR', CO or CH₂ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this invention.

Host cells may be prokaryotic cells or eukaryotic cells. Exemplary eukaryotic cells include mammalian cells, such as primate or non-primate animal cells; fungal cells, such as yeast; plant cells; and insect cells.

Any host cell susceptible to cell culture, and to expression of protein or polypeptides, may be utilized in accordance with the present invention. In certain embodiments, the host cell is mammalian. Mammalian cell lines available as hosts for expression are well known in the art and include many immortalized cell lines available from the American Type Culture Collection (ATCC). Nonlimiting exemplary mammalian cells include, but are not limited to, NS0 cells, HEK 293 and Chinese hamster ovary (CHO) cells, and their derivatives, such as 293-6E and CHO DG44 cells, CHO DXB11, and Potelligent® CHOK1SV cells (BioWa/Lonza, Allendale, NJ). Mammalian host cells also include, but are not limited to, human cervical carcinoma cells (HeLa, ATCC CCL 2), baby hamster kidney (BHK, ATCC CCL 10) cells, monkey kidney cells (COS), and human hepatocellular carcinoma cells (e.g., Hep G2). Other non-limiting examples of mammalian cells that may be used in accordance with the present invention include human retinoblasts (PER.C6®; CruCell, Leiden, The Netherlands); monkey kidney CV1 line transformed by SV40 (COS-7, ATCC CRL 1651); human embryonic kidney line 293 (HEK 293) or 293 cells subcloned for growth in suspension culture (Graham et al., 1977, J. Gen Virol. 36:59); mouse sertoli cells (TM4, Mather, 1980, Biol. Reprod. 23:243-251); monkey kidney cells (CV1 ATCC CCL 70); African green monkey kidney cells (VERO-76, ATCC CRL-1 587); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., 1982, Annals N.Y. Acad. Sci. 383:44-68); MRC 5 cells; FS4 cells; a human hepatoma line (Hep G2); and numerous myeloma cell lines, including, but not limited to, BALB/c mouse myeloma line (NS0/1, ECACC No: 85110503), NS0 cells and Sp2/0 cells.

Additionally, any number of commercially and non-commercially available cell lines that express polypeptides or proteins may be utilized in accordance with the present invention. One skilled in the art will appreciate that different cell lines might have different nutrition requirements and/or might require different culture conditions for optimal growth and polypeptide or protein expression, and will be able to modify conditions as needed.

The invention includes any eukaryotic expression system known in the art or disclosed herein for production of proteins of interest, such as expression in an insect cell system, a yeast expression system, or a mammalian cell system, such as, but not limited to, CHO cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

By the term "leader peptide" or "leader sequence" or "leader signal sequence" or "signal sequence", as used interchangeably herein, is meant any nucleic acid sequence, or amino acid sequence encoded thereby, that may be present on the 5' end of a nucleic acid molecule and/or at or near the N-terminus of a polypeptide, that when present may mediate the transport of the polypeptide to an organelle of destination, including, but not limited to, the secretion of the polypeptide from a cell. Such leader sequences include, but are not limited to, nucleic acid sequences comprising, e.g., ATGGGATGGAGCTGTATCATCCTCTTCTTGGTAGC-AACAGCTACAGGCGTGC ACTCC (SEQ ID NO: 187), and amino acid sequences encoded thereby, such as, but not limited to, MGWSCIILFLVATATGVHS (SEQ ID NO: 188). The invention encompasses these and any other leader signals (nucleic and amino acid sequences) known in the art or to be identified which can result in the transport of a polypeptide to the desired organelle, e.g., the endoplasmic reticulum, and/or secreted from the cell. Generally, the signal peptide is removed from and/or is not present in the mature polypeptide.

As used herein, "treatment" is an approach for obtaining beneficial or desired clinical results. For purposes of this invention, beneficial or desired clinical results include, but are not limited to, one or more of the following: improved survival rate (reduced mortality), reduction in inflammatory response to the disease, reduction in the amount of tissue fibrosis, improvement in the appearance of the disease lesions, limitation of the pathological lesions to focal sites, decreased extent of damage from the disease, decreased duration of the disease, and/or reduction in the number, extent, or duration of symptoms related to the disease. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease. In some embodiments, the disease, condition or disorder is a cancer.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated using the methods and compositions of the invention. Exemplary cancers whose growth can be treated, e.g., reduced, using the antibodies molecules disclosed herein include cancers typically responsive to immunotherapy.

"Ameliorating" means a lessening or improvement of one or more symptoms as compared to not administering an anti-αvβ8 integrin antibody. "Ameliorating" also includes shortening or reduction in duration of a symptom.

As used herein, an "effective dosage" or "effective amount" of drug, compound, or pharmaceutical composition is an amount sufficient to affect any one or more beneficial or desired results. In more specific aspects, an effective amount prevents, alleviates or ameliorates symptoms of disease, e.g., a cancer, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a αvβ8 integrin-mediated disease, disorder or condition, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

The antibodies, or antigen-binding fragments thereof, can be administered in combination with one or more therapies (e.g., referred to herein as a "second therapy"). By "in combination with," it is not intended to imply that the therapy or the therapeutic agents must be administered at the same time and/or formulated for delivery together, although these methods of delivery are within the scope described herein. The anti-αvβ8 integrin antibodies, or antigen-binding fragments thereof, can be administered concurrently with, prior to, or subsequent to, one or more other additional therapies or therapeutic agents. The anti-αvβ8 integrin antibodies, or antigen-binding fragments thereof, and the second therapy, e.g., other agent or therapeutic protocol, can be administered in any order. In general, each agent will be administered at a dose and/or on a time schedule determined for that agent. In will further be appreciated that the additional therapeutic agent utilized in this combination may be administered together in a single composition or administered separately in different compositions. In some embodiments, the levels utilized in combination will be lower than those utilized individually.

A "synergistic combination" or a combination that acts "synergistically," is a combination that exhibits increased effects that are not predicted when compared with a merely additive effect of the individual therapies combined.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats. In some embodiments, the individual is at risk for a disease, disorder or condition mediated by or associated with αvβ8 integrin binding to its receptor and signaling mediated thereby. In certain embodiments, the subject has a disorder or condition as described herein, e.g., a cancer.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by known conventional methods (see, for example, Remington's Pharmaceutical Sciences, 18th edition, A. Gennaro, ed., Mack Publishing Co., Easton, PA, 1990; and Remington, The Science and Practice of Pharmacy 20th Ed. Mack Publishing, 2000).

Exemplary methods and materials are described herein, although methods and materials similar or equivalent to those described herein can also be used in the practice or testing of the present invention. The materials, methods, and examples are illustrative only and not intended to be limiting.

II. Anti-αvβ8 Integrin Antibodies

The present invention relates to antibodies and antigen-binding fragments thereof, that bind to αvβ8 integrin. Preferably, the antibodies specifically bind to αvβ8 integrin, i.e., they bind to αvβ8 integrin but they do not detectably bind, or bind at a lower affinity, to other αv integrins (e.g., αvβ3 integrin, αvβ5 integrin and αvβ6 integrin). The invention further relates to anti-αvβ8 integrin antibodies that exhibit an altered effector function. In some embodiments, the altered effector function is decreased ADCC. In some embodiments, the altered effector function is decreased CDC. The invention also relates to compositions comprising such antibodies as well as uses for such antibodies, including therapeutic and pharmaceutical uses.

In one embodiment, the disclosure provides any of the following, or compositions (including pharmaceutical compositions) comprising, an antibody having a light chain sequence, or a fragment thereof, and a heavy chain, or a fragment thereof, derived from, but not identical to, the mouse hybridoma antibody ADWA-11 (also referred to as ADWA11, mADWA11, mADWA-11), as disclosed in U.S. Pat. No. 9,969,804, which is herein incorporated by reference in its entirety, and as set forth in, e.g., SEQ ID NO: 20-33 and 71-76 of the present description.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody fragment (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the anti-αvβ8 integrin antibody is a monoclonal antibody. In some embodiments, the anti-αvβ8 integrin antibody is a human or humanized antibody. In some embodiments, the anti-αvβ8 integrin antibody is a chimeric antibody.

The anti-αvβ8 integrin antibodies of the invention may be made by any method known in the art. General techniques for production of human and mouse antibodies are known in the art and/or are described herein.

Following initial identification, the activity of a candidate anti-αvβ8 integrin antibody can be further confirmed and refined by bioassays, known to test the targeted biological activities. In some embodiments, an in vitro cell assay is used to further characterize a candidate anti-αvβ8 integrin antibody. For example, bioassays can be used to screen candidates directly. Some of the methods for identifying and characterizing an anti-αvβ8 integrin antibody are described in detail in the Examples.

Table 1 below is a summary of amino acid and nucleotide sequences for the murine, chimeric, and humanized anti-αvβ8 integrin antibodies, e.g., as described herein. The amino acid and nucleotide sequences of the heavy and light chain CDRs, the amino acid and nucleotide sequences of the heavy and light chain variable regions, and the amino acid and nucleotide sequences of the heavy and light chains are shown in this Table. Generally, unless specifically indicated, the anti-αvβ8 integrin antibodies of the invention can include any combination of one or more Kabat CDRs and/or Chothia hypervariable loops as set forth in Table 1. In some embodiments, the anti-αvβ8 integrin antibodies of the invention can include any combination of one or more VH and/or VL sequences as set forth in Table 1. In some embodiments, the anti-αvβ8 integrin antibodies of the invention can include any combination of one or more framework regions (e.g., FR1, FR2, FR3, and FR4) as described in Table 1. It may be generally understood, and as indicated in Table 1, each VH and VL sequence typically includes three CDRs and four FRs, arranged from amino-terminus to carboxy-terminus in the following order: FR1, CDR1, FR2, CDR2, FR3, CDR3, FR4.

In some embodiments, where an anti-αvβ8 integrin antibody comprises a C-terminal lysine (K) amino acid residue on a heavy chain polypeptide (e.g., human IgG1 heavy chain comprises a terminal lysine), one skilled in the art would understand that the lysine residue may be clipped resulting in an antibody with a heavy chain lacking the C-terminal lysine residue. Additionally, the antibody heavy chain may be produced using a nucleic acid that does not encode the lysine. Thus, in some embodiments, an anti-αvβ8 integrin antibody comprises a heavy chain where the terminal lysine otherwise present is not present.

TABLE 1

Amino acid and nucleotide sequences for αvβ8 integrin antibodies and other peptides.

| Name | SEQ ID NO. | Sequence |
|---|---|---|
| ADWA11 2.4 VL VL amino acid sequence The underlined amino acid residues are the CDR sequences according to Kabat (also referred to as ADWA11_VK01_2.4) | 7 | DIQMTQSPSSLSASVGDRVTITCRSTKSLSHFNGNTYL FWYQQKPGKAPKRLIYYMSSLASGVPSRFSGSGSGTDF TLTISSLQPEDFATYYCQQSLEYPFTFGGGTKVEIK |
| ADWA11 2.4 CDR-L1 according to Kabat | 11 | RSTKSLSHFNGNTYLF |
| ADWA11 2.4 CDR-L2 according to Kabat | 12 | YYMSSLAS |
| ADWA11 2.4 CDR-L3 according to Kabat | 13 | QQSLEYPFT |
| ADWA11 2.4 CDR-L1 according to Chothia | 17 | STKSLSHFNGNTYL |
| ADWA11 2.4 CDR-L2 according to Chothia | 18 | YYMSS |
| ADWA11 2.4 CDR-L3 according to Chothia | 19 | QSLEYPFT |
| ADWA11 2.4 VH VH amino acid sequence The underlined amino acid residues are the CDR sequences according to Kabat | 6 | EVQLVESGGGLVQPGGSLRLSCAASGFNIKDYYMNWVR QAPGKGLEWVGWIDPDQGNTIYEPKFQGRFTISADTSK NSAYLQMNSLRAEDTAVYYCARRLLMDYWGQGTLVTVS S |
| ADWA11 2.4 CDR-H1 according to Kabat | 8 | DYYMN |
| ADWA11 2.4 CDR-H2 according to Kabat | 9 | WIDPDQGNTIYEPKFQG |
| ADWA11 2.4 CDR-H3 according to Kabat | 10 | RLLMDY |

TABLE 1-continued

Amino acid and nucleotide sequences for αvβ8 integrin antibodies and other peptides.

| Name | SEQ ID NO. | Sequence |
|---|---|---|
| ADWA11 2.4 CDR-H1 according to Chothia | 14 | GFNIKDYYMN |
| ADWA11 2.4 CDR-H2 according to Chothia | 15 | WIDPDQGN |
| ADWA11 2.4 CDR-H3 according to Chothia | 16 | RLLMDY |
| ADWA11 2.4 Light chain (LC) amino acid sequence VL sequence is underlined | 5 | DIQMTQSPSSLSASVGDRVTITCRSTKSLSHFNGNTYL FWYQQKPGKAPKRLIYYMSSLASGVPSRFSGSGSGTDF TLTISSLQPEDFATYYCQQSLEYPFTFGGGTKVEIKRT VAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC |
| ADWA11 2.4 Heavy chain (HC) amino acid sequence VH sequence is underlined | 2 | EVQLVESGGGLVQPGGSLRLSCAASGFNIKDYYMNWVR QAPGKGLEWVGWIDPDQGNTIYEPKFQGRFTISADTSK NSAYLQMNSLRAEDTAVYYCARRLLMDYWGQGTLVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKKVEPKSCDKTHTCPPCP APEAAGAPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPGK |
| ADWA11 2.4 Heavy chain amino acid sequence without terminal lysine residue VH sequence is underlined | 3 | EVQLVESGGGLVQPGGSLRLSCAASGFNIKDYYMNWVR QAPGKGLEWVGWIDPDQGNTIYEPKFQGRFTISADTSK NSAYLQMNSLRAEDTAVYYCARRLLMDYWGQGTLVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKKVEPKSCDKTHTCPPCP APEAAGAPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG |
| ADWA11 2.4 Light chain DNA sequence Nucleic acid residues encoding the VL are underlined Nucleic acid residues encoding the leader are in lowercase letters | 4 | atgggatggagctgtatcatcctcttcttggtagcaac agctacaggcgtgcactccGACATCCAGATGACCCAGT CCCCTTCCAGCCTGAGCGCTTCCGTGGGCGACAGGGTG ACCATCACCTGCAGGTCCACCAAGTCCCTGTCCCACTT CAACGGCAACACCTACCTGTTCTGGTACCAGCAGAAGC CCGGCAAGGCCCCCAAGAGGCTGATCTACTACATGTCC TCCCTGGCCTCCGGAGTGCCCTCCAGGTTCTCCGGATC CGGCTCCGGCACCGACTTCACCCTGACCATCTCCTCCC TGCAGCCCGAGGATTTCGCCACCTACTACTGCCAGCAG TCCCTGGAGTACCCCTTCACCTTCGGCGGCGGCACCAA GGTGGAGATCAAACGAACTGTGGCTGCACCATCTGTCT TCATCTTCCCGCCATCTGATGAGCAGTTGAAATCTGGA ACTGCCTCTGTTGTGTGCCTGCTGAATAACTTCTATCC CAGAGAGGCCAAAGTACAGTGGAAGGTGGATAACGCCC TCCAATCGGGTAACTCCCAGGAGAGTGTCACAGAGCAG GACAGCAAGGACAGCACCTACAGCCTCAGCAGCACCCT GACGCTGAGCAAAGCAGACTACGAGAAACACAAAGTCT ACGCCTGCGAAGTCACCCATCAGGGCCTGAGCTCGCCC GTCACAAAGAGCTTCAACAGGGGAGAGTGT |
| ADWA11 2.4 Light chain DNA sequence Nucleic acid residues encoding the VL are underlined | 185 | GACATCCAGATGACCCAGTCCCCTTCCAGCCTGAGCGC TTCCGTGGGCGACAGGGTGACCATCACCTGCAGGTCCA CCAAGTCCCTGTCCCACTTCAACGGCAACACCTACCTG TTCTGGTACCAGCAGAAGCCCGGCAAGGCCCCCAAGAG GCTGATCTACTACATGTCCTCCCTGGCCTCCGGAGTGC CCTCCAGGTTCTCCGGATCCGGCTCCGGCACCGACTTC ACCCTGACCATCTCCTCCCTGCAGCCCGAGGATTTCGC CACCTACTACTGCCAGCAGTCCCTGGAGTACCCCTTCA CCTTCGGCGGCGGCACCAAGGTGGAGATCAAACGAACT GTGGCTGCACCATCTGTCTTCATCTTCCCGCCATCTGA TGAGCAGTTGAAATCTGGAACTGCCTCTGTTGTGTGCC |

TABLE 1-continued

Amino acid and nucleotide sequences for αvβ8 integrin antibodies and other peptides.

| Name | SEQ ID NO. | Sequence |
|---|---|---|
| | | TGCTGAATAACTTCTATCCCAGAGAGGCCAAAGTACAG<br>TGGAAGGTGGATAACGCCCTCCAATCGGGTAACTCCCA<br>GGAGAGTGTCACAGAGCAGGACAGCAAGGACAGCACCT<br>ACAGCCTCAGCAGCACCCTGACGCTGAGCAAAGCAGAC<br>TACGAGAAACACAAAGTCTACGCCTGCGAAGTCACCCA<br>TCAGGGCCTGAGCTCGCCCGTCACAAAGAGCTTCAACA<br>GGGGAGAGTGT |
| ADWA11 2.4 VL DNA sequence | 186 | GACATCCAGATGACCCAGTCCCCTTCCAGCCTGAGCGC<br>TTCCGTGGGCGACAGGGTGACCATCACCTGCAGGTCCA<br>CCAAGTCCCTGTCCCACTTCAACGGCAACACCTACCTG<br>TTCTGGTACCAGCAGAAGCCCGGCAAGGCCCCCAAGAG<br>GCTGATCTACTACATGTCCTCCCTGGCCTCCGGAGTGC<br>CCTCCAGGTTCTCCGGATCCGGCTCCGGCACCGACTTC<br>ACCCTGACCATCTCCTCCCTGCAGCCCGAGGATTTCGC<br>CACCTACTACTGCCAGCAGTCCCTGGAGTACCCCTTCA<br>CCTTCGGCGGCGGCACCAAGGTGGAGATCAAA |
| ADWA11 2.4 Light chain and heavy chain leader DNA sequence | 187 | ATGGGATGGAGCTGTATCATCCTCTTCTTGGTAGCAAC<br>AGCTACAGGCGTGCACTCC |
| ADWA11 2.4 Light chain and heavy chain leader amino acid sequence | 188 | MGWSCIILFLVATATGVHS |
| ADWA11 2.4 Heavy Chain DNA sequence (with terminal lysine) Nucleic acid residues encoding the VH are underlined Nucleic acid residues encoding the leader are in lower case letters | 1 | atgggatggagctgtatcatcctcttcttggtagcaac<br>agctacaggcgtgcactccGAGGTGCAGCTGGTGGAAA<br>GCGGAGGAGGCCTGGTGCAGCCTGGAGGAAGCCTGAGG<br>CTGAGCTGTGCCGCCAGCGGCTTCAACATCAAGGACTA<br>CTACATGAACTGGGTGAGGCAGGCCCCTGGCAAAGGAC<br>TGGAGTGGGTGGGCTGGATCGACCCCGACCAGGGCAAC<br>ACCATCTACGAGCCCAAGTTCCAGGGCAGGTTCACCAT<br>CAGCGCCGACACCAGCAAGAACAGCGCCTACCTGCAGA<br>TGAACTCCCTGAGGGCCGAGGACACCGCCGTGTACTAC<br>TGCGCCAGGAGGCTGCTGATGGACTACTGGGGCCAGGG<br>CACACTGGTCACCGTCTCCTCAGCCTCCACCAAGGGCC<br>CATCGGTCTTCCCCCTGGCACCCTCCTCCAAGAGCACC<br>TCTGGGGGCACAGCGGCCCTGGGCTGCCTGGTCAAGGA<br>CTACTTCCCCGAACCGGTGACGGTGTCGTGGAACTCAG<br>GCGCCCTGACCAGCGGCGTGCACACCTTCCCGGCTGTC<br>CTACAGTCCTCAGGACTCTACTCCCTCAGCAGCGTGGT<br>GACCGTGCCCTCCAGCAGCTTGGGCACCCAGACCTACA<br>TCTGCAACGTGAATCACAAGCCCAGCAACACCAAGGTG<br>GACAAGAAAGTTGAGCCCAAATCTTGTGACAAAACTCA<br>CACATGCCCACCGTGCCCAGCACCTGAAGCCGCTGGGG<br>CACCGTCAGTCTTCCTCTTCCCCCCAAAACCCAAGGAC<br>ACCCTCATGATCTCCCGGACCCCTGAGGTCACATGCGT<br>GGTGGTGGACGTGAGCCACGAAGACCCTGAGGTCAAGT<br>TCAACTGGTACGTGGACGGCGTGGAGGTGCATAATGCC<br>AAGACAAAGCCGCGGGAGGAGCAGTACAACAGCACGTA<br>CCGTGTGGTCAGCGTCCTCACCGTCCTGCACCAGGACT<br>GGCTGAATGGCAAGGAGTACAAGTGCAAGGTCTCCAAC<br>AAAGCCCTCCCAGCCCCCATCGAGAAAACCATCTCCAA<br>AGCCAAAGGGCAGCCCCGAGAACCACAGGTGTACACCC<br>TGCCCCCATCCCGGGAGGAGATGACCAAGAACCAGGTC<br>AGCCTGACCTGCCTGGTCAAAGGCTTCTATCCCAGCGA<br>CATCGCCGTGGAGTGGGAGAGCAATGGGCAGCCGGAGA<br>ACAACTACAAGACCACGCCTCCCGTGCTGGACTCCGAC<br>GGCTCCTTCTTCCTCTATAGCAAGCTCACCGTGGACAA<br>GAGCAGGTGGCAGCAGGGGAACGTCTTCTCATGCTCCG<br>TGATGCATGAGGCTCTGCACAACCACTACACGCAGAAG<br>AGCCTCTCCCTGTCCCCGGAAAA |
| ADWA11 2.4 Heavy Chain DNA sequence (with terminal lysine) Nucleic acid residues encoding | 189 | GAGGTGCAGCTGGTGGAAAGCGGAGGAGGCCTGGTGCA<br>GCCTGGAGGAAGCCTGAGGCTGAGCTGTGCCGCCAGCG<br>GCTTCAACATCAAGGACTACTACATGAACTGGGTGAGG<br>CAGGCCCCTGGCAAAGGACTGGAGTGGGTGGGCTGGAT<br>CGACCCCGACCAGGGCAACACCATCTACGAGCCCAAGT<br>TCCAGGGCAGGTTCACCATCAGCGCCGACACCAGCAAG |

TABLE 1-continued

Amino acid and nucleotide sequences for αvβ8 integrin antibodies and other peptides.

| Name | SEQ ID NO. | Sequence |
|---|---|---|
| the VH are underlined | | AACAGCGCCTACCTGCAGATGAACTCCCTGAGGGCCGA<br>GGACACCGCCGTGTACTACTGCGCCAGGAGGCTGCTGA<br>TGGACTACTGGGGCCAGGGCACACTGGTCACCGTCTCC<br>TCAGCCTCCACCAAGGGCCCATCGGTCTTCCCCCTGGC<br>ACCCTCCTCCAAGAGCACCTCTGGGGGCACAGCGGCCC<br>TGGGCTGCCTGGTCAAGGACTACTTCCCCGAACCGGTG<br>ACGGTGTCGTGGAACTCAGGCGCCCTGACCAGCGGCGT<br>GCACACCTTCCCGGCTGTCCTACAGTCCTCAGGACTCT<br>ACTCCCTCAGCAGCGTGGTGACCGTGCCCTCCAGCAGC<br>TTGGGCACCCAGACCTACATCTGCAACGTGAATCACAA<br>GCCCAGCAACACCAAGGTGGACAAGAAAGTTGAGCCCA<br>AATCTTGTGACAAAACTCACACATGCCCACCGTGCCCA<br>GCACCTGAAGCCGCTGGGGCACCGTCAGTCTTCCTCTT<br>CCCCCCAAAACCCAAGGACACCCTCATGATCTCCCGGA<br>CCCCTGAGGTCACATGCGTGGTGGTGGACGTGAGCCAC<br>GAAGACCCTGAGGTCAAGTTCAACTGGTACGTGGACGG<br>CGTGGAGGTGCATAATGCCAAGACAAAGCCGCGGGAGG<br>AGCAGTACAACAGCACGTACCGTGTGGTCAGCGTCCTC<br>ACCGTCCTGCACCAGGACTGGCTGAATGGCAAGGAGTA<br>CAAGTGCAAGGTCTCCAACAAAGCCCTCCCAGCCCCCA<br>TCGAGAAAACCATCTCCAAAGCCAAAGGGCAGCCCCGA<br>GAACCACAGGTGTACACCCTGCCCCCATCCCGGGAGGA<br>GATGACCAAGAACCAGGTCAGCCTGACCTGCCTGGTCA<br>AAGGCTTCTATCCCAGCGACATCGCCGTGGAGTGGGAG<br>AGCAATGGGCAGCCGGAGAACAACTACAAGACCACGCC<br>TCCCGTGCTGGACTCCGACGGCTCCTTCTTCCTCTATA<br>GCAAGCTCACCGTGGACAAGAGCAGGTGGCAGCAGGGG<br>AACGTCTTCTCATGCTCCGTGATGCATGAGGCTCTGCA<br>CAACCACTACACGCAGAAGAGCCTCTCCCTGTCCCCCG<br>GAAAA |
| ADWA11 2.4 VH DNA sequence | 190 | GAGGTGCAGCTGGTGGAAAGCGGAGGAGGCCTGGTGCA<br>GCCTGGAGGAAGCCTGAGGCTGAGCTGTGCCGCCAGCG<br>GCTTCAACATCAAGGACTACTACATGAACTGGGTGAGG<br>CAGGCCCCTGGCAAAGGACTGGAGTGGGTGGGCTGGAT<br>CGACCCCGACCAGGGCAACACCATCTACGAGCCCAAGT<br>TCCAGGGCAGGTTCACCATCAGCGCCGACACCAGCAAG<br>AACAGCGCCTACCTGCAGATGAACTCCCTGAGGGCCGA<br>GGACACCGCCGTGTACTACTGCGCCAGGAGGCTGCTGA<br>TGGACTACTGGGGCCAGGGCACACTGGTCACCGTCTCC<br>TCA |
| ADWA11 2.4 Heavy Chain DNA sequence Nucleic acid without terminal lysine, residues encoding the VH are underlined Nucleic acid residues encoding the leader are in lower case | 183 | atgggatggagctgtatcatcctcttcttggtagcaac<br>agctacaggcgtgcactccGAGGTGCAGCTGGTGGAAA<br>GCGGAGGAGGCCTGGTGCAGCCTGGAGGAAGCCTGAGG<br>CTGAGCTGTGCCGCCAGCGGCTTCAACATCAAGGACTA<br>CTACATGAACTGGGTGAGGCAGGCCCCTGGCAAAGGAC<br>TGGAGTGGGTGGGCTGGATCGACCCCGACCAGGGCAAC<br>ACCATCTACGAGCCCAAGTTCCAGGGCAGGTTCACCAT<br>CAGCGCCGACACCAGCAAGAACAGCGCCTACCTGCAGA<br>TGAACTCCCTGAGGGCCGAGGACACCGCCGTGTACTAC<br>TGCGCCAGGAGGCTGCTGATGGACTACTGGGGCCAGGG<br>CACACTGGTCACCGTCTCCTCAGCCTCCACCAAGGGCC<br>CATCGGTCTTCCCCCTGGCACCCTCCTCCAAGAGCACC<br>TCTGGGGGCACAGCGGCCCTGGGCTGCCTGGTCAAGGA<br>CTACTTCCCCGAACCGGTGACGGTGTCGTGGAACTCAG<br>GCGCCCTGACCAGCGGCGTGCACACCTTCCCGGCTGTC<br>CTACAGTCCTCAGGACTCTACTCCCTCAGCAGCGTGGT<br>GACCGTGCCCTCCAGCAGCTTGGGCACCCAGACCTACA<br>TCTGCAACGTGAATCACAAGCCCAGCAACACCAAGGTG<br>GACAAGAAAGTTGAGCCCAAATCTTGTGACAAAACTCA<br>CACATGCCCACCGTGCCCAGCACCTGAAGCCGCTGGGG<br>CACCGTCAGTCTTCCTCTTCCCCCCAAAACCCAAGGAC<br>ACCCTCATGATCTCCCGGACCCCTGAGGTCACATGCGT<br>GGTGGTGGACGTGAGCCACGAAGACCCTGAGGTCAAGT<br>TCAACTGGTACGTGGACGGCGTGGAGGTGCATAATGCC<br>AAGACAAAGCCGCGGGAGGAGCAGTACAACAGCACGTA<br>CCGTGTGGTCAGCGTCCTCACCGTCCTGCACCAGGACT<br>GGCTGAATGGCAAGGAGTACAAGTGCAAGGTCTCCAAC<br>AAAGCCCTCCCAGCCCCCATCGAGAAAACCATCTCCAA<br>AGCCAAAGGGCAGCCCCGAGAACCACAGGTGTACACCC<br>TGCCCCCATCCCGGGAGGAGATGACCAAGAACCAGGTC<br>AGCCTGACCTGCCTGGTCAAAGGCTTCTATCCCAGCGA |

TABLE 1-continued

Amino acid and nucleotide sequences for αvβ8 integrin antibodies and other peptides.

| Name | SEQ ID NO. | Sequence |
|---|---|---|
| | | CATCGCCGTGGAGTGGGAGAGCAATGGGCAGCCGGAGA<br>ACAACTACAAGACCACGCCTCCCGTGCTGGACTCCGAC<br>GGCTCCTTCTTCCTCTATAGCAAGCTCACCGTGGACAA<br>GAGCAGGTGGCAGCAGGGGAACGTCTTCTCATGCTCCG<br>TGATGCATGAGGCTCTGCACAACCACTACACGCAGAAG<br>AGCCTCTCCCTGTCCCCCGGA |
| ADWA11 2.4<br>Heavy Chain DNA<br>sequence<br>Nucleic acid without<br>terminal lysine,<br>residues encoding<br>the VH are<br>underlined | 191 | GAGGTGCAGCTGGTGGAAAGCGGAGGAGGCCTGGTGCA<br><u>GCCTGGAGGAAGCCTGAGGCTGAGCTGTGCCGCCAGCG</u><br><u>GCTTCAACATCAAGGACTACTACATGAACTGGGTGAGG</u><br><u>CAGGCCCCTGGCAAAGGACTGGAGTGGGTGGGCTGGAT</u><br><u>CGACCCCGACCAGGGCAACACCATCTACGAGCCCAAGT</u><br><u>TCCAGGGCAGGTTCACCATCAGCGCCGACACCAGCAAG</u><br><u>AACAGCGCCTACCTGCAGATGAACTCCCTGAGGGCCGA</u><br><u>GGACACCGCCGTGTACTACTGCGCCAGGAGGCTGCTGA</u><br><u>TGGACTACTGGGGCCAGGGCACACTGGTCACCGTCTCC</u><br><u>TCA</u>GCCTCCACCAAGGGCCCATCGGTCTTCCCCCTGGC<br>ACCCTCCTCCAAGAGCACCTCTGGGGGCACAGCGGCCC<br>TGGGCTGCCTGGTCAAGGACTACTTCCCCGAACCGGTG<br>ACGGTGTCGTGGAACTCAGGCGCCCTGACCAGCGGCGT<br>GCACACCTTCCCGGCTGTCCTACAGTCCTCAGGACTCT<br>ACTCCCTCAGCAGCGTGGTGACCGTGCCCTCCAGCAGC<br>TTGGGCACCCAGACCTACATCTGCAACGTGAATCACAA<br>GCCCAGCAACACCAAGGTGGACAAGAAAGTTGAGCCCA<br>AATCTTGTGACAAAACTCACACATGCCCACCGTGCCCA<br>GCACCTGAAGCCGCTGGGGCACCGTCAGTCTTCCTCTT<br>CCCCCCAAAACCCAAGGACACCCTCATGATCTCCCGGA<br>CCCCTGAGGTCACATGCGTGGTGGTGGACGTGAGCCAC<br>GAAGACCCTGAGGTCAAGTTCAACTGGTACGTGGACGG<br>CGTGGAGGTGCATAATGCCAAGACAAAGCCGCGGGAGG<br>AGCAGTACAACAGCACGTACCGTGTGGTCAGCGTCCTC<br>ACCGTCCTGCACCAGGACTGGCTGAATGGCAAGGAGTA<br>CAAGTGCAAGGTCTCCAACAAAGCCCTCCCAGCCCCCA<br>TCGAGAAAACCATCTCCAAAGCCAAAGGGCAGCCCCGA<br>GAACCACAGGTGTACACCCTGCCCCCATCCCGGGAGGA<br>GATGACCAAGAACCAGGTCAGCCTGACCTGCCTGGTCA<br>AAGGCTTCTATCCCAGCGACATCGCCGTGGAGTGGGAG<br>AGCAATGGGCAGCCGGAGAACAACTACAAGACCACGCC<br>TCCCGTGCTGGACTCCGACGGCTCCTTCTTCCTCTATA<br>GCAAGCTCACCGTGGACAAGAGCAGGTGGCAGCAGGGG<br>AACGTCTTCTCATGCTCCGTGATGCATGAGGCTCTGCA<br>CAACCACTACACGCAGAAGAGCCTCTCCCTGTCCCCCG<br>GA |
| Mouse hybridoma<br>antibody ADWA-11<br>VL amino acid<br>sequence<br>The underlined amino<br>acid residues are<br>the CDR sequences<br>according to Kabat | 21 | DIVMTQAAPSVPVTPGESVSISC<u>RSTKSLLHFNGNTYL</u><br><u>FWF</u>LQRPGQSPQRLI<u>YYMSNLAS</u>GVPDRFSGRGSGTDF<br>TLRISRVEAEDVGVYYC<u>MQSLEYPFT</u>FGTGTKLEIK |
| Mouse hybridoma<br>antibody ADWA-11<br>VH amino acid<br>sequence<br>The underlined amino<br>acid residues are<br>the CDR sequences<br>according to Kabat | 20 | EVQLQQSGAELVRPGAFVKLSCKASGFNIK<u>DYYMN</u>WVL<br>QRPEQGLEWIG<u>WIDPDNGNTIYDPKFQG</u>KASITADTSS<br>NTAYLQLSSLTSEDTAVYYCAR<u>RLLMDY</u>WGQGTSVTVS<br>S |
| Mouse hybridoma<br>antibody ADWA-11<br>CDR-L1 according to<br>Kabat | 25 | RSTKSLLHFNGNTYLF |
| Mouse hybridoma<br>antibody ADWA-11<br>CDR-L2 according to<br>Kabat | 26 | YYMSNLAS |

TABLE 1-continued

Amino acid and nucleotide sequences for αvβ8 integrin antibodies and other peptides.

| Name | SEQ ID NO. | Sequence |
|---|---|---|
| Mouse hybridoma antibody ADWA-11 CDR-L3 according to Kabat | 27 | MQSLEYPFT |
| Mouse hybridoma antibody ADWA-11 Alternate Alternate CDR-L1 according to Kabat | 71 | RSTKSLLHFNGNTYLF |
| Mouse hybridoma antibody ADWA-11 Alternate Alternate CDR-L2 according to Kabat | 72 | YYMSNLAS |
| Mouse hybridoma antibody ADWA-11 Alternate Alternate CDR-L3 according to Kabat | 73 | MQSLEYPFT |
| Mouse hybridoma antibody ADWA-11 CDR-H1 according to Kabat | 22 | DYYMN |
| Mouse hybridoma antibody ADWA-11 CDR-H2 according to Kabat | 23 | WIDPDNGNTIYDPKFQG |
| Mouse hybridoma antibody ADWA-11 CDR-H3 according to Kabat | 24 | RLLMDY |
| Mouse hybridoma antibody ADWA-11 CDR-L1 according to Chothia | 31 | STKSLLHFNGNTYL |
| Mouse hybridoma antibody ADWA-11 CDR-L2 according to Chothia | 32 | YYMSN |
| Mouse hybridoma antibody ADWA-11 CDR-L3 according to Chothia | 33 | QSLEYPFT |
| Mouse hybridoma antibody ADWA-11 Alternate Alternate CDR-L1 according to Chothia | 74 | STKSLLHFNGNTYL |
| Mouse hybridoma antibody ADWA-11 Alternate Alternate CDR-L2 according to Chothia | 75 | YYMSN |
| Mouse hybridoma antibody ADWA-11 Alternate Alternate CDR-L3 according to Chothia | 76 | QSLEYPFT |

TABLE 1-continued

Amino acid and nucleotide sequences for αvβ8 integrin antibodies and other peptides.

| Name | SEQ ID NO. | Sequence |
|---|---|---|
| Mouse hybridoma antibody ADWA-11 CDR-H1 according to Chothia | 28 | GFNIKDYYMN |
| Mouse hybridoma antibody ADWA-11 CDR-H2 according to Chothia | 29 | WIDPDNGN |
| Mouse hybridoma antibody ADWA-11 CDR-H3 according to Chothia | 30 | RLLMDY |
| ADWA11_VK01 (1) (also referred to herein as adwa_VL_1.1 L46R) VL amino acid sequence | 47 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSLEYPFTFGQGTKVEIK |
| ADWA11_VK01_1a (1) L29I VL amino acid sequence | 48 | DIQMTQSPSSLSASVGDRVTITCRSTKSILHFNGNTYL FWYQQKPGKAPKRLIYYMSNLASGVPSRFSGSGSGTDF TLTISSLQPEDFATYYCMQSLEYPFTFGQGTKVEIK |
| ADWA11_VK01_1b (1) L30S VL amino acid sequence | 49 | DIQMTQSPSSLSASVGDRVTITCRSTKSLSHFNGNTYL FWYQQKPGKAPKRLIYYMSNLASGVPSRFSGSGSGTDF TLTISSLQPEDFATYYCMQSLEYPFTFGQGTKVEIK |
| ADWA11_VK01_1c (1) T36S VL amino acid sequence | 50 | DIQMTQSPSSLSASVGDRVTITCRSTKSLLHFNGNSYL FWYQQKPGKAPKRLIYYMSNLASGVPSRFSGSGSGTDF TLTISSLQPEDFATYYCMQSLEYPFTFGQGTKVEIK |
| ADWA11_VK01_2a (1) Y55A VL amino acid sequence | 51 | DIQMTQSPSSLSASVGDRVTITCRSTKSLLHFNGNTYL FWYQQKPGKAPKRLIYAMSNLASGVPSRFSGSGSGTDF TLTISSLQPEDFATYYCMQSLEYPFTFGQGTKVEIK |
| ADWA11_VK01_2b (1) M56A VL amino acid sequence | 52 | DIQMTQSPSSLSASVGDRVTITCRSTKSLLHFNGNTYL FWYQQKPGKAPKRLIYYASNLASGVPSRFSGSGSGTDF TLTISSLQPEDFATYYCMQSLEYPFTFGQGTKVEIK |
| ADWA11_VK01_2c (1) N58S VL amino acid sequence | 53 | DIQMTQSPSSLSASVGDRVTITCRSTKSLLHFNGNTYL FWYQQKPGKAPKRLIYYMSSLASGVPSRFSGSGSGTDF TLTISSLQPEDFATYYCMQSLEYPFTFGQGTKVEIK |
| ADWA11_VK01_2d (1) A60Q VL amino acid | 54 | DIQMTQSPSSLSASVGDRVTITCRSTKSLLHFNGNTYL FWYQQKPGKAPKRLIYYMSNLQSGVPSRFSGSGSGTDF TLTISSLQPEDFATYYCMQSLEYPFTFGQGTKVEIK |
| ADWA11_VK01_3a (1) M94Q VL amino acid sequence | 55 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCQQSLEYPFTFGQGTKVEIK |
| ADWA11_VK01_3b (1) L97Y VL amino acid sequence | 56 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSYEYPFTFGQGTKVEIK |
| ADWA11_VK01_3c (1) E98S VL amino acid sequence | 57 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSLSYPFTFGQGTKVEIK |

TABLE 1-continued

Amino acid and nucleotide sequences for αvβ8 integrin antibodies and other peptides.

| Name | SEQ ID NO. | Sequence |
|---|---|---|
| ADWA11_VK01_3d (1) Y99T VL amino acid sequence | 58 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSLETPFTFGQGTKVEIK |
| ADWA11_VK01_4a (1) F101L VL amino acid sequence | 59 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSLEYPLTFGQGTKVEIK |
| ADWA11_VK01_4b (1) F101W VL amino acid sequence | 60 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSLEYPWTFGQGTKVEIK |
| ADWA11_VK01_4c (1) Q105G VL amino acid sequence | 61 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSLEYPFTFGGGTKVEIK |
| ADWA11VK1 IGKV2-28 VL amino acid sequence | 62 | DIVMTQSPLSLPVTPGEPASISCRSTKSLLHFNGNTYL FWYLQKPGQSPQLLIYYMSNLASGVPDRFSGSGSGTDF TLKISRVEAEDVGVYYCMQSLEYPFTFGQGTKVEIK |
| ADWA11VK2 IGKV2-30 VL amino acid sequence | 63 | DVVMTQSPLSLPVTLGQPASISCRSTKSLLHFNGNTYL FWFQQRPGQSPRRLIYYMSNLASGVPDRFSGSGSGTDF TLKISRVEAEDVGVYYCMQSLEYPFTFGQGTKVEIK |
| ADWA11VK3 IGKV4-1 VL amino acid sequence | 64 | DIVMTQSPDSLAVSLGERATINCRSTKSLLHFNGNTYL FWYQQKPGQPPKLLIYYMSNLASGVPDRFSGSGSGTDF TLTISSLQAEDVAVYYCMQSLEYPFTFGQGTKVEIK |
| ADWA11VK4 IGKV1-39 VL amino acid sequence | 65 | DIQMTQSPSSLSASVGDRVTITCRSTKSLLHFNGNTYL FWYQQKPGKAPKLLIYYMSNLASGVPSRFSGSGSGTDF TLTISSLQPEDFATYYCMQSLEYPFTFGQGTKVEIK |
| ADWA11VK5 IGKV3-11 VL amino acid sequence | 66 | EIVLTQSPATLSLSPGERATLSCRSTKSLLHFNGNTYL FWYQQKPGQAPRLLIYYMSNLASGIPARFSGSGSGTDF TLTISSLEPEDFAVYYCMQSLEYPFTFGQGTKVEIK |
| ADWA11_VK01_2.1 VL amino acid sequence | 67 | DIQMTQSPSSLSASVGDRVTITCRSTKSLSHFNGNTYL FWYQQKPGKAPKRLIYYMSNLASGVPSRFSGSGSGTDF TLTISSLQPEDFATYYCQQSLEYPFTFGGGTKVEIK |
| ADWA11_VK01_2.2 VL amino acid sequence | 68 | DIQMTQSPSSLSASVGDRVTITCRSTKSLSHFNGNTYL FWYQQKPGKAPKRLIYYMSNLASGVPSRFSGSGSGTDF TLTISSLQPEDFATYYCMQSYEYPFTFGGGTKVEIK |
| ADWA11_VK01_2.3 VL amino acid sequence | 69 | DIQMTQSPSSLSASVGDRVTITCRSTKSLSHFNGNTYL FWYQQKPGKAPKRLIYYASNLASGVPSRFSGSGSGTDF TLTISSLQPEDFATYYCQQSLEYPFTFGGGTKVEIK |
| ADWA11VH1 IGHV1-46 VH amino acid sequence | 34 | QVQLVQSGAEVKKPGASVKVSCKASGFNIKDYYMNWVR QAPGQGLEWIGWIDPDNGNTIYDQKFQGRVTMTRDTST STVYMELSSLRSEDTAVYYCARRLLMDYWGQGTLVTVS S |
| ADWA11VH2 IGHV3-23 VH amino acid sequence | 35 | EVQLLESGGGLVQPGGSLRLSCAASGFNIKDYYMNWVR QAPGKGLEWIGWIDPDNGNTIYDDSVKGRFTISRDNSK NTLYLQMNSLRAEDTAVYYCARRLLMDYWGQGTLVTVS S |
| ADWA11VH3 IGHV3-30 VH amino acid sequence | 36 | QVQLVESGGGVVQPGRSLRLSCAASGFNIKDYYMNWVR QAPGKGLEWIGWIDPDNGNTIYDDSVKGRFTISRDNSK NTLYLQMNSLRAEDTAVYYCARRLLMDYWGQGTLVTVS S |
| ADWA11VH4 IGHV1-69 VH amino acid sequence | 37 | QVQLVQSGAEVKKPGSSVKVSCKASGFNIKDYYMNWVR QAPGQGLEWIGWIDPDNGNTIYDQKFQGRVTITADEST STAYMELSSLRSEDTAVYYCARRLLMDYWGQGTLVTVS |

TABLE 1-continued

Amino acid and nucleotide sequences for αvβ8 integrin antibodies and other peptides.

| Name | SEQ ID NO. | Sequence |
|---|---|---|
| ADWA11VH5 IGHV3-48 VH amino acid sequence | 38 | EVQLVESGGGLVQPGGSLRLSCAASGFNIKDYYMNWVR QAPGKGLEWIGWIDPDNGNTIYDDSVKGRFTISRDNAK NSLYLQMNSLRAEDTAVYYCARRLLMDYWGQGTLVTVS S |
| ADWA11 VH05_VK1 (also referred to herein as adwa_VH_1.5 T28N + F29I + R72A + A49G + L79A + N74T + A75S) VH amino acid sequence | 39 | EVQLVESGGGLVQPGGSLRLSCAASGFNIKDYYMNWVR QAPGKGLEWVGWIDPDNGNTIYDPKFQGRFTISADTSK NSAYLQMNSLRAEDTAVYYCARRLLMDYWGQGTLVTVS S |
| ADWA11VH5 D61E VH amino acid sequence | 40 | EVQLVESGGGLVQPGGSLRLSCAASGFNIKDYYMNWVR QAPGKGLEWVGWIDPDNGNTIYEPKFQGRFTISADTSK NSAYLQMNSLRAEDTAVYYCARRLLMDYWGQGTLVTVS S |
| ADWA11VH5 N55Q VH amino acid sequence | 41 | EVQLVESGGGLVQPGGSLRLSCAASGFNIKDYYMNWVR QAPGKGLEWVGWIDPDQGNTIYDPKFQGRFTISADTSK NSAYLQMNSLRAEDTAVYYCARRLLMDYWGQGTLVTVS S |
| ADWA11VH5 N28Q VH amino acid sequence | 42 | EVQLVESGGGLVQPGGSLRLSCAASGFQIKDYYMNWVR QAPGKGLEWVGWIDPDQGNTIYDPKFQGRFTISADTSK NSAYLQMNSLRAEDTAVYYCARRLLMDYWGQGTLVTVS S |
| ADWA11VH5 K30A VH amino acid sequence | 43 | EVQLVESGGGLVQPGGSLRLSCAASGFNIADYYMNWVR QAPGKGLEWVGWIDPDNGNTIYDPKFQGRFTISADTSK NSAYLQMNSLRAEDTAVYYCARRLLMDYWGQGTLVTVS S |
| ADWA11VH5 N57Q VH amino acid sequence | 44 | EVQLVESGGGLVQPGGSLRLSCAASGFNIKDYYMNWVR QAPGKGLEWVGWIDPDNGQTIYDPKFQGRFTISADTSK NSAYLQMNSLRAEDTAVYYCARRLLMDYWGQGTLVTVS S |
| ADWA11VH5 P62A VH amino acid sequence | 45 | EVQLVESGGGLVQPGGSLRLSCAASGFNIKDYYMNWVR QAPGKGLEWVGWIDPDNGNTIYDAKFQGRFTISADTSK NSAYLQMNSLRAEDTAVYYCARRLLMDYWGQGTLVTVS S |
| ADWA11VH5 K63A VH amino acid sequence | 46 | EVQLVESGGGLVQPGGSLRLSCAASGFNIKDYYMNWVR QAPGKGLEWVGWIDPDNGNTIYDPAFQGRFTISADTSK NSAYLQMNSLRAEDTAVYYCARRLLMDYWGQGTLVTVS S |
| Exemplary human integrin subunit alpha-V (ITGAV) amino acid sequence | 77 | MLLGTLLLILYILMLCRMFLLVGAPKANTTQPGIVEGG QVLKCDWSSTRRCQPIEFDATGNRDYAKDDPLEFKSHQ WFGASVRSKQDKILACAPLYHWRTEMKQEREPVGTCFL QDGTKTVEYAPCRSQDIDADGQGFCQGGFSIDFTKADR VLLGGPGSFYWQGQLISDQVAEIVSKYDPNVYSIKYNN QLATRTAQAIFDDSYLGYSVAVGDFNGDGIDDFVSGVP RAARTLGMVYIYDGKNMSSLYNFTGEQMAAYFGFSVAA TDINGDDYADVFIGAPLFMDRGSDGKLQEVGQVSVSLQ RASGDFQTTKLNGFEVFARFGSAIAPLGDLDQDGFNDI AIAAPYGGEDKKGIVYIFNGRSTGLNAVPSQILEGQWA ARSMPPSFGYSMKGATDIDKNGYPDLIVGAFGVDRAIL YRARPVITVNAGLEVYPSILNQDNKTCSLPGTALKVSC FNVRFCLKADGKGVLPRKLNFQVELLLDKLKQKGAIRR ALFLYSRSPSHSKNMTISRGGLMQCEELIAYLRDESEF RDKLTPITIFMEYRLDYRTAADTTGLQPILNQFTPANI SRQAHILLDCGEDNVCKPKLEVSVDSDQKKIYIGDDNP LTLIVKAQNQGEGAYEAELIVSIPLQADFIGVVRNNEA LARLSCAFKTENQTRQVVCDLGNPMKAGTQLLAGLRFS VHQQSEMDTSVKFDLQIQSSNLFDKVSPVVSHKVDLAV LAAVEIRGVSSPDHIFLPIPNWEHKENPETEEDVGPVV QHIYELRNNGPSSFSKAMLHLQWPYKYNNNTLLYILHY DIDGPMNCTSDMEINPLRIKISSLQTTEKNDTVAGQGE RDHLITKRDLALSEGDIHTLGCGVAQCLKIVCQVGRLD |

TABLE 1-continued

Amino acid and nucleotide sequences for αvβ8 integrin antibodies and other peptides.

| Name | SEQ ID NO. | Sequence |
|---|---|---|
| | | RGKSAILYVKSLLWTETFMNKENQNHSYSLKSSASFNV IEFPYKNLPIEDITNSTLVTTNVTWGIQPAPMPVPVWV IILAVLAGLLLLAVLVFVMYRMGFFKRVRPPQEEQERE QLQPHENGEGNSET |
| Exemplary human integrin subunit beta 8 (ITGB8) amino acid sequence | 78 | MCGSALAFFTAAFVCLQNDRRGPASFLWAAWVFSLVLG LGQGEDNRCASSNAASCARCLALGPECGWCVQEDFISG GSRSERCDIVSNLISKGCSVDSIEYPSVHVIIPTENEI NTQVTPGEVSIQLRPGAEANFMLKVHPLKKYPVDLYYL VDVSASMHNNIEKLNSVGNDLSRKMAFFSRDFRLGFGS YVDKTVSPYISIHPERIHNQCSDYNLDCMPPHGYIHVL SLTENITEFEKAVHRQKISGNIDTPEGGFDAMLQAAVC ESHIGWRKEAKRLLLVMTDQTSHLALDSKLAGIVVPND GNCHLKNNVYVKSTTMEHPSLGQLSEKLIDNNINVIFA VQGKQFHWYKDLLPLLPGTIAGEIESKAANLNNLVVEA YQKLISEVKVQVENQVQGIYFNITAICPDGSRKPGMEG CRNVTSNDEVLFNVTVTMKKCDVTGGKNYAIIKPIGFN ETAKIHIHRNCSCQCEDNRGPKGKCVDETFLDSKCFQC DENKCHFDEDQFSSESCKSHKDQPVCSGRGVCVCGKCS CHKIKLGKVYGKYCEKDDFSCPYHHGNLCAGHGECEAG RCQCFSGWEGDRCQCPSAAAQHCVNSKGQVCSGRGTCV CGRCECTDPRSIGRFCEHCPTCYTACKENWNCMQCLHP HNLSQAILDQCKTSCALMEQQHYVDQTSECFSSPSYLR IFFIIFIVTFLIGLLKVLIIRQVILQWNSNKIKSSSDY RVSASKKDKLILQSVCTRAVTYRREKPEEIKMDISKLN AHETFRCNF |
| Exemplary mouse integrin subunit alpha-V (ITGAV) amino acid sequence | 79 | MAAPGRLLLRPRPGGLLLLLPGLLLPLADAFNLDVESP AEYAGPEGSYFGFAVDFFEPSTSSRMFLLVGAPKANTT QPGIVEGGQVLKCECSSSRRCQPIEFDSTGNRDYAKDD PLEFKSHQWFGASVRSKQDKILACAPLYHWRTEMKQER EPVGTCFLQDGTKTVEYAPCRSKNIDADGQGFCQGGFS IDFTKADRVLLGGPGSFYWQGQLISDQVAEIISKYDPN VYSIKYNNQLATRTAQAIFDDSYLGYSVAVGDFNGDGI EDFVSGVPRAARTLGMVYIYDGKNMSSLHNFTGEQMAA YFGFSVAATDINGDDYADVFIGAPLFMDRGSDGKLQEV GQVSVSLQRAVGDFQTTKLNGFEVFARFGSAIAPLGDL DQDGFNDIAIAAPYGGEDKKGLVYIFNGRSTGLNSVPS QILEGQWAAQSMPPSFGYSMKGATDVDRNGYPDLVVGA FGVDRAVLYRARPVVTVNAGLEVYPSILNQDNKICPLP GTALKVSCFNVRFCLKADGKGTLPRKLHFQVELLLDKL KQKGAIRRALFLHNRSPVHSKTMTVFRGGQMCEELVA YLRDESEFRDKLTPITIFMEYRLDQRTAADATGLQPIL NQFTPANVSRQAHILLDCGEDNVCKPKLEVSVNSDQKK IYIGDDNPLTLTVKAQNQGEGAYEAELIVSIPPQADFI GVVRNNEALARLSCAFKTENQTRQVVCDLGNPMKAGTQ LLAGLRFSVHQQSEMDTSVKFDLKIQSSNSFDNVSPVV SYKVDLAVLAAVEIRGVSSPDHIFLPIPNWEYKENPET EEDVGPIVQHIYELRNNGPSSFSKAILNLQWPYKYNNN TLLYILHYDIDGPMNCTADTEINPLRIKTPEKNDTAAA GQGERNHLITKRDLTLREGDVHTLGCGIAKCLQITCQV GRLDRGKSAILYVKSLLWTETFMNKENQNHSYSLKSSA SFNIIEFPYKNLPIEDLFNSTLVITNITWGIQPAPMPV PVWVIILAVLAGLLLLAVLVFVMYRMGFFKRVRPPQEE QEREQLQPHENGEGNSET |
| Exemplary mouse integrin subunit beta 8 (ITGB8) amino acid sequence | 80 | MCGSALAFLTAALLSLHNCQRGPALVLGAAWVFSLVLG LGQSEHNRCGSANVVSCARCLQLGPECGWCVQEDFVSG GSGSERCDTVSSLISKGCPVDSIEYLSVHVVTSSENEI NTQVTPGEVSVQLHPGAEANFMLKVRPLKKYPVDLYYL VDVSASMHNNIEKLNSVGNDLSKKMALYSRDFRLGFGS YVDKTVSPYISIHPERIHNQCSDYNLDCMPPHGYIHVL SLTENITEFEKAVHRQKISGNIDTPEGGFDAMLQAAVC ESHIGWRKEAKRLLLVMTDQTSHLALDSKLAGIVVPND GNCHLKNNVYVKSTTMEHPSLGQLSEKLIDNNINVIFA VQGKQFHWYKDLLPLLPGAIAGEIESKAANLNNLVVEA YKKIISEVKVQLENQVHGVHFNITAICPDGARKPGISG CGNVTSNDEVLFNVTVVMKTCDIMGGKNYAIIKPIGFN ETTKVHIHRSCSCQCENHRGLKGQCAEAAPDPKCPQCD DSRCHFDEDQFPSETCKPQEDQPVCSGRGVCICGKCLC HKTKLGRVYGQYCEKDDFSCPYLHGDVCAGHGECEGGR CQCFSGWEGDRCQCPSAAQHCVNSKGQVCSGRGTCVC GRCECTDPRSIGRLCEHCPTCHLSCSENWNCLQCLHPH |

TABLE 1-continued

Amino acid and nucleotide sequences for αvβ8 integrin antibodies and other peptides.

| Name | SEQ ID NO. | Sequence |
|---|---|---|
| | | NLSQAALDQCKSSCAVMEQHRMDQTSECLSGPSYLRIF FIIFIVTFLIGLLKVLIIRQVILQWNNNKIKSSSDYRM SASKKDKLILQSVCTRAVTYRREKPEEIKMDISKLNAQ EAFRCNF |
| Exemplary cynomolgus integrin subunit alpha-V (ITGAV) amino acid sequence | 84 | MASPPRRRLRLGPRGLPLLLSGLLLPLCRAFNLDVDSP AEYSGPEGSYFGFAVDFFVPSASSRMFLLVGAPKANTT QPGIVEGGQVLKCDWSSTRRCQPIEFDATGNRDYAKDD PLEFKSHQWFGASVRSKQDKILACAPLYHWRTELKQER EPVGTCFLQDGTKTVEYAPCRSQDIDADGQGFCQGGFS IDFTKADRVLLGGPGSFYWQGQLISDQVAEIVSKYDPN VYSIKYNNQLATRTAQAIFDDSYLGYSVAVGDFNGDGI DDFVSGVPRAARTLGMVYIYDGKNMSSIYNFTGDQMAA YFGFSVAATDINGDDYADVFIGAPLFMDRGSDGKLQEV GQVSVSLQRASGDFQTTKLNGFEVFARFGSAIAPLGDL DQDGFNDIAIAAPYGGEDKKGIVYIFNGRSTGLNAVPS QILEGQWAARSMPPSFGYSMKGATDIDKNGYPDLIVGA FGVDRAILYRARPVITVNAGLEVYPSILNQDNKTCSLP GTALKVSCFNVRFCLKADGKGVLPRKLNFQVELLLDKL KQKGAIRRALFLYSRSPSHSKNMTISRGGLMQCEELIA YLRDESEFRDKLTPITIFMEYWLDYRTAADTTGLQPIL NQFTPANISRQAHILLLDCGEDNVCKPKLEVFVDSDQKK IYIGDDNPLTLIVKAQNQGEGAYEAELIVSIPLQADFI GVVRNSEALARLSCAFKTENQTRQVVCDLGNPMKAGTQ LLAGLRFSVHQQSEMDTSVKFDLQIQSSNLFDKVSPVV SHKVDLAVLAAVEIRGVSSPDHIFLPIPNWEHKENPET EEDVGPVVQHIYELRNNGPSSFSKAMLHLQWPYKYNNN TLLYILHYDIDGPMNCTSDMEINPLRIKISSLQATEKN DTVAGQGERDHLITKRDLALSEGDIHTLGCGVAQCLKI VCQVGRLDRGKSAILYVKSLLWTETFMNKENQNHSYSL KSSASFNVIEFPYKNLPIEDITNSTLVTTNVTWGIQPA PMPVPVWVIILAVLAGLLLLAVLVFVMYRMGFFKRVRP PQEEQEREQLQPHENGEGNSET |
| Exemplary cynomolgus integrin subunit beta 8 (ITGB8) amino acid sequence | 85 | MCGSALAFFTAAFVCLQNDRRGPASFLWAAWVLSLVLG LGQGEDNICASSNAASCARCLALGPECGWCVQEDFISG GSRSERCDIVSNLISKGCSVDSIEYPSVHVIIPTENEI NTQVTPGEVSIQLRPGAEANFMLKIHPLKKYPVDLYYL VDVSASMHNNIEKLNSVGNDLSRKMAFFSRDFRLGFGS YVDKTVSPYISIHPERIHNQCSDYNLDCMPPHGYIHVL SLTENITEFEKAVHRQKISGNIDTPEGGFDAMLQAAVC ESHIGWRKEAKRLLLVMTDQTSHLALDSKLAGIVVPND GNCHLKNNVYVKSTTMEHPSLGQLSEKLIDNNINVIFA VQGKQFHWYKDLLPLLPGTIAGEIESKAANLNNLVVEA YQKLISEVKVHVENQVQGVYFNITAICPDGSRKPGMEG CRNVTSNHEVLFNVTVTMKKCDVTGGKNYAIIKPIGFN ETAKIHIHRNCSCQCEDNRGPKGKCVDETFLDSKCFQC DENKCHFDEDQFSSESCKSHKDQPVCSGRGVCVCGKCS CHKIKLGKVYGKYCEKDDFSCPYHHGNLCAGHGECEAG RCQCFSGWEGDRCQCPSAAAQHCVNSKGQVCSGRGTCV CGRCECTDPRSIGRFCEHCPTCHTACKENWNCVQCLHP HNLSQAILDQCKTSCALMEQQHYVDQTSECFSSPSYLR IFFIIFIVTFLIGLLKVLIIRQVILQWNSNKIKSSSDY RVSASKKDKLILQSVCTRAVTYRREKPEEIKMDISKLN AHETFRCNF |
| Exemplary human wild type IgG1 Fc (includes portion of $C_H1$ and hinge, $C_H2$ and $C_H3$) Wild type LLGG effector function sequence is indicated in italics NST Asn297 N-linked glycosylation site | 81 XXX | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PE*LLGG*PSVFLFPPKPKDTLMISRTPEVTCVVVDVSHE DPEVKFNWYVDGVEVHNAKTKPREEQY<u>NST</u>YRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPG |
| Exemplary human IgG1 constant region Wild type LLGG effector function sequence is | 82 XXXX | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PE*LLGG*PSVFLFPPKPKDTLMISRTPEVTCVVVDVSHE DPEVKFNWYVDGVEVHNAKTKPREEQY<u>NST</u>YRVVSVLT |

TABLE 1-continued

Amino acid and nucleotide sequences for αvβ8 integrin antibodies and other peptides.

| Name | SEQ ID NO. | Sequence |
|---|---|---|
| indicated in italics NST Asn297 N-linked glycosylation site Includes terminal Lysine | | VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Exemplary human effectorless IgG1 constant region | 184 | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PEAAGAPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPG |
| Exemplary human effectorless IgG1 constant region nucleic acid sequence | 192 | GCCTCCACCAAGGGCCCATCGGTCTTCCCCCTGGCACC CTCCTCCAAGAGCACCTCTGGGGGCACAGCGGCCCTGG GCTGCCTGGTCAAGGACTACTTCCCCGAACCGGTGACG GTGTCGTGGAACTCAGGCGCCCTGACCAGCGGCGTGCA CACCTTCCCGGCTGTCCTACAGTCCTCAGGACTCTACT CCCTCAGCAGCGTGGTGACCGTGCCCTCCAGCAGCTTG GGCACCCAGACCTACATCTGCAACGTGAATCACAAGCC CAGCAACACCAAGGTGGACAAGAAAGTTGAGCCCAAAT CTTGTGACAAAACTCACACATGCCCACCGTGCCCAGCA CCTGAAGCCGCTGGGGCACCGTCAGTCTTCCTCTTCCC CCCAAAACCCAAGGACACCCTCATGATCTCCCGGACCC CTGAGGTCACATGCGTGGTGGTGGACGTGAGCCACGAA GACCCTGAGGTCAAGTTCAACTGGTACGTGGACGGCGT GGAGGTGCATAATGCCAAGACAAAGCCGCGGGAGGAGC AGTACAACAGCACGTACCGTGTGGTCAGCGTCCTCACC GTCCTGCACCAGGACTGGCTGAATGGCAAGGAGTACAA GTGCAAGGTCTCCAACAAAGCCCTCCCAGCCCCCATCG AGAAAACCATCTCCAAAGCCAAAGGGCAGCCCCGAGAA CCACAGGTGTACACCCTGCCCCCATCCCGGGAGGAGAT GACCAAGAACCAGGTCAGCCTGACCTGCCTGGTCAAAG GCTTCTATCCCAGCGACATCGCCGTGGAGTGGGAGAGC AATGGGCAGCCGGAGAACAACTACAAGACCACGCCTCC CGTGCTGGACTCCGACGGCTCCTTCTTCCTCTATAGCA AGCTCACCGTGGACAAGAGCAGGTGGCAGCAGGGGAAC GTCTTCTCATGCTCCGTGATGCATGAGGCTCTGCACAA CCACTACACGCAGAAGAGCCTCTCCCTGTCCCCCGGA |
| Exemplary human effectorless IgG1 constant region (with terminal lysine) | 181 | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCPA PEAAGAPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPRE PQVYTLPPSREEMTKNQVSLTCLVKGFYPSDIAVEWES NGQPENNYKTTPPVLDSDGSFFLYSKLTVDKSRWQQGN VFSCSVMHEALHNHYTQKSLSLSPGK |
| Exemplary human effectorless IgG1 constant region nucleic acid sequence (with terminal lysine) | 193 | GCCTCCACCAAGGGCCCATCGGTCTTCCCCCTGGCACC CTCCTCCAAGAGCACCTCTGGGGGCACAGCGGCCCTGG GCTGCCTGGTCAAGGACTACTTCCCCGAACCGGTGACG GTGTCGTGGAACTCAGGCGCCCTGACCAGCGGCGTGCA CACCTTCCCGGCTGTCCTACAGTCCTCAGGACTCTACT CCCTCAGCAGCGTGGTGACCGTGCCCTCCAGCAGCTTG GGCACCCAGACCTACATCTGCAACGTGAATCACAAGCC CAGCAACACCAAGGTGGACAAGAAAGTTGAGCCCAAAT CTTGTGACAAAACTCACACATGCCCACCGTGCCCAGCA CCTGAAGCCGCTGGGGCACCGTCAGTCTTCCTCTTCCC CCCAAAACCCAAGGACACCCTCATGATCTCCCGGACCC CTGAGGTCACATGCGTGGTGGTGGACGTGAGCCACGAA GACCCTGAGGTCAAGTTCAACTGGTACGTGGACGGCGT GGAGGTGCATAATGCCAAGACAAAGCCGCGGGAGGAGC AGTACAACAGCACGTACCGTGTGGTCAGCGTCCTCACC GTCCTGCACCAGGACTGGCTGAATGGCAAGGAGTACAA GTGCAAGGTCTCCAACAAAGCCCTCCCAGCCCCCATCG AGAAAACCATCTCCAAAGCCAAAGGGCAGCCCCGAGAA CCACAGGTGTACACCCTGCCCCCATCCCGGGAGGAGAT GACCAAGAACCAGGTCAGCCTGACCTGCCTGGTCAAAG |

TABLE 1-continued

Amino acid and nucleotide sequences for αvβ8 integrin antibodies and other peptides.

| Name | SEQ ID NO. | Sequence |
|---|---|---|
| | | GCTTCTATCCCAGCGACATCGCCGTGGAGTGGGAGAGC AATGGGCAGCCGGAGAACAACTACAAGACCACGCCTCC CGTGCTGGACTCCGACGGCTCCTTCTTCCTCTATAGCA AGCTCACCGTGGACAAGAGCAGGTGGCAGCAGGGGAAC GTCTTCTCATGCTCCGTGATGCATGAGGCTCTGCACAA CCACTACACGCAGAAGAGCCTCTCCCTGTCCCCCGGAA AA |
| Exemplary human IgG2 constant region | 70 | ASTKGPSVFPLAPCSRSTSESTAALGCLVKDYFPEPVT VSWNSGALTSGVHTFPAVLQSSGLYSLSSVVTVPSSNF GTQTYTCNVDHKPSNTKVDKTERKCCVECPPCPAPPVA GPSVFLFPPKPKDTLMISRTPEVTCVVVDVSHEDPEVQ FNWYVDGVEVHNAKTKPREEQFNSTFRVVSVLTVVHQD WLNGKEYKCKVSNKGLPAPIEKTISKTKGQPREPQVYT LPPSREEMTKNQVSLTCLVKGFYPSDIAVEWESNGQPE NNYKTTPPMLDSDGSFFLYSKLTVDKSRWQQGNVFSCS VMHEALHNHYTQKSLSLSPGK |
| Exemplary human kappa light chain constant region (Cκ) | 83 | RTVAAPSVFIFPPSDEQLKSGTASVVCLLNNFYPREAK VQWKVDNALQSGNSQESVTEQDSKDSTYSLSSTLTLSK ADYEKHKVYACEVTHQGLSSPVTKSFNRGEC |
| Exemplary human kappa light chain constant region (Cκ) nucleic acid sequence | 194 | CGAACTGTGGCTGCACCATCTGTCTTCATCTTCCCGCC ATCTGATGAGCAGTTGAAATCTGGAACTGCCTCTGTTG TGTGCCTGCTGAATAACTTCTATCCCAGAGAGGCCAAA GTACAGTGGAAGGTGGATAACGCCCTCCAATCGGGTAA CTCCCAGGAGAGTGTCACAGAGCAGGACAGCAAGGACA GCACCTACAGCCTCAGCAGCACCCTGACGCTGAGCAAA GCAGACTACGAGAAACACAAAGTCTACGCCTGCGAAGT CACCCATCAGGGCCTGAGCTCGCCCGTCACAAAGAGCT TCAACAGGGGAGAGTGT |
| Exemplary murine IgG1 heavy chain constant region | 86 | AKTTPPSVYPLAPGSAAQTNSMVTLGCLVKGYFPEPVT VTWNSGSLSSGVHTFPAVLQSDLYTLSSSVTVPSSTWP SETVTCNVAHPASSTKVDKKIVPRDCGCKPCICTVPPV SSVFIFPPKPKDVLTITLTPKVTCVVVDISKDDPEVQF SWFVDDVEVHTAQTQPREEQFNSTFRSVSELPIMHQDW LNGKAFACAVNSAAFPAPIEKTISKTKGRPKAPQVYTI PPPKEQMAKDKVSLTCMITDFFPEDITVEWQWNGQPAE NYKNTQPIMDTDGSYFVYSKLNVQKSNWEAGNTFTCSV LHEGLHNHHTEKSLSHSPGK |
| Exemplary murine light chain constant region | 87 | RADAAPTVSIFPPSSEQLTSGGASVVCFLNNFYPKDIN VKWKIDGSERQNGVLNSWTDQDSKDSTYSMSSTLTLTK DEYERHNSYTCEATHKTSTSPIVKSFNRNEC |
| adwa_VH_1.1 T28N + F29I | 88 | EVQLVESGGGLVQPGGSLRLSCAASGFniKDYYMNWVR QAPGKGLEWVAWIDPDNGNTIYDPKFQGRFTISRDNAK NSLYLQMNSLRAEDTAVYYCARRLLMDYWGQGTLVTVS S |
| adwa_VH_1.2 T28N + F29I + R72A | 89 | EVQLVESGGGLVQPGGSLRLSCAASGFniKDYYMNWVR QAPGKGLEWVAWIDPDNGNTIYDPKFQGRFTISaDNAK NSLYLQMNSLRAEDTAVYYCARRLLMDYWGQGTLVTVS S |
| adwa_VH_1.3 T28N + F29I + R72A + A49G + L79A | 90 | EVQLVESGGGLVQPGGSLRLSCAASGFniKDYYMNWVR QAPGKGLEWVgWIDPDNGNTIYDPKFQGRFTISaDNAK NSaYLQMNSLRAEDTAVYYCARRLLMDYWGQGTLVTVS S |
| adwa_VH_1.4 T28N + F29I + R72A + N74T + A75S | 91 | EVQLVESGGGLVQPGGSLRLSCAASGFniKDYYMNWVR QAPGKGLEWVAWIDPDNGNTIYDPKFQGRFTISaDtsK NSLYLQMNSLRAEDTAVYYCARRLLMDYWGQGTLVTVS S |
| adwa_VL_1.2 L46R + Y36F | 92 | DIQMTQSPSSLSASVGDRVTITCRSTKSLLHFNGNTYL FWfQQKPGKAPKrLIYYMSNLASGVPSRFSGSGSGTDF TLTISSLQPEDFATYYCMQSLEYPFTFGQGTKVEIK |

TABLE 1-continued

Amino acid and nucleotide sequences for αvβ8 integrin antibodies and other peptides.

| Name | SEQ ID NO. | Sequence |
|---|---|---|
| VH05-2(F64V) VK01 | 93 | EVQLVESGGGLVQPGGSLRLSCAASGFNIKDYYMNWVR QAPGKGLEWVGWIDPDQGNTIYEPKVQGRFTISADTSK NSAYLQMNSLRAEDTAVYYCARRLLMDYWGQGTLVTVS S |
| 5662_01 | 94 | EPKFQGRFTISADTS |
| 5662_02 | 95 | TAVYYCARRLLMDYW |
| 5662_03 | 96 | TAVYYSARRLLXDYW |
| 5662_04 | 97 | KSLLHFNGNTYLFWY |
| 5662_05 | 98 | PKRLIYYMSNLASGV |
| 5662_06 | 99 | PKRLIYYXSNLASGV |
| 5662_07 | 100 | LIYYMSNLASGVPSR |
| 5662_08 | 101 | LIYYXSNLASGVPSR |
| 5662_09 | 102 | FATYYCMQSLEYPFT |
| 5662_10 | 103 | FATYYSXQSLEYPFT |
| 5662_11 | 104 | EYPFTFGQGTKVEIK |
| 5662_12 | 105 | EPKVQGRFTISADTS |
| 5662_13 | 106 | KSLSHFNGNTYLFWY |
| 5662_14 | 107 | FATYYCQQSLEYPFT |
| 5662_15 | 108 | FATYYSQQSLEYPFT |
| 5662_16 | 109 | FATYYCMQSYEYPFT |
| 5662_17 | 110 | FATYYSXQSYEYPFT |
| 5662_18 | 111 | EYPFTFGGGTKVEIK |
| 5662_19 | 112 | KRLIYYASNLASGVP |
| 5662_20 | 113 | KRLIYYMSSLASGVP |
| 5662_21 | 114 | KRLIYYXSSLASGVP |
| 5662_22 | 115 | QGDSLRTYYASWYQQ |
| 5662_23 | 116 | VLVIYGKHKRPSGIP |
| 5662_24 | 117 | EADYYCMSRSIWGNP |
| 5662_25 | 118 | EADYYSXSRSIWGNP |
| 5662_26 | 119 | SETLSLTCAVSGYST |
| 5662_27 | 120 | GLEWIGSISHTGNTY |
| 5662_28 | 121 | NPPLKSRVTISVDTS |
| 5662_29 | 122 | DTAVVYCARGGGISR |
| ADWA 11 VK01 | 123 | DIQMTQSPSSLSASVGDRVTITCRSTKSLLHFNGNTYL FWYQQKPGKAPKRLIYYMSNLASGVPSRFSGSGSGTDF TLTISSLQPEDFATYYCMQSLEYPFTFGQGTKVEIKRT VAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC |
| ADWA11 VH05 | 124 | EVQLVESGGGLVQPGGSLRLSCAASGFNIKDYYMNWVR QAPGKGLEWVGWIDPDNGNTIYDPKFQGRFTISADTSK NSAYLQMNSLRAEDTAVYYCARRLLMDYWGQGTLVTVS |

TABLE 1-continued

Amino acid and nucleotide sequences for αvβ8 integrin antibodies and other peptides.

| Name | SEQ ID NO. | Sequence |
|---|---|---|
| | | SASTKGPSVFPLAPSSKSTSGGTAALGCLVKDYFPEPV<br>TVSWNSGALTSGVHTFPAVLQSSGLYSLSSVVTVPSSS<br>LGTQTYICNVNHKPSNTKVDKKVEPKSCDKTHTCPPCP<br>APEAAGAPSVFLFPPKPKDTLMISRTPEVTCVVVDVSH<br>EDPEVKFNWYVDGVEVHNAKTKPREEQYNSTYRVVSVL<br>TVLHQDWLNGKEYKCKVSNKALPAPIEKTISKAKGQPR<br>EPQVYTLPPSREEMTKNQVSLTCLVKGFYPSDIAVEWE<br>SNGQPENNYKTTPPVLDSDGSFFLYSKLTVDKSRWQQG<br>NVFSCSVMHEALHNHYTQKSLSLSPGK |
| ADWA11 VH05 without terminal lysine residue | 182 | EVQLVESGGGLVQPGGSLRLSCAASGFNIKDYYMNWVR<br>QAPGKGLEWVGWIDPDNGNTIYDPKFQGRFTISADTSK<br>NSAYLQMNSLRAEDTAVYYCARRLLMDYWGQGTLVTVS<br>SASTKGPSVFPLAPSSKSTSGGTAALGCLVKDYFPEPV<br>TVSWNSGALTSGVHTFPAVLQSSGLYSLSSVVTVPSSS<br>LGTQTYICNVNHKPSNTKVDKKVEPKSCDKTHTCPPCP<br>APEAAGAPSVFLFPPKPKDTLMISRTPEVTCVVVDVSH<br>EDPEVKFNWYVDGVEVHNAKTKPREEQYNSTYRVVSVL<br>TVLHQDWLNGKEYKCKVSNKALPAPIEKTISKAKGQPR<br>EPQVYTLPPSREEMTKNQVSLTCLVKGFYPSDIAVEWE<br>SNGQPENNYKTTPPVLDSDGSFFLYSKLTVDKSRWQQG<br>NVFSCSVMHEALHNHYTQKSLSLSPG |
| Wild type human IgG1 hinge | 125 | EPKSCDKTHTCPPCPAPELLGGP |
| Effector null (3m, triple mutant) variant human IgG1 hinge | 126 | EPKSCDKTHTCPPCPAPEAAGAP |
| IGHV3-07 (DP-54) heavy chain germline | 127 | EVQLVESGGGLVQPGGSLRLSCAASGFTFSSYWMSWVR<br>QAPGKGLEWVANIKQDGSEKYYVDSVKGRFTISRDNAK<br>NSLYLQMNSLRAEDTAVYYCAR |
| IGKV1-39 (DPK-9) light chain germline | 128 | DIQMTQSPSSLSASVGDRVTITCRASQSISSYLNWYQQ<br>KPGKAPKLLIYAASSLQSGVPSRFSGSGSGTDFTLTIS<br>SLQPEDFATYYCQQSYSTP |
| synthetic peptide HA derived from Influenza A hemagglutinin | 129 | PKYVKQNTLKLAT |
| TET 830 modified/T-helper epitope from tetanus toxoid | 130 | AQYIKANSKFIGITEL |
| IMGT - heavy chain | 195 | EVQLVESGGG LVQPGGSLRL SCAASGFTFS<br>SYWMSWVRQA PGKGLEWVAN IKQDGSEKYY<br>VDSVKGRFTI SRDNAKNSLY LQMNSLRAED<br>TAVYYCAR |
| IMGT - light chain | 196 | DIQMTQSPSS LSASVGDRVT ITCRASQSIS<br>----S-YLNW YQQKPGKAPK LLIYAASSLQ<br>SGVPSRFSGS GSGTDFTLTI SSLQPEDFAT<br>YYCQQSYSTP |

*In some peptides, methionine was replaced with norleucine.

TABLE 14

Exemplary heavy chain CDRs according to Kabat

| VH (SEQ ID NO) | CDR-H1 (SEQ ID NO) | CDR-H2 (SEQ ID NO) | CDR-H3 (SEQ ID NO) |
|---|---|---|---|
| Mouse ADWA-11 VH (SEQ ID NO: 20) | DYYMN (SEQ ID NO: 22) | WIDPDNGNTIYDPKFQG (SEQ ID NO: 23) | RLLMDY (SEQ ID NO: 24) |
| ADWA11 2.4 VH (SEQ ID NO: 6) | DYYMN (SEQ ID NO: 8) | WIDPDQGNTIYEPKFQG (SEQ ID NO: 9) | RLLMDY (SEQ ID NO: 10) |

TABLE 14-continued

Exemplary heavy chain CDRs according to Kabat

| VH (SEQ ID NO) | CDR-H1 (SEQ ID NO) | CDR-H2 (SEQ ID NO) | CDR-H3 (SEQ ID NO) |
|---|---|---|---|
| ADWA11VH1 IGHV1-46 (SEQ ID NO: 34) | DYYMN (SEQ ID NO: 8) | WIDPDNGNTIYDQKFQG (SEQ ID NO: 157) | RLLMDY (SEQ ID NO: 10) |
| ADWA11VH2 IGHV3-23 (SEQ ID NO: 35) | DYYMN (SEQ ID NO: 8) | WIDPDNGNTIYDDSVKG (SEQ ID NO: 158) | RLLMDY (SEQ ID NO: 10) |
| ADWA11VH3 IGHV3-30 (SEQ ID NO: 36) | DYYMN (SEQ ID NO: 8) | WIDPDNGNTIYDDSVKG (SEQ ID NO: 158) | RLLMDY (SEQ ID NO: 10) |
| ADWA11VH4 IGHV1-69 (SEQ ID NO: 37) | DYYMN (SEQ ID NO: 8) | WIDPDNGNTIYDQKFQG (SEQ ID NO: 157) | RLLMDY (SEQ ID NO: 10) |
| ADWA11VH5 IGHV3-48 (SEQ ID NO: 38) | DYYMN (SEQ ID NO: 8) | WIDPDNGNTIYDDSVKG (SEQ ID NO: 158) | RLLMDY (SEQ ID NO: 10) |
| ADWA11 VH05_VK1 (also referred to herein as adwa_VH_1.5 T28N + F29I + R72A + A49G + L79A +0 N74T + A75S) (SEQ ID NO: 39) | DYYMN (SEQ ID NO: 8) | WIDPDNGNTIYDPKFQG (SEQ ID NO: 23) | RLLMDY (SEQ ID NO: 10) |
| ADWA11VH5 D61E (SEQ ID NO: 40) | DYYMN (SEQ ID NO: 8) | WIDPDNGNTIYEPKFQG (SEQ ID NO: 160) | RLLMDY (SEQ ID NO: 10) |
| ADWA11VH5 N55Q (SEQ ID NO: 41) | DYYMN (SEQ ID NO: 8) | WIDPDQGNTIYDPKFQG (SEQ ID NO: 161) | RLLMDY (SEQ ID NO: 10) |
| ADWA11VH5 N28Q (SEQ ID NO: 42) | DYYMN (SEQ ID NO: 8) | WIDPDQGNTIYDPKFQG (SEQ ID NO: 161) | RLLMDY (SEQ ID NO: 10) |
| ADWA11VH5 K30A (SEQ ID NO: 43) | DYYMN (SEQ ID NO: 8) | WIDPDNGNTIYDPKFQG (SEQ ID NO: 23) | RLLMDY (SEQ ID NO: 10) |
| ADWA11VH5 N57Q (SEQ ID NO: 44) | DYYMN (SEQ ID NO: 8) | WIDPDNGQTIYDPKFQG (SEQ ID NO: 162) | RLLMDY (SEQ ID NO: 10) |
| ADWA11VH5 P62A (SEQ ID NO: 45) | DYYMN (SEQ ID NO: 8) | WIDPDNGNTIYDAKFQG (SEQ ID NO: 163) | RLLMDY (SEQ ID NO: 10) |
| ADWA11VH5 K63A (SEQ ID NO: 46) | DYYMN (SEQ ID NO: 8) | WIDPDNGNTIYDPAFQG (SEQ ID NO: 165) | RLLMDY (SEQ ID NO: 10) |
| adwa_VH_1.1 T28N + F29I (SEQ ID NO: 88) | DYYMN (SEQ ID NO: 8) | WIDPDNGNTIYDPKFQG (SEQ ID NO: 23) | RLLMDY (SEQ ID NO: 10) |
| adwa_VH_1.2 T28N + F29I + R72A (SEQ ID NO: 89) | DYYMN (SEQ ID NO: 8) | WIDPDNGNTIYDPKFQG (SEQ ID NO: 23) | RLLMDY (SEQ ID NO: 10) |
| adwa_VH_1.3 T28N + F29I + R72A + A49G + L79A (SEQ ID NO: 90) | DYYMN (SEQ ID NO: 8) | WIDPDNGNTIYDPKFQG (SEQ ID NO: 23) | RLLMDY (SEQ ID NO: 10) |
| adwa_VH_1.4 T28N + F29I + R72A + N74T + A75S (SEQ ID NO: 91) | DYYMN (SEQ ID NO: 8) | WIDPDNGNTIYDPKFQG (SEQ ID NO: 23) | RLLMDY (SEQ ID NO: 10) |
| VH05-2(F64V) VK01 (SEQ ID NO: 93) | DYYMN (SEQ ID NO: 8) | WIDPDQGNTIYEPKVQG (SEQ ID NO: 166) | RLLMDY (SEQ ID NO: 10) |

TABLE 15

Exemplary light chain CDRs according to Kabat

| VL (SEQ ID NO) | CDR-L1 (SEQ ID NO) | CDR-L2 (SEQ ID NO) | CDR-L3 (SEQ ID NO) |
|---|---|---|---|
| Mouse ADWA-11 VL (SEQ ID NO: 21) | RSTKSLLHFNGNTYLF (SEQ ID NO: 25) | YYMSNLAS (SEQ ID NO: 26) | MQSLEYPFT (SEQ ID NO: 27) |
| ADWA11 2.4 (SEQ ID NO: 7) | RSTKSLSHFNGNTYLF (SEQ ID NO: 11) | YYMSSLAS (SEQ ID NO: 12) | QQSLEYPFT (SEQ ID NO: 13) |
| ADWA11_VK01 (1) (also referred to herein as adwa_VL_1.1 L46R) (SEQ ID NO: 47) | RSTKSLLHFNGNTYLF (SEQ ID NO: 25) | YYMSNLAS (SEQ ID NO: 26) | MQSLEYPFT (SEQ ID NO: 27) |
| ADWA11_VK01_1a (1) L29I (SEQ ID NO: 48) | RSTKSILHFNGNTYLF (SEQ ID NO: 138) | YYMSNLAS (SEQ ID NO: 26) | MQSLEYPFT (SEQ ID NO: 27) |
| ADWA11_VK01_1b (1) L30S (SEQ ID NO: 49) | RSTKSLSHFNGNTYLF (SEQ ID NO: 11) | YYMSNLAS (SEQ ID NO: 26) | MQSLEYPFT (SEQ ID NO: 27) |
| ADWA11_VK01_1c (1) T36S (SEQ ID NO: 50) | RSTKSLLHFNGNSYLF (SEQ ID NO: 140) | YYMSNLAS (SEQ ID NO: 26) | MQSLEYPFT (SEQ ID NO: 27) |
| ADWA11_VK01_2a (1) Y55A (SEQ ID NO: 51) | RSTKSLLHFNGNTYLF (SEQ ID NO: 25) | YAMSNLAS (SEQ ID NO: 142) | MQSLEYPFT (SEQ ID NO: 27) |
| ADWA11_VK01_2b (1) M56A (SEQ ID NO: 52) | RSTKSLLHFNGNTYLF (SEQ ID NO: 25) | YYASNLAS (SEQ ID NO: 144) | MQSLEYPFT (SEQ ID NO: 27) |
| ADWA11_VK01_2c (1) N58S (SEQ ID NO: 53) | RSTKSLLHFNGNTYLF (SEQ ID NO: 25) | YYMSSLAS (SEQ ID NO: 12) | MQSLEYPFT (SEQ ID NO: 27) |
| ADWA11_VK01_2d (1) A60Q (SEQ ID NO: 54) | RSTKSLLHFNGNTYLF (SEQ ID NO: 25) | YYMSNLQS (SEQ ID NO: 146) | MQSLEYPFT (SEQ ID NO: 27) |
| ADWA11_VK01_3a (1) M94Q (SEQ ID NO: 55) | RSTKSLLHFNGNTYLF (SEQ ID NO: 25) | YYMSNLAS (SEQ ID NO: 26) | QQSLEYPFT (SEQ ID NO: 13) |
| ADWA11_VK01_3b (1) L97Y (SEQ ID NO: 56) | RSTKSLLHFNGNTYLF (SEQ ID NO: 25) | YYMSNLAS (SEQ ID NO: 26) | MQSYEYPFT (SEQ ID NO: 147) |
| ADWA11_VK01_3c (1) E98S (SEQ ID NO: 57) | RSTKSLLHFNGNTYLF (SEQ ID NO: 25) | YYMSNLAS (SEQ ID NO: 26) | MQSLSYPFT (SEQ ID NO: 149) |
| ADWA11_VK01_3d (1) Y99T (SEQ ID NO: 58) | RSTKSLLHFNGNTYLF (SEQ ID NO: 25) | YYMSNLAS (SEQ ID NO: 26) | MQSLETPFT (SEQ ID NO: 151) |
| ADWA11_VK01_4a (1) F101L (SEQ ID NO: 59) | RSTKSLLHFNGNTYLF (SEQ ID NO: 25) | YYMSNLAS (SEQ ID NO: 26) | MQSLEYPLT (SEQ ID NO: 153) |
| ADWA11_VK01_4b (1) F101W (SEQ ID NO: 60) | RSTKSLLHFNGNTYLF (SEQ ID NO: 25) | YYMSNLAS (SEQ ID NO: 26) | MQSLEYPWT (SEQ ID NO: 155) |
| ADWA11_VK01_4c (1) Q105G (SEQ ID NO: 61) | RSTKSLLHFNGNTYLF (SEQ ID NO: 25) | YYMSNLAS (SEQ ID NO: 26) | MQSLEYPFT (SEQ ID NO: 27) |
| ADWA11VK1 IGKV2-28 (SEQ ID NO: 62) | RSTKSLLHFNGNTYLF (SEQ ID NO: 25) | YYMSNLAS (SEQ ID NO: 26) | MQSLEYPFT (SEQ ID NO: 27) |
| ADWA11VK2 IGKV2-30 (SEQ ID NO: 63) | RSTKSLLHFNGNTYLF (SEQ ID NO: 25) | YYMSNLAS (SEQ ID NO: 26) | MQSLEYPFT (SEQ ID NO: 27) |

TABLE 15-continued

Exemplary light chain CDRs according to Kabat

| VL (SEQ ID NO) | CDR-L1 (SEQ ID NO) | CDR-L2 (SEQ ID NO) | CDR-L3 (SEQ ID NO) |
|---|---|---|---|
| ADWA11VK3 IGKV4-1 (SEQ ID NO: 64) | RSTKSLLHFNGNTYL F (SEQ ID NO: 25) | YYMSNLAS (SEQ ID NO: 26) | MQSLEYPFT (SEQ ID NO: 27) |
| ADWA11VK4 IGKV1-39 (SEQ ID NO: 65) | RSTKSLLHFNGNTYL F (SEQ ID NO: 25) | YYMSNLAS (SEQ ID NO: 26) | MQSLEYPFT (SEQ ID NO: 27) |
| ADWA11VK5 IGKV3-11 (SEQ ID NO: 66) | RSTKSLLHFNGNTYL F (SEQ ID NO: 25) | YYMSNLAS (SEQ ID NO: 26) | MQSLEYPFT (SEQ ID NO: 27) |
| ADWA11_VK01_2.1 (SEQ ID NO: 67) | RSTKSLSHFNGNTYL F (SEQ ID NO: 11) | YYMSNLAS (SEQ ID NO: 26) | QQSLEYPFT (SEQ ID NO: 13) |
| ADWA11_VK012.2 (SEQ ID NO: 68) | RSTKSLSHFNGNTYL F (SEQ ID NO: 11) | YYMSNLAS (SEQ ID NO: 26) | MQSYEYPFT (SEQ ID NO: 147) |
| ADWA11_VK01_2.3 (SEQ ID NO: 69) | RSTKSLSHFNGNTYL F (SEQ ID NO: 11) | YYASNLAS (SEQ ID NO: 144) | QQSLEYPFT (SEQ ID NO: 13) |
| adwa_VL_1.2 L46R + Y36F (SEQ ID NO: 92) | RSTKSLLHFNGNTYL F (SEQ ID NO: 25) | YYMSNLAS (SEQ ID NO: 26) | MQSLEYPFT (SEQ ID NO: 27) |

TABLE 16

Exemplary heavy chain CDRs according to Chothia

| VH (SEQ ID NO) | CDR-H1 (SEQ ID NO) | CDR-H2 (SEQ ID NO) | CDR-H3 (SEQ ID NO) |
|---|---|---|---|
| Mouse ADWA-11 VH (SEQ ID NO: 20) | GFNIKDYYMN (SEQ ID NO: 28) | WIDPDNGN (SEQ ID NO: 29) | RLLMDY (SEQ ID NO: 30) |
| ADWA11 2.4 VH (SEQ ID NO: 6) | GFNIKDYYMN (SEQ ID NO: 14) | WIDPDQGN (SEQ ID NO: 15) | RLLMDY (SEQ ID NO: 16) |
| ADWA11VH1 IGHV1-46 (SEQ ID NO: 34) | GFNIKDYYMN (SEQ ID NO: 14) | WIDPDNGN (SEQ ID NO: 29) | RLLMDY (SEQ ID NO: 16) |
| ADWA11VH2 IGHV3-23 (SEQ ID NO: 35) | GFNIKDYYMN (SEQ ID NO: 14) | WIDPDNGN (SEQ ID NO: 29) | RLLMDY (SEQ ID NO: 16) |
| ADWA11VH3 IGHV3-30 (SEQ ID NO: 36) | GFNIKDYYMN (SEQ ID NO: 14) | WIDPDNGN (SEQ ID NO: 29) | RLLMDY (SEQ ID NO: 16) |
| ADWA11VH4 IGHV1-69 (SEQ ID NO: 37) | GFNIKDYYMN (SEQ ID NO: 14) | WIDPDNGN (SEQ ID NO: 29) | RLLMDY (SEQ ID NO: 16) |
| ADWA11VH5 IGHV3-48 (SEQ ID NO: 38) | GFNIKDYYMN (SEQ ID NO: 14) | WIDPDNGN (SEQ ID NO: 29) | RLLMDY (SEQ ID NO: 16) |
| ADWA11 VH05_VK1 (also referred to herein as adwa_VH_1.5 T28N + F29I + R72A + A49G + L79A + N74T + A75S) (SEQ ID NO: 39) | GFNIKDYYMN (SEQ ID NO: 14) | WIDPDNGN (SEQ ID NO: 29) | RLLMDY (SEQ ID NO: 16) |
| ADWA11VH5 D61E (SEQ ID NO: 40) | GFNIKDYYMN (SEQ ID NO: 14) | WIDPDNGN (SEQ ID NO: 29) | RLLMDY (SEQ ID NO: 16) |
| ADWA11VH5 N55Q (SEQ ID NO: 41) | GFNIKDYYMN (SEQ ID NO: 14) | WIDPDQGN (SEQ ID NO: 15) | RLLMDY (SEQ ID NO: 16) |

TABLE 16-continued

Exemplary heavy chain CDRs according to Chothia

| VH (SEQ ID NO) | CDR-H1 (SEQ ID NO) | CDR-H2 (SEQ ID NO) | CDR-H3 (SEQ ID NO) |
| --- | --- | --- | --- |
| ADWA11VH5 N28Q (SEQ ID NO: 42) | GFNIKDYYMN (SEQ ID NO: 14) | WIDPDQGN (SEQ ID NO: 15) | RLLMDY (SEQ ID NO: 16) |
| ADWA11VH5 K30A (SEQ ID NO: 43) | GFNIADYYMN (SEQ ID NO: 159) | WIDPDNGN (SEQ ID NO: 29) | RLLMDY (SEQ ID NO: 16) |
| ADWA11VH5 N57Q (SEQ ID NO: 44) | GFNIKDYYMN (SEQ ID NO: 14) | WIDPDNGQ (SEQ ID NO: 164) | RLLMDY (SEQ ID NO: 16) |
| ADWA11VH5 P62A (SEQ ID NO: 45) | GFNIKDYYMN (SEQ ID NO: 14) | WIDPDNGN (SEQ ID NO: 29) | RLLMDY (SEQ ID NO: 16) |
| ADWA11VH5 K63A (SEQ ID NO: 46) | GFNIKDYYMN (SEQ ID NO: 14) | WIDPDNGN (SEQ ID NO: 29) | RLLMDY (SEQ ID NO: 16) |
| adwa_VH_1.1 T28N + F29I (SEQ ID NO: 88) | GFNIKDYYMN (SEQ ID NO: 14) | WIDPDNGN (SEQ ID NO: 29) | RLLMDY (SEQ ID NO: 16) |
| adwa_VH_1.2 T28N + F29I + R72A (SEQ ID NO: 89) | GFNIKDYYMN (SEQ ID NO: 14) | WIDPDNGN (SEQ ID NO: 29) | RLLMDY (SEQ ID NO: 16) |
| adwa_VH_1.3 T28N + F29I + R72A + A49G + L79A (SEQ ID NO: 90) | GFNIKDYYMN (SEQ ID NO: 14) | WIDPDNGN (SEQ ID NO: 29) | RLLMDY (SEQ ID NO: 16) |
| adwa_VH_1.4 T28N + F29I + R72A + N74T + A75S (SEQ ID NO: 91) | GFNIKDYYMN (SEQ ID NO: 14) | WIDPDNGN (SEQ ID NO: 29) | RLLMDY (SEQ ID NO: 16) |
| VH05-2(F64V) VK01 (SEQ ID NO: 93) | GFNIKDYYMN (SEQ ID NO: 14) | WIDPDQGN (SEQ ID NO: 15) | RLLMDY (SEQ ID NO: 16) |

TABLE 17

Exemplary light chain CDRs according to Chothia

| VL (SEQ ID NO) | CDR-L1 (SEQ ID NO) | CDR-L2 (SEQ ID NO) | CDR-L3 (SEQ ID NO) |
| --- | --- | --- | --- |
| Mouse ADWA-11 VL (SEQ ID NO: 21) | STKSLLHFNGNTYL (SEQ ID NO: 31) | YYMSN (SEQ ID NO: 32) | QSLEYPFT (SEQ ID NO: 33) |
| ADWA11 2.4 (SEQ ID NO: 7) | STKSLSHFNGNTYL (SEQ ID NO: 17) | YYMSS (SEQ ID NO: 18) | QSLEYPFT (SEQ ID NO: 19) |
| ADWA11_VK01 (1) (also referred to herein as adwa_VL_1.1 L46R) (47) | STKSLLHFNGNTYL (SEQ ID NO: 31) | YYMSN (SEQ ID NO: 32) | QSLEYPFT (SEQ ID NO: 19) |
| ADWA11_VK01_1a (1) L29I (SEQ ID NO: 48) | STKSILFIFNGNTYL (SEQ ID NO: 139) | YYMSN (SEQ ID NO: 32) | QSLEYPFT (SEQ ID NO: 19) |
| ADWA11_VK01_1b (1) L30S (SEQ ID NO: 49) | STKSLSHFNGNTYL (SEQ ID NO: 17) | YYMSN (SEQ ID NO: 32) | QSLEYPFT (SEQ ID NO: 19) |
| ADWA11_VK01_1c (1) T36S (SEQ ID NO: 50) | STKSLLHFNGNSYL (SEQ ID NO: 141) | YYMSN (SEQ ID NO: 32) | QSLEYPFT (SEQ ID NO: 19) |
| ADWA11_VK01_2a (1) Y55A (SEQ ID NO: 51) | STKSLLHFNGNTYL (SEQ ID NO: 31) | YAMSN (SEQ ID NO: 143) | QSLEYPFT (SEQ ID NO: 19) |
| ADWA11_VK01_2b (1) M56A (SEQ ID NO: 52) | STKSLLHFNGNTYL (SEQ ID NO: 31) | YYASN (SEQ ID NO: 145) | QSLEYPFT (SEQ ID NO: 19) |

TABLE 17-continued

Exemplary light chain CDRs according to Chothia

| VL (SEQ ID NO) | CDR-L1 (SEQ ID NO) | CDR-L2 (SEQ ID NO) | CDR-L3 (SEQ ID NO) |
|---|---|---|---|
| ADWA11_VK01_2c (1) N58S (SEQ ID NO: 53) | STKSLLHFNGNTYL (SEQ ID NO: 31) | YYMSS (SEQ ID NO: 18) | QSLEYPFT (SEQ ID NO: 19) |
| ADWA11_VK01_2d (1) A60Q (SEQ ID NO: 54) | STKSLLHFNGNTYL (SEQ ID NO: 31) | YYMSN (SEQ ID NO: 32) | QSLEYPFT (SEQ ID NO: 19) |
| ADWA11_VK01_3a (1) M94Q (SEQ ID NO: 55) | STKSLLHFNGNTYL (SEQ ID NO: 31) | YYMSN (SEQ ID NO: 32) | QSLEYPFT (SEQ ID NO: 19) |
| ADWA11_VK01_3b (1) L97Y (SEQ ID NO: 56) | STKSLLHFNGNTYL (SEQ ID NO: 31) | YYMSN (SEQ ID NO: 32) | QSYEYPFT (SEQ ID NO: 148) |
| ADWA11_VK01_3c (1) E98S (SEQ ID NO: 57) | STKSLLHFNGNTYL (SEQ ID NO: 31) | YYMSN (SEQ ID NO: 32) | QSLSYPFT (SEQ ID NO: 150) |
| ADWA11_VK01_3d (1) Y99T (SEQ ID NO: 58) | STKSLLHFNGNTYL (SEQ ID NO: 31) | YYMSN (SEQ ID NO: 32) | QSLETPFT (SEQ ID NO: 152) |
| ADWA11_VK01_4a (1) F101L (SEQ ID NO: 59) | STKSLLHFNGNTYL (SEQ ID NO: 31) | YYMSN (SEQ ID NO: 32) | QSLEYPLT (SEQ ID NO: 154) |
| ADWA11_VK01_4b (1) F101W (SEQ ID NO: 60) | STKSLLHFNGNTYL (SEQ ID NO: 31) | YYMSN (SEQ ID NO: 32) | QSLEYPWT (SEQ ID NO: 156) |
| ADWA11_VK01_4c (1) Q105G (SEQ ID NO: 61) | STKSLLHFNGNTYL (SEQ ID NO: 31) | YYMSN (SEQ ID NO: 32) | QSLEYPFT (SEQ ID NO: 19) |
| ADWA11VK1 IGKV2-28 (SEQ ID NO: 62) | STKSLLHFNGNTYL (SEQ ID NO: 31) | YYMSN (SEQ ID NO: 32) | QSLEYPFT (SEQ ID NO: 19) |
| ADWA11VK2 IGKV2-30 (SEQ ID NO: 63) | STKSLLHFNGNTYL (SEQ ID NO: 31) | YYMSN (SEQ ID NO: 32) | QSLEYPFT (SEQ ID NO: 19) |
| ADWA11VK3 IGKV4-1 (SEQ ID NO: 64) | STKSLLHFNGNTYL (SEQ ID NO: 31) | YYMSN (SEQ ID NO: 32) | QSLEYPFT (SEQ ID NO: 19) |
| ADWA11VK4 IGKV1-39 (SEQ ID NO: 65) | STKSLLHFNGNTYL (SEQ ID NO: 31) | YYMSN (SEQ ID NO: 32) | QSLEYPFT (SEQ ID NO: 19) |
| ADWA11VK5 IGKV3-11 (SEQ ID NO: 66) | STKSLLHFNGNTYL (SEQ ID NO: 31) | YYMSN (SEQ ID NO: 32) | QSLEYPFT (SEQ ID NO: 19) |
| ADWA11_VK01_2.1 (SEQ ID NO: 67) | STKSLSHFNGNTYL (SEQ ID NO: 17) | YYMSN (SEQ ID NO: 32) | QSLEYPFT (SEQ ID NO: 19) |
| ADWA11_VK012.2 (SEQ ID NO: 68) | STKSLSHFNGNTYL (SEQ ID NO: 17) | YYMSN (SEQ ID NO: 32) | QSYEYPFT (SEQ ID NO: 148) |
| ADWA11_VK012.3 (SEQ ID NO: 69) | STKSLSHFNGNTYL (SEQ ID NO: 17) | YYASN (SEQ ID NO: 145) | QSLEYPFT (SEQ ID NO: 19) |
| adwa_VL_1.2 L46R + Y36F (SEQ ID NO: 92) | STKSLLHFNGNTYL (SEQ ID NO: 31) | YYMSN (SEQ ID NO: 32) | QSLEYPFT (SEQ ID NO: 19) |

In some aspects, the antibody, or antigen-binding fragment thereof, further comprises a CDR-H1, a CDR-H2, and a CDR-H3 as set forth in the amino acid sequence of at least one of SEQ ID NOs: 8-10, 14-16, 22-24, or 28-30.

In some aspects, the antibody, or antigen binding fragment thereof, comprises a CDR-L1, a CDR-L2, a CDR-L3 as set forth in the amino acid sequence of SEQ ID NO: 7, and a CDR-H1, a CDR-H2, and a CDR-H3 as set forth in the amino acid sequence of SEQ ID NO: 6.

In some aspects, the antibody, or antigen binding fragment thereof, comprises a CDR-L1, a CDR-L2, a CDR-L3 as set forth in the amino acid sequence of SEQ ID NO: 7, and a CDR-H1, a CDR-H2, and a CDR-H3 as set forth in the amino acid sequence of SEQ ID NO: 20.

In some aspects, the antibody, or antigen binding fragment thereof, comprises a CDR-L1, a CDR-L2, a CDR-L3 as set forth in the amino acid sequence of SEQ ID NO: 7, and a CDR-H1, a CDR-H2, and a CDR-H3 as set forth in the amino acid sequence of any one of SEQ ID NOs: 34-46, 88-91 or 93.

In some aspects, the antibody, or antigen binding fragment thereof, comprises a CDR-L1, a CDR-L2, a CDR-L3 as set forth in the amino acid sequence of SEQ ID NO: 21, and a CDR-H1, a CDR-H2, and a CDR-H3 as set forth in the amino acid sequence of SEQ ID NO: 6.

In some aspects, the antibody, or antigen binding fragment thereof, comprises a CDR-L1, a CDR-L2, a CDR-L3 as set forth in the amino acid sequence of any one of SEQ ID NOs: 47-69 or 92, and a CDR-H1, a CDR-H2, and a CDR-H3 as set forth in the amino acid sequence of SEQ ID NO: 6.

In some aspects, the antibody, or antigen binding fragment thereof, comprises a CDR-L1, a CDR-L2, a CDR-L3 as set forth in the amino acid sequence of SEQ ID NO: 5, and a CDR-H1, a CDR-H2, and a CDR-H3 as set forth in the amino acid sequence of SEQ ID NO: 2.

In some aspects, the antibody, or antigen binding fragment thereof, comprises a CDR-L1, a CDR-L2, a CDR-L3 as set forth in the amino acid sequence of SEQ ID NO: 5, and a CDR-H1, a CDR-H2, and a CDR-H3 as set forth in the amino acid sequence of SEQ ID NO: 3.

In some aspects, the antibody, or antigen binding fragment thereof, comprises a CDR-L1, a CDR-L2, a CDR-L3 as set forth in the amino acid sequence of SEQ ID NO: 5, and a CDR-H1, a CDR-H2, and a CDR-H3 as set forth in the amino acid sequence of SEQ ID NO: 124 or SEQ ID NO: 182.

In some aspects, the antibody, or antigen binding fragment thereof, comprises a CDR-L1, a CDR-L2, a CDR-L3 as set forth in the amino acid sequence of SEQ ID NO: 123, and a CDR-H1, a CDR-H2, and a CDR-H3 as set forth in the amino acid sequence of SEQ ID NO: 124 or SEQ ID NO: 182.

In some aspects, the antibody, or antigen binding fragment thereof, comprises a CDR-L1, a CDR-L2, a CDR-L3 as set forth in the amino acid sequence of SEQ ID NO: 123, and a CDR-H1, a CDR-H2, and a CDR-H3 as set forth in the amino acid sequence of SEQ ID NO: 2 or SEQ ID NO: 3.

In some aspects, the antibody, or antigen-binding fragment thereof, comprises a CDR-L1, a CDR-L2, and a CDR-L3 as set forth in the amino acid sequence encoded by the insert of the plasmid deposited with the ATCC having the Accession number PTA-124918.

In some aspects, the antibody, or antigen-binding fragment thereof, comprises a CDR-H1, a CDR-H2, and a CDR-H3 as set forth in the amino acid sequence encoded by the insert of the plasmid deposited with the ATCC having Accession number PTA-124917.

In some aspects, the antibody, or antigen-binding fragment thereof, comprises a CDR-L1, a CDR-L2, and a CDR-L3 amino acid sequence encoded by the insert of the plasmid deposited with the ATCC having the Accession number Accession number PTA-124918, and a CDR-H1, a CDR-H2, and a CDR-H3 amino acid sequence encoded by the insert of the plasmid deposited with the ATCC having Accession number PTA-124917.

In some aspects, the antibody, or antigen-binding fragment thereof, comprises a light chain variable region comprising the amino acid sequence encoded by the insert of the plasmid deposited with the ATCC having the Accession number PTA-124918.

In some aspects, the antibody, or antigen-binding fragment thereof, comprises a heavy chain variable region comprising the amino acid sequence encoded by the insert of the plasmid deposited with the ATCC having the Accession number PTA-124917.

In some aspects, the antibody, or antigen binding fragment thereof, comprises a CDR-L1 comprising the amino acid sequence of SEQ ID NO:11, a CDR-L2 comprising the amino acid sequence of SEQ ID NO:12, a CDR-L3 comprising the amino acid sequence of SEQ ID NO:13, a CDR-H1 comprising the amino acid sequence of SEQ ID NO:8, a CDR-H2 comprising the amino acid sequence of SEQ ID NO:9, and a CDR-H3 comprising the amino acid sequence of SEQ ID NO:10.

In some aspects, the antibody, or antigen binding fragment thereof, comprises a CDR-L1 comprising the amino acid sequence of SEQ ID NO:17, a CDR-L2 comprising the amino acid sequence of SEQ ID NO:18, a CDR-L3 comprising the amino acid sequence of SEQ ID NO:19, a CDR-H1 comprising the amino acid sequence of SEQ ID NO:14, a CDR-H2 comprising the amino acid sequence of SEQ ID NO:15, and a CDR-H3 comprising the amino acid sequence of SEQ ID NO:16.

In some aspects, an antibody, or antigen-binding fragment thereof, may comprise a VH comprising an amino acid sequence at least 90% identical to the amino acid sequence of any one of SEQ ID NOs: 6, 34-46, 88-91 and 93 (e.g., SEQ ID NO: 6). The VH may comprise an amino acid sequence at least 91%, 92%, 93%, 94%, 95%, 96%, 97%, 98%, or 99%, identical to the amino acid sequence of any one of SEQ ID NOs: 6, 34-46, 88-91 and 93 (e.g., SEQ ID NO: 6). The VH may comprise the amino acid sequence of any one of SEQ ID NOs: 6, 34-46, 88-91 and 93 (e.g., SEQ ID NO: 6).

In some aspects, an antibody, or antigen-binding fragment thereof, may comprise a VH comprising an amino acid sequence at least 90% identical to the amino acid sequence of SEQ ID NO: 6. The VH may comprise an amino acid sequence at least 91%, 92%, 93%, 94%, 95%, 96%, 97%, 98%, or 99%, identical to the amino acid sequence of SEQ ID NO: 6. The VH may comprise the amino acid sequence of SEQ ID NO: 6. In some embodiments, an antibody, or antigen-binding fragment thereof, comprises a VH comprising the amino acid sequence of SEQ ID NO: 6. In some embodiments, an antibody, or antigen-binding fragment thereof, comprises a VH consisting of the amino acid sequence of SEQ ID NO: 6.

In some aspects, an antibody, or antigen-binding fragment thereof, may comprise a VL comprising an amino acid sequence at least 90% identical to the amino acid sequence of any one of SEQ ID NOs: 7, 47-69 and 92 (e.g., SEQ ID NO: 7). The VL may comprise an amino acid sequence at least 91%, 92%, 93%, 94%, 95%, 96%, 97%, 98%, or 99%, identical to the amino acid sequence of any one of SEQ ID NOs: 7, 47-69 and 92 (e.g., SEQ ID NO: 7). The VL may comprise the amino acid sequence of any one of SEQ ID NOs: 7, 47-69 and 92 (e.g., SEQ ID NO: 7).

In some aspects, an antibody, or antigen-binding fragment thereof, may comprise a VL comprising an amino acid sequence at least 90% identical to the amino acid sequence of SEQ ID NO: 7. The VL may comprise an amino acid sequence at least 91%, 92%, 93%, 94%, 95%, 96%, 97%, 98%, or 99%, identical to the amino acid sequence of SEQ ID NO: 7. The VL may comprise the amino acid sequence of SEQ ID NO: 7. In some embodiments, an antibody, or antigen-binding fragment thereof, comprises a VL comprising the amino acid sequence of SEQ ID NO: 7. In some embodiments, an antibody, or antigen-binding fragment thereof, comprises a VL consisting of the amino acid sequence of SEQ ID NO: 7.

In some aspects, an antibody, or antigen-binding fragment thereof, may comprise a heavy chain comprising a VH comprising the amino acid sequence of any one of SEQ ID NOs: 6, 34-46, 88-91 and 93 (e.g., SEQ ID NO: 6), and further comprising an IgG1 constant domain (e.g., an IgG1 constant domain comprising the amino acid sequence of any one of SEQ ID NO: 81, 82, 181 or 184). In some aspects, an antibody, or antigen-binding fragment, variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length heavy chain. In a further aspect, a variant shares at least 65%, at least 75%, at least 85%, at least 90%, at least 95%, at least 96%, at least 97%, at least 98%, or at least 99% sequence identity with the full length heavy chain, and wherein said antibody or antigen-binding fragment specifically binds αvβ8 integrin.

In some embodiments, an antibody, or antigen-binding fragment thereof, comprises a heavy chain comprising a VH comprising the amino acid sequence of SEQ ID NO: 6 and further comprises an IgG1 constant domain comprising the amino acid sequence of SEQ ID NO: 181 or SEQ ID NO: 184. In some embodiments, an antibody, or antigen-binding fragment thereof, comprises a VH consisting of the amino acid sequence of SEQ ID NO: 6 and further comprises an IgG1 constant domain consisting of the amino acid sequence of SEQ ID NO: 181 or SEQ ID NO: 184. In some embodiments, the antibody lacks effector function(s). In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa (e.g., encoded by the amino acid sequence of SEQ ID NO: 83) or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

In some embodiments, an antibody, or antigen-binding fragment thereof, comprises a light chain comprising a VL comprising the amino acid sequence of any one of SEQ ID NOs: 7, 47-69 and 92 (e.g., SEQ ID NO: 7), and further comprises an kappa constant domain comprising the amino acid sequence of SEQ ID NO: 83. In some embodiments, an antibody, or antigen-binding fragment thereof, comprises a light chain comprising a VL consisting of the amino acid sequence of SEQ ID NO: 7 and further comprises a kappa constant domain consisting of the amino acid sequence of SEQ ID NO: 83.

In some aspects, an antibody, or antigen-binding fragment thereof, comprises a heavy chain (HC) comprising an amino acid sequence at least 90%, 91%, 92%, 93%, 94%, 95%, 96%, 97%, 98%, or 99%, identical to the amino acid sequence of SEQ ID NO: 2. In some embodiments, an antibody, or antigen-binding fragment thereof, comprises a HC comprising the amino acid sequence of SEQ ID NO: 2. In some embodiments, an antibody, or antigen-binding fragment thereof, comprises a HC consisting of the amino acid sequence of SEQ ID NO: 2. In some embodiments, the antibody lacks effector function(s).

In some aspects, an antibody, or antigen-binding fragment thereof, comprises a heavy chain (HC) comprising an amino acid sequence at least 90%, 91%, 92%, 93%, 94%, 95%, 96%, 97%, 98%, or 99%, identical to the amino acid sequence of SEQ ID NO: 3. In some embodiments, an antibody, or antigen-binding fragment thereof, comprises a HC comprising the amino acid sequence of SEQ ID NO: 3. In some embodiments, an antibody, or antigen-binding fragment thereof, comprises a HC consisting of the amino acid sequence of SEQ ID NO: 3. In some embodiments, the antibody lacks effector function(s). In some aspects, an antibody, or antigen-binding fragment thereof, comprises a light chain (LC) comprising an amino acid sequence at least 90%, 91%, 92%, 93%, 94%, 95%, 96%, 97%, 98%, or 99%, identical to SEQ ID NO: 5. In some embodiments, an antibody, or antigen-binding fragment thereof, comprises a LC comprising the amino acid sequence of SEQ ID NO: 5. In some embodiments, an antibody, or antigen-binding fragment thereof, comprises a LC consisting of the amino acid sequence of SEQ ID NO: 5. In some embodiments, the antibody lacks effector function.

Germline Substitutions

In certain embodiments, the antibody, or antigen-binding fragment thereof, comprises the following heavy chain CDR sequences: (i) CDR-H1 comprising SEQ ID NO:22, CDR-H2 comprising SEQ ID NO:23, and CDR-H3 comprising SEQ ID NO:24; and/or (ii) the following light chain CDR sequences: CDR-L1 comprising SEQ ID NO:25 or 71, CDR-L2 comprising SEQ ID NO:26 or 72, and CDR-L3 comprising SEQ ID NO:27 or 73. In certain embodiments, the antibody, or antigen-binding fragment thereof, comprises the following heavy chain CDR sequences: (i) CDR-H1 comprising SEQ ID NO:28, CDR-H2 comprising SEQ ID NO:29, and CDR-H3 comprising SEQ ID NO:30; and/or (ii) the following light chain CDR sequences: CDR-L1 comprising SEQ ID NO:31 or 74, CDR-L2 comprising SEQ ID NO:32 or 75, and CDR-L3 comprising SEQ ID NO:33 or 76. These are mouse CDRs and, preferably, are grafted or otherwise added in the context of a human VH and VL domain. A wide variety of acceptor human germline sequences are available and the process for "humanizing" a non-human species antibody to use in humans will well-known in the art and also discussed elsewhere herein. Therefore, the skilled artisan would appreciate that the above mouse CDR sequences can be placed in the context of human V domain amino acid sequences. In doing so, changes to the acceptor human germline sequences are generally made to preserve antibody binding and other desirable characteristics of the original parent (i.e., donor) antibody. Both the CDRs and framework regions (FW) may be engineered as follows.

In certain embodiments, no more than 11, or no more than 10, no more than 9, no more than 8, no more than 7, no more than 6, no more than 5, no more than 4, no more than 3, no more than 2, or no more than 1 substitution is made in CDR-L1, relative to the amino acid sequence of SEQ ID NO: 25, 31, 71, or 74. In certain embodiments, no more than 6, no more than 5, no more than 4, no more than 3, no more than 3, no more than 2, or no more than one substitution is made in CDR-L2, relative to the amino acid sequence of SEQ ID NO: 26, 32, 72, or 75. In certain embodiments, no more than 8, no more than 7, no more than 6, no more than 5, no more than 4, no more than 3, no more than 3, no more than 2, or no more than one substitution is made in CDR-L3, relative to the amino acid sequence of SEQ ID NO: 27, 33, 73, 76. In some embodiments, no more than 10, no more than 9, no more than 8, no more than 7, no more than 6, no more than 5, no more than 4, no more than 3, no more than 2, or no more than 1 substitution is made in CDR-H1, relative to the amino acid sequence of SEQ ID NO: 22 or 28. In some embodiments, no more than no more than 17, no more than 16, no more than 15, no more than 14, no more than 13, no more than 12, no more than 11, or no more than one 10, no more than 9, no more than 8, no more than 7, no more than 6, no more than 5, no more than 4, no more than 3, no more than 2, or no more than 1 substitution is made in CDR-H2, relative to relative to the amino acid sequence of SEQ ID NO: 23 or 29. In some embodiments, no more than 12, no more than 11, or no more than 10, no more than 9, no more than 8, no more than 7, no more than 6, no more than 5, no more than 4, no more than 3, no more than 2, or no more than 1 substitution is made in CDR-H3, relative to the amino acid sequence of SEQ ID NO: 24 or 30. In certain embodiments, the substitution(s) do not change binding affinity ($K_D$) value by more than 1000-fold, more than 100-fold, or 10-fold. In certain embodiments, the substitution is a conservative substitution according to Table 1.

In certain embodiments, the substitution is human germline substitution in which a (donor) CDR residue is replaced with the corresponding human germline (acceptor) residue, to increase the human amino acid content and potentially reduce immunogenicity of the antibody as described in, e.g., US Patent Application Publication No. 2017/0073395 and Townsend et al., 2015, Proc. Nat. Acad. Sci. USA 112(50): 15354-15359).

Methods and libraries for introducing human germline residues in antibody CDRs are described in detail in US Patent Application Publication No. 2017/0073395, and Townsend et al., 2015, Proc. Natl. Acad. Sci. USA. 112(50): 15354-15359, and both are herein incorporated by reference in their entirety.

The antibody, or antigen-binding fragment thereof, may comprise a VH framework comprising a human germline VH framework sequence. The VH framework sequence can be from a human VH3 germline, a VH1 germline, a VH5 germline, or a VH4 germline. Preferred human germline heavy chain frameworks are frameworks derived from VH1, VH3, or VH5 germlines. For example, VH frameworks from the following germlines may be used: IGHV3-07, IGHV1-46, IGHV3-23, IGHV3-30, IGHV1-69, or IGHV3-48 (germline names are based on IMGT germline definition). Preferred human germline light chain frameworks are frameworks derived from VK or Vλ germlines. For example, VL frameworks from the following germlines may be used: IGKV1-39, IGKV2-28, IGKV2-30, IGKV4-1, or IGKV3-11 (germline names are based on IMGT germline definition). Alternatively, or in addition, the framework sequence may be a human germline consensus framework sequence, such as the framework of human Vλ1 consensus sequence, VK1 consensus sequence, VK2 consensus sequence, VK3 consensus sequence, VH3 germline consensus sequence, VH1 germline consensus sequence, VH5 germline consensus sequence, or VH4 germline consensus sequence. Sequences of human germline frameworks are available from various public databases, such as V-base, IMGT, NCBI, or Abysis.

The antibody, or antigen-binding fragment thereof, may comprise a VL framework comprising a human germline VL framework sequence. The VL framework may comprise one or more amino acid substitutions, additions, or deletions, while still retaining functional and structural similarity with the germline from which it was derived. In some aspects, the VL framework is at least 90%, at least 91%, at least 92%, at least 93%, at least 94%, at least 95%, at least 96%, at least 97%, at least 98%, at least 99%, or 100% identical to a human germline VL framework sequence. In some aspects, the antibody, or antigen binding fragment thereof, comprises a VL framework comprising 1, 2, 3, 4, 5, 6, 7, 8, 9, 10 amino acid substitutions, additions or deletions relative to the human germline VL framework sequence. In some aspects, the 1, 2, 3, 4, 5, 6, 7, 8, 9, or 10 amino acid substitutions, additions or deletions are only in the framework regions. In some aspects, the % identity is based on similarity with VL excluding those portions herein defined as CDRs.

The human germline VL framework may be the framework of DPK9 (IMGT name: IGKV1-39, e.g., SEQ ID NO:128). The human germline VL framework may be the framework of IGKV2-28. The human germline VL framework may be the framework of DPK18 (IMGT name: IGKV2-30). The human germline VL framework may be the framework of DPK24 (IMGT name: IGKV4-1). The human germline VL framework may be the framework of HK102_V1 (IMGT name: IGKV1-5). The human germline VL framework may be the framework of Vg_38K (IMGT name: IGKV3-11). The human germline VL framework may be the framework of human Vλ consensus sequence. The human germline VL framework may be the framework of human Vλ1 consensus sequence. The human germline VL framework may be the framework of human Vλ3 consensus sequence. The human germline VL framework may be the framework of human VK consensus sequence. The human germline VL framework may be the framework of human VK1 consensus sequence. The human germline VL framework may be the framework of human VK2 consensus sequence. The human germline VL framework may be the framework of human VK3 consensus sequence.

In some aspects, the VL framework is DPK9 (SEQ ID NO: 128). Other similar framework regions are also predicted to deliver advantageous antibodies of the invention comprising CDRs of SEQ ID NOs: 11-13 and 17-19; and CDRs specified by the following VL amino acid sequences: 7, 47-69 and 92, including, e.g., IGKV2-28, IGKV2-30, IGKV4-1, or IGKV3-11, which may comprise 99, 97, 97, 96, 80, 76, 66, 97, 97, 96, 76, and 74% identity respectively to the FW region of DPK-9 and one or fewer amino acid differences in common structural features (Kabat Numbering) (A) residues directly underneath CDR (Vernier Zone), L2, L4, L35, L36, L46, L47, L48, L49, L64, L66, L68, L69, L71, (B) VH/VL Chain packing Residues: L36, L38, L44, L46, L87 and (C) canonical CDR Structural support residues L2, L48, L64, L71 (see Lo, "Antibody Humanization by CDR Grafting", (2004) Antibody Engineering, Vol. 248, Methods in Molecular Biology pp 135-159 and O'Brien and Jones, "Humanization of Monoclonal Antibodies by CDR Grafting", (2003) Recombinant Antibodies for Cancer Therapy, Vol. 207, Methods in Molecular Biology pp 81-100). Particularly preferred are framework regions of IGKV2-28, IGKV2-30, IGKV4-1, or IGKV3-11 sharing 99, 97, 97, 96, 80, 76, 66% identity to DPK9 respectively and have no amino acid differences in these common structural features. In some aspects, the % identity is based on similarity with VL excluding those portions herein defined as CDRs.

The antibody, or antigen-binding fragment thereof, may comprise a VH framework comprising a human germline VH framework sequence. The VH framework may comprise one or more amino acid substitutions, additions, or deletions, while still retaining functional and structural similarity with the germline from which it was derived. In some aspects, the VH framework is at least 90%, at least 91%, at least 92%, at least 93%, at least 94%, at least 95%, at least 96%, at least 97%, at least 98%, at least 99%, or 100% identical to a human germline VH framework sequence. In some aspects, the antibody, or antigen binding fragment thereof, comprises a VH framework comprising 1, 2, 3, 4, 5, 6, 7, 8, 9, 10 amino acid substitutions, additions or deletions relative to the human germline VH framework sequence. In some aspects, the 1, 2, 3, 4, 5, 6, 7, 8, 9, or 10 amino acid substitutions, additions or deletions are only in the framework regions. In some aspects, the % identity is based on similarity with VH excluding those portions herein defined as CDRs.

The human germline VH framework may be, for example, the framework of IGHV3-07 (also known as DP-54), IGHV1-46, IGHV3-23, IGHV3-30, IGHV1-69, or IGHV3-48. The human germline VH framework may be the framework of human VH germline consensus sequence. The human germline VH framework may be the framework of human VH3 germline consensus sequence. The human germline VH framework may be the framework of human VH5 germline consensus sequence. The human germline VH framework may be the framework of human VH1 germline consensus sequence. The human germline VH framework may be the framework of human VH4 germline consensus sequence.

In some aspects, the VH framework is IGHV3-07 (SEQ ID NO: 127). Other similar framework regions are also predicted to deliver advantageous antibodies of the invention comprising CDRs of SEQ ID NOs:8-10 and 14-16, and CDRs specified by any of the following VH amino acid sequences: SEQ ID NOs: 6, 34-46, 88-91 and 93, including IGHV3-07, IGHV1-46, IGHV3-23, IGHV3-30, IGHV1-69, or IGHV3-48, which may comprise 93, 92, 92, 99, 97, 97, 96, 96, 94, 94, 93, 92% identity respectively to the FW region of DP-54 and one or fewer amino acid differences in common structural features (Kabat Numbering) (A) residues directly underneath CDR (Vernier Zone), H2, H47, H48, and H49, H67, H69, H71, H73, H93, H94, (B) VH/VL Chain packing Residues: H37, H39, H45, H47, H91, H93 and (C) canonical CDR Structural support residues H24, H71, H94 (see Lo 2004, and O'Brien and Jones 2003). Exemplary framework regions of DP-50, IGHV3-30*09, IGHV3-30*15 sharing 93, 92 and 92% identity to DP-54 respectively and have no amino acid differences in these common structural features. In some aspects, the % identity is based on similarity with VH excluding those portions herein defined as CDRs.

In certain embodiments, the antibody, or antigen-binding fragment thereof, described herein comprises (i) a VH comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:6, and/or (ii) a VL comprising an amino acid sequence that is at least 50%, at least 60%, at least 66%, at least 70%, at least 75%, at least 76%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:7. Any combination of these VL and VH sequences is also encompassed by the invention.

In certain embodiments, the antibody, or antigen-binding fragment thereof, described herein comprises (i) a HC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:2 or SEQ ID NO:3; and/or (ii) a LC comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:5. Any combination of these HC and LC sequences is also encompassed by the invention.

In certain embodiments, the antibody, or antigen-binding fragment thereof, described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

The invention further provides an antibody, or antigen-binding fragment thereof, that competes for binding to human αvβ8 integrin with Latency Associated Peptide (LAP). For example, if the binding of an antibody, or antigen-binding fragment thereof, to human αvβ8 integrin hinders the subsequent binding of LAP to the human αvβ8 integrin, then the antibody, or the antigen-binding fragment thereof, competes with LAP for human αvβ8 integrin binding.

The antibodies and antigen-binding fragments provided by the invention include monoclonal antibodies, polyclonal antibodies, antibody fragments (e.g., Fab, Fab', $F(ab')_2$, Fv, Fc, etc.), chimeric antibodies, bispecific antibodies, heteroconjugate antibodies, single chain (ScFv), mutants thereof, fusion proteins comprising an antibody fragment, domain antibodies (dAbs), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies and antigen-binding fragments may be murine, rat, human, or any other origin (including chimeric or humanized antibodies). In some embodiments, the antibody is a monoclonal antibody. In some embodiments, the antibody is a chimeric, humanized or human antibody. In certain embodiments, the antibody is a human antibody. In certain embodiments, the antibody is a humanized antibody.

Biological Activity of Anti-αvβ8 Integrin Antibodies

In addition to binding an epitope on αvβ8 integrin, the antibody, or antigen-binding fragment thereof, of the invention can mediate a biological activity. That is, the invention includes an isolated antibody, or antigen-binding fragment thereof, that specifically binds αvβ8 integrin and mediates at least one detectable activity selected from the following:

(i) binds specifically to αvβ8 integrin (e.g., αvβ8 integrin from human, mouse, cynomolgus monkey, and/or rat);
(ii) reduces an interaction between αvβ8 integrin and Latency Associated Peptide (LAP);
(iii) reduces TGF-β signaling;
(iv) effectively blocks the αvβ8 integrin-mediated TGFβ activation with an IC50≤10 nM;
(v) has a comparable Kd (within 5-fold) towards a non-human primate (NHP) orthologue;
(vi) selectivity binds human αvβ8 and does not detectably bind a homologue of αvβ8 (e.g., αvβ1, αvβ3, αvβ5 and αvβ6);
(vii) causes growth suppression and/or complete tumor regression in an animal model for a cancer chosen from squamous cell carcinoma, breast, and colon cancer, alone or in combination with an immunomodulatory, e.g., a modulators of checkpoint inhibitors, e.g., inhibitors of PD-1, PD-L1, CTLA-4, or an agonist of a stimulatory molecule, e.g., 4-1BB;
(viii) causes growth suppression and/or complete tumor regression in an animal model for a cancer in combination with an anti-cancer therapy, e.g., radiotherapy;
(ix) shows at least 60% reduction in tumor growth in a syngeneic tumor graft model, e.g., when administered at ≤10 mg/kg;
(x) increases an anti-tumor response in the presence of one or more immunomodulators, e.g., an antagonist of a checkpoint inhibitor or an agonist of a checkpoint activator, e.g., an antagonist of PD-1, PD-L1, or CTLA-4, or an activator of an immune response, e.g., 4-1BB agonist, when administered to a subject, e.g., a mouse or human subject;
(xi) has an efficacy that is not dependent upon the expression of αvβ8 integrin in a tumor model;
(xii) increases the abundance of CD8+ GzmB+ T cell in the tumor microenvironment, e.g., as a monotherapy;
(xiii) shows a decrease, e.g., at least a >80% decrease, in tumor growth when used in combination with an antagonist of a checkpoint inhibitor (e.g., an anti-PD-1 or anti-PD-L1 antibody), e.g., in a syngeneic model of squamous cell carcinoma, breast cancer, and/or colon cancer;
(xiv) shows a statistically significant improvement in overall survival of a subject, e.g., a human or a mouse, as determined by a Kaplan-Meier analysis;
(xv) shows suitable formulation properties, including a high degree of thermal stability and minimal aggregation at high concentration; or
(xvi) may show reproducible expression and purity in large-scale manufacturing conditions.

In some embodiments, the anti-αvβ8 integrin antibodies, or antigen-binding fragments thereof, has at least one of the following properties:

i. a binding affinity expressed as KD for human αvβ8 integrin that is less than the KD of the murine antibody ADWA11, e.g., less than 536 pM (e.g., 1, 5, 10, 20, 30, 40, 50, 60, 70, 80, 90, 100, 150, 200, 250, 300, 350, 370, 400, 450, 500, 510, 520, 530, 531, 532, 533, 534, or 535 pM);
ii. a KD for human αvβ8 integrin that is less than or equal to 100 pM (e.g., 1, 2, 3, 4, 5, 6, 7, 8, 9, 10, 15, 20, 30, 40, 50, 60, 70, 80, 90, or 100 pM), e.g., for purified human αvβ8 integrin;
iii. a KD for mouse αvβ8 integrin that is less than the KD of the murine antibody ADWA11, e.g., less than 489 pM (e.g., 1, 5, 10, 20, 30, 40, 50, 60, 70, 80, 90, 100, 150, 200, 250, 300, 350, 370, 400, 450, 460, 470, 480, 485, 486, 487, or 488 pM);
iv. a KD for cynomolgus monkey αvβ8 integrin that is less than the KD of the murine antibody ADWA11, e.g., less than 507 pM (e.g., 1, 5, 10, 20, 30, 40, 50, 60, 70, 80, 90, 100, 150, 200, 250, 300, 350, 370, 400, 450, 500, 501, 502, 503, 504, 505, or 506 pM);
v. a KD for rat αvβ8 integrin that is about 160 pM;
vi. shows approximately equivalent affinity for at least two, three, or all of human, cynomolgus, mouse, and rat αvβ8 integrin, e.g., with a KD that is less than 100 pM (e.g., 1, 2, 3, 4, 5, 6, 7, 8, 9, 10, 15, 20, 30, 40, 50, 60, 70, 80, 90 or 95 pM), e.g., as determined using a Biacore affinity assay;
vii. an IC50 for inhibiting TGFβ transactivation that is less than the murine antibody ADWA11, e.g., less than 183 pM (e.g., 1, 2, 3, 4, 5, 6, 7, 8, 9, 10, 15, 20, 30, 40, 50, 60, 70, 80, 90, 100, 110, 120, 130, 140, 150, 160, 170, 175, 180, 181, or 182 pM);
viii. an IC50 for inhibiting TGFβ transactivation in U251 cells of about 100, 120, 140, 160, 180, 200, 220, 240, 260, 280, 300, 320 or 340 pM;
ix. an EC50 for U251 cells of about 126 pM with a standard deviation of plus or minus 34 pM;
x. an EC50 for U251 cells of about 256 pM with a standard deviation of plus or minus 115 pM;
xi. an EC50 for C8-S cells of about 115 pM;
xii. an EC50 for C8-S cells of about 145 pM with a standard deviation of plus or minus 23.7 pM;
xiii. at least one predicted human pharmacokinetic (PK) parameter chosen from:
  a. a clearance from central compartment (CL) of about 0.12-0.15 mL/h/kg;
  b. an inter-compartmental distribution clearance (CLF) of about 0.15-0.51 mL/h/kg;
  c. a volume of distribution for the central compartment (V1) of about 36-39 mL/kg;
  d. a volume of distribution for the peripheral compartment (V2) of about 21-33 mL/kg; and/or
  e. a terminal half-life ($t_{1/2}$) of about 12-17 days; or
    xiv. shows no detectable binding to human Fcγ receptors or C1q.

In some embodiments, the anti-αvβ8 integrin antibodies, or antigen-binding fragments thereof, binds αvβ8 integrin+ cells (e.g., cells expressing αvβ8 integrin) with high apparent affinity. Apparent affinity binding can be assessed using flow cytometry to detect antibody binding to cells expressing the target protein (e.g., αvβ8 integrin). The cells can be transiently or stably transfected with a nucleic acid encoding αvβ8 integrin. Alternatively, the cells can be cells that naturally express αvβ8 integrin on their surface. Regardless of the sources of αvβ8 integrin+cells, the binding of the antibody to the cells can be readily assessed using a variety of art-recognized methods. The antibody, or antigen-binding fragment thereof, bind human αvβ8 integrin, cynomolgus monkey αvβ8 integrin, mouse αvβ8 integrin, rat αvβ8 integrin.

The invention includes an antibody, or antigen-binding fragment thereof, that specifically binds αvβ8 integrin and antagonizes an activity mediated by αvβ8 integrin (e.g., TGFβ signaling, which can be mediated by inhibiting the interaction of αvβ8 integrin with the Latency Associated Peptide (LAP)). There are many assays known in the art to determine the inhibition of an activity mediated by TGFβ signaling. One such assay is a TGFβ pathway trans-activation assay. In one example of such an assay, the expression of SMAD, which can serve as a marker of TGFβ signaling and pathway activation, in monitored via the use of a luciferase reporter. The ability of the anti-αvβ8 integrin antibody to bind αvβ8 integrin and antagonize the effect of TGFβ signaling (e.g., by inhibiting the interaction of αvβ8 integrin with LAP) is therefore assessed by measuring the level of SMAD expressed in the presence or absence of the antibody. Preferably, the antibody can mediate a dose-dependent decrease in luciferase with an EC50 of about 1 pM, about 2 pM, about 3 pM, about 4 pM, about 5 pM, about 6 pM, about 7 pM, about 8 pM, about 9 pM, about 10 pM, about 20 pM, about 30 pM, about 40 pM, about 50 pM, about 60 pM, about 70 pM, about 80 pM, about 90 pM, about 100 pM, about 125 pM, about 150 pM, about 175 pM, about 200, pM, about 225 pM, about 250 pM, about 275 pM, about 300 pM, about 400 pM, or about 500 pM (e.g., an EC50 of between about 1 pM and about 100 pM, e.g., an EC50 of between about 1 pM and about 200 pM, e.g., an EC50 of between about 1 pM and about 300 pM, e.g., an EC50 of between about 1 pM and about 400 pM, e.g., an EC50 of between about 1 pM and about 500 pM). More preferably, the antibody, or antigen-binding fragment thereof, inhibits TGFβ signaling (e.g., TGFβ transactivation, e.g., TGFβ transactivation of SMAD) with an EC50 of about 100 pM (e.g., an EC50 of between about 5 pM and about 175 pM, e.g., an EC50 of between about 25 pM and about 175 pM, e.g., an EC50 of about 100 pM, about 105 pM, about 110 pM, about 115 pM, about 120 pM, about 125 pM, about 130 pM, about 135 pM, about 140 pM, about 145 pM, about 150 pM, about 155 pM, about 160 pM, about 165 pM, about 170 pM, or about 175 pM). In some embodiments, the antibody, or antigen-binding fragment thereof, inhibits TGFβ signaling (e.g., TGFβ transactivation, e.g., TGFβ transactivation of SMAD) with an EC50 of less than about 5 nM (e.g., less than about 0.001, 0.01, 0.1, 0.2, 0.3, 0.4, 0.5, 0.6, 0.7, 0.8, 0.9, 1, 1.5, 2, 2.5, 3, 3.5, 4, 4.5, 5, 5.1, 5.5, 6, 7, 8, 9, 10, 15, 20, or 25 nM). In embodiments, the antibody, or antigen-binding fragment thereof, inhibits TGFβ signaling (e.g., TGFβ transactivation, e.g., TGFβ transactivation of SMAD) with an EC50 of about 5 nM (e.g., about 0.001, 0.01, 0.1, 0.2, 0.3, 0.4, 0.5, 0.6, 0.7, 0.8, 0.9, 1, 1.5, 2, 2.5, 3, 3.5, 4, 4.5, 5, 5.1, 5.5, 6, 7, 8, 9, 10, 15, 20, or 25 nM).

In some embodiments, an antibody, or antigen-binding fragment thereof, of the present disclosure inhibits TGFβ signaling with an EC50 of about 145+/−23.7 pM. In some embodiments, an antibody, or antigen-binding fragment thereof, of the present disclosure inhibits TGFβ signaling in C8-S with an EC50 of about 145+/−23.7 pM. In some embodiments, an antibody or antigen-binding fragment thereof, of the present disclosure inhibits TGFβ signaling in C8-S cells with an EC50 of about 110 pM to about 180 pM.

In some embodiments, an antibody, or antigen-binding fragment thereof, of the present disclosure inhibits TGFβ signaling with an EC50 of about 256+/−115 pM. In some embodiments, an antibody, or antigen-binding fragment thereof, of the present disclosure inhibits TGFβ signaling in U251 cells with an EC50 of about 256+/−115 pM. In some embodiments, an antibody or antigen-binding fragment thereof, of the present disclosure inhibits TGFβ signaling in U251 cells with an EC50 of about 80 pM to about 400 pM.

The invention encompasses an antibody, or antigen-binding fragment thereof, that binds human αvβ8 integrin but does not detectably bind human proteins αvβ3 integrin, αvβ5 integrin or αvβ6 integrin.

III. Anti-αvβ8 Integrin Antibody Expression and Production

Nucleic Acids Encoding Anti-αvβ8 Integrin Antibodies

The invention also provides polynucleotides encoding any of the antibodies, including antibody fragments and modified antibodies described herein. The invention also provides a method of making any of the polynucleotides described herein. Polynucleotides can be made and expressed by procedures known in the art.

The sequence of a desired antibody, defined antibody fragment, or antigen-binding fragment thereof, and nucleic acid encoding such antibody, or fragment thereof, can be determined using standard sequencing techniques. A nucleic acid sequence encoding a desired antibody, defined antibody fragment, or antigen-binding fragment thereof, may be inserted into various vectors (such as cloning and expression vectors) for recombinant production and characterization. A nucleic acid encoding the heavy chain, defined antibody fragment, or antigen-binding fragment of the heavy chain, and a nucleic acid encoding the light chain, defined antibody fragment, or antigen-binding fragment of the light chain, can be cloned into the same vector, or different vectors.

The polynucleotide encoding the amino acid sequences above, encodes an amino acid sequence at least 80%, 85%, 90%, 91%, 92%, 93%, 94%, 95%, 96%, 97%, 98%, or 99%, and more preferably identical to, the amino acid sequence of the antibodies, or antigen-binding fragment thereof, of the present invention as disclosed herein.

In some embodiments, the invention provides polynucleotides encoding one or more proteins comprising the amino acid sequence selected from the group consisting of: SEQ ID NOs:2, 3, and 5-76 (e.g., a polynucleotide comprising a sequence set forth in SEQ ID NO: 1, 4, 183, 185, 186, 189, 190 or 191), or a nucleotide sequence encoding an amino acid sequence at least 80%, 85%, 90%, 91%, 92%, 93%, 94%, 95%, 96%, 97%, 98%, or 99%, and more preferably identical to SEQ ID NOs:2, 3, 5-76, 88-93, 123, 124 and 182.

The invention provides polynucleotides comprising the nucleic acid sequence as set forth as one or more of SEQ ID NOs: 1, 183, 189 or 191 and encoding an antibody heavy chain or a nucleotide sequence at least 80%, 85%, 90%, 91%, 92%, 93%, 94%, 95%, 96%, 97%, 98%, or 99%, or identical to SEQ ID NOs: 1, 183, 189 or 191 and encoding an antibody heavy chain.

The invention provides polynucleotides comprising the nucleic acid sequence as set forth as one or more of SEQ ID NOs: 4 or 185 and encoding an antibody light chain or a nucleotide sequence at least 80%, 85%, 90%, 91%, 92%, 93%, 94%, 95%, 96%, 97%, 98%, or 99%, or identical to SEQ ID NOs: 4 or 185 and encoding an antibody light chain.

The invention provides polynucleotides comprising the nucleic acid sequence as set forth in SEQ ID NO: 190 and encoding an antibody heavy chain variable region, or a nucleotide sequence at least 80%, 85%, 90%, 91%, 92%, 93%, 94%, 95%, 96%, 97%, 98%, or 99%, or identical to SEQ ID NO: 190 and encoding an antibody heavy chain variable region.

The invention provides polynucleotides comprising the nucleic acid sequence as set forth in SEQ ID NO: 186 and encoding an antibody light chain variable region, or a nucleotide sequence at least 80%, 85%, 90%, 91%, 92%, 93%, 94%, 95%, 96%, 97%, 98%, or 99%, or identical to SEQ ID NO: 186 and encoding an antibody light chain variable region.

The invention provides polynucleotides comprising the nucleic acid sequence as set forth in SEQ ID NO: 192 or 193 and encoding an antibody heavy chain constant region, or a nucleotide sequence at least 80%, 85%, 90%, 91%, 92%, 93%, 94%, 95%, 96%, 97%, 98%, or 99%, or identical to SEQ ID NO: 192 or 193 and encoding an antibody heavy chain constant region.

The invention provides polynucleotides comprising the nucleic acid sequence as set forth in SEQ ID NO: 194 and encoding an antibody light chain constant region, or a nucleotide sequence at least 80%, 85%, 90%, 91%, 92%, 93%, 94%, 95%, 96%, 97%, 98%, or 99%, or identical to SEQ ID NO: 194 and encoding an antibody light chain constant region.

The invention provides a polynucleotide comprising the nucleic acid sequence as set forth as SEQ ID NO: 189. The invention provides a polynucleotide comprising the nucleic acid sequence as set forth as SEQ ID NO: 190. The invention provides a polynucleotide comprising the nucleic acid sequence as set forth as SEQ ID NO: 185.

The invention provides a polynucleotide comprising one or both of the nucleic acid sequence of the DNA insert of the plasmid deposited with the ATCC and having Accession No. PTA-124917, and/or Accession No. PTA-124918.

The invention provides a polynucleotide comprising the nucleic acid sequence of the insert in the plasmid deposited with the ATCC and having Accession No. PTA-124917, and/or Accession No. PTA-124918.

The invention provides cells comprising one or more nucleic acid molecules as set forth in SEQ ID NOs: 1, 183 and 4.

The invention provides cells comprising one or more nucleic acid molecules as set forth in SEQ ID NOs: 185, 189 and 190.

In another aspect, the invention provides polynucleotides and variants thereof encoding an anti-αvβ8 integrin antibody (e.g., an anti-human αvβ8 integrin antibody), wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid sequences disclosed herein. These amounts are not meant to be limiting and increments between the recited percentages are specifically envisioned as part of the disclosure.

The invention provides polypeptides encoded by the nucleic acid molecules described herein.

In one embodiment, the VH and VL domains, or antigen-binding fragment thereof, or full length HC or LC, are encoded by separate polynucleotides. Alternatively, both VH and VL, or antigen-binding fragment thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. In some embodiments, variants exhibit at least about 70% identity, in some embodiments, at least about 80% identity, in some embodiments, at least about 90% identity, and in some embodiments, at least about 95% identity to a polynucleotide sequence that encodes a native antibody or a fragment thereof. These amounts are not meant to be limiting and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity. Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 pg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations or alterations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

Vectors

In some embodiments, a vector is selected that is optimized for expression of polypeptides in CHO or CHO-derived cells, or in NSO cells. Exemplary such vectors are described, e.g., in Running Deer et al., Biotechnol. Prog. 20:880-889 (2004).

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen. Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Host Cells

The antibody, or antigen-binding fragment thereof, may be made recombinantly using a suitable host cell. A nucleic acid encoding the antibody or antigen-binding fragment thereof can be cloned into an expression vector, which can then be introduced into a host cell, such as $E.\ coli$ cell, a yeast cell, an insect cell, a simian COS cell, a Chinese hamster ovary (CHO) cell, or a myeloma cell where the cell does not otherwise produce an immunoglobulin protein, to obtain the synthesis of an antibody in the recombinant host cell. Preferred host cells include a CHO cell, a human embryonic kidney HEK-293 cell, or an Sp2.0 cell, among many cells well-known in the art. An antibody fragment can be produced by proteolytic or other degradation of a full-length antibody, by recombinant methods, or by chemical synthesis. A polypeptide fragment of an antibody, especially shorter polypeptides up to about 50 amino acids, can be conveniently made by chemical synthesis. Methods of chemical synthesis for proteins and peptides are known in the art and are commercially available.

In various embodiments, anti-$\alpha v \beta 8$ integrin heavy chains and/or anti-$\alpha v \beta 8$ integrin light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lecl3 CHO cells, and FUT8 CHO cells; PER.C6® cells (Crucell); and NSO cells. In some embodiments, anti-$\alpha v \beta 8$ integrin heavy chains and/or anti-$\alpha v \beta 8$ integrin light chains may be expressed in yeast. See, e.g., U.S. Publication No. US 2006/0270045 A1. In some embodiments, a particular eukaryotic host cell is selected based on its ability to make desired post-translational modifications to the anti-$\alpha v \beta 8$ integrin heavy chains and/or anti-$\alpha v \beta 8$ integrin light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

Anti-$\alpha v \beta 8$ integrin antibodies may be purified by any suitable method. Such methods include, but are not limited to, the use of affinity matrices or hydrophobic interaction chromatography. Suitable affinity ligands include ligands that bind antibody constant regions. For example, a Protein A, Protein G, Protein A/G, or an antibody affinity column may be used to bind the constant region and to purify an anti-$\alpha v \beta 8$ integrin antibody. Hydrophobic interactive chromatography, for example, a butyl or phenyl column, may also suitable for purifying some polypeptides. Many methods of purifying polypeptides are known in the art.

In some embodiments, an anti-$\alpha v \beta 8$ integrin antibody is produced in a cell-free system. Non-limiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

IV. Uses and Medical Therapies

Therapeutic Uses

In some aspects, the invention provides for therapeutic methods for inhibiting $\alpha v \beta 8$ integrin activity by using an anti-$\alpha v \beta 8$ integrin antibody or antigen-binding fragment thereof, wherein the therapeutic methods comprise administering a therapeutically effective amount of a pharmaceutical composition comprising an anti-$\alpha v \beta 8$ integrin antibody or antigen-binding fragment thereof. The disorder treated is any disease or condition which is improved, ameliorated, inhibited, or prevented by removal, inhibition, or reduction of $\alpha v \beta 8$ integrin activity or signaling. In particular, the anti-$\alpha v \beta 8$ integrin antibodies of the invention, including humanized and chimeric antibodies, can be used in the prevention, treatment, and/or amelioration of diseases, disorders, or conditions caused by and/or associated with aberrant (e.g., increased) $\alpha v \beta 8$ integrin activity and/or TGF$\beta$ signaling in a subject (e.g., within the tumor microenvironment of a subject having a cancer). In some embodiments, the disease, disorder, or condition comprises a respiratory condition (e.g., asthma), fibrosis, or anemia. In some embodiments, the disease, disorder, or condition is treatable or preventable with a vaccine.

In some aspects, the invention provides a method for the selective inhibition of $\alpha v \beta 8$-dependent latent-TGF$\beta$ activation in cells in the tumor microenvironment including, for example, dendritic cells, T regulatory cells, tumor associated macrophages, and/or the cells of the tumor itself. Without being bound by any particular theory, a more precise and selective antagonism of TGF$\beta$ activation within the immune system and/or the tumor microenvironment mediated by administration of an anti-$\alpha v \beta 8$ integrin antibody of the invention may contribute to an anti-tumor immune response in a subject without perturbing the broader homeostatic functions of TGF$\beta$. Such an anti-tumor immune response within a subject that does not perturb the broader homeostatic functions of TGF$\beta$ may be expected to provide safety and therapeutic advantages over systemic TGF$\beta$ inhibition.

The methods provided herein may also be used to reduced and/or attenuate TGF$\beta$ activity, (e.g., TGF$\beta$ tumor-promoting activity) in a subject (e.g., within a tumor microenvironment of a subject having a cancer). TGF$\beta$ activities influencing angiogenesis, metastasis, epithelial-mesenchymal transition, and/or suppression of infiltrating immune cells (e.g., tumor infiltrating lymphocytes, e.g., T cells, B cells, natural killer cells, macrophages, neutrophils, dendritic cells, mast cells, eosinophils, and basophils) within a tumor microenvironment may be reduced and/or attenuated by the administration of a therapeutically effective amount of an anti-αvβ8 integrin antibody of the invention to a subject (e.g., a subject having a cancer).

In some instances, administration of an anti-αvβ8 integrin antibody, or antigen-binding fragment thereof, to a subject having a cancer increases the amount (e.g., density as determined by an immunohistochemistry (IHC) analysis) of infiltrating immune cells, for example, CD45 total lymphocytes and myeloid cells, CD3 T cells, CD4 T cells, CD8 T cells, and GranzymeB expressing cells (e.g., activated CD8 and NK cells), in a tumor sample (e.g., a solid tumor sample) acquired from the subject. An increase in the amount (e.g., density) of infiltrating immune cells may be determined, for example, by immunohistochemistry (IHC) analysis of a tumor sample (e.g., a solid tumor sample) acquired from a subject having a cancer in comparison to the amount (e.g., density) of infiltrating immune cells acquired from a reference tumor sample (e.g., a tumor sample obtained from the same subject or a different subject having a similar cancer, wherein the tumor sample was acquired prior to an administration (e.g., a first administration, or a subsequent administration) of an anti-αvβ8 integrin antibody, or antigen-binding fragment thereof).

In one aspect, the invention relates to treatment of a subject in vivo using an anti-αvβ8 integrin antibody, or antigen-binding fragment thereof, such that growth of cancerous tumors is inhibited or reduced. In some embodiments, a subject treated in vivo using an anti-αvβ8 integrin antibody, or antigen-binding fragment thereof, has a primary cancer, for example a locally advanced cancer. In some embodiments, a subject treated in vivo using an anti-αvβ8 integrin antibody, or antigen-binding fragment thereof, has a recurrent cancer, for example a metastatic cancer.

In one aspect, the invention relates to in vivo treatment of a subject having a cancer, or tumor, that expresses αvβ8 integrin, integrin β8 (ITGβ8) and/or integrin αV (ITGαV) using an anti-αvβ8 integrin antibody, or antigen-binding fragment thereof. In some embodiments, expression of αvβ8, β8 integrin and/or αV integrin is protein expression. In some embodiments, expression of αvβ8, β8 integrin and/or αV integrin is mRNA expression. In some embodiments, expression of αvβ8, β8 integrin and/or αV integrin is increased expression relative to a level of αvβ8, β8 integrin and/or αV integrin expression in a normal tissue or sample, in a control tissue or sample, in a tissue or sample prior to treatment and/or a tissue or sample following treatment. In one embodiment, a tissue or sample used to determine relative expression levels of αvβ8, β8 integrin and/or αV integrin may be obtained from a subject with a cancer or tumor, from a different subject having the same type of cancer or tumor or a different type of cancer or tumor or from a subject without a cancer or tumor.

In some embodiments, mRNA expression of αvβ8, β8 integrin and/or αV integrin is increased expression relative to a level of expression in a normal tissue or sample, in a control tissue or sample, in a tissue or sample prior to treatment and/or a tissue or sample following treatment. In some embodiments, mRNA expression of αvβ8, β8 integrin and/or αV integrin is increased by about 5%, about 10%, about 20%, about 30%, about 40%, about 50%, about 60%, about 70%, about 80%, about 90%, about 100%, about 150%, about 200%, about 300%, about 400%, about 500% relative to a level of mRNA expression of αvβ8, β8 integrin and/or αV integrin in a normal tissue or sample, in a control tissue or sample, in a tissue or sample prior to treatment and/or a tissue or sample following treatment.

An anti-αvβ8 integrin antibody, or antigen-binding fragment thereof, may be used alone (e.g., as a monotherapy) to inhibit the growth of a cancerous tumor. Alternatively, an anti-αvβ8 integrin antibody, or antigen-binding fragment thereof, may be used in combination with one or more of: a standard of care treatment (e.g., for cancers or infectious disorders), another antibody or antigen-binding fragment thereof, an immunomodulator (e.g., an activator of a costimulatory molecule or an inhibitor of an inhibitory molecule); a vaccine, e.g., a therapeutic cancer vaccine; or other forms of cellular immunotherapy.

Accordingly, in one embodiment, the invention provides a method of inhibiting growth of tumor cells in a subject, comprising administering to the subject a therapeutically effective amount of an anti-αvβ8 integrin antibody, or antigen-binding fragment thereof, described herein.

In one embodiment, the methods are suitable for the treatment of cancer in vivo. To achieve enhancement of immunity, the anti-αvβ8 integrin antibody, or antigen-binding fragment thereof, can be administered together with an antigen of interest. When the anti-αvβ8 integrin antibody, or antigen-binding fragment thereof, is administered in combination with one or more agents, the combination can be administered in either order or simultaneously.

In another aspect, a method of treating a subject, e.g., reducing or ameliorating, a hyperproliferative condition or disorder (e.g., a cancer), e.g., solid tumor, a hematological cancer, soft tissue tumor, or a metastatic lesion, in a subject is provided. The method includes administering to the subject one or more anti-αvβ8 integrin antibodies, or antigen-binding fragments thereof, described herein, alone or in combination with other agents or therapeutic modalities. In some embodiments, the anti-αvβ8 integrin antibody, or antigen-binding fragment thereof, of the invention can be administered as a $1^{st}$ line therapy in treatment naïve subjects, or as a $2^{nd}$ line therapy following for example, relapse or progression of the cancer.

Exemplary cancers whose growth can be treated, e.g., reduced, using the antibodies molecules disclosed herein include cancers typically responsive to immunotherapy. Non-limiting examples of cancers for treatment include melanoma (e.g., metastatic malignant melanoma, skin cutaneous melanoma), renal cell cancer (RCC) (e.g., clear cell carcinoma, papillary cell carcinoma), prostate cancer (e.g., hormone refractory prostate adenocarcinoma), breast cancer, ovarian cancer (e.g., epithelial ovarian cancer, fallopian tube or primary peritoneal cancer), head and neck cancer (e.g., squamous cell carcinoma of the head and neck (SCCHN)), colon cancer, esophageal cancer (e.g., adenocarcinoma and squamous cell carcinoma), gastric cancer (e.g., adenocarcinoma of gastric and gastroesophageal junction), pancreatic cancer (e.g, pancreatic ductal adenocarcinoma), biliary duct cancer (e.g., cholangiocarcinoma); endometrial cancer (e.g., uterine corpus endometrial carcinoma), urothelial carcinoma and lung cancer (e.g., non-small cell lung cancer, squamous cell cancer). Additionally, refractory or recurrent malignancies can be treated using the antibody molecules described herein.

Examples of other cancers that can be treated include bone cancer, cutaneous or intraocular malignant melanoma, rectal cancer, anal cancer, testicular cancer, carcinoma of the cervix, carcinoma of the vagina, carcinoma of the vulva, Merkel cell cancer, Hodgkin lymphoma, non-Hodgkin lymphoma, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, multiple myeloma, myelodysplastic syndromes, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers. In some embodiments, the cancer is chosen from a renal cell carcinoma, an ovarian cancer, a head and neck squamous cell carcinoma, and a skin cancer (e.g., a melanoma, e.g., an advanced melanoma).

In some instances, the cancer is selected from the group consisting of a solid tumor, a hematological cancer (e.g., leukemia, lymphoma, myeloma, e.g., multiple myeloma), and a metastatic lesion. The cancer may be a solid tumor, for example, a solid tumor such as a malignancies, e.g., sarcomas and carcinomas, e.g., adenocarcinomas of the various organ systems, such as those affecting the lung (e.g., a non-small cell lung cancer (NSCLC)), breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck (e.g., head and neck squamous cell carcinoma (HNSCC), skin (e.g., melanoma, e.g., an advanced melanoma), pancreas, colon, rectal, a renal (e.g., a renal cell carcinoma), liver, cancer of the small intestine and cancer of the esophagus, gastro-esophageal cancer, thyroid cancer, and cervical cancer. In some instances, the cancer may be a lymphoproliferative disease (e.g., a post-transplant lymphoproliferative disease) or a hematological cancer, T-cell lymphoma, B-cell lymphoma, a non-Hodgkin lymphoma, or a leukemia (e.g., a myeloid leukemia or a lymphoid leukemia). In some instances, the cancer is an early, intermediate, late stage or metastatic cancer. In particular instances, the cancer is a renal cell carcinoma, an ovarian cancer, or a head and neck squamous cell carcinoma.

In other embodiments, the cancer is a hematological malignancy or cancer including but is not limited to a leukemia or a lymphoma. For example, the anti-αvβ8 integrin antibody, or antigen-binding fragment thereof, can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a cutaneous squamous cell carcinoma (cutaneous SCC) (e.g., metastatic cutaneous SCC), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, a non-Hodgkin's lymphoma, or a leukemia (e.g., a myeloid leukemia).

In another embodiment, the cancer is chosen from a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC or clear cell renal cell carcinoma).

In some embodiments, when the cancer is a skin cancer (e.g., a melanoma, e.g., an advanced melanoma, e.g., cutaneous squamous cell carcinoma, e.g., metastatic cutaneous squamous cell carcinoma).

In one embodiment, the cancer is a melanoma, e.g., an advanced melanoma. In one embodiment, the cancer is an advanced or unresectable melanoma that does not respond to other therapies.

In some embodiments, the cancer is a renal cancer, e.g., a renal cell carcinoma (RCC). In some instances, the renal cancer is a metastatic RCC, a clear cell renal cell carcinoma (ccRCC)), or a non-clear-cell renal cell carcinoma (ncRCC). In some instances, when the cancer is an RCC, e.g., ccRCC, an anti-αvβ8 integrin antibody, or antigen-binding fragment thereof, of the invention may be administered as a $1^{st}$ line or $2^{nd}$ line therapy.

In some embodiments, when the cancer is an ovarian cancer an anti-αvβ8 integrin antibody, or antigen-binding fragment thereof, of the invention may be administered as a $2^{nd}$ Line therapy for platinum-resistant patients.

In some embodiments, the cancer is platinum-resistant and/or recurrent cancer.

Methods and compositions disclosed herein are useful for treating metastatic lesions associated with the aforementioned cancers.

Combination Therapies

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies or antigen-binding fragments thereof to each of these entities may be used in combination with anti-αvβ8 integrin antibodies, or antigen-binding fragments thereof, to counteract the effects of the immunosuppressive agent and favor tumor immune responses by the host.

The antibodies or antigen binding fragments disclosed herein can be used in unconjugated forms or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., recombinant viral particles, e.g.; via a viral coat protein), or mixtures thereof.

In certain embodiments, an anti-αvβ8 integrin antibody, or antigen-binding fragment thereof, can be used in combination with other therapies to provide an unexpected synergistic therapeutic effect that can provide an effect greater than a merely additive effect of adding two individual therapies. For example, the combination therapy can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such synergistic combination therapies may advantageously utilize lower dosages of the administered therapeutic agents, thus avoiding possible toxicities or complications associated with the various monotherapies.

In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include antimicrotubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation).

Alternatively, or in combination with the aforesaid combinations, the methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

Exemplary non-limiting synergistic combinations and uses of an anti-αvβ8 integrin antibodies, or antigen-binding fragments thereof, include the following.

In certain embodiments, an anti-αvβ8 integrin antibody, or antigen-binding fragment thereof, is administered in combination with a modulator of a costimulatory molecule or an inhibitory molecule, e.g., a co-inhibitory ligand or receptor.

In one embodiment, an anti-αvβ8 integrin antibody, or antigen-binding fragment thereof, is administered in combination with a modulator, e.g., agonist, of a costimulatory molecule. In one embodiment, the agonist of the costimulatory molecule is chosen from an agonist (e.g., an agonistic antibody or antigen-binding fragment thereof, or soluble fusion) of 4-1BB (CD137), OX40, CD2, CD27, CDS, ICAM-1, LFA-1 (CD11a/CD18), ICOS (CD278), GITR, CD30, CD40, BAFFR, HVEM, CD7, LIGHT, NKG2C, SLAMF7, NKp80, CD160, or B7-H3.

In another embodiment, an anti-αvβ8 integrin antibody, or antigen-binding fragment thereof, is used in combination with an immunomodulator, e.g., a costimulatory molecule, e.g., an agonist or modulator associated with a positive signal that includes a costimulatory domain of 4-1BB (CD137), CD28, CD27, ICOS and GITR.

Exemplary GITR modulators include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726. In one embodiment, an anti-αvβ8 integrin antibody, or antigen-binding fragment thereof, is administered in combination with an inhibitor of an inhibitory molecule of an immune checkpoint molecule. It will be understood by those of ordinary skill in the art, that the term "immune checkpoints" means a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, LAG-3 and TIM-3, which directly inhibit immune cells. Immunotherapeutic agents which can act as immune checkpoint inhibitors useful in the methods of the present invention, include, but are not limited to, inhibitors of PD-1, PD-L1, PD-L2, CTLA4, TIM-3, LAG-3, VISTA, BTLA, TIGIT, LAIR1, CD160, 2B4, CEACAM, and/or TGF beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

In one embodiment, the inhibitor is a soluble ligand (e.g., a CTLA-4-Ig or a TIM-3-Ig), or an antibody or antibody fragment that binds to PD-1, PD-L1, PD-L2 or CTLA4. For example, an anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9). In one embodiment, an anti-αvβ8 integrin antibody, or antigen-binding fragment thereof, is administered after treatment, e.g., after treatment of a melanoma, with an anti-CTLA4 antibody (e.g., ipilimumab) with or without a BRAF inhibitor (e.g., vemurafenib or dabrafenib). Exemplary doses of an anti-CTLA-4 antibody, e.g., ipilimumab, of about 3 mg/kg.

Other antibodies which may be used to activate host immune responsiveness can be used in combination with an anti-αvβ8 integrin antibody, or antigen-binding fragment thereof. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with an anti-αvβ8 integrin antibody, or antigen-binding fragment thereof. Antibodies to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

In certain embodiments, an anti-αvβ8 integrin antibody, or antigen-binding fragment thereof, described herein is administered in combination with one or more inhibitors of PD-1, PD-L1 and/or PD-L2 known in the art. In one embodiment, an anti-αvβ8 integrin antibody, or antigen-binding fragment thereof, is administered concurrently with an immune checkpoint inhibitor (e.g., an anti-PD-1, anti-PD-L1 and/or anti-PD-L2 antibody, or antigen-binding fragment thereof) to a subject who has not been previously treated with an immune checkpoint inhibitor. In one embodiment, an anti-αvβ8 integrin antibody, or antigen-binding fragment thereof, is administered concurrently with an immune checkpoint inhibitor (e.g., an anti-PD-1, anti-PD-L1 and/or anti-PD-L2 antibody, or antigen-binding fragment thereof) to a subject who has been previously treated with an immune checkpoint inhibitor and in whom the cancer or tumor had progressed (e.g., locally advanced, metastasized). In one embodiment, an anti-αvβ8 integrin antibody, or antigen-binding fragment thereof, is administered biweekly (e.g., every 2 week) in a 28-day cycle and an immune checkpoint inhibitor is administered every 4 weeks on day 1 of each 28-day cycle. In one embodiment, an anti-αvβ8 integrin antibody, or antigen-binding fragment thereof, is administered biweekly on a 28-day cycle and an immune checkpoint inhibitor (e.g., an anti-PD-1, anti-PD-L1 and/or anti-PD-L2 antibody, or antigen-binding fragment thereof) is administered every 4 weeks on day 1 of each 28-day cycle to a subject who has a cancer or a tumor. In one embodiment, an immune checkpoint inhibitor is an anti-PD1 antibody, or antigen-binding fragment thereof, described in PCT Publication No. WO2016/092419, (e.g., RN888, as referred to as PF-06801591 or sasanlimab). In one embodiment, a cancer or tumor is squamous cell carcinoma, e.g., squamous cell carcinoma of the head or neck (SCCHN), renal cell carcinoma (RCC), breast cancer, or colon cancer.

An inhibitor of PD-1, PD-L1 and/or PD-L2 may be an antibody, an antigen binding fragment thereof, an immunoadhesin, a fusion protein, or oligopeptide. In some embodiments, an anti-PD-1 antibody is chosen from MDX-1106, Merck 3475 or CT-011. In one embodiment, an anti-PD-1 antibody is nivolumab/Opdivo®, pembrolizumab/Keytruda®, spartalizumab, pidilizumab, tislelizumab, AMP-224, AMP-514, cemiplimab, or sasanlimab (RN888, mAb7, PF-06801591). In one embodiment, an anti-PD-L1 antibody is MEDI4736, MPDL3280A (YW243.55.s70), BMS-936559 (MDX-1105), atezolizumab/Tecentriq®, durvalumab/Imfizi® or avelumab/Bavencio®. In one embodiment, the anti-PD-L1 antibody is not avelumab. In one embodiment, an anti-PD-1 antibody is described in PCT Publication No. WO2016/092419, including, but not limited to, mAb7 (also referred to as RN888, PF-06801591, or sasanlimab).

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224. In some embodiments, the PD-L1 inhibitor is an anti-PD-L1 antibody. In some embodiments, an anti-PD-L1 binding antagonist is chosen from YW243.55.s70 (also known as MPDL3280A, atezolizumab), MEDI-4736, MSB-0010718C, or MDX-1105. MDX-1105, also known as BMS-936559, is an anti-PD-L1 antibody described in WO2007/005874. Antibody YW243.55.s70 also referred to as MPDL3280A (heavy and light chain variable region sequences shown in SEQ ID Nos. 20 and 21, respectively) is an anti-PD-L1 described in WO 2010/077634.

MDX-1106, also known as MDX-1106-04, ONO-4538 or BMS-936558, is an anti-PD-1 antibody described in WO2006/121168. Merck 3745, also known as MK-3475 or SCH-900475, is an anti-PD-1 antibody described in WO2009/114335. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. In other embodiments, an anti-PD-1 antibody is pembrolizumab. Pembrolizumab (Trade name KEYTRUDA formerly lambrolizumab, also known as MK-3475) disclosed, e.g., in Hamid, O. et al. (2013) New England Journal of Medicine 369 (2): 134-44. AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP-514 (Amplimmune), among others, e.g., anti-PD-1 antibodies disclosed in U.S. Pat. No. 8,609,089, US 2010028330, and/or US 20120114649.

In some embodiments, an anti-PD-1 antibody is MDX-1106. Alternative names for MDX-1106 include MDX-1106-04, ONO-4538, BMS-936558 or nivolumab. In some embodiments, an anti-PD-1 antibody is nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Lambrolizumab (also referred to as pembrolizumab or MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A (also known as YW243.55.s70, and other human monoclonal antibodies to PD-L1 are disclosed in U.S. Pat. No. 7,943,743 and U.S Publication No. 20120039906. The sequences of YW243.55.s70 (heavy and light chain variable regions are shown in SEQ ID NOs 20 and 21) are also set forth in WO2010/077634 and U.S. Pat. No. 8,217,149). MDX1105

(also referred to as BMS-936559), and other anti-PD-L1 binding agents are disclosed in WO2007/005874.

In other embodiments, an anti-αvβ8 integrin antibody, or antigen-binding fragment thereof, is administered in combination with a cytokine, e.g., interleukin-21, interleukin-2, interleukin-12, or interleukin-15. In certain embodiments, the combination of anti-αvβ8 integrin antibody, or antigen-binding fragment thereof, and cytokine described herein is used to treat a cancer, e.g., a cancer as described herein (e.g., a solid tumor or melanoma).

In all of the methods described herein, anti-αvβ8 integrin antibodies, or antigen-binding fragments thereof, can be combined with other forms of immunotherapy such as cytokine treatment (e.g., interferons, GM-CSF, G-CSF, IL-2, IL-21), or bispecific antibody therapy, which provides for enhanced presentation of tumor antigens (see e.g., Holliger (1993) Proc. Natl. Acad. Sci. USA 90:6444-6448; Poljak (1994) Structure 2:1121-1123).

Exemplary immunomodulators that can be used in combination with an anti-αvβ8 integrin antibody, or antigen-binding fragment thereof, include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

In some embodiments, the cancer is ovarian cancer and an anti-αvβ8 integrin antibody, or antigen-binding fragment thereof, is administered in combination with an inhibitor of PARP1 (e.g., olaparib, rucaparib, niraparib, veliparib, iniparib, talazoparib, 3-aminobenzamide, CEP 9722, E7016, BSI-201, KU-0059436, AG014699, MK-4827, or BGB-290).

In some embodiments, the cancer is a head and neck cancer, e.g., a head and neck squamous cell carcinoma. In some embodiments, an anti-αvβ8 integrin antibody, or antigen-binding fragment thereof, is administered in combination with a radiation therapy.

Diagnostic Uses

Anti-αvβ8 integrin antibodies, or antigen-binding fragments thereof, of the present invention may also be used to detect and/or measure αvβ8 integrin, or αvβ8 integrin-expressing cells in a sample, e.g., for diagnostic purposes. For example, an anti-αvβ8 integrin antibody, or fragment thereof, may be used to diagnose a condition or disease characterized by aberrant expression (e.g., over-expression, under-expression, lack of expression, etc.) of αvβ8 integrin. Exemplary diagnostic assays for αvβ8 integrin may comprise, e.g., contacting a sample, obtained from a patient, with an anti-anti-αvβ8 integrin antibody, or antigen-binding fragment thereof, of the invention, wherein an anti-αvβ8 integrin antibody, or antigen-binding fragment thereof, is labeled with a detectable label or reporter molecule.

In one aspect, the present invention provides a diagnostic method for detecting the presence of an αvβ8 integrin protein in vitro (e.g., in a biological sample, such as a tissue biopsy, e.g., from a cancerous tissue) or in vivo (e.g., in vivo imaging in a subject). The method includes: (i) contacting the sample with an antibody, or antigen-binding fragment thereof, described herein, or administering to the subject, the antibody, or antigen-binding fragment thereof; (optionally) (ii) contacting a reference sample, e.g., a control sample (e.g., a control biological sample, such as plasma, tissue, biopsy) or a control subject)); and (iii) detecting formation of a complex between the antibody, or antigen-binding fragment thereof, and the sample or subject, or the control sample or subject, wherein a change, e.g., a statistically significant change, in the formation of the complex in the sample or subject relative to the control sample or subject is indicative of the presence of αvβ8 integrin in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids, or tissue samples.

Complex formation between the antibody molecule and αvβ8 integrin can be detected by measuring or visualizing either the binding molecule bound to the αvβ8 integrin antigen or unbound binding molecule. Conventional detection assays can be used, e.g., an enzyme-linked immunosorbent assays (ELISA), a radioimmunoassay (RIA) or tissue immunohistochemistry. Alternative to labeling the antibody, or antigen-binding fragment thereof, the presence of αvβ8 integrin can be assayed in a sample by a competition immunoassay utilizing standards labeled with a detectable substance and an unlabeled antibody molecule. In this assay, the biological sample, the labeled standards and the antibody, or antigen-binding fragment thereof, are combined and the amount of labeled standard bound to the unlabeled binding molecule is determined. The amount of αvβ8 integrin in the sample is inversely proportional to the amount of labeled standard bound to the antibody, or antigen-binding fragment thereof.

V. Compositions

The disclosure also provides pharmaceutical compositions comprising an effective amount of an anti-αvβ8 integrin antibodies described herein. Examples of such compositions, as well as how to formulate, are also described herein. In some embodiments, the composition comprises one or more anti-αvβ8 integrin antibodies. In some embodiments, an anti-αvβ8 integrin antibody recognizes αvβ8 integrin (e.g., αvβ8 integrin from a human, mouse, cynomolgus monkey, or rat). In some embodiments, an anti-αvβ8 integrin antibody is a humanized antibody. In some embodiments, an anti-αvβ8 integrin antibody is a chimeric antibody. In some embodiments, an anti-αvβ8 integrin antibody comprises a constant region that is capable of triggering a desired immune response, such as antibody-mediated lysis or ADCC.

The composition used in the present disclosure can further comprise pharmaceutically acceptable carriers, excipients, or stabilizers, in the form of lyophilized formulations or aqueous solutions.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by conventional methods (see, for example, Remington's Pharmaceutical Sciences, 18th edition, A.

Gennaro, ed., Mack Publishing Co., Easton, PA, 1990; and Remington, The Science and Practice of Pharmacy, 20th Ed., Mack Publishing, 2000).

Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

Anti-αvβ8 integrin antibodies and compositions thereof can also be used in conjunction with other agents, including an additional therapeutic agent (e.g., an inhibitor of an immune checkpoint molecule) that serves to enhance and/or complement the effectiveness of the agents.

The disclosure also provides compositions, including pharmaceutical compositions, comprising polynucleotides encoding antibodies of the disclosure. In some embodiments, the composition comprises an expression vector comprising a polynucleotide encoding an antibody as described herein.. In some embodiments, a composition comprises either or both of the polynucleotides of SEQ ID NOs: 1 or 4. In some embodiments, a composition comprises either or both of the polynucleotides of SEQ ID NOs: 183 or 4. In some embodiments, a composition comprises either or both of the polynucleotides of SEQ ID NOs: 185 or 189. In some embodiments, a composition comprises either or both of the polynucleotides of SEQ ID NOs: 185 or 191.

In another aspect, the polynucleotide can encode the VH, VL and/or both VH and VL of an antibody of the disclosure. That is, the composition comprises a single polynucleotide or more than one polynucleotide encoding the antibody, or antigen-binding fragment thereof, of the disclosure.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, PA (1985), which is incorporated herein by reference.

In one embodiment, an anti-αvβ8 integrin antibody, or antigen-binding fragment thereof, is formulated in a vial containing 100 mg of anti-αvβ8 integrin antibody, or antigen-binding fragment thereof, in 1 mL of aqueous buffered solution.

In one embodiment, an anti-αvβ8 integrin antibody, or antigen-binding fragment thereof, is administered in an intravenous formulation as a sterile aqueous solution containing about 0.1 mg/mL, about 1 mg/mL, about 2 mg/mL, about 3 mg/mL, about 4 mg/mL, 5 mg/mL, or in some embodiments, about 10 mg/mL, or in some embodiments, about 15 mg/mL, or in some embodiments, about 20 mg/mL of antibody, or in some embodiments, about 25 mg/mL, or in some embodiments, about 50 mg/mL, or in some embodiments, about 100 mg/mL and 5% dextrose. In some embodiments, an intravenous formulation is a sterile aqueous solution containing 0.1 mg/mL to 15 mg/mL of anti-αvβ8 integrin antibody, or antigen-binding fragment thereof in 5% dextrose. In some embodiments, an anti-αvβ8 integrin antibody, or antigen-binding fragment thereof is formulated in a composition containing sodium acetate, polysorbate 80, and sodium chloride at a pH ranging from about 5 to 6. In some embodiments, the intravenous formulation is a sterile aqueous solution containing 5 or 10 mg/mL of antibody, with 20 mM sodium acetate, 0.2 mg/mL polysorbate 80, and 140 mM sodium chloride at pH 5.5. Further, a solution comprising an antibody, or antigen-binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 50 mg/mL anti-αvβ8 integrin antibody or antigen-binding fragment of the present disclosure, 20 mM histidine, 8.5% sucrose, and 0.02% polysorbate 80, 0.005% EDTA at pH 5.8; in another embodiment a pharmaceutical composition of the present invention comprises the following components: 100 mg/mL anti-αvβ8 integrin antibody or antigen-binding fragment of the present disclosure, 10 mM histidine, 5% sucrose, and 0.01% polysorbate 80 at pH 5.8. This composition may be provided as a liquid formulation or as a lyophilized powder. When the powder is reconstituted at full volume, the composition retains the same formulation. Alternatively, the powder may be reconstituted at half volume, in which case the composition comprises 100 mg anti-αvβ8 integrin antibody or antigen-binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the antibody formulation. For example, a 0.01 mg/kg intravenous injection of an anti-αvβ8 integrin antibody, or antigen-binding fragment thereof, may be given as a bolus, and the rest of the antibody dose may be administered by intravenous injection. A predetermined dose of an anti-αvβ8 integrin antibody, or antigen-binding fragment thereof, may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

VI. Dosing/Administration

To prepare pharmaceutical or sterile compositions including an anti-αvβ8 integrin antibody, or antigen-binding fragment thereof of the disclosure, the antibody is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N. Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N. Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32; Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising anti-αvβ8 integrin antibodies or antigen-binding fragments thereof, of the disclosure can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, New Engl. J. Med. 349:427-434; Herold, et al., 2002, New Engl. J. Med. 346:1692-1698; Liu, et al., 1999, J. Neurol. Neurosurg. Psych. 67:451-456; Portielji, et al., 2003, Cancer. Immunol. Immunother. 52: 133-144). The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For anti-αvβ8 integrin antibodies or antigen-binding fragments thereof of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. In some embodiments, a dosage of an anti-αvβ8 integrin antibody or antigen-binding fragment thereof, administered to a patient in need thereof, is about 0.1 mg/kg, about 0.3 mg/kg, about 2 mg/kg or about 3.0 mg/kg of the patient's body weight. In some embodiments, a dosage of an anti-αvβ8 integrin antibody or antigen-binding fragment thereof, administered to a patient in need thereof, is about 0.4 mg/kg, about 4 mg/kg, about 40 mg/kg or about 100 mg/kg of the patient's body weight.

In some embodiments, a dosage of an anti-αvβ8 integrin antibody or antigen-binding fragment thereof, administered to a patient in need thereof every 14 days, is about 1 mg/kg to about 12 mg/kg of the patient's body weight. In some embodiments, a dosage of an anti-αvβ8 integrin antibody or antigen-binding fragment thereof, administered to a patient in need thereof every 14 days, is about 2 mg/kg of the patient's body weight. In some embodiments, a dosage of an anti-αvβ8 integrin antibody or antigen-binding fragment thereof, administered to a patient in need thereof every 14 days, is about 7 mg/kg of the patient's body weight.

In some embodiments, a dosage of an anti-αvβ8 integrin antibody or antigen-binding fragment thereof, administered to a patient in need thereof every 28 days, is about 1 mg/kg to about 20 mg/kg of the patient's body weight. In some embodiments, a dosage of an anti-αvβ8 integrin antibody or antigen-binding fragment thereof, administered to a patient in need thereof every 28 days, is about 4 mg/kg of the patient's body weight. In some embodiments, a dosage of an anti-αvβ8 integrin antibody or antigen-binding fragment thereof, administered to a patient in need thereof every 28 days, is about 12 mg/kg of the patient's body weight.

The dosage of an anti-αvβ8 integrin antibodies antibody or antigen-binding fragment thereof may be calculated using the patient's weight in kilograms (kg) multiplied by the dose to be administered in mg/kg. The dosage of the antibodies of the disclosure may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.1 µg/kg or less of a patient's body weight.

Unit dose of an anti-αvβ8 integrin antibodies or antigen-binding fragments thereof of the disclosure may be 0.1 mg to 200 mg, 0.1 mg to 175 mg, 0.1 mg to 150 mg, 0.1 mg to 125 mg, 0.1 mg to 100 mg, 0.1 mg to 75 mg, 0.1 mg to 50 mg, 0.1 mg to 30 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg. In one embodiment, an anti-αvβ8 integrin antibody, or antigen-binding fragment thereof of the disclosure is administered at a unit dose of about 100 mg, about 300 mg, about 500 mg, about 600 mg, about 800 mg, about 1200 mg, about 1400 mg or about 1600 mg.

The dosage of an anti-αvβ8 integrin antibodies or antigen-binding fragments thereof of the disclosure may achieve a serum titer of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 pg/mL in a subject. Alternatively, the dosage of the antibodies of the disclosure may achieve a serum titer of at least 0.1 µg/mL, at least 0.5 µg/mL, at least 1 µg/mL, at least, 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL in the subject.

Doses of anti-αvβ8 integrin antibodies, or antigen-binding fragments thereof of the disclosure may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316,024). In one embodiment, an anti-αvβ8 integrin antibody, or antigen-binding fragment thereof of the disclosure is administered intravenously. In one embodiment, an anti-αvβ8 integrin antibody, or antigen-binding fragment thereof of the disclosure is administered subcutaneously.

Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985, 309, 5,934,272, 5,874,064, 5,855,913, 5,290,540, and 4,880, 078; and PCT Publication Nos. WO 92/19244, WO 97/32572, WO 97/44013, WO 98/31346, and WO 99/66903, each of which is incorporated herein by reference their entirety. In one embodiment, an anti-αvβ8 antibody, or antigen-binding fragment thereof, or a composition of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If an anti-αvβ8 integrin antibodies, or antigen-binding fragments thereof, of the disclosure are administered in a controlled release or sustained release system, a pump may be used to achieve controlled or sustained release (see, Langer, supra; Sefton, 1987, CRC Crit. Ref. Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, FL. (1974); Controlled Drug Bioavailability, Drug Product Design and Performance, Smolen and Ball (eds.), Wiley, New York (1984); Ranger and Peppas, 1983, J., Macromol. ScL Rev. Macromol. Chem. 23:61; see also Levy et al., 1985, Science 11 225:190; During et al., 19Z9, Ann. Neurol. 25:351; Howard et al., 1989, J. Neurosurg. 71: 105); U.S. Pat. Nos. 5,679, 377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), polyvinyl alcohol), polyacrylamide, polyethylene glycol), polylactides (PLA), polyoeactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more antibodies of the disclosure or conjugates thereof. See, e.g., U.S. Pat. No. 4,526,938, International Patent Publication Nos. WO 91/05548, WO 96/20698, Ning et al., 1996, "Intratumoral Radioimmunotherapy of a Human Colon Cancer Xenograft Using a Sustained-Release Gel," Radiotherapy and Oncology 59:179-189, Song et al., 1995, "Antibody Mediated Lung Targeting of Long-Circulating Emulsions," PDA Journal of Pharmaceutical Science and Technology 50:372-397, Cleek et al., 1997, "Biodegradable Polymeric Carriers for a bFGF Antibody for Cardiovascular Application," Pro. Ml. Symp. Control. Rel. Bioact. Mater. 24:853-854, and Lam et al., 1997, "Microencapsulation of Recombinant Humanized Monoclonal Antibody for Local Delivery," Proc. Ml. Symp. Control Rel. Bioact. Mater. 24:759-160, each of which is incorporated herein by reference in their entirety.

If an anti-αvβ8 integrin antibody, or antigen-binding fragment thereof, of the disclosure is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising anti-αvβ8 integrin antibodies, or antigen-binding fragments thereof, are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with an additional therapeutic agent, e.g., an immune checkpoint molecule, a cytokine, a steroid, a chemotherapeutic agent, an antibiotic, or a radiation therapy, are well known in the art (see, e.g., Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott, Williams and Wilkins, Phila., Pa.).

An effective amount of therapeutic may decrease the symptoms by at least 10 percent; by at least 20 percent; at least about 30 percent; at least 40 percent, or at least 50 percent.

Additional therapies (e.g., prophylactic or therapeutic agents), which can be administered in combination with an anti-αvβ8 integrin antibodies, or antigen-binding fragments of the disclosure, may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the disclosure. The two or more therapies may be administered within one same patient visit.

Methods of administering the antibody molecules are known in the art and are described below. Suitable dosages of the molecules used will depend on the age and weight of the subject and the particular drug used. Dosages and therapeutic regimens of an anti-αvβ8 integrin antibody, or antigen-binding fragment thereof, antibody molecule can be determined by a skilled artisan. In certain embodiments, an anti-αvβ8 integrin antibody, or antigen-binding fragment thereof, is administered by injection (e.g., subcutaneously or intravenously) at a dose of about 1 to 30 mg/kg, e.g., about 5 to 25 mg/kg, about 10 to 20 mg/kg, about 10 to about 14 mg/k, about 5 to 9 mg/kg, about 7 mg/kg, or about 12 mg/kg. In some embodiments, an anti-αvβ8 integrin antibody, or antigen-binding fragment thereof, is administered at a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 30 mg/kg, or about 40 mg/kg. In some embodiments, an anti-αvβ8 integrin antibody, or antigen-binding fragment thereof, is administered at a dose of about 1-5 mg/kg, about 5-10 mg/kg, or about 10-15 mg/kg. In some embodiments, an anti-αvβ8 integrin antibody, or antigen-binding fragment thereof, is administered at a dose of about 0.5-2, 2-4, 2-5, 2-6, 2-7, 2-8, 2-9, 2-10, 2-15, 5-15, or 5-20 mg/kg.

The dosing schedule can vary from e.g., once a week to once every 2, 3, 4, 5, or 6 weeks. In one embodiment, an anti-αvβ8 integrin antibody, or antigen-binding fragment thereof, is administered at a dose from about 10 to 20 mg/kg (e.g., about 7 mg/kg or about 12 mg/kg) every other week (e.g., every two weeks or biweekly). In one embodiment, an anti-αvβ8 integrin antibody, or antigen-binding fragment thereof, is administered at a dose from about 10 to 20 mg/kg (e.g., about 7 mg/kg or about 12 mg/kg) once per month (e.g., every four weeks). In some embodiments, an anti-αvβ8 integrin antibody, or antigen-binding fragment thereof, or a pharmaceutical composition comprising the same, is administered intravenously. In some embodiments, an anti-αvβ8 integrin antibody, or antigen-binding fragment thereof, or a pharmaceutical composition comprising the same, is administered subcutaneously.

In some embodiments, an anti-αvβ8 integrin antibody, or antigen-binding fragment thereof of the disclosure is administered intravenously or subcutaneously on a biweekly basis. In one embodiment, an anti-αvβ8 integrin antibody, or antigen-binding fragment thereof of the disclosure is administered at a unit dose of about 100 mg, about 300 mg, about 800 mg, about 1200 mg or about 1600 mg intravenously or subcutaneously on a biweekly basis. In some embodiments, a subject is administered an anti-αvβ8 integrin antibody, or antigen-binding fragments thereof of the disclosure at a unit dose of about 100 mg, about 300 mg, about 800 mg, about 1200 mg or about 1600 mg intravenously on a biweekly basis and administered an anti-PD1 inhibitor every four weeks. In some embodiments, an anti-PD1 inhibitor is an antibody administered subcutaneously at a unit dose of 300 mg. In some embodiments, an anti-PD1 inhibitor is an anti-PD1 antibody described in PCT Publication No. WO2016/092419 (e.g., mAb7, also referred to as RN888, PF-06801591, or sasanlimab).

In some embodiments, an anti-αvβ8 integrin antibody, or antigen-binding fragment thereof, or a pharmaceutical composition comprising the same, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months. In some embodiments, an anti-αvβ8 integrin antibody, or antigen-binding fragment thereof, or a pharmaceutical composition comprising the same, is administered is administered every two weeks, e.g., up to 12 times (e.g., up to 10, 8, 6, 5, 4, or 3 times). In some embodiments, an anti-αvβ8 integrin antibody, or antigen-binding fragment thereof, or a pharmaceutical composition comprising the same, is administered is administered every four weeks, e.g., up to 12 times (e.g., up to 10, 8, 6, 5, 4, or 3 times).

In some embodiments, each administration of an anti-αvβ8 integrin antibody, or antigen-binding fragment thereof, comprises 5-10 mg/kg (e.g., 5, 6, 7, 8, 9, or 10 mg/kg) of the antibody, or the antigen-binding fragments thereof, e.g., each administration comprises about 7 mg/kg.

In some embodiments, the antibody, or an antigen-binding fragments thereof, is administered every four weeks, e.g., up to 6 times (e.g., up to 6, 5, 4, 3, 2, or 1 time).

In other embodiments, each administration of an anti-αvβ8 integrin antibody, or antigen-binding fragment thereof, comprises 10-15 mg/kg (e.g., 10, 11, 12, 13, 14, or 15 mg/kg) of the antibody, or the antigen-binding fragments thereof, e.g., each administration comprises about 12 mg/kg.

Anti-αvβ8 antibodies, or antigen-binding fragments thereof, of the disclosure and other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, anti-αvβ8 antibodies, or antigen-binding fragments thereof of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522, 811; 5,374,548; and 5,399,331. The liposomes may comprise one or more moieties which are selectively transported into specific cells or organs, thus enhance targeted drug delivery (see, e.g., V. V. Ranade, 1989, J. Clin. Pharmacol. 29:685). Exemplary targeting moieties include folate or biotin (see, e.g., U.S. Pat. No. 5,416,016); mannosides (Umezawa et al., Biochem. Biophys. Res. Commun. 153: 1038); antibodies (P. G. Bloeman et al., 1995, FEBS Lett. 357: 140; M. Owais et al., 1995, Antimicrob. Agents Chemother. 39: 180); surfactant protein A receptor (Briscoe et al. (1995) Am. J. Physiol. 1233: 134); pl20 (Schreier et al. (1994) J. Biol. Chem. 269:9090); see also K. Keinanen; M. L. Laukkanen, 1994, FEBS Lett. 346:123; Killion; Fidler, 1994; Immunomethods 4:273.

The disclosure provides protocols for the administration of pharmaceutical composition comprising anti-αvβ8 antibodies, or antigen-binding fragments thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising anti-αvβ8 integrin antibodies, or antigen-binding fragments thereof, of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

VII. Kits

The disclosure also provides kits comprising any or all of the antibodies described herein. Kits of the disclosure include one or more containers comprising an anti-αvβ8 integrin antibody, or antigen-binding fragment thereof, described herein and instructions for use in accordance with any of the methods of the disclosure described herein. Generally, these instructions comprise a description of administration of an antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing an applicator, e.g., single and multi-chambered pre-filled syringes (e.g., liquid syringes and lyosyringes), are included.

The instructions relating to the use of an anti-αvβ8 integrin antibody, or antigen-binding fragment thereof, generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-αvβ8 integrin antibody of the disclosure. The container may further comprise an additional therapeutic agent as described herein.

The kit may further comprise at least one anti-PD1 antibody, such as, but not limited to, nivolumab, pembrolizumab, spartlizumab, pidilizumab, tislelizumab, cemiplimab, sasanlimab (mAb7, RN888, PD-06801591), AMP-224, an AMP-514.

Kits may optionally provide additional components such as buffers and interpretive information. Normally, the kit comprises a container and a label or package insert(s) on or associated with the container.

The disclosure also provides diagnostic kits comprising any or all of the antibodies, or antigen-binding fragments thereof, described herein. The diagnostic kits are useful for, for example, detecting the presence of αvβ8 integrin in a sample. In some embodiments, a diagnostic kit can be used to identify an individual with a latent disease, disorder or condition that may put them at risk of developing αvβ8 integrin-mediated disease, disorder or condition or a αvβ8 integrin deficiency disease, disorder or condition. In some embodiments, a diagnostic kit can be used to detect the presence and/or level of αvβ8 integrin in an individual suspected of having a αvβ8 integrin mediated disease or a αvβ8 integrin deficiency disease, disorder or condition.

Diagnostic kits of the disclosure include one or more containers comprising an anti-αvβ8 integrin antibody, or antigen-binding fragment thereof, described herein and instructions for use in accordance with any of the methods of the disclosure described herein. Generally, these instructions comprise a description of use of an anti-αvβ8 integrin antibody, or antigen-binding fragment thereof, to detect the presence of αvβ8 integrin in individuals at risk for, or suspected of having, a αvβ8 integrin mediated disease or a αvβ8 integrin deficiency disease, disorder or condition. In some embodiments, an exemplary diagnostic kit can be configured to contain reagents such as, for example, an anti-αvβ8 integrin antibody, or antigen-binding fragment thereof, a negative control sample, a positive control sample, and directions for using the kit.

VIII. Equivalents

The foregoing description and following Examples detail certain specific embodiments of the disclosure and describes the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, kits, and compositions, it will be appreciated that various changes and modifications can be made without departing from the teachings herein and the claimed disclosure below. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

IX. General Techniques

It is to be understood that this invention is not limited to specific synthetic methods of making that may of course vary. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, NY (2001); Ausubel et al., Current Protocols in Molecular Biology, John Wiley & Sons, NY (2002); Harlow and Lane Using Antibodies: A Laboratory Manual, Cold Spring Harbor Laboratory Press, Cold Spring Harbor, NY (1998); Coligan et al., Short Protocols in Protein Science, John Wiley & Sons, NY (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

X. Biological Deposit

Representative materials of the present invention were deposited in the American Type Culture Collection, 10801 University Boulevard, Manassas, Va. 20110-2209, USA, on Feb. 13, 2018. Vector ADWA11 VH05-02-VH, having ATCC Accession No. PTA-124917, comprises a DNA insert encoding the heavy chain variable region of antibody ADWA11 2.4, also known as VH05-2_VK01(2.4) and ADWA11 5-2 2.4. Vector ADWA11 VK2.4-VL, having ATCC Accession No. PTA-124918, comprises a DNA insert encoding the light chain variable region of antibody ADWA11 2.4, also known as VH05-2_VK01(2.4) and ADWA11 5-2 2.4.

The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The owner of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Example 1: Generation of Anti-αvβ8 Integrin Mouse Hybridoma Antibodies

Mouse hybridoma antibodies against human αvβ8 integrin were generated according to the methods as generally described in U.S. Pat. No. 9,969,804, which is herein incorporated by reference in its entirety.

Briefly, integrin β8 knockout mice, which were crossed into the outbred CD1 background to permit post-natal survival, were immunized with recombinant human αvβ8 integrin (R&D Systems, 4135-AV-050) at a dosage of 50 μg per mouse every two weeks until acceptable titers of anti-αvβ8 antibodies were generated. The sera from immunized mice were then screened by solid phase immunoassay to identify mice for hybridoma generation.

Antibodies from generated hybridomas were further characterized by flow cytometry using SW480 cells transfected to express integrin αvβ8 or αvβ3 or αvβ6 as negative controls. Sw480 cells normally do not express any αv integrins except for αvβ5. The mouse hybridoma antibody ADWA-11 (also referred to as ADWA11) was identified, and to confirm the specificity of this antibody flow cytometry was performed on each cell line using labelled ADWA-11 or antibodies to αvβ5 (Alula) or αvβ3 (Axum-2) or αvβ6 (10D5) (Su et al., Am. J. Respir. Cell Mol. Biol. 36:377-386, 2007; Su et al., Am. J. Respir. Cell Mol. Biol. 185: 58-66, 2012; Huang et al., J. Cell Sci. 111 (Pt 15): 2189-2195).

Cell adhesion assays were also performed with U251 cells that express integrin αvβ8 on dishes coated with TGFβ1 latency associated peptide 1 μg/ml (Kueng et al., Anal. Biochem. 182: 16-19, 1989). Blockade of TGFβ activity was determined by TMLC luciferase assay, which utilizes mink lung epithelial cells expressing a TGFβ sensitive portion of PAI-1 promoter driving firefly luciferase expression (Abe et al., Anal. Biochem. 216:276-284, 1994). Based on the hybridoma screening performed generally as described herein, the mouse hybridoma antibody ADWA-11 was selected for further evaluation.

Example 2: Humanization of Anti-αvβ8 Integrin Mouse Hybridoma Antibodies

The mouse hybridoma antibody ADWA-11, as disclosed in U.S. Pat. No. 9,969,804, and as set forth in, e.g., SEQ ID NO: 20-33 and 71-76 of the present description, was humanized by grafting the murine CDR sequences into the various human germline frameworks as listed in Table 1, which included the light chain germline frameworks IGKV2-28, IGKV2-30, IGKV4-1, IGKV1-39 (also referred to herein as DPK9), and IGKV3-11, as well as the heavy chain germline frameworks IGHV3-7 (also referred to herein as DP54), IGHV1-46, IGHV3-23, IGHV3-30, IGHV1-69, and IGHV3-48 (see, e.g., IMGT database).

The humanized antibodies referred to herein as "Humanized ADWA-11" included a set of six murine CDR sequences as set forth in SEQ ID NOs: 20-33 and 71-76 grafted into a IGKV1-39 (e.g., DPK9) light chain germline framework and a IGHV3-7 (e.g., DP54) heavy chain germline framework. Other germlines framework variants were also tried, as shown below in Tables 1.1 and 1.2.

TABLE 1.1

| Humanized variant | SEP ID NO |
|---|---|
| ADWA11 IGHV1-46/IGKV1-39 | VH: SEQ ID NO: 34; VL: SEQ ID NO: 65 |
| ADWA11 IGHV1-46/IGKV2-28 | VH: SEQ ID NO: 34; VL: SEQ ID NO: 62 |
| ADWA11 IGHV1-46/IGKV3-11 | VH: SEQ ID NO: 34; VL: SEQ ID NO: 66 |
| ADWA11 IGHV1-46/IGKV2-30 | VH: SEQ ID NO: 34; VL: SEQ ID NO: 63 |
| ADWA11 IGHV1-46/IGKV4-1 | VH: SEQ ID NO: 34; VL: SEQ ID NO: 64 |
| ADWA11 IGHV1-69/IGKV1-39 | VH: SEQ ID NO: 37; VL: SEQ ID NO: 65 |
| ADWA11 IGHV1-69/IGKV2-28 | VH: SEQ ID NO: 37; VL: SEQ ID NO: 62 |
| ADWA11 IGHV1-69/IGKV3-11 | VH: SEQ ID NO: 37; VL: SEQ ID NO: 66 |
| ADWA11 IGHV1-69/IGKV2-30 | VH: SEQ ID NO: 37; VL: SEQ ID NO: 63 |
| ADWA11 IGHV1-69/IGKV4-1 | VH: SEQ ID NO: 37; VL: SEQ ID NO: 64 |
| ADWA11 IGHV3-30/IGKV1-39 | VH: SEQ ID NO: 36; VL: SEQ ID NO: 65 |
| ADWA11 IGHV3-30/IGKV2-28 | VH: SEQ ID NO: 36; VL: SEQ ID NO: 62 |
| ADWA11 IGHV3-30/IGKV3-11 | VH: SEQ ID NO: 36; VL: SEQ ID NO: 66 |
| ADWA11 IGHV3-30/IGKV2-30 | VH: SEQ ID NO: 36; VL: SEQ ID NO: 63 |
| ADWA11 IGHV3-30/IGKV4-1 | VH: SEQ ID NO: 36; VL: SEQ ID NO: 64 |
| ADWA11 IGHV3-23/IGKV1-39 | VH: SEQ ID NO: 35; VL: SEQ ID NO: 65 |
| ADWA11 IGHV3-23/IGKV2-28 | VH: SEQ ID NO: 35; VL: SEQ ID NO: 62 |
| ADWA11 IGHV3-23/IGKV3-11 | VH: SEQ ID NO: 35; VL: SEQ ID NO: 66 |
| ADWA11 IGHV3-23/IGKV2-30 | VH: SEQ ID NO: 35; VL: SEQ ID NO: 63 |
| ADWA11 IGHV3-23/IGKV4-1 | VH: SEQ ID NO: 35; VL: SEQ ID NO: 64 |
| ADWA11 IGHV3-48/IGKV1-39 | VH: SEQ ID NO: 38; VL: SEQ ID NO: 65 |
| ADWA11 IGHV3-48/IGKV2-28 | VH: SEQ ID NO: 38; VL: SEQ ID NO: 62 |
| ADWA11 IGHV3-48/IGKV3-11 | VH: SEQ ID NO: 38; VL: SEQ ID NO: 66 |
| ADWA11 IGHV3-48/IGKV2-30 | VH: SEQ ID NO: 38; VL: SEQ ID NO: 63 |
| ADWA11 IGHV3-48/IGKV4-1 | VH: SEQ ID NO: 38; VL: SEQ ID NO: 64 |
| ADWA11 chimeric control | |

TABLE 1.2

| Name | Corresponding germline | SEQ ID NO: | Sequence |
|---|---|---|---|
| ADWA11 VH1 | IGHV1-46 | 34 | QVQLVQSGAEVKKPGASVKVSCK ASGFNIKDYYMNWVRQAPGQGLE WIGWIDPDNGNTIYDQKFQGRVT MTRDTSTSTVYMELSSLRSEDTAV YYCARRLLMDYWGQGTLVTVSS |

TABLE 1.2-continued

| Name | Corresponding germline | SEQ ID NO: | Sequence |
|---|---|---|---|
| ADWA11 VH2 | IGHV3-23 | 35 | EVQLLESGGGLVQPGGSLRLSCAASGFNIKDYYMNWVRQAPGKGLEWIGWIDPDNGNTIYDDSVKGRFTISRDNSKNTLYLQMNSLRAEDTAVYYCARRLLMDYWGQGTLVTVSS |
| ADWA11 VH3 | IGHV3-30 | 36 | QVQLVESGGGVVQPGRSLRLSCAASGFNIKDYYMNWVRQAPGKGLEWIGWIDPDNGNTIYDDSVKGRFTISRDNSKNTLYLQMNSLRAEDTAVYYCARRLLMDYWGQGTLVTVSS |
| ADWA11 VH4 | IGHV1-69 | 37 | QVQLVQSGAEVKKPGSSVKVSCKASGFNIKDYYMNWVRQAPGQGLEWIGWIDPDNGNTIYDQKFQGRVTITADESTSTAYMELSSLRSEDTAVYYCARRLLMDYWGQGTLVTVSS |
| ADWA11 VH5 | IGHV3-48 | 38 | EVQLVESGGGLVQPGGSLRLSCAASGFNIKDYYMNWVRQAPGKGLEWIGWIDPDNGNTIYDDSVKGRFTISRDNAKNSLYLQMNSLRAEDTAVYYCARRLLMDYWGQGTLVTVSS |
| ADWA11 VK1 | IGKV2-28 | 62 | DIVMTQSPLSLPVTPGEPASISCRSTKSLLHFNGNTYLFWYLQKPGQSPQLLIYYMSNLASGVPDRFSGSGSGTDFTLKISRVEAEDVGVYYCMQSLEYPFTFGQGTKVEIK |
| ADWA11 VK2 | IGKV2-30 | 63 | DVVMTQSPLSLPVTLGQPASISCRSTKSLLHFNGNTYLFWFQQRPGQSPRRLIYYMSNLASGVPDRFSGSGSGTDFTLKISRVEAEDVGVYYCMQSLEYPFTFGQGTKVEIK |
| ADWA11 VK3 | IGKV4-1 | 64 | DIVMTQSPDSLAVSLGERATINCRSTKSLLHFNGNTYLFWYQQKPGQPPKLLIYYMSNLASGVPDRFSGSGSGTDFTLTISSLQAEDVAVYYCMQSLEYPFTFGQGTKVEIK |
| ADWA11 VK4 | IGKV1-39 | 65 | DIQMTQSPSSLSASVGDRVTITCRSTKSLLHFNGNTYLFWYQQKPGKAPKLLIYYMSNLASGVPSRFSGSGSGTDFTLTISSLQPEDFATYYCMQSLEYPFTFGQGTKVEIK |
| ADWA11 VK5 | IGKV3-11 | 66 | EIVLTQSPATLSLSPGERATLSCRSTKSLLHFNGNTYLFWYQQKPGQAPRLLIYYMSNLASGIPARFSGSGSGTDFTLTISSLEPEDFAVYYCMQSLEYPFTFGQGTKVEIK |

A sequence alignment comparing the heavy chain variable region and the light chain variable region amino acid sequences of the mouse hybridoma antibody ADWA-11 (referred to as "Hybridoma mADWA-11" and "mADWA11"), the Humanized ADWA-11 antibody ("huADWA11-2.4"), and the IGHV3-07 and IGKV1-39 germline sequences is shown in FIGS. 1A and 1B. The underlined amino acid residues are the CDR sequences according to Kabat and the bolded amino acid residues are the CDR sequences according to Chothia.

Example 3: Introduction of Framework Mutations into Humanized Anti-αvβ8 Integrin Antibodies In order to improve the binding affinity of the humanized ADWA-11 antibody for αvβ8 integrin as compared to the binding affinity of the mouse hybridoma antibody ADWA11, several variants were generated having framework substitutions in the heavy chain variable region (VH) and the light chain variable region (VL), as indicated in Table 2. The heavy chain residues described in this Example are numbered according to SEQ ID NO: 127. The light chain residues described in this Example are numbered according to SEQ ID NO: 128.

TABLE 2

Framework substitutions introduced into the humanized ADWA11 antibody

| Variant ADWA11 VH and VL regions | Alternative Name(s) | Amino acid substitution(s) relative to SEQ ID NO: 127 (for heavy chain residues) and SEQ ID NO: 128 (for light chain residues) |
|---|---|---|
| adwaVH1.1 (SEQ ID NO: 88) | ADWA11 VH01 | T28N, F29I |
| adwa_VH_1.2 (SEQ ID NO: 89) | ADWA11 VH02 | T28N, F29I, R72A |
| adwa_VH_1.3 (SEQ ID NO: 90) | ADWA11 VH03 | T28N, F29I, R72A, A49G, L79A |
| adwa_VH_1.4 (SEQ ID NO: 91) | ADWA11 VH04 | T28N, F29I, R72A, N74T, A75S |
| adwa_VH_1.5 (SEQ ID NO: 39) | ADWA11 VH05 ADWA11 VH05 VK1 | T28N, F29I, R72A, A49G, L79A, N74T, A75S |
| adwaVL1.1 (SEQ ID NO: 47) | ADWA11 VK01 ADWA11_VK01 (1) | L46R |
| adwa_VL_1.2 (SEQ ID NO: 92) | ADWA11 VK02 | L46R, Y36F |

Humanized ADWA11 antibody variants were generated by combining the various sets of framework substitutions listed in Table 2. Such combinations resulted in antibodies having the VH of ADWA11 VH01, ADWA11 VH02, ADWA11 VH03, ADWA11 VH04, or ADWA11 VH05, and the VL of either ADWA11 VK01 or ADWA11 VK02.

The humanized ADWA11 antibody variants ADWA11 VH01/VK01, ADWA11 VH02/VK01, ADWA11 VH03/VK01, ADWA11 VH03/VK02, and ADWA11 VH05/VK01 were generated and evaluated as generally described herein.

The humanized ADWA11 antibody variant designated ADWA11 VH01/VK01 included T28N and F29I substitutions in the VH (SEQ ID NO:88), and an L46R substitution in the VL (SEQ ID NO:47).

The humanized ADWA11 antibody variant ADWA11 VH02/VK01 included T28N, F29I, and R72A substitutions in the VH (SEQ ID NO:89), and an L46R substitution in the VL (SEQ ID NO:47).

The humanized ADWA11 antibody variant ADWA11 VH03/VK01 included T28N, F29I, R72A, A49G, and L79A substitutions in the VH (SEQ ID NO:90), and an L46R substitution in the VL (SEQ ID NO:47).

The humanized ADWA11 antibody variant ADWA11 VH03/VK02 included T28N, F29I, R72A, A49G, and L79A substitutions in the VH (SEQ ID NO:90), and L46R and Y36F substitutions in the VL (SEQ ID NO:92).

The humanized ADWA11 antibody variant ADWA11 VH05/VK01 included T28N, F29I, R72A, A49G, L79A, N74T, and A75S substitutions in the VH (SEQ ID NO: 39), and an L46R substitution in the VL (SEQ ID NO: 47).

The Fab binding affinities of ADWA11 VH01/VK01, ADWA11 VH02/VK01, ADWA11 VH03/VK01, ADWA11 VH03/VK02, and ADWA11 VH05/VK01 for αvβ8 integrin were determined and are listed in Table 3. Additionally, the IC50 values for inhibiting TGF-β activation were also determined for each antibody and are listed in Table 3.

TABLE 3

Characterization of humanized ADWA11 antibodies variants

| | Antibody Name(s) | Fab Affinity | | | | IgG Potency TGFB Assay |
|---|---|---|---|---|---|---|
| | | ka | kd | KD (M) | KD (PM) | IC50 (pM) |
| | Mouse hybridoma antibody ADWA-11 VH: SEQ ID NO: 20 VL: SEQ ID NO: 21 Also referred to as: Hybridoma mADWA-11 | 9.22E+04 | 4.86E−05 | 5.36E−10 | 536 | 183 (n = 3) |
| Humanized Variants (DP54/DPK9) | ADWA11 VH01/VK01 VH: SEQ ID NO: 88 VL: SEQ ID NO: 47 Also referred to as: VH01/VK01 Fab | 4.13E+04 | 2.51E−04 | 6.86E−09 | 6860 | 8473 (n = 2) |
| | ADWA11 VH02/VK01 VH: SEQ ID NO: 89 VL: SEQ ID NO: 47 Also referred to as: VH02/VK01 Fab | 1.30E+05 | 2.44E−04 | 1.89E−09 | 1890 | 1756 (n = 2) |
| | ADWA11 VH03/VK01 VH: SEQ ID NO: 90 VL: SEQ ID NO: 47 Also referred to as: VH03/VK01 Fab | 1.36E+05 | <1E−05 | 7.35E−11 | <100 | 138 |
| | ADWA11 VH03/VK02 VH: SEQ ID NO: 90 VL: SEQ ID NO: 92 Also referred to as: VH03/VK02 Fab | 1.40E+05 | 5.23E−05 | 3.73E−10 | 370 | 223 |
| | ADWA11 VH05/VK01 VH: SEQ ID NO: 39 VL: SEQ ID NO: 47 Also referred to as: VH05-2_VK01; VH05-2_VK01 parental; and VH05/VK01 Fab | 1.87E+05 | <1E−05 | 5.00E−11 | <100 | 148 (n = 3) |

As shown in Table 3, ADWA11 VH03/VK01, ADWA11 VH03/VK02, and ADWA11 VH05/VK01 each demonstrated an improved binding affinity for αvβ8 integrin as compared to the mouse hybridoma antibody ADWA-11. ADWA11 VH03/VK01 (GBT) and ADWA11 VH05/VK01 each bound to αvβ8 integrin with a KD of less than 100 pM, which represented at least a 5-fold lower KD value than the KD of 536 pM determined for the mouse hybridoma antibody ADWA-11. Further, ADWA11 VH03/VK01 and ADWA11 VH05/VK01 each demonstrated a lower IC50 value for inhibiting TGF-β transactivation, as compared to the mouse hybridoma antibody ADWA-11.

It was further determined, as generally described herein, that ADWA11 VH05/VK01 also retained the activity, specificity, and species cross reactivity of the mouse hybridoma antibody ADWA-11. Thus, this example demonstrates improved binding affinity of humanized ADWA-11 antibodies for αvβ8 integrin as compared to the binding affinity of the mouse hybridoma antibody ADWA11.

Example 4: Optimization of the Humanized ADWA11 Antibody Variants

Single amino acid substitutions, as listed in Table 4, were evaluated for their ability to improve the stability and/or to reduce the immunogenicity of the humanized antibody ADWA11 VH05/VK01. The heavy chain residues described in this Example are numbered according to ADWA11 VH05 (SEQ ID NO: 39). The light chain residues described in this Example are numbered according to ADWA11 VK01 (SEQ ID NO: 47).

TABLE 4

Single Amino Acid Substitutions

| Light Chain Substitutions relative to ADWA11 VK01 (SEQ ID NO: 47) | Heavy Chain Substitutions relative to ADWA11 VH05 (SEQ ID NO: 39) |
|---|---|
| L30S | K30A |
| Y55A | N55Q |
| M56A | N57Q |
| N58S | D61E |
| A60Q | P62A |
| M94Q | K63A |
| L97Y | F64V |
| F101L | |
| F101W | |
| Q105G | |

Figure 4A:
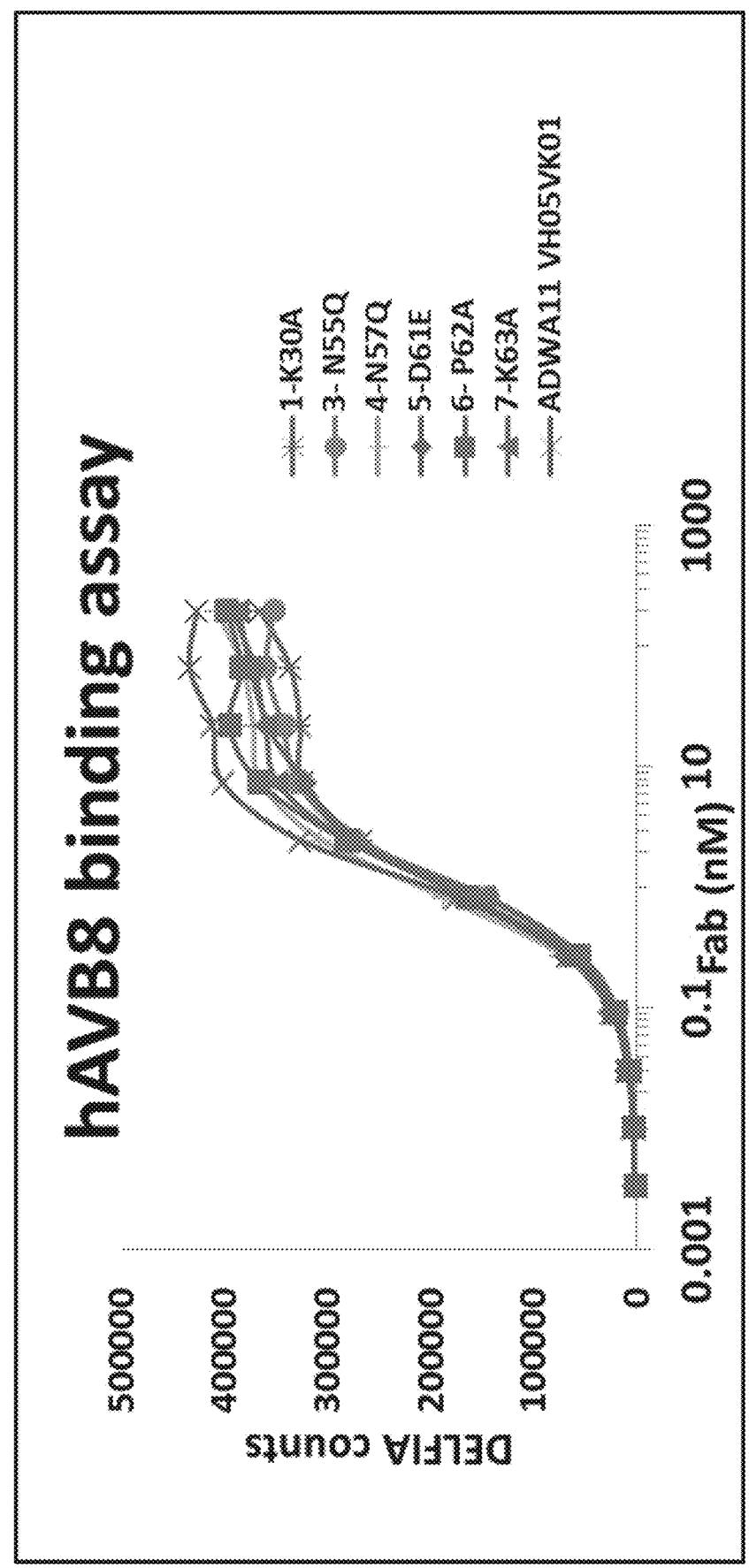
FIG. 4A shows a representative graph showing the binding affinity, as determined by ELISA, of ADWA11 VH05/VK01 Fabs having a K30A, N55Q, N57Q, D61E, P62A, or K63A amino acid substitution in the heavy chain variable region, to human αvβ8, as compared to the binding affinity of parental humanized ADWA11_VH05/VK01 (ADWA VH_1.5 and ADWA VL_1.1) antibody to human αvβ8. Fabs having a K30A, N55Q, N57Q, D61E, P62A, or K63A amino acid substitution in the heavy chain variable region retained binding affinity for human αvβ8.
Figure 4B:
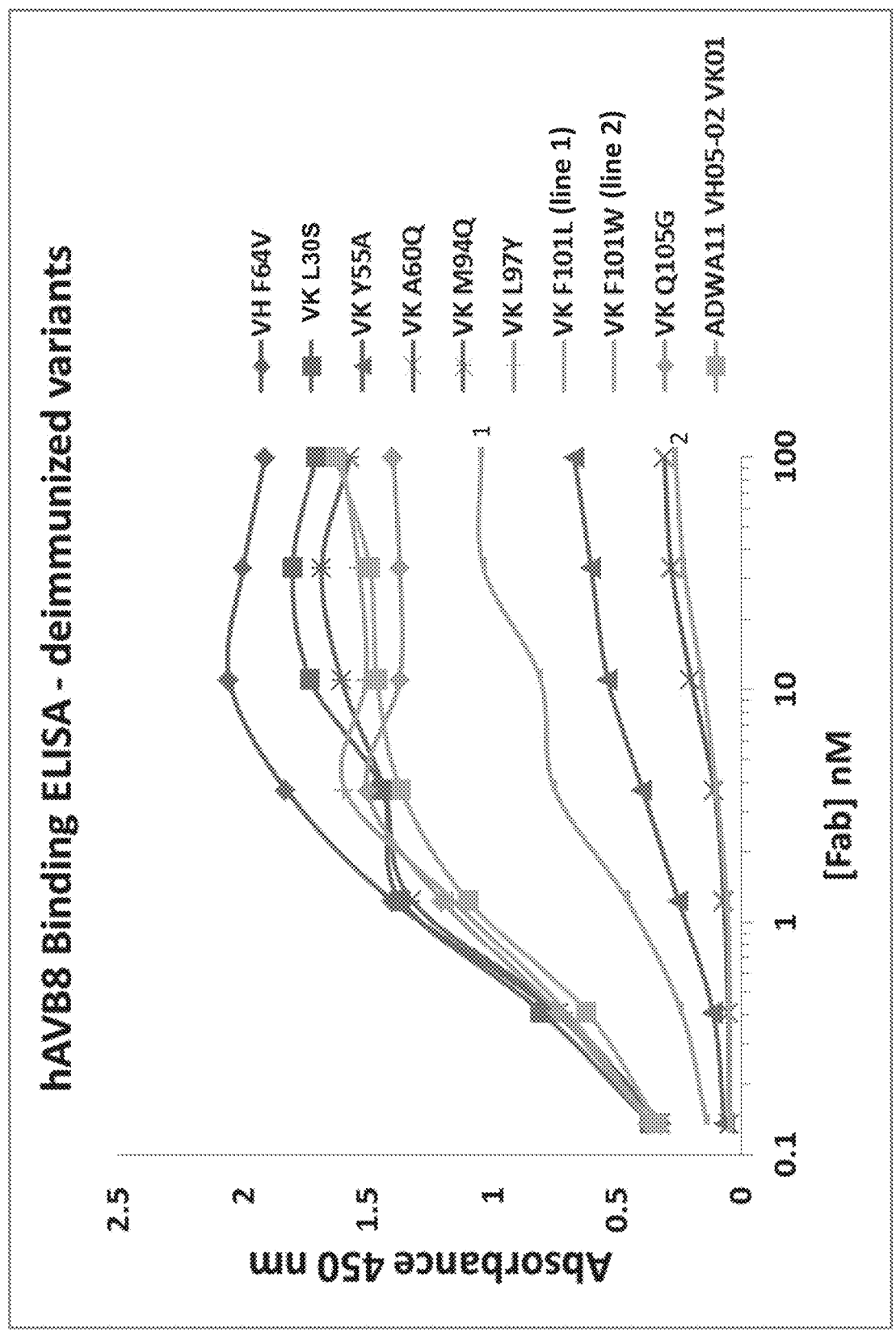
FIG. 4B shows a representative graph showing the binding affinity, as determined by ELISA, of ADWA11 VH05-2/VK01 Fabs having an amino acid substitution in either the heavy chain variable region (e.g., F64V), or the light chain variable region (e.g., L30S, Y55A, A60Q, M94Q, L97Y, F101L, F101W, or Q105G), to human αvβ8, as compared to the binding affinity of parental ADWA11 VH05-2/VK01 antibody to human αvβ8. Fabs having a Y55A, A60Q, F101L, or F101W amino acid substitution in the light chain variable region displayed a reduced binding affinity to human αvβ8, as compared to the humanized ADWA11 VH05-2/VK01 antibody. The other tested Fabs retained binding affinity for human αvβ8.
Figure 4C:
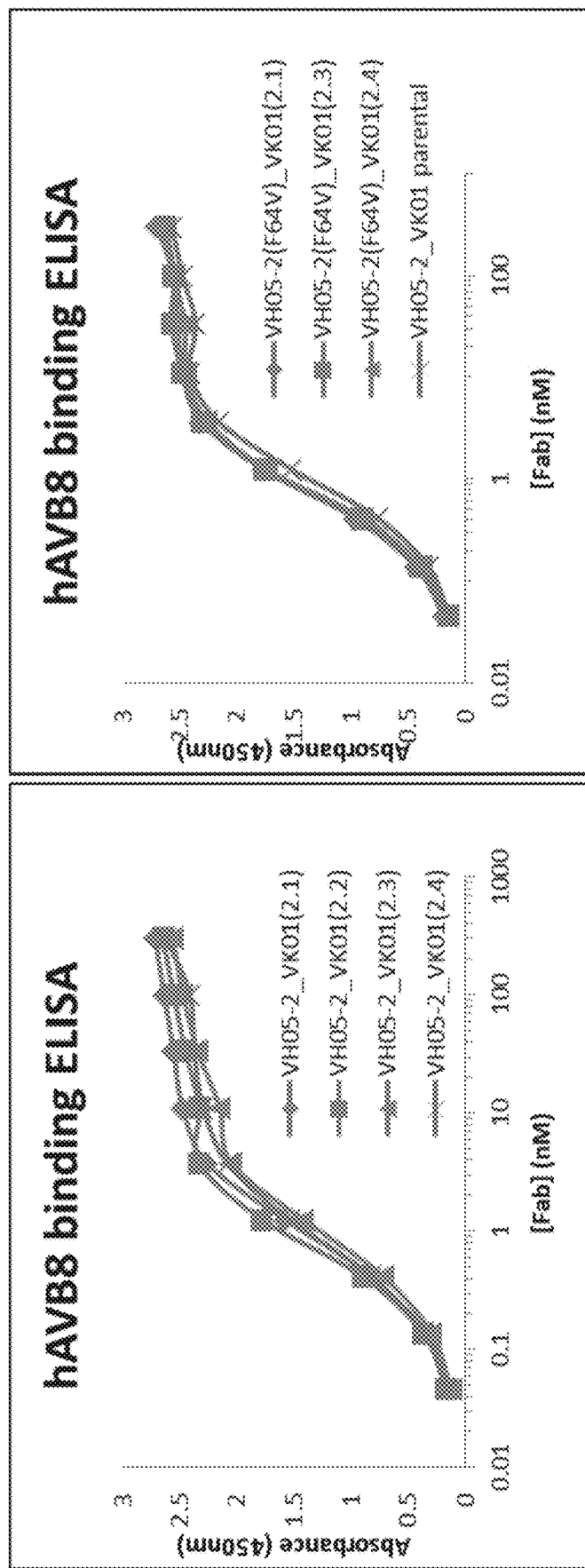
FIG. 4C shows representative graphs showing the binding affinity, as determined by ELISA, of ADWA11 VH05-2/VK01 Fabs referred to as VH05-2/VK01(2.1) (ADWA11 2.1), VH05-2/VK01(2.2) (ADWA 2.2), VH05-2/VK01(2.3) (ADWA 2.3), VH05-2/VK01(2.4) (ADWA 2.4), VH05-2 (F64V)/VK01(2.1), VH05-2(F64V)/VK01(2.3), and VH05-2(F64V)/VK01(2.4), having a combination of amino acid substitutions as shown in Table 5, to human αvβ8, and as compared to the parental antibody (VH05-2_VK01 parental). Each of the tested Fabs retained binding affinity for human αvβ8.

As shown further here, single substitutions that included K30A, N55Q, N57Q, D61E, or P62A in the variable region of the heavy chain, and L30S, M56A, N58S, M94Q, L97Y, or Q105G in the variable region of the light chain were found to retain the activity of the parental molecule (FIGS. 4A-4B). Additionally, combinations of different single amino acid substitutions as listed in Table 5 were also evaluated, and heavy chain sequences containing a double mutant including N55Q and D61E, or a triple mutant including N55Q, D61E, and F64V were found to retain the activity of the parental molecule, as described further herein (FIG. 4C).

More specifically, ADWA11 VH05/VK01 variants including the combinations of amino acid substitutions listed in Table 5, and referred to as ADWA11 2.1 ("2.1"), ADWA11 2.2 ("2.2"), ADWA11 2.3 ("2.3"), and ADWA11 2.4 ("2.4") were generated. The ADWA11 VH05-2/VK01 variants ADWA11 2.1 and ADWA11 2.4 were shown, as described further herein, to have more favorable expression and activity properties. This example demonstrates that single amino acid substitutions improved the stability and/or reduced the immunogenicity of the humanized antibody ADWA11 VH05/VK01.

TABLE 5

Combinations of Amino Acid Substitutions

| Clone Name | Alternative Name(s) | Light Chain Substitutions relative to ADWA11 VK01 (SEQ ID NO: 47) | Heavy Chain Substitutions relative to ADWA11 VH05 (SEQ ID NO: 39) |
|---|---|---|---|
| 2.1<br>VH: SEQ ID NO: 6<br>VL: SEQ ID NO: 67 | ADWA11 2.1<br>VH05-2_VK01(2.1) | L30S, M94Q, Q105G | N55Q, D61E |
| 2.2<br>VH: SEQ ID NO: 6<br>VL: SEQ ID NO: 68 | ADWA11 2.2<br>VH05-2_VK01(2.2) | L30S, L97Y, Q105G | N55Q, D61E |
| 2.3<br>VH: SEQ ID NO: 6<br>VL: SEQ ID NO: 69 | ADWA11 2.3<br>VH05-2_VK01(2.3) | L30S, M56S, M94Q, Q105G | N55Q, D61E |
| 2.4<br>VH: SEQ ID NO: 6<br>VL: SEQ ID NO: 7 | ADWA11 2.4<br>VH05-2_VK01(2.4)<br>ADWA11 5-2 2.4 | L30S, N58S, M94Q, Q105G | N55Q, D61E |
| 2.1 (F64V)<br>VH: SEQ ID NO: 93<br>VL: SEQ ID NO: 67 | ADWA11 2.1 (F64V)<br>VH05-2 (F64V)<br>VK01 (2.1) | L30S, M94Q, Q105G | N55Q, D61E, F64V |
| 2.2 (F64V)<br>VH: SEQ ID NO: 93<br>VL: SEQ ID NO: 68 | ADWA11 2.2 (F64V)<br>VH05-2 (F64V)<br>VK01 (2.2) | L30S, L97Y, Q105G | N55Q, D61E, F64V |
| 2.3 (F64V)<br>VH: SEQ ID NO: 93<br>VL: SEQ ID NO: 69 | ADWA11 2.3 (F64V)<br>VH05-2 (F64V)<br>VK01 (2.3) | L30S, M56S, M94Q, Q105G | N55Q, D61E, F64V |

TABLE 5-continued

Combinations of Amino Acid Substitutions

| Clone Name | Alternative Name(s) | Light Chain Substitutions relative to ADWA11 VK01 (SEQ ID NO: 47) | Heavy Chain Substitutions relative to ADWA11 VH05 (SEQ ID NO: 39) |
|---|---|---|---|
| 2.4 (F64V) VH: SEQ ID NO: 93 VL: SEQ ID NO: 7 | ADWA11 2.4 (F64V) VH05-2 (F64V) VK0 1 (2.4) | L30S, N58S, M94Q, Q105G | N55Q, D61E, F64V |

Example 5: Generation of Anti-αvβ8 Antibodies without Effector Function

Anti-αvβ8 integrin antibodies having reduced Fc-gamma receptor binding and reduced effector function (e.g., reduced antibody-dependent cell-mediated cytotoxicity (ADCC) and/or reduced complement dependent cytotoxicity (CDC) functions) were generated by subcloning a light chain variable region and a heavy chain variable region of the invention, and as listed in Table 1, into an immunoglobulin G (IgG) molecule.

To generate mouse antibodies without effector function, the variable regions from the mouse hybridoma antibody ADWA-11 were subcloned into a mouse IgG1 Fc backbone that contained E233P, E318A, K320A, and R322A single amino acid substitutions as outlined in U.S. Publication No. US2009/0155256. This antibody is referred to herein as ADWA-11_4mut, and as mIgG_4mut. ADWA-11_4mut binding to mouse αvβ8 was assessed using C8-S mouse astrocyte cells (ATCC) and blockade of TGFβ activation was determined using C8-S cells in co-culture TMLC luciferase assay.

To generate human antibodies without effector function, the variable regions from the humanized antibody ADWA11 VH05VK01 were subcloned into a human IgG1 Fc backbone (e.g., as described herein) that contained L234A, L235A, and G237A single amino acid substitutions in the hinge region, such that the hinge region comprised the amino acid sequence EPKSCDKTHTCPPCPAPEAAQAP (SEQ ID NO: 126) instead of the wild type hinge region amino acid sequence EPKSCDKTHTCPPCPAPELLGGP (SEQ ID NO: 125). This human monoclonal antibody without effector function is referred to herein as hIgG_VH05VK01.

Various features of the light chain (SEQ ID NO: 123) and heavy chain (SEQ ID NO: 124) of hIgG_VH05VK01 are identified in the sequences below.

```
Light Chain of ADWA11 VK01
                                  (SEQ ID NO: 123)
DIQMTQSPSSLSASVGDRVTITCRSTKSLLHFNGNTYLFWYQQKPGKAP

KRLIYYMSNLASGVPSRFSGSGSGTDFTLTISSLQPEDFATYYCMQSLE

YPFTFGQGTKVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

```
-continued
Heavy Chain of ADWA11 VH05
                                  (SEQ ID NO: 124)
EVQLVESGGGLVQPGGSLRLSCAASGFNIKDYYMNWVRQAPGKGLEWVG

WIDPDNGNTIYDPKFQGRFTISADTSKNSAYLQMNSLRAEDTAVYYCAR

RLLMDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCDKTHTCPPCPAPEAAGAPSVFLFPPKP

KDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSL

SPGK
```

In the above light chain and heavy chain sequences of humanized ADWA11VH05VK01, the CDR sequences are underlined; the N-linked glycosylation consensus sequence site is at amino acid residues N295, S296, and T297 of the heavy chain; a potential cleavage site is at amino acid residues D52 and P53 of the heavy chain; potential deamidation sites are at amino acid residues N33, G34, N35, and T36 of the light chain, and amino acid residues N57, T58, N77, S78, N84, and S85 of the heavy chain; a potential isomerization site is at amino acid residues D90 and T91 of the heavy chain; a potential methionine oxidation site is at amino acid residues M4 and M56 of the light chain, and M34, M102, and M426 of the heavy chain; the triple alanine mutant is at amino acid residues A232 A233, and A235 of the heavy chain; and the non-human residues outside the CDRs are amino acid residues R51 of the light chain, and G49, A72, T74, S75, and A79 of the heavy chain. The residues in the heavy chain and the light chain described in this Example are numbered according to SEQ ID NO: 124 and SEQ ID NO: 123, respectively.

Example 6: Evaluation of Anti-αvβ8 Integrin Antibodies by ELISA

ELISA Method

Biotinylated human αvβ8 integrin (50 μl of 0.6 μg/ml) was captured onto an ELISA plate coated with streptavidin. After blocking and washing, antibodies of interest (e.g., murine, chimera, or humanized variants) were added at various dilutions to different wells and incubated at room temperature for 1 hour. After washing, the detection antibody, anti-human IgG-HRP was added and incubated for 1 hour at room temperature. After washing, enzyme substrate (TMB) was added to develop the color for 10 minutes. The enzyme reaction was quenched by addition of 0.16 M sulfuric acid and the final signal intensity was measured at 450 nm.

Results

Figure 3A:
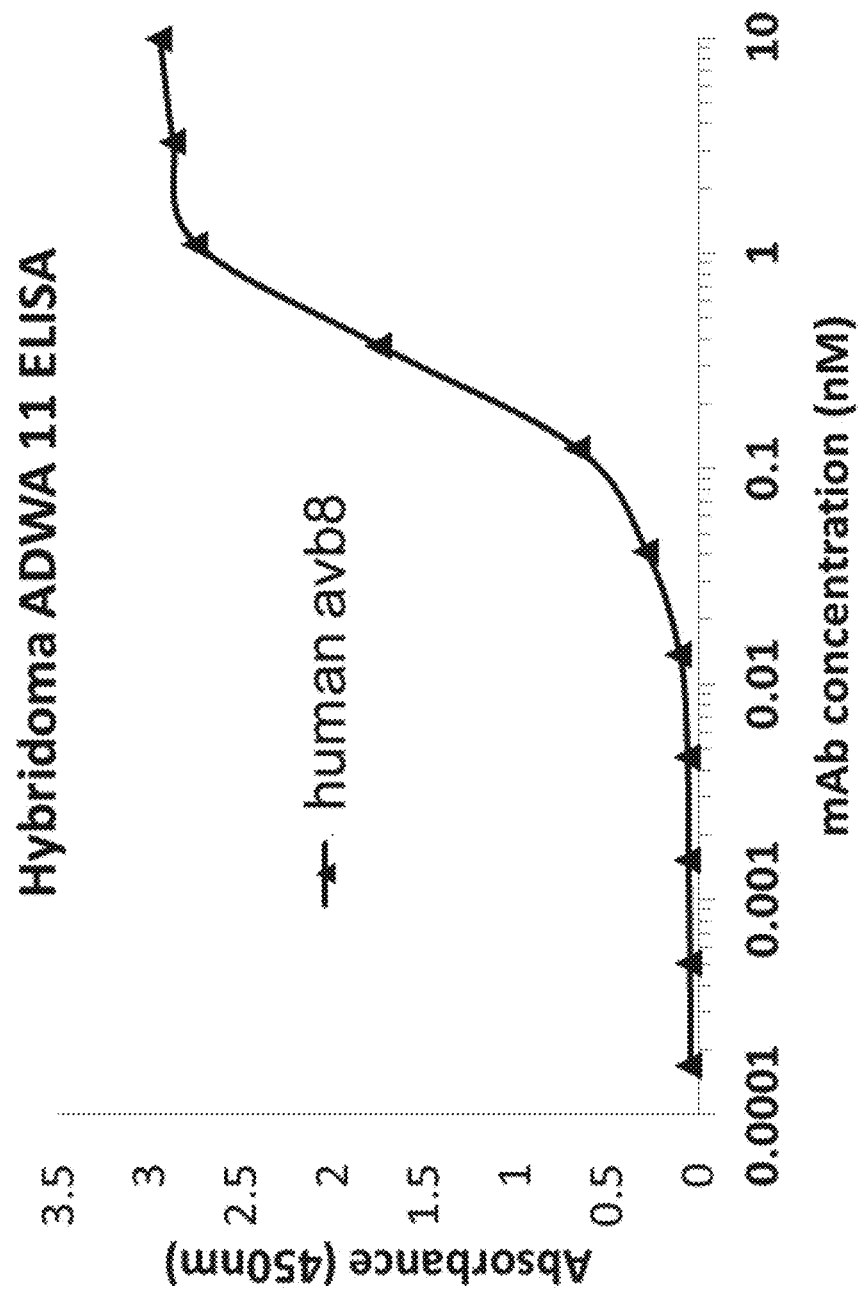
FIG. 3A shows a representative graph showing that the mouse hybridoma ADWA11 antibody bound to human αvβ8 as determined by ELISA.
Figure 3B:
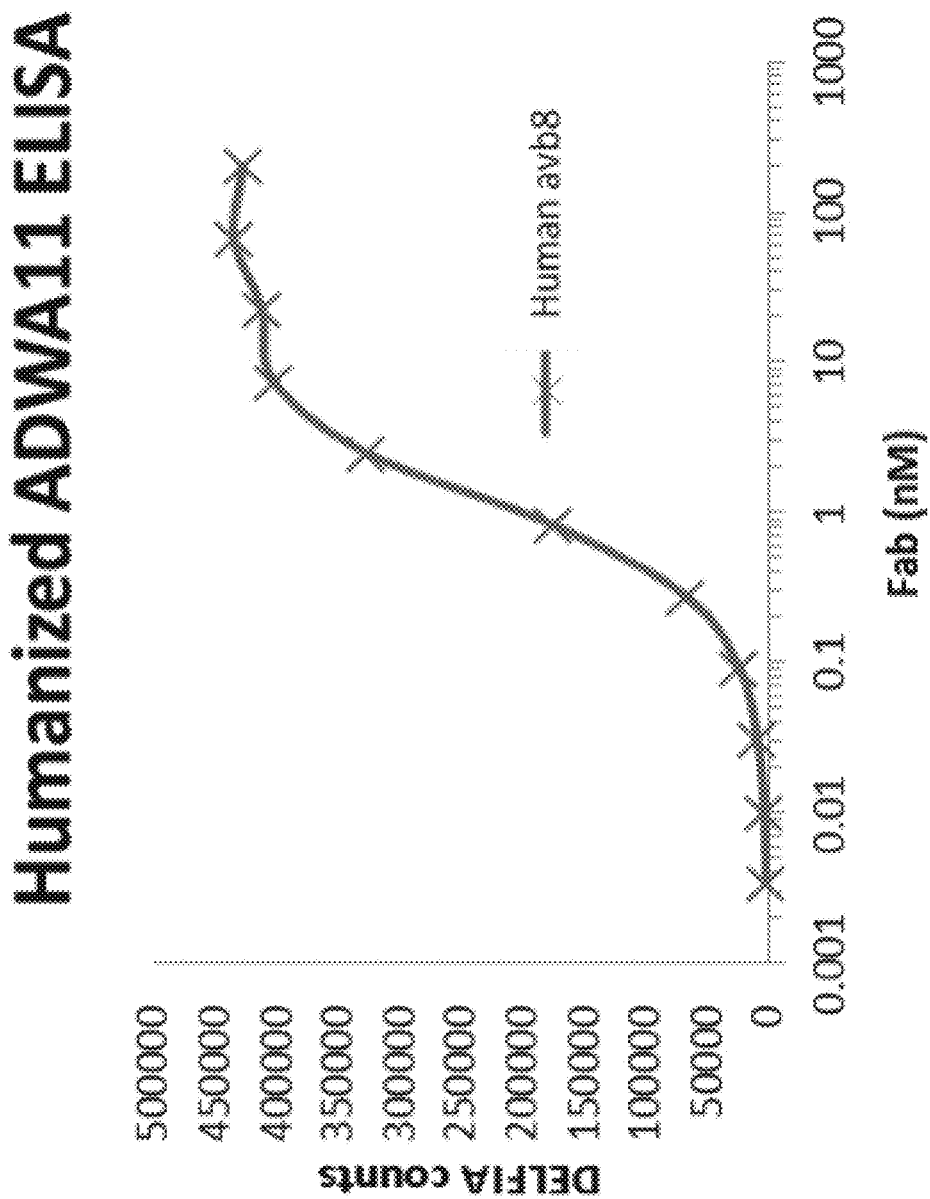
FIG. 3B shows a representative graph showing that the humanized antibody ADWA11 VH05/VK01(2.4) bound to human αvβ8 as determined by ELISA.

Mouse hybridoma antibodies confirmed to bind human αvβ8 (hαvβ8) integrin were counter screened for binding against the closely related integrins human αvβ3 and human αvβ6 to select murine antibodies that bind specifically to hαvβ8. The mouse hybridoma antibody ADWA11 was specific for hαvβ8 integrin and did not bind to the closely related integrins hαvβ3 or hαvβ6 (FIG. 2). However, the humanized ADWA11 antibody ADWA11 VH05/VK01 showed substantially improved affinity for αvβ8 integrin compared to the mouse hybridoma antibody ADWA11 (FIGS. 3A-3B).

Anti-αvβ8 integrin Fab molecules of ADWA11 VH05/VK01 having single or combinations of amino acids substitutions, as listed in Tables 4 and 5, were also evaluated by ELISA for binding to hαvβ8 integrin (FIGS. 4A-4C). As shown in FIG. 4A, Fabs having a K30A, N55Q, N57Q, D61E, P62A, or K63A single amino acid substitution in the heavy chain variable region retained binding affinity for hαvβ8. As shown in FIG. 4B, Fabs having a Y55A, A60Q, F101L, or F101W single amino acid substitution in the light chain variable region displayed a reduced binding affinity for hαvβ8, as compared to the parental antibody. As shown in FIG. 4C, Fabs having a combination of amino acid substitutions as listed in Table 5 retained binding affinity for hαvβ8.

This example demonstrates that humanized ADWA11 antibody ADWA11 VH05/VK01 showed substantially improved affinity for αvβ8 integrin compared to the mouse hybridoma antibody ADWA11 and some Fabs having single amino acid substitutions retained binding for hαvβ8.

Example 7: Evaluation of Anti-αvβ8 Integrin Antibodies by Biacore™

Method

Biotinylated recombinant αvβ8 integrin was captured on a streptavidin-coated Biacore™ chip (GE Healthcare Life Sciences) and the binding response versus time for Fab fragments was measured over a series of Fab concentrations. Representative background subtracted Biacore™ sensograms overlaid with the kinetic curve fits were obtained.

More specifically, recombinant αvβ8 integrin (e.g., R&D Systems) was biotin labeled via primary amines and immobilized on a Sensor Chip SA using a Biacore™ T200 instrument (GE Healthcare Life Sciences). Fab binding experiments were performed at 25° C. using a 30 µl/min flow rate in 0.01 M HEPES pH 7.4, 0.15 M NaCl, 1-2 mM $MgCl_2$, and 0.005% v/v surfactant P20 (HBS-P) buffer. Association was monitored for 5-10 minutes and dissociation for a further 15-20 minutes for each Fab concentration. After each injection, the chip surface was regenerated with IgG elution buffer (Thermo Fisher Scientific). All data was analyzed using the Biacore™ T200 Evaluation software. Data was dual background subtracted using the adjacent flow cell coupled with streptavidin without captured integrin, and buffer only injections. Kinetic constants for at least three experiments were obtained and reported as the mean.

Results

Figure 5:
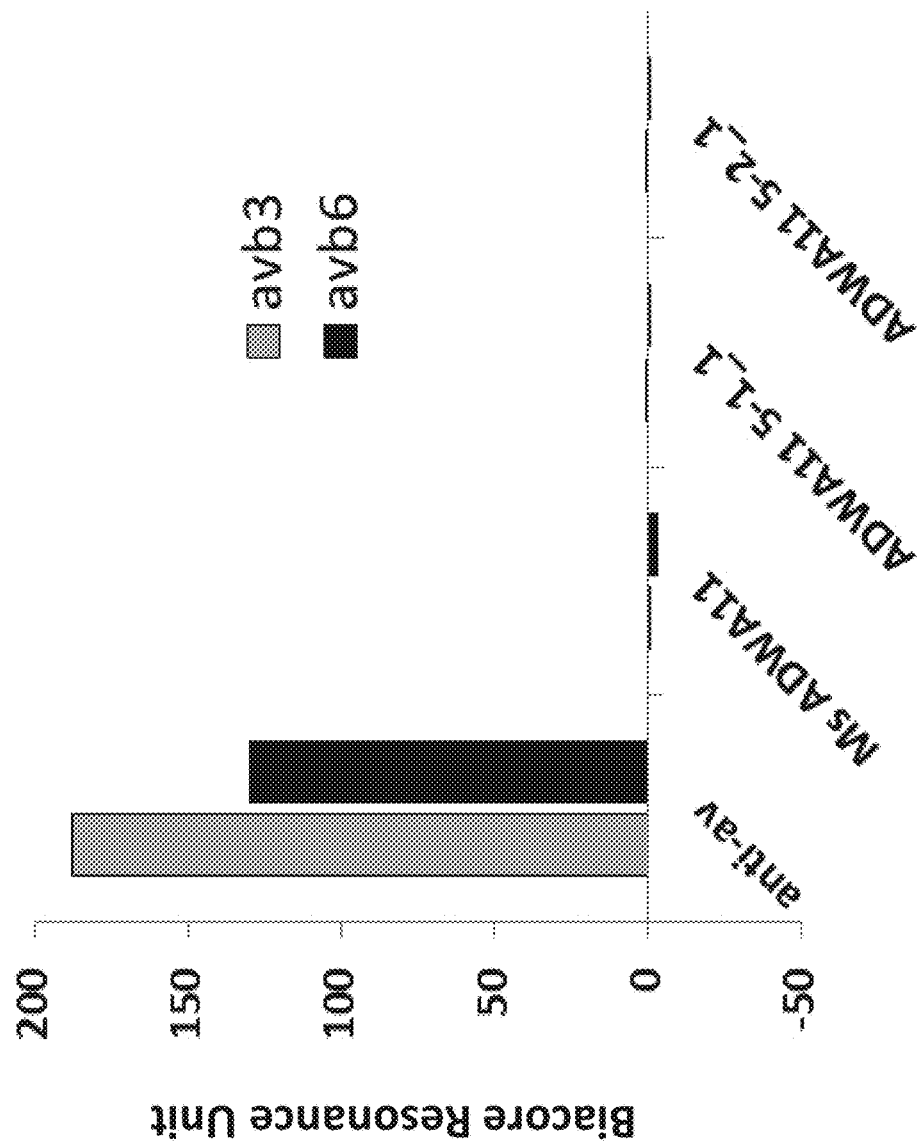
FIG. 5 shows a representative graph comparing the binding specificity of the mouse hybridoma ADWA11 ("MsADWA11" or "mADWA11") and humanized ADWA11 VH05-1/VK01 ("ADWA11 5-1_1") and ADWA11 VH05-2/VK01 ("ADWA11 5-2_1") for human integrins αvβ3 (avb3) and αvβ6 (avb6), as determined by Biacore. The ADWA11 antibodies did not bind integrins αvβ3 (avb3) and αvβ6 (avb6), while the control αV binding antibody ("anti-av") bound both αvβ3 and αvβ6.

Antibody binding to αvβ8 integrin from various species was evaluated. The mouse hybridoma ADWA-11 Fab and the humanized ADWA-11 VH05-2/VK01(2.4) Fab were both found to cross react with the αvβ8 integrin of other species. The mouse hybridoma ADWA-11 Fab cross reacted with human αvβ8 integrin, cynomolgus monkey αvβ8 integrin, and mouse αvβ8 integrin. The humanized ADWA-11 VH05-2/VK01(2.4) Fab cross reacted with human αvβ8 integrin, cynomolgus monkey αvβ8 integrin, and mouse αvβ8 integrin. Additionally, these antibodies were evaluated for their ability to bind to related integrins hαvβ3 or hαvβ6. These antibodies were specific for hαvβ8 and did not bind to the closely related integrins hαvβ3 or hαvβ6 in a Biacore assay, as shown in FIG. 5.

Figure 6A:
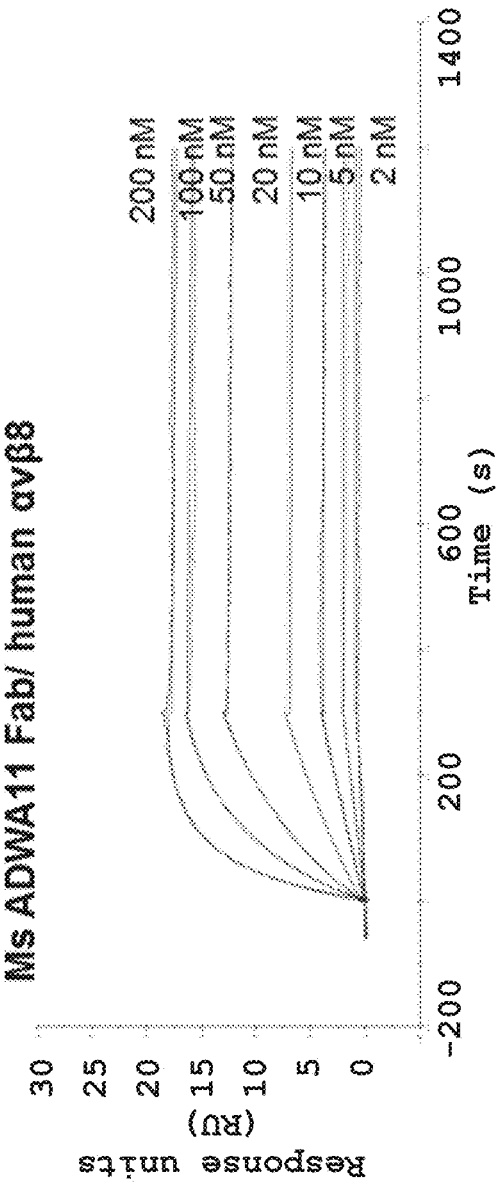
FIG. 6A shows a representative Biacore binding trace for the hybridoma ADWA11 ("Ms ADWA11") Fab to human αvβ8.
Figure 6B:
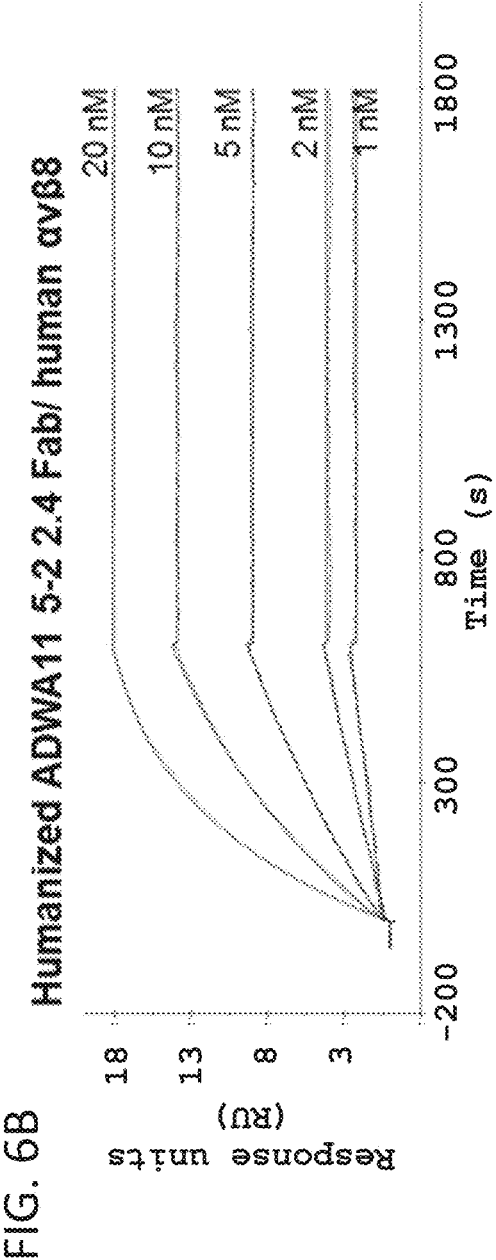
FIG. 6B shows a representative Biacore binding trace for the humanized ADWA11_5-2 2.4 Fab, also referred to as ADWA11 VH05-2/VK01(2.4) or "ADWA11 2.4" Fab to human αvβ8.

A comparison of the affinity measurements listed in Table 6 shows that the humanized ADWA-11 Fab had a lower KD for binding to both human αvβ8 integrin and mouse αvβ8 integrin, as compared to the KD of the mouse hybridoma ADWA-11 Fab for binding to human αvβ8 integrin and mouse αvβ8 integrin. More specifically, the humanized ADWA-11 Fab had about a 2.5-fold lower KD for binding to human αvβ8 integrin and about a 3.5-fold lower KD for binding to mouse αvβ8 integrin, as compared to the respective KD values of the mouse hybridoma ADWA-11 Fab. These data show an overall substantial affinity improvement for the humanized anti-αvβ8 antibody over the mouse hybridoma antibody (FIGS. 6A-6B and Table 6).

To evaluate the monomeric KD of the Fab ADWA11 2.4, also referred to herein as ADWA-11 VH05-2/VK01(2.4) and ADWA11 5-2 2.4, and the parental mouse IgG, recombinant human, cynomolgus, mouse, and rat αvβ8 was immobilized on a Biacore chip and the ka and kd of the Fabs were determined as generally described herein (Table 6). ADWA11 2.4 demonstrated an equivalent affinity for human, cynomolgus, mouse, and rat αvβ8 with a KD of <200 pM, however due to the very slow kd precise determination of KD was not possible. The parental mouse IgG demonstrated an equivalent affinity KD for human, cynomolgus, and mouse αvβ8 (KD of 489-536 pM) (rat was not tested) (FIG. 6C).

Additional Biacore experiments refined the estimated KD values for ADWA11 2.4 to a KD of <100 pM for human and cynomolgus αvβ8 and 70.8±19.9 pM (Average±Standard Deviation) for mouse αvβ8.

TABLE 6

| αvβ8 Integrin species affinity as assessed by Biacore (n > 3) | | | | |
| --- | --- | --- | --- | --- |
| Fab | αvβ8 species | ka (l/Ms) | kd (l/s) | KD |
| Mouse hybridoma antibody ADWA-11 | human | 9.22E + 04 | 4.86E − 05 | 5.36E − 7M |
| Also referred to herein as: | mouse | 1.03E + 05 | 5.03E − 05 | 4.89E − 7M |
| Mouse ADWA11 | cyno | 9.81E + 04 | 4.97E − 05 | 5.07E − 7M |
| ADWA11 5-2 2.4 | human | 1.61E + 05 | <3E − 05 | <2E − 010 |
| Also referred to as: | cyno | 1.72E + 05 | <2E − 05 | <2E − 010 |
| ADWA11 2.4 | mouse | 2.57E + 05 | 1.82E − 05 | <2E − 010 |
| VH05-2_VK01(2.4) | rat | 3.41E + 05 | <2E − 05 | <2E − 010 |
| Humanized ADWA11 | human | 1.73E + 05 | 3.61E − 05 | 2.09E − 7M |
| ADWA11 VH05-2_VK01 | mouse | 1.77E + 05 | 2.43E − 05 | 1.37E − 7M |
| VH: SEQ ID NO: 39 | human | 2.00E + 05 | 2.37E − 05 | 1.18E −10M |

TABLE 6-continued

αvβ8 Integrin species affinity as assessed by Biacore (n > 3)

| Fab | αvβ8 species | ka (l/Ms) | kd (l/s) | KD |
|---|---|---|---|---|
| VL: SEQ ID NO: 47 | mouse | 2.20E + 05 | <2E − 5 | <1E − 10M |
| Also referred to as: | rat | 1.94E + 05 | 3.10E − 05 | 1.60E − 10M |
| ADWA11 VH05/VK01 | cyno | 2.25E + 05 | <2E − 5 | <1E − 10M |
| VH05-2_VK01; | | | | |
| VH05-2_VK01 parental; and | | | | |
| VH05/VK01 Fab | | | | |

To evaluate the specificity of ADWA11 2.4, recombinant human αvβ6 and αvβ3 were immobilized on a Biacore chip and binding of the parental murine and humanized mAb variant of ADWA11 2.4 was determined. The parental hybridoma and humanized mAb did not bind αvβ3 or αvβ6, while binding to αvβ8 in separate BIAcore experiments was observed. A pan-Integrin αV antibody was used to demonstrate immobilization of αvβ3 or αvβ6 recombinant protein on the Biacore chip. Thus, this example also demonstrates the specificity of the humanized antibody for αvβ8.

Example 8: Evaluation of Anti-αvβ8 Integrin Antibodies in Cell Binding Assays Methods Cell binding experiments were performed with human glioblastoma U251 (Sigma) or C8-S(ATCC) cells cultured in MEM 10% hiFBS. The cells grown to 70-90% confluence were detached with 0.05% trypsin and washed two times with PBS containing 2% BSA.

For cell-binding experiments with HEK293-F cells overexpressing human αvβ3, αvβ5, αv6, αvβ8. HEK293-F cells transiently expressing full length human integrin beta 3 (Accession No. NP_000203.2), human integrin beta 5 (Accession No. NP_002204.2), human integrin beta 6 (Accession No. NP_000879.2), or human integrin beta 8 (Accession No. NP_002205.1) were prepared using proprietary vectors and vendor provided protocols. Cells were harvested after 4 days and analyzed for integrin expression. To characterize Integrin αvβ3, αvβ5, αvβ6, αvβ8 expression 100,000 cells were incubated in the indicated commercially available or directly conjugated proprietary antibodies for 30 minutes, along with LIVE/DEAD fixable cell stain (Invitrogen) at 1:2000 to distinguish live cells. Cells were spun down for five minutes at 300 g force. The cells were then washed twice with wash buffer (PBS+0.2% BSA) to remove excess unbound antibodies and an analysed on BD biosciences Fortessa flow cytometer Live cell-binding protocol: 100,000 cells were incubated with a dilution series of the anti-αvβ8 or human IgG1_3mut Isotype antibody for three to four hours on ice. The cells were spun down for five minutes at 300 g force. The cells were then washed three times with wash buffer (PBS+0.2% BSA) to remove excess unbound antibodies. After thorough washing, cells were incubated with Fab'2 anti-human Fc-PE (Invitrogen) or goat Fab'2 anti-mouse-APC (Jackson Labs) at 1:1000 dilution along with LIVE/DEAD fixable cell stain (Invitrogen) at 1:2000 to distinguish live cells. The whole content was incubated for 30 minutes on ice. After washing, the stained cells were analyzed on BD biosciences Fortessa flow cytometer (gated for live cells) using FlowJo analysis software. The mean fluorescence intensities (MFI) at different antibody concentrations were plotted for various antibodies.

Fixed cell-binding protocol: In some instances, cell binding experiments were performed with human glioblastoma U251 (Sigma) cells cultured in MEM or 10% hiFBS. The cells grown to 70-90% confluence were detached with 0.05% trypsin and washed two times with PBS containing 2% BSA. U251 (25,000 cells) were incubated with LIVE/DEAD fixable cell stain (Invitrogen) at 1:2000 to distinguish live cells. The cells were spun down for 5 minutes at 300 g force, and washed with wash buffer (PBS+0.2% BSA), followed by fixation with 2% paraformaldehyde for 10 minutes at room temperature. Fixed cells were wasted twice with wash buffer, followed by addition of a dilution series of anti-αvβ8 antibody of interest for 1 hour at 37 degrees. The cells were washed three times with wash buffer to remove excess unbound antibodies. After through washing, Fab'2 anti-human Fc-PE (Invitrogen) or anti-human Kappa Light Chain-APC (Invitrogen) detection antibody at 1:1000 dilutions was added to cells and incubated for 30 minutes on ice. After washing, the stained cells were analyzed on BD biosciences Fortessa flow cytometer (gated for live cells) using FlowJo analysis software. The mean fluorescence intensities (MFI) at different antibody concentrations were plotted for various antibodies.

Results

Figure 7A:
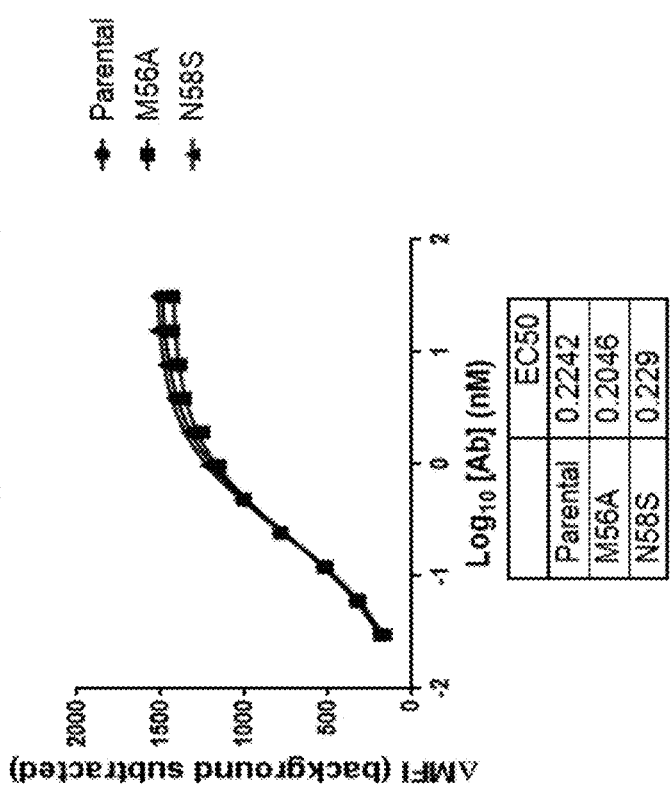
FIG. 7A shows a representative graph comparing U251 cell binding data for ADWA11 VH05-2/VK01 (Parental) Fabs ("ADWA11") having a single amino acid substitution in either the heavy chain variable region (e.g., F64V), or the light chain variable region (e.g., L30S, M94Q, L97Y, F101L, or Q105G). Fabs having a F101L amino acid substitution in the light chain variable region displayed reduced binding to U251 cells (human αvβ8), as compared to the parental antibody. The other tested Fabs retained binding to U251 cells (human αvβ8).
Figure 7B:
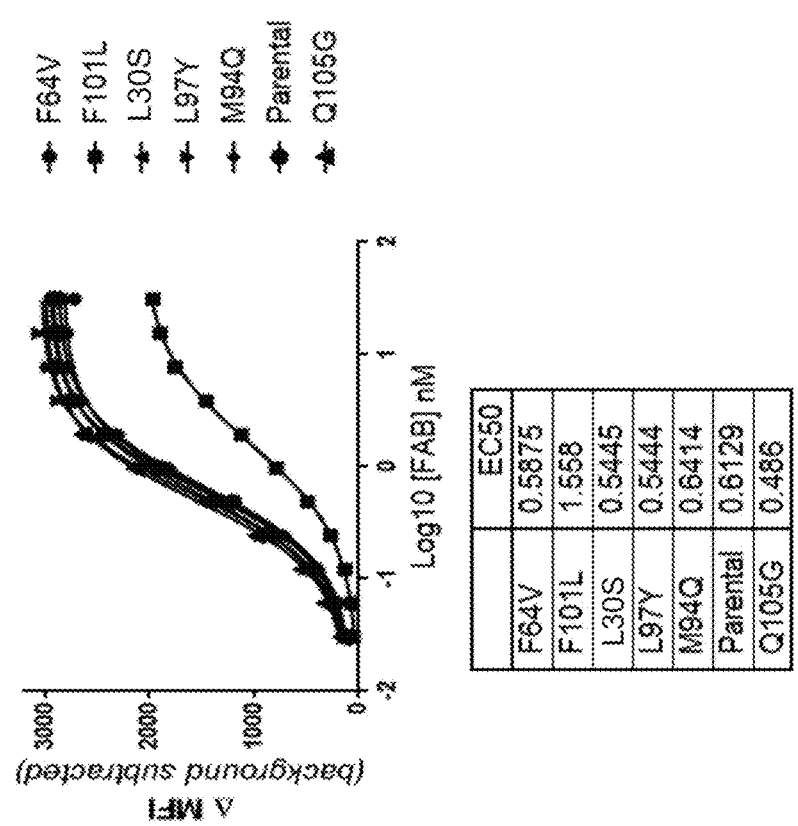
FIG. 7B shows a representative graph comparing U251 cell binding data for ADWA11 VH05-2/VK01 (Parental) Fabs ("ADWA11") having a single amino acid substitution in the light chain variable region (e.g., M56A or N58S). The M56A and N58S Fabs retained binding to U251 cells (human αvβ8).
Figure 7C:
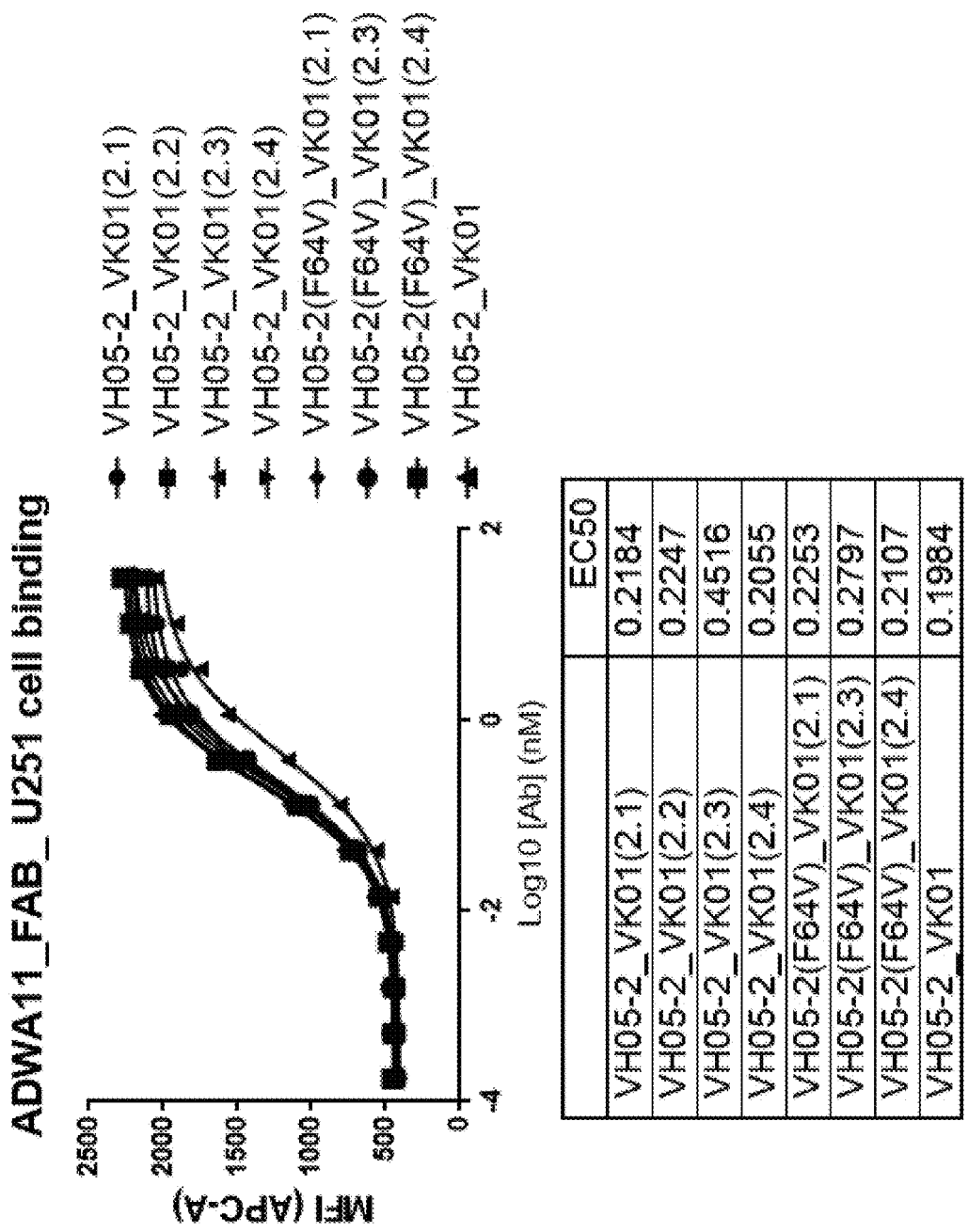
FIG. 7C shows a representative graph showing U251 cell binding data for ADWA11 VH05-2/VK01 Fabs ("ADWA11") having a combination of amino acid substitutions referred to as 2.1, 2.2, 2.3, 2.4, 2.1 (F64V), 2.3 (F64V), and 2.4 (F64V) according to Table 5, as compared to the parental antibody. Each of the tested Fabs retained binding to fixed U251 cells.

Fixed U251 cell binding data for ADWA11 VH05/VK01 Fabs having single amino acid substitutions in either the heavy chain variable region, including F64V, or the light chain variable region, including L30S, M94Q, L97Y, F101L, F101W, or Q105G, or a combination of amino acid substitutions referred to as 2.1, 2.2, 2.3, 2.4, 2.1 (F64V), 2.2 (F64V), 2.3 (F64V), and 2.4 (F64V) in Table 5 were obtained and compared to the parental antibody (FIGS. 7A-7C).

Figure 8:
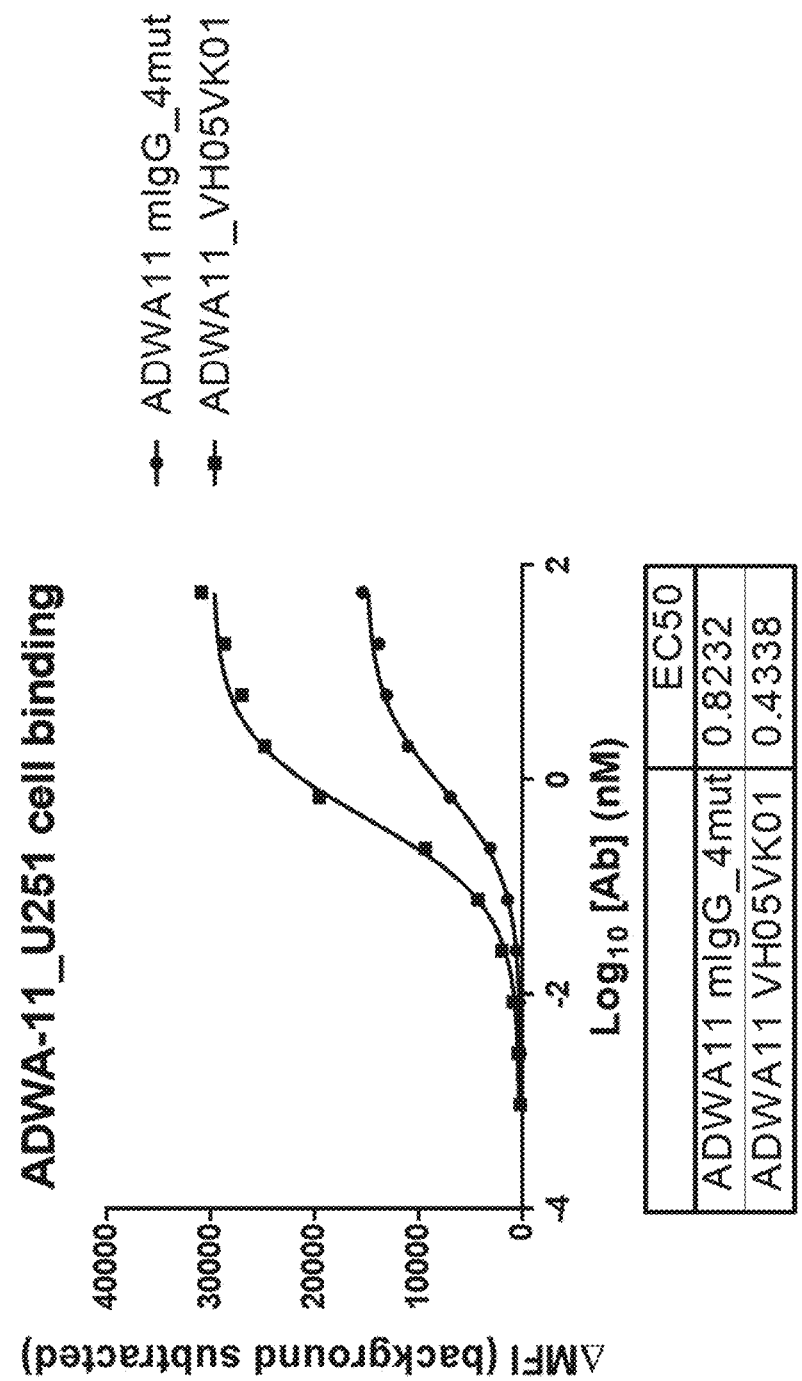
FIG. 8 shows a representative graph comparing the binding affinities of antibodies ADWA11 mIgG_4mut and ADWA11 VH05/VK01 to U251 cells.

U251 cell binding data was also obtained for the antibodies mIgG_4mut and hIgG_VH05VK01 (also referred to as ADWA11 2.4 and described further in Example 5)(FIG. 8). The apparent affinity of mIgG_4mut and hIgG_3mut_VH05VK01, for U251 cells is shown below in Table 7. These data demonstrate that hIgG_3mut_VH05VK01 was determined to have a higher affinity as compared to mIgG_4mut.

TABLE 7

Affinity values from U251 cell binding assay

| ADWA11 antibody | U251 app Kd (pM) |
|---|---|
| mIgG_4mut | 823 |
| hIgG 3mut VH05VK01 | 430 |

Figure 9A:
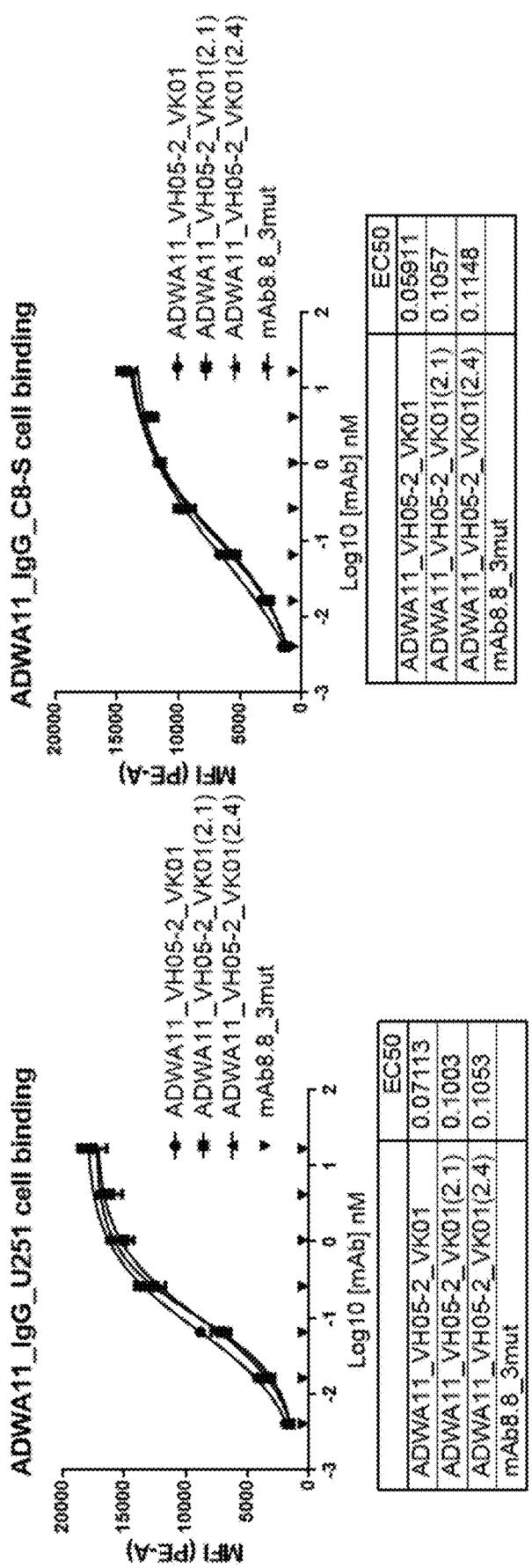
FIG. 9A shows representative graphs showing binding of ADWA11 VH05-2/VK01 having a combination of amino acid substitutions referred to as ADWA11_VH05-2/VK01 (2.1), and ADWA11_VH05-2/VK01(2.4) to U251 (human glioblastoma) or C8-S (mouse astrocyte) cells. The ADWA11 VH05-2/VK01(2.1) and ADWA11 VH05-2/VK01 (2.4) antibodies retained binding to U251 cells (human avb8) and C8-S (mouse avb8).

The apparent-affinity of ADWA11 2.4 for U251 (human glioblastoma) or C8-S (mouse astrocyte) cells was also evaluated in a cell-binding assay, according to the methods as generally described herein. Briefly, cells were incubated with a serial dilution of ADWA11 2.4 for 4 hours on ice, followed by detection on bound antibody with an anti-human-PE secondary antibody, and analyzed by flow cytometry. ADWA11 2.4 demonstrated saturable binding to human αvβ8 and mouse αvβ8-expressing cells, with an average EC50 in the U251 (human αvβ8) cell-binding assay of 126 μm with a standard deviation of plus or minus 34 pM (FIG. 9A; n=3).

In further studies, the EC50 of ADWA11 VH05-2/VK01 (2.4) binding to human U251 cells was determined to be 256±115 pM (average±standard deviation in seven independent experiments) and binding to mouse C8-S cells was determined to be 145 f 23.7 pM (average±standard deviation in four independent experiments).

Figure 9B:
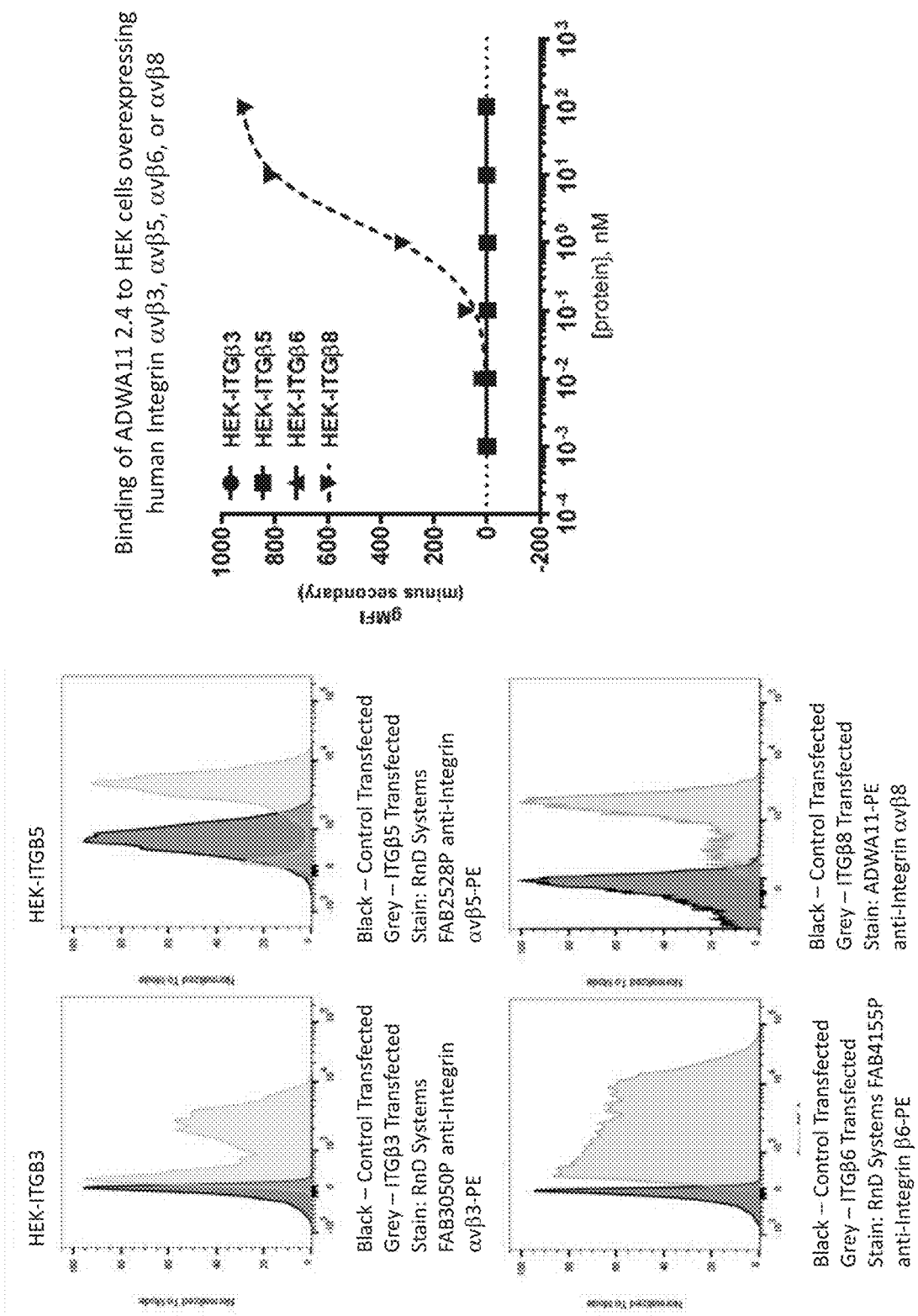
FIG. 9B shows representative graphs depicting binding of integrin specific antibodies, such as, ADWA11 VH05-2/VK01(2.4) to HEK cells expressing αvβ3, αvβ5, αvβ6, and αvβ8. Results show saturable binding of ADWA11 VH05-2/VK01(2.4) to HEK cells expressing αvβ8 and no binding to cells expressing αvβ3, αvβ5, αvβ6. There results demonstrate specific binding of ADWA11 VH05-2/VK01(2.4) to human αvβ8.

HEK293F cell-binding experiments with transiently overexpressed integrin β family members demonstrate ADWA11 2.4 specifically binds to cells expressing human αvβ8, but not αvβ3, αvβ5, or αvβ6 (FIG. 9B). Thus, ADWA11 2.4 demonstrated improved characteristics compared with the parent mouse antibody ADWA11 thereby suggesting that the humanized ADWA11 2.4 is a potential improved human therapeutic.

Example 9: Evaluation of Anti-αvβ8 Integrin Antibodies in a αvβ8 Induced TGF-β Activation Assays Methods The effect of anti-αvβ8 antibodies on TGF-β pathway trans-activation was measured using U251-MG (Sigma) and Mv1Lu-SMAD-luciferase reporter cells. In some experiments, C8-S mouse astrocyte cells were used instead of U251 cells. Briefly, mink lung epithelial cell line MvLu1 cells (ATCC) were transduced with Cignal SMAD reporter (luc) lentiviral particles (SABioscience) at a multiplicity of infection (MOI) of 50. Stable cell lines expressing the SMAD firefly luciferase construct were generated by culturing the cells in the complete growth media (MEM plus 10% fetal bovine serum (FBS) with L-glutamine+penicillin/streptomycin) supplemented with 2 μg/mL puromycin. For the experiment, U251 cells (5000 cells in 50 μL in MEM medium containing 2% charcoal-stripped FBS) were added to each well of a clear-bottom, white-walled TC-treated 96 well plate and incubated for 1 hr at 37° C. A dilution series of anti-αvβ8 antibodies, e.g., FAB antibodies, was prepared in MEM medium containing 2% charcoal-stripped FBS and added to the plated U251 cells, 25 μl per well. After an hour of incubation, Mv1Lu-SMAD-luciferase reporter cells were added (5000 cells/well in 25 μL) to each well and after 18 hours of incubation at 37° C. the luciferase activity was measured using Bright Glo reagent (Promega) according to manufactures suggested protocol. Luminescence was measured using an Envision plate reader with is integration time.

Results

Inhibitory activity of various antibodies on αvβ8 induced TGF-β transactivation of U251 cells was monitored by assessing decreased luciferase activity (FIG. 10A-10F).

Figure 10A:
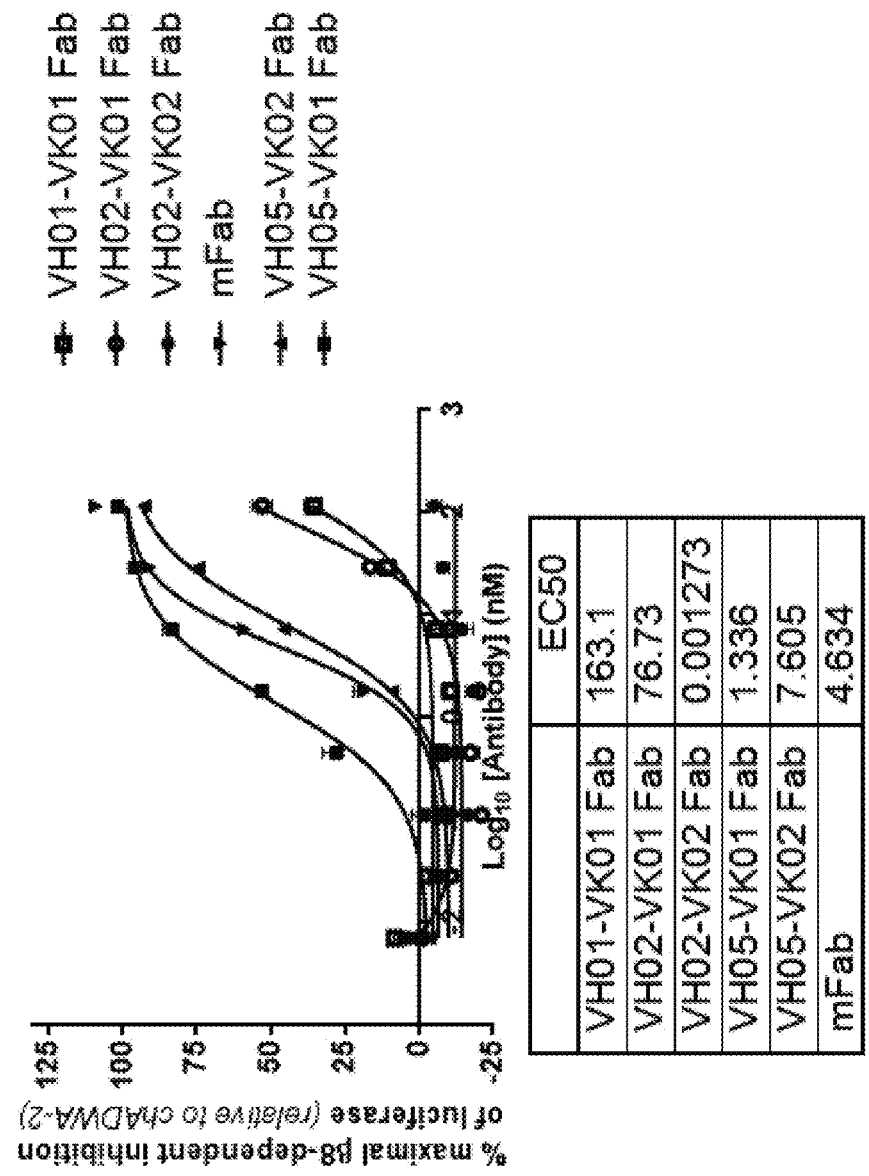
FIG. 10A shows a representative graph comparing the effect of mouse hybridoma ADWA11 ("mFab") and humanized ADWA11 Fabs: ADWA11 VH01/VK01, ADWA11 VH02/VK01, ADWA11 VH02/VK02, ADWA11 VH05/VK02, and ADWA11 VH05/VK01 on TGFβ trans-activation by U251 cells. The VH01/VK01, VH02/VK01, and VH02/VK02 Fabs displayed reduced activity, while VH05/VK01 retained activity, and VH05/VK02 demonstrated improved activity to block TGFβ activation in the U251 transactivation assay as compared to mouse hybridoma ADWA11 Fab ("mFab").

FIG. 10A depicts a comparison of antibodies generated as described in Example 3, and include a comparison between ADWA11 VH05/VK01 (also referred to as VH05-VK01 Fab) to the parental mouse hybridoma antibody ADWA11 (mFab). The EC50 value measured by apparent affinity in the TGF-β transactivation assay was improved from 4.6 nM for the parental mouse hybridoma antibody ADWA11 (mFab) to 1.3 nM for ADWA11 VH05/VK01 (also referred to as VH05-VK01 Fab).

Figure 10B:
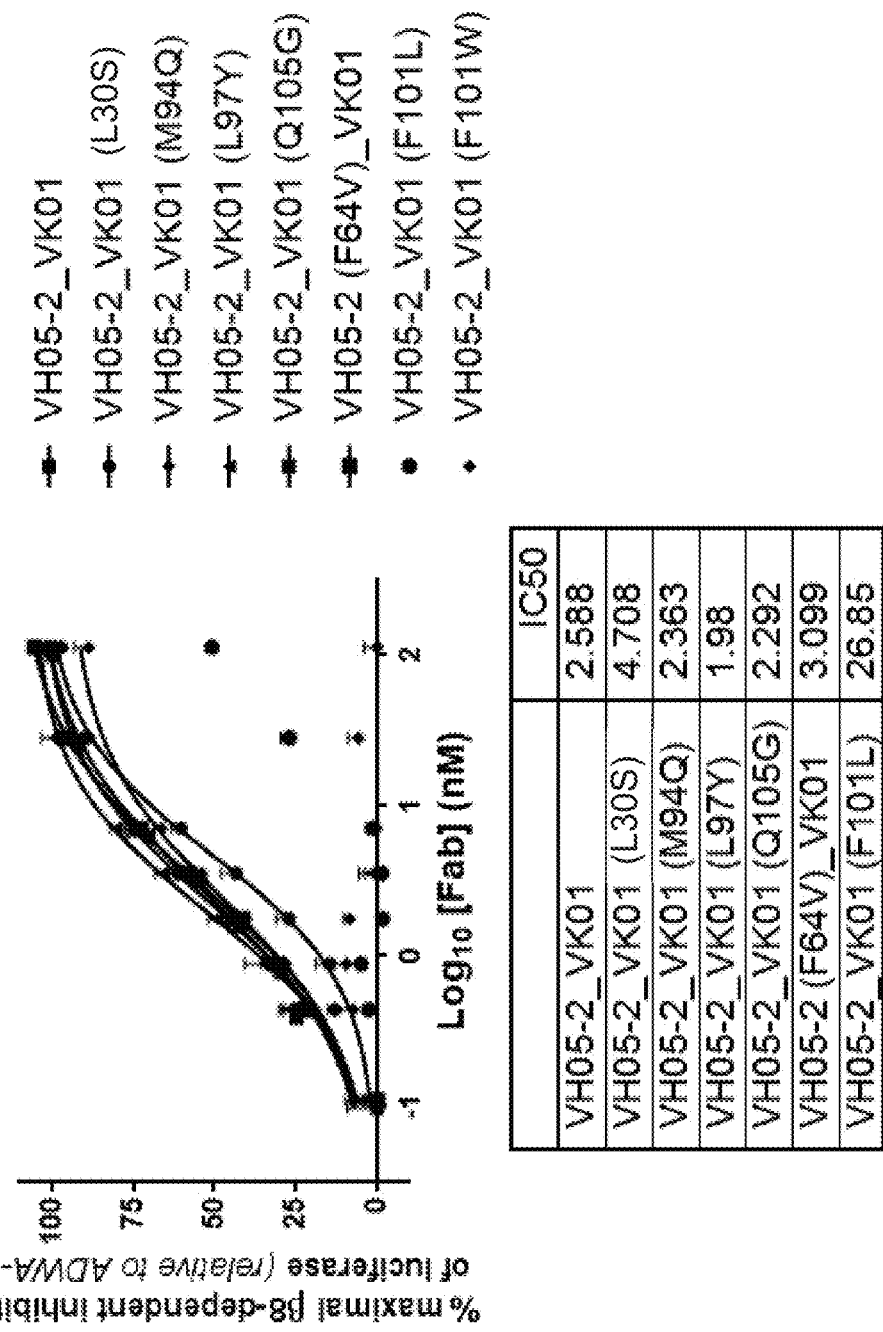
FIG. 10B shows a representative graph comparing the effect of the indicated ADWA11 VH05-2/VK01 Fabs having an amino acid substitution in either the heavy chain variable region (e.g., F64V), or the light chain variable region (e.g., L30S, M94Q, L97Y, F101L, F101W, or Q105G) on TGFβ transactivation in U251 cells. Fabs having a F101L or F101W single amino acid substitution in the light chain variable region displayed a reduced effect on TGFβ transactivation, as compared to the humanized parental ADWA11 VH05-2/VK01 Fab. The other tested Fabs retained activity in the TGFβ transactivation assay.
Figure 10C:
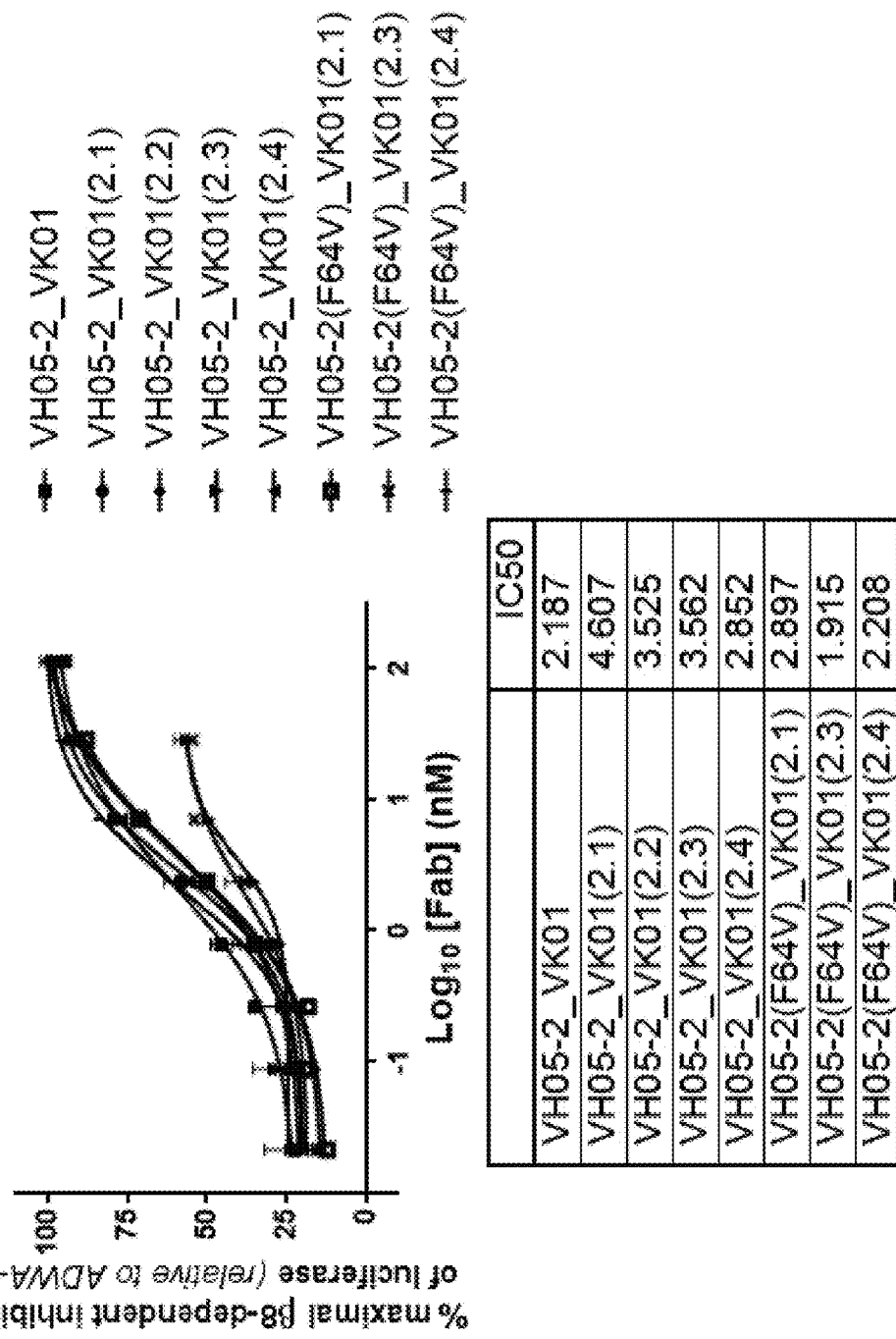
FIG. 10C shows a representative graph comparing the effect of ADWA11 VH05-2/VK01 Fabs having amino acid substitutions, including the combination of amino acid substitutions referred to as 2.1, 2.2, 2.3, 2.4, 2.1 (F64V), 2.3 (F64V), and 2.4 (F64V) according to Table 5. The VH02-2/VK01(2.3) and VH05-2(F64V)/VK01(2.3) Fabs displayed a reduced effect on TGFβ transactivation, as compared to the parental ADWA11 VH05-2/VK01 Fab. The other tested Fabs retained activity in the TGFβ transactivation assay.
Figure 10D:
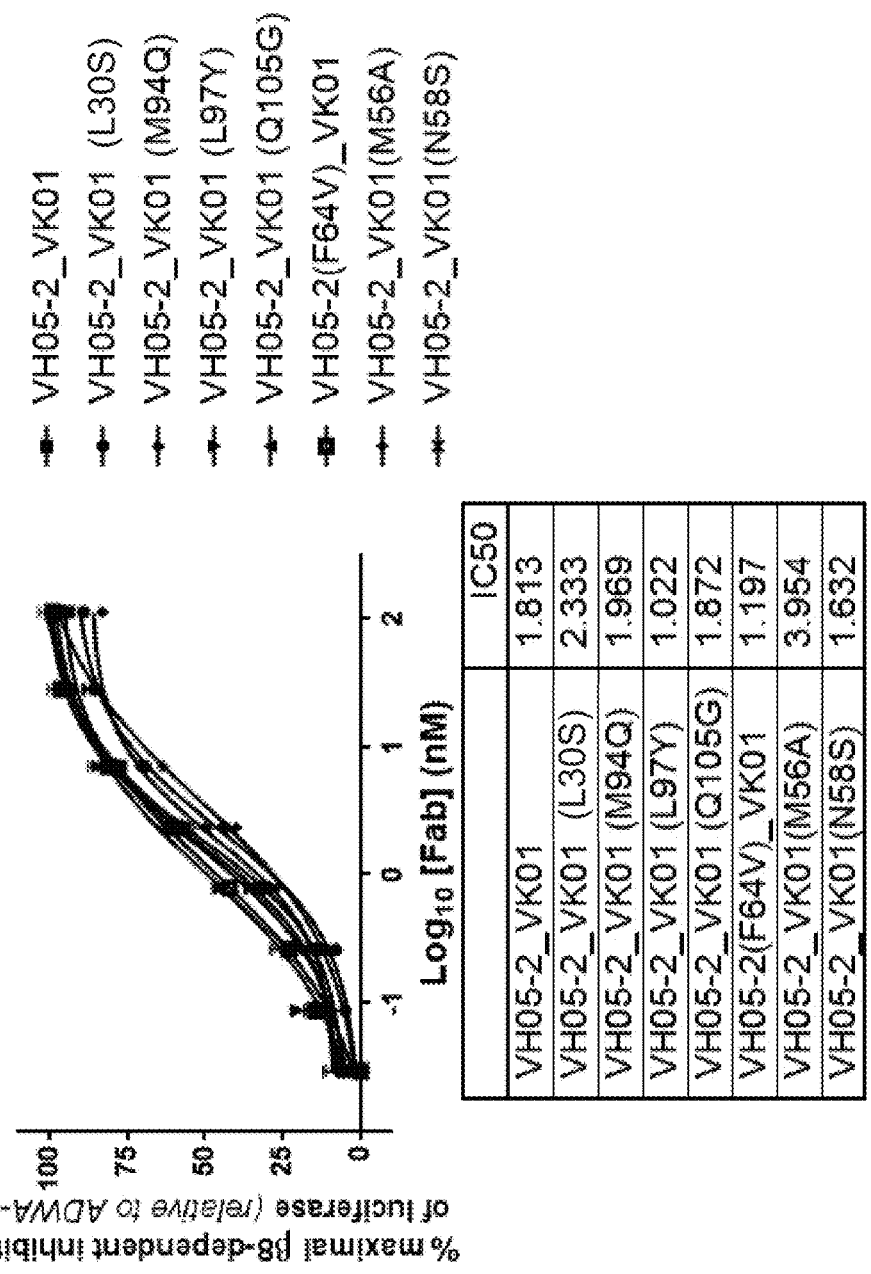
FIG. 10D shows a representative graph comparing the effect of ADWA11 VH05-2/VK01 (Parental) Fabs having the indicated amino acid substitution in the heavy chain variable region (e.g., F64V), or the light chain variable region (e.g., L30S, M94Q, L97Y, Q105G, M56A, or N58S). The tested Fabs retained activity in the TGFβ transactivation assay as compared to the parental ADWA11 VH05-2/VK01 Fab.

The impact of amino acid substitutions made in either the heavy chain variable region, or the light chain variable region of ADWA11 VH05/VK01 on TGFβ transactivation by U251 cells was also assessed (FIG. 10B-10D). Fabs having a F101L or F101W single amino acid substitution in the light chain variable region displayed a reduced TGFβ transactivation, as compared to the ADWA11 VH05/VK01 Fab.

Figure 10E:
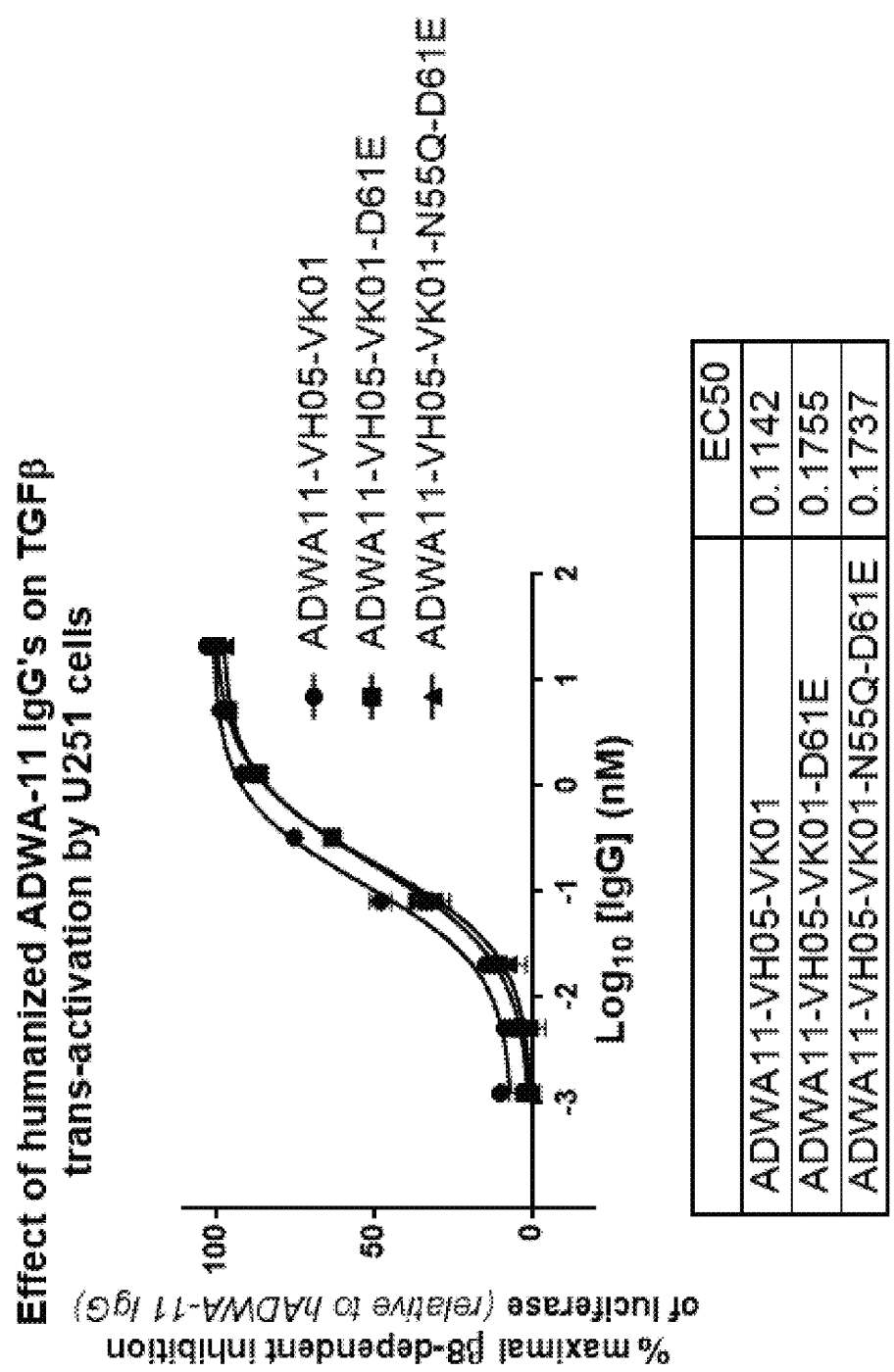
FIG. 10E shows a representative graph showing the effect of the humanized ADWA11 VH05/VK01, VH05/VK01-D61E (VH05-1/VK01), and VH05/VK01-N55Q-D61E (VH05-2/VK01) IgG on TGFβ transactivation by U251 cells. The tested antibodies retained activity in the TGFβ transactivation assay.

A comparison of the effect of humanized ADWA-11 IgG molecules on αvβ8 induced TGF-β transactivation of U251 cells was also monitored using the luciferase activity assay (FIG. 10E). These data show that the VH05/VK01-D61E and -N55Q-D61E mutants, have comparable effects on TGFβ transactivation.

Figure 10F:
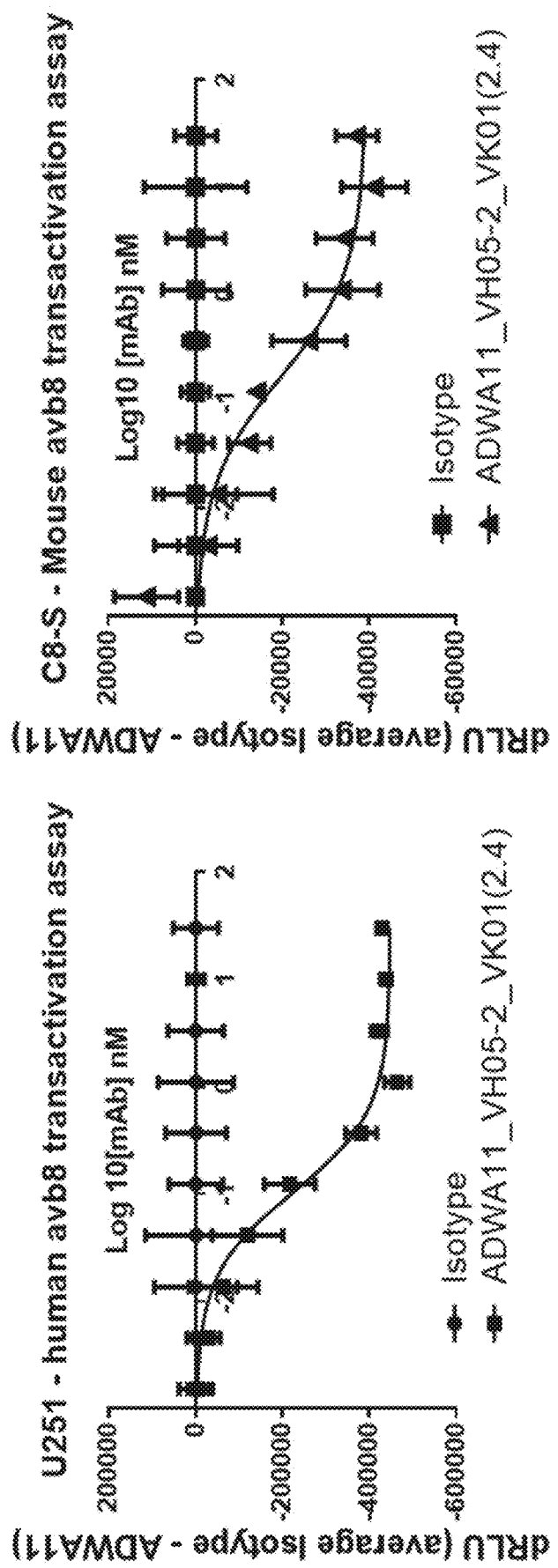
FIG. 10F depicts representative graphs showing the effect of ADWA11_VH05-2_VK01(2.4) on TGFβ transactivation by U251 cells (left panel) and C8-S (right panel), compared to the isotype control antibody. Additional experiments demonstrated the IC50 for ADWA11 VH05-2/VK01(2.4) in the TGFβ transactivation assay with U251 cells to be 199±93.6 pM (average±standard deviation).

To evaluate the potency of ADWA11_VH05-2_VK01 (2.4), alternatively referred to herein as ADWA11 2.4, a co-culture system was established with human and mouse cells that endogenously express αvβ8 with a TGFβ-sensitive luciferase reporter cell system. Briefly, U251 (human glioblastoma) or C8-S(mouse astrocyte) cells were plated with mink lung epithelial cell (Mv1Lu) stably transduced with Cignal SMAD reporter (luc) lentiviral particles (SABioscience) at a multiplicity of infection (MOI) of 50 (Mv1Lu-Smad cells). Mv1Lu-Smad cells respond to TGFβ generated by the U251 or C8-S cells, and inhibition of αvβ8 function can be monitored by a decrease in luciferase activity. FIG. 10F shows the effect of ADWA11 2.4 on TGFβ transactivation by U251 cells and C8-S, compared to an isotype negative control antibody.

These data demonstrate that ADWA11 2.4 is a more potent inhibitor of αvβ8 induced TGF-β transactivation than other antibodies, including the mouse ADWA11 monoclonal antibody. The IC50 for ADWA11 VH05-2/VK01(2.4) in the TGFβ transactivation assay with U251 cells was determined to be 199±93.6 pM (Average±Standard Deviation in five independent experiments).

Example 10: Evaluation of the Immunogenicity of Anti-αvβ8 Integrin Antibodies

The functional significance of peptides binding to Major Histocompatibility Complex (MHC) was evaluated by a T cell proliferation assay. CD4, a transmembrane glycoprotein expressed on T-helper cells, recognizes peptides bound MHC Class II molecules on the surface of antigen presenting cells (APC). This interaction results in proliferation of T-helper cells leading to an immune response. T-Cell proliferation was monitored by a decrease in the fluorescence intensity of the individual cells containing carboxyfluorescein succinimidyl ester (CFSE) dye. ProImmune's REVEAL® Immunogenicity System T cell assay uses flow cytometry methods to analyze division of CFSE dye labelled cells. PMBCs from various donors were incubated with CFSE to form intracellular fluorescent conjugates. Fluorescence intensity of CFSE is halved through each consecutive cell division, thus allowing measurement of cell proliferation. This reliable and reproducible CFSE-labelled T cell assay is useful to determine potential CD4-Tcell epitopes on MHCII presented peptides. Peptide controls derived from Influenza/Tetanus and Tuberculin Purified Protein Derivative (PPD) were used as positive controls for cell proliferation.

Twenty-nine peptides encompassing the CDRs were tested with PBMC derived from 51 donors for T-cells proliferation (Table 1, SEQ ID NOs: 94-122). The CFSE labelled PBMCs were incubated with test peptides for seven days and the extent of CD4+ T cells proliferation was monitored by Flow-cytometry method. The number of responders for the peptide derived from optimized molecule was compared with the number of responders for corresponding germline sequence peptides.

Reference antigens comprising known MHC class II epitopes were used in this study Tuberculin Purified Protein Derivative (PPD) is a derivative of *Mycobacterium tuberculosis*, and was used at a final assay concentration of 5 µg/ml. Approximately 70-100% of the PBMC donors are expected to react to this protein as a result of previous vaccination, i.e., through a memory immune response.

Keyhole Limpet Hemocyanin (KLH) is a recognized and potent naïve protein immunogen, used at a final concentration of 0.25 mg/ml in the assay. Typically between 50-80% of donors might be expected to react to this protein, presumably driven by a naïve immune response.

The synthetic peptide HA is derived from Influenza A hemagglutinin (PKYVKQNTLKLAT, residues 307-319; SEQ ID NO: 129) and was used at a final assay concentration of 5 µM. It is expected to elicit a response in up to 50% of donors. The synthetic peptide TT (AQYIKANSKFIGITEL (SEQ ID NO: 130), TET 830 modified/T-helper epitope from tetanus toxoid) is a universal human tetanus toxin T cell epitope that induces T-cell activation and is used as a helper peptide in vaccinations. It was used at a final assay concentration of 5 uM, with up to 45% of donors expected to respond.

Figure 11:
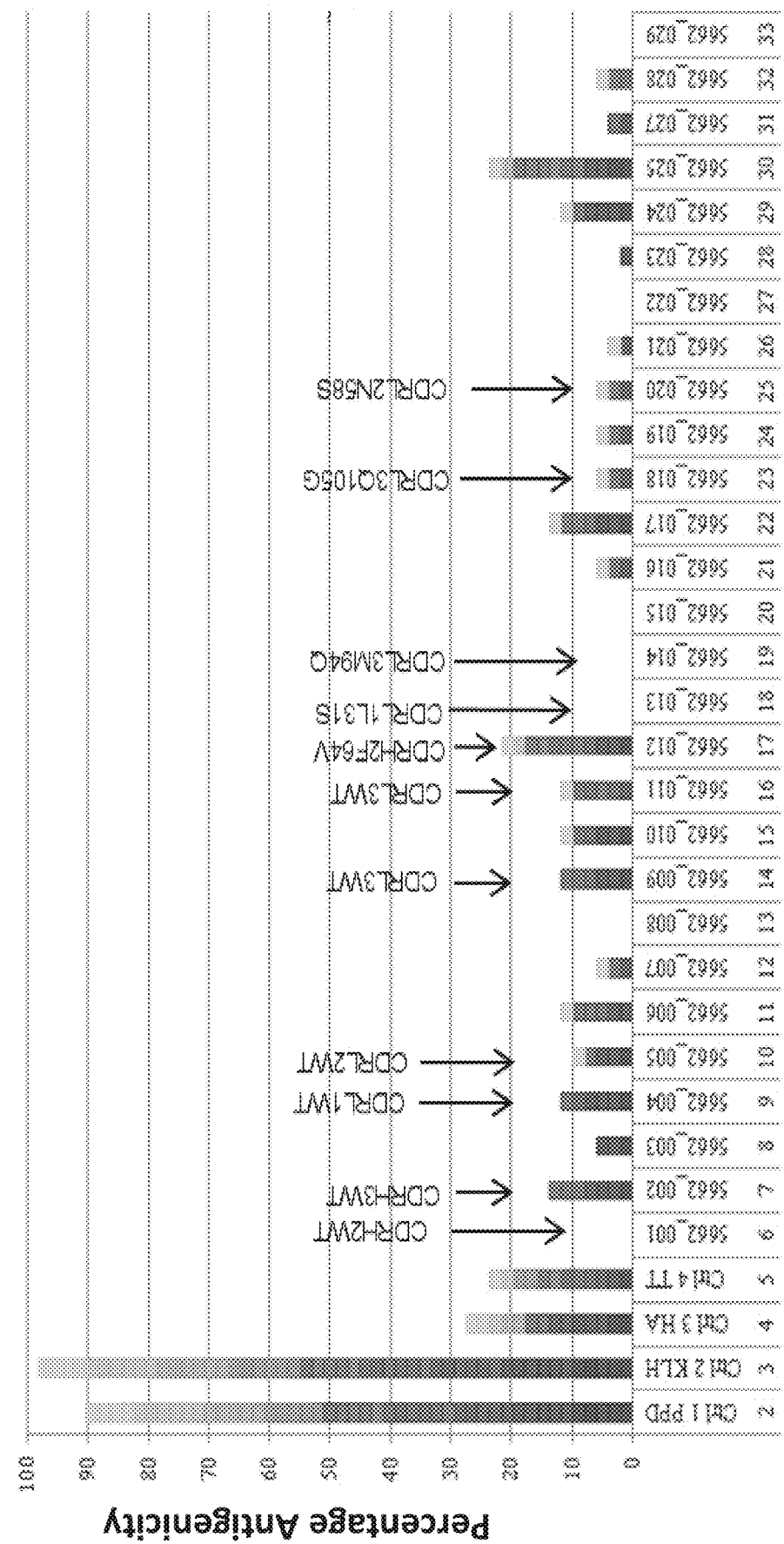
FIG. 11 shows a representative graph showing the percentage of responders (antigenicity) for different ADWA11 VH05-2VK01 CDR peptides compared to positive control peptides set forth in Table 1. Peptide antigenicity score was used to select possible CDR sequences with reduced immunogenicity risk.

The F64V substitution (SEQ ID NO: 105) in the heavy chain was found to increase the immunogenicity. Eleven of 51 donors' PBMCs responded in the CD4+ T cells proliferation assay and none of the donors were sensitive to the corresponding germline sequence. Other substitutions including Q105G (SEQ ID NO: 111), L30S (SEQ ID NO: 106), M94Q (SEQ ID NO: 107), and N58S (SEQ ID NO: 113) were found to reduce the immunogenicity each to a different extent as shown in Table 8. Percentage responder for different CDR peptides compared to positive control peptides are given in FIG. 11.

TABLE 8

| | Number of responders* for peptides corresponding to different substitution | |
|---|---|---|
| substitution | Original | After substitution |
| F64V | 0 | 11 |
| Q105G | 6 | 3 |
| L30S | 6 | 0 |
| M94Q | 6 | 0 |
| N58S | 5 | 3 |

*numbers of donors PBMC were responding in the CD4+ T cells proliferation assay

These data demonstrate that certain antibodies of the invention, including ADWA11 2.4, exhibit decreased T cell responses compared with the mouse parent mAb ADWA11. These results suggest that ADWA11 2.4 is an improved potential human therapeutic compared to its mouse parent antibody.

Example 11: Inhibition of αvβ8 Improves the Efficacy of Anti-PD-1 Therapy in the EMT6 Tumor Model Methods In this study, $3 \times 10^5$ EMT6 (ATCC) cells were implanted into the fourth mammary fat pad or subcutaneously in Balb/c mice (Charles River Laboratory). Mice were randomized into treatment groups when their tumors reached an average of 50 mm³ and then treatment was initiated. For treatment, mice received a dose of 10 mg/kg of the indicated antibodies 2A3_rat IgG ("2A3"; BioXcell), anti-PD-1 antibody ("PD1"; clone RMP1-14, BioXcell), 2B8_mIgG1_4mut ("2B8"), or ADWA11_mIgG1_4mut (ADWA11) by intravenous injection every four days for a total of three dosage administrations. Tumors were measured in two dimensions to monitor growth, where volume (V)=½ L×W², and L (length) is defined as the longest diameter of the tumor and W (width) is perpendicular to L. Tumor measurements were recorded 2-3 times per week until end of the study.

Results

Figure 12A:
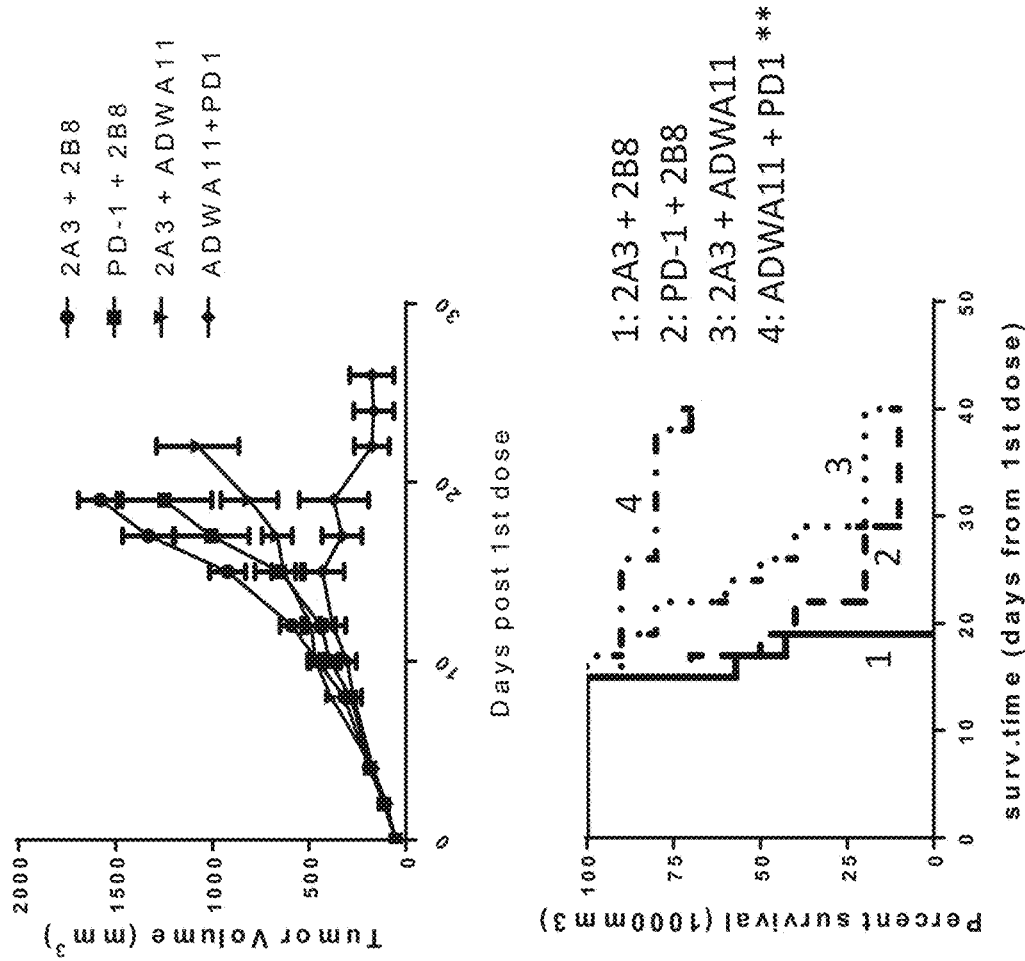
FIG. 12A shows representative graphs showing the efficacy of combinations of anti-αvβ8 antibody (ADWA11), anti-PD1 antibody ("PD-1", RMP1-14), mIgG1_4mut isotype (2B8), and rat IgG2a isotype (2A3) treatment in the EMT6 breast cancer tumor model. Tumor growth was measured using digital calipers three times per week and reported as tumor volume (length×width×width×0.5). Mean tumor volume+/−SEM in each treatment group was plotted until less than 8/10 of mice were remaining in each group. Survival was defined as the time to reach 1000 mm$^3$. The combination of anti-PD1 and ADWA11 inhibited tumor growth and improved overall survival to a greater extent than the other combinations tested.

Anti-αvβ8 (ADWA11) in combination with anti-PD1 therapy (ADA11+PD1) synergistically and significantly decreased tumor growth and improved survival over anti-PD1 or anti-αvβ8 monotherapy treatment groups (FIGS. 12A and 12B).

In the 10 mg/kg monotherapy dose group ADWA11 treatment resulted in a 47.1% tumor growth inhibition (TGI) on Day 13 of the study however, the TGI was transient and no mice reached the end of the study (0% survival at Day 51). Anti-PD1 monotherapy treatment resulted in a 15% TGI on Day 14 of the study and no mice reached the end of the study (0% survival at Day 51). By comparison, ADWA11 (10 mg/kg dose group) in combination with anti-PD-1 antibody resulted in a 90.0% TGI on Day 14 of the study and a 60% of mice reached the end of the study (60% survival at Day 51).

These results demonstrate for the first time that ADWA11 antibodies, including ADWA11 2.4, provide a synergistic therapeutic effect when combined with an inhibitor of PD-1, e.g., anti-PD-1 antibody. These data suggest that ADWA11 2.4 is a potential human therapeutic that can provide a synergistic therapeutic anti-tumor response when combined with a PD-1 inhibitor.

Example 12: Inhibition of αvβ8 Improves the Efficacy of 4-1BB and Anti-CTLA4 Therapy in the EMT6 Model Methods In this EMT6 tumor efficacy study, $1 \times 10^6$ EMT6 (ATCC) cells were implanted into the fourth mammary fat pad in Balb/c mice (Charles River Laboratory). Mice were randomized when tumors reached an average of 100 mm³ and treatment was initiated. Mice received i.v. dosing of 4-1BB (MAB9371 R&D Systems, 1 mg/kg Day 0 and Day 4), anti-CTLA4 (clone 9D9 BioXcell, 10 mg/kg Day 0, Day 4, and Day 8), anti-αvβ8 (ADWA11, 10 mg/kg Day 0, Day 4, and Day 8), 2B8_mIgG_4mut (10 mg/kg, Day 0, Day 4, and Day 8), or 2A3_rat IgG (BioXcell, 10 mg/kg Day 0, Day 4, and Day 8). Tumors were measured in two dimensions to monitor growth, where volume (V)=½L×W², and L (length) is defined as the longest diameter of the tumor and W (width) is perpendicular to L. Tumor measurements were recorded 2-3 times per week until end of the study.

Immunohistochemistry (IHC) analysis: 4 mm thickness formalin fixed paraffin embedded (FFPE) tumor tissue sections for CD8, CD45, and Granzyme B expression using custom protocols and Leica Bond-max automated IHC stainer. Images were acquired on a Leica/Aperio AT2 whole slide digital scanner using the 20× magnification setting. Images were analyzed using custom algorithms created in Visiopharm 7.2 software and optimized for each target of interest. Cell counting was carried out on the viable tissue and was normalized by the viable tissue area. Cell Density was calculated using the following equation: Cells/µm2= (#Positive Cells/Viable Tumor area (µm2))*1×106. Percent object density was calculated using the following equation: Area of staining (µm2)/Viable Tumor Area (µm2).

Results

Figure 13:
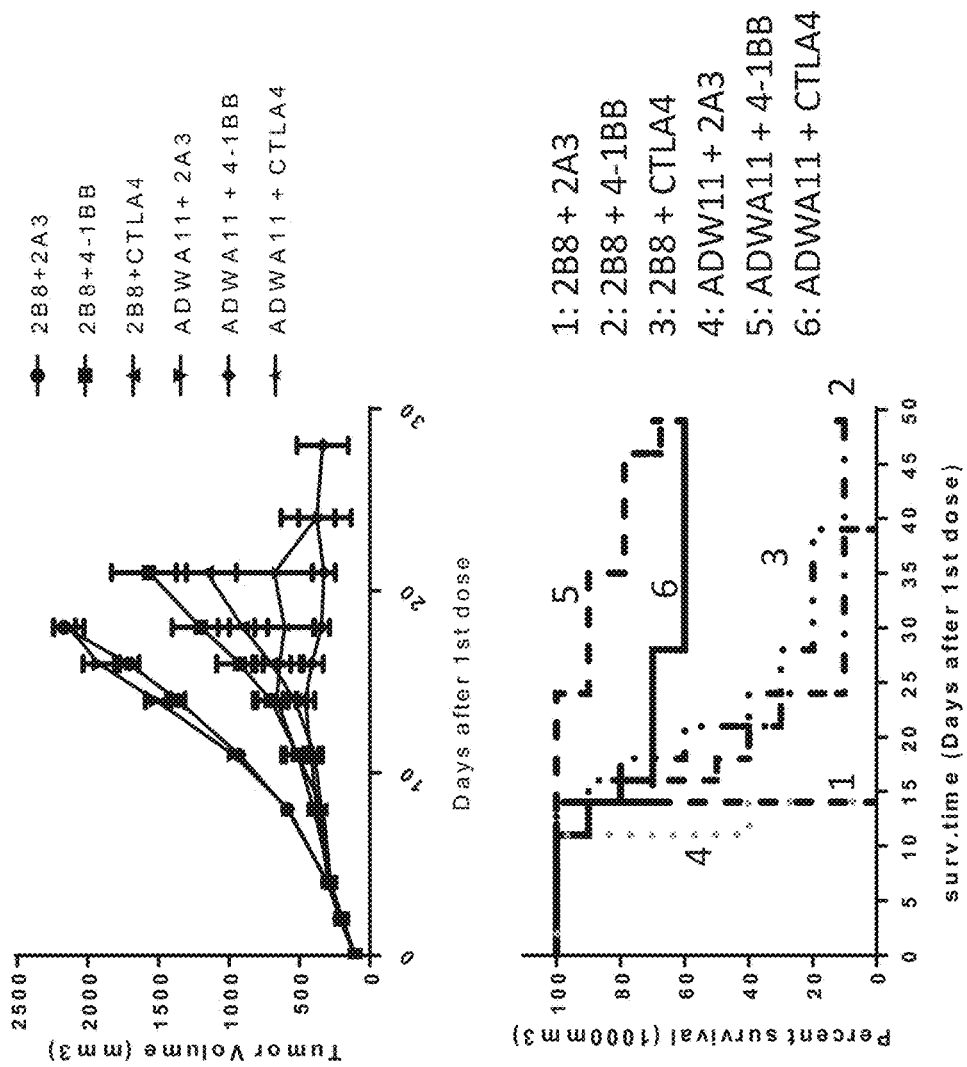
FIG. 13 shows representative graphs showing the efficacy of combinations of anti-αvβ8 (ADWA11), anti-41BB (MAB9371), anti-CTL4 (9D9), mIgG1_4mut isotype (2B8), and rat IgG2a isotype (2A3) treatment in an EMT6 tumor model. Tumor growth was measured using digital calipers three times per week and reported as tumor volume (length×width×width×0.5), mean tumor volume+/−SEM in each treatment group was plotted until less than 8/10 of mice were remaining in each group and survival was defined as the time to reach 1000 mm$^3$. The combination of anti-4-1BB and ADWA11 or anti-CLTA4 and ADWA11 treatment inhibited tumor growth and improved overall survival to a greater extent than the other combinations tested.

Anti-αvβ8 (ADWA11) in combination with anti-4-1BB or anti-CTLA4 significantly and synergistically decreased tumor growth and improved survival over anti-4-1BB, anti-CTLA4, or anti-αvβ8 monotherapy treatment groups (FIG. 13).

Figure 15:
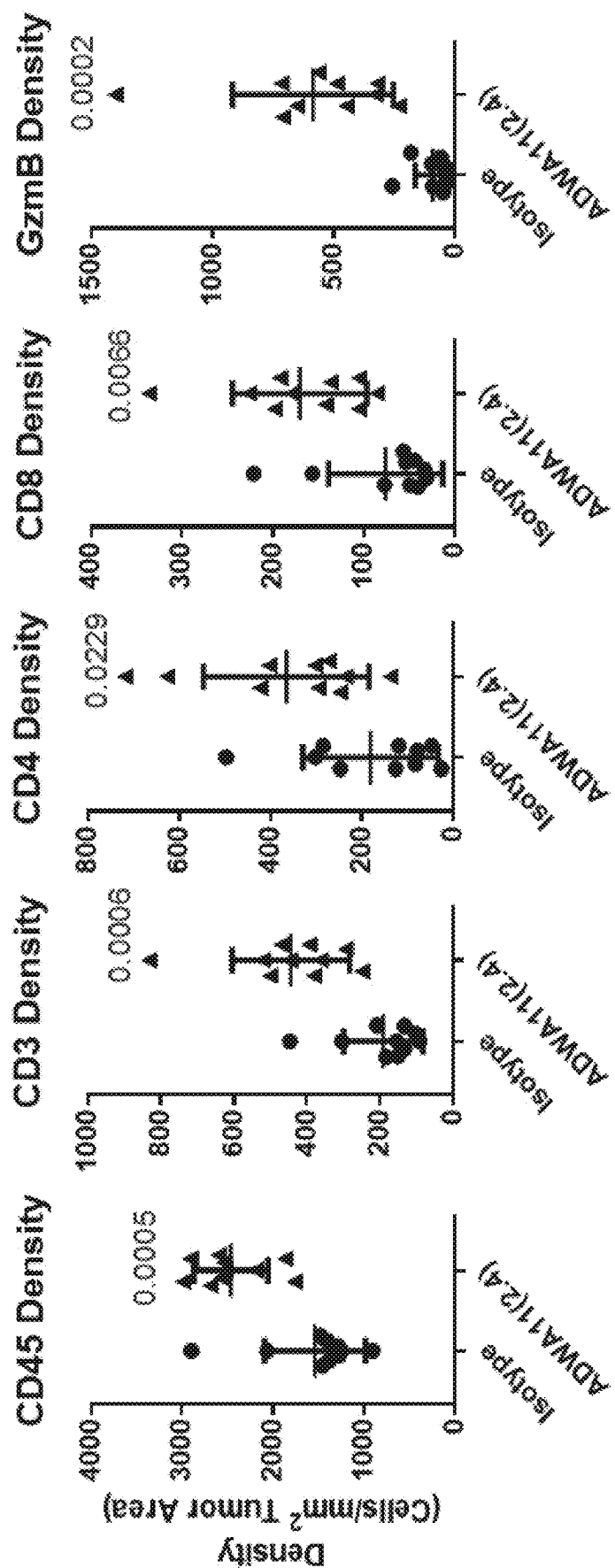
FIG. 15 depicts representative graphs showing IHC analysis of the density of CD45 (total lymphocytes and myeloid cells), CD3 (total T cells), CD4 T cells, CD8 T cells, and Granzyme B (activated CD8 and NK cells) in the EMT6 tumor model. ADWA11(2.4) (also referred to as ADWA11VH05-2/VK01(2.4) herein) treatment increased the density of all cell types analyzed. N=10 per group, p value for two-tailed t-test labelled on graph.

Changes in tumor infiltrating cell density after treatment with anti-αvβ8 antibody were assessed (FIG. 15). Lymphocyte abundance was quantified in the EMT6 tumor model by IHC analysis of the density of CD45 (total lymphocytes and myeloid cells), CD3 (total T cells), CD4 T cells, CD8 T cells, and Granzyme B (activated CD8 and NK cells) staining. These data demonstrated that anti-αvβ8 monotherapy increased the abundance of the total CD45+ cells, CD4+ T cell, and CD8+ T cells, and resulted in a very significant increase in the density of Granzyme B expressing cells (n=10 for each group).

Tumor lymphocyte abundance in tumor tissue was analyzed Day 11 (antibody treatment on Day 0, 3, 6, 9) from mice treated with Isotype control or ADWA11 (2.4) (FIG. 15). ADWA11 (2.4) treatment increased the density of total leukocytes (CD45+, 1540±558 vs 2470±407), CD8 T cell (CD8+, 76.3±62.7 vs 170±74.2) and cytotoxic cells (% Granzyme B density, 11.8±11.0 vs 106±35.1) in the tumor microenvironment (average number of cells CD45+, average number of cells CD8+, or average % Granzyme B staining area per mm²±standard deviation in Isotype vs ADWA11 (2.4) treatment)

These results demonstrate for the first time that ADWA11 antibodies, including ADWA11 2.4, provide a synergistic therapeutic effect when combined with an agonist of 4-1BB, e.g., anti-4-1BB antibody. These data suggest that ADWA11 2.4 is a potential human therapeutic that can provide a synergistic therapeutic anti-tumor response when combined with an agonist of 4-1BB.

These results also demonstrate for the first time that ADWA11 antibodies, including ADWA11 2.4, provide a synergistic therapeutic effect when combined with an inhibitor of CTLA4, e.g., anti-CTLA4 antibody. These data suggest that ADWA11 2.4 is a potential human therapeutic that can provide a synergistic therapeutic anti-tumor response when combined with an inhibitor of CTLA4.

Example 13: Inhibition of αvβ8 Improves the Efficacy of Radiation Therapy in the CT26 Tumor Model Methods CT26 tumor efficacy study: $4 \times 10^5$ CT26 (ATCC) cells were implanted subcutaneously into the flank of Balb/c mice (Charles River Laboratory). Mice were randomized when tumors reached an average of 100 mm³ and treatment was initiated. Mice received 10 mg/kg i.v. dose every 4 days, 3 total doses, of 2B8_mIgG1_4mut (in house) isotype control or ADWA11_mIgG1_4mut, and a single dose of 5Gy tumor targeted radiation on Day 5 after first dose. Tumors were measured in two dimensions to monitor growth, where volume (V)=½ L×W², and L (length) is defined as the longest diameter of the tumor and W (width) is perpendicular to L. Tumor measurements were recorded 2-3 times per week until end of the study.

qPCR analysis of gene expression: tumor tissue was collected and 30 mg of tissue was homogenized in 900 µL of lysis buffer supplied in the RNeasy Plus Mini Kit, using Omin Bead Ruptor. RNA from homogenized tumor samples was isolated using the RNeasy Plus Mini Kit and vendor recommended protocols. cDNA was synthesized using 2 µg of total RNA and the High-capacity cDNA reverse transcription kit, using vendor recommended protocols. Gene expression was analyzed using 50 ng of cDNA and gene-specific taqman primers, TaqMan Universal Master Mix II, and vendor recommended protocols. ViiA7 real-time qPCR system was used for qPCR studies. The threshold cycles (CT) for each sample was analyzed using the recommended comparative CT method and expression of target genes is reported as fold change of treatment group compared to isotype control group. A two-tailed unpaired Students T-test test was used to compare treatment group to the isotype control group with significance reported at <0.05.

Immunohistochemistry (IHC) analysis: 4 mm thickness formalin fixed paraffin embedded (FFPE) tumor tissue sections were prepared for CD8, CD45, and Granzyme B expression using custom protocols and Leica Bond-max automated IHC stainer. Images were acquired on a Leica/Aperio AT2 whole slide digital scanner using the 20× magnification setting. Images were analyzed using custom algorithms created in Visiopharm 7.2 software and optimized for each target of interest. Cell counting was carried out on the viable tissue and was normalized by the viable tissue area. Cell Density was calculated using the following equation: Cells/µm2=(#Positive Cells/Viable Tumor area (µm2))*1×106.

Results

Figure 14A:
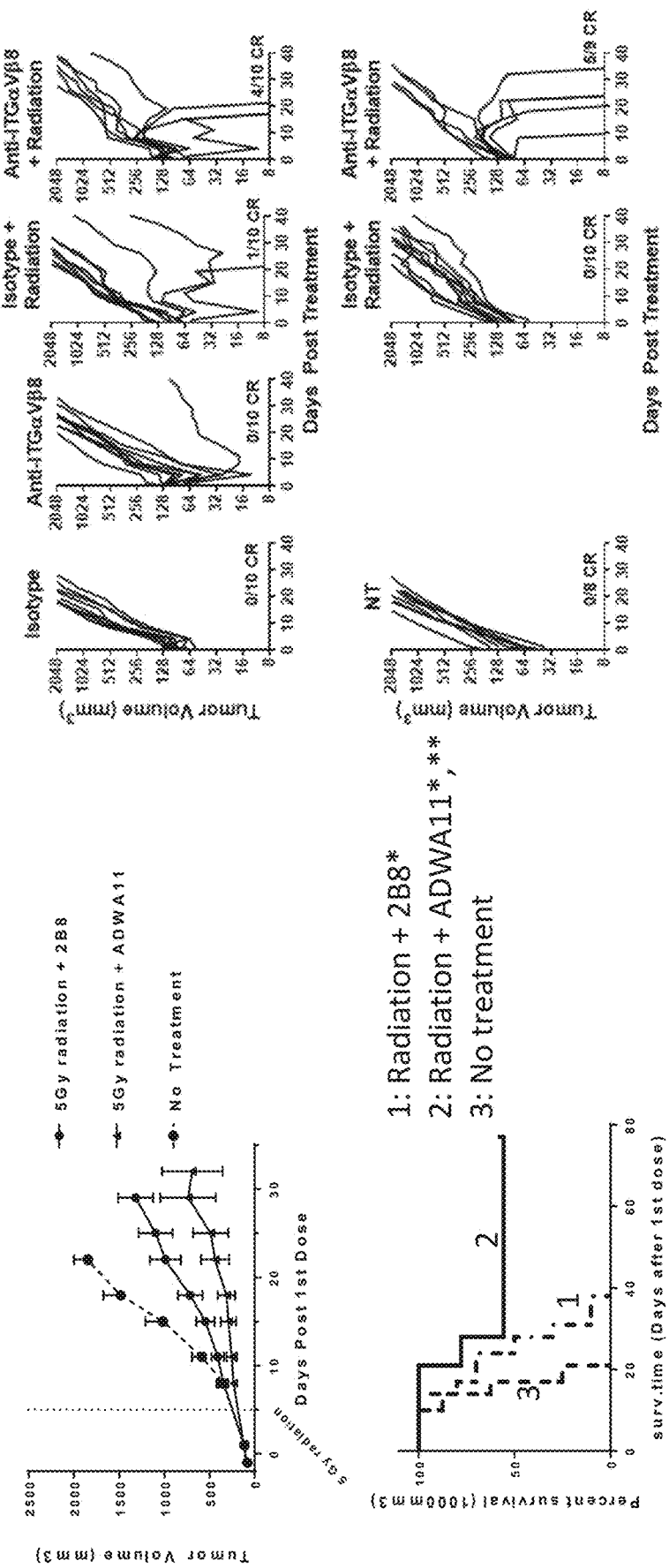
FIG. 14A depicts representative graphs showing that the combination of anti-αvβ8 antibody and radiation therapy (ADWA11+5Gy radiation group) inhibited tumor growth and improved overall survival to a greater extent than radiation therapy with an isotype control (mIgG4mut (2B8)+5Gy radiation group) in the CT26 tumor model. Tumor growth was measured using digital calipers 3 times per week and reported as tumor volume (length×width×width×0.5), mean tumor volume+/−SEM in each treatment group is plotted and survival was defined as the time to reach 1000 mm$^3$. *p<0.05 vs No Treatment, **P<0.05 vs radiation+2B8.

Anti-αvβ8 antibody (ADWA11) in combination with radiation therapy significantly decreased tumor growth and improved survival over radiation therapy alone (FIG. 14A).

In the CT26 studies, ADWA11 antibody (anti-ITGαVβ8) monotherapy resulted in a 64.3% TGI on Day 19 of the study, but the response was transient and only 1 out of 10 mice reached the end of the study (10% survival, Day 57). Radiation therapy alone (5 Gray (Gy) dose on Day 5) resulted in a 57.7% tumor growth inhibition (Day 18), and 1 out of 20 mice reached the end of the study (5% survival, Day 57). By comparison ADWA11 treatment in combination with radiation therapy resulted in an 87.7% tumor growth inhibition (Day 19, 10 mg/kg ADWA11 and 5 Gy radiation therapy dose group) and 9 out of 19 mice reached the end of the study (47.4% survival, Day 57).

To investigate the effect of ADWA11 on tumor lymphocyte abundance in the CT26 tumor model, tumor tissue was collected Day 12 (antibody treatment on Day 0, 4, 8) from mice treated with Isotype control or ADWA11 VH05-2/VK01 (anti-ITGαVβ8) and analyzed for lymphocyte markers by IHC (FIG. 14B, top panel). ADWA11 VH05-2/VK01 treatment increased the density of total CD45+ leukocytes; Isotype: 367±128, ADWA11 VH05-2/VK01: 695±94.8 (Average number of cells per mm²±standard deviation). CD8+ T cell; Isotype: 173±79.3, ADWA11 VH05-2/VK01: 374±80.4 (Average number of cells per mm2±standard deviation). Ganzyme B expressing cytotoxic cells, Isotype: 264±65.5, ADWA11 VH05-2/VK01: 514±91.7 (Average number of cells per mm2±standard deviation) in the tumor microenvironment. Additionally, anti-ADWA11 treatment in combination with radiation therapy increased the mRNA expression level of CD45 (3.86±0.979), CD8a (5.45±3.53), Granzyme B (4.21±1.02), and IFNγ (5.53±2.13) in the tumor microenvironment (Fold Change f standard deviation vs Isotype treatment group) (FIG. 14B, bottom panel).

These studies demonstrate that anti-ITGαVβ8 (ADWA11_mIgG1_4mut) treatment increases the abundance of activated lymphocytes in the tumor microenvironment, and in combination with tumor targeted radiation is efficacious at causing tumor regression and long-term survival.

These results also demonstrate for the first time that ADWA11 antibodies, including ADWA11 2.4, provide a synergistic therapeutic effect when combined with radiation therapy. These data suggest that ADWA11 2.4 is a potential human therapeutic that can provide a synergistic therapeutic anti-tumor response when combined with radiation therapy.

Example 14: Evaluation of Integrin αvβ8 as a Novel Suppressor of Tumor Immunity and Target for Tumor Immunotherapy In this study, a potent αvβ8 blocking monoclonal antibody (ADWA-11) that was generated by immunizing Itgb8 knockout mice with recombinant αvβ8, was used to examine whether inhibition of this integrin could facilitate anti-tumor immunity.

In non-neoplastic tissues, αvβ8 integrin is expressed on neuroepithelia, fibroblasts, dendritic cells, and T cells, and can activate latent transforming growth factor β (TGFβ), an important immunomodulator. As now shown herein, within carcinomas, myeloid cells express αvβ8 integrin and that a potent monoclonal antibody blocking αvβ8 (ADWA-11) causes growth suppression or complete tumor regression in syngeneic models of squamous cell carcinoma, breast and colon cancer, especially when combined with other immunomodulators (anti-PD1, anti-CTLA-4 or 4-1BB) or radiotherapy. Treatment with ADWA-11 increases tumor infiltration and Granzyme B expression of CD8+ T cells, and enhances the ratio of pro-inflammatory to suppressive tumor associated macrophages. Most human tumors express ITGβ8 mRNA and, as shown herein, there are high levels of surface αvβ8 expression on monocytes, macrophages, and dendritic cell subsets in biopsies of human ovarian and renal cell carcinomas. These findings identify αvβ8 integrin as a promising new target for cancer immunotherapy.

Figure 28:
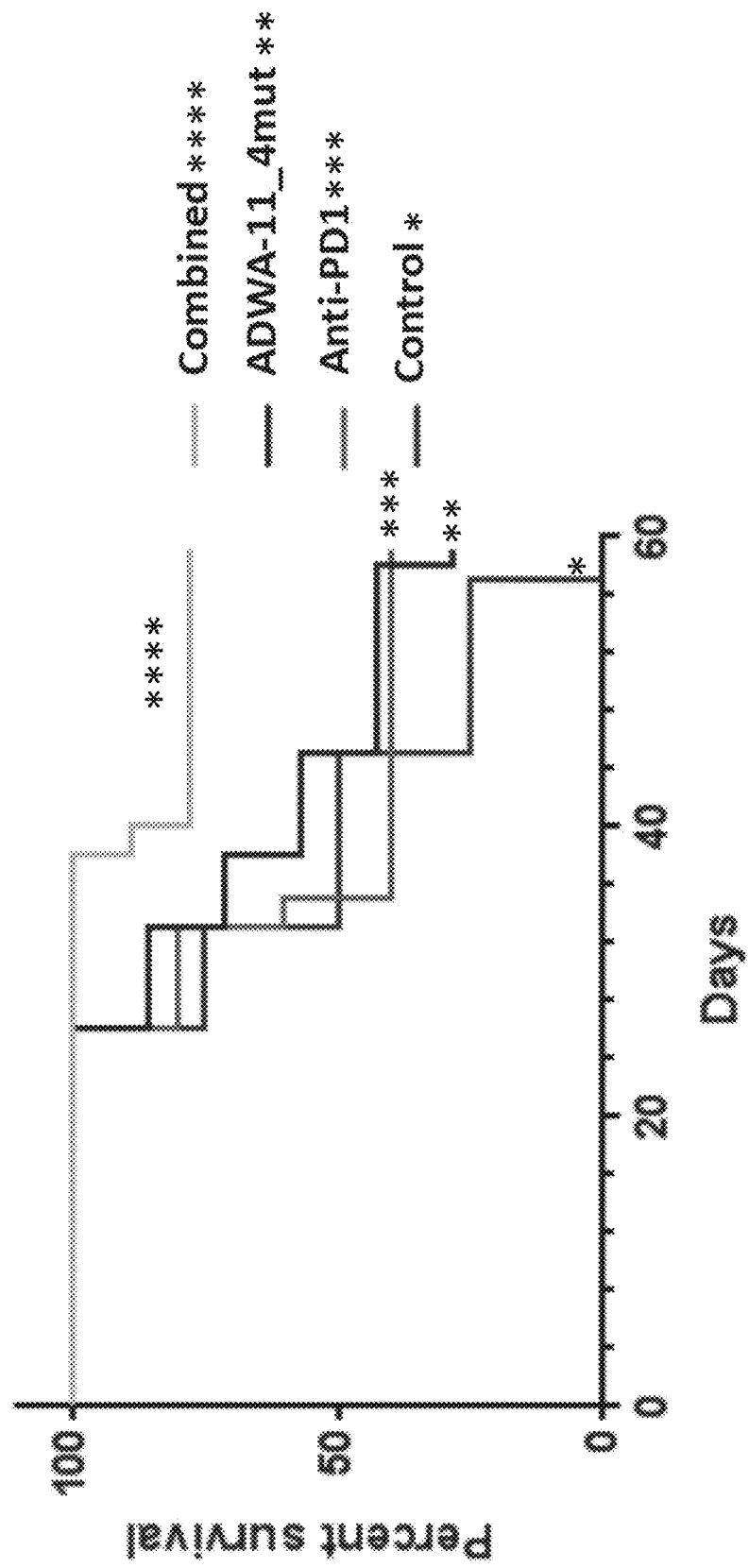
FIG. 28 depicts representative graphs showing Kaplan-Meier survival curves, using a tumor volume of 2000 mm³ as a cutoff for survival for the CCK168 tumor model. Treatment groups were isotype control, anti-PD1 antibody, ADWA11_4mut, and a combination of anti-PD1 antibody and ADWA11_4mut. A combination of anti-PD1 antibody and ADWA11_4mut treatment synergistically improved overall survival to a greater extent than anti-PD1 antibody, ADWA11_4mut, or isotype control treatment alone or the expected additive effects of combination treatments.
Figures 30A, 30B, 30C:
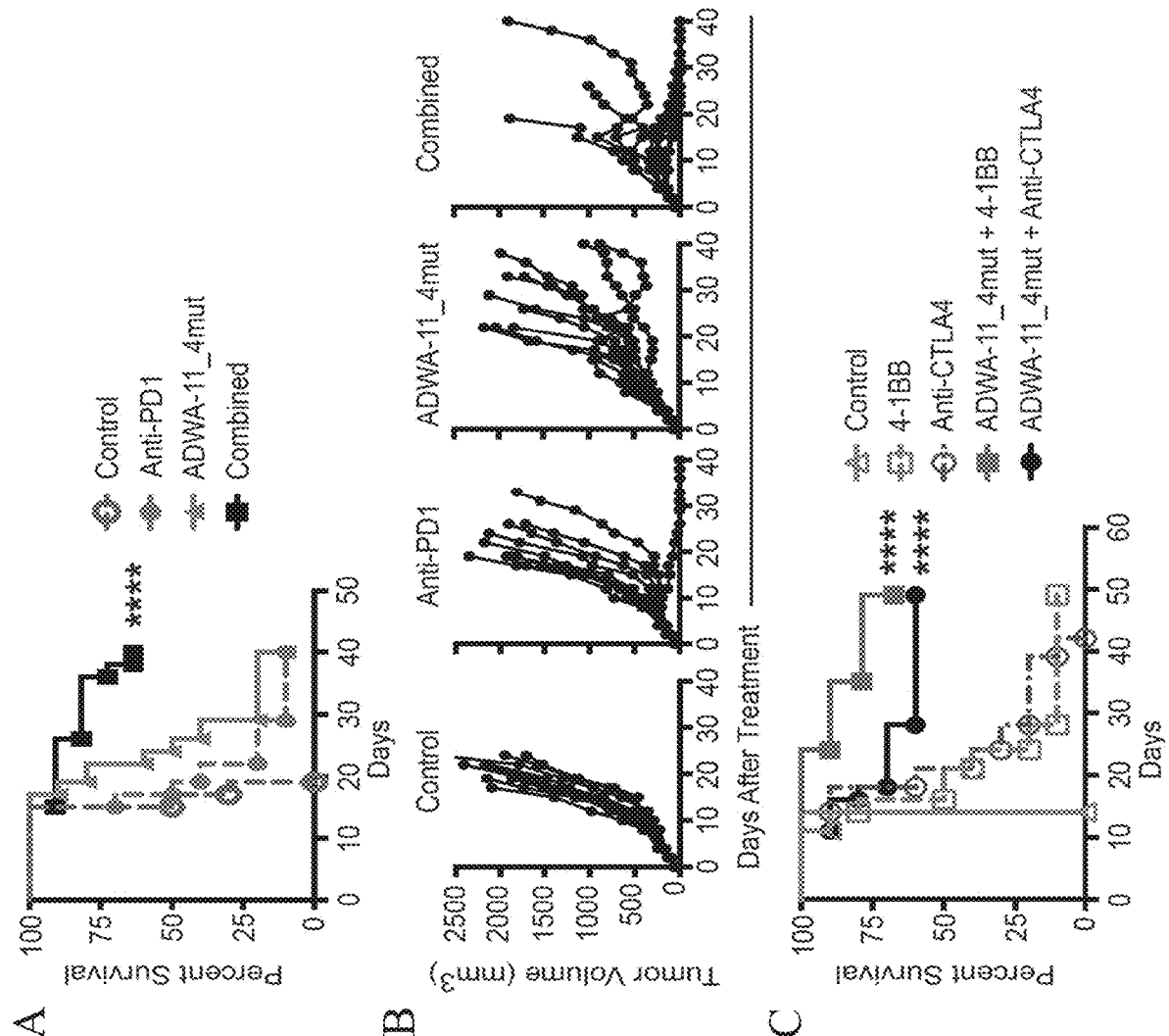
FIG. 30A shows graphs depicting representative survival curves and FIG. 30B shows graphs depicting representative individual growth curves in mice implanted orthotopically with EMT6 cells following treatment with isotype control antibody, ADWA11_4mut, 4-1BB, anti-CTLA4, anti-PD-1, or a combination of ADWA-11_4mut and 4-1BB, anti-CTLA4 or anti-PD-1. Data reported as percent survival, n=10 in each group. ****p<0.0001 by log-rank Mantel-Cox test
FIG. 30C shows graphs depicting representative survival curves and FIG. 30D shows graphs depicting representative individual growth curves for mice treated with anti-CTLA4 or activator of 4-1BB.
Figures 30D, 30E:
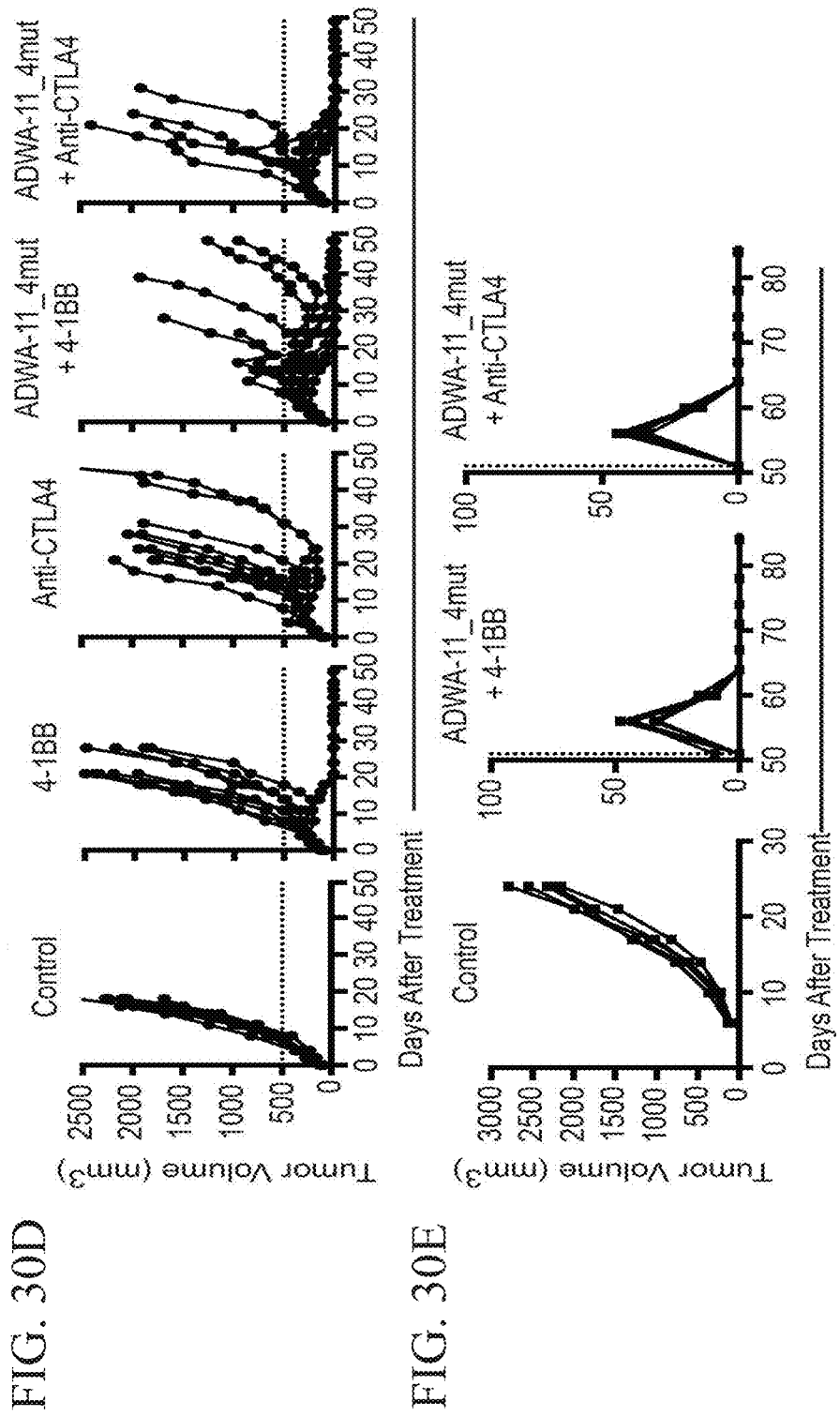
FIG. 30E shows representative graphs depicting results from tumor re-challenge in mice that survived 50 days with complete regression of tumors after treatment with the synergistic combination of ADWA-11_4mut and anti-CTLA4 or the synergistic combination of ADWA-11_4mut and activator of 4-1BB. Control mice were not previously exposed to tumor. Re-challenged mice were assessed for 30 days. n=5 control, n=6 ADWA-11_4mut+anti-CTLA4, n=5 ADWA-11_4mut+4-1BB.

Efficacious Synergistic Combination Immunotherapy with ADWA-11 and Anti-PD-1 in a Squamous Cell Carcinoma Model The effects of ADWA11 alone, or in combination with an anti-PD-1 antibody, were examined in a syngeneic tumor model of established squamous cell carcinoma (CCK168 cells) (FIG. 16A and FIG. 28). CCK168 cells, a chemically induced squamous cell carcinoma cell line derived from FVB mice, were injected subcutaneously into the dorsolateral right flank of syngeneic wild type FVB mice at a dosage of $1.5 \times 10^4$ cells/mouse.

Tumors were allowed to grow over 14 days. Mice selected for the experiment had tumor size of at least 5 mm in diameter and were optimally distributed based on tumor sizes, between different treatment groups using studylog software. Mice were weighed and tumor size was measured every other day for the duration of the study using a traceable digital caliper (Fisher Scientific, model #14-648-17). Mice were euthanized when tumor size reached or exceeded 2000 mm$^3$ or developed a large ulceration at the tumor site.

Mice were treated with hybridoma antibody ADWA11 or isotype-matched control antibodies on days 0 and 7 and with mouse anti-PD-1 antibody (RMP1-14, BioXcell) or its isotype-matched control antibody on days 0, 4 and 8 (day 0 being the first day of therapy). Appropriate antibody for each group and isotype control antibodies were injected intraperitoneally at doses of 10 mg/Kg for each antibody, ADWA11, anti-PD-1 antibody (RMP1-14, BioXcell), control antibody ADWA-21 (for ADWA11), and control 2A3 (BioXcell). Control ADWA-21 binds human but not mouse integrin-08.

CCK168 tumors demonstrated minimal responses to an anti-PD1 antibody, but five of ten mice treated with ADWA11 monotherapy showed tumor regression (FIG. 16B-16C). Combination therapy with ADWA11 and an anti-PD1 antibody induced complete regression of eight out of ten tumors, and significant increase in overall survival when mice were treated with hybridoma ADWA11 and an anti-PD1 antibody (FIG. 16B) or ADWA11_4mut_mIgG1 and anti-PD1 antibody (FIG. 28).

Surviving mice were observed for up to two years after tumor regression and none showed evidence of subsequent tumor regrowth. Thirteen mice from two replicate experiments with complete regression after combination therapy and 3 mice with complete regression after monotherapy with ADWA11 were re-challenged either once or twice with CCK168 cells and there was no tumor growth in any, demonstrating the development of long-term tumor immunity.

These results demonstrate for the first time that ADWA11 antibodies, including ADWA11 2.4, provide a synergistic therapeutic effect when combined with an inhibitor of PD-1, e.g., an anti-PD-1 antibody. These data suggest that ADWA11 2.4 is a potential human therapeutic that can provide a synergistic anti-tumor response when combined with a PD-1 inhibitor.

Figure 18A:
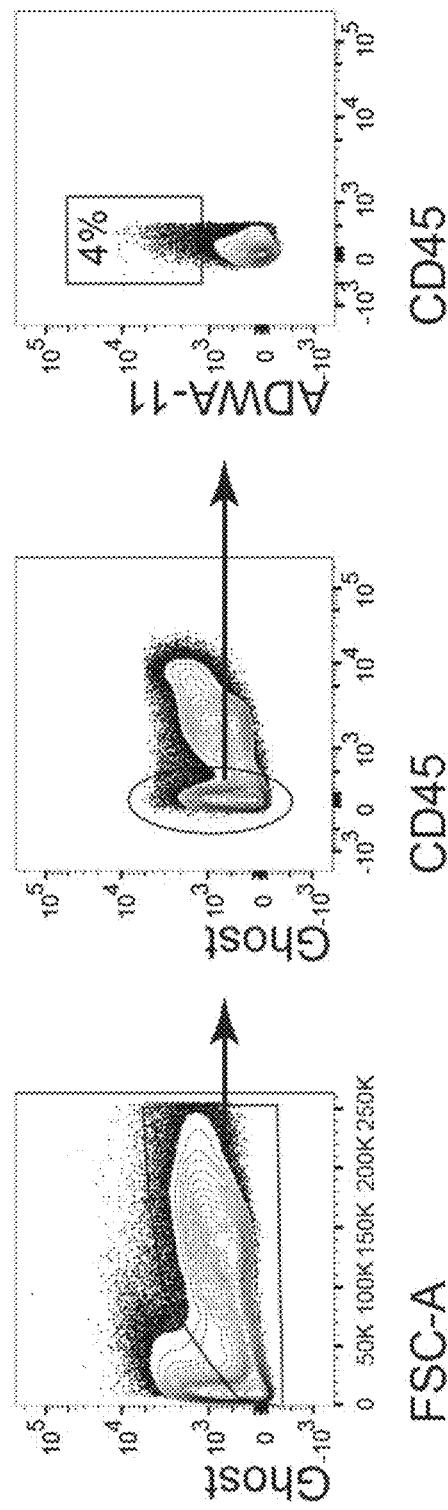
FIG. 18A depicts representative graphs showing ADWA11 staining on CD45-negative cells isolated from CCK168. Live single cells were analyzed for the presence of CD45. 4% of CD45 negative cells in the CCK168 tumor model were positive for αvβ8 expression using ADWA11 antibody.
Figure 18B:
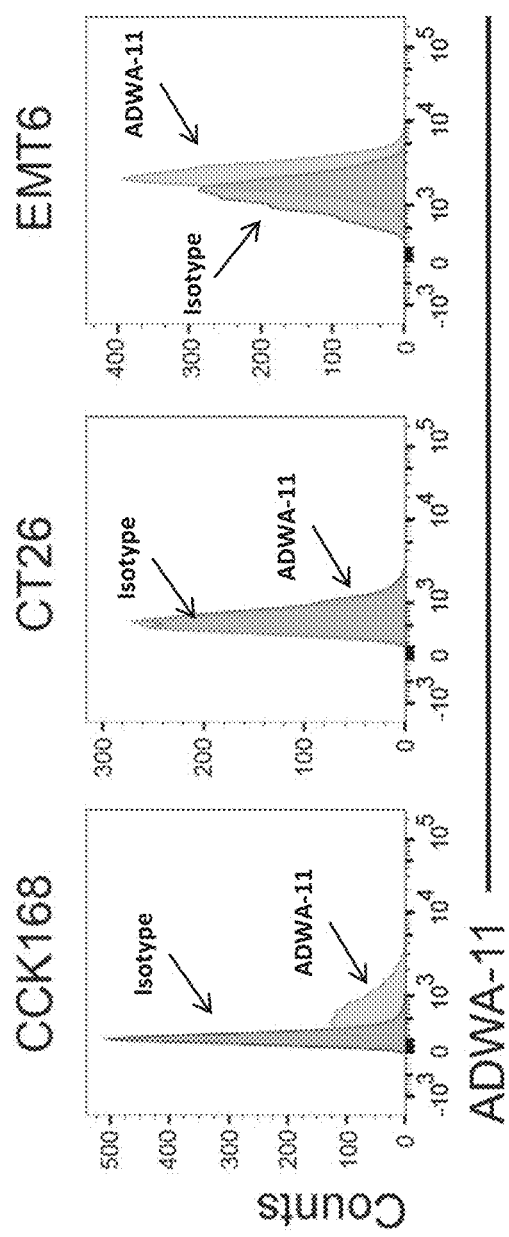
FIG. 18B depicts the expression of αvβ8 in the CCK168, CT26, and EMT6 cell lines. Live single cells were analyzed for αvβ8expression by flow cytometry using isotype and anti-αvβ8 (ALDWA11) staining antibodies. The CCK168 and EMT6 cell lines have detectable expression of αvβ8, while the CT26 cells line does not.
Figure 20:
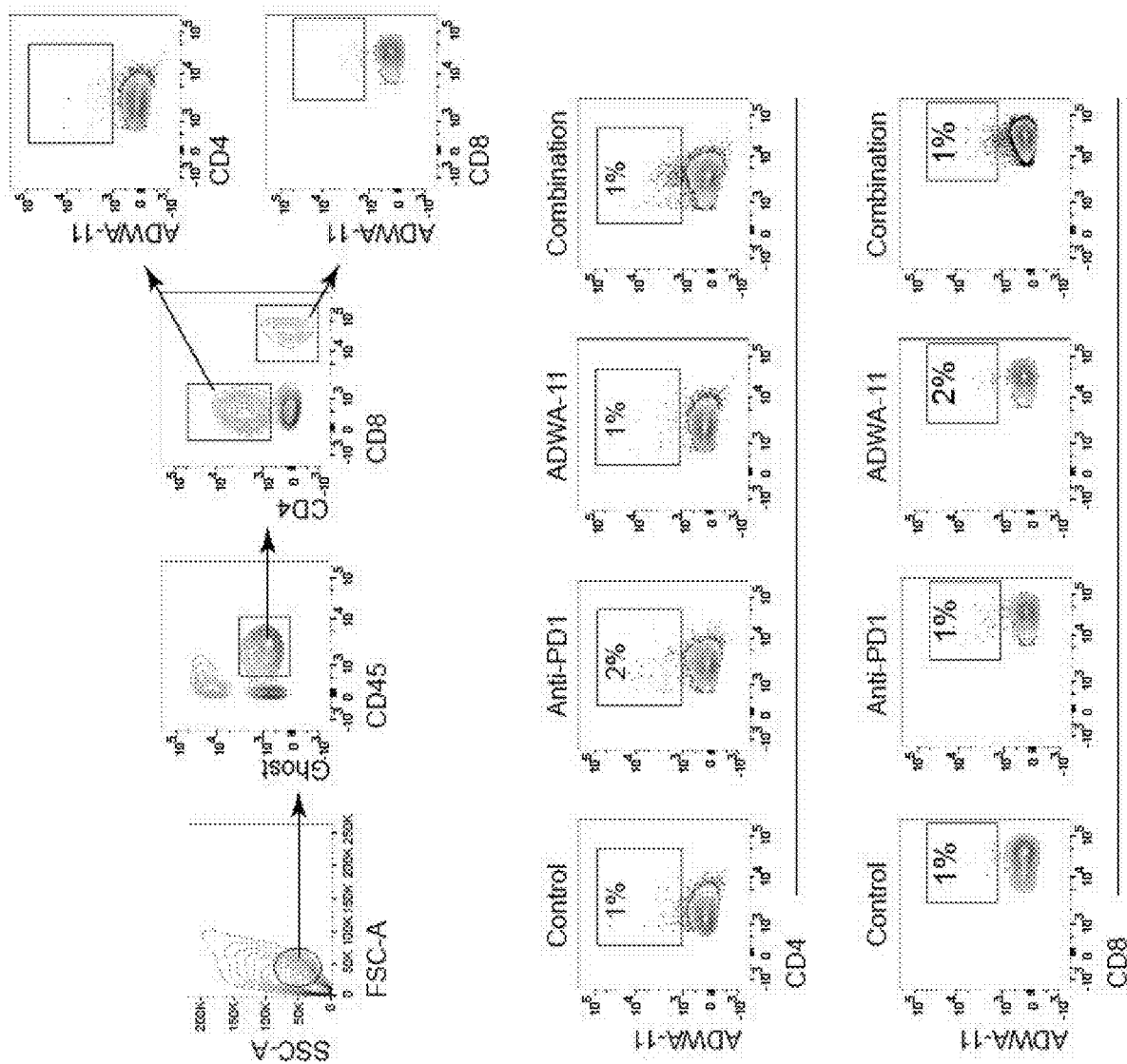
FIG. 20 depicts representative graphs showing ADWA11 staining on CD4+ and CD8+ T cells in the CCK168 tumor microenvironment. Live, single CD45+ cells were gated on CD4 and CD8 and stained with ADWA11. Representative plots are shown for mice from each of the 4 treatment groups.

Surface Integrin αvβ8 is Present on Myeloid Cells within the Tumor Microenvironment Flow cytometry was utilized to identify which cell types of the tumor express integrin β8, presumed to be expressed as an αvβ8 heterodimer (FIG. 17A and FIG. 17B). αvβ8 expression was readily detectable on greater than 80% of CD45+CD11b+F4/80+CD64+ macrophages and less than 20% of CD45+CD11b+F4/80−CD64−CD11c+MHCII$^{high}$ dendritic cells within CCK168 tumors (FIG. 17B). αvβ8 was expressed at similar levels in each of the macrophage subpopulations examined, including early infiltrating (pro-inflammatory) Ly6C+ cells and immunosuppressive CD206+ cells (FIG. 17B). αvβ8 was also expressed on CCK168 tumor cells in vitro (FIG. 18B). Low levels of expression of αvβ8 on CD45-tumor and stromal cells in vivo was also found (FIG. 18A). No expression of αvβ8 was found on intratumoral T cells (FIG. 20).

Animals

All animal studies were performed in accordance with approved protocols by the University of California, San Francisco, Institutional Animal Care and Use Committee of Pfizer, Inc. Institutional Animal Care and Use Committee. Wild type FVB/N mice used were either purchased from Jackson Laboratories (The Jackson Laboratories, stock #001800) or derived from our own breeding colony derived from this stock. Wild type Balb/c mice were purchased from Charles River Laboratories (Charles River Laboratories, strain code 028).

Human Tumor Processing

For all human samples, informed consent was obtained from all subjects, and work was performed in accordance with Institutional Review Board (IRB) approval. Fresh tissue was collected and processed through the UCSF Immunoprofiler workflow, a translational platform developed and optimized for profiling immune subsets within cancer. Briefly, tissue was acquired from the operating room and transported to the laboratory within 4 hours of excision. Tissue was vigorously minced (<1 mm chunks) and digested enzymatically (3 mg/ml collagenase A, 50 U/ml DNase I) based on developed standard operating procedures. Immune populations were subjected to multiplexed flow cytometry (>60 colors) to analyze proportionality and mean fluorescent intensities of known subsets and their expression of $\alpha v\beta 8$. All antibodies were purchased from BD Pharmingen, eBioscience, Invitrogen, or BioLegend. Anti-$\alpha v\beta 8$ antibody was generated as described previously. All flow cytometry including cell sorting was performed on a special-order BD FACSAria Fusion flow cytometer. Analysis of flow cytometry data was done using FlowJo.

Flow Cytometry Protocol

Subcutaneous tumors were isolated from the mice using scissors and blunt dissection. The tumors were placed in a petri dish with digestion cocktail of Collagenase XI (Sigma C9407) 2 mg/mL, Hyaluronidase (Sigma H3506) 0.5 mg/ML, and DNase (Sigma DN25) 0.1 mg/mL prepared in C10 media (RPMI 1640, Hepes 1%, Penicillin/Streptomycin $1\lambda$, fetal calf serum 10%, sodium pyruvate 1 mM, non-essential amino acids $1\lambda$, and beta-mercaptoethanol 0.45%). Tumors were minced using sterile scissors. The resultant slurry of cells were transferred into 50 mL conical tubes (Fisher Scientific #14-432-22) and the petri dish used to mince the tumor was rinsed with 2 mL C10 media to capture remaining cells. Cells were incubated in a shaker at 255 rpm for 45 minutes at 37° C. After incubation, 15 mL of C10 media was added to the digested tumor cells and gently vortexed for 15 seconds. The cell slurry was passed through a 100 μm mesh strainer (Falcon® #352360) into a clean 50 mL conical tube. Cells were pelleted by centrifugation for 5 minutes at 200 g at 4° C. and reconstituted in PBS. Cell counts were performed using a Countless II FL hemocytometer (Life Technologies).

Isolated single cell preps were used for cell surface and intracellular staining. After counting, $10 \times 10^6$ cells were transferred into each well of a v-shaped 96-well plate for staining. Live dead staining with Ghost Dye™ Violet 510 (TONBO bioscience #13-0870) at 1:1000 for 20 minutes at 4° C. Fc receptor and non-specific binding was blocked with anti-CD16/30 (eBioscience #14061) for 10 minutes at 4° C. Surface staining was performed for 20 minutes at 4° C. For intracellular staining, cells were incubated in Fix/Perm buffer (eBioscience #88-8824) for 20 minutes at room temperature followed by intracellular cytokine staining with antibody cocktails for 20 minutes at 4° C. After completion of staining, cells were transferred into flow cytometry buffer (PBS with 2% FBS, Penicillin/Streptomycin/Glutamate, EDTA 2 mM) for analysis.

Antibodies used for T cell staining experiments: ICOS FITC (eBioscience #11-9949-80), CD25 AF780 (eBioscience #47-0251-82), CD45.1 AF700 (BioLegend #110723), CD8 BV605 (BioLegend #100743), CD4 BV650 (BioLegend #100546), Ki-67 PE-Cy7 (BD Biosciences #561283), CTLA4 PE (BD Biosciences #553720), and FoxP3 PB-e450 (eBiosciences #48-5773-82).

Antibodies used for intracellular cytokine staining experiments: CD3 APC (eBioscience #17-0032-82), NK1.1 APC-AF780 (eBioscience #47-5941-80), CD45.1 AF700 (BioLegend #110723), CD4 BV650 (BioLegend #104729), CD8 BV605 (BioLegend #100546), IFN-7 FITC (eBioscience #11-7311-82), IL-17A PE-Cy7 (BioLegend #506921), Granzyme-B PE (eBioscience #12-8898-82), FasL PerCP-eFluor710 (eBioscience #46-5911-82), and FoxP3 PB-e450 (eBioscience #48-5773-82).

Antibodies used for myeloid cell staining experiments: Ly6G BV785 (BioLegend #127645), SiglecF BV785 (BD Biosciences #740956), CD90.2 BV785 (BioLegend #10533), B220 BV785 (BioLegend #103246), CD45.1 AF700 (BioLegend #110724), CD11b AF780 (eBioscience #47-0112-82), CD206 PerCP-Cy5.5 (BioLegend #141716), F4/80 PE (BioLegend #123109), CD11c BV650 (BioLegend #117339), Ly6C BV605 (BioLegend #128035), MHC-II PB-e450 (eBioscience #48-5321), CD24 PE-Cy7 (BioLegend #101822), CD103 FITC (eBioscience #11-1031-82), ADWA11 APC (custom conjugated in our laboratory), and CD64 FITC (BioLegend #139316).

Antibodies used for NK cell staining experiments: CD45.1 AF700 (BioLegend #110724), CD3 APC (eBioscience #17-0032-82), NK1.1 APC-AF780 (eBioscience #47-5941-80), CD314-NKG2D PE (eBioscience #12-5882-82), CD226-DNAM-1 PerCP-Cy5.5 (BioLegend #128814), CD335-NKp46 FITC (eBioscience #11-3351-82), CD107a-LAMP-1 PE-Cy7 (BioLegend #121620), and CD49b eFluor450 (eBioscience #48-5971-82).

For cell stimulation, cells were stimulated prior to cell surface and intracellular staining. Approximately $3 \times 10^6$ cells in 200 μl of C10 media per well were incubated in round-bottom 96-well plates overnight in a tissue culture incubator in 5% CO2 at 37° C. Stimulation cocktail (Inomycin, PMA, Brefeldin-A, and Monensin 500× stimulation cocktail Tombo #TNB4975-UL100) was added to cells which were incubated in tissue culture incubator in 5% CO2 at 37° C. for 4 hours. Cells were transferred to v-bottom wells for staining as outlined above. Flow cytometry was performed using a BD LSRFortessa™ (BD Biosciences) and analyzed using FlowJo™ (Tree Star Inc.).

Figure 19A:
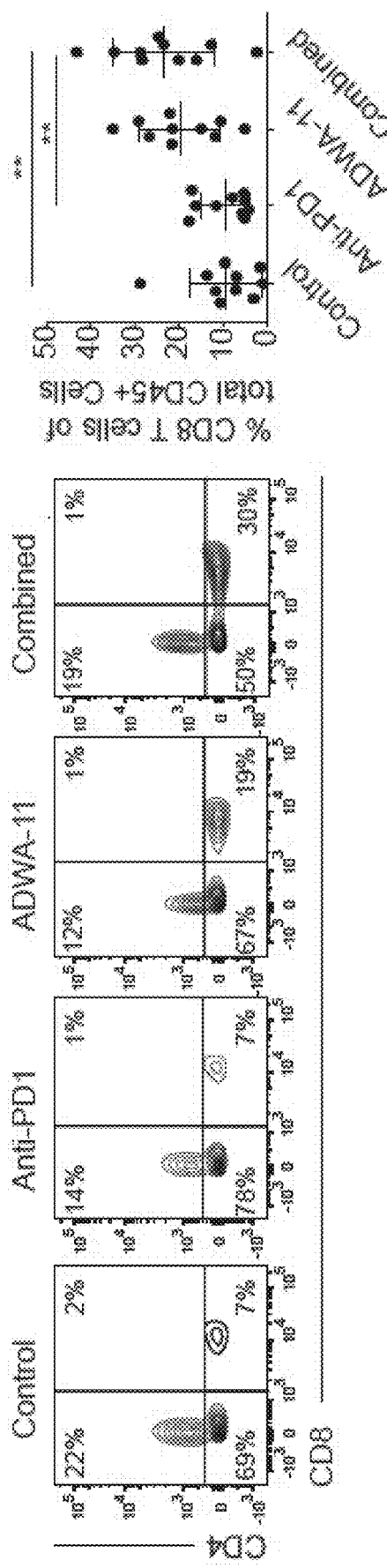
FIG. 19A depicts representative graphs showing total intratumoral CD8+ T cells numbers of mice with CCK168 tumors treated with control antibodies alone, anti-PD1, ADWA11 or combined anti-PD1 and ADWA11. Representative flow cytometry plots for CD4 and CD8 expression of all CD45+ cells are shown along with the ratio of CD8+ cells number to CD45+ cells for each mouse in each group.
Figure 19B:
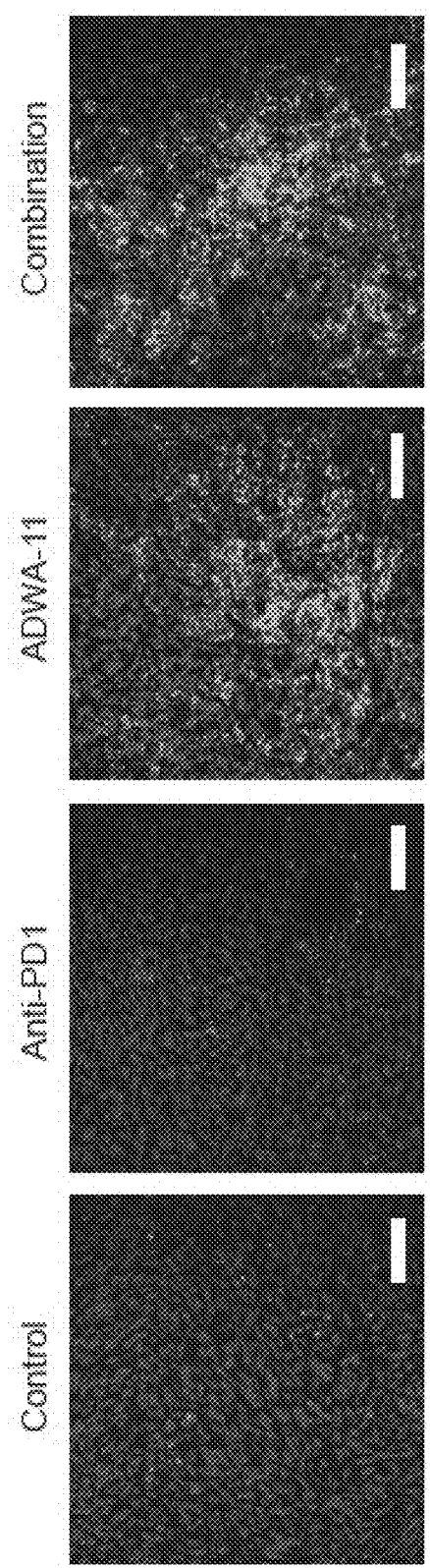
FIG. 19B shows representative immunofluorescence micrographs of CCK168 tumor sections harvested from mice in each treatment group, stained for anti-CD8 and DAPI. Scale bar, 50 μm.
Figure 19C:
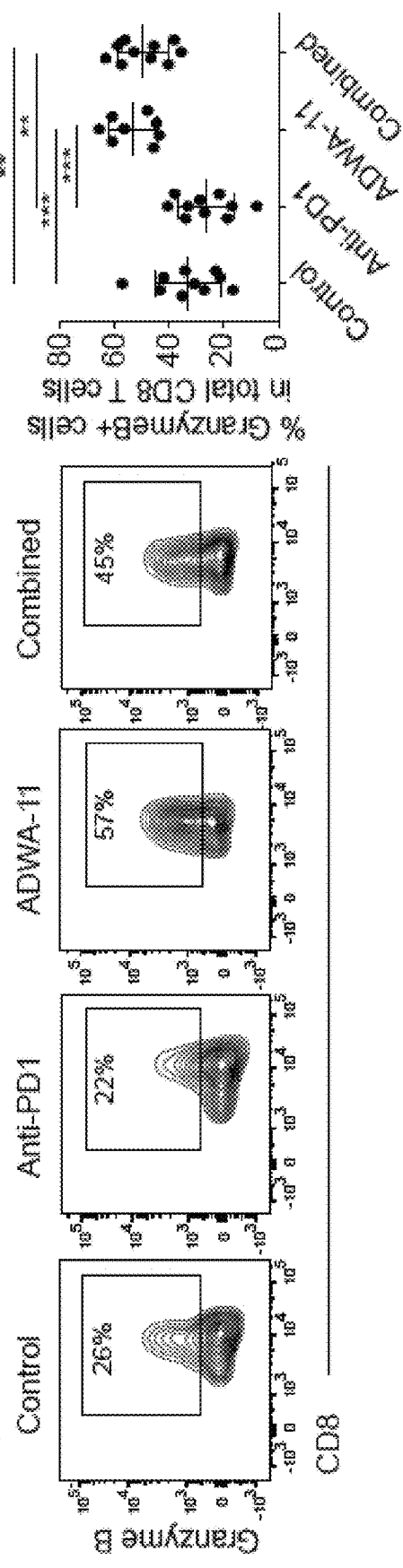
FIG. 19C shows representative flow cytometry plots showing intracellular staining for Granzyme B in cells gated for CD8 expression, along with the percentage of CD8+ cells expressing detectable Granzyme B in each mouse in each group.
Figure 19D:
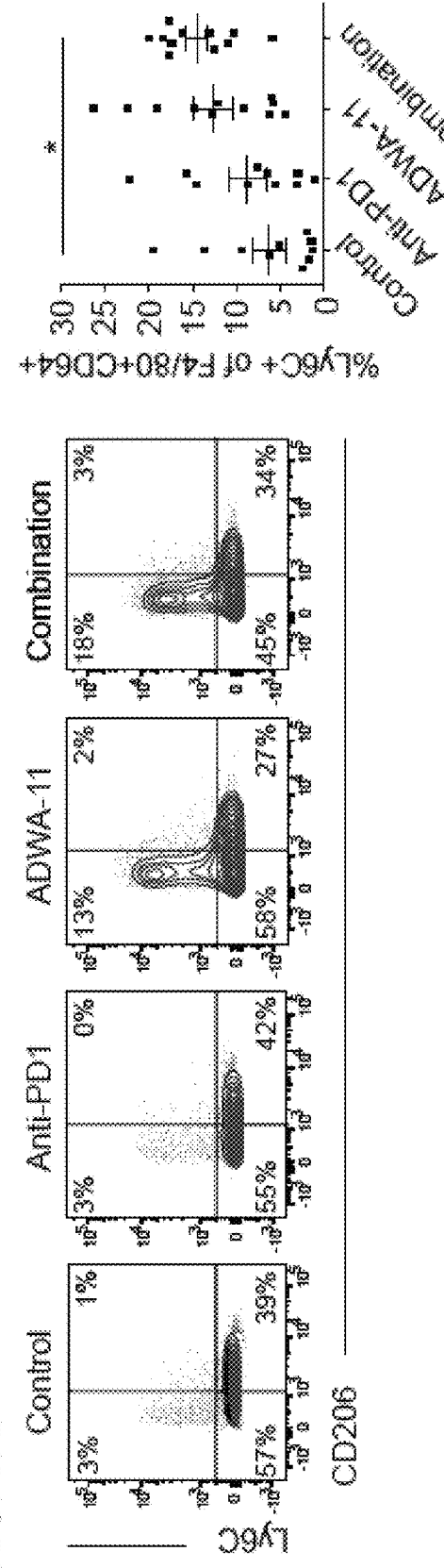
FIG. 19D shows representative flow cytometry plots showing immunostimulatory macrophages (Ly6c$^{high}$, CD206$^{low}$), and immunosuppressive macrophages (CD206$^{high}$, Ly6c$^{low}$) for cells gated as CD45+Ly6G-CD11b+CD64$^{high}$F4/80$^{high}$. Of the macrophage population, immunostimulatory macrophages were identified as Ly6C$^{high}$CD206$^{low}$ and immunosuppressive macrophages were identified as Ly6C$^{low}$CD206$^{high}$, along with percentage of immunostimulatory macrophages for each mouse. Data in graphs are mean±SEM, n=10 per group. *p<0.05, p<0.01, *p<0.001 by one-way ANOVA.

ADWA11 Increases Tumor Infiltration and Enhances Differentiation of Cytotoxic CD8+ T Cells, and Elevates the Ratio of Inflammatory Monocytes to Suppressive Macrophages The effects of ADWA11 (with or without anti-PD1) on the nature of the immune infiltrate were also characterized (Thomas et al., Cancer Cell 8:369-380, 2005; Wu et al., Cancer Immunol. Res. 2:487-500, 2014). Although treatment with anti-PD1 in this model had no effect on the total number of tumor CD8+ T cells, treatment with ADWA11 dramatically increased CD8 T cell infiltration, an effect that was most apparent by immunostaining excised tumors (FIGS. 19A-19B). ADWA11 also significantly increased the percentage of CD8+ T cells that expressed Granzyme B (FIG. 19C), whereas treatment with anti-PD1 had no effect. Inflammatory monocytes also contribute to tumor evasion of host immune responses. Ly6C is expressed on inflammatory monocytes and expression of Ly6C is diminished in tumor associated macrophages with suppressive properties in the tumor microenvironment (Franklin et al., Science 344:921-925, 2014; Movahedi et al., Cancer Res. 70:5728-5739). Further classification of the myeloid population showed that ADWA11 treatment specifically increased the accumulation of CD45+CD11b+CD11c−Ly6G−Ly6C$^{high}$CD206$^{low}$ inflammatory macrophages (FIG. 19D) (Ostuni et al., Trends Immunol. 36:229-239, 2015; Noy et al., Immunity 41:49-61, 2014). None of the treatments had significant effects on CD4+ T cell numbers, CD4+ FoxP3+ regulatory T cells, or interferon-γ expression by T cell subsets, at the time points analyzed, and we were unable to identify significant expression of IL-17 in any T cells subset (data not shown).

For immunostaining, tumors were harvested and fixed in 4% paraformaldehyde at 4° C. overnight. The fixed tumors were immersed in 30% sucrose solution at 4° C. overnight and embedded in O.C.T. compound (Tissue Tek® #4583), and cryosectioned at 15 µm. Frozen sections were stained by previously described protocols (Henderson et al., Nat. Med. 19:1617-1624, 2013; Rock et al., Proc. Natl. Acad. Sci. USA 108: E1475-1483, 2011). In brief, cryosections were permeabilized and blocked with 0.3% Triton X-100 and 3% BSA in PBS. Sections were incubated with primary antibodies overnight at room temperature, then with fluorophore-conjugated primary and secondary antibodies, and then mounted with Prolong Gold (Invitrogen).

Antibodies used for immunostaining: rat anti-F4/80 (Alexa Fluor 647-conjugated, Serotec, clone C1, 1:100), rabbit anti-phospho-Smad3 (Epitomics, 1880-1; 1:100), rat anti-CD8 (Alexa Fluor 488- or 594-conjugated, Biolegend, clone 53-6.7, 1:100). Alexa Fluor 488-, 555-, 647-conjugated donkey anti-rabbit, and anti-rat (Invitrogen). Confocal microscopy was performed on a Zeiss LSM780 and LSM5 Pascal microscopes.

All quantifications were done using high-resolution confocal images representing a thin (1 airy unit; ~1 µm) optical section of the sample. Images were analyzed using ImageJ software. Each group contained samples from at least 5 controls, and 5 treated (ADWA11) mice. Four images (fields sized 425.10×425.10 µm) from each tissue section were taken randomly, using the same confocal settings. Images were placed at identical thresholds, then the area covered by myofibroblast stains or phospho-Smad3 was calculated.

Figure 21A:
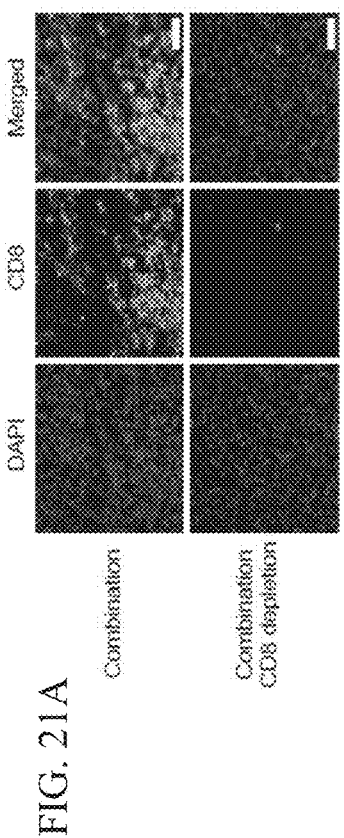
FIG. 21A shows representative graphs showing immunodepletion of CD8+ T cells. Micrographs show immunostaining with anti-CD8 counterstained with DAPI in CCK168 tumors isolated following combinatorial anti-PD-1/ADWA11 therapy with or without prior treatment with anti-CD8 depleting antibody or isotype control antibody.
Figure 21B:
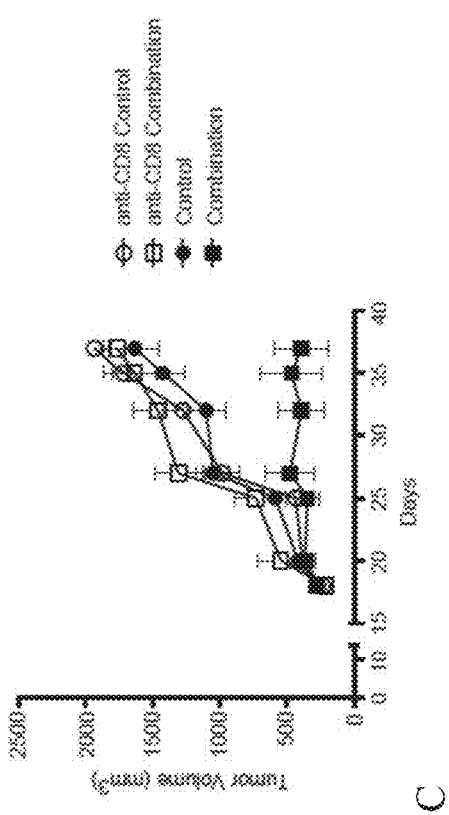
FIG. 21B shows representative graphs showing average tumor growth curves for CCK168 tumors pretreated with anti-CD8 depleting antibody or isotype control antibody 24 hours prior to ADWA11/anti-PD-1 combination therapy.
Figure 21C:
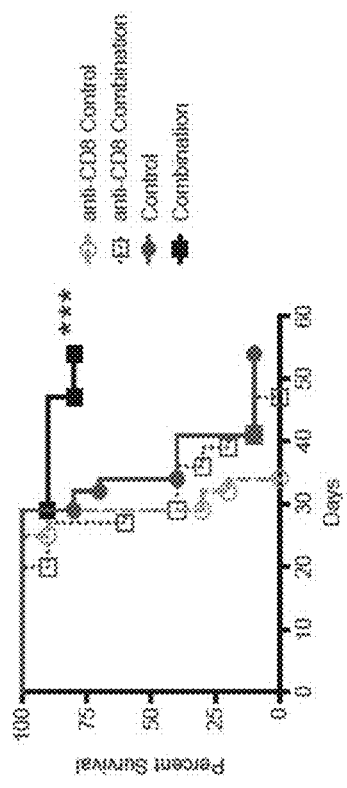
FIG. 21C shows representative graphs showing survival of mice harboring CCK168 tumors following ADWA11/anti-PD-1 combination therapy, pretreated one day earlier with either anti-CD8 depleting antibody or isotype control antibody. Data reported as percent survival, n=10 in each group. **p<0.01 by log-rank Mantel-Cox test.

The Beneficial Synergistic Effects of Combined ADWA11 and Anti-PD1 Therapy were Abrogated by CD8+ T Cell Depletion Since the most dramatic effects of ADWA11 therapy were observed on CD8+ T cells, herein it was sought to determine whether these cells drove the anti-tumor effects of ADWA11. CCK168 tumor-bearing mice were depleted of cytotoxic T cells using an anti-CD-8a (Bio X Cell® BE0004-1 Clone 53-6.72) antibody or control antibody at a dose of 10 mg/Kg was injected intraperitoneally 24 hours prior to each administration of therapeutic drugs, commencing at day 0. Combined ADWA11 (10 mg/Kg) and anti-PD1 (10 mg/Kg) were injected on days 1, 5, and 9. Immunostaining according to the methods described herein showed effective CD8 depletion (FIG. 21A), which completely abrogated the beneficial effects (e.g., survival and tumor regression) of combination therapy with ADWA11 and anti-PD1 (FIGS. 21B-21C).

These data suggest that CD8+ T cells are important in anti-avb8, e.g., ADWA11, mediated anti-tumor effects.

pSmad3, a Marker of Active TGFβ Signaling, is Present in CCK168 Tumor Cells and Cells of the Tumor Microenvironment, and Signaling is Broadly Inhibited by Treatment with ADWA11

Figure 22B:
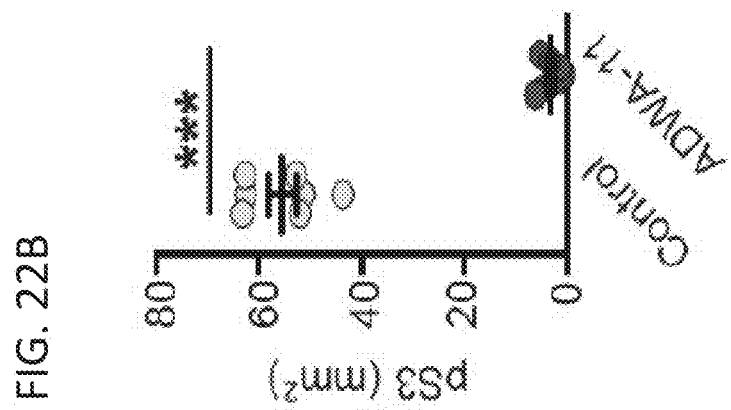
FIG. 22B shows representative graphs depicting quantification of pSmad3 (pS3) staining density in control and ADWA11 treated mice. ADWA11 treatment decreased pSmad3 density in CCK168 tumors.
Figure 22A:
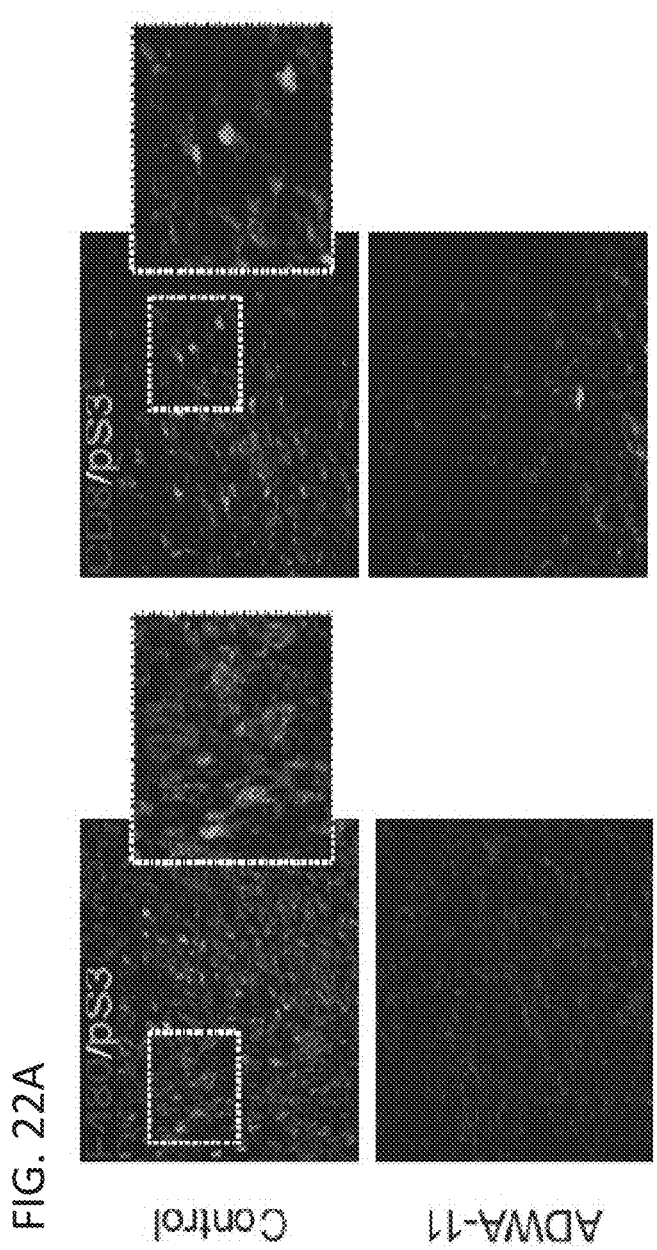
FIG. 22A shows representative graphs showing CCK168 tumors harvested from mice treated with either ADWA-11 or control antibody, and stained with antibodies to, CD8, F4/80 to detect macrophages and phospho-SMAD3 to detect TGFβ signaling (pS3). Low power merged images and images showing only pSMAD3 are shown to the left and enlarged merged images and images for each single antibody from boxed areas are shown to the right.

Because the best characterized in vivo function of αvβ8 integrin is local activation of latent TGFβ, it was sought to determine which cells in untreated tumors showed evidence of TGFβ signaling and whether this signaling would be inhibited or suppressed by ADWA11 therapy. To identify cell types within CCK168 tumors that are actively signaling from TGFβ receptors, immunostaining was used with an antibody to phosphorylated SMAD3, a proximal step in TGFβ signaling, as evidence that cells (CD8+ T cells, F4/80 macrophages and CD11c dendritic cells) were responding to active TGFβ. The CCK168 tumors examined had a rich network of macrophages (FIG. 22A) throughout the tumors and only small numbers of intercalated DCs. pSMAD3 was readily detected within the tumors, usually in cells adjacent to F4/80+ macrophages, but was not detected in macrophages themselves. CD8+ T cells were sparse in untreated mice and were substantially more abundant in tumors from mice treated with AWDA-11. pSMAD3 staining was not observed in these cells. In untreated tumors, high levels of pSMAD3 were seen throughout the tumor microenvironment; however, pSMAD3 staining was broadly inhibited by treatment with ADWA11 (FIG. 22A). Thus, without wishing to be bound by any particular theory, these data indicate that in some embodiments, αvβ8 activity is essential for TGFβ activation in these tumors, but that the effects of TGFβ, when activated by αvβ8, on CD8+ T cell accumulation, Granzyme B expression and macrophage subset distribution are indirect or occur outside the tumor microenvironment.

Effectorless ADWA11 Inhibits Tumor Growth, Improves Overall Survival and Induces Persistent Anti-Tumor Immunity in CCK168 Squamous Cell Carcinoma Model and CT-26 Carcinomas Initial studies were performed using a native murine antibody that could interact with Fc receptors. It was therefore possible that the anti-tumor effects of ADWA11 could be due to antibody-dependent-cellular-cytotoxicity (ADCC) of tumor cells or tumor infiltrating macrophages or dendritic cells. To determine the effect of ADCC on ADWA11 activity, a recombinant, Fc "effectorless" version of ADWA11 was generated, termed ADWA11_4mut, by introducing 4 substitutions into the IgG1 Fc domain of the mouse antibody to abrogate effector function. These substitutions had previously been shown to completely abrogate antibody binding to Fc receptors (Alegre et al., J. Immunol. 148: 3461-3468, 1992; Hezareh et al., J. Virol. 75: 12161-12168, 2001). The ADWA11_4mut was as effective as the wild type antibody in the CCK168 model (FIG. 28). In addition, the ADWA11_4mut antibody was tested for efficacy in two syngeneic tumor models (i.e., the CT26 and EMT6 tumor models).

CT-26 cells were chosen, in addition to CCK168, since the former completely lack detectable αvβ8 expression (FIG. 18B). CT-26 mouse colon carcinoma cells (ATCC® CRL-2638™) were injected at a dosage of $4\times10^5$ cells/mouse into the subcutaneous flank of female Balb/c mice (Charles River Labs). Tumors were allowed to grow to 50-100 mm³ in size for inclusion in the study. For these studies, ADWA11_4mut or isotype control 2B8_mIgG_4mut were injected on days 0, 4, 8, 12, anti-PD1 antibody (RMP1-14, BioXcell) or isotype control 2A3_rat IgG (BioXcell) were injected intravenously on days 0, 4, 8. All antibodies were dosed at 10 mg/Kg. On Day 5, all mice except the no radiation treatment control group, were exposed to tumor targeted 5 Gy dose of radiation. Tumor growth was measured twice per week with digital calipers and reported as volume (length×width×width×0.5). For the re-challenge experiment, on day 51 (post first antibody treatment) mice with a complete response and naïve mice were implanted on the contralateral flank with $2.5\times10^5$ CT26 cells in PBS and tumor growth was monitored as described above.

In both models, the ADWA11_mut4 was effective in driving an anti-tumor response (FIG. 28), demonstrating that ADCC function was not required for the ADWA11-mediated anti-tumor effect.

ADWA11 is Efficacious in Multiple Carcinoma Models and Enhances the Effects of Radiation Therapy and Anti-PD-1, Anti-CTLA-4 and 4-1BB Therapy The efficacy of ADWA11 in other solid tumor models and whether ADWA11 could more broadly enhance the beneficial effects of additional immunomodulatory therapies were determined. The ability of ADWA11 to enhance the effects of radiation therapy on CT-26 carcinomas was also examined, since this tumor had previously been shown to be radiosensitive, does not express αvβ8 either in vitro or in vivo, and has been shown to be responsive to a TGFB receptor small molecule inhibitor (Young et al., PloS One 11:e0157164, 2016). Using radiation doses that were only minimally effective as therapy, addition of either ADWA11_4mut or anti-PD-1 significantly increased tumor regression and overall survival of mice, with 5/9 and 3/10 complete responders, respectively (FIGS. 29A and 29B). Interestingly, the addition of anti-PD1 to ADWA11 added little additional benefit in this model, providing further evidence that inhibition of αvβ8 can be effective even in the absence of checkpoint inhibitors. The surviving mice which showed complete regression of primary tumors and that received either monotherapy or combination therapy were re-challenged on the contralateral side with the same CT-26 tumor cells at least 51 days after initial therapy. Minimal tumor growth was observed with the contralateral tumors in a few mice. The small tumors that did initially grow all subsequently showed complete regression, indicating that in some embodiments, successful treatment with ADWA11 can lead to long-term anti-tumor immunity, as has been previously described for other immunomodulators (Ascierto et al., J. Transl. Med. 15:205, 2017) (FIG. 29C). None of the primary tumors that were regressed showed re-growth.

ADWA11_4Mut is Efficacious in the EMT6 Breast Carcinoma Model and Enhances the Effects of Anti-CTLA-4 and Anti-4-1BB.

The EMT-6 model of breast carcinoma with an immune excluded tumor microenvironment and low levels of αvβ8 expression was used to examine the effects of anti-PD-1, anti-CTLA-4 (which has recently been shown to work through a different molecular mechanism than anti-PD1 (Wei et al., Cell 170:1120-1133, 2017), or an agonist of 4-1BB, a costimulatory receptor expressed on CD8+ T cells (Kang et al., Cancer Res. 2017) in combination with ADWA11_4mut.

ADWA11_4mut was also tested in the EMT-6 tumor model. $1 \times 10^6$ EMT6 cells (mouse epithelial mammary carcinoma cell line; ATCC®, CRL2755™) were injected into the fourth mammary fad pad of female Balb/c mice (Charles River Labs). Tumors were allowed to grow up to 50-100 mm$^3$ in size. Mice were randomized into antibody treatment groups and operators were blinded to treatment groups. ADWA11_4mut 10 mg/kg or control 2B8_mIgG4mut 10 mg/kg, anti-CTLA4 (9D9 BioXcell) or isotype control E.tenella-mIgG2b 10 mg/kg were injected on days 0, 4 and 8, and anti-4-1BB (MAB9371, R&D systems) 1 mg/kg was injected on days 0 and 4 through an intravenous route. Tumor growth was measured twice per week with digital calipers and reported as volume (length×width×width×0.5).

Anti-PD1, anti-CTLA4 or anti-41-BB monotherapy showed significant initial tumor regression, however only one mouse treated with anti-4-1BB and one treated with anti-PD1 had complete regression (FIG. 30A-D). In contrast, approximately 70% of mice treated with ADWA11 in combination with either anti-PD-1, anti-CTLA4 or anti-4-1BB had complete regression, long-term survival and resistance to EMT6 tumor cell re-challenge suggestive of long-term tumor immunity (FIG. 30E). For the re-challenge experiment, on day 51 (post first antibody treatment) mice with a complete response and naïve mice were implanted in the contralateral fat pad with $1 \times 10^6$ EMT-6 cells and tumor growth was monitored as described above.

These data demonstrate for the first time that ADWA11 antibodies, including ADWA11 2.4, provide a synergistic therapeutic effect when combined with an inhibitor of PD-1 or CTLA4 (e.g., an antagonist antibody that binds to PD-1 or CTLA-4 and thereby inhibits the effect of PD-1 or CTLA-4, respectively) and/or an agonist of 4-1BB (e.g., an agonist antibody that increases the biological activity of 4-1BB). These data suggest that ADWA11 2.4 is a potential human therapeutic that can provide a synergistic therapeutic anti-tumor response when combined with an inhibitor of, e.g., PD-1 or CTLA4, or an agonist of, e.g., 4-1BB.

Integrin αvβ8 Gene Expression and Staining in Human Tumors

Figure 23A:
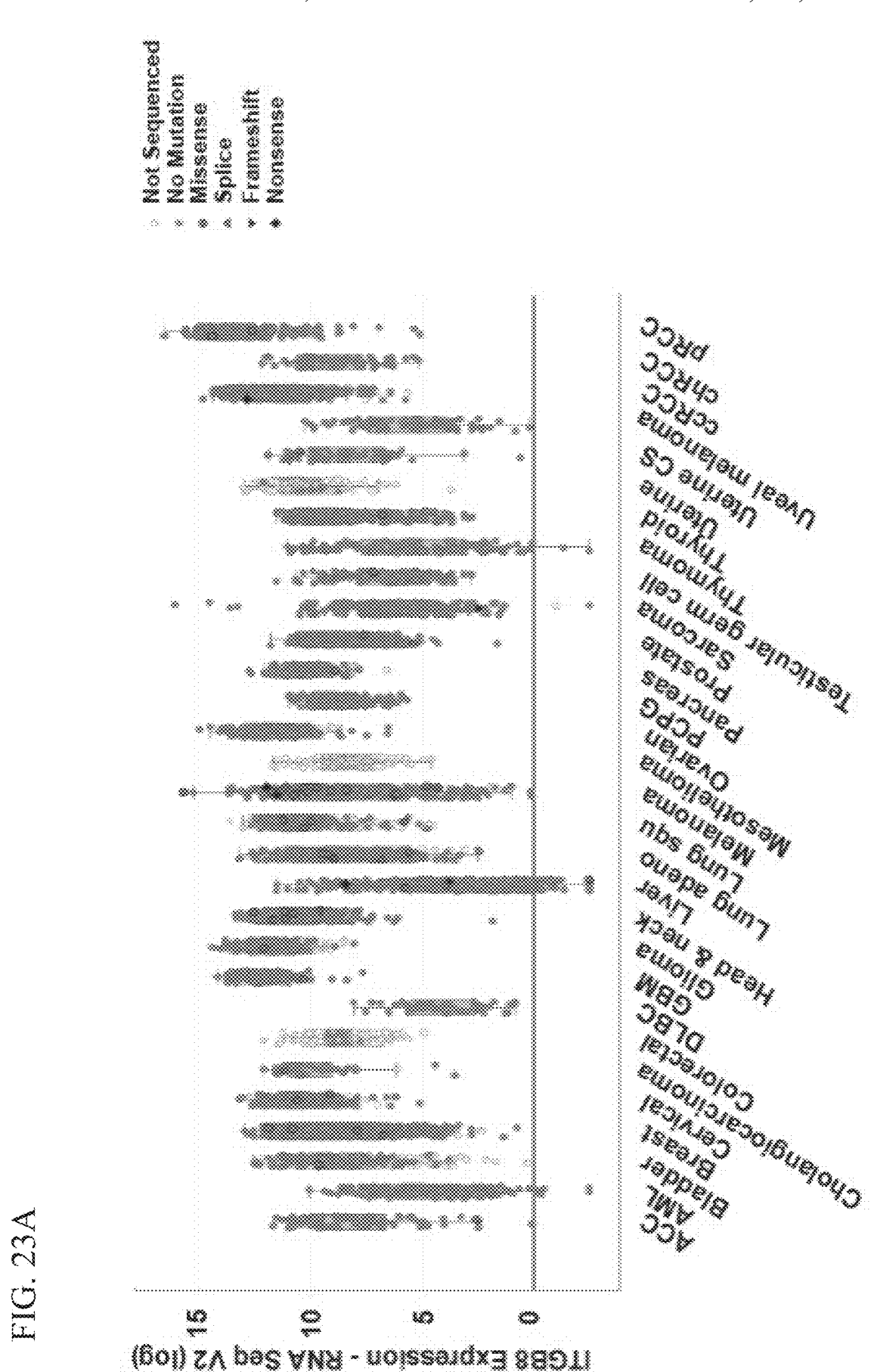
FIG. 23A shows representative graphs setting forth data extracted from The Cancer Genome Atlas (TCGA) for integrin-β8 mRNA expression in 30 different human cancers. Each dot represents an individual tumor sample. The results shown in this figure are based upon data generated by the TCGA Research Network.
Figure 23B:
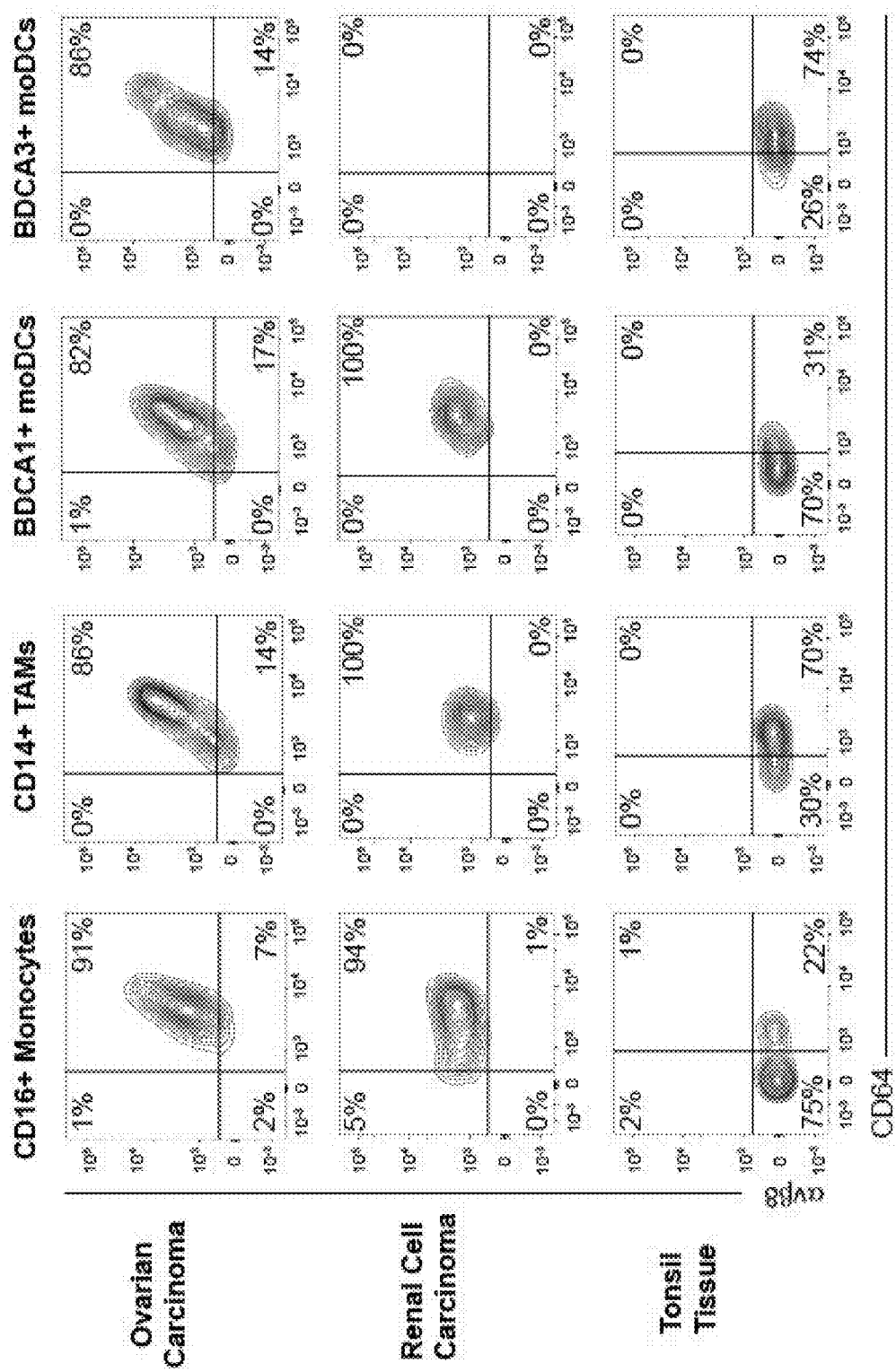
FIG. 23B shows representative graphs showing flow cytometry data of disaggregated cells from fresh, de-identified ovarian carcinoma and renal cell carcinomas gated for mature monocytes (CD16+ monocytes), tumor associated macrophages (CD14+ macrophages), two monocyte derived dendritic cell populations (BCDA1+ moDCs and BCDA3+ moDCs) or eosinophils and stained for expression of αvβ8. Tissues from normal tonsils were also analyzed as a control. Gating strategy is shown in FIG. 23C; n=2 for each tumor type.
Figure 23C:
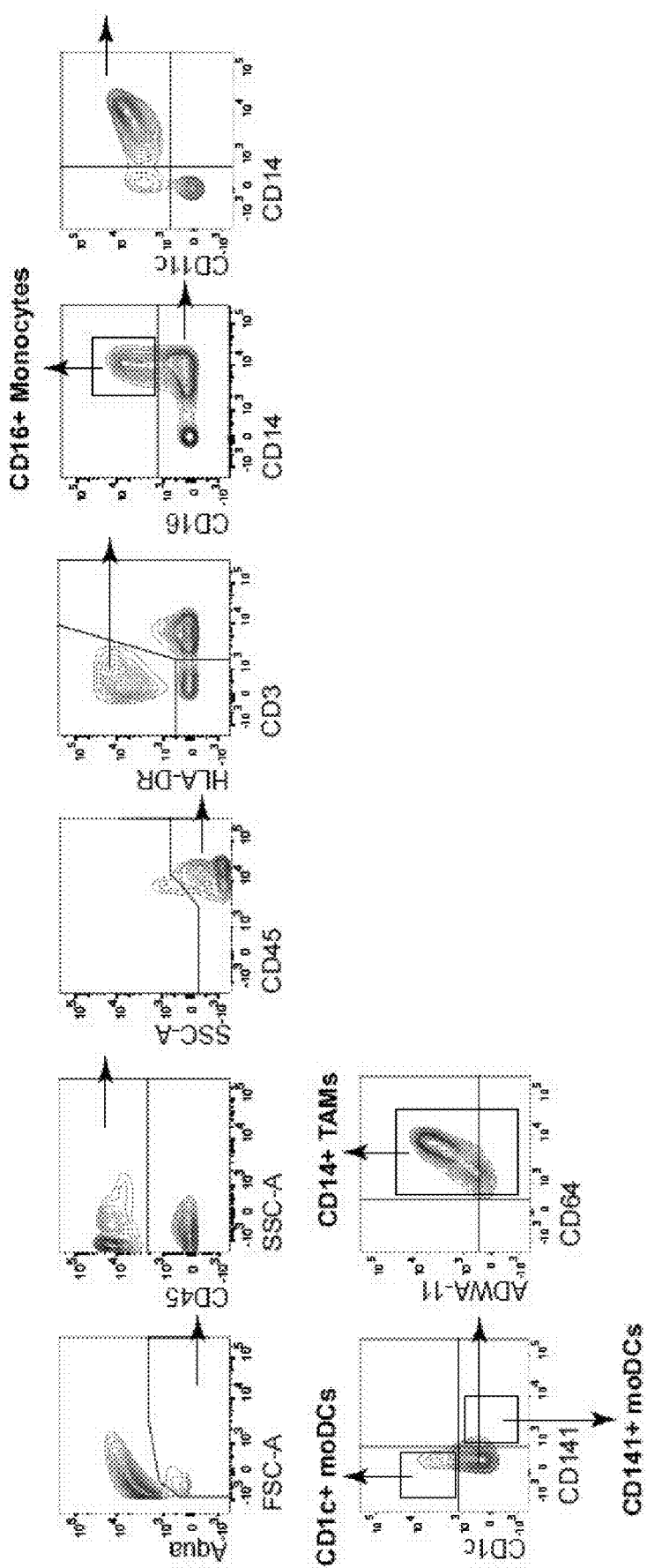
FIG. 23C are representative graphs showing the gating strategy for human tumor biopsy samples. Live single CD45+ cells were gated for SSC-A(hi) to remove granulocytes. SSC-A(lo) was gated for HLA-DR+CD3− and stained with CD14 and CD16. CD14+CD16+ were designated CD16+ monocytes. CD16− cells were further stained for CD11c. CD14+CD11c+ cells were further stained with CD1c and CD141. CD1c+CD141− were designated CD1c+ MoDC. CD141+CD1c− were designated CD141+ MoDC. CD1c−CD141− cells were further stained with CD64 and CD64+ population were designated CD14+TAMs.
Figure 24A:
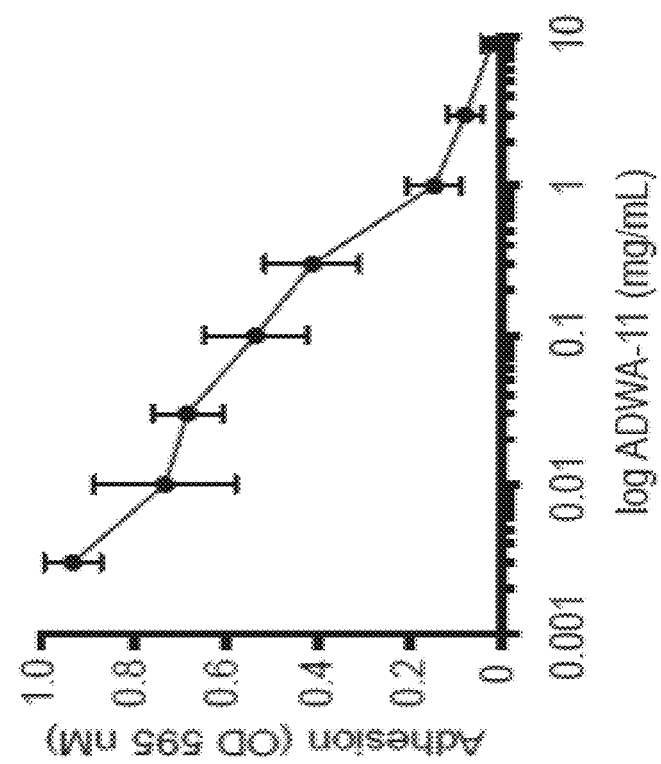
FIG. 24A shows a representative graph showing the results of a TMLC cell co-culture bioassays performed with concentrations of ADWA11 ranging from 0.01 to 10 mg/ml. TGFβ activity is reported as relative luciferase units based on PAI-1 luciferase reporter activity. n=3 per ADWA11 dose, repeated 3 times.
Figure 24B:
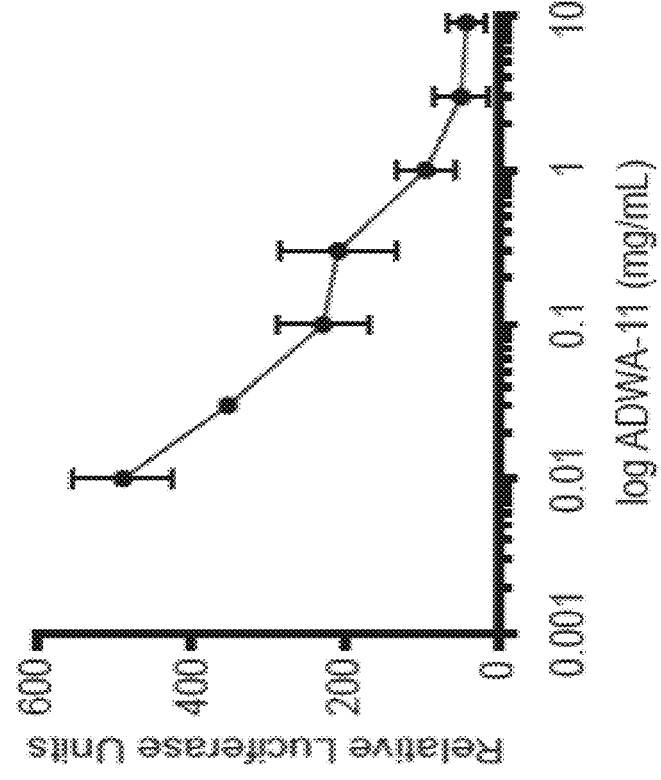
FIG. 24B shows a representative graph showing the results of a cell adhesion assays performed on dishes coated with the latency associated peptide (LAP) of TGFβ1 in the presence of ADWA-11 in concentrations from 0.001 to 10 mg/ml. Adherent cells were stained with crystal violet and adhesion expressed as absorbance at 595 nm. n=3 per ADWA11 dose, repeated 3 times.
Figure 24C:
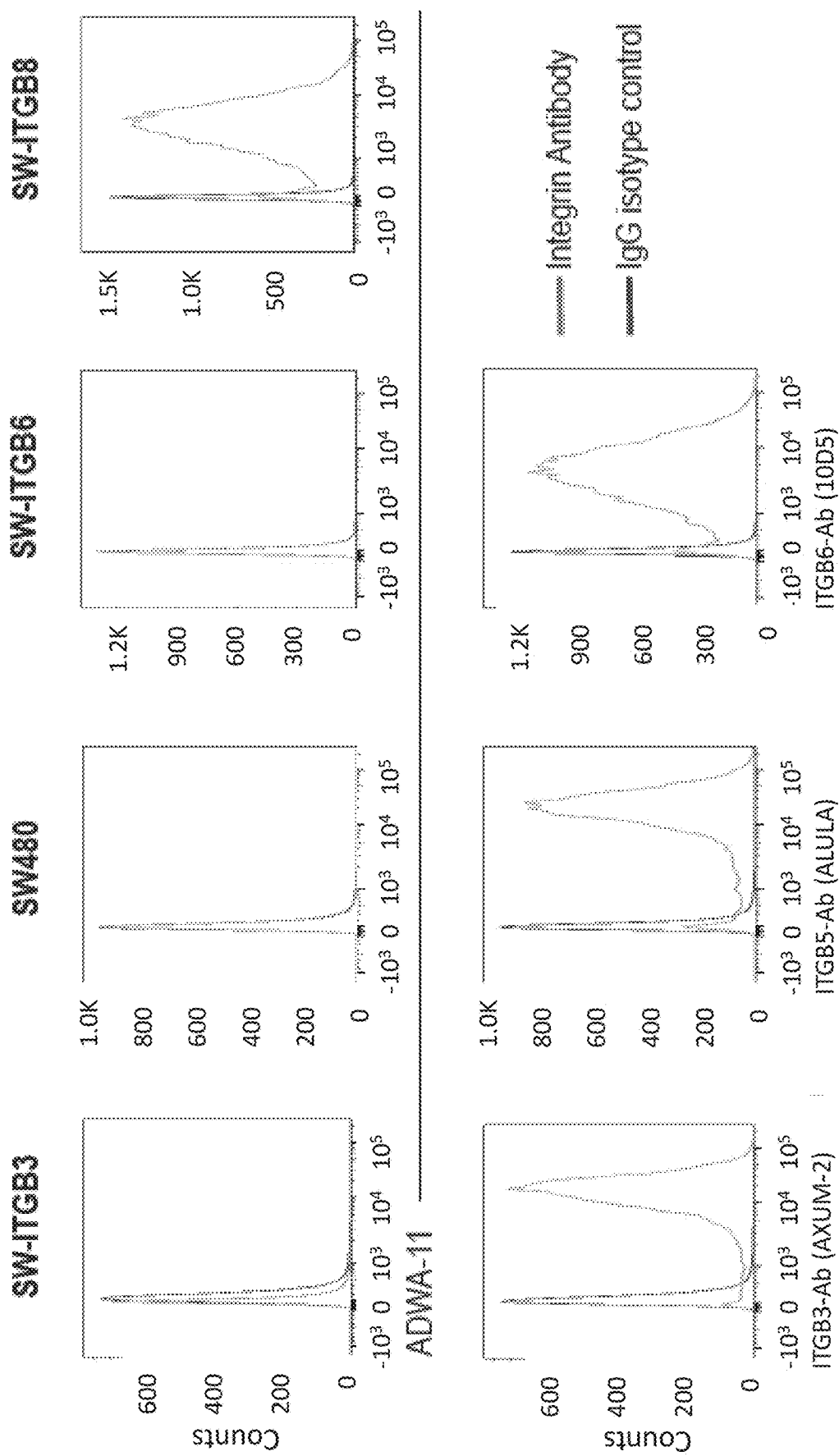
FIG. 24C depicts representative graphs showing that antibodies to integrin αvβ3, αvβ5, αvβ6, and αvβ8 were used for flow cytometry of wild type colon carcinoma cells, SW-480, that do not express any of these integrins or SW-480 cells transfected to express 03 (SW-itgb3), β6 (SW-itgb6), or β8 (SW-itgb8). Representative flow cytometry plots are shown for each antibody and cell type tested.

Interrogation of The Cancer Genome Atlas (TCGA) for ITGB8 mRNA expression revealed that nearly all human tumors, of the thirty tumor types examined, express detectable robust levels of ITGB8 mRNA, with the highest levels of expression detected in ovarian and renal cell carcinomas (FIG. 23A). ITGB8 expression in whole tumor lysates might reflect expression of αvβ8 on infiltrating immune cells. To test this, multi-panel flow cytometry was performed to assess expression of αvβ8 protein in single cells in specimens of freshly harvested and disaggregated human tumor resections and biopsies. Analysis of two human ovarian carcinomas and two renal cell carcinomas showed substantial αvβ8 expressed on CD16+ monocytes, CD14+ tumor associated macrophages and BCDA1+ and BCDA3+ monocyte-derived dendritic cells (FIG. 23B).

Discussion

As will be appreciated by one of ordinary skill in the art, ADWA11 is a monoclonal antibody specific for blocking αvβ8 integrin and is an effective anti-tumor immunotherapy when used alone. For example, ADWA11 demonstrated anti-tumor activity in a CCK168 cutaneous squamous cell carcinoma. Additionally or alternatively, ADWA11 in combination with an immunomodulator (e.g., anti-PD-1, anti-CTLA-4, and anti-4-1BB) or with radiotherapy demonstrated a powerful and synergistic enhanced anti-tumor activity in three syngeneic allograft models of epithelial carcinomas on three different mouse strains backgrounds. In some embodiments, inhibition of αvβ8 increased the number of CD8+ T cells in tumors and their cytotoxic differentiation, as assessed by expression of Granzyme B in these cells. Depletion of CD8+ T cells abrogated the anti-tumor effects of ADWA11 and anti-PD1 treatment, indicating that in some embodiments, enhanced tumor cell killing by CD8 T cells is critical for the efficacy of ADWA11. In addition to the effects on CD8+ T cells, ADWA11 increased the number of immunostimulatory monocytes in the tumor microenvironment (Franklin et al., Science 344:921-925, 2014; Movahedi et al., Cancer Res. 70:5728-5739, 2010; Ostuni, Trends Immunol. 36: 229-239, 2015; Noy et al., Immunity 41:49-61, 2014). Although there was no difference in the number of immunosuppressive macrophages, these macrophages, along with dendritic cells, expressed high levels of detectable αvβ8. Although the first tumor line tested, CCK168 cells, expressed significant surface levels of αvβ8 in vitro, little expression of αvβ8 was found by flow cytometry on non-hematopoietic cells from harvested tumors, indicating that in some embodiments, expression is lost when these malignant cells form tumors in vivo. Nevertheless, the possibility that the anti-tumor effects of ADWA11 were due to targeting of the malignant cell directly via ADCC, was excluded by replicating the findings using a recombinant, effectorless ADWA11 antibody in cells that do not express any detectable αvβ8 (i.e., CT-26 colon carcinoma cells). The effectorless antibody was able to suppress tumor growth in three tumor models, CCK168, CT-26 and EMT-6, of which CT-26 has undetectable expression of αvβ8. Furthermore, short-term therapy with ADWA11 led to long-term tumor suppression and resistance to subsequent re-challenge, indicating, in some embodiments, the induction of long-term anti-tumor immunity. Together, these data indicate that in some embodiments integrin αvβ8 blockade causes tumor suppression by blocking αvβ8 on innate immune cells or T regulatory cells to enhance adaptive immunity to tumors.

TGFβ activation by αvβ8 expressed on dendritic cells, regulatory T cells, fibroblasts, airway epithelial cells and neuroepithelium, has been shown previously (Travis et al., Nature 449:361-365, 2007; Melton et al., J. Clin. Invest. 120:4436-4444, 2010; Arnold et al., J. Neurosci. 32(4):1197-1206, 2012; Fenton et al., Mucosal Immunol. 10:624-634, 2017; Mu et al., J. Cell Biol. 157:493-507, 2002; Proctor et al., J. Neurosci. 25:9940-9948, 2005; Edwards et al., J. Immunol. 193:2843-2849, 2014), but defining the full range of integrin αvβ8 expression has been limited by the absence of reliable reagents for tissue staining. In the Examples set forth herein, newly developed antibodies capable of detecting integrin αvβ8 by flow cytometry were used to demonstrate that tumor associated macrophages and dendritic cells are the major cell types showing high cell surface staining for αvβ8 in murine carcinomas. This indicates that in some embodiments, expression on one or more of these cell types is important for αvβ8-mediated suppression of local anti-tumor immunity.

In the Examples set forth herein, αvβ8 expression on T cells, including regulatory T cells (Tregs), was not detected.

Activation of TGFβ by integrins, including αvβ8, is tightly spatially restricted, allowing αvβ8-expressing cells to present TGFβ locally to cells they directly contact (Travis et al., Nature 449:361-365, 2007; Munger et al., Cell 96:319-328, 1999). TGFβ has been described to suppress the activity of effector T cells. As demonstrated in the Examples set forth herein, CD8+ T cells are increased in ADWA11 treated tumors, are more likely to express Granzyme B, and are important for mediating the protective effects of ADWA11. In some embodiments, the suppressive effects of αvβ8 on innate immune cells is due to direct presentation of active TGFβ to CD8 T cells. However, immunostaining for pSMAD3 did not reveal evidence of TGFβ signaling in CD8+ T cells, but showed robust signaling in non-hematopoietic cells (e.g. tumor cells). Thus, in some embodiments, tumor cells and some other tumor associated non-hematopoietic cells (e.g., fibroblasts) are the functionally important cells that respond to TGFβ activated by αvβ8 and suppress local tumor immunity.

As described in the Examples set forth herein, αvβ8 integrin is broadly expressed on monocytes, macrophages and dendritic cells in multiple murine and human tumors and is a potent modulator of the anti-tumor immune response. Monotherapy (e.g., ADWA11) targeting this integrin is effective in some tumors. Furthermore, efficacy is synergistically enhanced by combining inhibition of αvβ8 (e.g., treatment with ADWA11) with either checkpoint inhibitors (e.g., anti-PD1 or anti-CTLA4) or an immune activator (e.g., anti-4-1BB) or by combining αvβ8 monotherapy with radiotherapy. Taken together, these results identify the αvβ8 integrin as a novel target for tumor immunotherapy.

Example 15: Further In Vivo Assessment of ADWA11 2.4

Summary of Tumor Models for Anti-αvβ8 Evaluation

In vivo efficacy was assessed using syngeneic tumor models in immunocompetent mice. Efficacy studies were performed with an effectorless version of the parental mouse hybridoma antibody ADWA11_4mut due to a strong anti-species drug response that limited exposure with ADWA11 2.4 which is humanized.

TABLE 9

Tumor models for anti-αvβ8 evaluation

| Model | Tumor microenvironment | Expression of αV integrins | TGFp pathway status |
|---|---|---|---|
| EMT6, breast cancer | Immune excluded tumor microenvironment model | Expresses both αvβ8 and αvβ6 | High TGFp pathway activation gene expression profile |
| CT26, colon cancer | Preexisting immune model | Does not express αvβ8 or αvβ6 | Low TGFp pathway activation gene expression profile |

Efficacy in the EMT6 Model

The EMT6 tumor model studies were conducted orthotopically ($4^{th}$ mammary fat pad) and treatment with anti-αvβ8 with or without checkpoint inhibitors was performed concurrently.

Charles River Balb/c mice (n=10 per group) were implanted with $3\times10^5$ or $1\times10^6$ EMT6 cells/mouse. Treatment was initiated at an average tumor volume of 50 mm$^3$, or 100 mm$^3$.

The murine parental anti-αvβ8 antibody ADWA11_4mut was dosed at 10 mg/kg once every four days for a total of three doses in all studies. Anti-PD1 antibody (clone RMP1-14, BioXcell) was dosed at 10 mg/kg once every four days for a total of three doses, 4-1BB agonist mAb (Clone MAB9371, R&D systems) was dosed at 1 mg/kg once every four days for a total of two doses, and anti-CTLA4 (Clone 9D9, BioXcell) was dosed at 10 mg/kg once every four days for a total of three doses.

Anti-αvβ8 monotherapy efficacy of ~50% tumor growth inhibition (TGI) (Day 10-20) was observed when $3\times10^5$ cells were implanted and treatment was initiated at 50 mm$^3$. However when $1\times10^6$ cells were implanted and treatment was initiated at 100 mm$^3$ anti-αvβ8 monotherapy TGI was not observed. The difference in anti-αvβ8 monotherapy TGI between the two studies is unclear; however, without wishing to be bound by any particular theory, the rapid tumor growth rate of this model when $1\times10^6$ cells were implanted could have limited the response or out competed the anti-tumor response of αvβ8-blockade. Importantly, anti-αvβ8 demonstrates a significant synergistic treatment effect with anti-PD1 (7/10 complete responses), 4-1BB agonist (5 complete responses), and anti-CTLA4 (6 complete responses), and resulted in an increased survival as compared to monotherapy and isotype control groups. Therefore, these data suggest that ADWA11 antibodies can provide an anti-tumor response in the EMT-6 tumor model.

Anti-CTLA4 or 4-1BB agonist monotherapy demonstrated significant response (~50% TGI, Day 8-20); however, the response was transient and tumors ultimately outgrew the response. To demonstrate that the combination treatments resulted in a cellular response to the EMT6 tumor, as compared to an anti-angiogenesis or anti-proliferative response, the mice with a complete response were re-challenged on Day 51 (after $1^{st}$ dose) with a second EMT6 tumor implant but without additional drug treatment. EMT6 tumors grew rapidly in naïve mice but were rapidly cleared in the complete responding mice, indicating in some embodiments, the development of cellular immunity to the tumor cells, e.g., direct tumor cell death, is not mediated by anti-angiogenesis or anti-proliferation.

Quantification of Lymphocyte Abundance in the EMT6 Tumor Model

To investigate the impact of anti-αvβ8 treatment on the EMT6 tumor microenvironment, the abundance of lymphocyte subsets was quantified by IHC. Briefly, Charles River Balb/c mice (n=10 per group) were implanted with 1×10$^6$ EMT6 cells and treatment was initiated at an average tumor volume of 100 mm$^3$ (Day 0). Anti-αvβ8 ADWA11 2.4 antibody was dosed at 10 mg/kg every three days (e.g., Day 0, Day 3, Day 6, and Day 9) for a total of four doses, and tumors were harvested on Day 11 (48 hours after the 4$^{th}$ dose).

Immunohistochemical (IHC) analysis of the density of CD45 (total lymphocytes and myeloid cells), CD3 (total T cells), CD4 T cells, CD8 T cells, and Granzyme B (activated CD8 and NK cells) staining demonstrated that anti-αvβ8 monotherapy increased the abundance of the total CD45, CD4 T cell, CD8 T cells, and very significantly increased the density of Granzyme B expressing cells (n=10 for each group) (FIG. 15). The IHC data indicated that in some embodiments, ADWA11 2.4 monotherapy is sufficient to change the tumor microenvironment, consistent with the expected mechanism of action (MOA) of αvβ8.

Efficacy in the CT26 Model

The CT26 model was selected based on the absence of αvβ8 expression, partial response to anti-PD1 therapy, and evidence in the literature for a synergistic TGI of a TGFβ small molecule inhibitor with suboptimal dose of radiation. Radiation therapy (RT) is of particular interest due to its ability to induce immunological cell death and de novo DC-T cell priming, where αvβ8 potentially plays an important role in shaping T-cell differentiation and activation. Briefly, Charles River Balb/c mice (n=10 for each group) were subcutaneously implanted with 4e5 cells and treatment was initiated at an average tumor volume of 100 mm$^3$.

The murine anti-αvβ8 effector null antibody ADWA11_4mut was dosed at 10 mg/kg Q4D×4, anti-PD1 (clone RMP1-14, BioXcell) was dosed at 10 mg/kg Q4D×3, and a 5Gy dose of tumor targeted radiation was performed 5 days after the first dose of mAbs. Including anti-αvβ8 with RT resulted in a significant increase in TGI with 5/9 mice showing a complete response. Including anti-PD1 with RT resulted a less significant TGI as compared to anti-αvβ8, with 3/10 mice demonstrating a complete response. The triple combination of RT, anti-αvβ8, and anti-PD1 resulted in a very significant TGI with 7/10 mice with a complete response. Similar to the EMT6 study, the mice with a complete response were immune to re-challenge with CT26 cells.

Immunophenotyping of the CT26 Tumor Infiltrating Cell Population

To investigate the impact of anti-αvβ8 treatment on the CT26 tumor microenvironment the abundance of lymphocyte subsets was quantified by flow cytometry. Briefly, Charles River Balb/c mice (n=6 for each group) subcutaneously implanted with 4e5 cells and treatment was initiated at an average tumor volume of 100 mm$^3$. Anti-αvβ8 ADWA11 2.4 was dosed at 10 mg/kg or 1 mg/kg Q3D×3, and tumors were harvested on Day 8 (48 hours after the 3$^{rd}$ dose). Tumors were dissociated and the lymphocyte population was quantified by CyTOF cytometry. Anti-αvβ8 (10 and 1 mg/kg) increased the abundance of CD8 T cells in the CD3 T cell gate. Additionally, the CD8 cells more frequently expressed Granzyme B, a marker of an activated phenotype.

Summary

Taken together, the EMT6 and CT26 efficacy and PD studies demonstrate: (1) that anti-αvβ8 synergistically increases the response to multiple checkpoint inhibitors; (2) that anti-αvβ8 efficacy is not dependent upon expression of αvβ8 by the tumor cell; and (3) that anti-αvβ8 ADWA11 2.4 monotherapy is sufficient to increase the abundance of CD8+ GzmB+ Tcell in a tumor microenvironment.

Example 16: ADWA11 2.4 Pharmacokinetics in Human FcRn Transgenic (TG32) Mice

The TG32 mouse model has been shown to be as good as monkey models for predicting human pharmacokinetics of IgG1 and IgG2 mAbs that exhibit linear pharmacokinetics. Pharmacokinetics of ADWA11 2.4 was assessed in TG32 mice following a single IV bolus dose administered at 0.1, 0.3, or 3 mg/kg. Serum drug concentrations were then measured. As shown in FIG. 25A and FIG. 25B, a clear trend of a dose-dependent decrease in antibody clearance was observed. This is typical for monoclonal antibodies that interact with cell surface targets and indicated that the target receptor, αvβ8, can act as a clearance mechanism. Consequently, two separate pharmacokinetic models were used to describe the linear (typical FcRn mediated antibody clearance mechanism) vs. non-linear (αvβ8-mediated) clearance pathways. For estimation of parameters for the linear clearance, a two-compartment population pharmacokinetic model was used to fit the 3 mg/kg data alone (FIG. 25A). For estimation of pharmacokinetic parameters for the non-linear clearance across multiple doses, a two-compartment saturable model (Michaelis Menten) was used to fit all the data (0.1, 0.3, 3 mg/kg) (FIG. 25B). The estimated linear and non-linear pharmacokinetic parameters are shown in Tables 10 and 11, respectively. The linear pharmacokinetic parameters are within the range observed for typical mAb in TG32 mice.

TABLE 10

Two-compartment pharmacokinetic parameters in TG32 mice (IV at 3 mg/kg)

| Parameter | Estimate | % CV |
| --- | --- | --- |
| CL (mL/h/kg) | 0.33 | 9.2 |
| CLD (mL/h/kg) | 2.3 | 13 |
| V1 (mL/kg) | 49 | 2.4 |
| V2 (mL/kg) | 38 | 9.6 |
| t½(day) | 7.6 | |

CL: clearance from central compartment; CLD: inter-compartmental distribution clearance; VI: volume of distribution for the central compartment; V2: volume of distribution for the peripheral compartment; t½, terminal half-life calculated based on estimated parameters.

TABLE 11

Two-compartment non-linear pharmacokinetic parameters in TG32 mice (IV at 0.1, 0.3, and 3 mg/kg)

| Parameter | Estimate | % CV |
| --- | --- | --- |
| Km (ng/mL) | 1659 | 25 |
| Vmax (ng/h/kg) | 6596 | 5 |
| CLD (mL/h/kg) | 3.4 | 20 |
| V1 (mL/kg) | 49 | 4 |
| V2 (mL/kg) | 48 | 8 |

Vmax: maximal rate; Km: substrate concentration to achieve half maximal rate; CLD inter-compartmental distribution clearance; VI: volume of distribution for the central compartment; V2: volume of distribution for the peripheral compartment.

Consistent with the observed target mediated drug disposition (TMDD) based on serum pharmacokinetics, a dose-dependent decrease in drug distribution into multiple tissues (due to saturating target binding), especially kidney, were also observed in a tissue distribution study.

Example 17: Pharmacokinetics in Non-Human Primates (NHP)

Figure 26:
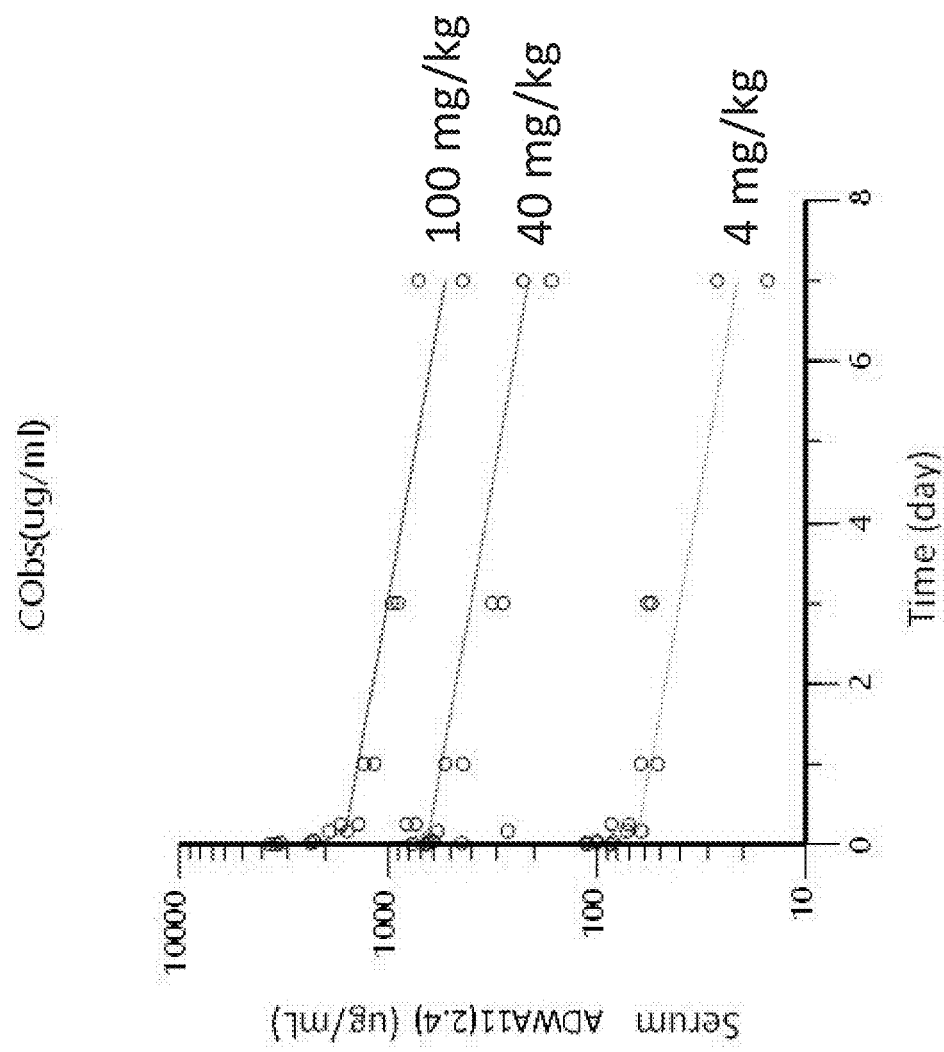
FIG. 26 shows representative graphs two-compartment pharmacokinetics of ADWA11 2.4 in cynomolgus monkeys following a single IV bolus administration at 4, 40, and 100 mg/kg, respectively. Circles: observed data. Lines: model fit.

Pharmacokinetics of ADWA11 2.4 was assessed in an NHP exploratory toxicology study following the first dose of a multiple dose administration study at 4, 40, or 100 mg/kg. As shown in FIG. 26, exposure of ADWA11 2.4 appears to be linear within this dose range, due to being above the saturating range for target mediated drug disposition (TMDD). A two-compartment linear model was used to fit the data (FIG. 26) and the estimated pharmacokinetics parameters were shown in Table 12. Whereas the observed CL and distribution volumes were within ranges for typical mAbs, the terminal $t_{1/2}$ appears to be on the short end of the range. Without wishing to be bound by any particular theory, this is likely due to the terminal phase not well defined as only sampled up to 7 days post dose (limit of ETS study design).

TABLE 12

Two-compartment pharmacokinetic parameters in NHP
(IV at 4, 40, and 100 mg/kg-first dose)

| Parameter | Estimate | % CV |
|---|---|---|
| CL (mL/h/kg) | 0.41 | 8.7 |
| CLD (mL/h/kg) | 15.9 | 25 |
| VI (mL/kg) | 35.6 | 12 |
| V2 (mL/kg) | 25.1 | 25 |
| t½ (day) | 4.3 | |

CL: clearance from central compartment; CLD: inter-compartmental distribution clearance; VI: volume of distribution for the central compartment; V2: volume of distribution for the peripheral compartment; t1/2, terminal half-life calculated based on estimated parameters.

Example 18: Pharmacokinetics of Murine Surrogate Antibody as Monotherapy, and when Co-Dosed with Anti-PD-1

Single dose pharmacokinetic data for the parental (mouse IgG) were not available, but exposures were measured at up to four time points in several efficacy studies and appear to be consistent across these studies. Exposures of the parental (mouse IgG) appear to be linear within the dose range investigated (1, 3, and 10 mg/kg), consistent with saturating TMDD as estimated in TG32 mice for the humanized antibody, ADWA11 2.4. A two compartment pharmacokinetic model was fitted to exposure data in the dose-response EMT6 tumor model study, estimating only CL while fixing the other parameters at the values reported above for humanized antibody in TG32 mouse. The estimated CL of the parental (mouse IgG) in these tumor bearing mice was 0.74 mL/hr/kg.

The exposure of the parental (mouse IgG) appears to be ~5-50× lower following repeated co-dosing study with anti-PD-1 antibody, compared to those dosed with murine surrogate antibody alone or co-dosed with control rat IgG 2A3. This phenomenon was observed in two separate studies using two different tumor models (CT26 and EMT6). The lower exposure is possibly due to increased ADA formation in the presence of anti-PD-1, as has been reported in PD-1 knockout mice (Nishimura H et al., 1998, International Immunol. 10(10): 1563-72). Increased ADA formation following anti-PD-1 antibody (Pembrolizumab) treatment has also been reported in the clinic.

Example 19: Human PK/Exposure Prediction

The human pharmacokinetic profile of ADW11 2.4 at doses saturating target mediated drug disposition (TMDD) was predicted by scaling linear pharmacokinetic parameters from TG32 mouse (Table 13). The projected linear human pharmacokinetic parameters are given in Table 13. In addition, a linear human CL of 0.12 mL/hr/kg was predicted based on the measured AC-SINS binding (Score=2, Section 2.4), using a platform PBPK model. A linear human CL of 0.086 mL/hr/kg was predicted by allometric scaling from NHP. These CL values are within 2× range to the prediction based on TG32 allometric scaling (0.15 mL/hr/kg), further supporting that at doses saturating TMDD, ADW11 2.4 will have a pharmacokinetic profile that is typical for monoclonal antibodies.

These results indicate that ADWA11 2.4 is a potential useful human therapeutic antibody.

TABLE 13

Projected human linear pharmacokinetic parameters for ADWA11 2.4

| Parameter | Scaling factor | Projected value |
|---|---|---|
| CL (mL/h/kg) | 0.9 | 0.15 |
| CLD (mL/h/kg) | 0.67 | 0.15 |
| VI (mL/kg) | 0.97 | 39 |
| V2 (mL/kg) | 0.93 | 21 |
| t½ (day) | NA | 12 |

CL: clearance from central compartment; CLD: inter-compartmental distribution clearance; VI: volume of distribution for the central compartment; V2: volume of distribution for the peripheral compartment; t1/2, terminal half-life calculated based on estimated parameters.

Additional single-dose ADWA11 (2.4) IV and SC PK and/or TK were characterized in male hFcRn TG32 mice (n=4 or 8/dose group and male cynomolgus monkeys (n=1/dose group) and the human pharmacokinetic parameters set forth previously herein were revised. More specifically, after single IV dosing (0.1, 0.3, and 3 mg/kg in TG32 mice and cynomolgus monkes), the PK of ADWA11 (2.4) was non-linear in both species with a trend of dose-dependent decrease in CL, consistent with saturable target-mediated drug disposition. At doses above saturable clearance, the PK of ADWA11 (2.4) is linear and consistent with a typical human IgG1 mAb. The mean PK and TK parameters after single SC dosing at 10 mg/kg, $T_{max}$ was observed at 240 hours post dose, and bioavailability was estimated to be approximately 100% based on comparison with dose-normalized $AUC_{inf}$ following single IV dosing at 3 mg/kg.

ADWA11 (2.4) is expected to be dose-dependent at lower doses than set forth previously elsewhere herein. That is, human PK of ADWA11 (2.4) was predicted based on allometric scaling of the cynomolgus monkey PK model that includes both linear and non-linear clearances. The revised predicted human PK parameters are as follows: 36 mL/kg for the volume of distribution for the central compartment, 33 mL/kg for volume of distribution for the peripheral compartment, 0.12 mL/kg/h for the clearance from central compartment (linear CL), 0.51 mL/kg/h for the inter-compartmental clearance, and the maximum rate of nonlinear elimination of 0.46 μg/mL/h and a Km of 0.42 μg/mL for the nonlinear clearance. This model predicts that the nonlinear clearance of ADWA11 (2.4) is likely to be saturated above 14 µg/mL plasma concentration with a predicted t½ of approximately 15 to 17 days.

Example 20: Pharmacokinetics-Pharmacodynamics Relationship and Prediction of Efficacious Human Dose In the absence of clear exposure-TGI responses in syngeneic mouse tumor models, the 10 mg/kg dose was considered the efficacious dose for estimation of an efficacious concentration. Using the pharmacokinetic model for the parental (mouse IgG), the average concentration ($C_{avg}$) was estimated to be 107 µg/mL at day 12 (4 days after the last dose in the study with Q4D×3 dosing at 10 mg/kg). Similar, though slightly higher, $C_{avg}$ values are estimated by calculating AUC using the linear trapezoid rule from the available exposure data.

Figure 27A:
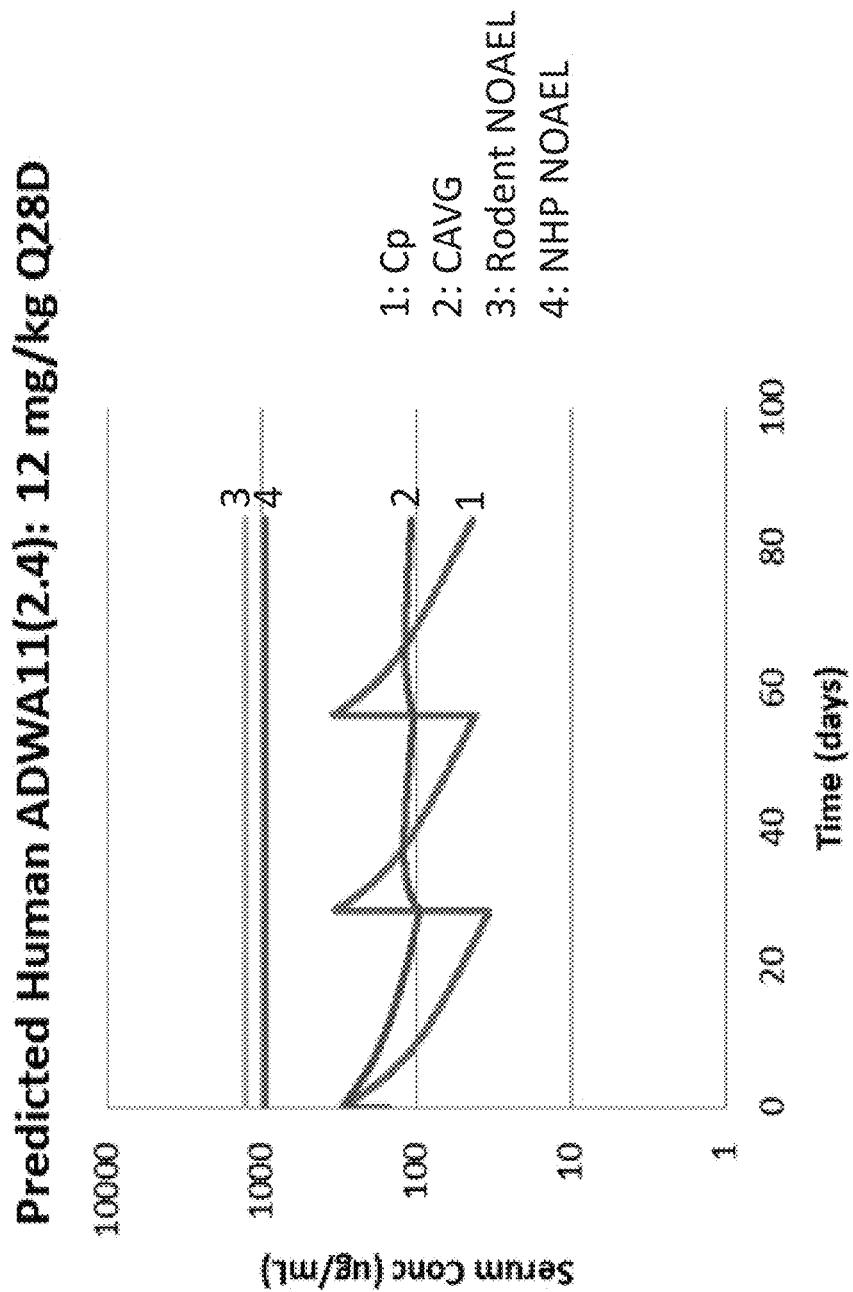
FIGS. 27A-27B show representative graphs illustrating predicted human ADWA11 2.4 pharmacokinetics following 12 mg/kg Q28D and 7 mg/kg Q14D. CP is the predicted plasma concentration; CAVG is the Cavg or average plasma concentration; Rodent NOAEL is the $C_{ave}$ no observed adverse effect level in rodents; and NHP NOAEL is the $C_{ave}$ no observed adverse effect level in nonhuman primates.
Figure 27B:
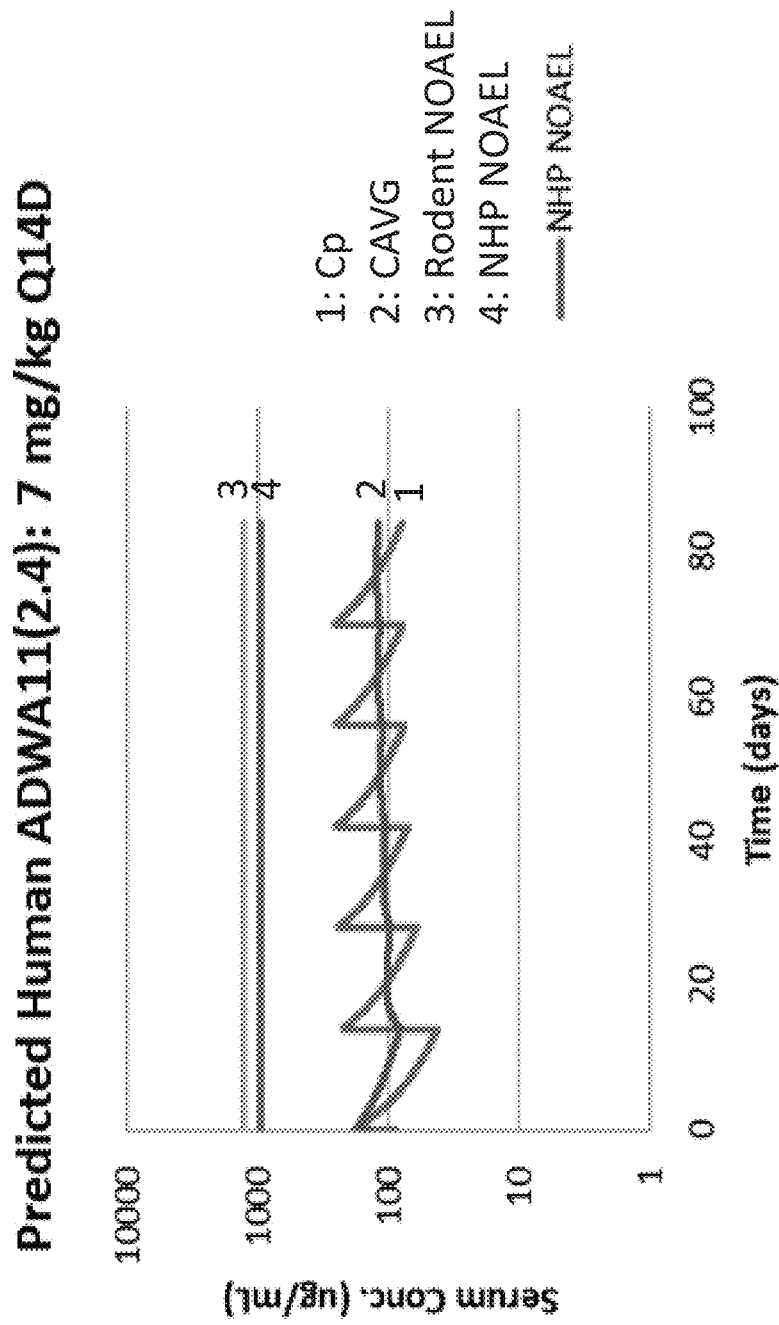

As typical antibody pharmacokinetics are expected for ADWA11 2.4 at these efficacious concentration levels, the two-compartment pharmacokinetic model with scaled TG32 mouse parameters (Table 13) were used for human dose prediction (Betts et al. MABS (2018) 1-14). In addition, human doses predicted using scaled NHP pharmacokinetic parameters differ by only about 20% from those predicted using the TG32 mouse. To match the Cn, an efficacious human IV dose of 7 mg/kg is predicted for Q14D×3 dosing, while an IV dose of 12 mg/kg is predicted for Q28D×3 dosing (FIGS. 27A-27B). The dose may also be tailored to particular patient populations, clinical indications and/or clinical signs and symptoms.

The human PK prediction of ADWA11 2.4 was refined based on allometric scaling from cynomolgus monkeys and outcome of additional preclinical efficacy studies. Efficacious dose prediction ($C_{eff}$) was determined as the plasma concentration that is equal to 10× of the half-maximal effect on tumor growth inhibition across different studies using the above 2 mouse tumor models. $C_{eff}$ was estimated to be in the range of 10-98 nM across all studies; therefore, a conservative approach was used to define 100 nM (the high end of the range) as the target $C_{eff}$. The human efficacious dose of ADWA11 2.4 is predicted to be approximately 2 mg/kg IV Q14D or 4 mg/kg IV Q28D, which was predicted to provide >IC90 tumor growth inhibition coverage at the estimated trough drug concentration (100 nM). The projected $C_{max}$, $C_{ave}$ and $C_{min}$ at steady state at the predicted efficacious doses are 84, 44 and 29 µg/mL following 2 mg/kg Q14D (IV), and 132, 45 and 21 µg/mL following 4 mg/kg Q28D (IV), respectively. The predicted human $t_{1/2}$ is approximately 15 to 17 days at the predicted efficacious dose.

These results support that ADWA11 2.4 is a potential useful human therapeutic antibody in that it can be dosed in amounts that are commercially feasible and reasonable to produce.

Example 21: Repeat-Dose Toxicokinetics in CD-1 Mouse

Toxicokinetic and anti-drug antibody evaluations were conducted after weekly intravenous (IV) or subcutaneous (SC) dosing of ADWA11 2.4 at 10 (IV), 100 (SC), or 200 (IV) mg/kg/week for a total of 4 doses to CD-1 mice (n=3/sex/dose group) as part of a GLP repeat-dose toxicity study.

There were no quantifiable concentrations of ADWA11 2.4 in samples collected and analyzed from the vehicle control group at any timepoint during the study. Based on a qualitative review of the data, there were no consistent sex-related differences in systemic exposure (as assessed by Cmax and AUC168) therefore, group mean toxicokinetic parameters are presented using combined data from both male and female CD-1 mice (Table 18).

| Overall mean toxicokinetic parameters for ADWA11 2.4 in CD-I mice. | | | | |
|---|---|---|---|---|
| Dose (mg/kg/week)/Route | Day | Cmax (ug/mL) | Tmax (hour) | AUC168 (ug·h/mL) |
| 10/IV | 1 | 199 | 0.54 | 15400 |
|  | 22 | 615 | 1.1 | 46400 |
| 100/SC | 1 | 871 | 72 | 104000 |
|  | 22 | 750 | 18 | 591000 |
| 200/IV | 1 | 5020 | 0.25 | 258000 |
|  | 22 | 6510 | 0.54 | 267000 |

$AUC_{168}$ = Area under the concentration-time curve from time 0 to 168 hours; $C_{max}$ = maximum observed concentration; $T_{max}$ = time at which Cmax was first observed.

Following IV dosing, systemic exposure increased with increasing dose in an approximately dose-proportional manner on Day 1, and a less than dose-proportional manner on Day 22. The mean accumulation ratios ($AUC_{168}$, Day 22/Day 1) were 3.0, 0.6, and 1.0 for 10 mg/kg/week (IV), 100 mg/kg/week (SC) and 200 mg/kg/week (IV), respectively. The lack of accumulation following repeat dosing at 100 mg/kg/week (SC) and 200 mg/kg/week (IV) could be related to the presence of ADA in animals in these dose groups.

The overall incidence of ADA induction to ADWA11 2.4 was 28% (5/18 animals). The incidence of ADA induction to ADWA11 2.4 was 0% (0/6 animals), 67% (4/6 animals) and 17% (1/6 animals) in CD-1 mice dosed with ADWA11 2.4 at 10 (IV), 100 (SC), or 200 (IV) mg/kg/week, respectively. In general, the exposure in the ADA-positive animals was similar or lower compared to the ADA-negative animals.

Example 22: Repeat-Dose Toxicokinetics in Cynomolgus Monkeys

Toxicokinetic and anti-drug antibody evaluations were conducted after weekly intravenous (IV) or subcutaneous (SC) dosing of ADWA11 2.4 at the doses of 8 (IV), 100 (SC) and 200 (IV) mg/kg/week for a total of 5 doses to cynomolgus monkeys as part of a GLP repeat-dose toxicity study.

There were no quantifiable concentrations of ADWA11 2.4 in samples collected and analyzed from the vehicle control group at any time point during the study, or any test article-dosed group prior to dosing on Day 1. There were no apparent sex-related differences in systemic exposures (as assessed by Cmax and AUC168) across dose groups; therefore, group mean TK parameters are discussed and presented using combined data from both male and female cynomolgus monkeys (Table 19).

TABLE 19

| Overall mean toxicokinetic parameters for ADWA11 2.4 in cynomolgus monkeys. | | | | |
|---|---|---|---|---|
| Dose (mg/kg/week)/Route | Day | Cmax (ug/mL) | Tmax (hour) | AUC168 (ug·h/mL) |
| 8/IV | 1 | 248 | 0.54 | 17300 |
|  | 22 | 394 | 6.3 | 44600 |
| 100/SC | 1 | 1270 | 72 | 161000 |
|  | 22 | 2880 | 32 | 393000 |
| 200/IV | 1 | 6200 | 1.1 | 479000 |
|  | 22 | 11400 | 2.7 | 1100000 |

$AUC_{168}$ = Area under the concentration-time curve from time 0 to 168 hours; $C_{max}$ = maximum observed concentration; $T_{max}$ = time at which Cmax was first observed.

Following weekly dosing at 8 (IV), 100 (SC) and 200 (IV) mg/kg, systemic exposure increased approximately dose-proportional on both Day 1 and Day 22, with accumulation ratios (Study Day 22/Study Day 1) ranging from approximately 2.3 to 2.6.

The overall incidence of ADA induction to ADWA11 2.4 was 39% (7/18 animals) across all dose groups. The incidence of ADA induction to ADAW11 2.4 was 17% (1/6), 33% (2/6) and 67% (4/6) for animals dosed with ADAW11 2.4 at 8 (IV), 100 (SC), or 200 (IV) mg/kg/week dose, respectively. In general, exposure was generally similar in ADA-positive animals compared to ADA-negative animals.

Example 23: Non-Clinical Toxicology in Mice and Cynomolgus Monkeys

AWA11 2.4 was administered to mice and cynomolgus monkeys in intravenous (IV) and subcutaneous (SC) studies up to 1 month in duration. The target organs identified in these studies included bone, spleen, and clinical chemistry changes, although the changes were not considered adverse. The no-adverse-effect levels (NOAELs) in the 1-month studies were 200 mg/kg/week IV ($C_{max}$ and AUC168 6510 µg/mL and 267000 µg·h/mL) for mice and ($C_{max}$ and AUC168 11,400 µg/mL and 1,100,000 µg·h/mL) cynomolgus monkeys, respectively.

Single-Dose Toxicity

ADWA11 2.4 was tolerated following a single SC dose of 10, 30, or 100 mg/kg in female CD-1 mice following by a 2 week observation phase. There were no test article-related finding during the study and mean systemic exposure increased with each dose in a dose-proportional manner as measured by area under the curve (AUC). At 100 mg/kg, the mean Cmax and AUC336 were 795 µg/mL and 148,000 µg*h/mL, respectively.

Repeat-Dose Toxicity

Study 1: In Study 1, female CD-1 mice were administered ADWA11 2.4 by IV bolus at doses of 0, 1, 10, or 100 mg/kg/dose on Days 1, 4, 8, 11, and 14. All mice survived the duration of study and all doses were tolerated. At 100 mg/kg/dose, there were test article-related differences in clinical chemistry parameters, compared with control mean, which included lower glucose (0.75×), and higher phosphorus (1.35×), globulin (1.09×), and blood urea nitrogen (1.18×) without any associated microscopic findings or clear dose relationship (glucose and phosphorus). At ≤10 mg/kg/dose, test article-related differences in clinical chemistry parameters included lower glucose (0.77× at 10 mg/kg/dose only) and higher phosphorus (1.26×), compared with control mean. Mean systemic exposure increased with increasing dose in an approximately dose proportional manner on Day 1 and Day 11. At 100 mg/kg/dose, the highest administered dose, the mean $C_{max}$ and AUC48 were 4510 µg/mL and 124,000 µg·h/mL on Day 11.

Study 2: In Study 2, cynomolgus monkeys were administered ADWA11 2.4 by IV bolus once weekly at doses of 0, 4, 40, or 100 mg/kg/dose on Days 1, 8, and 14. All monkeys survived the duration of the study and all doses were tolerated. The only test article-related findings were decreases in CD8+ naïve T cells in both the female (0.21× baseline) and male (0.44× baseline) monkeys in the 100 mg/kg/dose group but no changes were observed in the 4 or 40 mg/kg/dose groups. Mean systemic exposure increased with increasing dose in an approximately dose proportional manner on Day 1. At 100 mg/kg/dose, the highest administered dose, the mean $C_{max}$ and $AUC_{168}$ were 3550 µg/mL and 162,000 µg/mL on Day 1.

Study 3: In Study 3, ADWA11 2.4 was administered to male cynomolgus monkeys by IV bolus injection on Day 1 at doses of 0.1, 0.3, or 3 mg/kg, or by SC injection at 10 mg/kg. Subsequently, animals which were administered 0.1 or 0.3 mg/kg (IV) on Day 1 were also administered 30 or 100 mg/kg by SC injection, respectively, on Day 8. All administered doses/routes of administration were tolerated. There were no test article-related in-life observations (i.e., clinical signs, or changes in body weight or food consumption) over a 22- or 29-day observation period following dose administration. There was no evidence of erythema or edema at the injections sites.

Following single IV administration at 0.1, 0.3, and 3 mg/kg on Day 1, the systemic drug exposures increased dose-proportionally between 0.1 and 0.3 mg/kg, and more than dose proportionally between 0.3 and 3 mg/kg. Following single SC administration at 10 mg/kg on Day 1, or at 30 mg/kg and 100 mg/kg on Day 8, the systemic drug exposures increased dose-proportionally. The SC bioavailability relative to the 3 mg/kg IV dose was 103%, 79%, and 100% at 10, 30, and 100 mg/kg, respectively. Administration of ADWA11 2.4 at 0.1, 0.3, or 3 mg/kg (IV) or 10, 30, or 100 mg/kg (SC) to cynomolgus monkeys was tolerated and systemic exposure increased with dose.

Study 4: In Study 4, ADWA11 2.4 was administered once weekly to male and female CD-1 mice by either IV and/or SC doses of 0 (IV and SC), 10 (IV), 100 (SC), or 200 (IV) mg/kg/week for 1 month (5 total doses). Test article-related findings were limited to nonadverse alterations in clinical chemistry, immunophenotyping parameters in the spleen, and splenic weights.

All animals survived to scheduled necropsy with the exception of one 100 (SC) mg/kg/week male which was found dead on Day 5; however, the death of this animal was not deemed related to test article. Postmortem autolysis was observed in various organs and a cause of death 200 (IV) mg/kg/week group and included higher globin (1.15× to 1.16×) in both sexes, lower AG ratio (0.85×) in females, and higher total protein (1.11×) in males compared with concurrent controls. Administration of the mAb test article increased the systemic gamma globulin concentration and likely contributed to these alterations in serum proteins. Because of their small magnitude and a lack of associated microscopic or macroscopic findings, these observations in clinical chemistry parameters were nonadverse. In the spleen, test article-related lower numbers of CD8+ T cells (0.52×, 0.65×, and 0.60× control mean) in females and higher percentages of CD4+ T cells expressing the activation marker CD25 (1.62×, 1.90×, and 1.52× control mean) in males were noted at 10 (IV), 100 (SC), and 200 (IV) mg/kg/week, respectively on Day 30. Mean absolute and relative (to body and brain weights) spleen weights were lower (0.86× to 0.88× control) in females at 200 (IV) mg/kg/week. There were no correlating macroscopic or microscopic findings for the lower spleen weights. Based on a qualitative review of the data, there were no consistent sex-related differences in systemic exposure as assessed by $C_{max}$ and $AUC_{168}$. Systemic exposure increased with increasing IV or SC dose. After repeated dosing, exposures increased at 10 mg/kg/week (IV), decreased at 100 (SC) mg/kg/week, and remained the same at 200 (IV) mg/kg/week. The incidence of anti-drug antibodies (ADA) induction to ADWA11 2.4 was 0% (0/6), 67% (4/6) and 17% (1/6) at 10 (IV), 100 (SC), or 200 (IV) mg/kg/week, respectively. There was no evidence of ADWA11 2.4 related microscopic findings in the heart or skin one month after administration of ADWA11 2.4.

Following repeat dose administration, exposures in the ADA-positive animals were similar or slightly lower when compared with ADA-negative animals. The highest dose administered, 200 (IV) mg/kg/week, was identified as the no observed adverse effect level (NOAEL) based on a lack of adverse findings at any dose and was associated with a $C_{max}$ of 6,510 μg/mL, and $AUC_{168}$ of 267,000 μg·h/mL on Day 22.

Study 5: In Study 5, cynomolgus monkeys were administered ADWA11 2.4 as IV and/or SC doses of 0 (IV and SC), 8 (IV), 200 (IV), or 100 (SC) mg/kg/week for 1 month (5 total doses). There were no adverse test article-related findings in this study. Nonadverse test article-related findings included unilateral physeal dysplasia in the costochondral junction in males and alterations in serum proteins (increased globulin (up to 1.29×), total protein (up to 1.10×), and/or decreased albumin globulin ratio (down to 0.75×) in females at 100 (SC) mg/kg/week and both sexes at 200 (IV) mg/kg/week. Systemic exposure (as assessed by $C_{max}$ and $AUC_{168}$) was similar in males and females across dose groups and mean systemic exposure in IV dose groups increased with increasing dose in an approximately dose-proportional manner on Days 1 and 22. Exposures were higher after repeated dosing across groups. There was no evidence of ADWA11 2.4 related microscopic findings in the heart or skin one month after administration of ADWA11 2.4.

The incidence of ADA induction was 17% (1/6 animals), 33% (2/6 animals) and 67% (4/6 animals) for animals dosed with ADWA11 2.4 at 8 (IV), 100 (SC), or 200 (IV) mg/kg/week doses, respectively; the incidence of ADA induction to ADWA11 2.4 was 39% across all dose groups. Serum exposure was generally similar in ADA-positive animals compared with ADA-negative animals. Following once weekly IV or SC administration of ADWA11 2.4, 200 (IV) mg/kg/week was identified as the NOAEL in this 1-month toxicity study in monkeys based upon a lack of adverse findings in any in-life or postmortem evaluations. At 200 (IV) mg/kg/week, the mean $C_{max}$ was 11,400 μg/mL and the mean $AUC_{168}$ was 1,100,000 μg·h/mL on Day 22.

The NOAELs in the 1-month studies were 200 mg/kg IV for both mice (Cm and $AUC_{last}$ 6510 μg/mL and 267000 μg·h/mL) and cynomolgus monkeys ($C_{max}$ and $AUC_{last}$ 11,400 μg/mL and 1,100,000 μg·h/mL), respectively.

Example 24: In Vitro Complement Protein C1q and FcR Binding

The potential for ADWA11 2.4 to cause complement dependent cytotoxicity (CDC) and antibody-dependent cell-mediated cytotoxicity (ADCC) was investigated in in vitro screening assays via binding of C1q and Fc gamma receptors (FcγR), respectively. ADWA11 2.4 did not bind to C1q at the concentrations tested (up to 30 μg/mL) and therefor is considered to have a low potential for inducing CDC. ADWA11 2.4 binding to all FcγRs tested was similar or lower compared with binding to a negative control antibody and lower compared with binding to a positive control antibody. Therefore, ADWA11 2.4 is considered to have a low potential to elicit ADCC activity.

Example 25: In Vitro Cytokine Release Assay

An in vitro cytokine release assay was performed in whole blood and PBMC formats using samples from 8 human donors. No test-article related TNF, IL-6 or INF-7 release was observed following incubation with ADWA11 2.4. These data are consistent with the lack of changes in serum cytokine profiles following administration of ADWA11 2.4 in the mouse and monkey studies described above.

Example 26: Inhibition of αvβ8 Improves the Efficacy of Anti-PD-1 Therapy in the MC38 Tumor Model Methods:

In this study, the MC38 murine colon carcinoma cell line was maintained in Dulbecco's Modified Eagle Medium (DMEM) containing 10% fetal bovine serum, 2 mM glutamine, 100 units/mL penicillin G sodium, 100 μg/mL streptomycin sulfate, and 25 μg/mL gentamicin. The cells were cultured in tissue culture flasks in a humidified incubator at 37° C., with an atmosphere of 5% $CO_2$ and 95% air. On the day of tumor implantation, MC38 tumor cells were harvested during exponential growth and resuspended in phosphate buffered saline (PBS). Each mouse received $5×10^5$ cells in a 0.1 mL suspension subcutaneously (sc) in the right flank. Tumors were measured in two dimensions to monitor growth as the mean volume approached 80-120 $mm^3$ range. Volume (V)=½ L×$W^2$, and L (length) is defined as the longest diameter of the tumor and W (width) is perpendicular to L. On Day 1 of the study, animals were sorted into seven groups (n=10 per group) with group mean tumor volumes of 100 $mm^3$ and treated as described below. Tumor measurements were recorded 2-3 times per week until tumor volume reached greater than 1200 $mm^3$.

Quantitative PCR (qPCR) analysis of gene expression was performed on 30 mg of harvested tumor tissue homogenized in 900 μL of lysis buffer supplied in the RNeasy Plus Mini Kit, using Omin Bead Ruptor. RNA from homogenized tumor samples was isolated using the RNeasy Plus Mini Kit and vendor recommended protocols. RNA concentration was quantified using Epoch BioTek spectrophotometer and resuspended to 200 ng/μL with ddH20. cDNA was synthesized using 2 μg of total RNA and the High-capacity cDNA reverse transcription kit, using vendor recommended protocols. Gene expression was analyzed using 50 ng of cDNA and gene-specific taqman primers, TaqMan Universal Master Mix II, and vendor recommended protocols. ViiA7 real-time qPCR system was used for qPCR studies. The threshold cycles (CT) for each sample was analyzed using the recommended comparative CT method and expression of target genes is reported as fold change of treatment group compared to isotype control group. A two-tailed unpaired Students T-test test was used to compare treatment group to the isotype control group with significance reported at <0.05.

Figure 31A:
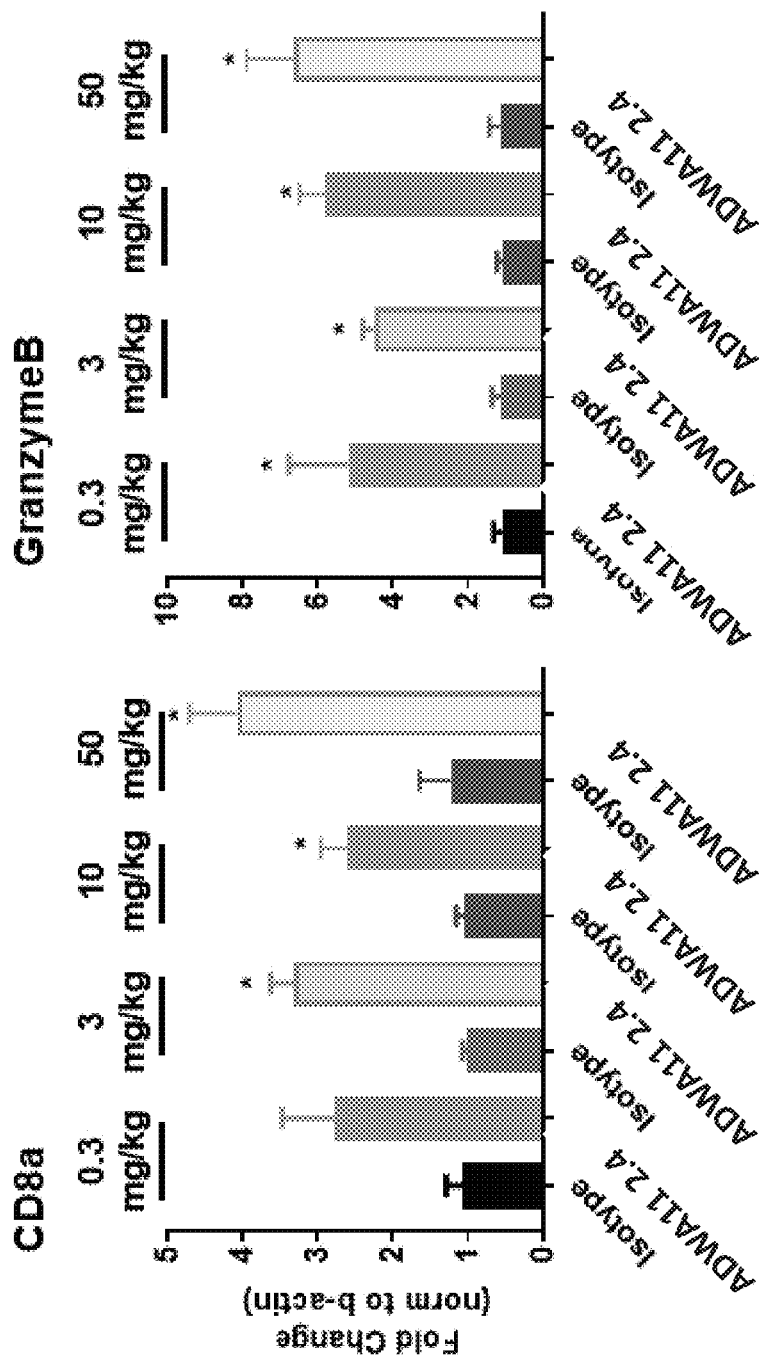
FIG. 31A depicts mRNA gene expression analysis in MC38 tumor tissue using CD8a and GranzymeB specific taqman probes. Tumor tissue was collected 12 days after the first dose of Isotype control or ADWA11 2.4 antibody at the indicated dosage level. Treatments were administered intravenously on Day 1, Day 5, and Day 9 of the study, 5 mice were included in each treatment group. *=p-value <0.05.

Results:

To investigate the effect of αvβ8-blockade on tumor lymphocyte abundance, tumor tissue was collected Day 12 (antibody treatment on Day 1, 5, 9) from mice treated with Isotype control or ADWA11 VH05-2/VK01(ADWA 2.4) and analyzed for lymphocyte marker mRNA expression by quantitative PCR. ADWA11 VH05-2/VK01(ADWA 2.4) treatment increased the expression level of CD8a (2.62±0.763) and Granzyme B (5.79±1.55) in the tumor microenvironment (Fold Change standard deviation vs Isotype group, 10 mg/kg treatment group) (FIG. 31A). These data demonstrate that treatment with ADWA11 2.4 antibody increases the abundance of activated lymphocytes, which play a role in tumor regression, in the tumor microenvironment.

Figure 31B:
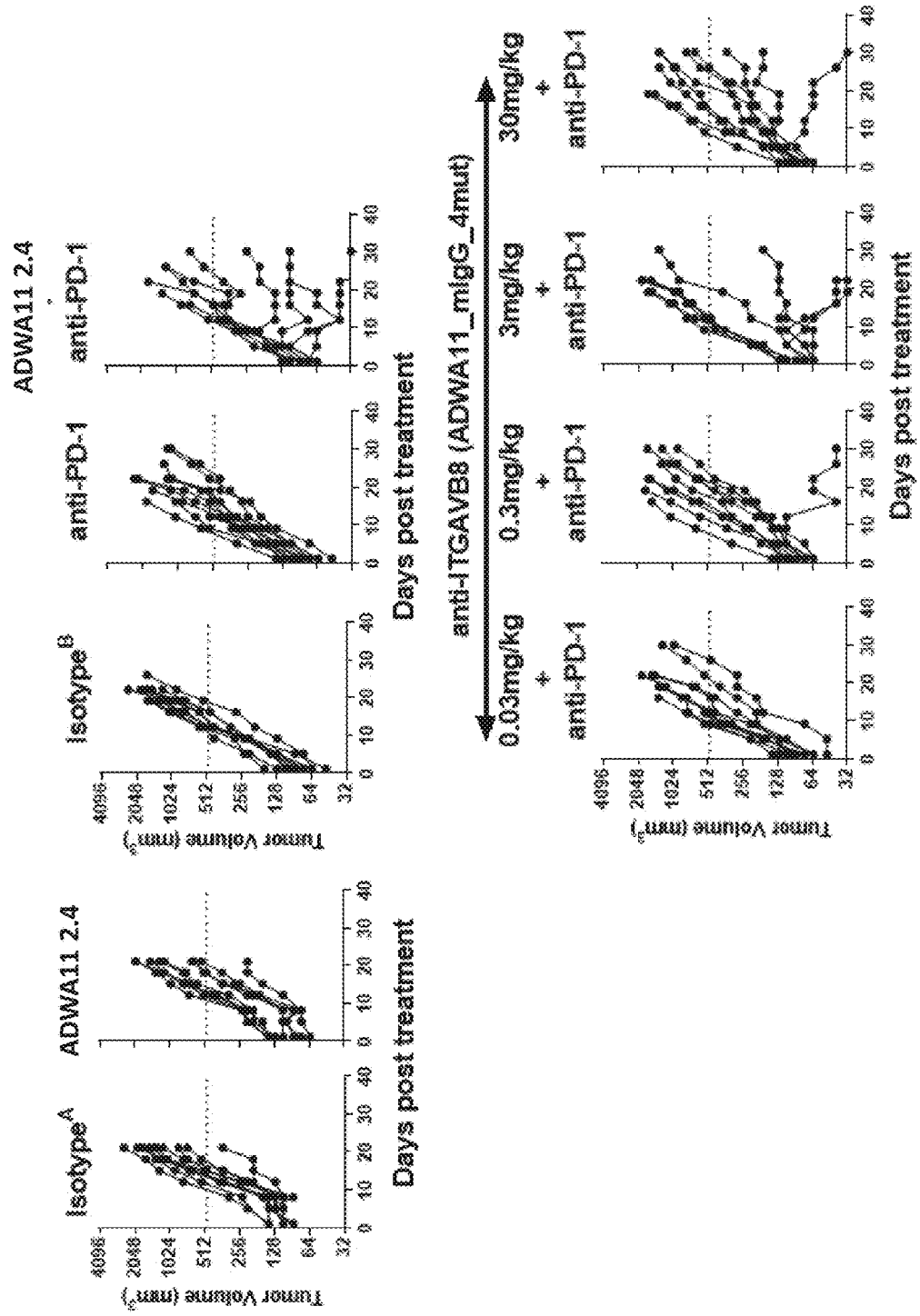
FIG. 31B shows representative graphs depicting tumor growth rate in the MC38 tumor model in Isotype (10 mg/kg), ADWA11 2.4 (10 mg/kg), anti-PD-1 antibody (RMP1-14, 10 mg/kg), and combined ADWA11 2.4 (10 mg/kg) and anti-PD1 antibody (RMP1-14, 10 mg/kg) treated mice. Additionally, representative graphs showing the tumor growth rate of MC38 tumors in mice treated with ADWA11 (anti-ITGAVB8 (ADWA11_mIgG_4mut) antibody at a 0.03, 0.3, 3, and 30 mg/kg dose in combination with 10 mg/kg of anti-PD-1 antibody (RMP1-14). For all graphs antibodies were administered on Day 1, 5, and 9 of the study.

ADWA11 2.4 treatment resulted in an 18% TGI on Day 15 of the study, while anti-PD-1 antibody (RMP1-14) treatment resulted in a 10.3% TGI on Day 16 of the study and no mice reached the end of the study (0% survival at Day 30). By comparison, ADWA11 2.4 in combination with anti-PD-1 resulted in a 35.8% TGI on Day 16 of the study and 60% of mice reached the end of the study (% survival at Day 30) (FIG. 31B top panel).

These results demonstrate that combination therapy of anti-PD1 and anti-αvβ8, as exemplified by the antibodies used herein, provides an unexpected synergistic antitumor effect. These data indicate that combination therapy of the novel anti-αvβ8 (e.g., ADWA11 2.4) antibodies disclosed herein and anti-PD-1 antibodies well-known in the art, provides a potential novel therapeuty for treatment of tumors.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety for all purposes. In the event that one or more of the incorporated literature and similar materials differs from or contradicts this application, including but not limited to defined terms, term usage, described techniques, or the like, this application controls.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating a cancer in a subject, comprising administering to the subject, a therapeutically effective amount of an antibody or antigen-binding fragment thereof, that specifically binds αvβ8 integrin, wherein the antibody or antigen-binding fragment thereof is at least one antibody or antigen-binding fragment thereof selected from the group consisting of:

(a) an antibody or antigen-binding fragment thereof, comprising a light chain complementarity determining region 1 (CDR-L1) comprising the amino acid sequence of SEQ ID NO: 11; a CDR-L2 comprising the amino acid sequence of SEQ ID NO: 12; a CDR-L3 comprising the amino acid sequence of SEQ ID NO: 13; a heavy chain CDR1 (CDR-H1) comprising the amino acid sequence of SEQ ID NO: 8; a CDR-H2 comprising the amino acid sequence of SEQ ID NO: 9; and a CDR-H3 comprising the amino acid sequence of SEQ ID NO: 10;

(b) an antibody or antigen-binding fragment thereof, comprising a CDR-L1 comprising the amino acid sequence of SEQ ID NO: 17; a CDR-L2 comprising the amino acid sequence of SEQ ID NO: 18; a CDR-L3 comprising the amino acid sequence of SEQ ID NO: 19; a CDR-H1 comprising the amino acid sequence of SEQ ID NO:14; a CDR-H2 comprising the amino acid sequence of SEQ ID NO: 15; and a CDR-H3 comprising the amino acid sequence of SEQ ID NO: 16;

(c) an antibody or antigen-binding fragment thereof, comprising a variable light (VL) region comprising the amino acid sequence encoded by the insert of the plasmid deposited with the ATCC and having Accession Number PTA-124918, and a variable heavy (VH) region comprising the amino acid sequence encoded by the insert of the plasmid deposited with the ATCC having Accession Number PTA-124917;

(d) an antibody or antigen-binding fragment thereof, comprising a VL region comprising the amino acid sequence of SEQ ID NO: 7, and a VH region comprising the amino acid sequence of SEQ ID NO: 6;

(e) an antibody or antigen-binding fragment thereof, comprising a VL region comprising the amino acid sequence of SEQ ID NO: 47 and a VH region comprising the amino acid sequence of SEQ ID NO: 39, or an antibody of antigen-binding fragment thereof, comprising a VL region comprising the amino acid sequence of SEQ ID NO: 92 and a VH region comprising the amino acid sequence of SEQ ID NO: 39;

(f) an antibody or antigen-binding fragment thereof, comprising a VL region comprising the amino acid sequence of SEQ ID NO: 67 and a VH region comprising the amino acid sequence of SEQ ID NO: 6, or an antibody of antigen-binding fragment thereof, comprising a VL region comprising the amino acid sequence of SEQ ID NO: 69 and a VH region comprising the amino acid sequence of SEQ ID NO: 6, or an antibody of antigen-binding fragment thereof, comprising a VL region comprising the amino acid sequence of SEQ ID NO: 7 and a VH region comprising the amino acid sequence of SEQ ID NO: 93, or an antibody of antigen-binding fragment thereof, comprising a VL region comprising the amino acid sequence of SEQ ID NO: 67 and a VH region comprising the amino acid sequence of SEQ ID NO: 93, or an antibody of antigen-binding fragment thereof, comprising a VL region comprising the amino acid sequence of SEQ ID NO: 69 and a VH region comprising the amino acid sequence of SEQ ID NO: 93;

(g) an antibody or antigen-binding fragment thereof, comprising a VL region comprising the amino acid sequence of SEQ ID NO: 47 and a VH region comprising the amino acid sequence of SEQ ID NO: 90, or an antibody of antigen-binding fragment thereof, comprising a VL region comprising the amino acid sequence of SEQ ID NO: 47 and a VH region comprising the amino acid sequence of SEQ ID NO: 6, or an antibody of antigen-binding fragment thereof, comprising a VL region comprising the amino acid sequence of SEQ ID NO: 92 and a VH region comprising the amino acid sequence of SEQ ID NO: 90;

(h) an antibody or antigen-binding fragment thereof, comprising a light chain (LC) region comprising the amino acid sequence of SEQ ID NO: 5, and a heavy chain (HC) region comprising the amino acid sequence of SEQ ID NO: 2;

(i) an antibody or antigen-binding fragment thereof, comprising a LC region comprising the amino acid sequence of SEQ ID NO: 5, and a HC region comprising the amino acid sequence of SEQ ID NO: 3;

(j) an antibody or antigen-binding fragment thereof, comprising a LC region comprising the amino acid sequence of SEQ ID NO: 123, and a HC region comprising the amino acid sequence of SEQ ID NO: 124 or 182;

(k) an antibody or antigen-binding fragment thereof, comprising a VL region encoded by the nucleic acid sequence of SEQ ID NO: 186, and a VH region encoded by the nucleic acid sequence of SEQ ID NO: 190; and (l) an antibody or antigen-binding fragment thereof, comprising a LC region encoded by the nucleic acid sequence of SEQ ID NO: 185, and a HC region encoded by the nucleic acid sequence of SEQ ID NO: 189 or 191.

2. The method of claim 1, further administering to the subject a cytotoxic agent, a cytostatic agent, a chemotherapeutic agent, a hormone treatment, a vaccine, an immunotherapy, surgery, radiation, thermotherapy, or a combination thereof.

3. The method of claim 2, wherein the further administering is simultaneous, sequential or separate from the administration of the therapeutically effective amount of the antibody or antigen-binding fragment thereof.

4. The method of claim 2, wherein the immunotherapy comprises a inhibitor of an immune checkpoint molecule selected from the group consisting of an anti-PD1 antibody, an anti-PD-L1 antibody, an anti-PD-L2 antibody, an anti-CTLA-4 antibody, a soluble CTLA-4 fusion protein and a combination thereof.

5. The method of claim 1, wherein the cancer is selected from the group consisting of squamous cell carcinoma of the head and neck, renal cell carcinoma with clear cell or papillary cell type, ovarian cancer, fallopian tube cancer, primary peritoneal cancer, gastric cancer, gastroesophageal junction cancer, esophageal cancer, lung squamous cell cancer, pancreatic ductal adenocarcinoma, cholangiocarcinoma, uterine cancer, melanoma, urothelial carcinoma and combinations thereof.

6. The method of claim 1, further comprising administering to the subject an inhibitor of PD1, PD-L1, or PD-L2.

7. The method of claim 6, wherein the cancer is a squamous cell carcinoma.

8. The method of claim 6, wherein the cancer is breast or colon cancer.

9. The method of claim 6, wherein the inhibitor is selected from the group consisting of an anti-PD1 antibody, an anti-PD-L1 antibody, and an anti-PD-L2 antibody.

10. The method of claim 1, wherein the antibody or antigen-binding fragment thereof comprises a CDR-L1 comprising the amino acid sequence of SEQ ID NO: 11; a CDR-L2 comprising the amino acid sequence of SEQ ID NO: 12; a CDR-L3 comprising the amino acid sequence of SEQ ID NO: 13; a CDR-H1 comprising the amino acid sequence of SEQ ID NO: 8; a CDR-H2 comprising the amino acid sequence of SEQ ID NO: 9; and a CDR-H3 comprising the amino acid sequence of SEQ ID NO: 10.

11. The method of claim 1, wherein the antibody or antigen-binding fragment thereof comprises a CDR-L1 comprising the amino acid sequence of SEQ ID NO: 17; a CDR-L2 comprising the amino acid sequence of SEQ ID NO: 18; a CDR-L3 comprising the amino acid sequence of SEQ ID NO: 19; a CDR-H1 comprising the amino acid sequence of SEQ ID NO: 14; a CDR-H2 comprising the amino acid sequence of SEQ ID NO: 15; and a CDR-H3 comprising the amino acid sequence of SEQ ID NO: 16.

12. The method of claim 1, wherein the antibody or antigen-binding fragment thereof comprises a VL region comprising the amino acid sequence of SEQ ID NO: 7, and a VH region comprising the amino acid sequence of SEQ ID NO: 6.

13. The method of claim 1, wherein the antibody or antigen-binding fragment thereof comprises a VL region comprising the amino acid sequence encoded by the insert of the plasmid deposited with the ATCC and having Accession Number PTA-124918, and a VH region comprising the amino acid sequence encoded by the insert of the plasmid deposited with the ATCC having Accession Number PTA-124917.

14. The method of claim 1, wherein the antibody or antigen-binding fragment thereof comprises a LC region comprising the amino acid sequence of SEQ ID NO: 5, and a HC region comprising the amino acid sequence of SEQ ID NO: 2 or 3.

15. The method of claim 1, where the antibody or antigen-binding fragment thereof comprises a VL region comprising a VL region comprising the amino acid sequence selected from the group consisting of SEQ ID NO: 47 and 92, and a VH region comprising the amino acid of SEQ ID NO: 39.

16. The method of claim 1, where the antibody or antigen-binding fragment thereof comprises a VL region comprising the amino acid sequence selected from the group consisting of SEQ ID NO: 7, 67, or 69, and a VH region comprising the amino acid sequence selected from the group consisting of SEQ ID NO: 6 and 93.

17. The method of claim 1, where the antibody or antigen-binding fragment thereof comprises a VL region comprising the amino acid sequence selected from the group consisting of SEQ ID NO: 47 and 92, and a VH region comprising the amino acid sequence selected from the group consisting of SEQ ID NO: and 90.

18. A method of improving survival rate of a subject having a cancer, decreasing the appearance of cancer lesions, decreasing the extent of tissue damage from the cancer, decreasing the duration of the cancer, and/or reducing the number, extent, or duration of symptoms related to the cancer, comprising administering to the subject, a therapeutically effective amount of an antibody or antigen-binding fragment thereof, that specifically binds αvβ8 integrin, wherein the antibody or antigen-binding fragment thereof is at least one antibody or antigen-binding fragment thereof selected from the group consisting of:

(a) an antibody or antigen-binding fragment thereof, comprising a light chain complementarity determining region 1 (CDR-L1) comprising the amino acid sequence of SEQ ID NO: 11; a CDR-L2 comprising the amino acid sequence of SEQ ID NO: 12; a CDR-L3 comprising the amino acid sequence of SEQ ID NO: 13; a heavy chain CDR1 (CDR-H1) comprising the amino acid sequence of SEQ ID NO: 8; a CDR-H2 comprising the amino acid sequence of SEQ ID NO: 9; and a CDR-H3 comprising the amino acid sequence of SEQ ID NO: 10;

(b) an antibody or antigen-binding fragment thereof, comprising a CDR-L1 comprising the amino acid sequence of SEQ ID NO: 17; a CDR-L2 comprising the amino acid sequence of SEQ ID NO: 18; a CDR-L3 comprising the amino acid sequence of SEQ ID NO: 19; a CDR-H1 comprising the amino acid sequence of SEQ ID NO:14; a CDR-H2 comprising the amino acid sequence of SEQ ID NO: 15; and a CDR-H3 comprising the amino acid sequence of SEQ ID NO: 16;

(c) an antibody or antigen-binding fragment thereof, comprising a variable light (VL) region comprising the amino acid sequence encoded by the insert of the plasmid deposited with the ATCC and having Accession Number PTA-124918, and a variable heavy (VH) region comprising the amino acid sequence encoded by the insert of the plasmid deposited with the ATCC having Accession Number PTA-124917;

(d) an antibody or antigen-binding fragment thereof, comprising a VL region comprising the amino acid sequence of SEQ ID NO: 7, and a VH region comprising the amino acid sequence of SEQ ID NO: 6;

(e) an antibody or antigen-binding fragment thereof, comprising a VL region comprising the amino acid sequence of SEQ ID NO: 47 and a VH region comprising the amino acid sequence of SEQ ID NO: 39, or an antibody of antigen-binding fragment thereof, comprising a VL region comprising the amino acid sequence of SEQ ID NO: 92 and a VH region comprising the amino acid sequence of SEQ ID NO: 39;

(f) an antibody or antigen-binding fragment thereof, comprising a VL region comprising the amino acid sequence of SEQ ID NO: 67 and a VH region comprising the amino acid sequence of SEQ ID NO: 6, or an antibody of antigen-binding fragment thereof, comprising a VL region comprising the amino acid sequence of SEQ ID NO: 69 and a VH region comprising the amino acid sequence of SEQ ID NO: 6, or an antibody of antigen-binding fragment thereof, comprising a VL region comprising the amino acid sequence of SEQ ID NO: 7 and a VH region comprising the amino acid sequence of SEQ ID NO: 93, or an antibody of antigen-binding fragment thereof, comprising a VL region comprising the amino acid sequence of SEQ ID NO: 67 and a VH region comprising the amino acid sequence of SEQ ID NO: 93, or an antibody of antigen-binding fragment thereof, comprising a VL region comprising the amino acid sequence of SEQ ID NO: 69 and a VH region comprising the amino acid sequence of SEQ ID NO: 93;

(g) an antibody or antigen-binding fragment thereof, comprising a VL region comprising the amino acid sequence of SEQ ID NO: 47 and a VH region comprising the amino acid sequence of SEQ ID NO: 90, or an antibody of antigen-binding fragment thereof, comprising a VL region comprising the amino acid sequence of SEQ ID NO: 47 and a VH region comprising the amino acid sequence of SEQ ID NO: 6, or an antibody of antigen-binding fragment thereof, comprising a VL region comprising the amino acid sequence of SEQ ID NO: 92 and a VH region comprising the amino acid sequence of 90;

(h) an antibody or antigen-binding fragment thereof, comprising a light chain (LC) region comprising the amino acid sequence of SEQ ID NO: 5, and a heavy chain (HC) region comprising the amino acid sequence of SEQ ID NO: 2;

(i) an antibody or antigen-binding fragment thereof, comprising a LC region comprising the amino acid sequence of SEQ ID NO: 5, and a HC region comprising the amino acid sequence of SEQ ID NO: 3;

(j) an antibody or antigen-binding fragment thereof, comprising a LC region comprising the amino acid sequence of SEQ ID NO: 123, and a HC region comprising the amino acid sequence of SEQ ID NO: 124 or 182;

(k) an antibody or antigen-binding fragment thereof, comprising a VL region encoded by the nucleic acid sequence of SEQ ID NO: 186, and a VH region encoded by the nucleic acid sequence of SEQ ID NO: 190; and (l) an antibody or antigen-binding fragment thereof, comprising a LC region encoded by the nucleic acid sequence of SEQ ID NO: 185, and a HC region encoded by the nucleic acid sequence of SEQ ID NO: 189 or 191.

19. A method of inhibiting αvβ8 integrin binding, comprising administering to a subject a therapeutically effective amount of an antibody or antigen-binding fragment thereof, that specifically binds αvβ8 integrin, wherein the antibody or antigen-binding fragment thereof is at least one antibody or antigen-binding fragment thereof selected from the group consisting of:

(a) an antibody or antigen-binding fragment thereof, comprising a light chain complementarity determining region 1 (CDR-L1) comprising the amino acid sequence of SEQ ID NO: 11; a CDR-L2 comprising the amino acid sequence of SEQ ID NO: 12; a CDR-L3 comprising the amino acid sequence of SEQ ID NO: 13; a heavy chain CDR1 (CDR-H1) comprising the amino acid sequence of SEQ ID NO: 8; a CDR-H2 comprising the amino acid sequence of SEQ ID NO: 9; and a CDR-H3 comprising the amino acid sequence of SEQ ID NO: 10;

(b) an antibody or antigen-binding fragment thereof, comprising a CDR-L1 comprising the amino acid sequence of SEQ ID NO: 17; a CDR-L2 comprising the amino acid sequence of SEQ ID NO: 18; a CDR-L3 comprising the amino acid sequence of SEQ ID NO: 19; a CDR-H1 comprising the amino acid sequence of SEQ ID NO:14; a CDR-H2 comprising the amino acid sequence of SEQ ID NO: 15; and a CDR-H3 comprising the amino acid sequence of SEQ ID NO: 16;

(c) an antibody or antigen-binding fragment thereof, comprising a variable light (VL) region comprising the amino acid sequence encoded by the insert of the plasmid deposited with the ATCC and having Accession Number PTA-124918, and a variable heavy (VH) region comprising the amino acid sequence encoded by the insert of the plasmid deposited with the ATCC having Accession Number PTA-124917;

(d) an antibody or antigen-binding fragment thereof, comprising a VL region comprising the amino acid sequence of SEQ ID NO: 7, and a VH region comprising the amino acid sequence of SEQ ID NO: 6;

(e) an antibody or antigen-binding fragment thereof, comprising a VL region comprising the amino acid sequence selected from the group consisting of SEQ ID NO: 62-66, and a VH region comprising the amino acid sequence selected from the group consisting of SEQ ID NO: 34-38;

(f) an antibody or antigen-binding fragment thereof, comprising a VL region comprising the amino acid sequence selected from the group consisting of SEQ ID NO: 47 and 92, and a VH region comprising the amino acid sequence selected from the group consisting of SEQ ID NO: 39 and 88-91;

(g) an antibody or antigen-binding fragment thereof, comprising a VL region comprising the amino acid sequence selected from the group consisting of SEQ ID NO: 7 and 67-69, and a VH region comprising the amino acid sequence selected from the group consisting of SEQ ID NO: 6 and 93;

(h) an antibody or antigen-binding fragment thereof, comprising a VL region comprising the amino acid sequence selected from the group consisting of SEQ ID NO: 7, 47-69 and 92, and a VH region comprising the amino acid sequence selected from the group consisting of SEQ ID NO: 6, 34-46, 88-91 and 93;

(i) an antibody or antigen-binding fragment thereof, comprising a light chain (LC) region comprising the amino acid sequence of SEQ ID NO: 5, and a heavy chain (HC) region comprising the amino acid sequence of SEQ ID NO: 2;
(j) an antibody or antigen-binding fragment thereof, comprising a LC region comprising the amino acid sequence of SEQ ID NO: 5, and a HC region comprising the amino acid sequence of SEQ ID NO: 3;
(k) an antibody or antigen-binding fragment thereof, comprising a LC region comprising the amino acid sequence of SEQ ID NO: 123, and a HC region comprising the amino acid sequence of SEQ ID NO: 124 or 182;
(l) an antibody or antigen-binding fragment thereof, comprising a VL region encoded by the nucleic acid sequence of SEQ ID NO: 186, and a VH region encoded by the nucleic acid sequence of SEQ ID NO: 190; and
(m) an antibody or antigen-binding fragment thereof, comprising a LC region encoded by the nucleic acid sequence of SEQ ID NO: 185, and a HC region encoded by the nucleic acid sequence of SEQ ID NO: 189 or 191.

20. The method of claim 19, where the subject has a cancer.

* * * * *

SEQUENCE LISTING

```
<160> NUMBER OF SEQ ID NOS: 197

<210> SEQ ID NO 1
<211> LENGTH: 1392
<212> TYPE: DNA
<213> ORGANISM: Artificial Sequence
<220> FEATURE:
<223> OTHER INFORMATION: Synthetic Construct

<400> SEQUENCE: 1
atgggatgga gctgtatcat cctcttcttg gtagcaacag ctacaggcgt gcactccgag      60
gtgcagctgg tggaaagcgg aggaggcctg gtgcagcctg gaggaagcct gaggctgagc     120
tgtgccgcca gcggcttcaa catcaaggac tactacatga actgggtgag gcaggcccct     180
ggcaaaggac tggagtgggt gggctggatc gaccccgacc agggcaacac catctacgag     240
cccaagttcc agggcaggtt caccatcagc gccgacacca gcaagaacag cgcctacctg     300
cagatgaact ccctgagggc cgaggacacc gccgtgtact actgcgccag gaggctgctg     360
atggactact ggggccaggg cacactggtc accgtctcct cagcctccac caagggccca     420
tcggtcttcc ccctggcacc ctcctccaag agcacctctg gggggcacagc ggccctgggc     480 tgcctggtca aggactactt ccccgaaccg gtgacggtgt cgtggaactc aggcgccctg     540
accagcggcg tgcacacctt cccggctgtc ctacagtcct caggactcta ctccctcagc     600
agcgtggtga ccgtgccctc cagcagcttg ggcacccaga cctacatctg caacgtgaat     660
cacaagccca gcaacaccaa ggtggacaag aaagttgagc ccaaatcttg tgacaaaact     720
cacacatgcc caccgtgccc agcacctgaa gccgctgggg gaccgtcagt cttcctcttc     780
cccccaaaac ccaaggacac cctcatgatc tcccggaccc ctgaggtcac atgcgtggtg     840
gtggacgtga gccacgaaga ccctgaggtc aagttcaact ggtacgtgga cggcgtggag     900
gtgcataatg ccaagacaaa gccgcgggag gagcagtaca acagcacgta ccgtgtggtc     960
agcgtcctca ccgtcctgca ccaggactgg ctgaatggca aggagtacaa gtgcaaggtc    1020
tccaacaaag ccctcccagc ccccatcgag aaaaccatct ccaaagccaa agggcagccc    1080
cgagaaccac aggtgtacac cctgccccca tcccgggagg agatgaccaa gaaccaggtc    1140
```

```
agcctgacct gcctggtcaa aggcttctat cccagcgaca tcgccgtgga gtgggagagc    1200
aatgggcagc cggagaacaa ctacaagacc acgcctcccg tgctggactc cgacggctcc    1260
ttcttcctct atagcaagct caccgtggac aagagcaggt ggcagcaggg gaacgtcttc    1320
tcatgctccg tgatgcatga ggctctgcac aaccactaca cgcagaagag cctctccctg    1380 tccccggaa aa                                                          1392
```

<210> SEQ ID NO 2
<211> LENGTH: 445
<212> TYPE: PRT
<213> ORGANISM: Artificial Sequence
<220> FEATURE:
<223> OTHER INFORMATION: Synthetic Construct

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Gln Gly Asn Thr Ile Tyr Glu Pro Lys Phe
    50                  55                  60

Gln Gly Arg Phe Thr Ile Ser Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

```
Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 3
<211> LENGTH: 444
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Gln Gly Asn Thr Ile Tyr Glu Pro Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 4
<211> LENGTH: 714
<212> TYPE: DNA
<213> ORGANISM: Artificial Sequence
<220> FEATURE:
<223> OTHER INFORMATION: Synthetic Construct

<400> SEQUENCE: 4
atgggatgga gctgtatcat cctcttcttg gtagcaacag ctacaggcgt gcactccgac      60
atccagatga cccagtcccc ttccagcctg agcgcttccg tgggcgacag ggtgaccatc     120
acctgcaggt ccaccaagtc cctgtcccac ttcaacggca cacctacct gttctggtac      180 cagcagaagc ccggcaaggc ccccaagagg ctgatctact acatgtcctc cctggcctcc     240
ggagtgccct ccaggttctc cggatccggc tccggcaccg acttcaccct gaccatctcc     300
tccctgcagc ccgaggattt cgccacctac tactgccagc agtccctgga gtacccttc      360 accttcggcg gcggcaccaa ggtggagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660 acccatcagg gcctgagctc gcccgtcaca aagagcttca cagggagga gtgt            714

<210> SEQ ID NO 5
<211> LENGTH: 219
<212> TYPE: PRT
<213> ORGANISM: Artificial Sequence
```

```
<220> FEATURE:
<223> OTHER INFORMATION: Synthetic Construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Ser His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Ser
                85                  90                  95

Leu Glu Tyr Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 6
<211> LENGTH: 115
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Gln Gly Asn Thr Ile Tyr Glu Pro Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
```

<210> SEQ ID NO 7
<211> LENGTH: 112
<212> TYPE: PRT
<213> ORGANISM: Artificial Sequence
<220> FEATURE:
<223> OTHER INFORMATION: Synthetic Construct

<400> SEQUENCE: 7

```
Asp Ile Gln Met Thr Gln Ser Pro Ser Ser Leu Ser Ala Ser Val Gly
1               5                   10                  15
Asp Arg Val Thr Ile Thr Cys Arg Ser Thr Lys Ser Leu Ser His Phe
            20                  25                  30
Asn Gly Asn Thr Tyr Leu Phe Trp Tyr Gln Gln Lys Pro Gly Lys Ala
        35                  40                  45
Pro Lys Arg Leu Ile Tyr Tyr Met Ser Ser Leu Ala Ser Gly Val Pro
    50                  55                  60
Ser Arg Phe Ser Gly Ser Gly Ser Gly Thr Asp Phe Thr Leu Thr Ile
65                  70                  75                  80
Ser Ser Leu Gln Pro Glu Asp Phe Ala Thr Tyr Tyr Cys Gln Gln Ser
                85                  90                  95
Leu Glu Tyr Pro Phe Thr Phe Gly Gly Gly Thr Lys Val Glu Ile Lys
            100                 105                 110
```

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

```
Asp Tyr Tyr Met Asn
1               5
```

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

```
Trp Ile Asp Pro Asp Gln Gly Asn Thr Ile Tyr Glu Pro Lys Phe Gln
1               5                   10                  15
Gly
```

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

```
Arg Leu Leu Met Asp Tyr
1               5
```

<210> SEQ ID NO 11
<211> LENGTH: 16
<212> TYPE: PRT
<213> ORGANISM: Artificial Sequence

```
<220> FEATURE:
<223> OTHER INFORMATION: Synthetic Construct

<400> SEQUENCE: 11

Arg Ser Thr Lys Ser Leu Ser His Phe Asn Gly Asn Thr Tyr Leu Phe
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Tyr Tyr Met Ser Ser Leu Ala Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Gln Gln Ser Leu Glu Tyr Pro Phe Thr
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Gly Phe Asn Ile Lys Asp Tyr Tyr Met Asn
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Trp Ile Asp Pro Asp Gln Gly Asn
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Arg Leu Leu Met Asp Tyr
1               5

<210> SEQ ID NO 17
<211> LENGTH: 14
<212> TYPE: PRT
<213> ORGANISM: Artificial Sequence
<220> FEATURE:
```

<223> OTHER INFORMATION: Synthetic Construct

<400> SEQUENCE: 17

Ser Thr Lys Ser Leu Ser His Phe Asn Gly Asn Thr Tyr Leu
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Tyr Tyr Met Ser Ser
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Gln Ser Leu Glu Tyr Pro Phe Thr
1               5

<210> SEQ ID NO 20
<211> LENGTH: 115
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Gln Gln Ser Gly Ala Glu Leu Val Arg Pro Gly Ala
1               5                   10                  15

Phe Val Lys Leu Ser Cys Lys Ala Ser Gly Phe Asn Ile Lys Asp Tyr
            20                  25                  30

Tyr Met Asn Trp Val Leu Gln Arg Pro Glu Gln Gly Leu Glu Trp Ile
        35                  40                  45

Gly Trp Ile Asp Pro Asp Asn Gly Asn Thr Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Leu Leu Met Asp Tyr Trp Gly Gln Gly Thr Ser Val Thr
            100                 105                 110

Val Ser Ser
        115

<210> SEQ ID NO 21
<211> LENGTH: 112
<212> TYPE: PRT
<213> ORGANISM: Artificial Sequence
<220> FEATURE:
<223> OTHER INFORMATION: Synthetic Construct

<400> SEQUENCE: 21

Asp Ile Val Met Thr Gln Ala Ala Pro Ser Val Pro Val Thr Pro Gly
1               5                   10                  15

-continued

```
Glu Ser Val Ser Ile Ser Cys Arg Ser Thr Lys Ser Leu Leu His Phe
             20                  25                  30

Asn Gly Asn Thr Tyr Leu Phe Trp Phe Leu Gln Arg Pro Gly Gln Ser
         35                  40                  45

Pro Gln Arg Leu Ile Tyr Tyr Met Ser Asn Leu Ala Ser Gly Val Pro
     50                  55                  60

Asp Arg Phe Ser Gly Arg Gly Ser Gly Thr Asp Phe Thr Leu Arg Ile
 65                  70                  75                  80

Ser Arg Val Glu Ala Glu Asp Val Gly Val Tyr Tyr Cys Met Gln Ser
                 85                  90                  95

Leu Glu Tyr Pro Phe Thr Phe Gly Thr Gly Thr Lys Leu Glu Ile Lys
            100                 105                 110
```

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

```
Asp Tyr Tyr Met Asn
1               5
```

<210> SEQ ID NO 23
<211> LENGTH: 17
<212> TYPE: PRT
<213> ORGANISM: Artificial Sequence
<220> FEATURE:
<223> OTHER INFORMATION: Synthetic Construct

<400> SEQUENCE: 23

```
Trp Ile Asp Pro Asp Asn Gly Asn Thr Ile Tyr Asp Pro Lys Phe Gln
1               5                   10                  15

Gly
```

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

```
Arg Leu Leu Met Asp Tyr
1               5
```

<210> SEQ ID NO 25
<211> LENGTH: 16
<212> TYPE: PRT
<213> ORGANISM: Artificial Sequence
<220> FEATURE:
<223> OTHER INFORMATION: Synthetic Construct

<400> SEQUENCE: 25

```
Arg Ser Thr Lys Ser Leu Leu His Phe Asn Gly Asn Thr Tyr Leu Phe
1               5                   10                  15
```

<210> SEQ ID NO 26
<211> LENGTH: 8
<212> TYPE: PRT
<213> ORGANISM: Artificial Sequence
<220> FEATURE:

```
<223> OTHER INFORMATION: Synthetic Construct

<400> SEQUENCE: 26

Tyr Tyr Met Ser Asn Leu Ala Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Met Gln Ser Leu Glu Tyr Pro Phe Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Gly Phe Asn Ile Lys Asp Tyr Tyr Met Asn
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Trp Ile Asp Pro Asp Asn Gly Asn
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Arg Leu Leu Met Asp Tyr
1               5

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Ser Thr Lys Ser Leu Leu His Phe Asn Gly Asn Thr Tyr Leu
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct
```

<400> SEQUENCE: 32

Tyr Tyr Met Ser Asn
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Gln Ser Leu Glu Tyr Pro Phe Thr
1               5

<210> SEQ ID NO 34
<211> LENGTH: 115
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met Asn Trp Val Arg Gln Ala Pro Gly Gln Gly Leu Glu Trp Ile
        35                  40                  45

Gly Trp Ile Asp Pro Asp Asn Gly Asn Thr Ile Tyr Asp Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 35
<211> LENGTH: 115
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Ile
        35                  40                  45

Gly Trp Ile Asp Pro Asp Asn Gly Asn Thr Ile Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys 85                  90                  95

Ala Arg Arg Leu Leu Met Asp Tyr Trp Gly Gln Gly Thr Leu Val Thr
                100                 105                 110

Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: Synthetic Construct

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Ile Lys Asp Tyr
                20                  25                  30

Tyr Met Asn Trp Val Arg Gln Ala Pro Gly Lys Gly Leu Glu Trp Ile
            35                  40                  45

Gly Trp Ile Asp Pro Asp Asn Gly Asn Thr Ile Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
                100                 105                 110

Val Ser Ser
        115

<210> SEQ ID NO 37
<211> LENGTH: 115
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Tyr
                20                  25                  30

Tyr Met Asn Trp Val Arg Gln Ala Pro Gly Gln Gly Leu Glu Trp Ile
            35                  40                  45

Gly Trp Ile Asp Pro Asp Asn Gly Asn Thr Ile Tyr Asp Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Leu Leu Met Asp Tyr Trp Gly Gln Gly Thr Leu Val Thr
                100                 105                 110

Val Ser Ser
        115

<210> SEQ ID NO 38
<211> LENGTH: 115

```
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Ile
        35                  40                  45

Gly Trp Ile Asp Pro Asp Asn Gly Asn Thr Ile Tyr Asp Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 39
<211> LENGTH: 115
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Asn Gly Asn Thr Ile Tyr Asp Pro Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 40
<211> LENGTH: 115
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
```

```
                  20                  25                  30

Tyr Met Asn Trp Val Arg Gln Ala Pro Gly Lys Gly Leu Glu Trp Val
            35                  40                  45

Gly Trp Ile Asp Pro Asp Asn Gly Asn Thr Ile Tyr Glu Pro Lys Phe
        50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
                100                 105                 110

Val Ser Ser
        115

<210> SEQ ID NO 41
<211> LENGTH: 115
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
                20                  25                  30

Tyr Met Asn Trp Val Arg Gln Ala Pro Gly Lys Gly Leu Glu Trp Val
            35                  40                  45

Gly Trp Ile Asp Pro Asp Gln Gly Asn Thr Ile Tyr Asp Pro Lys Phe
        50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
                100                 105                 110

Val Ser Ser
        115

<210> SEQ ID NO 42
<211> LENGTH: 115
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Gln Ile Lys Asp Tyr
                20                  25                  30

Tyr Met Asn Trp Val Arg Gln Ala Pro Gly Lys Gly Leu Glu Trp Val
            35                  40                  45

Gly Trp Ile Asp Pro Asp Gln Gly Asn Thr Ile Tyr Asp Pro Lys Phe
        50                  55                  60

Gln Gly Arg Phe Thr Ile Ser Ala Asp Thr Ser Lys Asn Ser Ala Tyr
65                  70                  75                  80
```

```
Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 43
<211> LENGTH: 115
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ala Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Asn Gly Asn Thr Ile Tyr Asp Pro Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 44
<211> LENGTH: 115
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Asn Gly Gln Thr Ile Tyr Asp Pro Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 45
```

```
<211> LENGTH: 115
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Asn Gly Asn Thr Ile Tyr Asp Ala Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 46
<211> LENGTH: 115
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Asn Gly Asn Thr Ile Tyr Asp Pro Ala Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 47
<211> LENGTH: 112
<212> TYPE: PRT
<213> ORGANISM: Artificial Sequence
<220> FEATURE:
<223> OTHER INFORMATION: Synthetic Construct

<400> SEQUENCE: 47

Asp Ile Gln Met Thr Gln Ser Pro Ser Ser Leu Ser Ala Ser Val Gly
1               5                   10                  15
```

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 48
<211> LENGTH: 112
<212> TYPE: PRT
<213> ORGANISM: Artificial Sequence
<220> FEATURE:
<223> OTHER INFORMATION: Synthetic Construct

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Ile Leu His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 49
<211> LENGTH: 112
<212> TYPE: PRT
<213> ORGANISM: Artificial Sequence
<220> FEATURE:
<223> OTHER INFORMATION: Synthetic Construct

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Ser His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 50
<211> LENGTH: 112
<212> TYPE: PRT
<213> ORGANISM: Artificial Sequence
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Ser Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 51
<211> LENGTH: 112
<212> TYPE: PRT
<213> ORGANISM: Artificial Sequence
<220> FEATURE:
<223> OTHER INFORMATION: Synthetic Construct

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Ala Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
            35                  40                  45

Pro Lys Arg Leu Ile Tyr Tyr Ala Ser Asn Leu Ala Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Met Gln Ser
                 85                  90                  95

Leu Glu Tyr Pro Phe Thr Phe Gly Gln Gly Thr Lys Val Glu Ile Lys
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: Synthetic Construct

<400> SEQUENCE: 53

Asp Ile Gln Met Thr Gln Ser Pro Ser Ser Leu Ser Ala Ser Val Gly
 1               5                  10                  15

Asp Arg Val Thr Ile Thr Cys Arg Ser Thr Lys Ser Leu Leu His Phe
                 20                  25                  30

Asn Gly Asn Thr Tyr Leu Phe Trp Tyr Gln Gln Lys Pro Gly Lys Ala
            35                  40                  45

Pro Lys Arg Leu Ile Tyr Tyr Met Ser Ser Leu Ala Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Met Gln Ser
                 85                  90                  95

Leu Glu Tyr Pro Phe Thr Phe Gly Gln Gly Thr Lys Val Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: Synthetic Construct

<400> SEQUENCE: 54

Asp Ile Gln Met Thr Gln Ser Pro Ser Ser Leu Ser Ala Ser Val Gly
 1               5                  10                  15

Asp Arg Val Thr Ile Thr Cys Arg Ser Thr Lys Ser Leu Leu His Phe
                 20                  25                  30

Asn Gly Asn Thr Tyr Leu Phe Trp Tyr Gln Gln Lys Pro Gly Lys Ala
            35                  40                  45

Pro Lys Arg Leu Ile Tyr Tyr Met Ser Asn Leu Gln Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Met Gln Ser
                 85                  90                  95

Leu Glu Tyr Pro Phe Thr Phe Gly Gln Gly Thr Lys Val Glu Ile Lys
            100                 105                 110

<210> SEQ ID NO 55

```
<211> LENGTH: 112
<212> TYPE: PRT
<213> ORGANISM: Artificial Sequence
<220> FEATURE:
<223> OTHER INFORMATION: Synthetic Construct

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Ser
                85                  90                  95

Leu Glu Tyr Pro Phe Thr Phe Gly Gln Gly Thr Lys Val Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: Synthetic Construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Tyr Glu Tyr Pro Phe Thr Phe Gly Gln Gly Thr Lys Val Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45
```

```
Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
 65              70                  75                      80

Ser Ser Leu Gln Pro Glu Asp Phe Ala Thr Tyr Tyr Cys Met Gln Ser
                85                  90                  95

Leu Ser Tyr Pro Phe Thr Phe Gly Gln Gly Thr Lys Val Glu Ile Lys
            100                 105                 110
```

<210> SEQ ID NO 58
<211> LENGTH: 112
<212> TYPE: PRT
<213> ORGANISM: Artificial Sequence
<220> FEATURE:
<223> OTHER INFORMATION: Synthetic Construct

<400> SEQUENCE: 58

```
Asp Ile Gln Met Thr Gln Ser Pro Ser Ser Leu Ser Ala Ser Val Gly
 1               5                  10                  15

Asp Arg Val Thr Ile Thr Cys Arg Ser Thr Lys Ser Leu Leu His Phe
             20                  25                  30

Asn Gly Asn Thr Tyr Leu Phe Trp Tyr Gln Gln Lys Pro Gly Lys Ala
         35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
 65              70                  75                      80

Ser Ser Leu Gln Pro Glu Asp Phe Ala Thr Tyr Tyr Cys Met Gln Ser
                85                  90                  95

Leu Glu Thr Pro Phe Thr Phe Gly Gln Gly Thr Lys Val Glu Ile Lys
            100                 105                 110
```

<210> SEQ ID NO 59
<211> LENGTH: 112
<212> TYPE: PRT
<213> ORGANISM: Artificial Sequence
<220> FEATURE:
<223> OTHER INFORMATION: Synthetic Construct

<400> SEQUENCE: 59

```
Asp Ile Gln Met Thr Gln Ser Pro Ser Ser Leu Ser Ala Ser Val Gly
 1               5                  10                  15

Asp Arg Val Thr Ile Thr Cys Arg Ser Thr Lys Ser Leu Leu His Phe
             20                  25                  30

Asn Gly Asn Thr Tyr Leu Phe Trp Tyr Gln Gln Lys Pro Gly Lys Ala
         35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
 65              70                  75                      80

Ser Ser Leu Gln Pro Glu Asp Phe Ala Thr Tyr Tyr Cys Met Gln Ser
                85                  90                  95

Leu Glu Tyr Pro Leu Thr Phe Gly Gln Gly Thr Lys Val Glu Ile Lys
            100                 105                 110
```

<210> SEQ ID NO 60
<211> LENGTH: 112
<212> TYPE: PRT
<213> ORGANISM: Artificial Sequence

```
<220> FEATURE:
<223> OTHER INFORMATION: Synthetic Construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Trp Thr Phe Gly Gln Gly Thr Lys Val Glu Ile Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gly Gly Thr Lys Val Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: Synthetic Construct

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Ser Thr Lys Ser Leu Leu His Phe
            20                  25                  30

Asn Gly Asn Thr Tyr Leu Phe Trp Tyr Leu Gln Lys Pro Gly Gln Ser
        35                  40                  45

Pro Gln Leu Leu Ile Tyr Tyr Met Ser Asn Leu Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Leu Glu Tyr Pro Phe Thr Phe Gly Gln Gly Thr Lys Val Glu Ile Lys
            100                 105                 110
```

<210> SEQ ID NO 63
<211> LENGTH: 112
<212> TYPE: PRT
<213> ORGANISM: Artificial Sequence
<220> FEATURE:
<223> OTHER INFORMATION: Synthetic Construct

<400> SEQUENCE: 63

```
Asp Val Val Met Thr Gln Ser Pro Leu Ser Leu Pro Val Thr Leu Gly
 1               5                  10                  15

Gln Pro Ala Ser Ile Ser Cys Arg Ser Thr Lys Ser Leu Leu His Phe
            20                  25                  30

Asn Gly Asn Thr Tyr Leu Phe Trp Phe Gln Gln Arg Pro Gly Gln Ser
         35                  40                  45

Pro Arg Arg Leu Ile Tyr Tyr Met Ser Asn Leu Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Leu Glu Tyr Pro Phe Thr Phe Gly Gln Gly Thr Lys Val Glu Ile Lys
            100                 105                 110
```

<210> SEQ ID NO 64
<211> LENGTH: 112
<212> TYPE: PRT
<213> ORGANISM: Artificial Sequence
<220> FEATURE:
<223> OTHER INFORMATION: Synthetic Construct

<400> SEQUENCE: 64

```
Asp Ile Val Met Thr Gln Ser Pro Asp Ser Leu Ala Val Ser Leu Gly
 1               5                  10                  15

Glu Arg Ala Thr Ile Asn Cys Arg Ser Thr Lys Ser Leu Leu His Phe
            20                  25                  30

Asn Gly Asn Thr Tyr Leu Phe Trp Tyr Gln Gln Lys Pro Gly Gln Pro
         35                  40                  45

Pro Lys Leu Leu Ile Tyr Tyr Met Ser Asn Leu Ala Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Met Gln Ser
                 85                  90                  95

Leu Glu Tyr Pro Phe Thr Phe Gly Gln Gly Thr Lys Val Glu Ile Lys
            100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
            20                  25                  30

Asn Gly Asn Thr Tyr Leu Phe Trp Tyr Gln Gln Lys Pro Gly Lys Ala
        35                  40                  45

Pro Lys Leu Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 66
<211> LENGTH: 112
<212> TYPE: PRT
<213> ORGANISM: Artificial Sequence
<220> FEATURE:
<223> OTHER INFORMATION: Synthetic Construct

<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys Arg Ser Thr Lys Ser Leu Leu His Phe
            20                  25                  30

Asn Gly Asn Thr Tyr Leu Phe Trp Tyr Gln Gln Lys Pro Gly Gln Ala
        35                  40                  45

Pro Arg Leu Leu Ile Tyr Tyr Met Ser Asn Leu Ala Ser Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 67
<211> LENGTH: 112
<212> TYPE: PRT
<213> ORGANISM: Artificial Sequence
<220> FEATURE:
<223> OTHER INFORMATION: Synthetic Construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Ser His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

```
Ser Ser Leu Gln Pro Glu Asp Phe Ala Thr Tyr Tyr Cys Gln Gln Ser
                85                  90                  95

Leu Glu Tyr Pro Phe Thr Phe Gly Gly Gly Thr Lys Val Glu Ile Lys
            100                 105                 110

<210> SEQ ID NO 68
<211> LENGTH: 112
<212> TYPE: PRT
<213> ORGANISM: Artificial Sequence
<220> FEATURE:
<223> OTHER INFORMATION: Synthetic Construct

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Ser His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Tyr Glu Tyr Pro Phe Thr Phe Gly Gly Gly Thr Lys Val Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Ser His Phe
            20                  25                  30

Asn Gly Asn Thr Tyr Leu Phe Trp Tyr Gln Gln Lys Pro Gly Lys Ala
        35                  40                  45

Pro Lys Arg Leu Ile Tyr Tyr Ala Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Ser
                85                  90                  95

Leu Glu Tyr Pro Phe Thr Phe Gly Gly Gly Thr Lys Val Glu Ile Lys
            100                 105                 110

<210> SEQ ID NO 70
<211> LENGTH: 325
<212> TYPE: PRT
<213> ORGANISM: Artificial Sequence
<220> FEATURE:
<223> OTHER INFORMATION: Synthetic Construct

<400> SEQUENCE: 70

Ala Ser Thr Lys Gly Pro Ser Val Phe Pro Leu Ala Pro Cys Ser Arg
```

```
            1               5                  10                 15
         Ser Thr Ser Glu Ser Thr Ala Ala Leu Gly Cys Leu Val Lys Asp Tyr
                     20                  25                  30

Phe Pro Glu Pro Val Thr Val Ser Trp Asn Ser Gly Ala Leu Thr Ser
                     35                  40                  45

Gly Val His Thr Phe Pro Ala Val Leu Gln Ser Ser Gly Leu Tyr Ser
                     50                  55                  60

Leu Ser Ser Val Val Thr Val Pro Ser Ser Asn Phe Gly Thr Gln Thr
         65                  70                  75                  80

Tyr Thr Cys Asn Val Asp His Lys Pro Ser Asn Thr Lys Val Asp Lys
                             85                  90                  95

Thr Glu Arg Lys Cys Cys Val Glu Cys Pro Pro Cys Pro Ala Pro Pro
                         100                 105                 110

Val Ala Gly Pro Ser Val Phe Leu Phe Pro Pro Lys Pro Lys Asp Thr
                         115                 120                 125

Leu Met Ile Ser Arg Thr Pro Glu Val Thr Cys Val Val Val Asp Val
         130                 135                 140

Ser His Glu Asp Pro Glu Val Gln Phe Asn Trp Tyr Val Asp Gly Val
         145                 150                 155                 160

Glu Val His Asn Ala Lys Thr Lys Pro Arg Glu Glu Gln Phe Asn Ser
                         165                 170                 175

Thr Phe Arg Val Val Ser Val Leu Thr Val Val His Gln Asp Trp Leu
                     180                 185                 190

Asn Gly Lys Glu Tyr Lys Cys Lys Val Ser Asn Lys Gly Leu Pro Ala
                     195                 200                 205

Pro Ile Glu Lys Thr Ile Ser Lys Thr Lys Gly Gln Pro Arg Glu Pro
         210                 215                 220

Gln Val Tyr Thr Leu Pro Pro Ser Arg Glu Glu Met Thr Lys Asn Gln
         225                 230                 235                 240

Val Ser Leu Thr Cys Leu Val Lys Gly Phe Tyr Pro Ser Asp Ile Ala
                         245                 250                 255

Val Glu Trp Glu Ser Asn Gly Gln Pro Glu Asn Asn Tyr Lys Thr Thr
                         260                 265                 270

Pro Pro Met Leu Asp Ser Asp Gly Ser Phe Phe Leu Tyr Ser Lys Leu
                     275                 280                 285

Thr Val Asp Lys Ser Arg Trp Gln Gln Gly Asn Val Phe Ser Cys Ser
                     290                 295                 300

Val Met His Glu Ala Leu His Asn His Tyr Thr Gln Lys Ser Leu Ser
         305                 310                 315                 320

Leu Ser Pro Gly Lys
                         325

<210> SEQ ID NO 71
<211> LENGTH: 16
<212> TYPE: PRT
<213> ORGANISM: Artificial Sequence
<220> FEATURE:
<223> OTHER INFORMATION: Synthetic Construct

<400> SEQUENCE: 71

Arg Ser Thr Lys Ser Leu Leu His Phe Asn Gly Asn Thr Tyr Leu Phe
1               5                   10                  15

<210> SEQ ID NO 72
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 72

Tyr Tyr Met Ser Asn Leu Ala Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct

<400> SEQUENCE: 73

Met Gln Ser Leu Glu Tyr Pro Phe Thr
1               5

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Ser Thr Lys Ser Leu Leu His Phe Asn Gly Asn Thr Tyr Leu
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Synthetic Construct

<400> SEQUENCE: 75

Tyr Tyr Met Ser Asn
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

Gln Ser Leu Glu Tyr Pro Phe Thr
1               5

<210> SEQ ID NO 77
<211> LENGTH: 1002
<212> TYPE: PRT
<213> ORGANISM: Artificial Sequence
<220> FEATURE:
<223> OTHER INFORMATION: Synthetic Construct

<400> SEQUENCE: 77

Met Leu Leu Gly Thr Leu Leu Ile Leu Tyr Ile Leu Met Leu Cys
1               5                   10                  15

Arg Met Phe Leu Leu Val Gly Ala Pro Lys Ala Asn Thr Thr Gln Pro
                20                  25                  30

Gly Ile Val Glu Gly Gly Gln Val Leu Lys Cys Asp Trp Ser Ser Thr
            35                  40                  45
```

```
Arg Arg Cys Gln Pro Ile Glu Phe Asp Ala Thr Gly Asn Arg Asp Tyr
            50                  55                  60

Ala Lys Asp Asp Pro Leu Glu Phe Lys Ser His Gln Trp Phe Gly Ala
 65                  70                  75                  80

Ser Val Arg Ser Lys Gln Asp Lys Ile Leu Ala Cys Ala Pro Leu Tyr
                85                  90                  95

His Trp Arg Thr Glu Met Lys Gln Glu Arg Glu Pro Val Gly Thr Cys
               100                 105                 110

Phe Leu Gln Asp Gly Thr Lys Thr Val Glu Tyr Ala Pro Cys Arg Ser
           115                 120                 125

Gln Asp Ile Asp Ala Asp Gly Gln Gly Phe Cys Gln Gly Gly Phe Ser
           130                 135                 140

Ile Asp Phe Thr Lys Ala Asp Arg Val Leu Leu Gly Gly Pro Gly Ser
145                 150                 155                 160

Phe Tyr Trp Gln Gly Gln Leu Ile Ser Asp Gln Val Ala Glu Ile Val
               165                 170                 175

Ser Lys Tyr Asp Pro Asn Val Tyr Ser Ile Lys Tyr Asn Asn Gln Leu
           180                 185                 190

Ala Thr Arg Thr Ala Gln Ala Ile Phe Asp Asp Ser Tyr Leu Gly Tyr
           195                 200                 205

Ser Val Ala Val Gly Asp Phe Asn Gly Asp Gly Ile Asp Asp Phe Val
210                 215                 220

Ser Gly Val Pro Arg Ala Ala Arg Thr Leu Gly Met Val Tyr Ile Tyr
225                 230                 235                 240

Asp Gly Lys Asn Met Ser Ser Leu Tyr Asn Phe Thr Gly Glu Gln Met
               245                 250                 255

Ala Ala Tyr Phe Gly Phe Ser Val Ala Ala Thr Asp Ile Asn Gly Asp
           260                 265                 270

Asp Tyr Ala Asp Val Phe Ile Gly Ala Pro Leu Phe Met Asp Arg Gly
           275                 280                 285

Ser Asp Gly Lys Leu Gln Glu Val Gly Gln Val Ser Val Ser Leu Gln
           290                 295                 300

Arg Ala Ser Gly Asp Phe Gln Thr Thr Lys Leu Asn Gly Phe Glu Val
305                 310                 315                 320

Phe Ala Arg Phe Gly Ser Ala Ile Ala Pro Leu Gly Asp Leu Asp Gln
                325                 330                 335

Asp Gly Phe Asn Asp Ile Ala Ile Ala Ala Pro Tyr Gly Gly Glu Asp
               340                 345                 350

Lys Lys Gly Ile Val Tyr Ile Phe Asn Gly Arg Ser Thr Gly Leu Asn
           355                 360                 365

Ala Val Pro Ser Gln Ile Leu Glu Gly Gln Trp Ala Ala Arg Ser Met
           370                 375                 380

Pro Pro Ser Phe Gly Tyr Ser Met Lys Gly Ala Thr Asp Ile Asp Lys
385                 390                 395                 400

Asn Gly Tyr Pro Asp Leu Ile Val Gly Ala Phe Gly Val Asp Arg Ala
               405                 410                 415

Ile Leu Tyr Arg Ala Arg Pro Val Ile Thr Val Asn Ala Gly Leu Glu
           420                 425                 430

Val Tyr Pro Ser Ile Leu Asn Gln Asp Asn Lys Thr Cys Ser Leu Pro
           435                 440                 445

Gly Thr Ala Leu Lys Val Ser Cys Phe Asn Val Arg Phe Cys Leu Lys
450                 455                 460
```

```
Ala Asp Gly Lys Gly Val Leu Pro Arg Lys Leu Asn Phe Gln Val Glu
465                 470                 475                 480

Leu Leu Leu Asp Lys Leu Lys Gln Lys Gly Ala Ile Arg Arg Ala Leu
            485                 490                 495

Phe Leu Tyr Ser Arg Ser Pro Ser His Ser Lys Asn Met Thr Ile Ser
            500                 505                 510

Arg Gly Gly Leu Met Gln Cys Glu Glu Leu Ile Ala Tyr Leu Arg Asp
            515                 520                 525

Glu Ser Glu Phe Arg Asp Lys Leu Thr Pro Ile Thr Ile Phe Met Glu
    530                 535                 540

Tyr Arg Leu Asp Tyr Arg Thr Ala Ala Asp Thr Thr Gly Leu Gln Pro
545                 550                 555                 560

Ile Leu Asn Gln Phe Thr Pro Ala Asn Ile Ser Arg Gln Ala His Ile
                565                 570                 575

Leu Leu Asp Cys Gly Glu Asp Asn Val Cys Lys Pro Lys Leu Glu Val
            580                 585                 590

Ser Val Asp Ser Asp Gln Lys Lys Ile Tyr Ile Gly Asp Asp Asn Pro
    595                 600                 605

Leu Thr Leu Ile Val Lys Ala Gln Asn Gln Gly Glu Gly Ala Tyr Glu
    610                 615                 620

Ala Glu Leu Ile Val Ser Ile Pro Leu Gln Ala Asp Phe Ile Gly Val
625                 630                 635                 640

Val Arg Asn Asn Glu Ala Leu Ala Arg Leu Ser Cys Ala Phe Lys Thr
                645                 650                 655

Glu Asn Gln Thr Arg Gln Val Val Cys Asp Leu Gly Asn Pro Met Lys
                660                 665                 670

Ala Gly Thr Gln Leu Leu Ala Gly Leu Arg Phe Ser Val His Gln Gln
            675                 680                 685

Ser Glu Met Asp Thr Ser Val Lys Phe Asp Leu Gln Ile Gln Ser Ser
    690                 695                 700

Asn Leu Phe Asp Lys Val Ser Pro Val Val Ser His Lys Val Asp Leu
705                 710                 715                 720

Ala Val Leu Ala Ala Val Glu Ile Arg Gly Val Ser Ser Pro Asp His
                725                 730                 735

Ile Phe Leu Pro Ile Pro Asn Trp Glu His Lys Glu Asn Pro Glu Thr
            740                 745                 750

Glu Glu Asp Val Gly Pro Val Val Gln His Ile Tyr Glu Leu Arg Asn
            755                 760                 765

Asn Gly Pro Ser Ser Phe Ser Lys Ala Met Leu His Leu Gln Trp Pro
    770                 775                 780

Tyr Lys Tyr Asn Asn Asn Thr Leu Leu Tyr Ile Leu His Tyr Asp Ile
785                 790                 795                 800

Asp Gly Pro Met Asn Cys Thr Ser Asp Met Glu Ile Asn Pro Leu Arg
                805                 810                 815

Ile Lys Ile Ser Ser Leu Gln Thr Thr Glu Lys Asn Asp Thr Val Ala
            820                 825                 830

Gly Gln Gly Glu Arg Asp His Leu Ile Thr Lys Arg Asp Leu Ala Leu
            835                 840                 845

Ser Glu Gly Asp Ile His Thr Leu Gly Cys Gly Val Ala Gln Cys Leu
    850                 855                 860

Lys Ile Val Cys Gln Val Gly Arg Leu Asp Arg Gly Lys Ser Ala Ile
865                 870                 875                 880

Leu Tyr Val Lys Ser Leu Leu Trp Thr Glu Thr Phe Met Asn Lys Glu
```

```
                    885                 890                 895
Asn Gln Asn His Ser Tyr Ser Leu Lys Ser Ala Ser Phe Asn Val
                900                 905                 910

Ile Glu Phe Pro Tyr Lys Asn Leu Pro Ile Glu Asp Ile Thr Asn Ser
                915                 920                 925

Thr Leu Val Thr Thr Asn Val Thr Trp Gly Ile Gln Pro Ala Pro Met
                930                 935                 940

Pro Val Pro Val Trp Val Ile Ile Leu Ala Val Leu Ala Gly Leu Leu
945                 950                 955                 960

Leu Leu Ala Val Leu Val Phe Val Met Tyr Arg Met Gly Phe Phe Lys
                965                 970                 975

Arg Val Arg Pro Pro Gln Glu Glu Gln Arg Glu Gln Leu Gln Pro
                980                 985                 990

His Glu Asn Gly Glu Gly Asn Ser  Glu Thr
                995                 1000

<210> SEQ ID NO 78
<211> LENGTH: 769
<212> TYPE: PRT
<213> ORGANISM: Artificial Sequence
<220> FEATURE:
<223> OTHER INFORMATION: Synthetic Construct

<400> SEQUENCE: 78

Met Cys Gly Ser Ala Leu Ala Phe Phe Thr Ala Ala Phe Val Cys Leu
1               5                   10                  15

Gln Asn Asp Arg Arg Gly Pro Ala Ser Phe Leu Trp Ala Ala Trp Val
                20                  25                  30

Phe Ser Leu Val Leu Gly Leu Gly Gln Gly Glu Asp Asn Arg Cys Ala
                35                  40                  45

Ser Ser Asn Ala Ala Ser Cys Ala Arg Cys Leu Ala Leu Gly Pro Glu
    50                  55                  60

Cys Gly Trp Cys Val Gln Glu Asp Phe Ile Ser Gly Gly Ser Arg Ser
65                  70                  75                  80

Glu Arg Cys Asp Ile Val Ser Asn Leu Ile Ser Lys Gly Cys Ser Val
                85                  90                  95

Asp Ser Ile Glu Tyr Pro Ser Val His Val Ile Ile Pro Thr Glu Asn
                100                 105                 110

Glu Ile Asn Thr Gln Val Thr Pro Gly Glu Val Ser Ile Gln Leu Arg
                115                 120                 125

Pro Gly Ala Glu Ala Asn Phe Met Leu Lys Val His Pro Leu Lys Lys
    130                 135                 140

Tyr Pro Val Asp Leu Tyr Tyr Leu Val Asp Val Ser Ala Ser Met His
145                 150                 155                 160

Asn Asn Ile Glu Lys Leu Asn Ser Val Gly Asn Asp Leu Ser Arg Lys
                165                 170                 175

Met Ala Phe Phe Ser Arg Asp Phe Arg Leu Gly Phe Gly Ser Tyr Val
                180                 185                 190

Asp Lys Thr Val Ser Pro Tyr Ile Ser Ile His Pro Glu Arg Ile His
                195                 200                 205

Asn Gln Cys Ser Asp Tyr Asn Leu Asp Cys Met Pro Pro His Gly Tyr
    210                 215                 220

Ile His Val Leu Ser Leu Thr Glu Asn Ile Thr Glu Phe Glu Lys Ala
225                 230                 235                 240

Val His Arg Gln Lys Ile Ser Gly Asn Ile Asp Thr Pro Glu Gly Gly
```

```
                    245                 250                 255
Phe Asp Ala Met Leu Gln Ala Ala Val Cys Glu Ser His Ile Gly Trp
                260                 265                 270

Arg Lys Glu Ala Lys Arg Leu Leu Val Met Thr Asp Gln Thr Ser
            275                 280                 285

His Leu Ala Leu Asp Ser Lys Leu Ala Gly Ile Val Val Pro Asn Asp
        290                 295                 300

Gly Asn Cys His Leu Lys Asn Asn Val Tyr Val Lys Ser Thr Thr Met
305                 310                 315                 320

Glu His Pro Ser Leu Gly Gln Leu Ser Glu Lys Leu Ile Asp Asn Asn
                325                 330                 335

Ile Asn Val Ile Phe Ala Val Gln Gly Lys Gln Phe His Trp Tyr Lys
                340                 345                 350

Asp Leu Leu Pro Leu Leu Pro Gly Thr Ile Ala Gly Glu Ile Glu Ser
                355                 360                 365

Lys Ala Ala Asn Leu Asn Asn Leu Val Val Glu Ala Tyr Gln Lys Leu
            370                 375                 380

Ile Ser Glu Val Lys Val Gln Val Glu Asn Gln Val Gln Gly Ile Tyr
385                 390                 395                 400

Phe Asn Ile Thr Ala Ile Cys Pro Asp Gly Ser Arg Lys Pro Gly Met
                    405                 410                 415

Glu Gly Cys Arg Asn Val Thr Ser Asn Asp Glu Val Leu Phe Asn Val
                420                 425                 430

Thr Val Thr Met Lys Lys Cys Asp Val Thr Gly Gly Lys Asn Tyr Ala
                435                 440                 445

Ile Ile Lys Pro Ile Gly Phe Asn Glu Thr Ala Lys Ile His Ile His
            450                 455                 460

Arg Asn Cys Ser Cys Gln Cys Glu Asp Asn Arg Gly Pro Lys Gly Lys
465                 470                 475                 480

Cys Val Asp Glu Thr Phe Leu Asp Ser Lys Cys Phe Gln Cys Asp Glu
                    485                 490                 495

Asn Lys Cys His Phe Asp Glu Asp Gln Phe Ser Ser Glu Ser Cys Lys
                500                 505                 510

Ser His Lys Asp Gln Pro Val Cys Ser Gly Arg Gly Val Cys Val Cys
            515                 520                 525

Gly Lys Cys Ser Cys His Lys Ile Lys Leu Gly Lys Val Tyr Gly Lys
            530                 535                 540

Tyr Cys Glu Lys Asp Asp Phe Ser Cys Pro Tyr His His Gly Asn Leu
545                 550                 555                 560

Cys Ala Gly His Gly Glu Cys Glu Ala Gly Arg Cys Gln Cys Phe Ser
                565                 570                 575

Gly Trp Glu Gly Asp Arg Cys Gln Cys Pro Ser Ala Ala Gln His
                580                 585                 590

Cys Val Asn Ser Lys Gly Gln Val Cys Ser Gly Arg Gly Thr Cys Val
                595                 600                 605

Cys Gly Arg Cys Glu Cys Thr Asp Pro Arg Ser Ile Gly Arg Phe Cys
            610                 615                 620

Glu His Cys Pro Thr Cys Tyr Thr Ala Cys Lys Glu Asn Trp Asn Cys
625                 630                 635                 640

Met Gln Cys Leu His Pro His Asn Leu Ser Gln Ala Ile Leu Asp Gln
                645                 650                 655

Cys Lys Thr Ser Cys Ala Leu Met Glu Gln Gln His Tyr Val Asp Gln
            660                 665                 670
```

```
Thr Ser Glu Cys Phe Ser Ser Pro Ser Tyr Leu Arg Ile Phe Phe Ile
            675                 680                 685

Ile Phe Ile Val Thr Phe Leu Ile Gly Leu Leu Lys Val Leu Ile Ile
        690                 695                 700

Arg Gln Val Ile Leu Gln Trp Asn Ser Asn Lys Ile Lys Ser Ser Ser
705                 710                 715                 720

Asp Tyr Arg Val Ser Ala Ser Lys Lys Asp Lys Leu Ile Leu Gln Ser
                725                 730                 735

Val Cys Thr Arg Ala Val Thr Tyr Arg Arg Glu Lys Pro Glu Glu Ile
                740                 745                 750

Lys Met Asp Ile Ser Lys Leu Asn Ala His Glu Thr Phe Arg Cys Asn
                755                 760                 765

Phe

<210> SEQ ID NO 79
<211> LENGTH: 1044
<212> TYPE: PRT
<213> ORGANISM: Artificial Sequence
<220> FEATURE:
<223> OTHER INFORMATION: Synthetic Construct

<400> SEQUENCE: 79

Met Ala Ala Pro Gly Arg Leu Leu Arg Pro Arg Pro Gly Gly Leu
1               5                   10                  15

Leu Leu Leu Leu Pro Gly Leu Leu Pro Leu Ala Asp Ala Phe Asn
                20                  25                  30

Leu Asp Val Glu Ser Pro Ala Glu Tyr Ala Gly Pro Glu Gly Ser Tyr
            35                  40                  45

Phe Gly Phe Ala Val Asp Phe Phe Glu Pro Ser Thr Ser Ser Arg Met
        50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Glu Cys Ser Ser Ser Arg Arg
                85                  90                  95

Cys Gln Pro Ile Glu Phe Asp Ser Thr Gly Asn Arg Asp Tyr Ala Lys
                100                 105                 110

Asp Asp Pro Leu Glu Phe Lys Ser His Gln Trp Phe Gly Ala Ser Val
                115                 120                 125

Arg Ser Lys Gln Asp Lys Ile Leu Ala Cys Ala Pro Leu Tyr His Trp
            130                 135                 140

Arg Thr Glu Met Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Lys Asn
                165                 170                 175

Ile Asp Ala Asp Gly Gln Gly Phe Cys Gln Gly Gly Phe Ser Ile Asp
                180                 185                 190

Phe Thr Lys Ala Asp Arg Val Leu Leu Gly Gly Pro Gly Ser Phe Tyr
            195                 200                 205

Trp Gln Gly Gln Leu Ile Ser Asp Gln Val Ala Glu Ile Ile Ser Lys
        210                 215                 220

Tyr Asp Pro Asn Val Tyr Ser Ile Lys Tyr Asn Asn Gln Leu Ala Thr
225                 230                 235                 240

Arg Thr Ala Gln Ala Ile Phe Asp Asp Ser Tyr Leu Gly Tyr Ser Val
                245                 250                 255
```

```
Ala Val Gly Asp Phe Asn Gly Asp Gly Ile Glu Asp Phe Val Ser Gly
            260                 265                 270

Val Pro Arg Ala Ala Arg Thr Leu Gly Met Val Tyr Ile Tyr Asp Gly
        275                 280                 285

Lys Asn Met Ser Ser Leu His Asn Phe Thr Gly Glu Gln Met Ala Ala
    290                 295                 300

Tyr Phe Gly Phe Ser Val Ala Ala Thr Asp Ile Asn Gly Asp Asp Tyr
305                 310                 315                 320

Ala Asp Val Phe Ile Gly Ala Pro Leu Phe Met Asp Arg Gly Ser Asp
                325                 330                 335

Gly Lys Leu Gln Glu Val Gly Gln Val Ser Val Ser Leu Gln Arg Ala
            340                 345                 350

Val Gly Asp Phe Gln Thr Thr Lys Leu Asn Gly Phe Glu Val Phe Ala
        355                 360                 365

Arg Phe Gly Ser Ala Ile Ala Pro Leu Gly Asp Leu Asp Gln Asp Gly
    370                 375                 380

Phe Asn Asp Ile Ala Ile Ala Ala Pro Tyr Gly Gly Glu Asp Lys Lys
385                 390                 395                 400

Gly Leu Val Tyr Ile Phe Asn Gly Arg Ser Thr Gly Leu Asn Ser Val
                405                 410                 415

Pro Ser Gln Ile Leu Glu Gly Gln Trp Ala Ala Gln Ser Met Pro Pro
            420                 425                 430

Ser Phe Gly Tyr Ser Met Lys Gly Ala Thr Asp Val Asp Arg Asn Gly
        435                 440                 445

Tyr Pro Asp Leu Val Val Gly Ala Phe Gly Val Asp Arg Ala Val Leu
    450                 455                 460

Tyr Arg Ala Arg Pro Val Val Thr Val Asn Ala Gly Leu Glu Val Tyr
465                 470                 475                 480

Pro Ser Ile Leu Asn Gln Asp Asn Lys Ile Cys Pro Leu Pro Gly Thr
                485                 490                 495

Ala Leu Lys Val Ser Cys Phe Asn Val Arg Phe Cys Leu Lys Ala Asp
            500                 505                 510

Gly Lys Gly Thr Leu Pro Arg Lys Leu His Phe Gln Val Glu Leu Leu
        515                 520                 525

Leu Asp Lys Leu Lys Gln Lys Gly Ala Ile Arg Arg Ala Leu Phe Leu
    530                 535                 540

His Asn Arg Ser Pro Val His Ser Lys Thr Met Thr Val Phe Arg Gly
545                 550                 555                 560

Gly Gln Met Gln Cys Glu Glu Leu Val Ala Tyr Leu Arg Asp Glu Ser
                565                 570                 575

Glu Phe Arg Asp Lys Leu Thr Pro Ile Thr Ile Phe Met Glu Tyr Arg
            580                 585                 590

Leu Asp Gln Arg Thr Ala Ala Asp Ala Thr Gly Leu Gln Pro Ile Leu
        595                 600                 605

Asn Gln Phe Thr Pro Ala Asn Val Ser Arg Gln Ala His Ile Leu Leu
    610                 615                 620

Asp Cys Gly Glu Asp Asn Val Cys Lys Pro Lys Leu Glu Val Ser Val
625                 630                 635                 640

Asn Ser Asp Gln Lys Lys Ile Tyr Ile Gly Asp Asp Asn Pro Leu Thr
                645                 650                 655

Leu Thr Val Lys Ala Gln Asn Gln Gly Glu Gly Ala Tyr Glu Ala Glu
            660                 665                 670

Leu Ile Val Ser Ile Pro Pro Gln Ala Asp Phe Ile Gly Val Val Arg
```

```
                675                 680                 685

Asn Asn Glu Ala Leu Ala Arg Leu Ser Cys Ala Phe Lys Thr Glu Asn
    690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
                725                 730                 735

Met Asp Thr Ser Val Lys Phe Asp Leu Lys Ile Gln Ser Ser Asn Ser
            740                 745                 750

Phe Asp Asn Val Ser Pro Val Ser Tyr Lys Val Asp Leu Ala Val
        755                 760                 765

Leu Ala Ala Val Glu Ile Arg Gly Val Ser Ser Pro Asp His Ile Phe
770                 775                 780

Leu Pro Ile Pro Asn Trp Glu Tyr Lys Glu Asn Pro Glu Thr Glu Glu
785                 790                 795                 800

Asp Val Gly Pro Ile Val Gln His Ile Tyr Glu Leu Arg Asn Asn Gly
                805                 810                 815

Pro Ser Ser Phe Ser Lys Ala Ile Leu Asn Leu Gln Trp Pro Tyr Lys
            820                 825                 830

Tyr Asn Asn Asn Thr Leu Leu Tyr Ile Leu His Tyr Asp Ile Asp Gly
        835                 840                 845

Pro Met Asn Cys Thr Ala Asp Thr Glu Ile Asn Pro Leu Arg Ile Lys
850                 855                 860

Thr Pro Glu Lys Asn Asp Thr Ala Ala Gly Gln Gly Glu Arg Asn
865                 870                 875                 880

His Leu Ile Thr Lys Arg Asp Leu Thr Leu Arg Glu Gly Asp Val His
                885                 890                 895

Thr Leu Gly Cys Gly Ile Ala Lys Cys Leu Gln Ile Thr Cys Gln Val
            900                 905                 910

Gly Arg Leu Asp Arg Gly Lys Ser Ala Ile Leu Tyr Val Lys Ser Leu
        915                 920                 925

Leu Trp Thr Glu Thr Phe Met Asn Lys Glu Asn Gln Asn His Ser Tyr
930                 935                 940

Ser Leu Lys Ser Ser Ala Ser Phe Asn Ile Ile Glu Phe Pro Tyr Lys
945                 950                 955                 960

Asn Leu Pro Ile Glu Asp Leu Phe Asn Ser Thr Leu Val Thr Thr Asn
                965                 970                 975

Ile Thr Trp Gly Ile Gln Pro Ala Pro Met Pro Val Pro Val Trp Val
            980                 985                 990

Ile Ile Leu Ala Val Leu Ala Gly  Leu Leu Leu Ala  Val Leu Val
        995                 1000                 1005

Phe Val  Met Tyr Arg Met Gly  Phe Phe Lys Arg Val  Arg Pro Pro
    1010                 1015                 1020

Gln Glu  Glu Gln Glu Arg Glu  Gln Leu Gln Pro His  Glu Asn Gly
    1025                 1030                 1035

Glu Gly  Asn Ser Glu Thr
    1040

<210> SEQ ID NO 80
<211> LENGTH: 767
<212> TYPE: PRT
<213> ORGANISM: Artificial Sequence
<220> FEATURE:
<223> OTHER INFORMATION: Synthetic Construct
```

-continued

```
<400> SEQUENCE: 80

Met Cys Gly Ser Ala Leu Ala Phe Leu Thr Ala Ala Leu Leu Ser Leu
1               5                   10                  15

His Asn Cys Gln Arg Gly Pro Ala Leu Val Leu Gly Ala Ala Trp Val
            20                  25                  30

Phe Ser Leu Val Leu Gly Leu Gly Gln Ser Glu His Asn Arg Cys Gly
        35                  40                  45

Ser Ala Asn Val Val Ser Cys Ala Arg Cys Leu Gln Leu Gly Pro Glu
    50                  55                  60

Cys Gly Trp Cys Val Gln Glu Asp Phe Val Ser Gly Gly Ser Gly Ser
65                  70                  75                  80

Glu Arg Cys Asp Thr Val Ser Ser Leu Ile Ser Lys Gly Cys Pro Val
                85                  90                  95

Asp Ser Ile Glu Tyr Leu Ser Val His Val Val Thr Ser Ser Glu Asn
            100                 105                 110

Glu Ile Asn Thr Gln Val Thr Pro Gly Glu Val Ser Val Gln Leu His
        115                 120                 125

Pro Gly Ala Glu Ala Asn Phe Met Leu Lys Val Arg Pro Leu Lys Lys
    130                 135                 140

Tyr Pro Val Asp Leu Tyr Tyr Leu Val Asp Val Ser Ala Ser Met His
145                 150                 155                 160

Asn Asn Ile Glu Lys Leu Asn Ser Val Gly Asn Asp Leu Ser Lys Lys
                165                 170                 175

Met Ala Leu Tyr Ser Arg Asp Phe Arg Leu Gly Phe Gly Ser Tyr Val
            180                 185                 190

Asp Lys Thr Val Ser Pro Tyr Ile Ser Ile His Pro Glu Arg Ile His
        195                 200                 205

Asn Gln Cys Ser Asp Tyr Asn Leu Asp Cys Met Pro Pro His Gly Tyr
    210                 215                 220

Ile His Val Leu Ser Leu Thr Glu Asn Ile Thr Glu Phe Glu Lys Ala
225                 230                 235                 240

Val His Arg Gln Lys Ile Ser Gly Asn Ile Asp Thr Pro Glu Gly Gly
                245                 250                 255

Phe Asp Ala Met Leu Gln Ala Ala Val Cys Glu Ser His Ile Gly Trp
            260                 265                 270

Arg Lys Glu Ala Lys Arg Leu Leu Leu Val Met Thr Asp Gln Thr Ser
        275                 280                 285

His Leu Ala Leu Asp Ser Lys Leu Ala Gly Ile Val Val Pro Asn Asp
    290                 295                 300

Gly Asn Cys His Leu Lys Asn Asn Val Tyr Val Lys Ser Thr Thr Met
305                 310                 315                 320

Glu His Pro Ser Leu Gly Gln Leu Ser Glu Lys Leu Ile Asp Asn Asn
                325                 330                 335

Ile Asn Val Ile Phe Ala Val Gln Gly Lys Gln Phe His Trp Tyr Lys
            340                 345                 350

Asp Leu Leu Pro Leu Leu Pro Gly Ala Ile Ala Gly Glu Ile Glu Ser
        355                 360                 365

Lys Ala Ala Asn Leu Asn Asn Leu Val Val Glu Ala Tyr Lys Lys Ile
    370                 375                 380

Ile Ser Glu Val Lys Val Gln Leu Glu Asn Gln Val His Gly Val His
385                 390                 395                 400

Phe Asn Ile Thr Ala Ile Cys Pro Asp Gly Ala Arg Lys Pro Gly Ile
                405                 410                 415
```

```
Ser Gly Cys Gly Asn Val Thr Ser Asn Asp Glu Val Leu Phe Asn Val
            420                 425                 430

Thr Val Val Met Lys Thr Cys Asp Ile Met Gly Gly Lys Asn Tyr Ala
            435                 440                 445

Ile Ile Lys Pro Ile Gly Phe Asn Glu Thr Thr Lys Val His Ile His
450                 455                 460

Arg Ser Cys Ser Cys Gln Cys Glu Asn His Arg Gly Leu Lys Gly Gln
465                 470                 475                 480

Cys Ala Glu Ala Ala Pro Asp Pro Lys Cys Pro Gln Cys Asp Asp Ser
                485                 490                 495

Arg Cys His Phe Asp Glu Asp Gln Phe Pro Ser Glu Thr Cys Lys Pro
                500                 505                 510

Gln Glu Asp Gln Pro Val Cys Ser Gly Arg Gly Val Cys Ile Cys Gly
            515                 520                 525

Lys Cys Leu Cys His Lys Thr Lys Leu Gly Arg Val Tyr Gly Gln Tyr
            530                 535                 540

Cys Glu Lys Asp Asp Phe Ser Cys Pro Tyr Leu His Gly Asp Val Cys
545                 550                 555                 560

Ala Gly His Gly Glu Cys Glu Gly Gly Arg Cys Gln Cys Phe Ser Gly
                565                 570                 575

Trp Glu Gly Asp Arg Cys Gln Cys Pro Ser Ala Ser Ala Gln His Cys
                580                 585                 590

Val Asn Ser Lys Gly Gln Val Cys Ser Gly Arg Gly Thr Cys Val Cys
            595                 600                 605

Gly Arg Cys Glu Cys Thr Asp Pro Arg Ser Ile Gly Arg Leu Cys Glu
            610                 615                 620

His Cys Pro Thr Cys His Leu Ser Cys Ser Glu Asn Trp Asn Cys Leu
625                 630                 635                 640

Gln Cys Leu His Pro His Asn Leu Ser Gln Ala Ala Leu Asp Gln Cys
                645                 650                 655

Lys Ser Ser Cys Ala Val Met Glu Gln His Arg Met Asp Gln Thr Ser
                660                 665                 670

Glu Cys Leu Ser Gly Pro Ser Tyr Leu Arg Ile Phe Phe Ile Ile Phe
            675                 680                 685

Ile Val Thr Phe Leu Ile Gly Leu Leu Lys Val Leu Ile Ile Arg Gln
            690                 695                 700

Val Ile Leu Gln Trp Asn Asn Asn Lys Ile Lys Ser Ser Ser Asp Tyr
705                 710                 715                 720

Arg Met Ser Ala Ser Lys Lys Asp Lys Leu Ile Leu Gln Ser Val Cys
                725                 730                 735

Thr Arg Ala Val Thr Tyr Arg Arg Glu Lys Pro Glu Glu Ile Lys Met
            740                 745                 750

Asp Ile Ser Lys Leu Asn Ala Gln Glu Ala Phe Arg Cys Asn Phe
            755                 760                 765

<210> SEQ ID NO 81
<211> LENGTH: 329
<212> TYPE: PRT
<213> ORGANISM: Artificial Sequence
<220> FEATURE:
<223> OTHER INFORMATION: Synthetic Construct

<400> SEQUENCE: 81

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 82
<211> LENGTH: 330
<212> TYPE: PRT
<213> ORGANISM: Artificial Sequence
<220> FEATURE:
<223> OTHER INFORMATION: Synthetic Construct

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 83
<211> LENGTH: 107
<212> TYPE: PRT
<213> ORGANISM: Artificial Sequence
<220> FEATURE:
<223> OTHER INFORMATION: Synthetic Construct

<400> SEQUENCE: 83

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 84
<211> LENGTH: 1048
<212> TYPE: PRT
<213> ORGANISM: Artificial Sequence
<220> FEATURE:
<223> OTHER INFORMATION: Synthetic Construct

<400> SEQUENCE: 84

```
Met Ala Ser Pro Pro Arg Arg Leu Arg Leu Gly Pro Arg Gly Leu
1               5                   10                  15

Pro Leu Leu Leu Ser Gly Leu Leu Pro Leu Cys Arg Ala Phe Asn
                20                  25                  30

Leu Asp Val Asp Ser Pro Ala Glu Tyr Ser Gly Pro Glu Gly Ser Tyr
                35                  40                  45

Phe Gly Phe Ala Val Asp Phe Phe Val Pro Ser Ala Ser Ser Arg Met
50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
                100                 105                 110

Asp Asp Pro Leu Glu Phe Lys Ser His Gln Trp Phe Gly Ala Ser Val
                115                 120                 125

Arg Ser Lys Gln Asp Lys Ile Leu Ala Cys Ala Pro Leu Tyr His Trp
                130                 135                 140

Arg Thr Glu Leu Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Gln Asp
                165                 170                 175

Ile Asp Ala Asp Gly Gln Gly Phe Cys Gln Gly Gly Phe Ser Ile Asp
                180                 185                 190

Phe Thr Lys Ala Asp Arg Val Leu Leu Gly Gly Pro Gly Ser Phe Tyr
                195                 200                 205

Trp Gln Gly Gln Leu Ile Ser Asp Gln Val Ala Glu Ile Val Ser Lys
                210                 215                 220

Tyr Asp Pro Asn Val Tyr Ser Ile Lys Tyr Asn Asn Gln Leu Ala Thr
225                 230                 235                 240

Arg Thr Ala Gln Ala Ile Phe Asp Asp Ser Tyr Leu Gly Tyr Ser Val
                245                 250                 255

Ala Val Gly Asp Phe Asn Gly Asp Gly Ile Asp Asp Phe Val Ser Gly
                260                 265                 270

Val Pro Arg Ala Ala Arg Thr Leu Gly Met Val Tyr Ile Tyr Asp Gly
                275                 280                 285

Lys Asn Met Ser Ser Ile Tyr Asn Phe Thr Gly Asp Gln Met Ala Ala
                290                 295                 300

Tyr Phe Gly Phe Ser Val Ala Ala Thr Asp Ile Asn Gly Asp Asp Tyr
305                 310                 315                 320

Ala Asp Val Phe Ile Gly Ala Pro Leu Phe Met Asp Arg Gly Ser Asp
                325                 330                 335
```

```
Gly Lys Leu Gln Glu Val Gly Gln Val Ser Val Ser Leu Gln Arg Ala
            340                 345                 350

Ser Gly Asp Phe Gln Thr Thr Lys Leu Asn Gly Phe Glu Val Phe Ala
            355                 360                 365

Arg Phe Gly Ser Ala Ile Ala Pro Leu Gly Asp Leu Asp Gln Asp Gly
370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
                405                 410                 415

Pro Ser Gln Ile Leu Glu Gly Gln Trp Ala Ala Arg Ser Met Pro Pro
            420                 425                 430

Ser Phe Gly Tyr Ser Met Lys Gly Ala Thr Asp Ile Asp Lys Asn Gly
            435                 440                 445

Tyr Pro Asp Leu Ile Val Gly Ala Phe Gly Val Asp Arg Ala Ile Leu
            450                 455                 460

Tyr Arg Ala Arg Pro Val Ile Thr Val Asn Ala Gly Leu Glu Val Tyr
465                 470                 475                 480

Pro Ser Ile Leu Asn Gln Asp Asn Lys Thr Cys Ser Leu Pro Gly Thr
                485                 490                 495

Ala Leu Lys Val Ser Cys Phe Asn Val Arg Phe Cys Leu Lys Ala Asp
            500                 505                 510

Gly Lys Gly Val Leu Pro Arg Lys Leu Asn Phe Gln Val Glu Leu Leu
            515                 520                 525

Leu Asp Lys Leu Lys Gln Lys Gly Ala Ile Arg Arg Ala Leu Phe Leu
            530                 535                 540

Tyr Ser Arg Ser Pro Ser His Ser Lys Asn Met Thr Ile Ser Arg Gly
545                 550                 555                 560

Gly Leu Met Gln Cys Glu Glu Leu Ile Ala Tyr Leu Arg Asp Glu Ser
            565                 570                 575

Glu Phe Arg Asp Lys Leu Thr Pro Ile Thr Ile Phe Met Glu Tyr Trp
            580                 585                 590

Leu Asp Tyr Arg Thr Ala Ala Asp Thr Thr Gly Leu Gln Pro Ile Leu
            595                 600                 605

Asn Gln Phe Thr Pro Ala Asn Ile Ser Arg Gln Ala His Ile Leu Leu
            610                 615                 620

Asp Cys Gly Glu Asp Asn Val Cys Lys Pro Lys Leu Glu Val Phe Val
625                 630                 635                 640

Asp Ser Asp Gln Lys Lys Ile Tyr Ile Gly Asp Asp Asn Pro Leu Thr
                645                 650                 655

Leu Ile Val Lys Ala Gln Asn Gln Gly Glu Gly Ala Tyr Glu Ala Glu
            660                 665                 670

Leu Ile Val Ser Ile Pro Leu Gln Ala Asp Phe Ile Gly Val Val Arg
            675                 680                 685

Asn Ser Glu Ala Leu Ala Arg Leu Ser Cys Ala Phe Lys Thr Glu Asn
            690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
            725                 730                 735

Met Asp Thr Ser Val Lys Phe Asp Leu Gln Ile Gln Ser Ser Asn Leu
            740                 745                 750
```

Phe Asp Lys Val Ser Pro Val Ser His Lys Val Asp Leu Ala Val
            755                 760                 765

Leu Ala Ala Val Glu Ile Arg Gly Val Ser Ser Pro Asp His Ile Phe
        770                 775                 780

Leu Pro Ile Pro Asn Trp Glu His Lys Glu Asn Pro Glu Thr Glu Glu
785                 790                 795                 800

Asp Val Gly Pro Val Val Gln His Ile Tyr Glu Leu Arg Asn Asn Gly
                805                 810                 815

Pro Ser Ser Phe Ser Lys Ala Met Leu His Leu Gln Trp Pro Tyr Lys
            820                 825                 830

Tyr Asn Asn Asn Thr Leu Leu Tyr Ile Leu His Tyr Asp Ile Asp Gly
        835                 840                 845

Pro Met Asn Cys Thr Ser Asp Met Glu Ile Asn Pro Leu Arg Ile Lys
    850                 855                 860

Ile Ser Ser Leu Gln Ala Thr Glu Lys Asn Asp Thr Val Ala Gly Gln
865                 870                 875                 880

Gly Glu Arg Asp His Leu Ile Thr Lys Arg Asp Leu Ala Leu Ser Glu
                885                 890                 895

Gly Asp Ile His Thr Leu Gly Cys Gly Val Ala Gln Cys Leu Lys Ile
            900                 905                 910

Val Cys Gln Val Gly Arg Leu Asp Arg Gly Lys Ser Ala Ile Leu Tyr
        915                 920                 925

Val Lys Ser Leu Leu Trp Thr Glu Thr Phe Met Asn Lys Glu Asn Gln
    930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
                965                 970                 975

Val Thr Thr Asn Val Thr Trp Gly Ile Gln Pro Ala Pro Met Pro Val
            980                 985                 990

Pro Val Trp Val Ile Ile Leu Ala Val Leu Ala Gly Leu Leu Leu Leu
        995                 1000                1005

Ala Val Leu Val Phe Val Met Tyr Arg Met Gly Phe Phe Lys Arg
        1010                1015                1020

Val Arg Pro Pro Gln Glu Glu Gln Glu Arg Glu Gln Leu Gln Pro
        1025                1030                1035

His Glu Asn Gly Glu Gly Asn Ser Glu Thr
        1040                1045

<210> SEQ ID NO 85
<211> LENGTH: 769
<212> TYPE: PRT
<213> ORGANISM: Artificial Sequence
<220> FEATURE:
<223> OTHER INFORMATION: Synthetic Construct

<400> SEQUENCE: 85

Met Cys Gly Ser Ala Leu Ala Phe Phe Thr Ala Ala Phe Val Cys Leu
1               5                   10                  15

Gln Asn Asp Arg Arg Gly Pro Ala Ser Phe Leu Trp Ala Ala Trp Val
            20                  25                  30

Leu Ser Leu Val Leu Gly Leu Gly Gln Gly Glu Asp Asn Ile Cys Ala
        35                  40                  45

Ser Ser Asn Ala Ala Ser Cys Ala Arg Cys Leu Ala Leu Gly Pro Glu
    50                  55                  60

```
Cys Gly Trp Cys Val Gln Glu Asp Phe Ile Ser Gly Gly Ser Arg Ser
 65                  70                  75                  80

Glu Arg Cys Asp Ile Val Ser Asn Leu Ile Ser Lys Gly Cys Ser Val
                 85                  90                  95

Asp Ser Ile Glu Tyr Pro Ser Val His Val Ile Pro Thr Glu Asn
            100                 105                 110

Glu Ile Asn Thr Gln Val Thr Pro Gly Glu Val Ser Ile Gln Leu Arg
            115                 120                 125

Pro Gly Ala Glu Ala Asn Phe Met Leu Lys Ile His Pro Leu Lys Lys
        130                 135                 140

Tyr Pro Val Asp Leu Tyr Tyr Leu Val Asp Val Ser Ala Ser Met His
145                 150                 155                 160

Asn Asn Ile Glu Lys Leu Asn Ser Val Gly Asn Asp Leu Ser Arg Lys
                165                 170                 175

Met Ala Phe Phe Ser Arg Asp Phe Arg Leu Gly Phe Gly Ser Tyr Val
            180                 185                 190

Asp Lys Thr Val Ser Pro Tyr Ile Ser Ile His Pro Glu Arg Ile His
        195                 200                 205

Asn Gln Cys Ser Asp Tyr Asn Leu Asp Cys Met Pro Pro His Gly Tyr
210                 215                 220

Ile His Val Leu Ser Leu Thr Glu Asn Ile Thr Glu Phe Glu Lys Ala
225                 230                 235                 240

Val His Arg Gln Lys Ile Ser Gly Asn Ile Asp Thr Pro Glu Gly Gly
                245                 250                 255

Phe Asp Ala Met Leu Gln Ala Ala Val Cys Glu Ser His Ile Gly Trp
            260                 265                 270

Arg Lys Glu Ala Lys Arg Leu Leu Leu Val Met Thr Asp Gln Thr Ser
        275                 280                 285

His Leu Ala Leu Asp Ser Lys Leu Ala Gly Ile Val Val Pro Asn Asp
    290                 295                 300

Gly Asn Cys His Leu Lys Asn Asn Val Tyr Val Lys Ser Thr Thr Met
305                 310                 315                 320

Glu His Pro Ser Leu Gly Gln Leu Ser Glu Lys Leu Ile Asp Asn Asn
                325                 330                 335

Ile Asn Val Ile Phe Ala Val Gln Gly Lys Gln Phe His Trp Tyr Lys
            340                 345                 350

Asp Leu Leu Pro Leu Leu Pro Gly Thr Ile Ala Gly Glu Ile Glu Ser
        355                 360                 365

Lys Ala Ala Asn Leu Asn Asn Leu Val Val Glu Ala Tyr Gln Lys Leu
370                 375                 380

Ile Ser Glu Val Lys Val His Val Glu Asn Gln Val Gln Gly Val Tyr
385                 390                 395                 400

Phe Asn Ile Thr Ala Ile Cys Pro Asp Gly Ser Arg Lys Pro Gly Met
                405                 410                 415

Glu Gly Cys Arg Asn Val Thr Ser Asn His Glu Val Leu Phe Asn Val
            420                 425                 430

Thr Val Thr Met Lys Lys Cys Asp Val Thr Gly Gly Lys Asn Tyr Ala
        435                 440                 445

Ile Ile Lys Pro Ile Gly Phe Asn Glu Thr Ala Lys Ile His Ile His
    450                 455                 460

Arg Asn Cys Ser Cys Gln Cys Glu Asp Asn Arg Gly Pro Lys Gly Lys
465                 470                 475                 480

Cys Val Asp Glu Thr Phe Leu Asp Ser Lys Cys Phe Gln Cys Asp Glu
```

```
                    485                 490                 495
Asn Lys Cys His Phe Asp Glu Asp Gln Phe Ser Ser Glu Ser Cys Lys
                500                 505                 510

Ser His Lys Asp Gln Pro Val Cys Ser Gly Arg Gly Val Cys Val Cys
            515                 520                 525

Gly Lys Cys Ser Cys His Lys Ile Lys Leu Gly Lys Val Tyr Gly Lys
        530                 535                 540

Tyr Cys Glu Lys Asp Asp Phe Ser Cys Pro Tyr His His Gly Asn Leu
545                 550                 555                 560

Cys Ala Gly His Gly Glu Cys Glu Ala Gly Arg Cys Gln Cys Phe Ser
                565                 570                 575

Gly Trp Glu Gly Asp Arg Cys Gln Cys Pro Ser Ala Ala Ala Gln His
            580                 585                 590

Cys Val Asn Ser Lys Gly Gln Val Cys Ser Gly Arg Gly Thr Cys Val
        595                 600                 605

Cys Gly Arg Cys Glu Cys Thr Asp Pro Arg Ser Ile Gly Arg Phe Cys
        610                 615                 620

Glu His Cys Pro Thr Cys His Thr Ala Cys Lys Glu Asn Trp Asn Cys
625                 630                 635                 640

Val Gln Cys Leu His Pro His Asn Leu Ser Gln Ala Ile Leu Asp Gln
                645                 650                 655

Cys Lys Thr Ser Cys Ala Leu Met Glu Gln Gln His Tyr Val Asp Gln
                660                 665                 670

Thr Ser Glu Cys Phe Ser Ser Pro Ser Tyr Leu Arg Ile Phe Phe Ile
            675                 680                 685

Ile Phe Ile Val Thr Phe Leu Ile Gly Leu Leu Lys Val Leu Ile Ile
        690                 695                 700

Arg Gln Val Ile Leu Gln Trp Asn Ser Asn Lys Ile Lys Ser Ser Ser
705                 710                 715                 720

Asp Tyr Arg Val Ser Ala Ser Lys Lys Asp Lys Leu Ile Leu Gln Ser
                725                 730                 735

Val Cys Thr Arg Ala Val Thr Tyr Arg Arg Glu Lys Pro Glu Glu Ile
            740                 745                 750

Lys Met Asp Ile Ser Lys Leu Asn Ala His Glu Thr Phe Arg Cys Asn
        755                 760                 765

Phe

<210> SEQ ID NO 86
<211> LENGTH: 324
<212> TYPE: PRT
<213> ORGANISM: Artificial Sequence
<220> FEATURE:
<223> OTHER INFORMATION: Synthetic Construct

<400> SEQUENCE: 86

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80
```

```
Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Pro Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Ala Phe Ala Cys Ala Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105
```

<210> SEQ ID NO 88
<211> LENGTH: 115
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Ala Trp Ile Asp Pro Asp Asn Gly Asn Thr Ile Tyr Asp Pro Lys Phe
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 89
<211> LENGTH: 115
<212> TYPE: PRT
<213> ORGANISM: Artificial Sequence
<220> FEATURE:
<223> OTHER INFORMATION: Synthetic Construct

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Ala Trp Ile Asp Pro Asp Asn Gly Asn Thr Ile Tyr Asp Pro Lys Phe
    50                  55                  60

Gln Gly Arg Phe Thr Ile Ser Ala Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 90
<211> LENGTH: 115
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Gln Pro Gly Gly

```
                1               5                  10                  15
Ser Leu Arg Leu Ser Cys Ala Ala Ser Gly Phe Asn Ile Lys Asp Tyr
                20                  25                  30

Tyr Met Asn Trp Val Arg Gln Ala Pro Gly Lys Gly Leu Glu Trp Val
            35                  40                  45

Gly Trp Ile Asp Pro Asp Asn Gly Asn Thr Ile Tyr Asp Pro Lys Phe
        50                  55                  60

Gln Gly Arg Phe Thr Ile Ser Ala Asp Asn Ala Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
                100                 105                 110

Val Ser Ser
        115
```

<210> SEQ ID NO 91
<211> LENGTH: 115
<212> TYPE: PRT
<213> ORGANISM: Artificial Sequence
<220> FEATURE:
<223> OTHER INFORMATION: Synthetic Construct

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
                20                  25                  30

Tyr Met Asn Trp Val Arg Gln Ala Pro Gly Lys Gly Leu Glu Trp Val
            35                  40                  45

Ala Trp Ile Asp Pro Asp Asn Gly Asn Thr Ile Tyr Asp Pro Lys Phe
        50                  55                  60

Gln Gly Arg Phe Thr Ile Ser Ala Asp Thr Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
                100                 105                 110

Val Ser Ser
        115
```

<210> SEQ ID NO 92
<211> LENGTH: 112
<212> TYPE: PRT
<213> ORGANISM: Artificial Sequence
<220> FEATURE:
<223> OTHER INFORMATION: Synthetic Construct

<400> SEQUENCE: 92

```
Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
                20                  25                  30

Asn Gly Asn Thr Tyr Leu Phe Trp Phe Gln Gln Lys Pro Gly Lys Ala
            35                  40                  45

Pro Lys Arg Leu Ile Tyr Tyr Met Ser Asn Leu Ala Ser Gly Val Pro
        50                  55                  60
```

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
                85                  90                  95

Leu Glu Tyr Pro Phe Thr Phe Gly Gln Gly Thr Lys Val Glu Ile Lys
            100                 105                 110

<210> SEQ ID NO 93
<211> LENGTH: 115
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Gln Gly Asn Thr Ile Tyr Glu Pro Lys Val
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser
        115

<210> SEQ ID NO 94
<211> LENGTH: 15
<212> TYPE: PRT
<213> ORGANISM: Artificial Sequence
<220> FEATURE:
<223> OTHER INFORMATION: Synthetic Construct

<400> SEQUENCE: 94

Glu Pro Lys Phe Gln Gly Arg Phe Thr Ile Ser Ala Asp Thr Ser
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic Construct

<400> SEQUENCE: 95

Thr Ala Val Tyr Tyr Cys Ala Arg Arg Leu Leu Met Asp Tyr Trp
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)

<223> OTHER INFORMATION: Xaa can be any naturally occurring amino acid

<400> SEQUENCE: 96

Thr Ala Val Tyr Tyr Ser Ala Arg Arg Leu Leu Xaa Asp Tyr Trp
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic Construct

<400> SEQUENCE: 97

Lys Ser Leu Leu His Phe Asn Gly Asn Thr Tyr Leu Phe Trp Tyr
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic Construct

<400> SEQUENCE: 98

Pro Lys Arg Leu Ile Tyr Tyr Met Ser Asn Leu Ala Ser Gly Val
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 99

Pro Lys Arg Leu Ile Tyr Tyr Xaa Ser Asn Leu Ala Ser Gly Val
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic Construct

<400> SEQUENCE: 100

Leu Ile Tyr Tyr Met Ser Asn Leu Ala Ser Gly Val Pro Ser Arg
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid

<400> SEQUENCE: 101

Leu Ile Tyr Tyr Xaa Ser Asn Leu Ala Ser Gly Val Pro Ser Arg
1               5                   10                  15

```
<210> SEQ ID NO 102
<211> LENGTH: 15
<212> TYPE: PRT
<213> ORGANISM: Artificial Sequence
<220> FEATURE:
<223> OTHER INFORMATION: Synthetic Construct

<400> SEQUENCE: 102

Phe Ala Thr Tyr Tyr Cys Met Gln Ser Leu Glu Tyr Pro Phe Thr
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa can be any naturally occurring amino acid

<400> SEQUENCE: 103

Phe Ala Thr Tyr Tyr Ser Xaa Gln Ser Leu Glu Tyr Pro Phe Thr
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic Construct

<400> SEQUENCE: 104

Glu Tyr Pro Phe Thr Phe Gly Gln Gly Thr Lys Val Glu Ile Lys
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic Construct

<400> SEQUENCE: 105

Glu Pro Lys Val Gln Gly Arg Phe Thr Ile Ser Ala Asp Thr Ser
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic Construct

<400> SEQUENCE: 106

Lys Ser Leu Ser His Phe Asn Gly Asn Thr Tyr Leu Phe Trp Tyr
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic Construct

<400> SEQUENCE: 107
```

```
Phe Ala Thr Tyr Tyr Cys Gln Gln Ser Leu Glu Tyr Pro Phe Thr
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic Construct

<400> SEQUENCE: 108

Phe Ala Thr Tyr Tyr Ser Gln Gln Ser Leu Glu Tyr Pro Phe Thr
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic Construct

<400> SEQUENCE: 109

Phe Ala Thr Tyr Tyr Cys Met Gln Ser Tyr Glu Tyr Pro Phe Thr
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa can be any naturally occurring amino acid

<400> SEQUENCE: 110

Phe Ala Thr Tyr Tyr Ser Xaa Gln Ser Tyr Glu Tyr Pro Phe Thr
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic Construct

<400> SEQUENCE: 111

Glu Tyr Pro Phe Thr Phe Gly Gly Gly Thr Lys Val Glu Ile Lys
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic Construct

<400> SEQUENCE: 112

Lys Arg Leu Ile Tyr Tyr Ala Ser Asn Leu Ala Ser Gly Val Pro
1               5                   10                  15

<210> SEQ ID NO 113
<211> LENGTH: 15
<212> TYPE: PRT
<213> ORGANISM: Artificial Sequence
<220> FEATURE:
```

```
<223> OTHER INFORMATION: Synthetic Construct

<400> SEQUENCE: 113

Lys Arg Leu Ile Tyr Tyr Met Ser Ser Leu Ala Ser Gly Val Pro
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa can be any naturally occurring amino acid

<400> SEQUENCE: 114

Lys Arg Leu Ile Tyr Tyr Xaa Ser Ser Leu Ala Ser Gly Val Pro
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic Construct

<400> SEQUENCE: 115

Gln Gly Asp Ser Leu Arg Thr Tyr Tyr Ala Ser Trp Tyr Gln Gln
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic Construct

<400> SEQUENCE: 116

Val Leu Val Ile Tyr Gly Lys His Lys Arg Pro Ser Gly Ile Pro
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic Construct

<400> SEQUENCE: 117

Glu Ala Asp Tyr Tyr Cys Met Ser Arg Ser Ile Trp Gly Asn Pro
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa can be any naturally occurring amino acid

<400> SEQUENCE: 118

Glu Ala Asp Tyr Tyr Ser Xaa Ser Arg Ser Ile Trp Gly Asn Pro
1               5                   10                  15
```

```
<210> SEQ ID NO 119
<211> LENGTH: 15
<212> TYPE: PRT
<213> ORGANISM: Artificial Sequence
<220> FEATURE:
<223> OTHER INFORMATION: Synthetic Construct

<400> SEQUENCE: 119

Ser Glu Thr Leu Ser Leu Thr Cys Ala Val Ser Gly Tyr Ser Thr
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic Construct

<400> SEQUENCE: 120

Gly Leu Glu Trp Ile Gly Ser Ile Ser His Thr Gly Asn Thr Tyr
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Synthetic Construct

<400> SEQUENCE: 121

Asn Pro Pro Leu Lys Ser Arg Val Thr Ile Ser Val Asp Thr Ser
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Synthetic Construct

<400> SEQUENCE: 122

Asp Thr Ala Val Val Tyr Cys Ala Arg Gly Gly Gly Ile Ser Arg
1               5                   10                  15

<210> SEQ ID NO 123
<211> LENGTH: 219
<212> TYPE: PRT
<213> ORGANISM: Artificial Sequence
<220> FEATURE:
<223> OTHER INFORMATION: Synthetic Construct

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Phe
                20                  25                  30

Asn Gly Asn Thr Tyr Leu Phe Trp Tyr Gln Gln Lys Pro Gly Lys Ala
            35                  40                  45

Pro Lys Arg Leu Ile Tyr Tyr Met Ser Asn Leu Ala Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Ser
```

```
                85                  90                  95
Leu Glu Tyr Pro Phe Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 124
<211> LENGTH: 445
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Asn Gly Asn Thr Ile Tyr Asp Pro Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
```

```
                225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 125
<211> LENGTH: 23
<212> TYPE: PRT
<213> ORGANISM: Artificial Sequence
<220> FEATURE:
<223> OTHER INFORMATION: Synthetic Construct

<400> SEQUENCE: 125

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 126
<211> LENGTH: 23
<212> TYPE: PRT
<213> ORGANISM: Artificial Sequence
<220> FEATURE:
<223> OTHER INFORMATION: Synthetic Construct

<400> SEQUENCE: 126

Glu Pro Lys Ser Cys Asp Lys Thr His Thr Cys Pro Pro Cys Pro Ala
1               5                   10                  15

Pro Glu Ala Ala Gly Ala Pro
            20

<210> SEQ ID NO 127
<211> LENGTH: 98
<212> TYPE: PRT
<213> ORGANISM: Artificial Sequence
<220> FEATURE:
```

<223> OTHER INFORMATION: Synthetic Construct

<400> SEQUENCE: 127

Glu Val Gln Leu Val Glu Ser Gly Gly Gly Leu Val Gln Pro Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 128
<211> LENGTH: 95
<212> TYPE: PRT
<213> ORGANISM: Artificial Sequence
<220> FEATURE:
<223> OTHER INFORMATION: Synthetic Construct

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 129
<211> LENGTH: 13
<212> TYPE: PRT
<213> ORGANISM: Artificial Sequence
<220> FEATURE:
<223> OTHER INFORMATION: Synthetic Construct

<400> SEQUENCE: 129

Pro Lys Tyr Val Lys Gln Asn Thr Leu Lys Leu Ala Thr
1               5                   10

<210> SEQ ID NO 130
<211> LENGTH: 16
<212> TYPE: PRT
<213> ORGANISM: Artificial Sequence
<220> FEATURE:
<223> OTHER INFORMATION: Synthetic Construct

<400> SEQUENCE: 130

Ala Gln Tyr Ile Lys Ala Asn Ser Lys Phe Ile Gly Ile Thr Glu Leu
1               5                   10                  15

```
<210> SEQ ID NO 131
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 131

Trp Ile Asp Pro Asp Xaa Gly Asn Thr Ile Tyr Xaa Pro Lys Phe Gln
1               5                   10                  15

Gly

<210> SEQ ID NO 132
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa can be any naturally occurring amino acid

<400> SEQUENCE: 132

Arg Ser Thr Lys Ser Leu Xaa His Phe Asn Gly Asn Thr Tyr Leu Phe
1               5                   10                  15

<210> SEQ ID NO 133
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid

<400> SEQUENCE: 133

Tyr Tyr Met Ser Xaa Leu Ala Ser
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 134

Xaa Gln Ser Leu Glu Tyr Pro Phe Thr
1               5

<210> SEQ ID NO 135
<211> LENGTH: 8
<212> TYPE: PRT
<213> ORGANISM: Artificial Sequence
<220> FEATURE:
```

<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid

<400> SEQUENCE: 135

Trp Ile Asp Pro Asp Xaa Gly Asn
1               5

<210> SEQ ID NO 136
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid

<400> SEQUENCE: 136

Ser Thr Lys Ser Leu Xaa His Phe Asn Gly Asn Thr Tyr Leu
1               5                   10

<210> SEQ ID NO 137
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid

<400> SEQUENCE: 137

Tyr Tyr Met Ser Xaa
1               5

<210> SEQ ID NO 138
<211> LENGTH: 16
<212> TYPE: PRT
<213> ORGANISM: Artificial Sequence
<220> FEATURE:
<223> OTHER INFORMATION: Synthetic Construct

<400> SEQUENCE: 138

Arg Ser Thr Lys Ser Ile Leu His Phe Asn Gly Asn Thr Tyr Leu Phe
1               5                   10                  15

<210> SEQ ID NO 139
<211> LENGTH: 14
<212> TYPE: PRT
<213> ORGANISM: Artificial Sequence
<220> FEATURE:
<223> OTHER INFORMATION: Synthetic Construct

<400> SEQUENCE: 139

Ser Thr Lys Ser Ile Leu His Phe Asn Gly Asn Thr Tyr Leu
1               5                   10

<210> SEQ ID NO 140
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 140

Arg Ser Thr Lys Ser Leu Leu His Phe Asn Gly Asn Ser Tyr Leu Phe
1               5                   10                  15

<210> SEQ ID NO 141
<211> LENGTH: 14
<212> TYPE: PRT
<213> ORGANISM: Artificial Sequence
<220> FEATURE:
<223> OTHER INFORMATION: Synthetic Construct

<400> SEQUENCE: 141

Ser Thr Lys Ser Leu Leu His Phe Asn Gly Asn Ser Tyr Leu
1               5                   10

<210> SEQ ID NO 142
<211> LENGTH: 8
<212> TYPE: PRT
<213> ORGANISM: Artificial Sequence
<220> FEATURE:
<223> OTHER INFORMATION: Synthetic Construct

<400> SEQUENCE: 142

Tyr Ala Met Ser Asn Leu Ala Ser
1               5

<210> SEQ ID NO 143
<211> LENGTH: 5
<212> TYPE: PRT
<213> ORGANISM: Artificial Sequence
<220> FEATURE:
<223> OTHER INFORMATION: Synthetic Construct

<400> SEQUENCE: 143

Tyr Ala Met Ser Asn
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic Construct

<400> SEQUENCE: 144

Tyr Tyr Ala Ser Asn Leu Ala Ser
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic Construct

<400> SEQUENCE: 145

Tyr Tyr Ala Ser Asn
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic Construct

<400> SEQUENCE: 146
```

Tyr Tyr Met Ser Asn Leu Gln Ser
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic Construct

<400> SEQUENCE: 147

Met Gln Ser Tyr Glu Tyr Pro Phe Thr
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic Construct

<400> SEQUENCE: 148

Gln Ser Tyr Glu Tyr Pro Phe Thr
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic Construct

<400> SEQUENCE: 149

Met Gln Ser Leu Ser Tyr Pro Phe Thr
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic Construct

<400> SEQUENCE: 150

Gln Ser Leu Ser Tyr Pro Phe Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Construct

<400> SEQUENCE: 151

Met Gln Ser Leu Glu Thr Pro Phe Thr
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic Construct

<400> SEQUENCE: 152

Gln Ser Leu Glu Thr Pro Phe Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Met Gln Ser Leu Glu Tyr Pro Leu Thr
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic Construct

<400> SEQUENCE: 154

Gln Ser Leu Glu Tyr Pro Leu Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic Construct

<400> SEQUENCE: 155

Met Gln Ser Leu Glu Tyr Pro Trp Thr
1               5

<210> SEQ ID NO 156
<211> LENGTH: 8
<212> TYPE: PRT
<213> ORGANISM: Artificial Sequence
<220> FEATURE:
<223> OTHER INFORMATION: Synthetic Construct

<400> SEQUENCE: 156

Gln Ser Leu Glu Tyr Pro Trp Thr
1               5

<210> SEQ ID NO 157
<211> LENGTH: 17
<212> TYPE: PRT
<213> ORGANISM: Artificial Sequence
<220> FEATURE:
<223> OTHER INFORMATION: Synthetic Construct

<400> SEQUENCE: 157

Trp Ile Asp Pro Asp Asn Gly Asn Thr Ile Tyr Asp Gln Lys Phe Gln
1               5                   10                  15

Gly

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct

<400> SEQUENCE: 158

```
Trp Ile Asp Pro Asp Asn Gly Asn Thr Ile Tyr Asp Asp Ser Val Lys
1               5                   10                  15

Gly

<210> SEQ ID NO 159
<211> LENGTH: 10
<212> TYPE: PRT
<213> ORGANISM: Artificial Sequence
<220> FEATURE:
<223> OTHER INFORMATION: Synthetic Construct

<400> SEQUENCE: 159

Gly Phe Asn Ile Ala Asp Tyr Tyr Met Asn
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Synthetic Construct

<400> SEQUENCE: 160

Trp Ile Asp Pro Asp Asn Gly Asn Thr Ile Tyr Glu Pro Lys Phe Gln
1               5                   10                  15

Gly

<210> SEQ ID NO 161
<211> LENGTH: 17
<212> TYPE: PRT
<213> ORGANISM: Artificial Sequence
<220> FEATURE:
<223> OTHER INFORMATION: Synthetic Construct

<400> SEQUENCE: 161

Trp Ile Asp Pro Asp Gln Gly Asn Thr Ile Tyr Asp Pro Lys Phe Gln
1               5                   10                  15

Gly

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Trp Ile Asp Pro Asp Asn Gly Gln Thr Ile Tyr Asp Pro Lys Phe Gln
1               5                   10                  15

Gly

<210> SEQ ID NO 163
<211> LENGTH: 17
<212> TYPE: PRT
<213> ORGANISM: Artificial Sequence
<220> FEATURE:
<223> OTHER INFORMATION: Synthetic Construct

<400> SEQUENCE: 163

Trp Ile Asp Pro Asp Asn Gly Asn Thr Ile Tyr Asp Ala Lys Phe Gln
1               5                   10                  15

Gly
```

```
<210> SEQ ID NO 164
<211> LENGTH: 8
<212> TYPE: PRT
<213> ORGANISM: Artificial Sequence
<220> FEATURE:
<223> OTHER INFORMATION: Synthetic Construct

<400> SEQUENCE: 164

Trp Ile Asp Pro Asp Asn Gly Gln
1               5

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165

Trp Ile Asp Pro Asp Asn Gly Asn Thr Ile Tyr Asp Pro Ala Phe Gln
1               5                   10                  15

Gly

<210> SEQ ID NO 166
<211> LENGTH: 17
<212> TYPE: PRT
<213> ORGANISM: Artificial Sequence
<220> FEATURE:
<223> OTHER INFORMATION: Synthetic Construct

<400> SEQUENCE: 166

Trp Ile Asp Pro Asp Gln Gly Asn Thr Ile Tyr Glu Pro Lys Val Gln
1               5                   10                  15

Gly

<210> SEQ ID NO 167
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid

<400> SEQUENCE: 167

Trp Ile Asp Pro Asp Xaa Gly Xaa Thr Ile Tyr Xaa Xaa Xaa Xaa Xaa
1               5                   10                  15

Gly

<210> SEQ ID NO 168
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (6)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 168

Arg Ser Thr Lys Ser Xaa Xaa His Phe Asn Gly Asn Xaa Tyr Leu Phe
1               5                   10                  15

<210> SEQ ID NO 169
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 169

Tyr Xaa Xaa Ser Xaa Leu Xaa Ser
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 170

Xaa Gln Ser Xaa Xaa Xaa Pro Xaa Thr
1               5

<210> SEQ ID NO 171
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
```

```
<222> LOCATION: (15)..(15)
<223> OTHER INFORMATION: Xaa can be any naturally occurring amino acid

<400> SEQUENCE: 171

Trp Ile Asp Pro Asp Xaa Gly Asn Thr Ile Tyr Xaa Pro Lys Xaa Gln
1               5                   10                  15

Gly

<210> SEQ ID NO 172
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa can be any naturally occurring amino acid

<400> SEQUENCE: 172

Arg Ser Thr Lys Ser Leu Xaa His Phe Asn Gly Asn Thr Tyr Leu Phe
1               5                   10                  15

<210> SEQ ID NO 173
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 173

Tyr Tyr Xaa Ser Xaa Leu Ala Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 174

Xaa Gln Ser Xaa Glu Tyr Pro Phe Thr
1               5

<210> SEQ ID NO 175
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
```

```
<223> OTHER INFORMATION: Xaa can be any naturally occurring amino acid

<400> SEQUENCE: 175

Gly Phe Asn Ile Xaa Asp Tyr Tyr Met Asn
1               5                   10

<210> SEQ ID NO 176
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 176

Trp Ile Asp Pro Asp Xaa Gly Xaa
1               5

<210> SEQ ID NO 177
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 177

Ser Thr Lys Ser Xaa Xaa His Phe Asn Gly Asn Xaa Tyr Leu
1               5                   10

<210> SEQ ID NO 178
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 178

Tyr Xaa Xaa Ser Xaa
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 179

Tyr Tyr Xaa Ser Xaa
1               5

<210> SEQ ID NO 180
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 180

Gln Ser Xaa Glu Tyr Pro Phe Thr
1               5

<210> SEQ ID NO 181
<211> LENGTH: 330
<212> TYPE: PRT
<213> ORGANISM: Artificial Sequence
<220> FEATURE:
<223> OTHER INFORMATION: Synthetic Construct

<400> SEQUENCE: 181

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 182
<211> LENGTH: 444
<212> TYPE: PRT
<213> ORGANISM: Artificial Sequence
<220> FEATURE:
<223> OTHER INFORMATION: Synthetic Construct

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30

Tyr Met Asn Trp Val Arg Gln Ala Pro Gly Lys Gly Leu Glu Trp Val
        35                  40                  45

Gly Trp Ile Asp Pro Asp Asn Gly Asn Thr Ile Tyr Asp Pro Lys Phe
    50                  55                  60

Gln Gly Arg Phe Thr Ile Ser Ala Asp Thr Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Leu Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
```

```
                  245                 250                 255
Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 183
<211> LENGTH: 1389
<212> TYPE: DNA
<213> ORGANISM: Artificial Sequence
<220> FEATURE:
<223> OTHER INFORMATION: Synthetic Construct

<400> SEQUENCE: 183
atgggatgga gctgtatcat cctcttcttg gtagcaacag ctacaggcgt gcactccgag     60
gtgcagctgg tggaaagcgg aggaggcctg gtgcagcctg aggaagcct gaggctgagc    120 tgtgccgcca gcggcttcaa catcaaggac tactacatga actgggtgag gcaggccct    180 ggcaaaggac tggagtgggt gggctggatc gaccccgacc agggcaacac catctacgag    240
cccaagttcc agggcaggtt caccatcagc gccgacacca gcaagaacag cgcctacctg    300
cagatgaact ccctgagggc cgaggacacc gccgtgtact actgcgccag gaggctgctg    360
atggactact ggggccaggg cacactggtc accgtctcct cagcctccac caagggccca    420
tcggtcttcc ccctggcacc ctcctccaag agcacctctg ggggcacagc ggccctgggc    480
tgcctggtca aggactactt ccccgaaccg gtgacggtgt cgtggaactc aggcgccctg    540
accagcggcg tgcacacctt cccggctgtc ctacagtcct caggactcta ctccctcagc    600
agcgtggtga ccgtgccctc agcagcttg gcacccaga cctacatctg caacgtgaat    660
cacaagccca gcaacaccaa ggtggacaag aaagttgagc ccaaatcttg tgacaaaact    720
cacacatgcc caccgtgccc agcacctgaa gccgctgggg gaccgtcagt cttcctcttc    780
cccccaaaac ccaaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
```

```
agcgtcctca ccgtcctgca ccaggactgg ctgaatggca aggagtacaa gtgcaaggtc    1020
tccaacaaag ccctcccagc ccccatcgag aaaaccatct ccaaagccaa agggcagccc    1080
cgagaaccac aggtgtacac cctgccccca tcccgggagg agatgaccaa gaaccaggtc    1140
agcctgacct gcctggtcaa aggcttctat cccagcgaca tcgccgtgga gtgggagagc    1200
aatgggcagc cggagaacaa ctacaagacc acgcctcccg tgctggactc cgacggctcc    1260
ttcttcctct atagcaagct caccgtggac aagagcaggt ggcagcaggg gaacgtcttc    1320
tcatgctccg tgatgcatga ggctctgcac aaccactaca cgcagaagag cctctccctg    1380
tcccccgga                                                             1389
```

<210> SEQ ID NO 184
<211> LENGTH: 329
<212> TYPE: PRT
<213> ORGANISM: Artificial Sequence
<220> FEATURE:
<223> OTHER INFORMATION: Synthetic Construct

<400> SEQUENCE: 184

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

|  | 275 | | | | 280 | | | | 285 | | | |
|---|---|---|---|---|---|---|---|---|---|---|---|---|
| Leu | Tyr | Ser | Lys | Leu | Thr | Val | Asp | Lys | Ser | Arg | Trp | Gln | Gln | Gly | Asn |
| | | | | 290 | | | | | 295 | | | | | 300 | |

| Val | Phe | Ser | Cys | Ser | Val | Met | His | Glu | Ala | Leu | His | Asn | His | Tyr | Thr |
|---|---|---|---|---|---|---|---|---|---|---|---|---|---|---|---|
| 305 | | | | | 310 | | | | | 315 | | | | | 320 |

Gln Lys Ser Leu Ser Leu Ser Pro Gly
            325

<210> SEQ ID NO 185
<211> LENGTH: 657
<212> TYPE: DNA
<213> ORGANISM: Artificial Sequence
<220> FEATURE:
<223> OTHER INFORMATION: Synthetic Construct

<400> SEQUENCE: 185

```
gacatccaga tgacccagtc cccttccagc ctgagcgctt ccgtgggcga cagggtgacc      60
atcacctgca ggtccaccaa gtccctgtcc cacttcaacg gcaacaccta cctgttctgg     120
taccagcaga agcccggcaa ggcccccaag aggctgatct actacatgtc ctccctggcc     180
tccggagtgc cctccaggtt ctccggatcc ggctccggca ccgacttcac cctgaccatc     240
tcctccctgc agcccgagga tttcgccacc tactactgcc agcagtccct ggagtacccc     300
ttcaccttcg gcggcggcac caaggtggag atcaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657
```

<210> SEQ ID NO 186
<211> LENGTH: 336
<212> TYPE: DNA
<213> ORGANISM: Artificial Sequence
<220> FEATURE:
<223> OTHER INFORMATION: Synthetic Construct

<400> SEQUENCE: 186

```
gacatccaga tgacccagtc cccttccagc ctgagcgctt ccgtgggcga cagggtgacc      60
atcacctgca ggtccaccaa gtccctgtcc cacttcaacg gcaacaccta cctgttctgg     120
taccagcaga agcccggcaa ggcccccaag aggctgatct actacatgtc ctccctggcc     180
tccggagtgc cctccaggtt ctccggatcc ggctccggca ccgacttcac cctgaccatc     240
tcctccctgc agcccgagga tttcgccacc tactactgcc agcagtccct ggagtacccc     300
ttcaccttcg gcggcggcac caaggtggag atcaaa                               336
```

<210> SEQ ID NO 187
<211> LENGTH: 57
<212> TYPE: DNA
<213> ORGANISM: Artificial Sequence
<220> FEATURE:
<223> OTHER INFORMATION: Synthetic Construct

<400> SEQUENCE: 187

```
atgggatgga gctgtatcat cctcttcttg gtagcaacag ctacaggcgt gcactcc         57
```

<210> SEQ ID NO 188

```
<211> LENGTH: 19
<212> TYPE: PRT
<213> ORGANISM: Artificial Sequence
<220> FEATURE:
<223> OTHER INFORMATION: Synthetic Construct

<400> SEQUENCE: 188

Met Gly Trp Ser Cys Ile Ile Leu Phe Leu Val Ala Thr Ala Thr Gly
1               5                   10                  15

Val His Ser

<210> SEQ ID NO 189
<211> LENGTH: 1335
<212> TYPE: DNA
<213> ORGANISM: Artificial Sequence
<220> FEATURE:
<223> OTHER INFORMATION: Synthetic Construct

<400> SEQUENCE: 189
gaggtgcagc tggtggaaag cggaggaggc ctggtgcagc ctggaggaag cctgaggctg      60
agctgtgccg ccagcggctt caacatcaag gactactaca tgaactgggt gaggcaggcc     120
cctggcaaag gactggagtg ggtgggctgg atcgaccccg accagggcaa caccatctac     180
gagcccaagt tccagggcag gttcaccatc agcgccgaca ccagcaagaa cagcgcctac     240
ctgcagatga actccctgag ggccgaggac accgccgtgt actactgcgc caggaggctg     300
ctgatggact actggggcca gggcacactg gtcaccgtct cctcagcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagccgctg ggcaccgtc agtcttcctc     720 ttccccccaa acccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca agccctccc agccccatc gagaaaacca tctccaaagc caaagggcag    1020
ccccgagaac cacaggtgta caccctgccc ccatcccggg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtcccccg gaaaa                                                     1335

<210> SEQ ID NO 190
<211> LENGTH: 345
<212> TYPE: DNA
<213> ORGANISM: Artificial Sequence
<220> FEATURE:
<223> OTHER INFORMATION: Synthetic Construct

<400> SEQUENCE: 190
```

| | |
|---|---|
| gaggtgcagc tggtggaaag cggaggaggc ctggtgcagc tggaggaag cctgaggctg | 60 |
| agctgtgccg ccagcggctt caacatcaag gactactaca tgaactgggt gaggcaggcc | 120 |
| cctggcaaag gactggagtg ggtgggctgg atcgaccccg accagggcaa caccatctac | 180 |
| gagcccaagt tccagggcag gttcaccatc agcgccgaca ccagcaagaa cagcgcctac | 240 |
| ctgcagatga actccctgag ggccgaggac accgccgtgt actactgcgc caggaggctg | 300 |
| ctgatggact actggggcca gggcacactg gtcaccgtct cctca | 345 |

<210> SEQ ID NO 191
<211> LENGTH: 1332
<212> TYPE: DNA
<213> ORGANISM: Artificial Sequence
<220> FEATURE:
<223> OTHER INFORMATION: Synthetic Construct

<400> SEQUENCE: 191

| | |
|---|---|
| gaggtgcagc tggtggaaag cggaggaggc ctggtgcagc tggaggaag cctgaggctg | 60 |
| agctgtgccg ccagcggctt caacatcaag gactactaca tgaactgggt gaggcaggcc | 120 |
| cctggcaaag gactggagtg ggtgggctgg atcgaccccg accagggcaa caccatctac | 180 |
| gagcccaagt tccagggcag gttcaccatc agcgccgaca ccagcaagaa cagcgcctac | 240 |
| ctgcagatga actccctgag ggccgaggac accgccgtgt actactgcgc caggaggctg | 300 |
| ctgatggact actggggcca gggcacactg gtcaccgtct cctcagcctc caccaagggc | 360 |
| ccatcggtct tccccctggc accctcctcc aagagcacct ctgggggcac agcggccctg | 420 |
| ggctgcctgg tcaaggacta cttccccgaa ccggtgacgg tgtcgtggaa ctcaggcgcc | 480 |
| ctgaccagcg gcgtgcacac cttcccggct gtcctacagt cctcaggact ctactccctc | 540 |
| agcagcgtgg tgaccgtgcc ctccagcagc ttgggcaccc agacctacat ctgcaacgtg | 600 |
| aatcacaagc ccagcaacac caaggtggac aagaaagttg agcccaaatc ttgtgacaaa | 660 |
| actcacacat gcccaccgtg cccagcacct gaagccgctg ggcaccgtc agtcttcctc | 720 |
| ttccccccaa aacccaagga caccctcatg atctcccgga cccctgaggt cacatgcgtg | 780 |
| gtggtggacg tgagccacga agaccctgag gtcaagttca actggtacgt ggacggcgtg | 840 |
| gaggtgcata atgccaagac aaagccgcgg gaggagcagt acaacagcac gtaccgtgtg | 900 |
| gtcagcgtcc tcaccgtcct gcaccaggac tggctgaatg gcaaggagta caagtgcaag | 960 |
| gtctccaaca aagccctccc agcccccatc gagaaaacca tctccaaagc caaagggcag | 1020 |
| ccccgagaac acaggtgta caccctgccc ccatcccggg aggagatgac caagaaccag | 1080 |
| gtcagcctga cctgcctggt caaaggcttc tatcccagcg acatcgccgt ggagtgggag | 1140 |
| agcaatgggc agccggagaa caactacaag accacgcctc ccgtgctgga ctccgacggc | 1200 |
| tccttcttcc tctatagcaa gctcaccgtg gacaagagca ggtggcagca ggggaacgtc | 1260 |
| ttctcatgct ccgtgatgca tgaggctctg cacaaccact acacgcagaa gagcctctcc | 1320 |
| ctgtccccg ga | 1332 |

<210> SEQ ID NO 192
<211> LENGTH: 987
<212> TYPE: DNA
<213> ORGANISM: Artificial Sequence
<220> FEATURE:
<223> OTHER INFORMATION: Synthetic Construct

<400> SEQUENCE: 192

| | |
|---|---|
| gcctccacca agggcccatc ggtcttcccc ctggcaccct cctccaagag cacctctggg | 60 |

```
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaagc cgctggggca      360
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcggagga gcagtacaac      540 agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgcccccatc ccgggaggag      720
atgaccaaga accaggtcag cctgacctgc ctggtcaaag cttctatcc cagcgacatc       780 gccgtggagt gggagagcaa tgggcagccg gagaacaact acaagaccac gcctcccgtg      840
ctggactccg acggctcctt cttcctctat agcaagctca ccgtggacaa gagcaggtgg      900
cagcagggga acgtcttctc atgctccgtg atgcatgagg ctctgcacaa ccactacacg      960
cagaagagcc tctccctgtc ccccgga                                         987
```

<210> SEQ ID NO 193
<211> LENGTH: 990
<212> TYPE: DNA
<213> ORGANISM: Artificial Sequence
<220> FEATURE:
<223> OTHER INFORMATION: Synthetic Construct

<400> SEQUENCE: 193

```
gcctccacca agggcccatc ggtcttcccc ctggcaccct cctccaagag cacctctggg       60
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaagc cgctggggca      360
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcggagga gcagtacaac      540 agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgcccccatc ccgggaggag      720
atgaccaaga accaggtcag cctgacctgc ctggtcaaag cttctatcc cagcgacatc       780 gccgtggagt gggagagcaa tgggcagccg gagaacaact acaagaccac gcctcccgtg      840
ctggactccg acggctcctt cttcctctat agcaagctca ccgtggacaa gagcaggtgg      900
cagcagggga acgtcttctc atgctccgtg atgcatgagg ctctgcacaa ccactacacg      960
cagaagagcc tctccctgtc ccccggaaaa                                      990
```

<210> SEQ ID NO 194

<211> LENGTH: 321
<212> TYPE: DNA
<213> ORGANISM: Artificial Sequence
<220> FEATURE:
<223> OTHER INFORMATION: Synthetic Construct

<400> SEQUENCE: 194

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321
```

<210> SEQ ID NO 195
<211> LENGTH: 98
<212> TYPE: PRT
<213> ORGANISM: Artificial Sequence
<220> FEATURE:
<223> OTHER INFORMATION: Synthetic Construct

<400> SEQUENCE: 195

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg
```

<210> SEQ ID NO 196
<211> LENGTH: 95
<212> TYPE: PRT
<213> ORGANISM: Artificial Sequence
<220> FEATURE:
<223> OTHER INFORMATION: Synthetic Construct

<400> SEQUENCE: 196

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
            85                  90                  95
```

```
<210> SEQ ID NO 197
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 197

Gln Ser Xaa Xaa Xaa Pro Xaa Thr
1               5
```